US012391957B2

(12) United States Patent
Durbin et al.

(10) Patent No.: US 12,391,957 B2
(45) Date of Patent: Aug. 19, 2025

(54) RECOMBINANT NEWCASTLE DISEASE VIRUSES AND USES THEREOF FOR THE PREVENTION OF RSV DISEASE OR HUMAN METAPNEUMOVIRUS DISEASE

(71) Applicants: ICAHN SCHOOL OF MEDICINE AT MOUNT SINAI, New York, NY (US); RUTGERS, THE STATE UNIVERSITY OF NEW JERSEY, New Brunswick, NJ (US)

(72) Inventors: Joan E. Durbin, Sergeantsville, NJ (US); Russell K. Durbin, Sergeantsville, NJ (US); Adolfo Garcia-Sastre, New York, NY (US); Ignacio Mena, New York, NY (US); Peter Palese, New York, NY (US)

(73) Assignees: ICAHN SCHOOL OF MEDICINE AT MOUNT SINAI, New York, NY (US); RUTGERS, THE STATE UNIVERSITY OF NEW JERSEY, New Brunswick, NJ (US)

( * ) Notice: Subject to any disclaimer, the term of this patent is extended or adjusted under 35 U.S.C. 154(b) by 1098 days.

(21) Appl. No.: 17/268,403

(22) PCT Filed: Aug. 16, 2019

(86) PCT No.: PCT/US2019/046837

§ 371 (c)(1),
(2) Date: Feb. 12, 2021

(87) PCT Pub. No.: WO2020/037215

PCT Pub. Date: Feb. 20, 2020

(65) Prior Publication Data

US 2021/0198323 A1 Jul. 1, 2021

Related U.S. Application Data

(60) Provisional application No. 62/765,242, filed on Aug. 17, 2018.

(51) Int. Cl.
*C07K 14/08* (2006.01)
*A61K 39/12* (2006.01)
(Continued)

(52) U.S. Cl.
CPC .............. *C12N 15/86* (2013.01); *A61K 39/12* (2013.01); *C07K 14/08* (2013.01); *C12N 15/113* (2013.01);
(Continued)

(58) Field of Classification Search
None
See application file for complete search history.

(56) References Cited

U.S. PATENT DOCUMENTS 4,444,887 A 4/1984 Hoffman
4,474,893 A 10/1984 Reading
(Continued)

FOREIGN PATENT DOCUMENTS

AU 2002307971 B2 5/2008
CN 101787373 A 7/2010
(Continued)

OTHER PUBLICATIONS

Martinez-Sobrido et al. (Journal of Virology. 2006; 80 (3): 1130-1139).*
(Continued)

*Primary Examiner* — Shanon A. Foley
(74) *Attorney, Agent, or Firm* — Bryan D. Zerhusen, Esq.; Nicholas R. Herrel, Esq.; CANTOR COLBURN LLP

(57) ABSTRACT

Described herein are recombinant Newcastle disease viruses ("NDVs") comprising a packaged genome, wherein the packaged genome comprises a transgene encoding a respiratory syncytial virus ("RSV") F protein or human metapneumovirus ("hMPV") F protein. Also described herein are
(Continued)

Figure 1A:
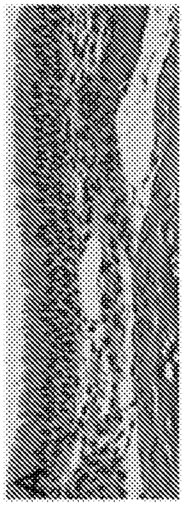
Figure 1E:
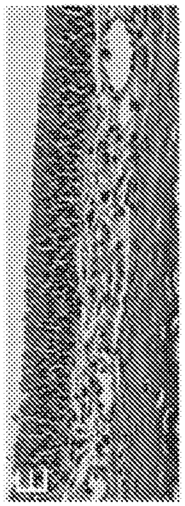
Figure 1B:
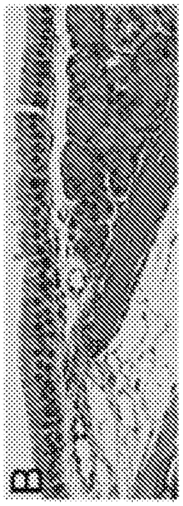
Figure 1F:
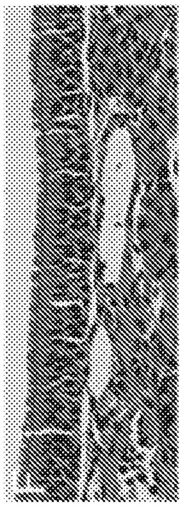
Figure 1C:
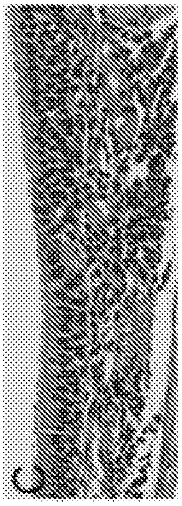

recombinant NDVs comprising a packaged genome, wherein the packaged genome comprises a transgene encoding a chimeric F protein, wherein the chimeric F protein comprises (i) an RSV F protein ectodomain and NDV F protein transmembrane and cytoplasmic domains; or (ii) an hMPV F protein ectodomain and NDV F protein transmembrane and cytoplasmic domains. The recombinant NDVs and compositions thereof are useful for the immunizing against RSV or hMPV as well as the prevention of RSV disease or hMPV disease.

18 Claims, 29 Drawing Sheets

Specification includes a Sequence Listing.

(51) Int. Cl.
*C07K 16/10* (2006.01)
*C12N 15/113* (2010.01)
*C12N 15/86* (2006.01)
*A61K 39/00* (2006.01)

(52) U.S. Cl.
CPC .. *A61K 2039/505* (2013.01); *A61K 2039/543* (2013.01)

(56) References Cited

U.S. PATENT DOCUMENTS 4,676,980 A 6/1987 Segal et al.
4,714,681 A 12/1987 Reading
4,716,111 A 12/1987 Osband et al.
4,816,397 A 3/1989 Boss et al.
4,816,567 A 3/1989 Cabilly et al.
4,925,648 A 5/1990 Hansen et al.
5,122,464 A 6/1992 Wilson et al.
5,166,057 A 11/1992 Palese et al.
5,223,409 A 6/1993 Ladner et al.
5,225,539 A 7/1993 Winter
5,273,745 A 12/1993 Schirrmacher
5,403,484 A 4/1995 Ladner et al.
5,413,923 A 5/1995 Kucherlapati et al.
5,427,908 A 6/1995 Dower et al.
5,516,637 A 5/1996 Huang et al.
5,530,101 A 6/1996 Queen et al.
5,545,806 A 8/1996 Lonberg et al.
5,565,332 A 10/1996 Hoogenboom et al.
5,569,825 A 10/1996 Lonberg et al.
5,571,698 A 11/1996 Ladner et al.
5,573,920 A 11/1996 Randle
5,580,717 A 12/1996 Dower et al.
5,585,089 A 12/1996 Queen et al.
5,601,819 A 2/1997 Wong et al.
5,625,126 A 4/1997 Lonberg et al.
5,633,425 A 5/1997 Lonberg et al.
5,658,727 A 8/1997 Barbas et al.
5,661,016 A 8/1997 Lonberg et al.
5,698,426 A 12/1997 Huse
5,731,168 A 3/1998 Carter et al.
5,733,743 A 3/1998 Stuart et al.
5,750,753 A 5/1998 Kimae et al.
5,766,886 A 6/1998 Studnicka et al.
5,780,225 A 7/1998 Wigler et al.
5,786,199 A 7/1998 Palese
5,807,715 A 9/1998 Morrison et al.
5,814,318 A 9/1998 Lonberg et al.
5,820,871 A 10/1998 Palese et al.
5,821,047 A 10/1998 Garrard et al.
5,854,037 A 12/1998 Palese et al.
5,891,680 A 4/1999 Lieschke et al.
5,939,598 A 8/1999 Kucherlapati et al.
5,969,108 A 10/1999 McCafferty et al.
6,005,079 A 12/1999 Casterman et al.
6,146,642 A 11/2000 Garcia-Sastre et al.
6,190,901 B1 2/2001 Sundick et al.
6,287,554 B1 9/2001 Sundick et al.
6,329,511 B1 12/2001 Vasquez et al.
6,331,415 B1 12/2001 Cabilly et al.
6,407,213 B1 6/2002 Carter et al.
6,451,323 B1 9/2002 Garcia-Sastre et al.
6,544,785 B1 4/2003 Palese et al.
6,635,416 B2 10/2003 Palese et al.
6,649,372 B1 11/2003 Palese et al.
6,669,943 B1 12/2003 Palese et al.
6,719,979 B2 4/2004 Peeters et al.
6,737,522 B2 5/2004 Sundick et al.
6,811,784 B2 11/2004 Haller et al.
6,852,522 B1 2/2005 Palese et al.
6,896,881 B1 5/2005 Russell et al.
7,052,685 B1 5/2006 Rook
7,056,689 B1 6/2006 Lorence et al.
7,060,430 B2 6/2006 Palese et al.
7,141,550 B2 11/2006 Molling et al.
7,223,389 B2 5/2007 Zakay-Rones et al.
7,244,558 B1 7/2007 Samal et al.
7,332,169 B2 2/2008 Peeters et al.
7,384,774 B2 6/2008 Palese et al.
7,442,379 B2 10/2008 Garcia-sastre et al.
7,442,527 B2 10/2008 Palese et al.
7,470,426 B1 12/2008 Roberts et al.
7,488,802 B2 2/2009 Collins et al.
7,494,808 B2 2/2009 Palese et al.
7,547,442 B2 6/2009 Peeters et al.
7,709,226 B2 5/2010 Foote
7,736,640 B2 6/2010 Lorence et al.
7,780,962 B2 8/2010 Roberts et al.
7,833,774 B2 11/2010 Palese et al.
7,858,081 B2 12/2010 Bernard et al.
8,043,612 B2 10/2011 Roberts et al.
8,105,578 B2 1/2012 Roberts et al.
8,124,084 B2 2/2012 Lefrancois et al.
8,163,879 B2 4/2012 Wong et al.
8,168,757 B2 5/2012 Finnefrock et al.
8,326,547 B2 12/2012 Liu et al.
8,354,509 B2 1/2013 Craven et al.
8,475,790 B2 7/2013 Jure-Kunkel
8,486,418 B2 7/2013 Bublot et al.
8,490,289 B2 7/2013 Nystrom et al.
8,492,118 B2 7/2013 Wong et al.
8,507,222 B2 8/2013 Wong et al.
8,591,881 B2 11/2013 Palese et al.
8,709,417 B2 4/2014 Allison et al.
8,765,462 B2 7/2014 Medin et al.
8,871,191 B2 10/2014 Pavlakis et al.
8,900,587 B2 12/2014 Craven et al.
8,940,288 B2 1/2015 Lefrancois et al.
8,952,136 B2 2/2015 Carven et al.
9,217,136 B2 12/2015 Palese et al.
9,370,563 B2 6/2016 Morales et al.
9,375,475 B2 6/2016 Allison et al.
9,387,242 B2 7/2016 Palese et al.
9,476,033 B2 10/2016 Samal et al.
9,616,118 B2 4/2017 Bublot et al.
9,642,298 B1 5/2017 Martin
9,821,016 B2 11/2017 Lauer et al.
9,937,196 B2 4/2018 Samal et al.
10,023,637 B2 7/2018 Allison et al.
10,251,922 B2 4/2019 Palese et al.
10,308,913 B2 6/2019 Palese et al.
10,383,936 B2 8/2019 Samal et al.
10,519,426 B2 12/2019 Cheng et al.
2002/0052030 A1 5/2002 Wonderling et al.
2002/0150554 A1 10/2002 Sundick et al.
2003/0044384 A1 3/2003 Roberts et al.
2003/0078410 A1 4/2003 Garcia-sastre et al.
2003/0224017 A1 12/2003 Samal et al.
2004/0005545 A1 1/2004 Fouchier et al.
2004/0234552 A1 11/2004 Peeters et al.
2005/0042664 A1 2/2005 Wu et al.
2005/0048549 A1 3/2005 Cao et al.
2005/0191617 A1 9/2005 Inoue et al.
2005/0235134 A1 10/2005 O'Sullivan

(56) References Cited

U.S. PATENT DOCUMENTS

| | | | |
|---|---|---|---|
| 2005/0238622 | A1 | 10/2005 | Axelrod et al. |
| 2006/0159695 | A1 | 7/2006 | Delvecchio et al. |
| 2006/0216310 | A1 | 9/2006 | Lorence et al. |
| 2008/0057037 | A1 | 3/2008 | Roberts et al. |
| 2008/0206201 | A1 | 8/2008 | Beier et al. |
| 2009/0061521 | A1 | 3/2009 | Palese et al. |
| 2009/0081161 | A1 | 3/2009 | Roberts et al. |
| 2009/0082299 | A1 | 3/2009 | Felber et al. |
| 2009/0175826 | A1 | 7/2009 | Subbiah et al. |
| 2009/0214590 | A1 | 8/2009 | Sundick et al. |
| 2009/0238791 | A1 | 9/2009 | Jacques et al. |
| 2009/0280144 | A1 | 11/2009 | Garcia-sastre et al. |
| 2010/0092430 | A1 | 4/2010 | Beier et al. |
| 2010/0297072 | A1 | 11/2010 | DePinho et al. |
| 2011/0020282 | A1 | 1/2011 | Beier et al. |
| 2011/0044937 | A1 | 2/2011 | Bell et al. |
| 2011/0081311 | A1 | 4/2011 | Pavlakis et al. |
| 2011/0081374 | A1 | 4/2011 | Bublot et al. |
| 2011/0158938 | A1 | 6/2011 | Bernard et al. |
| 2011/0189189 | A1 | 8/2011 | Jure-Kunkel |
| 2012/0034242 | A1 | 2/2012 | Jooss et al. |
| 2012/0058141 | A1 | 3/2012 | Palese et al. |
| 2012/0058538 | A1 | 3/2012 | Palese et al. |
| 2012/0064112 | A1 | 3/2012 | Samal et al. |
| 2012/0071859 | A1 | 3/2012 | Morgan et al. |
| 2012/0114648 | A1 | 5/2012 | Langermann et al. |
| 2012/0122185 | A1 | 5/2012 | Palese et al. |
| 2013/0084264 | A1 | 4/2013 | Schrier et al. |
| 2013/0108665 | A1 | 5/2013 | Liang |
| 2014/0044678 | A1 | 2/2014 | Palese et al. |
| 2014/0134128 | A1 | 5/2014 | Wong et al. |
| 2014/0159960 | A1 | 6/2014 | Mueller |
| 2014/0186303 | A1 | 7/2014 | Subbiah et al. |
| 2014/0205560 | A1 | 7/2014 | Wong et al. |
| 2014/0219955 | A1 | 8/2014 | Wong et al. |
| 2014/0242025 | A1 | 8/2014 | Wong et al. |
| 2014/0271677 | A1 | 9/2014 | Palese et al. |
| 2014/0271699 | A1* | 9/2014 | Kwong ................ C07K 14/005 435/254.11 |
| 2014/0377221 | A1 | 12/2014 | Tufaro et al. |
| 2015/0017121 | A1 | 1/2015 | Becher et al. |
| 2015/0093357 | A1 | 4/2015 | Lefrancois et al. |
| 2015/0132257 | A1 | 5/2015 | Wong et al. |
| 2015/0133531 | A1 | 5/2015 | Wiegand |
| 2015/0139945 | A1 | 5/2015 | Lefrancois et al. |
| 2015/0152188 | A1 | 6/2015 | Morisseau et al. |
| 2015/0250837 | A1 | 9/2015 | Nolin et al. |
| 2016/0015760 | A1 | 1/2016 | Palese et al. |
| 2016/0068823 | A1 | 3/2016 | Palese et al. |
| 2016/0137721 | A1 | 5/2016 | Palese et al. |
| 2016/0208222 | A1 | 7/2016 | Cheng et al. |
| 2017/0037379 | A1 | 2/2017 | Palese et al. |
| 2017/0247425 | A1 | 8/2017 | Ungerechts et al. |
| 2017/0285037 | A1 | 10/2017 | Kulangara et al. |
| 2018/0078592 | A1 | 3/2018 | Palese et al. |
| 2018/0251555 | A1 | 9/2018 | Allison et al. |
| 2018/0256655 | A1 | 9/2018 | Palese et al. |
| 2018/0280455 | A1 | 10/2018 | Palese et al. |
| 2020/0061184 | A1 | 2/2020 | Palese et al. |
| 2021/0198323 | A1* | 7/2021 | Durbin .................... A61P 31/14 |

FOREIGN PATENT DOCUMENTS

| | | | |
|---|---|---|---|
| CN | 102740887 | A | 10/2012 |
| CN | 105734023 | A | 7/2016 |
| CN | 106166294 | A | 11/2016 |
| DE | 3922444 | A1 | 1/1991 |
| EP | 0239400 | B1 | 8/1994 |
| EP | 0702085 | A1 | 3/1996 |
| EP | 0780475 | B1 | 6/1997 |
| EP | 0974660 | A1 | 1/2000 |
| EP | 0592106 | B1 | 11/2004 |
| EP | 0519596 | B1 | 2/2005 |
| EP | 1248654 | B1 | 10/2005 |
| EP | 1032269 | B1 | 8/2007 |
| EP | 1486211 | B1 | 10/2008 |
| EP | 2085092 | A1 | 8/2009 |
| EP | 0702085 | B2 | 1/2010 |
| EP | 2669381 | A1 | 12/2013 |
| EP | 2579884 | B1 | 6/2014 |
| EP | 2393921 | B1 | 7/2015 |
| EP | 2987856 | A1 | 2/2016 |
| EP | 2766035 | B1 | 3/2018 |
| JP | 2012-527465 | A | 11/2012 |
| WO | WO 1986005807 | A1 | 10/1986 |
| WO | WO 1989001036 | A1 | 2/1989 |
| WO | WO 1990002809 | A1 | 3/1990 |
| WO | WO 1991000360 | A1 | 1/1991 |
| WO | WO 1991009967 | A1 | 7/1991 |
| WO | WO 1991010737 | A1 | 7/1991 |
| WO | WO 1991010741 | A1 | 7/1991 |
| WO | WO 1992000373 | A1 | 1/1992 |
| WO | WO 1992001047 | A1 | 1/1992 |
| WO | WO 1992008802 | A1 | 5/1992 |
| WO | WO 1992018619 | A1 | 10/1992 |
| WO | WO 1992022324 | A1 | 12/1992 |
| WO | WO 1993011236 | A1 | 6/1993 |
| WO | WO 1993017105 | A1 | 9/1993 |
| WO | WO 1993017715 | A1 | 9/1993 |
| WO | WO 1994004678 | A1 | 3/1994 |
| WO | WO 1994004690 | A1 | 3/1994 |
| WO | WO 1994025591 | A1 | 11/1994 |
| WO | WO 1994025627 | A1 | 11/1994 |
| WO | WO 1995015982 | A2 | 6/1995 |
| WO | WO 1995015982 | A3 | 6/1995 |
| WO | WO 1995020401 | A1 | 8/1995 |
| WO | WO 1996033735 | A1 | 10/1996 |
| WO | WO 1996034096 | A1 | 10/1996 |
| WO | WO 1996034625 | A1 | 11/1996 |
| WO | WO 1997006270 | A1 | 2/1997 |
| WO | WO 1997012032 | A1 | 4/1997 |
| WO | WO 1997013844 | A1 | 4/1997 |
| WO | WO 1997014433 | A1 | 4/1997 |
| WO | WO 1998002530 | A1 | 1/1998 |
| WO | WO 1998013501 | A2 | 4/1998 |
| WO | WO 1998013501 | A3 | 4/1998 |
| WO | WO 1998016654 | A1 | 4/1998 |
| WO | WO 1998024893 | A2 | 6/1998 |
| WO | WO 1998024893 | A3 | 6/1998 |
| WO | WO 1998046645 | A2 | 10/1998 |
| WO | WO 1998046645 | A3 | 10/1998 |
| WO | WO 1998050433 | A2 | 11/1998 |
| WO | WO 1998050433 | A3 | 11/1998 |
| WO | WO 1998053078 | A1 | 11/1998 |
| WO | WO 1999002657 | A1 | 1/1999 |
| WO | WO 1999015672 | A1 | 4/1999 |
| WO | WO 1999018799 | A1 | 4/1999 |
| WO | WO 1999066045 | A1 | 12/1999 |
| WO | WO 2000062735 | A2 | 10/2000 |
| WO | WO 2000062735 | A3 | 10/2000 |
| WO | WO 2000067786 | A1 | 11/2000 |
| WO | WO 2001004333 | A1 | 1/2001 |
| WO | WO 2001020989 | A1 | 3/2001 |
| WO | WO 2001044301 | A1 | 6/2001 |
| WO | WO 2002081621 | A2 | 10/2002 |
| WO | WO 2002081621 | A3 | 10/2002 |
| WO | WO 2002102404 | A1 | 12/2002 |
| WO | WO 2003092579 | A2 | 11/2003 |
| WO | WO 2003092579 | A3 | 11/2003 |
| WO | WO 2006/042156 | * | 4/2006 |
| WO | WO 2006050984 | A2 | 5/2006 |
| WO | WO 2006050984 | A3 | 5/2006 |
| WO | WO 2007001677 | A2 | 1/2007 |
| WO | WO 2007001677 | A3 | 1/2007 |
| WO | WO 2007008918 | A2 | 1/2007 |
| WO | WO 2007008918 | A3 | 1/2007 |
| WO | WO 2007064802 | A1 | 6/2007 |
| WO | WO 2007084342 | A2 | 7/2007 |
| WO | WO 2007084342 | A3 | 7/2007 |
| WO | WO 2007113648 | A2 | 10/2007 |
| WO | WO 2007113648 | A3 | 10/2007 |
| WO | WO 2008011726 | A1 | 1/2008 |
| WO | WO 2008156712 | A1 | 12/2008 |

(56) References Cited

FOREIGN PATENT DOCUMENTS

| | | | |
|---|---|---|---|
| WO | WO 2009002562 | A2 | 12/2008 |
| WO | WO 2009002562 | A3 | 12/2008 |
| WO | WO 2009095167 | A1 | 8/2009 |
| WO | WO 2009101149 | A2 | 8/2009 |
| WO | WO 2009101149 | A3 | 8/2009 |
| WO | WO 2010091262 | A1 | 8/2010 |
| WO | WO 2010135242 | A1 | 11/2010 |
| WO | WO 2011022656 | A2 | 2/2011 |
| WO | WO 2011022656 | A3 | 2/2011 |
| WO | WO 2011041613 | A2 | 4/2011 |
| WO | WO 2011041613 | A3 | 4/2011 |
| WO | WO 2011119628 | A2 | 9/2011 |
| WO | WO 2011119628 | A3 | 9/2011 |
| WO | WO 2011154476 | A1 | 12/2011 |
| WO | WO 2012000188 | A1 | 1/2012 |
| WO | WO 2012000443 | A1 | 1/2012 |
| WO | WO 2012142529 | A2 | 10/2012 |
| WO | WO 2012142529 | A3 | 10/2012 |
| WO | WO 2013053775 | A1 | 4/2013 |
| WO | WO 2013112942 | A1 | 8/2013 |
| WO | WO 2013178344 | A1 | 12/2013 |
| WO | WO 2014047350 | A1 | 3/2014 |
| WO | WO 2014066527 | A2 | 5/2014 |
| WO | WO 2014066527 | A3 | 5/2014 |
| WO | WO 2014158811 | A1 | 10/2014 |
| WO | WO 2014170032 | A1 | 10/2014 |
| WO | WO 2015018528 | A1 | 2/2015 |
| WO | WO 2015018529 | A1 | 2/2015 |
| WO | WO 2015032755 | A1 | 3/2015 |
| WO | WO 2015127501 | A1 | 9/2015 |
| WO | WO 2015131994 | A1 | 9/2015 |
| WO | WO 2016018920 | A1 | 2/2016 |
| WO | WO 2016048903 | A1 | 3/2016 |
| WO | WO 2016094377 | A1 | 6/2016 |
| WO | WO 2017019894 | A1 | 2/2017 |
| WO | WO 2017019896 | A1 | 2/2017 |
| WO | WO 2017019897 | A1 | 2/2017 |
| WO | WO 2017062953 | A1 | 4/2017 |
| WO | WO 2017083291 | A1 | 5/2017 |
| WO | WO 2017118867 | A1 | 7/2017 |
| WO | WO 2017123981 | A1 | 7/2017 |
| WO | WO 2017190112 | A1 | 11/2017 |
| WO | WO 2018027316 | A1 | 2/2018 |
| WO | WO 2018209194 | A2 | 11/2018 |
| WO | WO 2018209194 | A3 | 11/2018 |
| WO | WO 2018218151 | A1 | 11/2018 |
| WO | WO 2019197275 | A1 | 10/2019 |
| WO | WO 2019209859 | A1 | 10/2019 |
| WO | WO 2020/012037 | * | 1/2020 |
| WO | WO 2020014591 | A1 | 1/2020 |
| WO | WO 2020037215 | A1 | 2/2020 |
| WO | WO 2020043835 | A1 | 3/2020 |
| WO | WO 2020079427 | A1 | 4/2020 |

OTHER PUBLICATIONS

SEQ ID No. 6 alignment with Geneseq db access No. AEH30839 Apr. 2006.*
SEQ ID No. 3 alignment with Genesdeq db access No. AAZ44617 Apr. 2000.*
SEQ ID No. 10 alignment with Genesdeq db access BBN47024 Nov. 2014.*
SEQ ID No. 9 alignment with GenEmbl db access AF295543 2001.*
SEQ ID No. 1 alignment with Geneseq db access AEH30838 2006.*
SEQ ID No. 17 UniPtot db acc No. Q8B9N8_9MONO 2003.*
SEQ ID No. 16 alignment with GenEmbl db access AY145301 2003.*
SEQ ID No. 20 alignment with GenEmbl db access AY845400 2005.*
McGinnes et al. (Journal of Virology. 2011; 366-377).*
Kim et al. (Viruses. 2016; 8 (7): 183).*
Instant SEQ 21 alignment with Geneseq db access ARL59598 by Bu et al. in CN1869234-2008.*
Abolnik et al., 2012, "Full genomic sequence of an African avian paramyxovirus type 4 strain isolated from a wild duck," Virus Genes, 45(3):537-541.
Afonso et al., 2016, "Taxonomy of the order Mononegavirales: update 2016," Arch Virol., 161(8):2351-2360.
Aigner et al., "An effective tumor vaccine optimized for costimulation via bispecific and trispecific fusion proteins," Int. J. Oncol., 32(4): 777-789 (2008).
Akhras et al., 2010, "Human metapneumovirus and respiratory syncytial virus: subtle differences but comparable severity," Infect. Dis. Rep., 2(2):e12 (5 pages).
Alexander et al., 1978, "Relationship of parakeet/Netherlands/449/75 virus to other avian paramyxoviruses," Res. Vet. Sci., 25(1):105-106.
Alexander et al., 1981, "Characterization of viruses from doves representing a new serotype of avian paramyxoviruses," Arch. Virol., 68(3-4):265-269.
Alexander, "Newcastle disease, Newcastle disease virus—an avian paramyxovirus," Kluwer Academic Publishers, Dordrecht, The Netherlands, pp. 1-22 (1988).
Al-Lazikani et al., "Standard conformations for the canonical structures of immunoglobulins," J. Mol. Biol., 273(4):927-948 (1997).
Alper et al., 2009, "Rate of concurrent otitis media in upper respiratory tract infections with specific viruses," Arch. Otolaryngol. Head Neck Surg., 135(1):17-21.
Altomonte et al., "Engineered newcastle disease virus as an improved oncolytic agent against hepatocellular carcinoma," Mol. Ther., 18: 275-284 (2010).
Andral et al., 1984, "Isolation of avian paramyxovirus 2 and 3 from turkeys in Brittany," Vet. Rec., 114(23):570-571.
Annels et al., "Oncolytic Immunotherapy for Bladder Cancer Using Coxsackie A21 Virus," Mol. Ther. Oncolytics, 9:1-12 (2018).
Assudani et al., "Immunotherapeutic potential of DISC-HSV and OX40L in cancer," Cancer Immunol. Immunother., 55:104-111 (2006).
Ayers et al., "IFN-γ-related mRNA profile predicts clinical response to PD-1 blockade," J. Clin. Invest., 127(8):2930-2940 (2017).
Ayllon et al., 2013, "Rescue of Recombinant Newcastle Disease Virus from cDNA," J. Vis. Exp., (80):e50830.
Baca et al., "Antibody humanization using monovalent phage display," J. Biol. Chem., 272(16):10678-10684 (1997).
Bai et al., 2002, "Dendritic cells pulsed with viral oncolysates potently stimulate autologous T cells from cancer patients," Int. J. Oncol., 21(4):685-694.
Bankowski et al., 1981, "Effect of paramyxovirus yucaipa on fertility, hatchability, and poult yield of turkeys," Avian. Dis., 25(2):517-520.
Barber et al. "Restoring function in exhausted CD8 T cells during chronic viral infection," Nature 439:682-687, with Supplemental Material attached (2006).
Bart et al., "Role of interferon in the anti-melanoma effects of poly (I).poly (C) and Newcastle disease virus," Nat. New. Biol., 245:229-230 (1973).
Bauzon et al., 2014, "Armed therapeutic viruses—a disruptive therapy on the horizon of cancer immunotherapy," Front. Immunol., 5(74):1-10.
Blackburn et al., "Tissue-specific differences in PD-1 and PD-L1 expression during chronic viral infection: implications for CD8 T-cell exhaustion," J. Virol., 84(4):2078-2089 (2010) (Epub Dec. 2, 2009).
Blake et al., "Automated kinetic exclusion assays to quantify protein binding interactions in homogeneous solution," Anal. Biochem., 272(2):123-134 (1999).
Bohle et al., 1990, "Postoperative active specific immunization in colorectal cancer patients with virus-modified autologous tumor-cell vaccine. First clinical results with tumor-cell vaccines modified with live but avirulent Newcastle disease virus," Cancer, 66(7):1517-1523.
Bohnsack et al., "Adaptation of the Immune-Related Response Criteria: irRECIST," ESMO, Abstract 4958, pp. 1-8 (2014).
Boisseau, 1993, "Basis for the evaluation of the microbiological risks due to veterinary drug residues in food," Vet. Microbiol., 35(3-4):187-192.

(56) References Cited

OTHER PUBLICATIONS

Brahmer et al., "Phase I study of single-agent anti-programmed death-1 (MDX-1106) in refractory solid tumors: safety, clinical activity, pharmacodynamics, and immunologic correlates," J. Clin. Oncol., 28(19):3167-3175 (2010).
Brahmer et al., "Safety and activity of anti-PD-L1 antibody in patients with advanced cancer," N. Engl. J. Med., 366(26):2455-2465 (2012).
Briand et al., 2012, "Complete genome sequence of a novel avian paramyxovirus," J Virol., 86(14):7710.
Brinkmann et al., "Phage display of disulfide-stabilized Fv fragments," J. Immunol. Methods, 182(1):41-50 (1995).
Brown et al., "Role of PD-1 in regulating acute infections," Curr. Opin. Immunol., 22(3):397-401 (2010).
Bryant et al., "Development of intermediate-grade (mantle cell) and low-grade (small lymphocytic and marginal zone) human non-Hodgkin's lymphomas xenotransplanted in severe combined immunodeficiency mouse models," Lab. Invest., 80:557-573 (2000).
Buchman et al., 2002, "Nasal and otologic effects of experimental respiratory syncytial virus infection in adults," Am. J. Otolaryngol., 23(2):70-75.
Buijs et al., "Recombinant Immunomodulating Lentogenic or Mesogenic Oncolytic Newcastle Disease Virus for Treatment of Pancreatic Adenocarcinoma," Viruses, 7:2980-2998 (2015).
Burton et al., "Human antibodies from combinatorial libraries," Adv. Immunol., 57:191-280 (1994).
Calain et al., "The Rule of Six, a Basic Feature for Efficient Replication of Sendai Virus Defective Interfering RNA," J. Virol., 67(8):4822-4830 (1993).
Caldas et al., "Design and synthesis of germline-based hemi-humanized single-chain Fv against the CD18 surface antigen," Protein Eng., 13(5):353-360 (2000).
Capua et al., 2004, "Isolation of an avian paramyxovirus type 9 from migratory waterfowl in Italy," Vet. Rec., 155(5):156.
Car et al., "The Toxicology of Interleukin-12: A Review," Toxicol. Pathol., 27(1):58-63 (1999).
Carnero et al., 2009, "Optimization of human immunodeficiency virus gag expression by newcastle disease virus vectors for the induction of potent immune responses," J Virol., 83(2):584-597 (Epub Nov. 12, 2008).
Carpenter et al., "Non-Fc receptor-binding humanized anti-CD3 antibodies induce apoptosis of activated human T cells," J. Immunol., 165(11):6205-6213 (2000).
Carthon et al., "Preoperative CTLA-4 blockade: tolerability and immune monitoring in the setting of a presurgical clinical trial," Clin. Canc. Res., 16(10):2861-2871 (2010).
Caruso et al., "Adenovirus-mediated interleukin-12 gene therapy for metastatic colon carcinoma," Proc. Natl. Acad. Sci. USA, 93:11302-11306 (1996).
Cassel et al., 1965, "Newcastle Disease Virus as an Antineoplastic Agent," Cancer, 18:863-868.
Chaiwatpongsakorn et al., 2011, "Soluble respiratory syncytial virus fusion protein in the fully cleaved, pretriggered state is triggered by exposure to low-molarity buffer," J. Virol., 85(8):3968-3977.
Chen et al., "CD4 T Cells Require ICOS-Mediated P13K Signaling to Increase T-Bet Expression in the Setting of Anti-CTLA-4 Therapy," Cancer Immunol. Res., 2(2):167-176 (2013).
Cheng et al., "Genetic Modification of Oncolytic Newcastle Disease Virus for Cancer Therapy." J. Virol., 90(1):5343-5352 (2016).
Cho et al., 2018, "Co-expression of the Hemagglutinin and Neuraminidase by Heterologous Newcastle Disease Virus Vectors Protected Chickens against H5 Clade 2.3.4.4 HPAI Viruses," Sci. Rep., 8(1):16854 (9 pages).
Chothia et al., "Canonical structures for the hypervariable regions of immunoglobulins," J. Mol. Biol., 196(4):901-917 (1987).
Chothia et al., "Conformations of immunoglobulin hypervariable regions," Nature, 342:877-883 (1989).
Chothia et al., "Structural repertoire of the human VH segments," J. Mol. Biol., 227(3):799-817 (1992).
Chumakov et al., "Oncolytic Enteroviruses," Mol. Biol. (Mosk), 46(5):639-650 (2012).
Clinical Trial NCT01295827, "Study of Pembrolizumab (MK-3475) in Participants With Progressive Locally Advanced or Metastatic Carcinoma, Melanoma, or Non-small Cell Lung Carcinoma (P07990/MK-3475-001/Keynote-001) (Keynote-001)," Merck Sharp & Dohme Corp., updated Sep. 13, 2018 (13 pages).
Cloud et al., 1980, "Characterization of Nine Avian Paramyxoviruses," Avian Dis., 24(1):139-152.
Colbère-Garapin et al., "A new dominant hybrid selective marker for higher eukaryotic cells," J. Mol. Biol., 150(1):1-14 (1981).
Copeland et al., 2005, "Functional chimeras of human immunodeficiency virus type 1 Gp120 and influenza A virus (H3) hemagglutinin," J Virol., 79(10):6459-6471.
Crouse et al., "Expression and amplification of engineered mouse dihydrofolate reductase minigenes," Mol. Cell Biol., 3(2):257-266 (1983).
Crowe, 2001, "Respiratory syncytial virus vaccine development," Vaccine, 20 Suppl 1:S32-S37.
Csatary et al., "MTH-68/H oncolytic viral treatment in human high-grade gliomas," J. Neurooncol., 67:83-93 (2004).
Cuadrado-Castano et al., 2015, "Enhancement of the proapoptotic properties of newcastle disease virus promotes tumor remission in syngeneic murine cancer models," Mol Cancer Ther., 14(5):1247-1258.
Cuadrado-Castano et al., 2015, "The therapeutic effect of death: Newcastle disease virus and its antitumor potential," Virus Res., 209:56-66.
Cull et al., "Screening for receptor ligands using large libraries of peptides linked to the C terminus of the lac repressor," Proc. Natl. Acad. Sci. USA, 89(5):1865-1869 (1992).
Cuoto et al., "Anti-BA46 monoclonal antibody Mc3: humanization using a novel positional consensus and in vivo and in vitro characterization," Cancer Res., 55(8):1717-1722 (1995).
Cuoto et al., "Designing human consensus antibodies with minimal positional templates," Cancer Res., 55(23 Suppl):5973s-5977s (1995).
Curran et al, "Combination CTLA-4 blockade and 4-1BB activation enhances tumor rejection by increasing T-cell infiltration, proliferation, and cytokine production," PLoS One, 6(4):e19499 (2011).
Curran et al., "PD-1 and CTLA-4 combination blockade expands infiltrating T cells and reduces regulatory T and myeloid cells within B16 melanoma tumors," Proc. Natl. Acad. Sci. USA, 107(9):4275-4280 (2010).
Cwirla et al., "Peptides on phage: a vast library of peptides for identifying ligands," Proc. Natl. Acad. Sci. USA, 87(16):6378-6382 (1990).
De Leeuw et al., "Virulence of Newcastle disease virus is determined by the cleavage site of the fusion protein and by both the stem region and globular head of the haemagglutinin-neuraminidase protein," J. Gen. Virol., 86(5): 1759-1769 (2005).
De Sousa Linhares et al., "Not All Immune Checkpoints Are Created Equal," Front. Immunol., 9:1909 (2018).
Dezfouli et al., "Enhancing CTL responses to melanoma cell vaccines in vivo: synergistic increases obtained using IFNgamma primed and IFNbeta treated B7-1+ B16-F10 melanoma cells," Immunol. Cell. Biol., 81(6):459-471 (2003).
Diamond et al., "Type I interferon is selectively required by dendritic cells for immune rejection of tumors," J. Exp. Med., 208(10):1989-2003 (2011).
Dias et al., "Targeted cancer immunotherapy with oncolytic adenovirus coding for a fully human monoclonal antibody specific for CTLA-4," Gen Ther., 19(10):988-998 (2012).
Dortmans et al., "Virulence of Newcastle disease virus: what is known so far?" Vet. Res., 42:122 (2011).
Dortmans et al., 2012, "Newcastle disease virus outbreaks: vaccine mismatch or inadequate application?," Vet. Microbiol., 160(1-2):17-22.
Douin-Echinard et al., "Enhancement of anti-tumor immunity by injection of fibroblasts genetically engineered to produce IL-12 and to express CD70," Gene Therapy of Cancer, edited by Walden et al., Plenum Press, New York, 353-357 (1998).
Doyle et al., 1927, "A Hitherto Unrecorded Disease of Fowls Due to a Filter-passing Virus," J. Comp. Pathol. Ther., 40:144-169.

(56) References Cited

OTHER PUBLICATIONS

Dulos et al., 2012, "PD-1 blockade augments Th1 and Th17 and suppresses Th2 responses in peripheral blood from patients with prostate and advanced melanoma cancer," J Immunother, 35(2):169-178.
Dupraz et al., "Dominant negative MyD88 proteins inhibit interleukin-1β/interferon-γ-mediated induction of nuclear factor κB-dependent nitrite production and apoptosis in β cells," J. Biol. Chem., 275:37672-37678 (2000).
Durbin et al., 1996, "Targeted disruption of the mouse Stat1 gene results in compromised innate immunity to viral disease," Cell, 84(3):443-450.
Eisenhauer et al., "New response evaluation criteria in solid tumours: revised RECIST guideline (version 1.1)," Eur. J. Cancer, 45:228-247 (2009).
Elankumaran et al., "Type I interferon-sensitive recombinant newcastle disease virus for oncolytic virotherapy," J. Virol., 84:3835-3844 (2010).
Elmberg et al., 2017, "Potential disease transmission from wild geese and swans to livestock, poultry and humans: a review of the scientific literature from a One Health perspective," Infect Ecol Epidemiol., 7(1):1300450 (21 pages).
Esper et al., 2003, "Human metapneumovirus infection in the United States: clinical manifestations associated with a newly emerging respiratory infection in children," Pediatrics, 111(6 Pt 1):1407-1410.
Fan et al., "Engagement of the ICOS pathway markedly enhances efficacy of CTLA-4 blockade in cancer immunotherapy," J. Exp. Med., 211(4):715-725 (2014).
Fecci et al., "Systemic CTLA-4 blockade ameliorates glioma-induced changes to the CD4+ T cell compartment without affecting regulatory T-cell function," Clin. Cancer Res., 13: 2158-2167 (2007).
Felici et al., "Selection of antibody ligands from a large library of oligopeptides expressed on a multivalent exposition vector," J. Mol. Biol., 222(2):301-310 (1991).
Fields et al., "Adenoviridae and Their Replication," Fundamental Virology, 2nd Edition, Raven Press, Chapter 31, pp. 771-813 (1991).
Fiola et al., "Tumor selective replication of Newcastle disease virus: association with defects of tumor cells in antiviral defence," Int. J. Cancer, 119(2): 328-338 (2006).
Fisher et al., "IL-6 trans-signaling licenses mouse and human tumor microvascular gateways for trafficking of cytotoxic T cells," J. Clin. Invest., 121(10):3846-3859 (2011).
Fodde et al., "Disease model: familial adenomatous polyposis," Trends Mol. Med., 7:369-373 (2001).
Fodor et al., "Multiplexed biochemical assays with biological chips," Nature, 364(6437):555-556 (1993).
Foecking et al., "Powerful and versatile enhancer-promoter unit for mammalian expression vectors," Gene, 45(1):101-105 (1986).
Foote et al., "Antibody framework residues affecting the conformation of the hypervariable loops," J. Mol. Biol., 224(2):487-499 (1992).
Fournier et al., "Oncolytic Newcastle Disease Virus as Cutting Edge between Tumor and Host," Biology, 2:936-975 (2013).
Fournier et al., 2012, "Analysis of three properties of Newcastle disease virus for fighting cancer: tumor-selective replication, anti-tumor cytotoxicity, and immunostimulation," Methods Mol Biol., 797:177-204.
Foy et al., "Regulation of interferon regulatory factor-3 by the hepatitis C virus serine protease," Science, 300(5622):1145-1148 (2003).
Franciszkiewicz et al., "Role of chemokines and chemokine receptors in shaping the effector phase of the antitumor immune response," Cancer Res., 72(24):6325-6332 (2012).
Fransen et al., "Controlled Local Delivery of CTLA-4 Blocking Antibody Induces CD8+ T-Cell-Dependent Tumor Eradication and Decreases Risk of Toxic Side Effects," Clin. Cancer Res., 19(19):5381-5389 (2013).
Freeman et al., "Phase I/II trial of intravenous NDV-HUJ oncolytic virus in recurrent glioblastoma multiforme," Mol. Ther., 13:221-228 (2006).
Fu et al., "The ICOS/ICOSL Pathway is Required for Optimal Antitumor Responses Mediated by Anti-CTLA-4 Therapy," Cancer Res., 71:5445-5454 (2011).
Fuertes et al., "Host type I IFN signals are required for antitumor CD8+ T cell responses through CD8{alpha} + dendritic cells," J. Exp. Med., 208(10):2005-2016 (2011).
Fujimoto et al., 2012, "Induction and maintenance of anti-influenza antigen-specific nasal secretory IgA levels and serum IgG levels after influenza infection in adults," Influenza Other Respir. Viruses, 6(6):396-403.
Galivo et al., "Interference of CD40L-Mediated Tumor Immunotherapy by Oncolytic Vesicular Stomatitis Virus," Human Gene Therapy, 21:439-450 (2010).
Gambotto et al., "Induction of antitumor immunity by direct intratumoral injection of a recombinant adenovirus vector expressing interleukin-12," Cancer Gene Ther., 6(1):45-53 (1999).
Ganar et al., 2014, "Newcastle disease virus: current status and our understanding, " Virus Res., 184:71-81.
Gao et al., "Expression of transgenes from newcastle disease virus with a segmented genome," J. Virol., 82(6): 2692-2698 (2008).
Garcia-Sastre et al., "Introduction of foreign sequences into the genome of influenza A virus," Dev. Biol. Stand., 82:237-246 (1994).
Garcia-Sastre et al., "Use of a mammalian internal ribosomal entry site element for expression of a foreign protein by a transfectant influenza virus," J. Virol., 68:6254-6261 (1994).
Garcia-Sastre et al., 1995, "Influenza virus vectors," Biologicals, 23(2):171-178.
Gardiner et al., "A Randomized, Double-Blind, Placebo-Controlled Assessment of BMS-936558, a Fully Human Monoclonal Antibody to Programmed Death-1 (PD-1), in Patients with Chronic Hepatitis C Virus Infection," PLoS One, 8(5):e63818 (2013).
Genbank Accession No. AAA52578.1, "GM-CSF [*Homo sapiens*]," Nov. 8, 1994.
Genbank Accession No. AAB19466.1, "granulocyte-macrophage colony-stimulating factor [Canis lupus familiaris]," May 7, 1993.
Genbank Accession No. AAB41697.1, "interleukin-15 [Rattus norvegicus]," Feb. 1, 1997.
Genbank Accession No. AAB60398.1, "interleukin-15 [Macaca mulatta]," Feb. 3, 1996.
Genbank Accession No. AAB94536.1, "interleukin-15 [Rattus norvegicus]," Jan. 2, 1998.
Genbank Accession No. AAC06041.1, "granulocyte-macrophage colony-stimulating factor [Felis catus]," Mar. 19, 1998.
Genbank Accession No. AAD00274.1, "CD70 [Mus musculus]," Jan. 5, 1999.
Genbank Accession No. AAG16626.1, "granulocyte-macrophage colony-stimulating factor [Macaca mulatta]," Dec. 23, 2002.
Genbank Accession No. AAH18149.1, "Interleukin 15 [*Homo sapiens*]," Jul. 15, 2006.
Genbank Accession No. AAH23698.1, "Interleukin 15 [Mus musculus]," Jul. 15, 2006.
Genbank Accession No. AAI00964.1, "Interleukin 15 [*Homo sapiens*]," Oct. 4, 2006.
Genbank Accession No. AAS67141.1, "fusion protein [Avian avulavirus 1]," Mar. 22, 2004.
Genbank Accession No. AAS67147.1, "fusion protein [Avian avulavirus 1]," Mar. 22, 2004.
Genbank Accession No. AAS67153.1, "fusion protein [Avian avulavirus 1]," Mar. 22, 2004.
Genbank Accession No. AAS67159.1, "fusion protein [Avian avulavirus 1]," Mar. 22, 2004.
Genbank Accession No. AAS67165.1, "fusion protein [Avian avulavirus 1]," Mar. 22, 2004.
Genbank Accession No. ACJ53752.1, "fusion protein [Avian avulavirus 1]," Nov. 25, 2008.
Genbank Accession No. ACJ53758.1, "fusion protein [Avian avulavirus 1]," Nov. 25, 2008.
Genbank Accession No. ACK57498.1, "fusion protein [Avian avulavirus 1]," Apr. 19, 2011.

(56) References Cited

OTHER PUBLICATIONS

Genbank Accession No. ADF59234.1, "fusion protein [Avian avulavirus 1]," Aug. 16, 2011.
Genbank Accession No. AF124443.1, "Newcastle disease virus isolate Roakin matrix protein mRNA, complete cds," Mar. 6, 2000.
Genbank Accession No. AF163440.1, "Newcastle disease virus fusion glycoprotein precursor, gene, complete cds," Jul. 6, 1999.
Genbank Accession No. AF309418.1, "Newcastle disease virus B1, complete genome," Dec. 2, 2000.
Genbank Accession No. AIA66858.1, "NBS-LRR resistance protein, partial [Solanum viarum]," Jun. 4, 2014.
Genbank Accession No. AIA66951.1, "fusion protein [Avian avulavirus 1]," Jun. 4, 2014.
Genbank Accession No. AIO82815.1, "PPIC-type PPIASE domain protein [Burkholderia pseudomallei]," Dec. 1, 2014.
Genbank Accession No. AIQ82815.1, "E7 [Human papillomavirus type 16]," Sep. 29, 2014.
Genbank Accession No. AKN79013.1, "E6 [Human papillomavirus type 16]," Jul. 4, 2015.
Genbank Accession No. AY143159.1, "Newcastle disease virus strain MET95 hemagglutinin-neuraminidase protein HN gene, complete cds," Jul. 25, 2003.
Genbank Accession No. AY351959.1, "Newcastle disease virus hemagglutinin-neuraminidase gene, complete cds," Aug. 25, 2003.
Genbank Accession No. AY390310.1, "Newcastle disease virus strain YG97 from goose fusion protein gene, partial cds," Jul. 26, 2016.
Genbank Accession No. AY845400.2, "Newcastle disease virus strain LaSota, complete genome," Mar. 17, 2005,.
Genbank Accession No. CAA26820.1, "GM-CSF [Mus musculus]," Sep. 24, 2008.
Genbank Accession No. CAA62616.1, "interleukin-15 [*Homo sapiens*]," Nov. 14, 2006.
Genbank Accession No. CAG46642.1, "CD86, partial [*Homo sapiens*]," Jul. 26, 2016.
Genbank Accession No. CAI41082.1, "interleukin 15 receptor, alpha [*Homo sapiens*]," Jan. 13, 2009.
Genbank Accession No. EF033114.1, "Macaca mulatta interleukin 15 receptor alpha (IL15Ra) mRNA, complete cds, alternatively spliced," Nov. 12, 2006.
Genbank Accession No. EU293914.1, "Newcastle disease virus strain Italien, complete genome," Jun. 24, 2008.
Genbank Accession No. EU338414.1, "Avian paramyxovirus 2 strain APMV-2/Chicken/California/Yucaipa/56, complete genome," Sept. 3, 2008.
Genbank Accession No. EU622637.2, "Avian paramyxovirus 6 strain APMV-6/duck/HongKong/18/199/77, complete genome," Feb. 25, 2011.
Genbank Accession No. EU782025.1, "Avian paramyxovirus 3 strain turkey/Wisconsin/68, complete genome," Mar. 26, 2010.
Genbank Accession No. FJ177514.1, "Avian paramyxovirus 4 strain APMV-4/duck/Hongkong/D3/75, complete genome," Nov. 4, 2008.
Genbank Accession No. FJ231524.1, "Avian paramyxovirus 7 strain APMV-7/dove/Tennessee/4/75, complete genome," Sep. 10, 2009.
Genbank Accession No. FJ619036.1, "Avian paramyxovirus 8 isolate APMV-8/Goose/Delaware/1053/76, complete genome," Jun. 1, 2009.
Genbank Accession No. JF950510.1, Newcastle disease virus strain LaSota, complete genome, Aug. 10, 2011.
Genbank Accession No. JN571485.1, "Avian paramyxovirus 4 strain APMV4/mallard/Belgium/15129/07, complete genome," Dec. 8, 2011.
Genbank Accession No. JX133079.1, "Avian paramyxovirus 4 isolate APMV-4/Egyptian goose/South Africa/N1468/2010, complete genome," Apr. 4, 2013.
Genbank Accession No. JX987283.1, "Avian paramyxovirus 4 strain APMV-4/duck/Delaware/549227/2010, complete genome," Mar. 12, 2013.
Genabnk Accession No. KC439346.1, "Avian paramyxovirus 4 strain APMV4/duck/China/G302/2012, complete genome," Apr. 19, 2013.
Genbank Accession No. KM058635.1, "Human papillomavirus type 16 isolate IR-32 E7 (E7) gene, complete cds," Sep. 29, 2014.
Genbank Accession No. KP677555.1, "Human papillomavirus type 16 isolate Af2-ZOAASSOUMOU3 E6 (E6) gene, complete cds," Jul. 4, 2015.
Genbank Accession No. KU601399.1, "Avian paramyxovirus 4 isolate Uria_aalge/Russia/Tyuleniy_Island/115/2015, complete genome," Jul. 30, 2016.
Genbank Accession No. M11220.1, "Human granulocyte-macrophage colony stimulating factor (GM-CSF) mRNA," Nov. 8, 1994.
Genbank Accession No. NC_002617.1, "Newcastle disease virus B1, complete genome," Nov. 30, 2009.
Genbank Accession No. NC_025390.1, "Avian paramyxovirus 9 strain duck/New York/22/1978, complete genome," Aug. 13, 2018.
Genbank Accession No. NG_016779.1, "*Homo sapiens* interleukin 2 (IL2), RefSeqGene on chromosome 4," Dec. 4, 2019.
Genbank Accession No. NM_000402.2, "*Homo sapiens* glucose-6-phosphate dehydrogenase (G6PD), nuclear gene encoding mitochondrial protein, mRNA," May 7, 2006.
Genbank Accession No. NM_000585.4, "*Homo sapiens* interleukin 15 (IL15), transcript variant 3, mRNA," May 6, 2017.
Genbank Accession No. NM_000586.3, "*Homo sapiens* interleukin 2 (IL2), mRNA," Apr. 30, 2017.
Genbank Accession No. NM_000590.1, "*Homo sapiens* interleukin 9 (IL9), mRNA," May 6, 2017.
Genbank Accession No. NM_000594.3, "*Homo sapiens* tumor necrosis factor (TNF), mRNA," May 7, 2017.
Genbank Accession No. NM_000619.2, "*Homo sapiens* interferon gamma (IFNG), mRNA," May 13, 2017.
Genbank Accession No. NM_000758.3, "*Homo sapiens* colony stimulating factor 2 (CSF2), mRNA," Oct. 13, 2018.
Genbank Accession No. NM_000758.4, "*Homo sapiens* colony stimulating factor 2 (CSF2), mRNA," Feb. 16, 2020.
Genbank Accession No. NM_000880.3, "*Homo sapiens* interleukin 7 (IL7), transcript variant 1, mRNA," May 10, 2017.
Genbank Accession No. NM_000882.3, "*Homo sapiens* interleukin 12A (IL12A), mRNA," Apr. 30, 2017.
Genbank Accession No. NM_000937.2, "*Homo sapiens* polymerase (RNA) II (DNA directed) polypeptide A, 220kDa (POLR2A), mRNA," Feb. 11, 2008.
Genbank Accession No. NM_001024736.1, "*Homo sapiens* CD276 molecule (CD276), transcript variant 1, mRNA," May 7, 2017.
Genbank Accession No. NM_001090.2, "*Homo sapiens* ATP binding cassette subfamily F member 1 (ABCF1), transcript variant 2, mRNA," Apr. 27, 2017.
Genbank Accession No. NM_001099270.1, "*Homo sapiens* zinc finger and BTB domain containing 34 (ZBTB34), mRNA," Apr. 30, 2017.
Genbank Accession No. NM_001172085.1, "*Homo sapiens* TATA-box binding protein (TBP), transcript variant 2, mRNA," Apr. 17, 2017.
Genbank Accession No. NM_001199886.1, "*Homo sapiens* interleukin 7 (IL7), transcript variant 2, mRNA," May 10, 2017.
Genbank Accession No. NM_001199887.1, "*Homo sapiens* interleukin 7 (IL7), transcript variant 3, mRNA," May 10, 2017.
Genbank Accession No. NM_001199888.1, "*Homo sapiens* interleukin 7 (IL7), transcript variant 4, mRNA," May 10, 2017.
Genbank Accession No. NM_001207006.2, "*Homo sapiens* interleukin 21 (IL21), transcript variant 2, mRNA," May 7, 2017.
Genbank Accession No. NM_001242.4, "*Homo sapiens* CD27 molecule (CD27), mRNA," Apr. 28, 2017.
Genbank Accession No. NM_001252.3, "*Homo sapiens* CD70 molecule (CD70), mRNA," Jan. 11, 2014.
Genbank Accession No. NM_001267706.1, "*Homo sapiens* CD274 molecule (CD274), transcript variant 2, mRNA," Apr. 23, 2017.
Genbank Accession No. NM_001314029.1, "*Homo sapiens* CD274 molecule (CD274), transcript variant 4, mRNA," Apr. 23, 2017.
Genbank Accession No. NM_001768.5, "*Homo sapiens* CD8a molecule (CD8A), transcript variant 1, mRNA," Sep. 28, 2008.

(56) References Cited

OTHER PUBLICATIONS

Genbank Accession No. NM_002122.3, "*Homo sapiens* major histocompatibility complex, class II, DQ alpha 1 (HLA-DQA1), mRNA," May 7, 2017.
Genbank Accession No. NM_002124.1, "*Homo sapiens* major histocompatibility complex, class II, DR beta 1 (HLA-DRB1), mRNA," Jul. 31, 2007.
Genbank Accession No. NM_002164.3, "*Homo sapiens* indoleamine-pyrrole 2,3 dioxygenase (INDO), mRNA," Aug. 6, 2007.
Genbank Accession No. NM_002187.2, "*Homo sapiens* interleukin 12B (IL12B), mRNA," May 6, 2017.
Genbank Accession No. NM_002189.4, "*Homo sapiens* interleukin 15 receptor subunit alpha (IL15RA), transcript variant 1, mRNA," Jan. 2, 2020.
Genbank Accession No. NM_002190.2, "*Homo sapiens* interleukin 17A (IL17A), mRNA," May 7, 2017.
Genbank Accession No. NM_002286.5, "*Homo sapiens* lymphocyte activating 3 (LAG3), mRNA," May 7, 2017.
Genbank Accession No. NM_002416.1, "*Homo sapiens* chemokine (C-X-C motif) ligand 9 (CXCL9), mRNA," Sep. 25, 2014.
Genbank Accession No. NM_002801.2, "*Homo sapiens* proteasome (prosome, macropain) subunit, beta type, 10 (PSMB10), mRNA," Feb. 10, 2011.
Genbank Accession No. NM_002985.2, "*Homo sapiens* C-C motif chemokine ligand 5 (CCL5), transcript variant 1, mRNA," May 6, 2017.
Genbank Accession No. NM_003326.3, "*Homo sapiens* tumor necrosis factor (ligand) superfamily, member 4 (TNFSF4), mRNA," May 4, 2014.
Genbank Accession No. NM_003811.3, "*Homo sapiens* TNF superfamily member 9 (TNFSF9), mRNA," Mar. 4, 2017.
Genbank Accession No. NM_004072.1, "*Homo sapiens* chemokine-like receptor 1 (CMKLR1), mRNA," Jul. 13, 2008.
Genbank Accession No. NM_004152.2, "*Homo sapiens* ornithine decarboxylase antizyme 1 (OAZ1), mRNA," Jul. 4, 2014.
Genbank Accession No. NM_004168.1, "*Homo sapiens* succinate dehydrogenase complex, subunit A, flavoprotein (Fp) (SDHA), nuclear gene encoding mitochondrial protein, mRNA," Jun. 3, 2007.
Genbank Accession No. NM_005018.2, "*Homo sapiens* programmed cell death 1 (PDCD1), mRNA," May 6, 2017.
Genbank Accession No. NM_005191.3, "*Homo sapiens* CD80 molecule (CD80), mRNA," May 6, 2017.
Genbank Accession No. NM_005516.4, "*Homo sapiens* major histocompatibility complex, class I, E (HLA-E), mRNA," Jul. 5, 2010.
Genbank Accession No. NM_005601.3, "*Homo sapiens* natural killer cell granule protein 7 (NKG7), mRNA," Apr. 26, 2017.
Genbank Accession No. NM_006564.1, "*Homo sapiens* C-X-C motif chemokine receptor 6 (CXCR6), mRNA," Apr. 25, 2017.
Genbank Accession No. NM_007315.2, "*Homo sapiens* signal transducer and activator of transcription 1, 91kDa (STAT1), transcript variant alpha, mRNA," Apr. 29, 2008.
Genbank Accession No. NM_008357.2, "Mus musculus interleukin 15 (I115), transcript variant 1, mRNA," Dec. 28, 2019.
Genbank Accession No. NM_008358.2, "Mus musculus interleukin 15 receptor, alpha chain (I115ra), transcript variant 1, mRNA," Jan. 12, 2020.
Genbank Accession No. NM_009404.3, "Mus musculus tumor necrosis factor (ligand) superfamily, member 9 (Tnfsf9), mRNA," Apr. 29, 2017.
Genbank Accession No. NM_009452.2, "Mus musculus tumor necrosis factor (ligand) superfamily, member 4 (Tnfsf4), mRNA," May 12, 2017.
Genbank Accession No. NM_009855.2, "Mus musculus CD80 antigen (Cd80), mRNA," Apr. 28, 2017.
Genbank Accession No. NM_009969.4, "Mus musculus colony stimulating factor 2 (granulocyte-macrophage) (Csf2), mRNA," Jan. 27, 2020.

Genbank Accession No. NM_011617.2, "Mus musculus CD70 antigen (Cd70), mRNA," Sept. 1, 2016.
Genbank Accession No. NM_014143.3, "*Homo sapiens* CD274 molecule (CD274), transcript variant 1, mRNA," Apr. 30, 2017.
Genbank Accession No. NM_015259.4, "*Homo sapiens* inducible T-cell co-stimulator ligand (ICOSLG), mRNA," Sept. 2, 2013.
Genbank Accession No. NM_015527.3, "*Homo sapiens* TBC1 domain family member 10B (TBC1D10B), mRNA," May 2, 2017.
Genbank Accession No. NM_015790.3, "Mus musculus icos ligand (ICOSL), mRNA," Feb. 15, 2015.
Genbank Accession No. NM_017970.3, "*Homo sapiens* NRDE-2, necessary for RNA interference, domain containing (NRDE2), mRNA," May 10, 2017.
Genbank Accession No. NM_018955.2, "*Homo sapiens* ubiquitin B (Ubb), mRNA," Apr. 17, 2013.
Genbank Accession No. NM_019388.3, "Mus musculus CD86 antigen (Cd86), mRNA," May 2, 2017.
Genbank Accession No. NM_020525.4, "*Homo sapiens* interleukin 22 (IL22), mRNA," Apr. 26, 2017.
Genbank Accession No. NM_021803.3, "*Homo sapiens* interleukin 21 (IL21), transcript variant 1, mRNA," May 7, 2017.
Genbank Accession No. NM_025239.3, "*Homo sapiens* programmed cell death 1 ligand 2 (PDCDILG2), mRNA," May 3, 2017.
Genbank Accession No. NM_052902.2, "*Homo sapiens* serine/threonine kinase 11 interacting protein (STK11IP), mRNA," Mar. 22, 2015.
Genbank Accession No. NM_053852.1, "Rattus norvegicus colony stimulating factor 2 (Csf2), mRNA," Dec. 28, 2019.
Genbank Accession No. NM_172175.2, "*Homo sapiens* interleukin 15 (IL15), transcript variant 2, mRNA," May 6, 2017.
Genbank Accession No. NM_173799.2, "Homo sapiens T cell immunoreceptor with Ig and ITIM domains (TIGIT), mRNA," Jun. 18, 2009.
Genbank Accession No. NP_000576.1, "interleukin-15 isoform 1 preproprotein [*Homo sapiens*]," Feb. 9, 2020.
Genbank Accession No. NP_000577.2, "interleukin-2 precursor [*Homo sapiens*]," Feb. 3, 2020.
Genbank Accession No. NP_000749.2, "granulocyte-macrophage colony-stimulating factor precursor [*Homo sapiens*]," Feb. 16, 2020.
Genbank Accession No. NP_001009207.1, "interleukin-15 precursor [Felis catus]," Dec. 25, 2019.
Genbank Accession No. NP_001243.1, "CD70 antigen isoform 1 [*Homo sapiens*]," Oct. 8, 2016.
Genbank Accession No. NP_001254635.1, "programmed cell death 1 ligand 1 isoform b precursor [*Homo sapiens*]," Apr. 23, 2017.
Genbank Accession No. NP_001300958.1, "programmed cell death 1 ligand 1 isoform c precursor [*Homo sapiens*]," Apr. 23, 2017.
Genbank Accession No. NP_002178.2, "interleukin-12 subunit beta precursor [*Homo sapiens*]," May 6, 2017.
Genbank Accession No. NP_002180.1, "interleukin-15 receptor subunit alpha isoform 1 precursor [*Homo sapiens*]," Jan. 2, 2020.
Genbank Accession No. NP_003317.1, "tumor necrosis factor ligand superfamily member 4 isoform 1 [*Homo sapiens*]," Jul. 4, 2014.
Genbank Accession No. NP_003802.1, "tumor necrosis factor ligand superfamily member 9 [*Homo sapiens*]," Mar. 4, 2017.
Genbank Accession No. NP_005009.2, "programmed cell death protein 1 precursor [*Homo sapiens*]," May 6, 2017.
Genbank Accession No. NP_005182.1, "T-lymphocyte activation antigen CD80 precursor [*Homo sapiens*]," Apr. 30, 2017.
Genbank Accession No. NP_032383.1, "interleukin-15 preproprotein [Mus musculus]," Dec. 28, 2019.
Genbank Accession No. NP_032384.1, "interleukin-15 receptor subunit alpha isoform 1 precursor [Mus musculus], " Jan. 12, 2020.
Genbank Accession No. NP_033430.1, "tumor necrosis factor ligand superfamily member 9 [Mus musculus]," Apr. 29, 2017.
Genbank Accession No. NP_033478.1, "tumor necrosis factor ligand superfamily member 4 [Mus musculus]," May 12, 2017.
Genbank Accession No. NP_033985.3, "T-lymphocyte activation antigen CD80 precursor [Mus musculus]," Apr. 28, 2017.

(56) References Cited

OTHER PUBLICATIONS

Genbank Accession No. NP_034099.2, "granulocyte-macrophage colony-stimulating factor precursor [Mus musculus]," Jan. 27, 2020.
Genbank Accession No. NP_054862.1, "programmed cell death 1 ligand 1 isoform a precursor [*Homo sapiens*]," Apr. 30, 2017.
Genbank Accession No. NP_056074.1, "ICOS ligand isoform a precursor [*Homo sapiens*]," Apr. 23, 2017.
Genbank Accession No. NP_056605.1, "ICOS ligand precursor [Mus musculus]," Feb. 15, 2015.
Genbank Accession No. NP_056606.1, "F-box only protein 8 [Mus musculus]," Apr. 8, 2003.
Genbank Accession No. NP_062261.3, "T-lymphocyte activation antigen CD86 precursor [Mus musculus]," May 2, 2017.
Genbank Accession No. NP_079515.2, "programmed cell death 1 ligand 2 precursor [Homo sapiens]," May 3, 2017.
Genbank Accession No. NP_446304.1, "granulocyte-macrophage colony-stimulating factor precursor [Rattus norvegicus]," Dec. 28, 2019.
Genbank Accession No. U25837.1, "Newcastle disease virus isolate Ulster matrix protein mRNA, complete cds," Jul. 12, 1996.
Genbank Accession No. X03021.1, "Human gene for granulocyte-macrophage colony stimulating factor (GM-CSF)," Feb. 10, 1999.
Genbank Accession No., NP_000873.2, "interleukin-12 subunit alpha precursor [*Homo sapiens*]," Apr. 30, 2017.
Ghaneh et al., "Adenovirus-mediated transfer of p53 and p16(INK4a) results in pancreatic cancer regression in vitro and in vivo," Gene Ther., 8:199-208 (2001).
Gillies et al., "High-level expression of chimeric antibodies using adapted cDNA variable region cassettes," J. Immunol. Methods, 125(1-2):191-202 (1989).
Ginting et al., 2017, "Proinflammatory response induced by Newcastle disease virus in tumor and normal cells," Oncolytic Virother, 6:21-30.
Gitiban et al., 2005, "Chinchilla and murine models of upper respiratory tract infections with respiratory syncytial virus," J. Virol., 79(10):6035-6042.
Goff et al., "A Majority of Infectious Newcastle Disease Virus Particles Contain a Single Genome, while a Minority Contain Multiple Genomes," J. Virol., 86(19):10852-10856 (2012).
Gogoi et al., 2017, "Avian Paramyxovirus: A Brief Review," Transbound. Emerg. Dis., 64(1):53-67 (Epub 2015).
Gomez et al., 2009, "Phase-I study MEDI-534, of a live, attenuated intranasal vaccine against respiratory syncytial virus and parainfluenza-3 virus in seropositive children," Pediatr. Infect. Dis. J., 28(7):655-658.
Grieves et al., 2015, "Acute and Chronic Airway Disease After Human Respiratory Syncytial Virus Infection in Cotton Rats (*Sigmodon hispidus*)," Comp. Med., 65(4):315-326.
Gruber et al., "Efficient tumor cell lysis mediated by a bispecific single chain antibody expressed in Escherichia coli," J. Immunol., 152(11):5368-5374 (1994).
Grund et al., 2014, "Avian paramyoxvirus-8 immunization reduces viral shedding after homologous APMV-8 challenge but fails to protect against Newcastle disease," Virol. J., 11:179 (6 pages).
Guo et al., "Oncolytic immunotherapy: dying the right way is a key to eliciting potent antitumor immunity," Front. Oncol., 4(74):1-11 (2014).
Haas et al., "Bispecific antibodies increase T-cell stimulatory capacity in vitro of human autologous virus-modified tumor vaccine," Clin. Cancer Res., 4(3):721-730 (1998).
Haas et al., "A tumor vaccine containing ant-CD# and anti-CD28 bispecific antibodies triggers strong and durable antitumor activity in human lymphocytes," Int. J. Cancer, 188(3): 658-667 (2006).
Haas et al., "An effective strategy of human tumor vaccine modification by coupling bispecific costimulatory molecules," Cancer Gene Therapy, 6(3):254-262 (1999).
Habibi et al., 2015, "Impaired Antibody-mediated Protection and Defective IgA B-Cell Memory in Experimental Infection of Adults with Respiratory Syncytial Virus," Am. J. Respir. Crit. Care Med., 191(9):1040-1049.
Hall et al., 1991, "Immunity to and frequency of reinfection with respiratory syncytial virus," J. Infect. Dis., 163(4):693-698.
Hall et al., 2001, "Respiratory syncytial virus infections in previously healthy working adults," Clin. Infect. Dis., 33(6):792-796.
Hallak et al., 2000, "Iduronic acid-containing glycosaminoglycans on target cells are required for efficient respiratory syncytial virus infection," Virology, 271(2):264-275.
Hamid et al., "Safety and Tumor Responses with Lambrolizumab (Anti-PD-1) in Melanoma," N. Engl. J. Med., 369(2):134-144 (2013).
Hamid et al., 2016, "1050PD—Combination of MEDI0680, an anti-PD-1 antibody, with durvalumab, an anti-PD-L1 antibody: A phase 1, open-label study in advanced malignancies," Ann. Oncol., 27(suppl. 6):vi359-vi378 (1 page).
He et al., "Humanization and pharmacokinetics of a monoclonal antibody with specificity for both E- and P-selectin," J. Immunol., 160(2):1029-1035 (1998).
Heery et al., "Phase I open-label, multiple ascending dose trial of MSB0010718C, an anti-PD-L1 monoclonal antibody, in advanced solid malignancies," J. Clin. Oncol., 32(suppl. 5S):abstract 3064 (2014).
Heicappell et al., 1986, "Prevention of metastatic spread by post-operative immunotherapy with virally modified autologous tumor cells. I. Parameters for optimal therapeutic effects," Int. J. Cancer, 37(4):569-577.
Hemminki et al., "Oncolytic Immunotherapy: Where Are We Clinically? ," Scientifica, 2014, Article ID 862925 (2014).
Herber et al., "Squamous epithelial hyperplasia and carcinoma in mice transgenic for the human papillomavirus type 16 E7 oncogene," J. Virol., 70:1873-1881 (1996).
Herbst et al., "Predictive correlates of response to the anti-PD-L1 antibody MPDL3280A in cancer patients," Nature, 515(7528):563-567 (2014).
Herbst et al., "A study of MPDL3280A, an engineered PD-L1 antibody in patients with locally advanced or metastatic tumors," J. Clin. Oncol., 31(suppl):abstract 3000 (2013).
Hines et al., 2012, "Avian paramyxovirus serotype-1: a review of disease distribution, clinical symptoms, and laboratory diagnostics," Vet Med Int., 2012:708216 (17 pages).
Hirano et al., "Blockade of B7-H1 and PD-1 by Monoclonal Antibodies Potentiates Cancer Therapeutic Immunity," Cancer Res., 65(3):1089-1096 (2005).
Hirschhorn-Cymerman et al., "Induction of tumoricidal function in CD4+ T cells is associated with concomitant memory and terminally differentiated phenotype," J. Exp. Med., 209(11):2113-2126 (2012).
Hofmeyer et al., "The PD-1/PD-L1 (B7-H1) Pathway in Chronic Infection-Induced Cytotoxic T Lymphocyte Exhaustion," J. Biomed. Biotechnol., 2011:451694 (2011).
Holliger et al., ""Diabodies": small bivalent and bispecific antibody fragments," Proc. Natl. Acad. Sci. USA, 90(14):6444-6448 (1993).
Hollinger et al., "Engineered antibody fragments and the rise of single domains," Nature Biotech., 23(9):1126-1136 (2005).
Hosokawa et al., "In vivo analysis of mammary and non-mammary tumorigenesis in MMTV-cyclin D1 transgenic mice deficient in p53," Transgenic Res., 10:471-478 (2001).
Hotte et al., "An optimized clinical regimen for the oncolytic virus PV701," Clin. Cancer Res., 13:977-985 (2007).
Hou et al., 2009, "Study on the effect of Newcastle disease virus vaccine and interleukin-12 to the tranjsplantable nude mice model of human ovarian cancer," Chin. J. Cancer Prev. Treat., 16(18):1375-1378 (in Chinese with English abstract).
Houdebine, "Production of Pharmaceutical Proteins by Transgenic Animals." Comp. Immunol. Microbiol. Infect. Dis., 32(2):107-121 (2009).
Hough et al., "A model for spontaneous B-lineage lymphomas in IgHmu-HOX11 transgenic mice," Proc. Natl. Acad. Sci USA, 95:13853-13858 (1998).

(56) References Cited

OTHER PUBLICATIONS

Houghten et al. "The use of synthetic peptide combinatorial libraries for the identification of bioactive peptides," Biotechniques, 13(3):412-421 (1992).
Huang et al., "Newcastle disease virus V protein is associated with viral pathogenesis and functions as an alpha interferon antagonist," J. Virol., 77:8676-8685 (2003).
Huang et al., "Preclinical validation: LV/IL-12 transduction of patient leukemia cells for immunotherapy of AML," Mol. Ther., 3:16074 (2016).
Huard et al., "CD4/major histocompatibility complex class II interaction analyzed with CD4- and lymphocyte activation gene-3 (LAG-3)-Ig fusion proteins," Eur. J. Immunol., 25:2718-2721 (1995).
Infante et al., "Clinical and pharmacodynamic (PD) results of a phase I trial with AMP-224 (B7-DC Fc) that binds to the PD-1 receptor," J. Clin. Oncol., 31(suppl):abstract 3044 (2013).
Inouye et al., "Up-promoter mutations in the lpp gene of *Escherichia coli*," Nucleic Acids Res., 13(9):3101-3110 (1985).
International Nonproprietary Names for Pharmaceutical Substances (INN), 2013, WHO Drug Information, vol. 27, No. 2, List 109, pp. 135-209.
International Search Report and Written Opinion for International Patent Application No. PCT/US2019/041568 (Pub No. WO 202001459) mailed Nov. 20, 2019 (12 pages).
International Search Report and Written Opinion for International Patent Application No. PCT/US2019/046837 (Pub. No. WO 2020037215) mailed Jan. 2, 2020 (13 pages).
Ishida et al., "Induced expression of PD-1, a novel member of the immunoglobulin gene superfamily, upon programmed cell death," Embo. J., 11:3887-3895 (1992).
Iwai et al., "PD-1 Inhibits Antiviral Immunity at the Effector Phase in the Liver," J. Exp. Med., 198(1):39-50 (2003).
Iwai et al., "Involvement of PD-L1 on tumor cells in the escape from host immune system and tumor immunotherapy by PD-L1 blockade," Proc. Natl. Acad. Sci USA, 99:12293-12297 (2002).
Jarahian et al., 2009, "Activation of natural killer cells by newcastle disease virus hemagglutinin-neuraminidase," J Virol., 83(16):8108-8121.
Jones et al., "Molecular interactions within the IL-6/IL-12 cytokine/receptor superfamily," Immunol. Res., 51(1):5-14 (2011).
Kabat et al., "Attempts to locate complementarity-determining residues in the variable positions of light and heavy chains," Ann. NY Acad. Sci., 190:382-393 (1971).
Kado et al., "Intestinal Microflora Are Necessary for Development of Spontaneous Adenocarcinoma of the Large Intestine in T-Cell Receptor ß Chain and p53 Double-Knockout Mice," Cancer Res., 61:2395-2398 (2001).
Kamphorst et al., "Rescue of exhausted CD8 T cells by PD-1-targeted therapies is CD28-dependent," Science, 355(6332):1423-1427 (2017).
Kapczynski et al., 2013, "Immune responses of poultry to Newcastle disease virus," Dev Comp Immunol., 41(3):447-453.
Karamendin et al., 2016, "Complete Genome Sequence of a Novel Avian Paramyxovirus (APMV-13) Isolated from a Wild Bird in Kazakhstan," Genome Announc., 4(3). pii:e00167-16 (2 pages).
Karcher et al., 2004, "Antitumor vaccination in patients with head and neck squamous cell carcinomas with autologous virus-modified tumor cells," Cancer Res., 64(21):8057-8061.
Kato et al., "Cell type-specific involvement of RIG-I in antiviral response," Immunity, 23(1):19-28 (2005).
Kettleborough et al., "Isolation of tumor cell-specific single-chain Fv from immunized mice using phage-antibody libraries and the re-construction of whole antibodies from these antibody fragments," Eur. J. Immunol., 24:952-958 (1994).
KEYTRUDA® (pembrolizumab) Prescribing Information, revised Aug. 2018 (52 pages).
KEYTRUDA® (pembrolizumab) Prescribing Information, revised Dec. 2015 (25 pages).
KEYTRUDA® (pembrolizumab) Prescribing Information, revised Jan. 2020 (85 pages).
KEYTRUDA® (pembrolizumab) Prescribing Information, revised Jun. 2018 (53 pages).
KEYTRUDA® (pembrolizumab) Prescribing Information, revised Oct. 2016 (26 pages).
Khattar et al., "A Y526Q mutation in the Newcastle disease virus HN protein reduces its functional activities and attenuates virus replication and pathogenicity," J. Virol., 83:7779-7782 (2009).
Kilpatrick et al., "Rapid development of affinity matured monoclonal antibodies using RIMMS," Hybridoma, 16(4):381-389 (1997).
Kim et al., "Evaluation of fusion protein cleavage site sequences of Newcastle disease virus in genotype matched vaccines," PLOS One, 12(3):e0173965 (2017).
Kim et al., "Expression and characterization of a recombinant Fab fragment derived from an anti-human alpha-fetoprotein monoclonal antibody," Mol. Cells., 11:158-163 (2001).
Kim et al., "LaSota fusion (F) cleavage motif-mediated fusion activity is affected by other regions of the F protein from different genotype Newcastle disease virus in a chimeric virus: implication for virulence attenuation," J. Gen. Virol., 97(6):1297-1304 (2016).
Kim et al., 1969, "Respiratory syncytial virus disease in infants despite prior administration of antigenic inactivated vaccine," Am. J. Epidemiol., 89(4):422-434.
Kim et al., 2012, "Replication, neurotropism, and pathogenicity of avian paramyxovirus serotypes 1-9 in chickens and ducks," PLoS One. 2012;7(4):e34927 (13 pages).
Kim et al., 2013, "Mutations in the fusion protein cleavage site of avian paramyxovirus serotype 4 confer increased replication and syncytium formation in vitro but not increased replication and pathogenicity in chickens and ducks," PLoS One, 8(1):e50598 (15 pages).
Kim et al., 2017, "A novel chimeric Newcastle disease virus vectored vaccine against highly pathogenic avian influenza virus," Virology, 503:31-36.
Kohler, "Immunoglobulin chain loss in hybridoma lines," Proc. Natl. Acad. Sci. USA, 77(4):2197-2199 (1980).
Korppi et al., 2004, "Respiratory morbidity 20 years after RSV infection in infancy," Pediatr. Pulmonol., 38(2):155-160.
Kostelny et al., "Formation of a bispecific antibody by the use of leucine zippers," J. Immunol., 148(5):1547-1553 (1992).
Kozbor et al., "A human hybrid myeloma for production of human monoclonal antibodies," J. Immunol., 133(6):3001-3005 (1984).
Krishnamurthy et al., "Differentially regulated interferon response determines the outcome of Newcastle disease virus infection in normal and tumor cell lines," J. Virology, 80:5145-5155 (2006).
Kulangara et al., "Development of the combined positive score (CPS) for the evaluation of PD-L1 in solid tumors with the immunohistochemistry assay PD-L1 IHC 22C3 pharmDx," J. Clin. Oncol., 35(15_suppl):e 14589 (2017).
Kumar et al., 2010, "Experimental avian paramyxovirus serotype-3 infection in chickens and turkeys," Vet Res., 41(5):72 (14 pages).
Kumar et al., 2011, "Evaluation of the Newcastle disease virus F and HN proteins in protective immunity by using a recombinant avian paramyxovirus type 3 vector in chickens," J. Virol., 85(13):6521-6534 (retracted).
Kumar et al., 2020, "Retraction for Kumar et al., "Evaluation of the Newcastle Disease Virus F and HN Proteins in Protective Immunity by Using a Recombinant Avian Paramyxovirus Type 3 Vector in Chickens"," J. Virol., 94(6):e01867-19 (1 page).
Kuraguchi et al., "Tumor-associated Apc mutations in Mlh1-/- Apc1638N mice reveal a mutational signature of Mlhl deficiency," Oncogene, 19(50):5755-5763 (2001).
Lam et al., "A new type of synthetic peptide library for identifying ligand-binding activity," Nature, 354(6348):82-84 (1991).
Lam et al., 2011, "Safety and clinical usage of newcastle disease virus in cancer therapy," J Biomed Biotechnol, 2011:718710 (13 pages).
Lamb et al., Paramyxoviridae: The Viruses and Their Replication. In B.N. Fields, D.M. Knipe, & P.M. Howley (Eds.), Fundamental Virology, pp. 577-604, Philadelphia, PA (1996).
Leach et al., "Enhancement of antitumor immunity by CTLA-4 blockade," Science, 271:1734-1736 (1996).

(56) References Cited

OTHER PUBLICATIONS

Lee et al., "Isolation of cDNA for a human granulocyte-macrophage colony-stimulating factor by functional expression in mammalian cells," Proc. Natl. Acad. Sci. USA, 82(13):4360-4364 (1985).
Lefranc et al., "IMGT, the international ImMunoGeneTics database," Nucl. Acids Res., 27(1):209-212 (1999).
Lefranc, "The IMGT unique numbering for immunoglobulins, T-cell receptors, and Ig-like domains," Immunologist, 7:132-136 (1999).
Lei et al., "An oncolytic adenovirus expressing granulocyte macrophage colony-stimulating factor shows improved specificity and efficacy for treating human solid tumors," Cancer Gene Therapy, 16:33-43 (2009).
Leonard et al., "Effects of single-dose interleukin-12 exposure on interleukin-12-associated toxicity and interferon-gamma production," Blood, 90(7):2541-2548 (1997).
Li et al, "Therapeutic effects of a fusogenic Newcastle disease virus in treating head and neck cancer," Head Neck, 33(10):1394-1399 (2011).
Li et al., "Decreased dependence on receptor recognition for the fusion promotion activity of L289A-mutated newcastle disease virus fusion protein correlates with a monoclonal antibody-detected conformational change," J. Virol., 79(2):1180-1190 (2005).
Li et al., 1999, "Recombinant influenza A virus vaccines for the pathogenic human A/Hong Kong/97 (H5N1) viruses," J. Infect. Dis., 179(5):1132-1138.
Li et al., 2005, "Chimeric influenza virus hemagglutinin proteins containing large domains of the Bacillus anthracis protective antigen: protein characterization, incorporation into infectious influenza viruses, and antigenicity," J. Virol., 79(15):10003-10012.
Liang et al., 2003, "Application of autologous tumor cell vaccine and NDV vaccine in treatment of tumors of digestive tract," World J Gastroenterol., 9(3):495-498.
Lieschke et al., "Bioactive murine and human interleukin-12 fusion proteins which retain antitumor activity in vivo," Nature, 15: 35-40 (1997).
Lipson et al., "Durable Cancer Regression Off-treatment and Effective Re-induction Therapy with an Anti-PD-1 Antibody," Clin. Cancer Res., 19(2):462-468 (2013).
Liu et al., "Adenovirus-mediated intratumoral expression of immunostimulatory proteins in combination with systemic Treg inactivation induces tumor-destructive immune responses in mouse models," Cancer Gene Ther., 18(6):407-418 (2011).
Liu et al., "ICP34.5 deleted herpes simplex virus with enhanced oncolytic, immune stimulating, and anti-tumour properties," Gene Therapy, 10:292-303 (2003).
Liu et al., 2018, "Chimeric Newcastle disease virus-vectored vaccine protects chickens against H9N2 avian influenza virus in the presence of pre-existing NDV immunity," Arch. Virol., 163(12):3365-3371.
Logan et al., "Adenovirus tripartite leader sequence enhances translation of mRNAs late after infection," Proc. Natl. Acad. Sci. USA, 81:3655-3659 (1984).
Lorence et al., "Phase 1 clinical experience using intravenous administration of PV701, an oncolytic Newcastle disease virus," Curr. Cancer Drug Targets, 7:157-167 (2007).
Lorence et al., 1988, "Newcastle disease virus as an antineoplastic agent: induction of tumor necrosis factor-alpha and augmentation of its cytotoxicity," J. Natl. Cancer Inst., 80(16):1305-1312.
Lotze et al., "Cytokine Gene Therapy of Cancer Using Interleukin-12: Murine and Clinical Trials," Ann. N.Y. Acad. Sci., 795:440-454 (1995).
Lowy et al., "Isolation of Transforming DNA: Cloning the Hamster aprt Gene," Cell 22:817-823 (1980).
Lutzky, "A phase 1 study of MEDI4736, an anti-PD-L1 antibody, in patients with advanced solid tumors," J. Clin. Oncol., 32(suppl 5S):abstract 3001 (2014).
Maamary et al., 2011, "Newcastle disease virus expressing a dendritic cell-targeted HIV gag protein induces a potent gag-specific immune response in mice," J Virol., 85(5):2235-2246.
MacCallum et al., "Antibody-antigen interactions: contact analysis and binding site topography," J. Mol. Biol., 262(5):732-745 (1996).
Maeda et al., "Live bivalent vaccine for parainfluenza and influenza virus infections," J. Viral., 79(11):6674-6679 (2005).
Mansour et al., "Oncolytic specificity of newcastle disease virus is mediated by selectivity for apoptosis-resistant cells," J. Virol., 85(12):6015-6023 (2011).
Martin, "Protein Sequence and Structure Analysis of Antibody Variable Domains," Antibody Engineering, Kontermann et al. eds., Springer-Verlag, Berlin, Chapter 31, pp. 33-51 (2001).
Martinez-Sobrido et al., 2006, "Protection against respiratory syncytial virus by a recombinant Newcastle disease virus vector," J Virol., 80(3):1130-1139.
Mazur et al., 2015, "Lower respiratory tract infection caused by respiratory syncytial virus: current management and new therapeutics," Lancet Respir. Med., 3(11):888-900.
Mazzolini et al., "Adenoviral Gene Transfer of Interleukin 12 into Tumors Synergizes with Adoptive T Cell Therapy Both at the Induction and Effector Level," Human Gene Ther., 11:113-125 (2000).
Mazzolini et al., "Regression of colon cancer and induction of antitumor immunity by intratumoral injection of adenovirus expressing interleukin-12," Cancer Gene Ther., 6(6):514-522 (1999).
Mcdermott et al., "Atezolizumab, an Anti-Programmed Death-Ligand 1 Antibody, in Metastatic Renal Cell Carcinoma: Long-Term Safety, Clinical Activity, and Immune Correlates From a Phase Ia Study," J. Clin. Oncol., 34(8):833-842 (2016).
Menne et al., "A comparison of signal sequence prediction methods using a test set of signal peptides," Bioinfomratics, 16(8):741-742 (2000).
Meseck et al., "A Functional Recombinant Human 4-1BB Ligand for Immune Costimulatory Therapy of Cancer," J. Immunother., 34(2):175-182 (2011).
Miller et al., 2010, "Evidence for a new avian paramyxovirus serotype 10 detected in rockhopper penguins from the Falkland Islands," J Virol., 84(21):11496-11504.
Mills et al., 1971, "Experimental respiratory syncytial virus infection of adults. Possible mechanisms of resistance to infection and illness" J. Immunol., 107(1):123-130.
Milstein et al., "Hybrid hybridomas and their use in immunohistochemistry," Nature, 305:537-540 (1983).
Morea et al., "Antibody modeling: implications for engineering and design," Methods, 20(3):267-279 (2000).
Morgan et al., "Human gene therapy," Annu. Rev. Biochem., 62:191-217 (1993).
Morris et al., "Lung-specific expression in mice of a dominant negative mutant form of the p53 tumor suppressor protein," J. La. State Med. Soc., 150(4):179-185 (1998).
Morrison, "Transfectomas provide novel chimeric antibodies," Science, 229(4719):1202-1207 (1985).
Mulligan et al., "Selection for animal cells that express the *Escherichia coli* gene coding for xanthine-guanine phosphoribosyltransferase," Proc. Natl. Acad. Sci. USA, 78:2072-2076 (1981).
Mulligan, "The basic science of gene therapy," Science, 260:926-932 (1993).
Muranski et al., "Tumor-specific Th17-polarized cells eradicate large established melanoma," Blood, 112(2):362-373 (2008).
Murawski et al., "Newcastle disease virus-like particles containing respiratory syncytial virus G protein induced protection in BALB/c mice, with No. evidence of immunopathology", J. Virol., 84(2):1110-1123 (2010).
Mustaffa-Babjee et al., 1974, "A pathogenic paramyxovirus from a budgerigar (*Melopsittacus undulatus*), " Avian Dis., 18(2):226-230.
Muyldermans, "Single domain camel antibodies: current status," J. Biotechnol., 74(4):277-302 (2001).
Naganawa et al., "Generation of mouse-human hybridomas secreting human monoclonal antibodies to Japanese cedar pollen allergen Cry j1," Hum. Antibodies, 14:27-31 (2005).
Nakaya et al., "Recombinant Newcastle disease virus as a vaccine vector," J. Virol., 75:11868-11873 (2001).
Narvaiza et al., "Intratumoral Coinjection of Two Adenoviruses, One Encoding the Chemokine IFN-γ-Inducible Protein-10 and

(56) References Cited

OTHER PUBLICATIONS

Another Encoding IL-12, Results in Marked Antitumoral Synergy," J. Immunol., 164(6):3112-3122 (2000).
Nguyen et al., 2020, "Oncolytic Virus Encoding a Master Pro-Inflammatory Cytokine Interleukin 12 in Cancer Immunotherapy," Cells, 9(2), 400.
Niu et al., "Recombinant Newcastle Disease virus Expressing IL15 Demonstrates Promising Antitumor Efficiency in Melanoma Model," Technol. Cancer Res. Treatment, 14(5):607-615 (2015).
Nolden et al., 2016, "Reverse genetics in high throughput: rapid generation of complete negative strand RNA virus cDNA clones and recombinant viruses thereof," Sci Rep., 6:23887 (15 pages).
Nuttall et al., "Immunoglobulin VH domains and beyond: design and selection of single-domain binding and targeting reagents," Curr. Pharm. Biotechnol., 1(3):253-263 (2000).
O'Hare et al., "Transformation of mouse fibroblasts to methotrexate resistance by a recombinant plasmid expressing a prokaryotic dihydrofolate reductase," Proc. Natl. Acad. Sci. USA 78:1527-1531 (1981).
OPDIVO® (nivolumab) Prescribing Information, revised Apr. 2018 (83 pages).
OPDIVO® (nivolumab) Prescribing Information, revised Dec. 2014 (20 pages).
OPDIVO® (nivolumab) Prescribing Information, revised Sep. 2019 (31 pages).
Oseledchyk et al., "Lysis-independent potentiation of immune checkpoint blockade by oncolytic virus," Oncotarget 9(47):28702-28716 with Supplementary Materials (2 pages) (2018).
Overwijk et al., "Tumor regression and autoimmunity after reversal of a functionally tolerant state of self-reactive CD8+ T cells," J. Exp. Med., 198(4):568-580 (2003).
Padlan, "A possible procedure for reducing the immunogenicity of antibody variable domains while preserving their ligand-binding properties," Mol. Immunol., 28:489-498 (1991).
Paramore et al., 2004, "Economic impact of respiratory syncytial virus-related illness in the US: an analysis of national databases," Pharmacoeconomics, 22(5):275-284.
Pardoll, "The blockade of immune checkpoints in cancer immunotherapy," Nat. Rev. Cancer, 12(4):252-264 (2012).
Park et al., "Engineered viral vaccine constructs with dual specificity: avian influenza and Newcastle disease," Proc. Natl. Acad. Sci. (USA), 103:8203-8208 (2006).
Park et al., "Newcastle disease virus V protein is a determinant of host range restriction," J. Virol., 77(17):9522-9532 (2003).
Park et al., 2003, "Newcastle disease virus (NDV)-based assay demonstrates interferon-antagonist activity for the NDV V protein and the Nipah virus V, W, and C proteins," J Virol., 77(2):1501-1511.
Patent Cooperation Treaty, International Search Report for PCT/US2006/045859, dated Mar. 28, 2007.
Patent Cooperation Treaty, International Search Report for PCT/US2010/023335, dated Jun. 7, 2010.
Patent Cooperation Treaty, International Search Report for PCT/US2014/020299, dated Aug. 15, 2014.
Patent Cooperation Treaty, International Search Report for PCT/US2018/032255, dated Nov. 19, 2018.
Patent Cooperation Treaty, Written Opinion for PCT/US2006/045859, dated Mar. 28, 2007.
Patent Cooperation Treaty, Written Opinion for PCT/US2010/023335, dated Jun. 7, 2010.
Patent Cooperation Treaty, Written Opinion for PCT/US2014/020299, dated Jul. 19, 2014.
Patent Cooperation Treaty, Written Opinion for PCT/US2018/032255, dated Nov. 19, 2018.
Pecora et al., "Phase I trial of intravenous administration of PV701, an oncolytic virus, in patients with advanced solid cancers," J. Clon. Oncol., 20:2251-2266 (2002).
Pedersen et al., "Comparison of surface accessible residues in human and murine immunoglobulin Fv domains. Implication for humanization of murine antibodies," J. Mol. Biol., 235(3):959-973 (1994).
Peeters et al., "Generation of a recombinant chimeric Newcastle disease virus vaccine that allows serological differentiation between vaccinated and infected animals," Vaccine, 19:1616-1627 (2001).
Peeters et al., "Rescue of Newcastle disease virus from cloned cDNA: evidence that cleavability of the fusion protein is a major determinant for virulence," J. Virol., 73(6):5001-5009 (1999).
Peggs et al., "Cancer immunotherapy: co-stimulatory agonists and co-inhibitory antagonists," Clin. Immunol., 157(1):9-19 (2009).
Pelaia et al., 2006, "Respiratory infections and asthma," Respir. Med., 100(5):775-784 (Epub 2005).
Persic et al., "An integrated vector system for the eukaryotic expression of antibodies or their fragments after selection from phage display libraries," Gene, 187:9-18 (1997).
Phuangsab et al., "Newcastle disease virus therapy of human tumor xenografts: antitumor effects of local or systemic administration," Cancer Lett., 172:27-36 (2001).
Plitt et al., "Cancer therapy with Newcastle disease virus: rationale for new immunotherapeutic combinations," Clinical Investigation, 5(1):75-87 (2015).
Polack et al., 2002, "A role for immune complexes in enhanced respiratory syncytial virus disease," J. Exp. Med., 196(6):859-865.
Pomer et al., 1995, "Tumor response and 4 year survival-data of patients with advanced renal-cell carcinoma treated with autologous tumor vaccine and subcutaneous R-IL-2 and IFN-alpha(2b)," Int. J. Oncol., 6(5):947-954.
Proudfoot, "Transcriptional interference and termination between duplicated $\alpha$-globin gene constructs suggests a novel mechanism for gene regulation," Nature, 322(7):562-565 (1986).
Puhler et al., "Generation of a recombinant oncolytic Newcastle disease virus and expression of a full IgG antibody from two transgenes," Gene Ther., 15:371-383 (2008).
Puzanov et al., "Phase 1 results of a phase 1b/2, multicenter, open-label trial to evaluate safety and efficacy of talimogene laherparepvec (T-VEC) and ipilimumab (ipi) vs ipi alone in previously untreated, unresected stage IIIB-IV melanoma," J. Immunother. Cancer, 1(Suppl 1):P84 (2013).
Quetglas et al., "Virotherapy with a Semliki Forest Virus-Based Vector Encoding IL12 Synergizes with PD-1/PD-L1 Blockade," Cancer Immunol. Res., 3(5):449-454 (2015).
Quezada et al., "CTLA4 blockade and GM-CSF combination immunotherapy alters the intratumor balance of effector and regulatory T cells," J. Clin. Invest., 116(7): 1935-1945 (2006).
Quinn et al., "Rapid quantitation of recombinant retrovirus produced by packaging cell clones," Biotechniques, 23(6):1038-1044 (1997).
Ravindra et al., "Newcastle disease virus as an oncolytic agent," Indian J. Med. Rres., 130(5):507-513 (2009).
Ren et al., 2016, "Recombinant Newcastle Disease Virus Encoding IL-12 and/or IL-2 as Potential Candidate for Hepatoma Carcinoma Therapy," Technol. Cancer Res. Treat., 15(5):NP83-NP94.
Ribas et al., "Oncolytic Virotherapy Promotes Intratumoral T Cell Infiltration and Improves Anti-PD-1 Immunotherapy," Cell, 170(6):1109-1119 (2017).
Riechmann et al., "Single domain antibodies: comparison of camel VH and camelised human VH domains," J. Immunol. Methods, 231:25-38 (1999).
Robbins et al., "Human tumor antigens recognized by T cells," Curr. Opin. Immunol., 8(5):628-636 (1996).
Robert et al., "Ipilimumab plus dacarbazine for previously untreated metastatic melanoma," N. Engl. J. Med., 364(26):2517-2526 (2011).
Roguska et al., "A comparison of two murine monoclonal antibodies humanized by CDR-grafting and variable domain resurfacing," Protein Eng., 9(10):895-904 (1996).
Roguska et al., "Humanization of murine monoclonal antibodies through variable domain resurfacing," Proc. Natl. Acad. Sci USA, 91(3):969-973 (1994).
Romer-Oberdorfer et al., 1999, "Generation of recombinant lentogenic Newcastle disease virus from cDNA" J Gen Virol., 80(Pt 11):2987-2995.

(56) References Cited

OTHER PUBLICATIONS

Ruther et al., "Easy identification of cDNA clones," EMBO J., 2(10):1791-1794 (1983).
Saif et al., 1997, "Natural and experimental infection of turkeys with avian paramyxovirus-7," Avian Dis., 41(2):326-329.
Sandhu et al., 2003, "Influenza A Virus Infection of Domestic Ducks," JSTOR, 47:93-99.
Santerre et al., "Expression of prokaryotic genes for hygromycin B and G418 resistance as dominant-selection markers in mouse L cells," Gene, 30:147-156 (1984).
Sapoznik et al. "Novel anti-melanoma immunotherapies: disarming tumor escape mechanisms," Clin Dev Immunol., 2012: 818214. doi: 10.1155/2012/818214. Epub Apr. 23, 2012 (2012).
Sawai et al., "Direct production of the Fab fragment derived from the sperm immobilizing antibody using polymerase chain reaction and cDNA expression vectors," A. J. Reprod. Immunol., 34(1):26-34 (1995).
Scapin et al., "Structure of full-length human anti-PD1 therapeutic IgG4 antibody pembrolizumab,"Nat. Struct. Mol. Biol., 22(12):953-958 (2015).
Schickli et al., "Plasmid-only rescue of influenza A virus vaccine candidates," Phil. Trans. R. Soc. Lond., 356:1965-1973 (2001).
Schirrmacher et al., "Antitumor effects of Newcastle Disease Virus in vivo: Local versus systemic effects," Int. J. Oncol., 18:945-952 (2001).
Schirrmacher et al., "Newcastle disease virus: a promising vector for viral therapy, immune therapy, and gene therapy of cancer," Methods Mol. Biol., 542: 565-605 (2009).
Schirrmacher et al., 1998, "Immunization with virus-modified tumor cells" Semin. Oncol., 25(6):677-696.
Schirrmacher et al., 1999, "Human tumor cell modification by virus infection: an efficient and safe way to produce cancer vaccine with pleiotropic immune stimulatory properties when using Newcastle disease virus," Gene Ther., 6(1):63-73.
Schirrmacher et al., 2014, "Long-term remission of prostate cancer with extensive bone metastases upon immuno- and virotherapy: A case report," Oncol Lett., 8(6):2403-2406.
Schirrmacher et al., 2014, "Multimodal cancer therapy involving oncolytic newcastle disease virus, autologous immune cells, and bi-specific antibodies," Front Oncol., 4:224 (5 pages).
Schirrmacher, 2016, "Fifty Years of Clinical Application of Newcastle Disease Virus: Time to Celebrate!" Biomedicines, 4(3), 14 pages.
Scott et al., "Searching for peptide ligands with an epitope library," Science, 249(4967):386-390 (1990).
Seliger et al., "Characterization of the major histocompatibility complex class I deficiencies in B16 melanoma cells," Cancer Res., 61(3):1095-1099 (2001).
Senne et al., 2004, "Control of Newcastle disease by vaccination," Dev. Biol. (Basel), 119:165-170.
Seppi et al., "Direct determination of oxygen by HPLC. 2. Chamber and sample application system for determination of o(2) at trace levels," Anal. Chem., 69(21):4476-4481 (1997).
Sergel et al., "A Single Amino Acid Change in the Newcastle Disease Virus Fusion Protein Alters the Requirement for HN Protein in Fusion," J. Virol., 74(11):5101-5107 (2000).
Sharma et al., "Triggering the interferon antiviral response through an ikk-related pathway," Science, 300(5622):1148-1151 (2003).
Shenk, "Adenoviridae: The Viruses and Their Replication," Fundamental Virology, Fields et al. eds., Lippincott-Raven, Philadelphia, PA, pp. 979-1016 (1996).
Shim et al., "Inhibitory Receptors Induced by VSV Viroimmunotherapy Are Not Necessarily Targets for Improving Treatment Efficacy," Mol. Ther., 25(4):962-975 (2017).
Shinmoto et al., "Generation of mouse-human hybridomas secreting antibodies against peanut allergen Ara h1," Cytotechnology, 46(1):19-23 (2004).
Shinoff et al., 2008, "Young infants can develop protective levels of neutralizing antibody after infection with respiratory syncytial virus," J. Infect. Dis., 198(7):1007-1015.
Shinohara et al., "Structure and chromosomal localization of the human PD-1 gene (PDCD1)," Genomics, 23:704-706 (1994).
Shnyrova et al., 2007, "Vesicle formation by self-assembly of membrane-bound matrix proteins into a fluidlike budding domain," J Cell Biol., 179(4):627-633.
Shortridge et al., 1980, "Isolation and properties of viruses from poultry in Hong Kong which represent a new (sixth) distinct group of avian paramyxoviruses," J Gen Virol., 49(2):255-262.
Sigurs et al., 2000, "Respiratory syncytial virus bronchiolitis in infancy is an important risk factor for asthma and allergy at age 7," Am. J. Respir. Crit. Care Med., 161(5):1501-1507.
Sigurs et al., 2005, "Severe respiratory syncytial virus bronchiolitis in infancy and asthma and allergy at age 13," Am. J. Respir. Crit. Care Med., 171(2):137-141 (Epub 2004).
Silberhumer et al., "Genetically engineered oncolytic Newcastle disease virus effectively induces sustained remission of malignant pleural mesothelioma," Mol. Cancer Ther., 9(10):2761-2769 (2010).
Simoes et al., 2003, "Impact of severe disease caused by respiratory syncytial virus in children living in developed countries," Pediatr. Infect. Dis. J., 22(2 Suppl):S13-S20.
Simpson et al., "Regulation of CD4 T cell activation and effector function by inducible costimulator (ICOS)," Curr. Opin. Immunol., 22(3):326-332 (2010).
Sinkovics et al., "Newcastle disease virus (NDV): brief history of its oncolytic strains," J. Clin. Virol,. 16:1-15 (2000).
Song et al., "Antitumor efficacy of viral therapy using genetically engineered Newcastle disease virus [NDV(F3aa)-GFP] for peritoneally disseminated gastric cancer," J. Mol. Med. (Berl)., 88(6):589-596 (2010).
Spranger et al., "Up-regulation of PD-L1, IDO, and T(regs) in the melanoma tumor microenvironment is driven by CD8(+) T cells," Sci. Transl. Med., 5(200):200ra116 (2013).
Stanislawek et al., 2002, "Avian paramyxoviruses and influenza viruses isolated from mallard ducks (*Anas platyrhynchos*) in New Zealand," Arch. Virol., 147(7):1287-1302.
Steglich et al., 2013, "Chimeric newcastle disease virus protects chickens against avian influenza in the presence of maternally derived NDV immunity," PLoS One, 8(9):e72530 (14 pages).
Steiner et al., 2004, "Antitumor vaccination of patients with glioblastoma multiforme: a pilot study to assess feasibility, safety, and clinical benefit," J Clin Oncol., 22(21):4272-4281.
Studnicka et al., "Human-engineered monoclonal antibodies retain full specific binding activity by preserving non-CDR complementarity-modulating residues," Protein Eng., 7(6):805-814 (1994).
Su et al., "Immunoadjuvant activities of a recombinant chicken IL-12 in chickens vaccinated with Newcastle disease virus recombinant HN protein," Veterinary Microbiology, 151:220-228 (2011).
Subbiah et al., 2010, "Pathogenesis of two strains of avian paramyxovirus serotype 2, Yucaipa and Bangor, in chickens and turkeysm," Avian Dis., 54(3):1050-1057.
Suresh et al., "Bispecific monoclonal antibodies from hybrid hybridomas," Methods Enzymol., 121:210-228 (1986).
Swann et al., "Type I IFN contributes to NK cell homeostasis, activation, and antitumor function," J. Immunol., 178(12):7540-7549 (2007).
Swayne et al., "Recombinant paramyxovirus type 1-avian influenza-H7 virus as a vaccine for protection of chickens against influenza and Newcastle disease," Avian Dis., 47:1047-1050 (2003).
Swayne, 2003, "Vaccines for List A poultry diseases: emphasis on avian influenza," Dev. Biol. (Basel), 114:201-212.
Szybalska et al., "Genetics of human cess line. IV. DNA-mediated heritable transformation of a biochemical trait," Proc. Natl. Acad. Sci. USA 48:2026-2034 (1992).
Tan et al., ""Superhumanized" antibodies: reduction of immunogenic potential by complementarity-determining region grafting with human germline sequences: application to an anti-CD28," J. Immunol., 169(2):1119-1125 (2002).
Tang et al., "Use of a peptide mimotope to guide the humanization of MRK-16, an anti-P-glycoprotein monoclonal antibody," J. Biol. Chem., 274(39): 27371-27378 (1999).
TECENTRIQ® (atezolizumab), Prescribing Information, revised Oct. 2016 (23 pages).

(56) References Cited

OTHER PUBLICATIONS

TECENTRIQ™ (atezolizumab), Prescribing Information, May 2016 (17 pages).
Terregino et al., 2013, Antigenic and genetic analyses of isolate APMV/wigeon/Italy/3920-1/2005 indicate that it represents a new avian paramyxovirus (APMV-12), Arch. Virol., 158(11):2233-2243.
Therasse et al., "New guidelines to evaluate the response to treatment in solid tumors. European Organization for Research and Treatment of Cancer, National Cancer Institute of the United States, National Cancer Institute of Canada," J. Natl. Cancer Inst., 92(3):205-216 (2000).
Tolstoshev, "Gene therapy, concepts, current trials and future directions," Ann. Rev. Pharmacol. Toxicol., 32:573-596 (1993).
Topalian et al., "Safety, activity, and immune correlates of anti-PD-1 antibody in cancer," New Eng. J. Med., 366:2443-2454 (2012).
Tramontano et al., "Framework residue 71 is a major determinant of the position and conformation of the second hypervariable region in the VH domains of immunoglobulins," J. Mol. Biol., 215(1):175-182 (1990).
Traunecker et al., "Bispecific single chain molecules (Janusins) target cytotoxic lymphocytes on HIV infected cells," EMBO J., 10(12):3655-3659 (1991).
Tumeh et al., "PD-1 blockade induces responses by inhibiting adaptive immune resistance," Nature, 515(7528):568-571 (2014). (Extended Data Figures 1-6 and Extended Data Tables 1-4 attached).
Tumova et al., 1979, "A hitherto unreported paramyxovirus of turkeys," Res. Vet. Sci., 27(2):135-140.
Turk et al., "Concomitant tumor immunity to a poorly immunogenic melanoma is prevented by regulatory T cells," J. Exp. Med., 200(6):771-782 (2004).
Tuve et al., "In situ adenovirus vaccination engages T effector cells against cancer," Vaccine, 27:4225-4239 (2009).
UniProtKB/Swiss-Prot No. Q60819.1, "RecName: Full=Interleukin-15 receptor subunit alpha; Short=IL-15 receptor subunit alpha; Short=IL-15R-alpha; Short=IL-15RA; AltName: CD_antigen=CD215; Contains: RecName: Full=Soluble interleukin-15 receptor subunit alpha; Short=sIL-15 receptor subunit alpha; Short=sIL-15R-alpha; Short=sIL-15RA; Flags: Precursor," Oct. 16, 2019.
U.S. Appl. No. 14/205,776, Final Office Action dated Sep. 23, 2016.
U.S. Appl. No. 14/205,776, Non-Final Office Action dated Mar. 4, 2016.
U.S. Appl. No. 14/205,776, Amendment and Response dated Jan. 8, 2016.
U.S. Appl. No. 14/205,776, Amendment under 37 C.F.R. 1.111 dated Jun. 9, 2015.
U.S. Appl. No. 14/205,776, Final Office Action dated Aug. 10, 2015.
U.S. Appl. No. 14/205,776, Non-Final Office Action dated Jan. 28, 2015.
U.S. Appl. No. 14/774,962, Non-Final Office Action mailed Nov. 9, 2016.
U.S. Appl. No. 15/588,251, Non-Final Office Action dated Jul. 16, 2018.
U.S. Appl. No. 15/789,340, Amendment and Response dated May 17, 2019.
U.S. Appl. No. 15/789,340, Final Office Action dated Jun. 14, 2019.
U.S. Appl. No. 15/789,340, Non-Final Office Action date Feb. 19, 2019.
U.S. Appl. No. 15/789,539, Amendment and Response dated Oct. 30, 2018.
U.S. Appl. No. 15/789,539, Non-Final Office Action mailed Jul. 30, 2018.
U.S. Appl. No. 15/789,539, Notice of Allowance mailed Dec. 11, 2018.
Vail et al., "Spontaneously occurring tumors of companion animals as models for human cancer," Cancer Invest., 18:781-792 (2000).
Van Den Hoogen et al., 2001, "A newly discovered human pneumovirus isolated from young children with respiratory tract disease, " Nat. Med., 7(6):719-724.
Van Heeke et al., "Expression of human asparagine synthetase in Escherichia coli," J. Biol. Chem., 264(10):5503-5509 (1989).
Velu et al., "Role of PD-1 co-inhibitory pathway in HIV infection and potential therapeutic options," Retrovirology, 12:14 (2015).
Verma et al., "Gene therapy—promises, problems and prospects," Nature, 389:239-242 (1997).
Vigil et al., "Recombinant Newcastle disease virus as a vaccine vector for cancer therapy," Molecular Therapy, 16(11):1883-1890 (2008).
Vigil et al., "Use of reverse genetics to enhance the oncolytic properties of Newcastle disease virus," Cancer Research, 67(17):8285-8292 (2007).
Vlasak et al., "Use of flow cytometry for characterization of human cytomegalovirus vaccine particles," Vaccine, 34:2321-2328 (2016).
Von Heijne, "A new method for predicting signal sequence cleavage sites," Nucleic Acids Res., 14(11):4683-4690 (1986).
Von Heijne, "Patterns of amino acids near signal-sequence cleavage sites," Eur. J. Biochem., 133(1):17-21 (1983).
Wagner et al., 1989, "Serum immunoglobulin G antibody subclass response to respiratory syncytial virus F and G glycoproteins after first, second, and third infections," J. Clin. Microbiol., 27(3):589-592.
Waitz et al., "Potent induction of tumor immunity by combining tumor cryoablation with anti-CTLA-4 therapy," Cancer Res., 72(2):430-439 (2012).
Wakamatsu et al., "Convergent and divergent effects of costimulatory molecules in conventional and regulatory CD4+ T cells," Proc. Natl. Acad. Sci. USA, 110(3):1023-1028 (2013).
Wakamatsu et al., "The effect on pathogenesis of Newcastle disease virus LaSota strain from a mutation of the fusion cleavage site to a virulent sequence," Avian Dis., 50(4):483-488 (2006).
Walsh et al., 2004, "Humoral and mucosal immunity in protection from natural respiratory syncytial virus infection in adults," J. Infect. Dis., 190(2):373-378.
Walter et al., "Targeted inhibition of interferon-dependent intercellular adhesion molecule-1 (ICAM-1) expression using dominant-negative stat1," J. Biol. Chem., 272(45):28582-28589 (1997).
Walter et al., "Two avirulent, lentogenic strains of Newcastle disease virus are cytotoxic for some human pancreatic tumor lines in vitro," J. Pancreas, 13(5):502-513 (2012).
Wang et al., "A Novel, Clinically Relevant Animal Model of Metastatic Pancreatic Adenocarcinoma Biology and Therapy," Int. J. Pancreatol., 29(1):37-46 (2001).
Wang et al., "Impact of modification of cleavage site of fusion protein and foreign gene insertion on the virulence of Newcastle Disease Virus LaSota vaccine strain," Wei Sheng Wu Xue Bao, 48(3):362-368 (2008). (English abstract attached).
Washburn et al., 2002, "Human tumor cell infection by Newcastle Disease Virus leads to upregulation of HLA and cell adhesion molecules and to induction of interferons, chemokines and finally apoptosis," Int. J. Oncol., 21(1):85-93.
Weber et al., "Viral suppression of the interferon system," Biochimie, 89(6-7):836-842 (2007).
Webster et al., 1976, "Ortho- and paramyxoviruses from migrating feral ducks: characterization of a new group of influenza A viruses," J Gen Virol., 32(2):217-225.
Welliver et al., 1980, "The antibody response to primary and secondary infection with respiratory syncytial virus: kinetics of class-specific responses," J. Pediatr., 96(5):808-813.
Wheelock et al., 1964, "Observations on the repeated administration of viruses to a patient with acute leukemia. A preliminary report," N. Engl. J. Med., 271:645-651.
Wigler et al, "Transformation of mammalian cells with an amplifiable dominant-acting gene," Proc Natl. Acad. Sci. USA, 77:3567-3570 (1980).
Wigler et al., "Transfer of purified herpes virus thymidine kinase gene to cultured mouse cells," Cell, 11(1):223-232 (1977).
Wilden et al., "Expression of RIG-I, IRF3, IFN-beta and IRF7 determines resistance or susceptibility of cells to infection by Newcastle Disease Virus," Int. J. Oncol., 34(4):971-982 (2009).
Wold et al., "Adenovirus vectors for gene therapy, vaccination and cancer gene therapy," Curr. Gene Ther., 13(6):421-433 (2013).
Woller et al., "Oncolytic viruses as anticancer vaccines," Front. Oncol., 4(188):1-13 (2014).

(56) References Cited

OTHER PUBLICATIONS

Woolcock et al., 1996, "Isolation of paramyxovirus serotype 7 from ostriches (*Struthio camelus*)," Avian Dis., 40(4):945-949.
Wren et al., "SIGNAL-Sequence Information and GeNomic Analysis," Comput. Methods Programs Biomed., 68(2):177-181 (2002).
Wright et al., 1976, "Evaluation of a live, attenuated respiratory syncytial virus vaccine in infants," J. Pediatr., 88(6):931-936.
Wright et al., 1982, "Administration of a highly attenuated, live respiratory syncytial virus vaccine to adults and children," Infect. Immun., 37(1):397-400.
Wu et al., "Delivery systems for gene therapy," Biotherapy, 3(1):87-95 (1991).
Yamaki et al., "The potential of recombinant vesicular stomatitis virus-mediated virotherapy against metastatic colon cancer," Int. J. Mol. Med., 31:299-306 (2013).
Yamamoto et al., 2015, "Characterization of novel avian paramyxovirus strain APMV/Shimane67 isolated from migratory wild geese in Japan," J Vet Med Sci., 77(9):1079-1085.
Yamane et al., 1982, "Characterization of avian paramyxoviruses isolated from feral ducks in northern Japan: the presence of three distinct viruses in nature," Microbiol Immunol., 26(7):557-568.
Yao et al., "Reviving exhausted T lymphocytes during chronic virus infection by B7-H1 blockade," Trends Mol. Med., 12(6):244-246 (2006).
Ying et al., "Adenovirus-mediated intratumoral expression of immunostimulatory proteins in combination with systemic Treg inactivation induces tumor-destructive immune responses in mouse models," Cancer Gene Ther., 18(6):407-418 (2011).
Yoneyama et al., "The RNA helicase RIG-I has an essential function in double-stranded RNA-induced innate antiviral responses," Nature Immunol., 5:730-737 (2004).
Yoshida et al., 2017, "Avian Paramyxovirus Type-3 as a Vaccine Vector: Identification of a Genome Location for High Level Expression of a Foreign Gene," Front Microbiol., 8:693 (8 pages).
Yoshida et al., 2019, "Novel avian paramyxovirus-based vaccine vectors expressing the Ebola virus glycoprotein elicit mucosal and humoral immune responses in guinea pigs," Sci. Rep., 9(1):5520 (10 pages).
Zamarin et al., "Potentiation of immunomodulatory antibody therapy with oncolytic viruses for treatment of cancer," Mol. Therapy-Oncolytics, 1:14004; doi: 10.1038/mto.2014.4. (2014).
Zamarin et al., "Upregulation of PD-L1 in tumor microenvironment is a resistance mechanism for onolytic virus immunotherapy," J. Immunother. Cancer, 5(Suppl 2):87 (2017).
Zamarin et al., "Enhancement of Oncolytic Properties of Genetically-Engineered Fusogenic Newcastle Disease Virus through Antagonism of Cellular Innate Immune Responses," Mol. Ther., 16(Suppl. 1), Abstract #43 (2008).
Zamarin et al., "Enhancement of oncolytic properties of recombinant Newcastle disease virus through antagonism of cellular innate immune responses," Mol. Ther., 17(4):697-706 (2009).
Zamarin et al., "Genetically engineered Newcastle disease virus for malignant melanoma therapy," Gene Ther., 16(6):796-804 (2009).
Zamarin et al., "Intratumoral modulation of the inducible co-stimulator ICOS by recombinant oncolytic virus promotes systemic anti-tumour immunity," Nat. Commun., 8:14340 (2017).
Zamarin et al., "Localized oncolytic virotherapy inflames distant tumors and synergizes with immune checkpoint blockade leading to systemic tumor rejection," J. Immunother. Cancer, 1(Suppl 1):09 (2013).
Zamarin et al., "Oncolytic Newcastle disease virus for cancer therapy: old challenges and new directions," Future Microbiol., 7:347-367 (2012).
Zamarin et al., "PD-L1 in tumor microenvironment mediates resistance to oncolytic immunotherapy," J. Clin. Invest., 128(4):1413-1428, with Supplemental Materials (2018).
Zamarin et al., 2014, "Localized oncolytic virotherapy overcomes systemic tumor resistance to immune checkpoint blockade immunotherapy," Sci. Transl. Med., 6(226):226ra32 , with Supplemental Materials (109 pages).
Zamarin et al., 2017, "P415: Upregulation of PD-L1 in tumor microenvironment is a resistance mechanism for onolytic virus immunotherapy," J. Immunother. Cancer, 5(Suppl 2):87, p. 202.
Zhang et al., "Anti-Oncogene and Tumor Suppressor Gene Therapy—Examples from a Lung Cancer Animal Model," In-Vivo, 8:755-769 (1994).
Zhao et al., "P and M gene junction is the optimal insertion site in Newcastle disease virus vaccine vector for foreign gene expression," J. Gen. Virol., 96(Pt 1):40-45 (2015) (Epub Oct. 1, 2014).
Zhao et al., 2008, "Recombinant Newcastle disease virus expressing human interleukin-2 serves as a potential candidate for tumor therapy," Virus Res., 136(1-2):75-80.
Zimmer et al., "A chimeric respiratory syncytial virus fusion protein functionally replaces the F and HN glycoproteins in recombinant sendai virus," J Virol., 79(16):10467-10477 (2005).
Zitvogel et al., "Type I interferons in anticancer immunity," Nature Rev. Innumol., 15:405-414 (2015).

* cited by examiner prime boost mock

NDV

NDV-F mock

NDV

NDV-F

FIG. 3A
mock
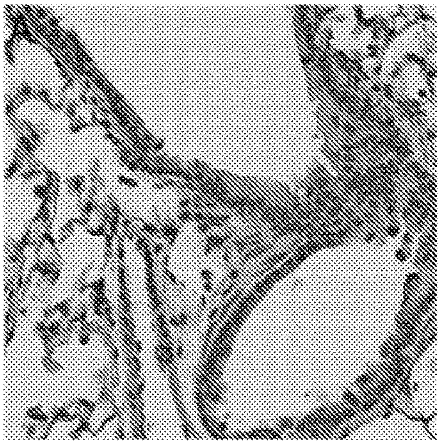
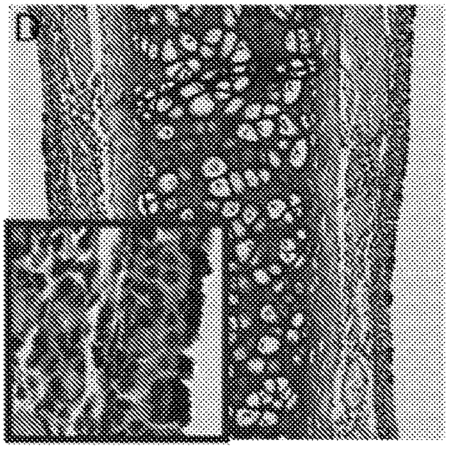
FIG. 3D
FIG. 3B
NDV
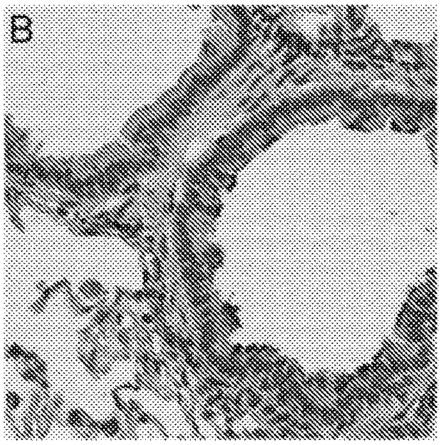
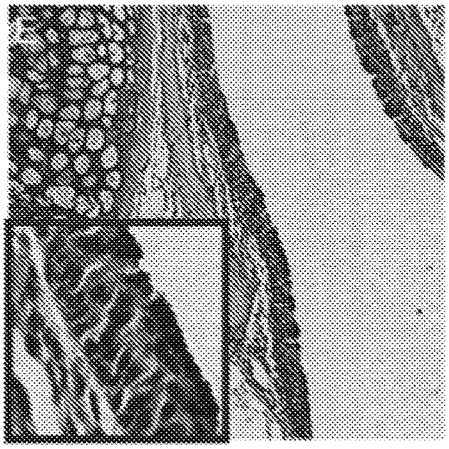
FIG. 3E
FIG. 3C
NDV-F
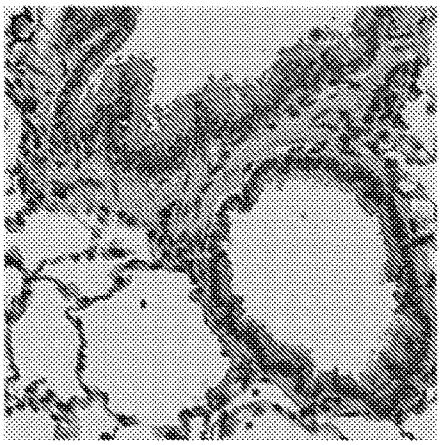
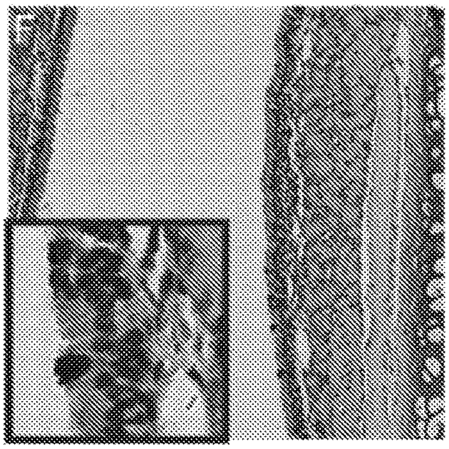
FIG. 3F

ALIGNMENT OF NUCLEIC ACID SEQUENCE ENCODING HUMAN RSV F PROTEIN AND CODON OPTIMIZED NUCLEIC ACID SEQUENCE ENCODING HUMAN RSV F PROTEIN

```
wt       1 ATGGAGTTGCTAATCCTCAAAGCAAATGCAATTACCACAATCCTCACTGC   50
           ||||||.||||.|||||.||.||.||.||.||.||||||.|||||.||.||
opt      1 ATGGAGCTGCTGATCCTGAAGGCCAACGCCATCACCACCATCCTGACCGC   50

wt      51 AGTCACATTTTGTTTTGCTTCTGGTCAAAACATCACTGAAGAATTTTATC  100
           .||.||.||.||.||.||....||.||.||||||.||.||.||.||.|
opt     51 CGTGACCTTCTGCTTCGCCAGCGGCCAGAACATCACCGAGGAGTTCTACC  100

wt     101 AATCAACATGCAGTGCAGTTAGCAAAGGCTATCTTAGTGCTCTGAGAACT  150
           |.  .||.|||||.||.||.|||||.|||||.||.||.||.|||.|.||.
opt    101 AGAGCACCTGCAGCGCCGTGAGCAAGGGCTACCTGAGCGCCCTGCGCACC  150

wt     151 GGTTGGTATACCAGTGTTATAACTATAGAATTAAGTAATATCAAGGAAAA  200
           ||.|||||.|||||.||.||.||.||.||..|.||.||.||||||||.||
opt    151 GGCTGGTACACCAGCGTGATCACCATCGAGCTGAGCAACATCAAGGAGAA  200

wt     201 TAAGTGTAATGGAACAGATGCTAAGGTAAAATTGATAAAACAAGAATTAG  250
            |||||.||.||.||.||.|.|||||.||..||||.||.||.||..|.|
opt    201 CAAGTGCAACGGCACCGACGCCAAGGTGAAGCTGATCAAGCAGGAGCTGG  250

wt     251 ATAAATATAAAAATGCTGTAACAGAATTGCAGTTGCTCATGCAAAGCACA  300
           |.||.||.||.||.||.||.||.||..|||||.||||.|||||.|||||.
opt    251 ACAAGTACAAGAACGCCGTGACCGAGCTGCAGCTGCTGATGCAGAGCACC  300

wt     301 CCAGCAACAAACAATCGAGCCAGAAGAGAACTACCAAGGTTTATGAATTA  350
           ||.||.||.|||||.||.|||.|..|.||.||.||..|.||.|||||.||
opt    301 CCCGCCACCAACAACCGCGCCCGCCGCGAGCTGCCCCGCTTCATGAACTA  350

wt     351 TACACTCAACAATGCCAAAAAAACCAATGTAACATTAAGCAAGAAAAGGA  400
            ||.||.|||||.|||||.||.|||||.||.||..|.||||||||..|.|
opt    351 CACCCTGAACAACGCCAAGAAGACCAACGTGACCCTGAGCAAGAAGCGCA  400

wt     401 AAAGAAGATTTCTTGGTTTTTTGTTAGGTGTTGGATCTGCAATCGCCAGT  450
           |. |..|.||.||.||.||..||.|.||.||.||....||.||||||||
opt    401 AGCGCCGCTTCCTGGGCTTCCTGCTGGGCGTGGGCAGCGCCATCGCCAGC  450

wt     451 GGCGTTGCTGTATCTAAGGTCCTGCACCTAGAAGGGGAAGTGAACAAGAT  500
           |||||.|| ||....|||||.||||||||.||.||.||.||||||||||||
opt    451 GGCGTGGCCGTGAGCAAGGTGCTGCACCTGGAGGGCGAGGTGAACAAGAT  500

wt     501 CAAAAGTGCTCTACTATCCACAAACAAGGCTGTAGTCAGCTTATCAAATG  550
           |||.||.||.||.||...|||.||||||||.||.||.|||.|....||.|
opt    501 CAAGAGCGCCCTGCTGAGCACCAACAAGGCCGTGGTGAGCCTGAGCAACG  550

wt     551 GAGTTAGTGTCTTAACCAGCAAAGTGTTAGACCTCAAAAACTATATAGAT  600
           |.||.||.||..|.||||||||.|||.|.|||||.||.|||||.||.||.
opt    551 GCGTGAGCGTGCTGACCAGCAAGGTGCTGGACCTGAAGAACTACATCGAC  600

wt     601 AAACAATTGTTACCTATTGTGAACAAGCAAAGCTGCAGCATATCAAATAT  650
           ||.||..||.|.||.||.|||||||||.|||||||||||....||.||
opt    601 AAGCAGCTGCTGCCCATCGTGAACAAGCAGAGCTGCAGCATCAGCAACAT  650
```

FIG. 16A

```
wt     651 AGCAACTGTGATAGAGTTCCAACAAAAGAACAACAGACTACTAGAGATTA  700
           .||.||.|||||.||||||||.||.||||||||||.|.||.||.|||||.|
opt    651 CGCCACCGTGATCGAGTTCCAGCAGAAGAACAACCGCCTGCTGGAGATCA  700

wt     701 CCAGGGAATTTAGTGTTAATGCAGGTGTAACTACACCTGTAAGCACTTAC  750
           ||.|.||.||.||.||.||.||.||.||.||.||.||.||.||.|||||.|||
opt    701 CCCGCGAGTTCAGCGTGAACGCCGGCGTGACCACCCCCGTGAGCACCTAC  750

wt     751 ATGTTAACTAATAGTGAATTATTGTCATTAATCAATGATATGCCTATAAC  800
           |||.|.||.||.||.||..|..||....|.|||||.||.|||||.||.||
opt    751 ATGCTGACCAACAGCGAGCTGCTGAGCCTGATCAACGACATGCCCATCAC  800

wt     801 AAATGATCAGAAAAAGTTAATGTCCAACAATGTTCAAATAGTTAGACAGC  850
           .||.||.|||||.|||.|.|||..||||||.||.||.||.||..|.||||
opt    801 CAACGACCAGAAGAAGCTGATGAGCAACAACGTGCAGATCGTGCGCCAGC  850

wt     851 AAAGTTACTCTATCATGTCCATAATAAAAGAGGAAGTCTTAGCATATGTA  900
           |.||.|||...||||||..|||.||.||.|||||.||..|.||.||.||.
opt    851 AGAGCTACAGCATCATGAGCATCATCAAGGAGGAGGTGCTGGCCTACGTG  900

wt     901 GTACAATTACCACTATATGGTGTTATAGATACACCCTGTTGGAAACTACA  950
           ||.||..|.||.||.||.||.||.||.||.||.|||||.|||||.||.||
opt    901 GTGCAGCTGCCCCTGTACGGCGTGATCGACACCCCCTGCTGGAAGCTGCA  950

wt     951 CACATCCCCTCTATGTACAACCAACACAAAAGAAGGGTCCAACATCTGTT  1000
           |||...|||.||.||.||.||||||||.||.||.||...|||||||||..
opt    951 CACCAGCCCCCTGTGCACCACCAACACCAAGGAGGGCAGCAACATCTGCC  1000

wt    1001 TAACAAGAACTGACAGAGGATGGTACTGTGACAATGCAGGATCAGTATCT  1050
           |.||..|.||.|||||.||.||||||||.|||||.||.||....||....
opt   1001 TGACCCGCACCGACAGGGGCTGGTACTGCGACAACGCCGGCAGCGTGAGC  1050

wt    1051 TTCTTCCCACAAGCTGAAACATGTAAAGTTCAATCAAATCGAGTATTTTG  1100
           ||||||||.||.||.||.||.||.||.||.||....||.||.||.||.||
opt   1051 TTCTTCCCCCAGGCCGAGACCTGCAAGGTGCAGAGCAACCGCGTGTTCTG  1100

wt    1101 TGACACAATGAACAGTTTAACATTACCAAGTGAAGTAAATCTCTGCAATG  1150
           .|||||.||||||||..|.||..|.||.||.||.||.||.||.|||||.|
opt   1101 CGACACCATGAACAGCCTGACCCTGCCCAGCGAGGTGAACCTGTGCAACG  1150

wt    1151 TTGACATATTCAACCCCAAATATGATTGTAAAATTATGACTTCAAAAACA  1200
           |.|||||.|||||||||||.||.||.||.||.||.|||||....||.||.
opt   1151 TGGACATCTTCAACCCCAAGTACGACTGCAAGATCATGACCAGCAAGACC  1200

wt    1201 GATGTAAGCAGCTCCGTTATCACATCTCTAGGAGCCATTGTGTCATGCTA  1250
           ||.||.||||||..|||.|||||....||.||.|||||.|||...|||||
opt   1201 GACGTGAGCAGCAGCGTGATCACCAGCCTGGGCGCCATCGTGAGCTGCTA  1250

wt    1251 TGGCAAAACTAAATGTACAGCATCCAATAAAAATCGTGGAATCATAAAGA  1300
           .|||||.||.||.||.||.||...|||.||.||..|.||.|||||.||||
opt   1251 CGGCAAGACCAAGTGCACCGCCAGCAACAAGAACAGGGGCATCATCAAGA  1300

wt    1301 CATTTTCTAACGGGTGCGATTATGTATCAAATAAAGGGGTGGACACTGTG  1350
           |.||....|||||.|||||.||.||....||.||.||.||||||||.|||
opt   1301 CCTTCAGCAACGGCTGCGACTACGTGAGCAACAAGGGCGTGGACACCGTG  1350

wt    1351 TCTGTAGGTAACACATTATATTATGTAAATAAGCAAGAAGGTAAAAGTCT  1400
           ...||.||.|||||..|.||.||.||.||.|||||.||.||.||.||.||
opt   1351 AGCGTGGGCAACACCCTGTACTACGTGAACAAGCAGGAGGGCAAGAGCCT  1400
```

FIG. 16B

```
wt        1401 CTATGTAAAAGGTGAACCAATAATAAATTTCTATGACCCATTAGTATTCC  1450
               .||.||.||.||.||.||.||.||.||.|||||.|||||..|.||.||||
opt       1401 GTACGTGAAGGGCGAGCCCATCATCAACTTCTACGACCCCCTGGTGTTCC  1450

wt        1451 CCTCTGATGAATTTGATGCATCAATATCTCAAGTCAACGAGAAGATTAAC  1500
               ||...||.||.||.||.||....||....||.||.|||||||||||.|||
opt       1451 CCAGCGACGAGTTCGACGCCAGCATCAGCCAGGTGAACGAGAAGATCAAC  1500

wt        1501 CAGAGCCTAGCATTTATTCGTAAATCCGATGAATTATTACATAATGTAAA  1550
               ||||||||.||.||.||.||.||...|||.||..|..|.||.||.||.||
opt       1501 CAGAGCCTGGCCTTCATCCGCAAGAGCGACGAGCTGCTGCACAACGTGAA  1550

wt        1551 TGCTGGTAAATCCACCATAAATATCATGATAACTACTATAATTATAGTGA  1600
               .||.||.||...||||||.||.||||||||.||.||.||.||.||.||||
opt       1551 CGCCGGCAAGAGCACCATCAACATCATGATCACCACCATCATCATCGTGA  1600

wt        1601 TTATAGTAATATTGTTATCATTAATTGCTGTTGGACTGCTCTTATACTGT  1650
               |.||.||.||..||.|.....|.||.||.||.||.|||||..|.|||||.
opt       1601 TCATCGTGATCCTGCTGAGCCTGATCGCCGTGGGCCTGCTGCTGTACTGC  1650

wt        1651 AAGGCCAGAAGCACACCAGTCACACTAAGCAAAGATCAACTGAGTGGTAT  1700
               ||||||.|.|||||.||.||.||.||.|||||.||.||.|||||.||.||
opt       1651 AAGGCCCGCAGCACCCCCGTGACCCTGAGCAAGGACCAGCTGAGCGGCAT  1700

wt        1701 AAATAATATTGCATTTAGTAACTAA  1725
               .||.||.||.||.||.||.||||||
opt       1701 CAACAACATCGCCTTCAGCAACTAA  1725
```

FIG. 16C

ALIGNMENT OF WILD-TYPE NUCLEIC ACID SEQUENCE ENCODING BOVINE RSV F PROTEIN AND CODON OPTIMIZED NUCLEIC ACID SEQUENCE ENCODING BOVINE RSV F PROTEIN

```
wt                1 ATGGCGACAACAGCCATGAGGATGATCATCAGCATTATCTTCATCTCTAC  50
                    |||||.||.||.||||||.|.||||||||||||||.|||||||||...||
codon-optimiz     1 ATGGCCACCACCGCCATGCGCATGATCATCAGCATCATCTTCATCAGCAC  50

wt               51 CTATGTGACACATATCACTTTATGCCAAAACATAACAGAAGAATTTTATC 100
                    |||.|||||.||.|||||..|.|||||.|||||.||.||.||.||.||.|
codon-optimiz    51 CTACGTGACCCACATCACCCTGTGCCAGAACATCACCGAGGAGTTCTACC 100

wt              101 AATCAACATGCAGTGCAGTTAGTAGAGGTTACCTTAGTGCATTAAGAACT 150
                    |....||.|||||.||.||.|||.|.||.|||||.||.||..|..|.||.
codon-optimiz   101 AGAGCACCTGCAGCGCCGTGAGTCGCGGCTACCTGAGCGCCCTGCGCACC 150

wt              151 GGATGGTATACAAGTGTGGTAACAATAGAGTTGAGCAAAATACAAAAAAA 200
                    ||.|||||.||.||.|||||.||.||.|||.|||||||.||.||.||.||
codon-optimiz   151 GGCTGGTACACCAGCGTGGTGACCATCGAGCTGAGCAAGATCCAGAAGAA 200

wt              201 TGTGTGTAATAGTACTGATTCAAAAGTGAAATTAATAAAGCAAGAACTAG 250
                    .|||||.||.||.||.||....||.|||||..|.||.|||||.||.||.|
codon-optimiz   201 CGTGTGCAACAGCACCGACAGCAAGGTGAAGCTGATCAAGCAGGAGCTGG 250

wt              251 AAAGATACAACAATGCAGTAGTGGAATTGCAGTCACTTATGCAAAATGAA 300
                    |..|.||||||||.||.||.|||||..|||||...||.|||||.||.||.
codon-optimiz   251 AGCGCTACAACAACGCCGTGGTGGAGCTGCAGAGCCTGATGCAGAACGAG 300

wt              301 CCGGCCTCCTTCAGTAGAGCAAAAAGAGGGATACCAGAGTTGATACATTA 350
                    ||.|||..||||||..|.||.||..|.||.||.||.|||.||||.||.||
codon-optimiz   301 CCCGCCAGCTTCAGCCGCGCCAAGCGCGGCATCCCCGAGCTGATCCACTA 350

wt              351 TACAAGAAACTCTACAAAAAAGTTTTATGGGCTAATGGGCAAGAAGAGAA 400
                    .||..|.|||...||.||.|||||.||.||.||.||||||||||||.|.|
codon-optimiz   351 CACCCGCAACAGCACCAAGAAGTTCTACGGCCTGATGGGCAAGAAGCGCA 400

wt              401 AAAGGAGATTTTTAGGATTCTTGCTAGGTATTGGATCTGCTATTGCAAGT 450
                    |..|..|.||..|.||.|||.||||.||.||.||....||.||.||.||.
codon-optimiz   401 AGCGCCGCTTCCTGGGCTTCCTGCTGGGCATCGGCAGCGCCATCGCCAGC 450

wt              451 GGTGTAGCAGTGTCCAAAGTACTACACCTGGAGGGAGAGGTGAATAAAAT 500
                    ||.||.||.|||..|||.||.||.|||||||||||.||||||||.||.||
codon-optimiz   451 GGCGTGGCCGTGAGCAAGGTGCTGCACCTGGAGGGCGAGGTGAACAAGAT 500

wt              501 TAAAAATGCACTGCTATCCACAAATAAAGCAGTAGTTAGTCTATCCAATG 550
                    .||.||.||.|||||...|||.||.||.||.||.||.||.||...|||.|
codon-optimiz   501 CAAGAACGCCCTGCTGAGCACCAACAAGGCCGTGGTGAGCCTGAGCAACG 550

wt              551 GAGTTAGTGTCCTTACTAGCAAAGTACTTGATCTAAAGAACTATATAGAC 600
                    |.||.||.||.||.||.|||||.||.||.||.||.||||||||.||.|||
codon-optimiz   551 GCGTGAGCGTGCTGACCAGCAAGGTGCTGGACCTGAAGAACTACATCGAC 600

wt              601 AAAGAGCTTCTACCTAAAGTTAACAATCATGATTGTAGGATATCCAAAAT 650
                    ||.|||||.||.||.||.||.|||||.||.||.||..|.||...|||.||
codon-optimiz   601 AAGGAGCTGCTGCCCAAGGTGAACAACCACGACTGCCGCATCAGCAAGAT 650

wt              651 AGAAACTGTGATAGAATTCCAACAAAAAAACAATAGATTGTTAGAAATTG 700
                    .||.||.|||||.||.|||||.||.||.|||||..|..||.|.||.||.|
```

FIG. 17A

```
codon-optimiz    651 CGAGACCGTGATCGAGTTCCAGCAGAAGAACAACCGCCTGCTGGAGATCG    700

wt               701 CTAGGGAATTTAGTGTAAATGCTGGTATTACCACACCTCTCAGTACATAC    750
                     |..|.||.||.||.||.||.||.||.||.|||||.||.||.||.||.|||
codon-optimiz    701 CCCGCGAGTTCAGCGTGAACGCCGGCATCACCACCCCCCTGAGCACCTAC    750

wt               751 ATGTTGACCAATAGTGAATTACTATCACTAATTAATGATATGCCTATAAC    800
                     |||.|||||||.||.||..|.||....||.||.||.||.|||||.||.||
codon-optimiz    751 ATGCTGACCAACAGCGAGCTGCTGAGCCTGATCAACGACATGCCCATCAC    800

wt               801 GAATGACCAAAAAAAGCTAATGTCAAGTAATGTTCAAATAGTCAGGCAAC    850
                     .||.|||||.||.|||||.|||...||.||.||.||.||.||..|.||.|
codon-optimiz    801 CAACGACCAGAAGAAGCTGATGAGCAGCAACGTGCAGATCGTGCGCCAGC    850

wt               851 AGAGTTATTCCATTATGTCAGTGGTCAAAGAAGAAGTCATAGCTTATGTT    900
                     ||||.||...|||.|||...|||||.||.||.||.||.||.||.||.||.
codon-optimiz    851 AGAGCTACAGCATCATGAGCGTGGTGAAGGAGGAGGTGATCGCCTACGTG    900

wt               901 GTACAATTGCCTATTTATGGAGTTATAGACACCCCCTGTTGGAAACTACA    950
                     ||.||..||||.||.||.||.||.||.|||||||||||.|||||.||.||
codon-optimiz    901 GTGCAGCTGCCCATCTACGGCGTGATCGACACCCCCTGCTGGAAGCTGCA    950

wt               951 CACCTCTCCGTTATGCACCACTGATAATAAAGAAGGGTCAAACATCTGCT   1000
                     ||||...||..|.||||||||.||.||.||.||.||....|||||||||.
codon-optimiz    951 CACCAGCCCCCTGTGCACCACCGACAACAAGGAGGGCAGCAACATCTGCC   1000

wt              1001 TAACTAGGACAGATCGTGGGTGGTATTGTGACAATGCAGGCTCTGTGTCT   1050
                     |.||..|.||.|||||.||.|||||.||.|||||.||.||.|...|||...
codon-optimiz   1001 TGACCCGCACCGATCGCGGCTGGTACTGCGACAACGCCGGCAGCGTGAGC   1050

wt              1051 TTTTTCCCACAGACAGAGACATGTAAGGTACAATCAAATAGAGTGTTCTG   1100
                     ||.|||||.|||||.||||||.||.|||||.||....||..|.||||||||
codon-optimiz   1051 TTCTTCCCCCAGACCGAGACCTGCAAGGTGCAGAGCAACCGCGTGTTCTG   1100

wt              1101 TGACACAATGAACAGTTTAACTCTGCCTACTGACGTTAACTTATGCAACA   1150
                     .|||||.||||||||..|.||.|||||.||.|||||.|||.|.|||||||
codon-optimiz   1101 CGACACCATGAACAGCCTGACCCTGCCCACCGACGTGAACCTGTGCAACA   1150

wt              1151 CTGACATATTCAATACAAAGTATGACTGTAAAATAATGACATCTAAAACT   1200
                     |.|||||.|||||.||.|||||.|||||.||.||.|||||....||.||.
codon-optimiz   1151 CCGACATCTTCAACACCAAGTACGACTGCAAGATCATGACCAGCAAGACC   1200

wt              1201 GACATAAGTAGCTCTGTGATAACTTCAATTGGAGCTATTGTATCATGCTA   1250
                     |||||.||.|||...|||||.||....||.||.||.||.||....|||||
codon-optimiz   1201 GACATCAGCAGCAGCGTGATCACCAGCATCGGCGCCATCGTGAGCTGCTA   1250

wt              1251 TGGGAAGACAAAATGTACAGCTTCTAATAAAAATCGTGGAATCATAAAGA   1300
                     .||.|||||.||.||.||.||....||.||.|||||.||.|||||.||||
codon-optimiz   1251 CGGCAAGACCAAGTGCACCGCCAGCAACAAGAATCGCGGCATCATCAAGA   1300

wt              1301 CTTTTTCCAATGGGTGTGATTATGTATCAAACAAAGGAGTAGATACTGTA   1350
                     |.||...|||.||.||.||.||.||....|||||.||.||.||.||.||.
codon-optimiz   1301 CCTTCAGCAACGGCTGCGACTACGTGAGCAACAAGGGCGTGGACACCGTG   1350

wt              1351 TCTGTTGGTAACACACTATATTATGTAAATAAGCTAGAGGGGAAAGCACT   1400
                     ...||.||.|||||.||.||.||.||.||.|||||.|||||.||.||.||
codon-optimiz   1351 AGCGTGGGCAACACCCTGTACTACGTGAACAAGCTGGAGGGCAAGGCCCT   1400

wt              1401 CTATATAAAGGGTGAACCAATTATTAATTACTATGATCCACTAGTGTTTC   1450
                     .||.||.|||||.||.||.||.||.||.|||||.||.||.||.|||||.|
```

FIG. 17B

```
codon-optimiz   1401 GTACATCAAGGGCGAGCCCATCATCAACTACTACGACCCCCTGGTGTTCC   1450

wt              1451 CTTCTGATGAGTTTGATGCATCAATTGCCCAAGTAAACGCAAAAATAAAC   1500
                     |....||.|||||.||.||....||.|||||.||.|||||.||.||.|||
codon-optimiz   1451 CCAGCGACGAGTTCGACGCCAGCATCGCCCAGGTGAACGCCAAGATCAAC   1500

wt              1501 CAAAGCCTGGCCTTCATACGTCGATCTGATGAGTTACTTCACAGTGTAGA   1550
                     ||.||||||||||||||.||.||....||.|||.|.||.|||||.||.||
codon-optimiz   1501 CAGAGCCTGGCCTTCATCCGCCGCAGCGACGAGCTGCTGCACAGCGTGGA   1550

wt              1551 TGTAGGAAAATCCACCACAAATGTAGTAATTACTACTATTATCATAGTGA   1600
                     .||.||.||...||||||.||.||.||.||.||.||.||.|||||.||||
codon-optimiz   1551 CGTGGGCAAGAGCACCACCAACGTGGTGATCACCACCATCATCATCGTGA   1600

wt              1601 TAGTTGTAGTGATATTAATGTTAATAGCTGTAGGATTACTGTTTTACTGT   1650
                     |.||.||.|||||..|.|||.|.||.||.||.||..|.|||||.|||||.
codon-optimiz   1601 TCGTGGTGGTGATCCTGATGCTGATCGCCGTGGGCCTGCTGTTCTACTGC   1650

wt              1651 AAGACCAAGAGTACTCCTATCATGTTAGGGAAGGATCAGCTCAGTGGTAT   1700
                     |||||||||||.||.||.||||||.|.||.|||||.|||||.||.||.||
codon-optimiz   1651 AAGACCAAGAGCACCCCCATCATGCTGGGCAAGGACCAGCTGAGCGGCAT   1700

wt              1701 CAACAATCTTTCCTTTAGTAAATGA   1725
                     ||||||.||...|||.||.||.|.|
codon-optimiz   1701 CAACAACCTGAGCTTCAGCAAGTAA   1725
```

FIG. 17C

ALIGNMENT OF WILD-TYPE NUCLEIC ACID SEQUENCE ENCODING HMPV F PROTEIN AND CODON OPTIMIZED NUCLEIC ACID SEQUENCE ENCODING HMPV F PROTEIN

```
wt_huMPV-F          1 ATGTCTTGGAAAGTGGTGATCATTTTTTCATTGCTAATAACACCTCAACA     50
                      |||...|||||.|||||||||||.||.....||||.||.||.||.||.||
codon-optimiz       1 ATGAGCTGGAAGGTGGTGATCATCTTCAGCCTGCTGATCACCCCCCAGCA     50

wt_huMPV-F         51 CGGTCTTAAAGAGAGCTACCTAGAAGAATCATGTAGCACTATAACTGAGG    100
                      |||.||.||.|||||||||||.||.||. ..||.|||||.||.||.||||
codon-optimiz      51 CGGCCTGAAGGAGAGCTACCTGGAGGAGAGCTGCAGCACCATCACCGAGG    100

wt_huMPV-F        101 GATATCTTAGTGTTCTGAGGACAGGTTGGTATACCAACGTTTTTACATTA    150
                      |.||.||.|| ||.|||||.||.|| |||||.||||||||.||.||..|.
codon-optimiz     101 GCTACCTGAGCGTGCTGAGAACCGGCTGGTACACCAACGTGTTCACCCTG    150

wt_huMPV-F        151 GAGGTGGGTGATGTAGAAAACCTTACATGTTCTGATGGACCTAGCCTAAT    200
                      ||||||||.||.||.||.|||||.||.||....||.||.||.|||||.||
codon-optimiz     151 GAGGTGGGCGACGTGGAGAACCTGACCTGCAGCGACGGCCCCAGCCTGAT    200

wt_huMPV-F        201 AAAAACAGAATTAGATCTGACCAAAAGTGCACTAAGAGAGCTCAAAACAG    250
                      .||.||.||..|.|| ||||||||.||.||.||.||||||||.||.||.|
codon-optimiz     201 CAAGACCGAGCTGGACCTGACCAAGAGCGCCCTGAGAGAGCTGAAGACCG    250

wt_huMPV-F        251 TCTCTGCTGACCAATTGGCAAGAGAGGAACAAATTGAGAATCCCAGACAA    300
                      |....||.|||||..||||.||||||||.||.||.|||||.||||||||.
codon-optimiz     251 TGAGCGCCGACCAGCTGGCCAGAGAGGAGCAGATCGAGAACCCCAGACAG    300

wt_huMPV-F        301 TCTAGGTTTGTTCTAGGAGCAATAGCACTCGGTGTTGCAACAGCAGCTGC    350
                      ...||.||.||.||.||.||.||.||.||.||.||.||.||.||.||.||
codon-optimiz     301 AGCAGATTCGTGCTGGGCGCCATCGCCCTGGGCGTGGCCACCGCCGCCGC    350

wt_huMPV-F        351 AGTCACAGCAGGTGTTGCAATTGCCAAAACCATCCGGCTTGAGAGTGAAG    400
                      .||.||.||.||.||.||.|| |||||.||||||.| ||.|||||.||.|
codon-optimiz     351 CGTGACCGCCGGCGTGGCCATCGCCAAGACCATCAGACTGGAGAGCGAGG    400

wt_huMPV-F        401 TCACAGCAATTAAGAATGCCCTCAAAACGACCAATGAAGCAGTATCTACA    450
                      |.||.||.||.|||||.|||||.||.||.|||||.||.||.||....||.
codon-optimiz     401 TGACCGCCATCAAGAACGCCCTGAAGACCACCAACGAGGCCGTGAGCACC    450

wt_huMPV-F        451 TTGGGGAATGGAGTTCGAGTGTTGGCAACTGCAGTGAGAGAGCTGAAAGA    500
                      .||||.||.||.||..|||||.||||.||.||.||||||||||||||.||
codon-optimiz     451 CTGGGCAACGGCGTGAGAGTGCTGGCCACCGCCGTGAGAGAGCTGAAGGA    500

wt_huMPV-F        501 CTTTGTGAGCAAGAATTTAACTCGTGCAATCAACAAAAACAAGTGCGACA    550
                      |||.|||||||||||..|.||..|.||.|||||||| |||||||||||||
codon-optimiz     501 CTTCGTGAGCAAGAACCTGACCAGAGCCATCAACAAGAACAAGTGCGACA    550

wt_huMPV-F        551 TTGATGACCTAAAAATGGCCGTTAGCTTCAGTCAATTCAACAGAAGGTTT    600
                      |.||.||||| ||.||||||||.||||||||.||.|||||||||||.||.
codon-optimiz     551 TCGACGACCTGAAGATGGCCGTGAGCTTCAGCCAGTTCAACAGAAGATTC    600

wt_huMPV-F        601 CTAAATGTTGTGCGGCAATTTTCAGACAATGCTGGAATAACACCAGCAAT    650
                      ||.|| ||.|||.|.||.||....|||||.||.||.||.||.||.||.||
codon-optimiz     601 CTGAACGTGGTGAGACAGTTCAGCGACAACGCCGGCATCACCCCCGCCAT    650

wt_huMPV-F        651 ATCTTTGGACTTAATGACAGATGCTGAACTAGCCAGGGCCGTTTCTAACA    700
                      .....|||||.|.|||||.||.||.||.||.|||||.|||||....||||
```

FIG. 19A

```
codon-optimiz     651  CAGCCTGGACCTGATGACCGACGCCGAGCTGGCCAGAGCCGTGAGCAACA   700

wt_huMPV-F        701  TGCCGACATCTGCAGGACAAATAAAATTGATGTTGGAGAACCGCGCGATG   750
                       ||||.||....||.||.||.||.||..|||||.||||||||.|.||.|||
codon-optimiz     701  TGCCCACCAGCGCCGGCCAGATCAAGCTGATGCTGGAGAACAGAGCCATG   750

wt_huMPV-F        751  GTGCGAAGAAAGGGGTTCGGAATCCTGATAGGGGTCTACGGGAGCTCTGT   800
                       |||.||||||||||.|||||.||||||||.||.||.|||||.|||...||
codon-optimiz     751  GTGAGAAGAAAGGGCTTCGGCATCCTGATCGGCGTGTACGGCAGCAGCGT   800

wt_huMPV-F        801  AATTTACATGGTGCAGCTGCCAATCTTTGGCGTTATAGACACGCCTTGCT   850
                       .||.|||||||||||||||||.|||||.|||||.||.|||||.||.||||
codon-optimiz     801  GATCTACATGGTGCAGCTGCCCATCTTCGGCGTGATCGACACCCCCTGCT   850

wt_huMPV-F        851  GGATAGTAAAAGCAGCCCCTTCTTGTTCCGAAAAAAAGGGAAACTATGCT   900
                       ||||.||.||.||.|||||....||...|||.||.|||||.|||||.||.
codon-optimiz     851  GGATCGTGAAGGCCGCCCCCAGCTGCAGCGAGAAGAAGGGCAACTACGCC   900

wt_huMPV-F        901  TGCCTCTTAAGAGAAGACCAAGGGTGGTATTGTCAGAATGCAGGGTCAAC   950
                       |||||..|.|||||.|||||.||.|||||.||.|||||.||.||....||
codon-optimiz     901  TGCCTGCTGAGAGAGGACCAGGGCTGGTACTGCCAGAACGCCGGCAGCAC   950

wt_huMPV-F        951  TGTTTACTACCCAAATGAGAAAGACTGTGAAACAAGAGGAGACCATGTCT  1000
                       .||.||||||||.||.|||||.|||||.||.||.||.|||||.|||||.||.|
codon-optimiz     951  CGTGTACTACCCCAACGAGAAGGACTGCGAGACCAGAGGCGACCACGTGT  1000

wt_huMPV-F       1001  TTTGCGACACAGCAGCAGGAATTAATGTTGCTGAGCAATCAAAGGAGTGC  1050
                       |.||||||||.||.||.||.||.||.||.||.|||||....|||||||||
codon-optimiz    1001  TCTGCGACACCGCCGCCGGCATCAACGTGGCCGAGCAGAGCAAGGAGTGC  1050

wt_huMPV-F       1051  AACATCAACATATCCACTACAAATTACCCATGCAAAGTCAGCACAGGAAG  1100
                       |||||||||||...|||.||.||.|||||.|||||.||.|||||.||.||
codon-optimiz    1051  AACATCAACATCAGCACCACCAACTACCCCTGCAAGGTGAGCACCGGCAG  1100

wt_huMPV-F       1101  ACATCCTATCAGTATGGTTGCACTGTCTCCTCTTGGGGCTCTGGTTGCTT  1150
                       |||.||.|||||.|||||.||.|||...||.||.||.||.|||||.||.|
codon-optimiz    1101  ACACCCCATCAGCATGGTGGCCCTGAGCCCCCTGGGCGCCCTGGTGGCCT  1150

wt_huMPV-F       1151  GCTACAAAGGAGTAAGCTGTTCCATTGGCAGCAACAGAGTAGGGATCATC  1200
                       |||||||.||.||.|||||...|||.||||||||||||||.||.||||||
codon-optimiz    1151  GCTACAAGGGCGTGAGCTGCAGCATCGGCAGCAACAGAGTGGGCATCATC  1200

wt_huMPV-F       1201  AAGCAGCTGAACAAAGGTTGCTCCTATATAACCAACCAAGATGCAGACAC  1250
                       ||||||||||||||.||.|||..|||.||.||||||||.||.||.|||||
codon-optimiz    1201  AAGCAGCTGAACAAGGGCTGCAGCTACATCACCAACCAGGACGCCGACAC  1250

wt_huMPV-F       1251  AGTGACAATAGACAACACTGTATATCAGCTAAGCAAAGTTGAGGGTGAAC  1300
                       .|||||.||.||||||||.||.||.|||||.|||||.||.|||||.||.|
codon-optimiz    1251  CGTGACCATCGACAACACCGTGTACCAGCTGAGCAAGGTGGAGGGCGAGC  1300

wt_huMPV-F       1301  AGCATGTTATAAAAGGCAGACCAGTGTCAAGCAGCTTTGATCCAATCAAG  1350
                       ||||.||.||.||.||||||||.|||...||||||||.||.||.||||||
codon-optimiz    1301  AGCACGTGATCAAGGGCAGACCCGTGAGCAGCAGCTTCGACCCCATCAAG  1350

wt_huMPV-F       1351  TTTCCTGAAGATCAATTCAATGTTGCACTTGACCAAGTTTTTGAGAGCAT  1400
                       ||.||.||.||.||.|||||.||.||.||.|||||.||.||.||||||||
codon-optimiz    1351  TTCCCCGAGGACCAGTTCAACGTGGCCCTGGACCAGGTGTTCGAGAGCAT  1400

wt_huMPV-F       1401  TGAAAACAGCCAGGCCTTGGTAGATCAATCAAACAGAATCCTAAGCAGTG  1450
                       .||.||||||||||||.||||.||.||....|||||||||||.|||||.|
```

FIG. 19B

```
codon-optimiz    1401 CGAGAACAGCCAGGCCCTGGTGGACCAGAGCAACAGAATCCTGAGCAGCG   1450

wt_huMPV-F       1451 CAGAGAAAGGGAATACTGGCTTCATCATTGTAATAATTCTAATTGCTGTC   1500
                      |.|||||.||.||.||.||.|||||||||||.||.||.||.||.||.||.
codon-optimiz    1451 CCGAGAAGGGCAACACCGGCTTCATCATCGTGATCATCCTGATCGCCGTG   1500

wt_huMPV-F       1501 CTTGGCTCTAGCATGATCCTAGTGAGCATCTTCATTATAATCAAGAAAAC   1550
                      ||.|||...||||||||||.||||||||||||||.||.||||||||.||
codon-optimiz    1501 CTGGGCAGCAGCATGATCCTGGTGAGCATCTTCATCATCATCAAGAAGAC   1550

wt_huMPV-F       1551 AAAGAAACCAACGGGAGCACCTCCAGAGCTGAGTGGTGTCACAAACAATG   1600
                      .|||||.||.||.||.||.||.||.||.|||||||||.||.||.||.|||||.|
codon-optimiz    1551 CAAGAAGCCCACCGGCGCCCCCCCCGAGCTGAGCGGCGTGACCAACAACG   1600

wt_huMPV-F       1601 GCTTCATACCACACAGTTAG   1620
                      |||||||.||.|||||.|..
codon-optimiz    1601 GCTTCATCCCCCACAGCTGA   1620
```

FIG. 19C

SEQUENCE LISTING

```
<160> NUMBER OF SEQ ID NOS: 63

<210> SEQ ID NO 1
<211> LENGTH: 1725
<212> TYPE: DNA
<213> ORGANISM: Human respiratory syncytial virus

<400> SEQUENCE: 1

atggagttgc taatcctcaa agcaaatgca attaccacaa tcctcactgc agtcacattt     60

tgttttgctt ctggtcaaaa catcactgaa gaattttatc aatcaacatg cagtgcagtt    120

agcaaaggct atcttagtgc tctgagaact ggttggtata ccagtgttat aactatagaa    180

ttaagtaata tcaaggaaaa taagtgtaat ggaacagatg ctaaggtaaa attgataaaa    240

caagaattag ataaatataa aaatgctgta acagaattgc agttgctcat gcaaagcaca    300

ccagcaacaa acaatcgagc cagaagagaa ctaccaaggt ttatgaatta tacactcaac    360

aatgccaaaa aaaccaatgt aacattaagc aagaaaagga aaagaagatt tcttggtttt    420

ttgttaggtg ttggatctgc aatcgccagt ggcgttgctg tatctaaggt cctgcaccta    480

gaaggggaag tgaacaagat caaaagtgct ctactatcca caaacaaggc tgtagtcagc    540

ttatcaaatg gagttagtgt cttaaccagc aaagtgttag acctcaaaaa ctatatagat    600

aaacaattgt tacctattgt gaacaagcaa agctgcagca tatcaaatat agcaactgtg    660

atagagttcc aacaaaagaa caacagacta ctagagatta ccagggaatt tagtgttaat    720

gcaggtgtaa ctacacctgt aagcacttac atgttaacta atagtgaatt attgtcatta    780

atcaatgata tgcctataac aaatgatcag aaaaagttaa tgtccaacaa tgttcaaata    840

gttagacagc aaagttactc tatcatgtcc ataataaaag aggaagtctt agcatatgta    900

gtacaattac cactatatgg tgttatagat acaccctgtt ggaaactaca cacatcccct    960

ctatgtacaa ccaacacaaa agaagggtcc aacatctgtt taacaagaac tgacagagga   1020
```

tggtactgtg acaatgcagg atcagtatct ttcttcccac aagctgaaac atgtaaagtt 1080
caatcaaatc gagtattttg tgacacaatg aacagtttaa cattaccaag tgaagtaaat 1140
ctctgcaatg ttgacatatt caaccccaaa tatgattgta aaattatgac ttcaaaaaca 1200
gatgtaagca gctccgttat cacatctcta ggagccattg tgtcatgcta tggcaaaact 1260
aaatgtacag catccaataa aaatcgtgga atcataaaga cattttctaa cgggtgcgat 1320
tatgtatcaa ataaaggggt ggacactgtg tctgtaggta acacattata ttatgtaaat 1380
aagcaagaag gtaaaagtct ctatgtaaaa ggtgaaccaa taataaattt ctatgaccca 1440
ttagtattcc cctctgatga atttgatgca tcaatatctc aagtcaacga gaagattaac 1500
cagagcctag catttattcg taaatccgat gaattattac ataatgtaaa tgctggtaaa 1560
tccaccataa atatcatgat aactactata attatagtga ttatagtaat attgttatca 1620
ttaattgctg ttggactgct cttatactgt aaggccagaa gcacaccagt cacactaagc 1680
aaagatcaac tgagtggtat aaataatatt gcatttagta actaa 1725

<210> SEQ ID NO 2
<211> LENGTH: 1725
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 2
atggagctgc tgatcctgaa ggccaacgcc atcaccacca tcctgaccgc cgtgaccttc 60
tgcttcgcca gcggccagaa catcaccgag gagttctacc agagcacctg cagcgccgtg 120
agcaagggct acctgagcgc cctgcgcacc ggctggtaca ccagcgtgat caccatcgag 180
ctgagcaaca tcaaggagaa caagtgcaac ggcaccgacg ccaaggtgaa gctgatcaag 240
caggagctgg acaagtacaa gaacgccgtg accgagctgc agctgctgat gcagagcacc 300
cccgccacca acaaccgcgc ccgccgcgag ctgccccgct tcatgaacta caccctgaac 360
aacgccaaga agaccaacgt gaccctgagc aagaagcgca agcgccgctt cctgggcttc 420
ctgctgggcg tgggcagcgc catcgccagc ggcgtggccg tgagcaaggt gctgcacctg 480
gagggcgagg tgaacaagat caagagcgcc ctgctgagca ccaacaaggc cgtggtgagc 540
ctgagcaacg gcgtgagcgt gctgaccagc aaggtgctgg acctgaagaa ctacatcgac 600
aagcagctgc tgcccatcgt gaacaagcag agctgcagca tcagcaacat cgccaccgtg 660
atcgagttcc agcagaagaa caaccgcctg ctggagatca cccgcgagtt cagcgtgaac 720
gccggcgtga ccacccccgt gagcacctac atgctgacca acagcgagct gctgagcctg 780
atcaacgaca tgcccatcac caacgaccag aagaagctga tgagcaacaa cgtgcagatc 840
gtgcgccagc agagctacag catcatgagc atcatcaagg aggaggtgct ggcctacgtg 900
gtgcagctgc ccctgtacgg cgtgatcgac accccctgct ggaagctgca caccagcccc 960
ctgtgcacca ccaacaccaa ggagggcagc aacatctgcc tgacccgcac cgacaggggc 1020
tggtactgcg acaacgccgg cagcgtgagc ttcttccccc aggccgagac ctgcaaggtg 1080
cagagcaacc gcgtgttctg cgacaccatg aacagcctga ccctgcccag cgaggtgaac 1140
ctgtgcaacg tggacatctt caaccccaag tacgactgca agatcatgac cagcaagacc 1200
gacgtgagca gcagcgtgat caccagcctg ggcgccatcg tgagctgcta cggcaagacc 1260
aagtgcaccg ccagcaacaa gaacaggggc atcatcaaga ccttcagcaa cggctgcgac 1320

```
tacgtgagca acaagggcgt ggacaccgtg agcgtgggca acaccctgta ctacgtgaac   1380

aagcaggagg gcaagagcct gtacgtgaag ggcgagccca tcatcaactt ctacgacccc   1440

ctggtgttcc ccagcgacga gttcgacgcc agcatcagcc aggtgaacga gaagatcaac   1500

cagagcctgg ccttcatccg caagagcgac gagctgctgc acaacgtgaa cgccggcaag   1560

agcaccatca acatcatgat caccaccatc atcatcgtga tcatcgtgat cctgctgagc   1620

ctgatcgccg tgggcctgct gctgtactgc aaggcccgca gcacccccgt gaccctgagc   1680

aaggaccagc tgagcggcat caacaacatc gccttcagca actaa                    1725
```

<210> SEQ ID NO 3
<211> LENGTH: 16950
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 3

```
accaaacaga gaatccgtga gttacgataa aaggcgaagg agcaattgaa gtcgcacggg     60

tagaaggtgt gaatctcgag tgcgagcccg aagcacaaac tcgagaaagc cttctgccaa    120

catgtcttcc gtatttgatg agtacgaaca gctcctcgcg gctcagactc gccccaatgg    180

agctcatgga gggggagaaa aagggagtac cttaaaagta gacgtcccgg tattcactct    240

taacagtgat gacccagaag atagatggag ctttgtggta ttctgcctcc ggattgctgt    300

tagcgaagat gccaacaaac cactcaggca aggtgctctc atatctcttt tatgctccca    360

ctcacaggta atgaggaacc atgttgccct tgcagggaaa cagaatgaag ccacattggc    420

cgtgcttgag attgatggct ttgccaacgg cacgccccag ttcaacaata ggagtggagt    480

gtctgaagag agagcacaga gatttgcgat gatagcagga tctctccctc gggcatgcag    540

caacggaacc ccgttcgtca cagccggggc cgaagatgat gcaccagaag acatcaccga    600

taccctggag aggatcctct ctatccaggc tcaagtatgg gtcacagtag caaaagccat    660

gactgcgtat gagactgcag atgagtcgga aacaaggcga atcaataagt atatgcagca    720

aggcagggtc caaaagaaat acatcctcta ccccgtatgc aggagcacaa tccaactcac    780

gatcagacag tctcttgcag tccgcatctt tttggttagc gagctcaaga gaggccgcaa    840

cacggcaggt ggtacctcta cttattataa cctggtaggg gacgtagact catacatcag    900

gaataccggg cttactgcat tcttcttgac actcaagtac ggaatcaaca ccaagacatc    960

agcccttgca cttagtagcc tctcaggcga catccagaag atgaagcagc tcatgcgttt   1020

gtatcggatg aaaggagata atgcgccgta catgacatta cttggtgata gtgaccagat   1080

gagctttgcg cctgccgagt atgcacaact ttactccttt gccatgggta tggcatcagt   1140

cctagataaa ggtactggga aataccaatt tgccagggac tttatgagca catcattctg   1200

gagacttgga gtagagtacg ctcaggctca gggaagtagc attaacgagg atatggctgc   1260

cgagctaaag ctaaccccag cagcaaggag gggcctggca gctgctgccc aacgggtctc   1320

cgaggagacc agcagcatag acatgcctac tcaacaagtc ggagtcctca ctgggcttag   1380

cgaggggggg tcccaagctc tacaaggcgg atcgaataga tcgcaagggc aaccagaagc   1440

cggggatggg gagacccaat tcctggatct gatgagagcg gtagcaaata gcatgaggga   1500

ggcgccaaac tctgcacagg gcactcccca atcggggcct cccccaactc ctgggccatc   1560

ccaagataac gacaccgact gggggtattg atggacaaaa cccagcctgc ttccacaaaa   1620
```

-continued

```
acatcccaat gccctcaccc gtagtcgacc cctcgatttg cggctctata tgaccacacc   1680
ctcaaacaaa catccccctc tttcctccct cccccctgctg tacaactacg tacgccctag   1740
ataccacagg cacaatgcgg ctcactaaca atcaaaacag agccgaggga attagaaaaa   1800
agtacgggta gaagagggat attcagagat cagggcaagt ctcccgagtc tctgctctct   1860
cctctacctg atagaccagg acaaacatgg ccacctttac agatgcagag atcgacgagc   1920
tatttgagac aagtggaact gtcattgaca acataattac agcccagggt aaaccagcag   1980
agactgttgg aaggagtgca atcccacaag gcaagaccaa ggtgctgagc gcagcatggg   2040
agaagcatgg gagcatccag ccaccggcca gtcaagacaa ccccgatcga caggacagat   2100
ctgacaaaca accatccaca cccgagcaaa cgaccccgca tgacagcccg ccggccacat   2160
ccgccgacca gccccccacc caggccacag acgaagccgt cgacacacag ctcaggaccg   2220
gagcaagcaa ctctctgctg ttgatgcttg acaagctcag caataaatcg tccaatgcta   2280
aaaagggccc atggtcgagc cccaagaggg ggaatcacca acgtccgact caacagcagg   2340
ggagtcaacc cagtcgcgga aacagtcagg aaagaccgca gaaccaagtc aaggccgccc   2400
ctggaaacca gggcacagac gtgaacacag catatcatgg acaatgggag gagtcacaac   2460
tatcagctgg tgcaacccct catgctctcc gatcaaggca gagccaagac aataccttg    2520
tatctgcgga tcatgtccag ccacctgtag actttgtgca agcgatgatg tctatgatgg   2580
aggcgatatc acagagagta agtaaggttg actatcagct agatcttgtc ttgaaacaga   2640
catcctccat ccctatgatg cggtccgaaa tccaacagct gaaaacatct gttgcagtca   2700
tggaagccaa cttgggaatg atgaagattc tggatcccgg ttgtgccaac atttcatctc   2760
tgagtgatct acgggcagtt gcccgatctc acccggtttt agtttcaggc cctggagacc   2820
cctctcccta tgtgacacaa ggaggcgaaa tggcacttaa taaactttcg caaccagtgc   2880
cacatccatc tgaattgatt aaacccgcca ctgcatgcgg gcctgatata ggagtggaaa   2940
aggacactgt ccgtgcattg atcatgtcac gcccaatgca cccgagttct tcagccaagc   3000
tcctaagcaa gttagatgca gccgggtcga tcgaggaaat caggaaaatc aagcgccttg   3060
ctctaaatgg ctaattacta ctgccacacg tagcgggtcc ctgtccactc ggcatcacac   3120
ggaatctgca ccgagttccc ccccgcggtt agaaaaaaata cgggtagaac cgccaccatg   3180
gagctgctga tcctgaaggc caacgccatc accaccatcc tgaccgccgt gaccttctgc   3240
ttcgccagcg gccagaacat caccgaggag ttctaccaga gcacctgcag cgccgtgagc   3300
aagggctacc tgagcgccct gcgcaccggc tggtacacca gcgtgatcac catcgagctg   3360
agcaacatca aggagaacaa gtgcaacggc accgacgcca aggtgaagct gatcaagcag   3420
gagctggaca agtacaagaa cgccgtgacc gagctgcagc tgctgatgca gagcaccccc   3480
gccaccaaca accgcgcccg ccgcgagctg ccccgcttca tgaactacac cctgaacaac   3540
gccaagaaga ccaacgtgac cctgagcaag aagcgcaagc gccgcttcct gggcttcctg   3600
ctgggcgtgg gcagcgccat cgccagcggc gtggccgtga gcaaggtgct gcacctggag   3660
ggcgaggtga acaagatcaa gagcgccctg ctgagcacca acaaggccgt ggtgagcctg   3720
agcaacggcg tgagcgtgct gaccagcaag gtgctggacc tgaagaacta catcgacaag   3780
cagctgctgc ccatcgtgaa caagcagagc tgcagcatca gcaacatcgc caccgtgatc   3840
gagttccagc agaagaacaa ccgcctgctg gagatcaccc gcgagttcag cgtgaacgcc   3900
ggcgtgacca cccccgtgag cacctacatg ctgaccaaca gcgagctgct gagcctgatc   3960
```

-continued

```
aacgacatgc ccatcaccaa cgaccagaag aagctgatga gcaacaacgt gcagatcgtg   4020
cgccagcaga gctacagcat catgagcatc atcaaggagg aggtgctggc ctacgtggtg   4080
cagctgcccc tgtacggcgt gatcgacacc ccctgctgga agctgcacac cagcccccctg   4140
tgcaccacca acaccaagga gggcagcaac atctgcctga cccgcaccga caggggctgg   4200
tactgcgaca acgccggcag cgtgagcttc ttcccccagg ccgagacctg caaggtgcag   4260
agcaaccgcg tgttctgcga caccatgaac agcctgaccc tgcccagcga ggtgaacctg   4320
tgcaacgtgg acatcttcaa ccccaagtac gactgcaaga tcatgaccag caagaccgac   4380
gtgagcagca gcgtgatcac cagcctgggc gccatcgtga gctgctacgg caagaccaag   4440
tgcaccgcca gcaacaagaa caggggcatc atcaagacct tcagcaacgg ctgcgactac   4500
gtgagcaaca agggcgtgga caccgtgagc gtgggcaaca ccctgtacta cgtgaacaag   4560
caggagggca agagcctgta cgtgaagggc gagcccatca tcaacttcta cgacccccctg   4620
gtgttcccca gcgacgagtt cgacgccagc atcagccagg tgaacgagaa gatcaaccag   4680
agcctggcct tcatccgcaa gagcgacgag ctgctgcaca acgtgaacgc cggcaagagc   4740
accatcaaca tcatgatcac caccatcatc atcgtgatca tcgtgatcct gctgagcctg   4800
atcgccgtgg gcctgctgct gtactgcaag gcccgcagca cccccgtgac cctgagcaag   4860
gaccagctga gcggcatcaa caacatcgcc ttcagcaact aaccccccgc ggacccaagg   4920
tccaactctc caagcggcaa tcctctctcg cttcctcagc cccactgaat gatcgcgtaa   4980
ccgtaattaa tctagctaca tttaagatta agaaaaaata cgggtagaat tggagtgccc   5040
caattgtgcc aagatggact catctaggac aattgggctg tactttgatt ctgcccattc   5100
ttctagcaac ctgttagcat ttccgatcgt cctacaagac acaggagatg ggaagaagca   5160
aatcgccccg caatatagga tccagcgcct tgacttgtgg actgatagta aggaggactc   5220
agtattcatc accacctatg gattcatctt tcaagttggg aatgaagaag ccaccgtcgg   5280
catgatcgat gataaaccca agcgcgagtt actttccgct gcgatgctct gcctaggaag   5340
cgtcccaaat accggagacc ttattgagct ggcaagggcc tgtctcacta tgatagtcac   5400
atgcaagaag agtgcaacta atactgagag aatggttttc tcagtagtgc aggcacccca   5460
agtgctgcaa agctgtaggg ttgtggcaaa caaatactca tcagtgaatg cagtcaagca   5520
cgtgaaagcg ccagagaaga ttcccgggag tggaaccccta gaatacaagg tgaactttgt   5580
ctccttgact gtggtaccga agagggatgt ctacaagatc ccagctgcag tattgaaggt   5640
ttctggctcg agtctgtaca atcttgcgct caatgtcact attaatgtgg aggtagaccc   5700
gaggagtcct ttggttaaat ctctgtctaa gtctgacagc ggatactatg ctaacctctt   5760
cttgcatatt ggacttatga ccactgtaga taggaagggg aagaaagtga catttgacaa   5820
gctggaaaag aaaataagga gccttgatct atctgtcggg ctcagtgatg tgctcgggcc   5880
ttccgtgttg gtaaaagcaa gaggtgcacg gactaagctt ttggcacctt tcttctctag   5940
cagtgggaca gcctgctatc ccatagcaaa tgcttctcct caggtggcca agatactctg   6000
gagtcaaacc gcgtgcctgc ggagcgttaa aatcattatc caagcaggta cccaacgcgc   6060
tgtcgcagtg accgccgacc acgaggttac ctctactaag ctggagaagg ggcacaccct   6120
tgccaaatac aatcctttta agaaataagc tgcgtctctg agattgcgct ccgcccactc   6180
acccagatca tcatgacaca aaaaactaat ctgtcttgat tatttacagt tagtttacct   6240
gtctatcaag ttagaaaaaa cacgggtaga agattctgga tcccggttgg cgccctccag   6300
gtgcaagatg ggctccagac cttctaccaa gaacccagca cctatgatgc tgactatccg   6360
```

```
ggttgcgctg gtactgagtt gcatctgtcc ggcaaactcc attgatggca ggcctcttgc   6420
agctgcagga attgtggtta caggagacaa agccgtcaac atatacacct catcccagac   6480
aggatcaatc atagttaagc tcctcccgaa tctgcccaag gataaggagg catgtgcgaa   6540
agccccccttg gatgcataca acaggacatt gaccactttg ctcacccccc ttggtgactc   6600
tatccgtagg atacaagagt ctgtgactac atctggaggg gggagacagg ggcgccttat   6660
aggcgccatt attggcggtg tggctcttgg ggttgcaact gccgcacaaa taacagcggc   6720
cgcagctctg atacaagcca aacaaaatgc tgccaacatc ctccgactta aagagagcat   6780
tgccgcaacc aatgaggctg tgcatgaggt cactgacgga ttatcgcaac tagcagtggc   6840
agttgggaag atgcagcagt ttgttaatga ccaatttaat aaaacagctc aggaattaga   6900
ctgcatcaaa attgcacagc aagttggtgt agagctcaac ctgtacctaa ccgaattgac   6960
tacagtattc ggaccacaaa tcacttcacc tgctttaaac aagctgacta ttcaggcact   7020
ttacaatcta gctggtggaa atatggatta cttattgact aagttaggtg tagggaacaa   7080
tcaactcagc tcattaatcg gtagcggctt aatcaccggt aaccctattc tatacgactc   7140
acagactcaa ctcttgggta tacaggtaac tctaccttca gtcgggaacc taaataatat   7200
gcgtgccacc tacttggaaa ccttatccgt aagcacaacc aggggatttg cctcggcact   7260
tgtcccaaaa gtggtgacac aggtcggttc tgtgatagaa gaacttgaca cctcatactg   7320
tatagaaact gacttagatt tatattgtac aagaatagta acgttcccta tgtcccctgg   7380
tatttattcc tgcttgagcg gcaatacgtc ggcctgtatg tactcaaaga ccgaaggcgc   7440
acttactaca ccatacatga ctatcaaagg ttcagtcatc gccaactgca agatgacaac   7500
atgtagatgt gtaaaccccc cgggtatcat atcgcaaaac tatggagaag ccgtgtctct   7560
aatagataaa caatcatgca atgttttatc cttaggcggg ataactttaa ggctcagtgg   7620
ggaattcgat gtaacttatc agaagaatat ctcaatacaa gattctcaag taataataac   7680
aggcaatctt gatatctcaa ctgagcttgg gaatgtcaac aactcgatca gtaatgcttt   7740
gaataagtta gaggaaagca acagaaaact agacaaagtc aatgtcaaac tgactagcac   7800
atctgctctc attacctata tcgttttgac tatcatatct cttgtttttg gtatacttag   7860
cctgattcta gcatgctacc taatgtacaa gcaaaaggcg caacaaaaga ccttattatg   7920
gcttgggaat aatactctag atcagatgag agccactaca aaaatgtgaa cacagatgag   7980
gaacgaaggt ttccctaata gtaatttgtg tgaaagttct ggtagtctgt cagttcagag   8040
agttaagaaa aaactaccgg ttgtagatga ccaaaggacg atatacgggt agaacggtaa   8100
gagaggccgc ccctcaattg cgagccaggc ttcacaacct ccgttctacc gcttcaccga   8160
caacagtcct caatcatgga ccgcgccgtt agccaagttg cgttagagaa tgatgaaaga   8220
gaggcaaaaa atacatggcg cttgatattc cggattgcaa tcttattctt aacagtagtg   8280
accttggcta tatctgtagc ctccctttta tatagcatgg gggctagcac acctagcgat   8340
cttgtaggca taccgactag gatttccagg gcagaagaaa agattacatc tacacttggt   8400
tccaatcaag atgtagtaga taggatatat aagcaagtgg cccttgagtc tccgttggca   8460
ttgttaaata ctgagaccac aattatgaac gcaataacat ctctctctta tcagattaat   8520
ggagctgcaa acaacagtgg gtggggggca cctatccatg acccagatta tatagggggg   8580
ataggcaaag aactcattgt agatgatgct agtgatgtca catcattcta tccctctgca   8640
tttcaagaac atctgaattt tatcccggcg cctactacag gatcaggttg cactcgaata   8700
```

-continued

```
ccctcatttg acatgagtgc tacccattac tgctacaccc ataatgtaat attgtctgga   8760
tgcagagatc actcacattc atatcagtat ttagcacttg gtgtgctccg gacatctgca   8820
acagggaggg tattcttttc tactctgcgt tccatcaacc tggacgacac ccaaaatcgg   8880
aagtcttgca gtgtgagtgc aactcccctg ggttgtgata tgctgtgctc gaaagtcacg   8940
gagacagagg aagaagatta taactcagct gtccctacgc ggatggtaca tgggaggtta   9000
gggttcgacg gccagtacca cgaaaaggac ctagatgtca caacattatt cggggactgg   9060
gtggccaact acccaggagt agggggtgga tcttttattg acagccgcgt atggttctca   9120
gtctacggag ggttaaaacc caattcaccc agtgacactg tacaggaagg gaaatatgtg   9180
atatacaagc gatacaatga cacatgccca gatgagcaag actaccagat tcgaatggcc   9240
aagtcttcgt ataagcctgg acggtttggt gggaaacgca tacagcaggc tatcttatct   9300
atcaaggtgt caacatcctt aggcgaagac ccggtactga ctgtaccgcc caacacagtc   9360
acactcatgg gggccgaagg cagaattctc acagtaggga catctcattt cttgtatcaa   9420
cgagggtcat catacttctc tcccgcgtta ttatatccta tgacagtcag caacaaaaca   9480
gccactcttc atagtcctta tacattcaat gccttcactc ggccaggtag tatcccttgc   9540
caggcttcag caagatgccc caactcgtgt gttactggag tctatacaga tccatatccc   9600
ctaatcttct atagaaacca caccttgcga ggggtattcg ggacaatgct tgatggtgta   9660
caagcaagac ttaaccctgc gtctgcagta ttcgatagca catcccgcag tcgcattact   9720
cgagtgagtt caagcagtac caaagcagca tacacaacat caacttgttt taaagtggtc   9780
aagactaata agacctattg tctcagcatt gctgaaatat ctaatactct cttcggagaa   9840
ttcagaatcg tcccgttact agttgagatc ctcaaagatg acggggttag agaagccagg   9900
tctggctagt tgagtcaatt ataaaggagt tggaaagatg gcattgtatc acctatcttc   9960
tgcgacatca agaatcaaac cgaatgccgg cgcgtgctcg aattccatgt tgccagttga  10020
ccacaatcag ccagtgctca tgcgatcaga ttaagccttg tcaatagtct cttgattaag  10080
aaaaaatgta agtggcaatg agatacaagg caaaacagct catggttaac aatacgggta  10140
ggacatggcg agctccggtc ctgaaagggc agagcatcag attatcctac cagagtcaca  10200
cctgtcttca ccattggtca agcacaaact actctattac tggaaattaa ctgggctacc  10260
gcttcctgat gaatgtgact tcgaccacct cattctcagc cgacaatgga aaaaaatact  10320
tgaatcggcc tctcctgata ctgagagaat gataaaactc ggaagggcag tacaccaaac  10380
tcttaaccac aattccagaa taaccggagt gctccaccccc aggtgtttag aagaactggc  10440
taatattgag gtcccagatt caaccaacaa atttcggaag attgagaaga agatccaaat  10500
tcacaacacg agatatggag aactgttcac aaggctgtgt acgcatatag agaagaaact  10560
gctggggtca tcttggtcta acaatgtccc ccggtcagag gagttcagca gcattcgtac  10620
ggatccggca ttctggtttc actcaaaatg gtccacagcc aagtttgcat ggctccatat  10680
aaaacagatc cagaggcatc tgatggtggc agctaggaca aggtctgcgg ccaacaaatt  10740
ggtgatgcta acccataagg taggccaagt ctttgtcact cctgaacttg tcgttgtgac  10800
gcatacgaat gagaacaagt tcacatgtct tacccaggaa cttgtattga tgtatgcaga  10860
tatgatggag ggcagagata tggtcaacat aatatcaacc acggcggtgc atctcagaag  10920
cttatcagag aaaattgatg acattttgcg gttaatagac gctctggcaa aagacttggg  10980
taatcaagtc tacgatgttg tatcactaat ggagggattt gcatacggag ctgtccagct  11040
actcgagccg tcaggtacat ttgcaggaga tttcttcgca ttcaacctgc aggagcttaa  11100
```

agacattcta attggcctcc tccccaatga tatagcagaa tccgtgactc atgcaatcgc 11160
tactgtattc tctggtttag aacagaatca agcagctgag atgttgtgtc tgttgcgtct 11220
gtggggtcac ccactgcttg agtcccgtat tgcagcaaag gcagtcagga gccaaatgtg 11280
cgcaccgaaa atggtagact ttgatatgat ccttcaggta ctgtctttct tcaagggaac 11340
aatcatcaac gggtacagaa agaagaatgc aggtgtgtgg ccgcgagtca aagtggatac 11400
aatatatggg aaggtcattg ggcaactaca tgcagattca gcagagattt cacacgatat 11460
catgttgaga gagtataaga gtttatctgc acttgaattt gagccatgta tagaatatga 11520
ccctgtcacc aacctgagca tgttcctaaa agacaaggca atcgcacacc ccaacgataa 11580
ttggcttgcc tcgtttaggc ggaaccttct ctccgaagac cagaagaaac atgtaaaaga 11640
agcaacttcg actaatcgcc tcttgataga gtttttagag tcaaatgatt ttgatccata 11700
taaagagatg gaatatctga cgacccttga gtaccttaga gatgacaatg tggcagtatc 11760
atactcgctc aaggagaagg aagtgaaagt taatggacgg atcttcgcta agctgacaaa 11820
gaagttaagg aactgtcagg tgatggcgga agggatccta gccgatcaga ttgcaccttt 11880
ctttcaggga aatggagtca ttcaggatag catatccttg accaagagta tgctagcgat 11940
gagtcaactg tcttttaaca gcaataagaa acgtatcact gactgtaaag aaagagtatc 12000
ttcaaaccgc aatcatgatc cgaaaagcaa gaaccgtcgg agagttgcaa ccttcataac 12060
aactgacctg caaaagtact gtcttaattg gagatatcag acaatcaaat tgttcgctca 12120
tgccatcaat cagttgatgg gcctacctca cttcttcgaa tggattcacc taagactgat 12180
ggacactacg atgttcgtag gagacccttt caatcctcca agtgacccta ctgactgtga 12240
cctctcaaga gtccctaatg atgacatata tattgtcagt gccagagggg gtatcgaagg 12300
attatgccag aagctatgga caatgatctc aattgctgca atccaacttg ctgcagctag 12360
atcgcattgt cgtgttgcct gtatggtaca gggtgataat caagtaatag cagtaacgag 12420
agaggtaaga tcagacgact ctccggagat ggtgttgaca cagttgcatc aagccagtga 12480
taatttcttc aaggaattaa ttcatgtcaa tcatttgatt ggccataatt tgaaggatcg 12540
tgaaaccatc aggtcagaca cattcttcat atacagcaaa cgaatcttca aagatggagc 12600
aatcctcagt caagtcctca aaaattcatc taaattagtg ctagtgtcag gtgatctcag 12660
tgaaaacacc gtaatgtcct gtgccaacat tgcctctact gtagcacggc tatgcgagaa 12720
cgggcttccc aaagacttct gttactattt aaactatata atgagttgtg tgcagacata 12780
ctttgactct gagttctcca tcaccaacaa ttcgcacccc gatcttaatc agtcgtggat 12840
tgaggacatc tcttttgtgc actcatatgt tctgactcct gcccaattag gggactgag 12900
taaccttcaa tactcaaggc tctacactag aaatatcggt gacccgggga ctactgcttt 12960
tgcagagatc aagcgactag aagcagtggg attactgagt cctaacatta tgactaatat 13020
cttaactagg ccgcctggga atggagattg ggccagtctg tgcaacgacc catactcttt 13080
caattttgag actgttgcaa gcccaaatat tgttcttaag aaacatacgc aaagagtcct 13140
atttgaaact tgttcaaatc ccttattgtc tggagtgcac acagaggata atgaggcaga 13200
agagaaggca ttggctgaat tcttgcttaa tcaagaggtg attcatcccc gcgttgcgca 13260
tgccatcatg gaggcaagct ctgtaggtag gagaaagcaa attcaagggc ttgttgacac 13320
aacaaacacc gtaattaaga ttgcgcttac taggaggcca ttaggcatca agaggctgat 13380
gcggatagtc aattattcta gcatgcatgc aatgctgttt agagacgatg tttttcctc 13440

```
cagtagatcc aaccacccct tagtctcttc taatatgtgt tctctgacac tggcagacta  13500
tgcacggaat agaagctggt cacctttgac gggaggcagg aaaatactgg gtgtatctaa  13560
tcctgatacg atagaactcg tagagggtga gattcttagt gtaagcggag ggtgtacaag  13620
atgtgacagc ggagatgaac aatttacttg gttccatctt ccaagcaata tagaattgac  13680
cgatgacacc agcaagaatc ctccgatgag ggtaccatat ctcgggtcaa agacacagga  13740
gaggagagct gcctcacttg caaaaatagc tcatatgtcg ccacatgtaa aggctgccct  13800
aagggcatca tccgtgttga tctgggctta tggggataat gaagtaaatt ggactgctgc  13860
tcttacgatt gcaaaatctc ggtgtaatgt aaacttagag tatcttcggt tactgtcccc  13920
tttacccacg gctgggaatc ttcaacatag actagatgat ggtataactc agatgacatt  13980
cacccctgca tctctctaca gggtgtcacc ttacattcac atatccaatg attctcaaag  14040
gctgttcact gaagaaggag tcaaagaggg gaatgtggtt taccaacaga tcatgctctt  14100
gggtttatct ctaatcgaat cgatctttcc aatgacaaca accaggacat atgatgagat  14160
cacactgcac ctacatagta aatttagttg ctgtatcaga gaagcacctg ttgcggttcc  14220
tttcgagcta cttggggtgg taccggaact gaggacagtg acctcaaata agtttatgta  14280
tgatcctagc cctgtatcgg agggagactt tgcgagactt gacttagcta tcttcaagag  14340
ttatgagctt aatctggagt catatcccac gatagagcta atgaacattc tttcaatatc  14400
cagcgggaag ttgattggcc agtctgtggt ttcttatgat gaagatacct ccataaagaa  14460
tgacgccata atagtgtatg acaatacccg aaattggatc agtgaagctc agaattcaga  14520
tgtggtccgc ctatttgaat atgcagcact tgaagtgctc ctcgactgtt cttaccaact  14580
ctattacctg agagtaagag gcctggacaa tattgtctta tatatgggtg atttatacaa  14640
gaatatgcca ggaattctac tttccaacat tgcagctaca atatctcatc ccgtcattca  14700
ttcaaggtta catgcagtgg gcctggtcaa ccatgacgga tcacaccaac ttgcagatac  14760
ggattttatc gaaatgtctg caaaactatt agtatcttgc acccgacgtg tgatctccgg  14820
cttatattca ggaaataagt atgatctgct gttcccatct gtcttagatg ataacctgaa  14880
tgagaagatg cttcagctga tatcccggtt atgctgtctg tacacggtac tctttgctac  14940
aacaagagaa atcccgaaaa taagaggctt aactgcagaa gagaaatgtt caatactcac  15000
tgagtattta ctgtcggatg ctgtgaaacc attacttagc cccgatcaag tgagctctat  15060
catgtctcct aacataatta cattcccagc taatctgtac tacatgtctc ggaagagcct  15120
caatttgatc agggaaaggg aggacaggga tactatcctg gcgttgttgt tcccccaaga  15180
gccattatta gagttccctt ctgtgcaaga tattggtgct cgagtgaaag atccattcac  15240
ccgacaacct gcggcatttt tgcaagagtt agatttgagt gctccagcaa ggtatgacgc  15300
attcacactt agtcagattc atcctgaact cacatctcca aatccggagg aagactactt  15360
agtacgatac ttgttcagag ggatagggac tgcatcttcc tcttggtata aggcatctca  15420
tctcctttct gtacccgagg taagatgtgc aagacacggg aactccttat acttagctga  15480
agggagcgga gccatcatga gtcttctcga actgcatgta ccacatgaaa ctatctatta  15540
caatacgctc ttttcaaatg agatgaaccc cccgcaacga catttcgggc cgaccccaac  15600
tcagtttttg aattcggttg tttataggaa tctacaggcg gaggtaacat gcaaagatgg  15660
atttgtccaa gagttccgtc cattatggag agaaaataca gaggaaagcg acctgacctc  15720
agataaagta gtggggtata ttacatctgc agtgccctac agatctgtat cattgctgca  15780
ttgtgacatt gaaattcctc cagggtccaa tcaaagctta ctagatcaac tagctatcaa  15840
```

tttatctctg attgccatgc attctgtaag ggagggcggg gtagtaatca tcaaagtgtt 15900
gtatgcaatg ggatactact ttcatctact catgaacttg tttgctccgt gttccacaaa 15960
aggatatatt ctctctaatg gttatgcatg tcgaggagat atggagtgtt acctggtatt 16020
tgtcatgggt tacctgggcg ggcctacatt tgtacatgag gtggtgagga tggcgaaaac 16080
tctggtgcag cggcacggta cgcttttgtc taaatcagat gagatcacac tgaccaggtt 16140
attcacctca cagcggcagc gtgtgacaga catcctatcc agtcctttac caagattaat 16200
aaagtacttg aggaagaata ttgacactgc gctgattgaa gccgggggac agcccgtccg 16260
tccattctgt gcggagagtc tggtgagcac gctagcgaac ataactcaga taacccagat 16320
catcgctagt cacattgaca cagttatccg gtctgtgata tatatggaag ctgagggtga 16380
tctcgctgac acagtatttc tatttacccc ttacaatctc tctactgacg ggaaaaagag 16440
gacatcactt aaacagtgca cgagacagat cctagaggtt acaatactag gtcttagagt 16500
cgaaaatctc aataaaatag gcgatataat cagcctagtg cttaaaggca tgatctccat 16560
ggaggacctt atcccactaa ggacatactt gaagcatagt acctgcccta aatatttgaa 16620
ggctgtccta ggtattacca aactcaaaga aatgtttaca gacacttctg tactgtactt 16680
gactcgtgct caacaaaaat tctacatgaa aactataggc aatgcagtca aaggatatta 16740
cagtaactgt gactcttaac gaaaatcaca tattaatagg ctcctttttt ggccaattgt 16800
attcttgttg atttaatcat attatgttag aaaaaagttg aaccctgact ccttaggact 16860
cgaattcgaa ctcaaataaa tgtcttaaaa aaaggttgcg cacaattatt cttgagtgta 16920
gtctcgtcat tcaccaaatc tttgtttggt 16950

<210> SEQ ID NO 4
<211> LENGTH: 1740
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 4
atggagctgc tgatcctgaa ggccaacgcc atcaccacca tcctgaccgc cgtgaccttc 60
tgcttcgcca gcggccagaa catcaccgag gagttctacc agagcacctg cagcgccgtg 120
agcaagggct acctgagcgc cctgcgcacc ggctggtaca ccagcgtgat caccatcgag 180
ctgagcaaca tcaaggagaa caagtgcaac ggcaccgacg ccaaggtgaa gctgatcaag 240
caggagctgg acaagtacaa gaacgccgtg accgagctgc agctgctgat gcagagcacc 300
cccgccacca acaaccgcgc ccgccgcgag ctgccccgct tcatgaacta caccctgaac 360
aacgccaaga agaccaacgt gaccctgagc aagaagcgca agcgccgctt cctgggcttc 420
ctgctgggcg tgggcagcgc catcgccagc ggcgtggccg tgagcaaggt gctgcacctg 480
gagggcgagg tgaacaagat caagagcgcc ctgctgagca ccaacaaggc cgtggtgagc 540
ctgagcaacg gcgtgagcgt gctgaccagc aaggtgctgg acctgaagaa ctacatcgac 600
aagcagctgc tgcccatcgt gaacaagcag agctgcagca tcagcaacat cgccaccgtg 660
atcgagttcc agcagaagaa caaccgcctg ctggagatca cccgcgagtt cagcgtgaac 720
gccggcgtga ccacccccgt gagcacctac atgctgacca acagcgagct gctgagcctg 780
atcaacgaca tgcccatcac caacgaccag aagaagctga tgagcaacaa cgtgcagatc 840
gtgcgccagc agagctacag catcatgagc atcatcaagg aggaggtgct ggcctacgtg 900
gtgcagctgc ccctgtacgg cgtgatcgac accccctgct ggaagctgca caccagcccc 960
ctgtgcacca ccaacaccaa ggagggcagc aacatctgcc tgacccgcac cgacaggggc 1020
tggtactgcg acaacgccgg cagcgtgagc ttcttccccc aggccgagac ctgcaaggtg 1080
cagagcaacc gcgtgttctg cgacaccatg aacagcctga ccctgcccag cgaggtgaac 1140
ctgtgcaacg tggacatctt caaccccaag tacgactgca agatcatgac cagcaagacc 1200
gacgtgagca gcagcgtgat caccagcctg ggcgccatcg tgagctgcta cggcaagacc 1260
aagtgcaccg ccagcaacaa gaacaggggc atcatcaaga ccttcagcaa cggctgcgac 1320
tacgtgagca acaagggcgt ggacaccgtg agcgtgggca acaccctgta ctacgtgaac 1380
aagcaggagg gcaagagcct gtacgtgaag ggcgagccca tcatcaactt ctacgacccc 1440
ctggtgttcc ccagcgacga gttcgacgcc agcatcagcc aggtgaacga gaagatcaac 1500
cagagcctgg ccttcatccg caagagcgac gagctgctgc acaacgtgaa cgccggcaag 1560
agcaccatca acgttaacct cattacctat atcgttttga ctatcatatc tcttgttttt 1620
ggtatactta gcctgattct agcatgctac ctaatgtaca agcaaaaggc gcaacaaaag 1680
accttattat ggcttgggaa taataccta gatcagatga gagccactac aaaaatgtga 1740

<210> SEQ ID NO 5
<211> LENGTH: 17073
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 5
accaaacaga gaatccgtga gttacgataa aaggcgaagg agcaattgaa gtcgcacggg 60
tagaaggtgt gaatctcgag tgcgagcccg aagcacaaac tcgagaaagc cttctgccaa 120
catgtcttcc gtatttgatg agtacgaaca gctcctcgcg gctcagactc gccccaatgg 180
agctcatgga gggggagaaa aagggagtac cttaaaagta gacgtcccgg tattcactct 240
taacagtgat gacccagaag atagatggag ctttgtggta ttctgcctcc ggattgctgt 300
tagcgaagat gccaacaaac cactcaggca aggtgctctc atatctcttt tatgctccca 360
ctcacaggta atgaggaacc atgttgccct tgcagggaaa cagaatgaag ccacattggc 420
cgtgcttgag attgatggct ttgccaacgg cacgccccag ttcaacaata ggagtggagt 480
gtctgaagag agagcacaga gatttgcgat gatagcagga tctctccctc gggcatgcag 540
caacggaacc ccgttcgtca cagccggggc cgaagatgat gcaccagaag acatcaccga 600
taccctggag aggatcctct ctatccaggc tcaagtatgg gtcacagtag caaaagccat 660
gactgcgtat gagactgcag atgagtcgga aacaaggcga atcaataagt atatgcagca 720
aggcagggtc caaaagaaat acatcctcta ccccgtatgc aggagcacaa tccaactcac 780
gatcagacag tctcttgcag tccgcatctt tttggttagc gagctcaaga gaggccgcaa 840
cacggcaggt ggtacctcta cttattataa cctggtaggg gacgtagact catacatcag 900
gaataccggg cttactgcat tcttcttgac actcaagtac ggaatcaaca ccaagacatc 960
agcccttgca cttagtagcc tctcaggcga catccagaag atgaagcagc tcatgcgttt 1020
gtatcggatg aaaggagata atgcgccgta catgacatta cttggtgata gtgaccagat 1080
gagctttgcg cctgccgagt atgcacaact ttactccttt gccatgggta tggcatcagt 1140
cctagataaa ggtactggga aataccaatt tgccagggac tttatgagca catcattctg 1200

-continued

```
gagacttgga gtagagtacg ctcaggctca gggaagtagc attaacgagg atatggctgc   1260
cgagctaaag ctaaccccag cagcaaggag gggcctggca gctgctgccc aacgggtctc   1320
cgaggagacc agcagcatag acatgcctac tcaacaagtc ggagtcctca ctgggcttag   1380
cgaggggggg tcccaagctc tacaaggcgg atcgaataga tcgcaagggc aaccagaagc   1440
cggggatggg gagacccaat tcctggatct gatgagagcg gtagcaaata gcatgaggga   1500
ggcgccaaac tctgcacagg gcactcccca atcggggcct cccccaactc ctgggccatc   1560
ccaagataac gacaccgact gggggtattg atggacaaaa cccagcctgc ttccacaaaa   1620
acatcccaat gccctcaccc gtagtcgacc cctcgatttg cggctctata tgaccacacc   1680
ctcaaacaaa catccccctc tttcctccct ccccctgctg tacaactacg tacgccctag   1740
ataccacagg cacaatgcgg ctcactaaca atcaaaacag agccgaggga attagaaaaa   1800
agtacgggta gaagagggat attcagagat cagggcaagt ctcccgagtc tctgctctct   1860
cctctacctg atagaccagg acaaacatgg ccacctttac agatgcagag atcgacgagc   1920
tatttgagac aagtggaact gtcattgaca acataattac agcccagggt aaaccagcag   1980
agactgttgg aaggagtgca atcccacaag gcaagaccaa ggtgctgagc gcagcatggg   2040
agaagcatgg gagcatccag ccaccggcca gtcaagacaa ccccgatcga caggacagat   2100
ctgacaaaca accatccaca cccgagcaaa cgaccccgca tgacagcccg ccggccacat   2160
ccgccgacca gccccccacc caggccacag acgaagccgt cgacacacag ctcaggaccg   2220
gagcaagcaa ctctctgctg ttgatgcttg acaagctcag caataaatcg tccaatgcta   2280
aaaagggccc atggtcgagc cccaagaggg ggaatcacca acgtccgact caacagcagg   2340
ggagtcaacc cagtcgcgga aacagtcagg aaagaccgca gaaccaagtc aaggccgccc   2400
ctggaaacca gggcacagac gtgaacacag catatcatgg acaatgggag gagtcacaac   2460
tatcagctgg tgcaacccct catgctctcc gatcaaggca gagccaagac aatacccttg   2520
tatctgcgga tcatgtccag ccacctgtag actttgtgca agcgatgatg tctatgatgg   2580
aggcgatatc acagagagta agtaaggttg actatcagct agatcttgtc ttgaaacaga   2640
catcctccat ccctatgatg cggtccgaaa tccaacagct gaaaacatct gttgcagtca   2700
tggaagccaa cttgggaatg atgaagattc tggatcccgg ttgtgccaac atttcatctc   2760
tgagtgatct acgggcagtt gcccgatctc acccggtttt agtttcaggc cctggagacc   2820
cctctcccta tgtgacacaa ggaggcgaaa tggcacttaa taaactttcg caaccagtgc   2880
cacatccatc tgaattgatt aaacccgcca ctgcatgcgg gcctgatata ggagtggaaa   2940
aggacactgt ccgtgcattg atcatgtcac gcccaatgca cccgagttct tcagccaagc   3000
tcctaagcaa gttagatgca gccgggtcga tcgaggaaat caggaaaatc aagcgccttg   3060
ctctaaatgg ctaattacta ctgccacacg tagcgggtcc ctgtccactc ggcatcacac   3120
ggaatctgca ccgagttccc ccccgcggac ccaaggtcca actctccaag cggcaatcct   3180
ctctcgcttc ctcagcccca ctgaatgatc gcgtaaccgt aattaatcta gctacattta   3240
agattaagaa aaaatacggg tagaattgga gtgccccact agtgccacca tggagctgct   3300
gatcctgaag gccaacgcca tcaccaccat cctgaccgcc gtgaccttct gcttcgccag   3360
cggccagaac atcaccgagg agttctacca gagcacctgc agcgccgtga gcaagggcta   3420
cctgagcgcc ctgcgcaccg gctggtacac cagcgtgatc accatcgagc tgagcaacat   3480
caaggagaac aagtgcaacg gcaccgacgc caaggtgaag ctgatcaagc aggagctgga   3540
```

-continued

```
caagtacaag aacgccgtga ccgagctgca gctgctgatg cagagcaccc ccgccaccaa   3600
caaccgcgcc cgccgcgagc tgccccgctt catgaactac accctgaaca acgccaagaa   3660
gaccaacgtg accctgagca agaagcgcaa gcgccgcttc ctgggcttcc tgctgggcgt   3720
gggcagcgcc atcgccagcg gcgtggccgt gagcaaggtg ctgcacctgg agggcgaggt   3780
gaacaagatc aagagcgccc tgctgagcac caacaaggcc gtggtgagcc tgagcaacgg   3840
cgtgagcgtg ctgaccagca aggtgctgga cctgaagaac tacatcgaca agcagctgct   3900
gcccatcgtg aacaagcaga gctgcagcat cagcaacatc gccaccgtga tcgagttcca   3960
gcagaagaac aaccgcctgc tggagatcac ccgcgagttc agcgtgaacg ccggcgtgac   4020
cacccccgtg agcacctaca tgctgaccaa cagcgagctg ctgagcctga tcaacgacat   4080
gcccatcacc aacgaccaga agaagctgat gagcaacaac gtgcagatcg tgcgccagca   4140
gagctacagc atcatgagca tcatcaagga ggaggtgctg gcctacgtgg tgcagctgcc   4200
cctgtacggc gtgatcgaca cccccctgctg gaagctgcac accagccccc tgtgcaccac   4260
caacaccaag gagggcagca acatctgcct gacccgcacc gacaggggct ggtactgcga   4320
caacgccggc agcgtgagct tcttccccca ggccgagacc tgcaaggtgc agagcaaccg   4380
cgtgttctgc gacaccatga acagcctgac cctgcccagc gaggtgaacc tgtgcaacgt   4440
ggacatcttc aaccccaagt acgactgcaa gatcatgacc agcaagaccg acgtgagcag   4500
cagcgtgatc accagcctgg gcgccatcgt gagctgctac ggcaagacca agtgcaccgc   4560
cagcaacaag aacaggggca tcatcaagac cttcagcaac ggctgcgact acgtgagcaa   4620
caagggcgtg gacaccgtga gcgtgggcaa caccctgtac tacgtgaaca agcaggaggg   4680
caagagcctg tacgtgaagg gcgagcccat catcaacttc tacgaccccc tggtgttccc   4740
cagcgacgag ttcgacgcca gcatcagcca ggtgaacgag aagatcaacc agagcctggc   4800
cttcatccgc aagagcgacg agctgctgca caacgtgaac gccggcaaga gcaccatcaa   4860
cgttaacctc attacctata tcgttttgac tatcatatct cttgtttttg gtatacttag   4920
cctgattcta gcatgctacc taatgtacaa gcaaaaggcg caacaaaaga ccttattatg   4980
gcttgggaat aataccctag atcagatgag agccactaca aaaatgtgac cgcggaccca   5040
aggtccaact ctccaagcgg caatcctctc tcgcttcctc agccccactg aatgatcgcg   5100
taaccgtaat taatctagct acatttaaga ttaagaaaaa atacgggtag aattggagtg   5160
ccccaattgt gccaagatgg actcatctag gacaattggg ctgtactttg attctgccca   5220
ttcttctagc aacctgttag catttccgat cgtcctacaa gacacaggag atgggaagaa   5280
gcaaatcgcc ccgcaatata ggatccagcg ccttgacttg tggactgata gtaaggagga   5340
ctcagtattc atcaccacct atggattcat ctttcaagtt gggaatgaag aagccaccgt   5400
cggcatgatc gatgataaac ccaagcgcga gttactttcc gctgcgatgc tctgcctagg   5460
aagcgtccca aataccggag accttattga gctggcaagg gcctgtctca ctatgatagt   5520
cacatgcaag aagagtgcaa ctaatactga gagaatggtt ttctcagtag tgcaggcacc   5580
ccaagtgctg caaagctgta gggttgtggc aaacaaatac tcatcagtga atgcagtcaa   5640
gcacgtgaaa gcgccagaga agattcccgg gagtggaacc ctagaataca aggtgaactt   5700
tgtctccttg actgtggtac cgaagaggga tgtctacaag atcccagctg cagtattgaa   5760
ggtttctggc tcgagtctgt acaatcttgc gctcaatgtc actattaatg tggaggtaga   5820
cccgaggagt cctttggtta aatctctgtc taagtctgac agcggatact atgctaacct   5880
cttcttgcat attggactta tgaccactgt agataggaag gggaagaaag tgacatttga   5940
```

-continued caagctggaa aagaaaataa ggagccttga tctatctgtc gggctcagtg atgtgctcgg 6000
gccttccgtg ttggtaaaag caagaggtgc acggactaag cttttggcac ctttcttctc 6060
tagcagtggg acagcctgct atcccatagc aaatgcttct cctcaggtgg ccaagatact 6120
ctggagtcaa accgcgtgcc tgcggagcgt taaaatcatt atccaagcag gtacccaacg 6180
cgctgtcgca gtgaccgccg accacgaggt tacctctact aagctggaga aggggcacac 6240
ccttgccaaa tacaatcctt ttaagaaata agctgcgtct ctgagattgc gctccgccca 6300
ctcacccaga tcatcatgac acaaaaaact aatctgtctt gattatttac agttagttta 6360
cctgtctatc aagttagaaa aaacacgggt agaagattct ggatcccggt tggcgccctc 6420
caggtgcaag atgggctcca gaccttctac caagaaccca gcacctatga tgctgactat 6480
ccgggttgcg ctggtactga gttgcatctg tccggcaaac tccattgatg gcaggcctct 6540
tgcagctgca ggaattgtgg ttacaggaga caaagccgtc aacatataca cctcatccca 6600
gacaggatca atcatagtta agctcctccc gaatctgccc aaggataagg aggcatgtgc 6660
gaaagccccc ttggatgcat acaacaggac attgaccact ttgctcaccc cccttggtga 6720
ctctatccgt aggatacaag agtctgtgac tacatctgga ggggggagac aggggcgcct 6780
tataggcgcc attattggcg gtgtggctct tggggttgca actgccgcac aaataacagc 6840
ggccgcagct ctgatacaag ccaaacaaaa tgctgccaac atcctccgac ttaaagagag 6900
cattgccgca accaatgagg ctgtgcatga ggtcactgac ggattatcgc aactagcagt 6960
ggcagttggg aagatgcagc agtttgttaa tgaccaattt aataaaacag ctcaggaatt 7020
agactgcatc aaaattgcac agcaagttgg tgtagagctc aacctgtacc taaccgaatt 7080
gactacagta ttcggaccac aaatcacttc acctgcttta aacaagctga ctattcaggc 7140
actttacaat ctagctggtg gaaatatgga ttacttattg actaagttag gtgtagggaa 7200
caatcaactc agctcattaa tcggtagcgg cttaatcacc ggtaacccta ttctatacga 7260
ctcacagact caactcttgg gtatacaggt aactctacct tcagtcggga acctaaataa 7320
tatgcgtgcc acctacttgg aaaccttatc cgtaagcaca accaggggat ttgcctcggc 7380
acttgtccca aaagtggtga cacaggtcgg ttctgtgata gaagaacttg acacctcata 7440
ctgtatagaa actgacttag atttatattg tacaagaata gtaacgttcc ctatgtcccc 7500
tggtatttat tcctgcttga gcggcaatac gtcggcctgt atgtactcaa agaccgaagg 7560
cgcacttact acaccataca tgactatcaa aggttcagtc atcgccaact gcaagatgac 7620
aacatgtaga tgtgtaaacc ccccgggtat catatcgcaa aactatggag aagccgtgtc 7680
tctaatagat aaacaatcat gcaatgtttt atccttaggc gggataactt taaggctcag 7740
tggggaattc gatgtaactt atcagaagaa tatctcaata caagattctc aagtaataat 7800
aacaggcaat cttgatatct caactgagct tgggaatgtc aacaactcga tcagtaatgc 7860
tttgaataag ttagaggaaa gcaacagaaa actagacaaa gtcaatgtca aactgactag 7920
cacatctgct ctcattacct atatcgtttt gactatcata tctcttgttt ttggtatact 7980
tagcctgatt ctagcatgct acctaatgta caagcaaaag gcgcaacaaa agaccttatt 8040
atggcttggg aataatactc tagatcagat gagagccact acaaaaatgt gaacacagat 8100
gaggaacgaa ggtttcccta atagtaattt gtgtgaaagt tctggtagtc tgtcagttca 8160
gagagttaag aaaaaactac cggttgtaga tgaccaaagg acgatatacg ggtagaacgg 8220
taagagaggc cgcccctcaa ttgcgagcca ggcttcacaa cctccgttct accgcttcac 8280

-continued

```
cgacaacagt cctcaatcat ggaccgcgcc gttagccaag ttgcgttaga gaatgatgaa   8340
agagaggcaa aaaatacatg gcgcttgata ttccggattg caatcttatt cttaacagta   8400
gtgaccttgg ctatatctgt agcctccctt ttatatagca tgggggctag cacacctagc   8460
gatcttgtag gcataccgac taggatttcc agggcagaag aaaagattac atctacactt   8520
ggttccaatc aagatgtagt agataggata tataagcaag tggcccttga gtctccgttg   8580
gcattgttaa atactgagac cacaattatg aacgcaataa catctctctc ttatcagatt   8640
aatggagctg caaacaacag tgggtggggg gcacctatcc atgacccaga ttatataggg   8700
gggataggca aagaactcat tgtagatgat gctagtgatg tcacatcatt ctatccctct   8760
gcatttcaag aacatctgaa ttttatcccg gcgcctacta caggatcagg ttgcactcga   8820
ataccctcat ttgacatgag tgctacccat tactgctaca cccataatgt aatattgtct   8880
ggatgcagag atcactcaca ttcatatcag tatttagcac ttggtgtgct ccggacatct   8940
gcaacaggga gggtattctt ttctactctg cgttccatca acctggacga cacccaaaat   9000
cggaagtctt gcagtgtgag tgcaactccc ctgggttgtg atatgctgtg ctcgaaagtc   9060
acggagacag aggaagaaga ttataactca gctgtcccta cgcggatggt acatgggagg   9120
ttagggttcg acggccagta ccacgaaaag gacctagatg tcacaacatt attcggggac   9180
tgggtggcca actacccagg agtagggggt ggatctttta ttgacagccg cgtatggttc   9240
tcagtctacg gagggttaaa acccaattca cccagtgaca ctgtacagga agggaaatat   9300
gtgatataca agcgatacaa tgacacatgc ccagatgagc aagactacca gattcgaatg   9360
gccaagtctt cgtataagcc tggacggttt ggtgggaaac gcatacagca ggctatctta   9420
tctatcaagg tgtcaacatc cttaggcgaa gacccggtac tgactgtacc gcccaacaca   9480
gtcacactca tgggggccga aggcagaatt ctcacagtag ggacatctca tttcttgtat   9540
caacgagggt catcatactt ctctcccgcg ttattatatc ctatgacagt cagcaacaaa   9600
acagccactc ttcatagtcc ttatacattc aatgccttca ctcggccagg tagtatccct   9660
tgccaggctt cagcaagatg ccccaactcg tgtgttactg gagtctatac agatccatat   9720
cccctaatct tctatagaaa ccacaccttg cgaggggtat tcgggacaat gcttgatggt   9780
gtacaagcaa gacttaaccc tgcgtctgca gtattcgata gcacatcccg cagtcgcatt   9840
actcgagtga gttcaagcag taccaaagca gcatacacaa catcaacttg ttttaaagtg   9900
gtcaagacta ataagaccta ttgtctcagc attgctgaaa tatctaatac tctcttcgga   9960
gaattcagaa tcgtcccgtt actagttgag atcctcaaag atgacggggt tagagaagcc  10020
aggtctggct agttgagtca attataaagg agttggaaag atggcattgt atcacctatc  10080
ttctgcgaca tcaagaatca aaccgaatgc cggcgcgtgc tcgaattcca tgttgccagt  10140
tgaccacaat cagccagtgc tcatgcgatc agattaagcc ttgtcaatag tctcttgatt  10200
aagaaaaaat gtaagtggca atgagataca aggcaaaaca gctcatggtt aacaatacgg  10260
gtaggacatg gcgagctccg gtcctgaaag ggcagagcat cagattatcc taccagagtc  10320
acacctgtct tcaccattgg tcaagcacaa actactctat tactggaaat taactgggct  10380
accgcttcct gatgaatgtg acttcgacca cctcattctc agccgacaat ggaaaaaaat  10440
acttgaatcg gcctctcctg atactgagag aatgataaaa ctcggaaggg cagtacacca  10500
aactcttaac cacaattcca gaataaccgg agtgctccac cccaggtgtt tagaagaact  10560
ggctaatatt gaggtcccag attcaaccaa caaatttcgg aagattgaga agaagatcca  10620
aattcacaac acgagatatg gagaactgtt cacaaggctg tgtacgcata tagagaagaa  10680
```

```
actgctgggg tcatcttggt ctaacaatgt cccccggtca gaggagttca gcagcattcg  10740
tacggatccg gcattctggt ttcactcaaa atggtccaca gccaagtttg catggctcca  10800
tataaaacag atccagaggc atctgatggt ggcagctagg acaaggtctg cggccaacaa  10860
attggtgatg ctaacccata aggtaggcca agtctttgtc actcctgaac ttgtcgttgt  10920
gacgcatacg aatgagaaca agttcacatg tcttacccag gaacttgtat tgatgtatgc  10980
agatatgatg gagggcagag atatggtcaa cataaatatca accacggcgg tgcatctcag  11040
aagcttatca gagaaaattg atgacatttt gcggttaata gacgctctgg caaaagactt  11100
gggtaatcaa gtctacgatg ttgtatcact aatggaggga tttgcatacg gagctgtcca  11160
gctactcgag ccgtcaggta catttgcagg agatttcttc gcattcaacc tgcaggagct  11220
taaagacatt ctaattggcc tcctccccaa tgatatagca gaatccgtga ctcatgcaat  11280
cgctactgta ttctctggtt tagaacagaa tcaagcagct gagatgttgt gtctgttgcg  11340
tctgtggggt cacccactgc ttgagtcccg tattgcagca aaggcagtca ggagccaaat  11400
gtgcgcaccg aaaatggtag actttgatat gatccttcag gtactgtctt tcttcaaggg  11460
aacaatcatc aacgggtaca gaaagaagaa tgcaggtgtg tggccgcgag tcaaagtgga  11520
tacaatatat gggaaggtca ttgggcaact acatgcagat tcagcagaga tttcacacga  11580
tatcatgttg agagagtata agagtttatc tgcacttgaa tttgagccat gtatagaata  11640
tgaccctgtc accaacctga gcatgttcct aaaagacaag gcaatcgcac accccaacga  11700
taattggctt gcctcgttta ggcggaacct tctctccgaa gaccagaaga aacatgtaaa  11760
agaagcaact tcgactaatc gcctcttgat agagttttta gagtcaaatg attttgatcc  11820
atataaagag atggaatatc tgacgaccct tgagtacctt agagatgaca atgtggcagt  11880
atcatactcg ctcaaggaga aggaagtgaa agttaatgga cggatcttcg ctaagctgac  11940
aaagaagtta aggaactgtc aggtgatggc ggaagggatc ctagccgatc agattgcacc  12000
tttctttcag ggaaatggag tcattcagga tagcatatcc ttgaccaaga gtatgctagc  12060
gatgagtcaa ctgtctttta acagcaataa gaaacgtatc actgactgta aagaaagagt  12120
atcttcaaac cgcaatcatg atccgaaaag caagaaccgt cggagagttg caaccttcat  12180
aacaactgac ctgcaaaagt actgtcttaa ttggagatat cagacaatca aattgttcgc  12240
tcatgccatc aatcagttga tgggcctacc tcacttcttc gaatggattc acctaagact  12300
gatggacact acgatgttcg taggagaccc tttcaatcct ccaagtgacc ctactgactg  12360
tgacctctca agagtcccta atgatgacat atatattgtc agtgccagag gggtatcga  12420
aggattatgc cagaagctat ggacaatgat ctcaattgct gcaatccaac ttgctgcagc  12480
tagatcgcat tgtcgtgttg cctgtatggt acagggtgat aatcaagtaa tagcagtaac  12540
gagagaggta agatcagacg actctccgga gatggtgttg acacagttgc atcaagccag  12600
tgataatttc ttcaaggaat taattcatgt caatcatttg attggccata atttgaagga  12660
tcgtgaaacc atcaggtcag acacattctt catatacagc aaacgaatct tcaaagatgg  12720
agcaatcctc agtcaagtcc tcaaaaattc atctaaatta gtgctagtgt caggtgatct  12780
cagtgaaaac accgtaatgt cctgtgccaa cattgcctct actgtagcac ggctatgcga  12840
gaacgggctt cccaaagact tctgttacta tttaaactat ataatgagtt gtgtgcagac  12900
atactttgac tctgagttct ccatcaccaa caattcgcac cccgatctta atcagtcgtg  12960
gattgaggac atctcttttg tgcactcata tgttctgact cctgcccaat taggggggact  13020
```

-continued

```
gagtaacctt caatactcaa ggctctacac tagaaatatc ggtgacccgg ggactactgc  13080
ttttgcagag atcaagcgac tagaagcagt gggattactg agtcctaaca ttatgactaa  13140
tatcttaact aggccgcctg ggaatggaga ttgggccagt ctgtgcaacg acccatactc  13200
tttcaatttt gagactgttg caagcccaaa tattgttctt aagaaacata cgcaaagagt  13260
cctatttgaa acttgttcaa atcccttatt gtctggagtg cacacagagg ataatgaggc  13320
agaagagaag gcattggctg aattcttgct taatcaagag gtgattcatc cccgcgttgc  13380
gcatgccatc atggaggcaa gctctgtagg taggagaaag caaattcaag ggcttgttga  13440
cacaacaaac accgtaatta agattgcgct tactaggagg ccattaggca tcaagaggct  13500
gatgcggata gtcaattatt ctagcatgca tgcaatgctg tttagagacg atgtttttc  13560
ctccagtaga tccaaccacc ccttagtctc ttctaatatg tgttctctga cactggcaga  13620
ctatgcacgg aatagaagct ggtcaccttt gacgggaggc aggaaaatac tgggtgtatc  13680
taatcctgat acgatagaac tcgtagaggg tgagattctt agtgtaagcg gagggtgtac  13740
aagatgtgac agcggagatg aacaatttac ttggttccat cttccaagca atatagaatt  13800
gaccgatgac accagcaaga atcctccgat gagggtacca tatctcgggt caaagacaca  13860
ggagaggaga gctgcctcac ttgcaaaaat agctcatatg tcgccacatg taaaggctgc  13920
cctaagggca tcatccgtgt tgatctgggc ttatggggat aatgaagtaa attggactgc  13980
tgctcttacg attgcaaaat ctcggtgtaa tgtaaactta gagtatcttc ggttactgtc  14040
ccctttaccc acggctggga atcttcaaca tagactagat gatggtataa ctcagatgac  14100
attcacccct gcatctctct acagggtgtc accttacatt cacatatcca atgattctca  14160
aaggctgttc actgaagaag gagtcaaaga ggggaatgtg gtttaccaac agatcatgct  14220
cttgggttta tctctaatcg aatcgatctt tccaatgaca acaaccagga catatgatga  14280
gatcacactg cacctacata gtaaatttag ttgctgtatc agagaagcac ctgttgcggt  14340
tcctttcgag ctacttgggg tggtaccgga actgaggaca gtgacctcaa ataagtttat  14400
gtatgatcct agccctgtat cggagggaga ctttgcgaga cttgacttag ctatcttcaa  14460
gagttatgag cttaatctgg agtcatatcc cacgatagag ctaatgaaca ttctttcaat  14520
atccagcggg aagttgattg gccagtctgt ggtttcttat gatgaagata cctccataaa  14580
gaatgacgcc ataatagtgt atgacaatac ccgaaattgg atcagtgaag ctcagaattc  14640
agatgtggtc cgcctatttg aatatgcagc acttgaagtg ctcctcgact gttcttacca  14700
actctattac ctgagagtaa gaggcctgga caatattgtc ttatatatgg gtgatttata  14760
caagaatatg ccaggaattc tactttccaa cattgcagct acaatatctc atcccgtcat  14820
tcattcaagg ttacatgcag tgggcctggt caaccatgac ggatcacacc aacttgcaga  14880
tacggatttt atcgaaatgt ctgcaaaact attagtatct tgcacccgac gtgtgatctc  14940
cggcttatat tcaggaaata agtatgatct gctgttccca tctgtcttag atgataacct  15000
gaatgagaag atgcttcagc tgatatcccg gttatgctgt ctgtacacgg tactctttgc  15060
tacaacaaga gaaatcccga aaataagagg cttaactgca gaagagaaat gttcaatact  15120
cactgagtat ttactgtcgg atgctgtgaa accattactt agccccgatc aagtgagctc  15180
tatcatgtct cctaacataa ttacattccc agctaatctg tactacatgt ctcggaagag  15240
cctcaatttg atcagggaaa gggaggacag ggatactatc ctggcgttgt tgttccccca  15300
agagccatta ttagagttcc cttctgtgca agatattggt gctcgagtga aagatccatt  15360
cacccgacaa cctgcggcat ttttgcaaga gttagatttg agtgctccag caaggtatga  15420
```

```
cgcattcaca cttagtcaga ttcatcctga actcacatct ccaaatccgg aggaagacta  15480

cttagtacga tacttgttca gagggatagg gactgcatct tcctcttggt ataaggcatc  15540

tcatctcctt tctgtacccg aggtaagatg tgcaagacac gggaactcct tatacttagc  15600

tgaagggagc ggagccatca tgagtcttct cgaactgcat gtaccacatg aaactatcta  15660

ttacaatacg ctcttttcaa atgagatgaa ccccccgcaa cgacatttcg ggccgacccc  15720

aactcagttt ttgaattcgg ttgtttatag gaatctacag gcggaggtaa catgcaaaga  15780

tggatttgtc caagagttcc gtccattatg gagagaaaat acagaggaaa gcgacctgac  15840

ctcagataaa gtagtggggt atattacatc tgcagtgccc tacagatctg tatcattgct  15900

gcattgtgac attgaaattc ctccagggtc caatcaaagc ttactagatc aactagctat  15960

caatttatct ctgattgcca tgcattctgt aagggagggc ggggtagtaa tcatcaaagt  16020

gttgtatgca atgggatact actttcatct actcatgaac ttgtttgctc cgtgttccac  16080

aaaaggatat attctctcta atggttatgc atgtcgagga gatatggagt gttacctggt  16140

atttgtcatg ggttacctgg gcgggcctac atttgtacat gaggtggtga ggatggcgaa  16200

aactctggtg cagcggcacg gtacgctttt gtctaaatca gatgagatca cactgaccag  16260

gttattcacc tcacagcggc agcgtgtgac agacatccta tccagtcctt taccaagatt  16320

aataaagtac ttgaggaaga atattgacac tgcgctgatt gaagccgggg gacagcccgt  16380

ccgtccattc tgtgcggaga gtctggtgag cacgctagcg aacataactc agataaccca  16440

gatcatcgct agtcacattg acacagttat ccggtctgtg atatatatgg aagctgaggg  16500

tgatctcgct gacacagtat ttctatttac cccttacaat ctctctactg acgggaaaaa  16560

gaggacatca cttaaacagt gcacgagaca gatcctagag gttacaatac taggtcttag  16620

agtcgaaaat ctcaataaaa taggcgatat aatcagccta gtgcttaaag gcatgatctc  16680

catggaggac cttatcccac taaggacata cttgaagcat agtacctgcc ctaaatattt  16740

gaaggctgtc ctaggtatta ccaaactcaa agaaatgttt acagacactt ctgtactgta  16800

cttgactcgt gctcaacaaa aattctacat gaaaactata ggcaatgcag tcaaaggata  16860

ttacagtaac tgtgactctt aacgaaaatc acatattaat aggctccttt tttggccaat  16920

tgtattcttg ttgatttaat catattatgt tagaaaaaag ttgaaccctg actccttagg  16980

actcgaattc gaactcaaat aaatgtctta aaaaaaggtt gcgcacaatt attcttgagt  17040

gtagtctcgt cattcaccaa atctttgttt ggt                               17073
```

<210> SEQ ID NO 6
<211> LENGTH: 574
<212> TYPE: PRT
<213> ORGANISM: Human respiratory syncytial virus

<400> SEQUENCE: 6

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80
```

-continued

```
Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Ser Asn Ile Ala Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Val
    370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Gln Glu Gly
    450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495
```

```
Glu Lys Ile Asn Gln Ser Leu Ala Phe Ile Arg Lys Ser Asp Glu Leu
            500                 505                 510

Leu His Asn Val Asn Ala Gly Lys Ser Thr Ile Asn Ile Met Ile Thr
        515                 520                 525

Thr Ile Ile Ile Val Ile Ile Val Ile Leu Leu Ser Leu Ile Ala Val
    530                 535                 540

Gly Leu Leu Leu Tyr Cys Lys Ala Arg Ser Thr Pro Val Thr Leu Ser
545                 550                 555                 560

Lys Asp Gln Leu Ser Gly Ile Asn Asn Ile Ala Phe Ser Asn
                565                 570


<210> SEQ ID NO 7
<211> LENGTH: 579
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Ser Asn Ile Ala Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285
```

```
Met Ser Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Val
    370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Gln Glu Gly
    450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu His Asn Val Asn Ala Gly Lys Ser Thr Ile Asn Val Asn Leu Ile
        515                 520                 525

Thr Tyr Ile Val Leu Thr Ile Ile Ser Leu Val Phe Gly Ile Leu Ser
    530                 535                 540

Leu Ile Leu Ala Cys Tyr Leu Met Tyr Lys Gln Lys Ala Gln Gln Lys
545                 550                 555                 560

Thr Leu Leu Trp Leu Gly Asn Asn Thr Leu Asp Gln Met Arg Ala Thr
                565                 570                 575

Thr Lys Met


<210> SEQ ID NO 8
<211> LENGTH: 553
<212> TYPE: PRT
<213> ORGANISM: Newcastle disease virus

<400> SEQUENCE: 8

Met Gly Ser Arg Pro Ser Thr Lys Asn Pro Ala Pro Met Thr Leu Thr
1               5                   10                  15

Ile Arg Val Ala Leu Val Leu Ser Cys Ile Cys Pro Ala Asn Ser Ile
            20                  25                  30

Asp Gly Arg Pro Leu Ala Ala Ala Gly Ile Val Val Thr Gly Asp Lys
        35                  40                  45

Ala Val Asn Ile Tyr Thr Ser Ser Gln Thr Gly Ser Ile Ile Val Lys
    50                  55                  60

Leu Leu Pro Asn Leu Pro Lys Asp Lys Glu Ala Cys Ala Lys Ala Pro
65                  70                  75                  80
```

-continued

```
Leu Asp Ala Tyr Asn Arg Thr Leu Thr Thr Leu Leu Thr Pro Leu Gly
                85                  90                  95

Asp Ser Ile Arg Arg Ile Gln Glu Ser Val Thr Thr Ser Gly Gly Gly
            100                 105                 110

Arg Gln Gly Arg Leu Ile Gly Ala Ile Ile Gly Gly Val Ala Leu Gly
        115                 120                 125

Val Ala Thr Ala Ala Gln Ile Thr Ala Ala Ala Ala Leu Ile Gln Ala
    130                 135                 140

Lys Gln Asn Ala Ala Asn Ile Leu Arg Leu Lys Glu Ser Ile Ala Ala
145                 150                 155                 160

Thr Asn Glu Ala Val His Glu Val Thr Asp Gly Leu Ser Gln Leu Ala
                165                 170                 175

Val Ala Val Gly Lys Met Gln Gln Phe Val Asn Asp Gln Phe Asn Lys
            180                 185                 190

Thr Ala Gln Glu Leu Asp Cys Ile Lys Ile Ala Gln Gln Val Gly Val
        195                 200                 205

Glu Leu Asn Leu Tyr Leu Thr Glu Leu Thr Thr Val Phe Gly Pro Gln
    210                 215                 220

Ile Thr Ser Pro Ala Leu Asn Lys Leu Thr Ile Gln Ala Leu Tyr Asn
225                 230                 235                 240

Leu Ala Gly Gly Asn Met Asp Tyr Leu Leu Thr Lys Leu Gly Val Gly
                245                 250                 255

Asn Asn Gln Leu Ser Ser Leu Ile Gly Ser Gly Leu Ile Thr Gly Asn
            260                 265                 270

Pro Ile Leu Tyr Asp Ser Gln Thr Gln Leu Leu Gly Ile Gln Val Thr
        275                 280                 285

Leu Pro Ser Val Gly Asn Leu Asn Asn Met Arg Ala Thr Tyr Leu Glu
    290                 295                 300

Thr Leu Ser Val Ser Thr Thr Arg Gly Phe Ala Ser Ala Leu Val Pro
305                 310                 315                 320

Lys Val Val Thr Gln Val Gly Ser Val Ile Glu Glu Leu Asp Thr Ser
                325                 330                 335

Tyr Cys Ile Glu Thr Asp Leu Asp Leu Tyr Cys Thr Arg Ile Val Thr
            340                 345                 350

Phe Pro Met Ser Pro Gly Ile Tyr Ser Cys Leu Ser Gly Asn Thr Ser
        355                 360                 365

Ala Cys Met Tyr Ser Lys Thr Glu Gly Ala Leu Thr Thr Pro Tyr Met
    370                 375                 380

Thr Ile Lys Gly Ser Val Ile Ala Asn Cys Lys Met Thr Thr Cys Arg
385                 390                 395                 400

Cys Val Asn Pro Pro Gly Ile Ile Ser Gln Asn Tyr Gly Glu Ala Val
                405                 410                 415

Ser Leu Ile Asp Lys Gln Ser Cys Asn Val Leu Ser Leu Gly Gly Ile
            420                 425                 430

Thr Leu Arg Leu Ser Gly Glu Phe Asp Val Thr Tyr Gln Lys Asn Ile
        435                 440                 445

Ser Ile Gln Asp Ser Gln Val Ile Ile Thr Gly Asn Leu Asp Ile Ser
    450                 455                 460

Thr Glu Leu Gly Asn Val Asn Asn Ser Ile Ser Asn Ala Leu Asn Lys
465                 470                 475                 480

Leu Glu Glu Ser Asn Arg Lys Leu Asp Lys Val Asn Val Lys Leu Thr
                485                 490                 495
```

-continued

```
Ser Thr Ser Ala Leu Ile Thr Tyr Ile Val Leu Thr Ile Ile Ser Leu
            500                 505                 510

Val Phe Gly Ile Leu Ser Leu Ile Leu Ala Cys Tyr Leu Met Tyr Lys
        515                 520                 525

Gln Lys Ala Gln Gln Lys Thr Leu Leu Trp Leu Gly Asn Asn Thr Leu
    530                 535                 540

Asp Gln Met Arg Ala Thr Thr Lys Met
545                 550
```

<210> SEQ ID NO 9
<211> LENGTH: 1725
<212> TYPE: DNA
<213> ORGANISM: Bovine respiratory syncytial virus

<400> SEQUENCE: 9

```
atggcgacaa cagccatgag gatgatcatc agcattatct tcatctctac ctatgtgaca     60

catatcactt tatgccaaaa cataacagaa gaattttatc aatcaacatg cagtgcagtt    120

agtagaggtt accttagtgc attaagaact ggatggtata caagtgtggt aacaatagag    180

ttgagcaaaa tacaaaaaaa tgtgtgtaat agtactgatt caaaagtgaa attaataaag    240

caagaactag aaagatacaa caatgcagta gtggaattgc agtcacttat gcaaaatgaa    300

ccggcctcct tcagtagagc aaaaagaggg ataccagagt tgatacatta tacaagaaac    360

tctacaaaaa agttttatgg gctaatgggc aagaagagaa aaaggagatt tttaggattc    420

ttgctaggta ttggatctgc tattgcaagt ggtgtagcag tgtccaaagt actacacctg    480

gagggagagg tgaataaaat taaaaatgca ctgctatcca caaataaagc agtagttagt    540

ctatccaatg gagttagtgt ccttactagc aaagtacttg atctaaagaa ctatatagac    600

aaagagcttc tacctaaagt taacaatcat gattgtagga tatccaaaat agaaactgtg    660

atagaattcc aacaaaaaaa caatagattg ttagaaattg ctagggaatt tagtgtaaat    720

gctggtatta ccacacctct cagtacatac atgttgacca atagtgaatt actatcacta    780

attaatgata tgcctataac gaatgaccaa aaaaagctaa tgtcaagtaa tgttcaaata    840

gtcaggcaac agagttattc cattatgtca gtggtcaaag aagaagtcat agcttatgtt    900

gtacaattgc ctatttatgg agttatagac accccctgtt ggaaactaca cacctctccg    960

ttatgcacca ctgataataa agaagggtca aacatctgct taactaggac agatcgtggg   1020

tggtattgtg acaatgcagg ctctgtgtct tttttcccac agacagagac atgtaaggta   1080

caatcaaata gagtgttctg tgacacaatg aacagtttaa ctctgcctac tgacgttaac   1140

ttatgcaaca ctgacatatt caatacaaag tatgactgta aaataatgac atctaaaact   1200

gacataagta gctctgtgat aacttcaatt ggagctattg tatcatgcta tgggaagaca   1260

aaatgtacag cttctaataa aaatcgtgga atcataaaga ctttttccaa tgggtgtgat   1320

tatgtatcaa acaaaggagt agatactgta tctgttggta acacactata ttatgtaaat   1380

aagctagagg ggaaagcact ctatataaag ggtgaaccaa ttattaatta ctatgatcca   1440

ctagtgtttc cttctgatga gtttgatgca tcaattgccc aagtaaacgc aaaaataaac   1500

caaagcctgg ccttcatacg tcgatctgat gagttacttc acagtgtaga tgtaggaaaa   1560

tccaccacaa atgtagtaat tactactatt atcatagtga tagttgtagt gatattaatg   1620

ttaatagctg taggattact gttttactgt aagaccaaga gtactcctat catgttaggg   1680

aaggatcagc tcagtggtat caacaatctt tcctttagta aatga                   1725
```

```
<210> SEQ ID NO 10
<211> LENGTH: 574
<212> TYPE: PRT
<213> ORGANISM: Bovine respiratory syncytial virus

<400> SEQUENCE: 10

Met Ala Thr Thr Ala Met Arg Met Ile Ile Ser Ile Ile Phe Ile Ser
1               5                   10                  15

Thr Tyr Val Thr His Ile Thr Leu Cys Gln Asn Ile Thr Glu Glu Phe
            20                  25                  30

Tyr Gln Ser Thr Cys Ser Ala Val Ser Arg Gly Tyr Leu Ser Ala Leu
        35                  40                  45

Arg Thr Gly Trp Tyr Thr Ser Val Val Thr Ile Glu Leu Ser Lys Ile
    50                  55                  60

Gln Lys Asn Val Cys Asn Ser Thr Asp Ser Lys Val Lys Leu Ile Lys
65                  70                  75                  80

Gln Glu Leu Glu Arg Tyr Asn Asn Ala Val Val Glu Leu Gln Ser Leu
                85                  90                  95

Met Gln Asn Glu Pro Ala Ser Phe Ser Arg Ala Lys Arg Gly Ile Pro
            100                 105                 110

Glu Leu Ile His Tyr Thr Arg Asn Ser Thr Lys Lys Phe Tyr Gly Leu
        115                 120                 125

Met Gly Lys Lys Arg Lys Arg Arg Phe Leu Gly Phe Leu Leu Gly Ile
    130                 135                 140

Gly Ser Ala Ile Ala Ser Gly Val Ala Val Ser Lys Val Leu His Leu
145                 150                 155                 160

Glu Gly Glu Val Asn Lys Ile Lys Asn Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Glu Leu Leu Pro Lys Val Asn
        195                 200                 205

Asn His Asp Cys Arg Ile Ser Lys Ile Glu Thr Val Ile Glu Phe Gln
    210                 215                 220

Gln Lys Asn Asn Arg Leu Leu Glu Ile Ala Arg Glu Phe Ser Val Asn
225                 230                 235                 240

Ala Gly Ile Thr Thr Pro Leu Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Ser Asn Val Gln Ile Val Arg Gln Gln Ser Tyr Ser Ile
        275                 280                 285

Met Ser Val Val Lys Glu Glu Val Ile Ala Tyr Val Val Gln Leu Pro
    290                 295                 300

Ile Tyr Gly Val Ile Asp Thr Pro Cys Trp Lys Leu His Thr Ser Pro
305                 310                 315                 320

Leu Cys Thr Thr Asp Asn Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Thr Glu Thr Cys Lys Val Gln Ser Asn Arg Val Phe Cys Asp
        355                 360                 365

Thr Met Asn Ser Leu Thr Leu Pro Thr Asp Val Asn Leu Cys Asn Thr
    370                 375                 380
```

```
Asp Ile Phe Asn Thr Lys Tyr Asp Cys Lys Ile Met Thr Ser Lys Thr
385                 390                 395                 400

Asp Ile Ser Ser Ser Val Ile Thr Ser Ile Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Leu Glu Gly
    450                 455                 460

Lys Ala Leu Tyr Ile Lys Gly Glu Pro Ile Ile Asn Tyr Tyr Asp Pro
465                 470                 475                 480

Leu Val Phe Pro Ser Asp Glu Phe Asp Ala Ser Ile Ala Gln Val Asn
                485                 490                 495

Ala Lys Ile Asn Gln Ser Leu Ala Phe Ile Arg Arg Ser Asp Glu Leu
            500                 505                 510

Leu His Ser Val Asp Val Gly Lys Ser Thr Thr Asn Val Val Ile Thr
        515                 520                 525

Thr Ile Ile Ile Val Ile Val Val Val Ile Leu Met Leu Ile Ala Val
    530                 535                 540

Gly Leu Leu Phe Tyr Cys Lys Thr Lys Ser Thr Pro Ile Met Leu Gly
545                 550                 555                 560

Lys Asp Gln Leu Ser Gly Ile Asn Asn Leu Ser Phe Ser Lys
                565                 570
```

<210> SEQ ID NO 11
<211> LENGTH: 1725
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 11

```
atggccacca ccgccatgcg catgatcatc agcatcatct tcatcagcac ctacgtgacc     60

cacatcaccc tgtgccagaa catcaccgag gagttctacc agagcacctg cagcgccgtg    120

agtcgcggct acctgagcgc cctgcgcacc ggctggtaca ccagcgtggt gaccatcgag    180

ctgagcaaga tccagaagaa cgtgtgcaac agcaccgaca gcaaggtgaa gctgatcaag    240

caggagctgg agcgctacaa caacgccgtg gtggagctgc agagcctgat gcagaacgag    300

cccgccagct tcagccgcgc caagcgcggc atccccgagc tgatccacta cacccgcaac    360

agcaccaaga agttctacgg cctgatgggc aagaagcgca agcgccgctt cctgggcttc    420

ctgctgggca tcggcagcgc catcgccagc ggcgtggccg tgagcaaggt gctgcacctg    480

gagggcgagg tgaacaagat caagaacgcc ctgctgagca ccaacaaggc cgtggtgagc    540

ctgagcaacg gcgtgagcgt gctgaccagc aaggtgctgg acctgaagaa ctacatcgac    600

aaggagctgc tgcccaaggt gaacaaccac gactgccgca tcagcaagat cgagaccgtg    660

atcgagttcc agcagaagaa caaccgcctg ctggagatcg cccgcgagtt cagcgtgaac    720

gccggcatca ccacccccct gagcacctac atgctgacca acagcgagct gctgagcctg    780

atcaacgaca tgcccatcac caacgaccag aagaagctga tgagcagcaa cgtgcagatc    840

gtgcgccagc agagctacag catcatgagc gtggtgaagg aggaggtgat cgcctacgtg    900

gtgcagctgc ccatctacgg cgtgatcgac accccctgct ggaagctgca caccagcccc    960
```

ctgtgcacca ccgacaacaa ggagggcagc aacatctgcc tgacccgcac cgatcgcggc 1020
tggtactgcg acaacgccgg cagcgtgagc ttcttccccc agaccgagac ctgcaaggtg 1080
cagagcaacc gcgtgttctg cgacaccatg aacagcctga ccctgcccac cgacgtgaac 1140
ctgtgcaaca ccgacatctt caacaccaag tacgactgca agatcatgac cagcaagacc 1200
gacatcagca gcagcgtgat caccagcatc ggcgccatcg tgagctgcta cggcaagacc 1260
aagtgcaccg ccagcaacaa gaatcgcggc atcatcaaga ccttcagcaa cggctgcgac 1320
tacgtgagca acaagggcgt ggacaccgtg agcgtgggca acaccctgta ctacgtgaac 1380
aagctggagg gcaaggccct gtacatcaag ggcgagccca tcatcaacta ctacgacccc 1440
ctggtgttcc ccagcgacga gttcgacgcc agcatcgccc aggtgaacgc caagatcaac 1500
cagagcctgg ccttcatccg ccgcagcgac gagctgctgc acagcgtgga cgtgggcaag 1560
agcaccacca acgtggtgat caccaccatc atcatcgtga tcgtggtggt gatcctgatg 1620
ctgatcgccg tgggcctgct gttctactgc aagaccaaga gcacccccat catgctgggc 1680
aaggaccagc tgagcggcat caacaacctg agcttcagca agtaa 1725

<210> SEQ ID NO 12
<211> LENGTH: 16950
<212> TYPE: DNA
<213> ORGANISM: Bovine respiratory syncytial virus

<400> SEQUENCE: 12
accaaacaga gaatccgtga gttacgataa aaggcgaagg agcaattgaa gtcgcacggg 60
tagaaggtgt gaatctcgag tgcgagcccg aagcacaaac tcgagaaagc cttctgccaa 120
catgtcttcc gtatttgatg agtacgaaca gctcctcgcg gctcagactc gccccaatgg 180
agctcatgga gggggagaaa aagggagtac cttaaaagta gacgtcccgg tattcactct 240
taacagtgat gacccagaag atagatggag ctttgtggta ttctgcctcc ggattgctgt 300
tagcgaagat gccaacaaac cactcaggca aggtgctctc atatctcttt tatgctccca 360
ctcacaggta atgaggaacc atgttgccct tgcagggaaa cagaatgaag ccacattggc 420
cgtgcttgag attgatggct ttgccaacgg cacgccccag ttcaacaata ggagtggagt 480
gtctgaagag agagcacaga gatttgcgat gatagcagga tctctccctc gggcatgcag 540
caacggaacc ccgttcgtca cagccggggc cgaagatgat gcaccagaag acatcaccga 600
taccctggag aggatcctct ctatccaggc tcaagtatgg gtcacagtag caaaagccat 660
gactgcgtat gagactgcag atgagtcgga aacaaggcga atcaataagt atatgcagca 720
aggcagggtc caaaagaaat acatcctcta ccccgtatgc aggagcacaa tccaactcac 780
gatcagacag tctcttgcag tccgcatctt tttggttagc gagctcaaga gaggccgcaa 840
cacggcaggt ggtacctcta cttattataa cctggtaggg gacgtagact catacatcag 900
gaataccggg cttactgcat tcttcttgac actcaagtac ggaatcaaca ccaagacatc 960
agcccttgca cttagtagcc tctcaggcga catccagaag atgaagcagc tcatgcgttt 1020
gtatcggatg aaaggagata atgcgccgta catgacatta cttggtgata gtgaccagat 1080
gagctttgcg cctgccgagt atgcacaact ttactccttt gccatgggta tggcatcagt 1140
cctagataaa ggtactggga aataccaatt tgccagggac tttatgagca catcattctg 1200
gagacttgga gtagagtacg ctcaggctca gggaagtagc attaacgagg atatggctgc 1260
cgagctaaag ctaaccccag cagcaaggag gggcctggca gctgctgccc aacgggtctc 1320
cgaggagacc agcagcatag acatgcctac tcaacaagtc ggagtcctca ctgggcttag 1380
cgaggggggg tcccaagctc tacaaggcgg atcgaataga tcgcaagggc aaccagaagc 1440
cggggatggg gagacccaat tcctggatct gatgagagcg gtagcaaata gcatgaggga 1500
ggcgccaaac tctgcacagg gcactcccca atcggggcct cccccaactc ctgggccatc 1560
ccaagataac gacaccgact gggggtattg atggacaaaa cccagcctgc ttccacaaaa 1620
acatcccaat gccctcaccc gtagtcgacc cctcgatttg cggctctata tgaccacacc 1680
ctcaaacaaa catccccctc tttcctccct cccccctgctg tacaactacg tacgccctag 1740
ataccacagg cacaatgcgg ctcactaaca atcaaaacag agccgaggga attagaaaaa 1800
agtacgggta gaagagggat attcagagat cagggcaagt ctcccgagtc tctgctctct 1860
cctctacctg atagaccagg acaaacatgg ccacctttac agatgcagag atcgacgagc 1920
tatttgagac aagtggaact gtcattgaca acataattac agcccagggt aaaccagcag 1980
agactgttgg aaggagtgca atcccacaag gcaagaccaa ggtgctgagc gcagcatggg 2040
agaagcatgg gagcatccag ccaccggcca gtcaagacaa ccccgatcga caggacagat 2100
ctgacaaaca accatccaca cccgagcaaa cgaccccgca tgacagcccg ccggccacat 2160
ccgccgacca gccccccacc caggccacag acgaagccgt cgacacacag ctcaggaccg 2220
gagcaagcaa ctctctgctg ttgatgcttg acaagctcag caataaatcg tccaatgcta 2280
aaaagggccc atggtcgagc cccaagaggg ggaatcacca acgtccgact caacagcagg 2340
ggagtcaacc cagtcgcgga aacagtcagg aaagaccgca gaaccaagtc aaggccgccc 2400
ctggaaacca gggcacagac gtgaacacag catatcatgg acaatgggag gagtcacaac 2460
tatcagctgg tgcaacccct catgctctcc gatcaaggca gagccaagac aatacccttg 2520
tatctgcgga tcatgtccag ccacctgtag actttgtgca agcgatgatg tctatgatgg 2580
aggcgatatc acagagagta agtaaggttg actatcagct agatcttgtc ttgaaacaga 2640
catcctccat ccctatgatg cggtccgaaa tccaacagct gaaaacatct gttgcagtca 2700
tggaagccaa cttgggaatg atgaagattc tggatcccgg ttgtgccaac atttcatctc 2760
tgagtgatct acgggcagtt gcccgatctc acccggtttt agtttcaggc cctggagacc 2820
cctctcccta tgtgacacaa ggaggcgaaa tggcacttaa taaactttcg caaccagtgc 2880
cacatccatc tgaattgatt aaacccgcca ctgcatgcgg gcctgatata ggagtggaaa 2940
aggacactgt ccgtgcattg atcatgtcac gcccaatgca cccgagttct tcagccaagc 3000
tcctaagcaa gttagatgca gccgggtcga tcgaggaaat caggaaaatc aagcgccttg 3060
ctctaaatgg ctaattacta ctgccacacg tagcgggtcc ctgtccactc ggcatcacac 3120
ggaatctgca ccgagttccc ccccgcggtt agaaaaaata cgggtagaac cgccaccatg 3180
gcgacaacag ccatgaggat gatcatcagc attatcttca tctctaccta tgtgacacat 3240
atcactttat gccaaaacat aacagaagaa ttttatcaat caacatgcag tgcagttagt 3300
agaggttacc ttagtgcatt aagaactgga tggtatacaa gtgtggtaac aatagagttg 3360
agcaaaatac aaaaaaatgt gtgtaatagt actgattcaa aagtgaaatt aataaagcaa 3420
gaactagaaa gatacaacaa tgcagtagtg gaattgcagt cacttatgca aaatgaaccg 3480
gcctccttca gtagagcaaa aagagggata ccagagttga tacattatac aagaaactct 3540
acaaaaaagt tttatgggct aatgggcaag aagagaaaaa ggagattttt aggattcttg 3600
ctaggtattg gatctgctat tgcaagtggt gtagcagtgt ccaaagtact acacctggag 3660
ggagaggtga ataaaattaa aaatgcactg ctatccacaa ataaagcagt agttagtcta 3720

-continued

```
tccaatggag ttagtgtcct tactagcaaa gtacttgatc taaagaacta tatagacaaa   3780
gagcttctac ctaaagttaa caatcatgat tgtaggatat ccaaaataga aactgtgata   3840
gaattccaac aaaaaaacaa tagattgtta gaaattgcta gggaatttag tgtaaatgct   3900
ggtattacca cacctctcag tacatacatg ttgaccaata gtgaattact atcactaatt   3960
aatgatatgc ctataacgaa tgaccaaaaa aagctaatgt caagtaatgt tcaaatagtc   4020
aggcaacaga gttattccat tatgtcagtg gtcaaagaag aagtcatagc ttatgttgta   4080
caattgccta tttatggagt tatagacacc ccctgttgga aactacacac ctctccgtta   4140
tgcaccactg ataataaaga agggtcaaac atctgcttaa ctaggacaga tcgtgggtgg   4200
tattgtgaca atgcaggctc tgtgtctttt ttcccacaga cagagacatg taaggtacaa   4260
tcaaatagag tgttctgtga cacaatgaac agtttaactc tgcctactga cgttaactta   4320
tgcaacactg acatattcaa tacaaagtat gactgtaaaa taatgacatc taaaactgac   4380
ataagtagct ctgtgataac ttcaattgga gctattgtat catgctatgg gaagacaaaa   4440
tgtacagctt ctaataaaaa tcgtggaatc ataaagactt tttccaatgg gtgtgattat   4500
gtatcaaaca aaggagtaga tactgtatct gttggtaaca cactatatta tgtaaataag   4560
ctagagggga aagcactcta tataaagggt gaaccaatta ttaattacta tgatccacta   4620
gtgtttcctt ctgatgagtt tgatgcatca attgcccaag taaacgcaaa aataaaccaa   4680
agcctggcct tcatacgtcg atctgatgag ttacttcaca gtgtagatgt aggaaaatcc   4740
accacaaatg tagtaattac tactattatc atagtgatag ttgtagtgat attaatgtta   4800
atagctgtag gattactgtt ttactgtaag accaagagta ctcctatcat gttagggaag   4860
gatcagctca gtggtatcaa caatctttcc tttagtaaat gacccccccgc ggacccaagg   4920
tccaactctc caagcggcaa tcctctctcg cttcctcagc cccactgaat gatcgcgtaa   4980
ccgtaattaa tctagctaca tttaagatta agaaaaaata cgggtagaat tggagtgccc   5040
caattgtgcc aagatggact catctaggac aattgggctg tactttgatt ctgcccattc   5100
ttctagcaac ctgttagcat ttccgatcgt cctacaagac acaggagatg ggaagaagca   5160
aatcgccccg caatatagga tccagcgcct tgacttgtgg actgatagta aggaggactc   5220
agtattcatc accacctatg gattcatctt tcaagttggg aatgaagaag ccaccgtcgg   5280
catgatcgat gataaaccca agcgcgagtt actttccgct gcgatgctct gcctaggaag   5340
cgtcccaaat accggagacc ttattgagct ggcaagggcc tgtctcacta tgatagtcac   5400
atgcaagaag agtgcaacta atactgagag aatggttttc tcagtagtgc aggcacccca   5460
agtgctgcaa agctgtaggg ttgtggcaaa caaatactca tcagtgaatg cagtcaagca   5520
cgtgaaagcg ccagagaaga ttcccgggag tggaacccta gaatacaagg tgaactttgt   5580
ctccttgact gtggtaccga agagggatgt ctacaagatc ccagctgcag tattgaaggt   5640
ttctggctcg agtctgtaca atcttgcgct caatgtcact attaatgtgg aggtagaccc   5700
gaggagtcct ttggttaaat ctctgtctaa gtctgacagc ggatactatg ctaacctctt   5760
cttgcatatt ggacttatga ccactgtaga taggaagggg aagaaagtga catttgacaa   5820
gctggaaaag aaaataagga gccttgatct atctgtcggg ctcagtgatg tgctcgggcc   5880
ttccgtgttg gtaaaagcaa gaggtgcacg gactaagctt ttggcacctt tcttctctag   5940
cagtgggaca gcctgctatc ccatagcaaa tgcttctcct caggtggcca agatactctg   6000
gagtcaaacc gcgtgcctgc ggagcgttaa aatcattatc caagcaggta cccaacgcgc   6060
tgtcgcagtg accgccgacc acgaggttac ctctactaag ctggagaagg ggcacaccct   6120
```

-continued

```
tgccaaatac aatcctttta agaaataagc tgcgtctctg agattgcgct ccgcccactc   6180
acccagatca tcatgacaca aaaaactaat ctgtcttgat tatttacagt tagtttacct   6240
gtctatcaag ttagaaaaaa cacgggtaga agattctgga tcccggttgg cgccctccag   6300
gtgcaagatg ggctccagac cttctaccaa gaacccagca cctatgatgc tgactatccg   6360
ggttgcgctg gtactgagtt gcatctgtcc ggcaaactcc attgatggca ggcctcttgc   6420
agctgcagga attgtggtta caggagacaa agccgtcaac atatacacct catcccagac   6480
aggatcaatc atagttaagc tcctcccgaa tctgcccaag gataaggagg catgtgcgaa   6540
agccccccttg gatgcataca acaggacatt gaccactttg ctcacccccc ttggtgactc   6600
tatccgtagg atacaagagt ctgtgactac atctggaggg gggagacagg ggcgccttat   6660
aggcgccatt attggcggtg tggctcttgg ggttgcaact gccgcacaaa taacagcggc   6720
cgcagctctg atacaagcca aacaaaatgc tgccaacatc ctccgactta aagagagcat   6780
tgccgcaacc aatgaggctg tgcatgaggt cactgacgga ttatcgcaac tagcagtggc   6840
agttgggaag atgcagcagt ttgttaatga ccaatttaat aaaacagctc aggaattaga   6900
ctgcatcaaa attgcacagc aagttggtgt agagctcaac ctgtacctaa ccgaattgac   6960
tacagtattc ggaccacaaa tcacttcacc tgctttaaac aagctgacta ttcaggcact   7020
ttacaatcta gctggtggaa atatggatta cttattgact aagttaggtg tagggaacaa   7080
tcaactcagc tcattaatcg gtagcggctt aatcaccggt aaccctattc tatacgactc   7140
acagactcaa ctcttgggta tacaggtaac tctaccttca gtcgggaacc taaataatat   7200
gcgtgccacc tacttggaaa ccttatccgt aagcacaacc aggggatttg cctcggcact   7260
tgtcccaaaa gtggtgacac aggtcggttc tgtgatagaa gaacttgaca cctcatactg   7320
tatagaaact gacttagatt tatattgtac aagaatagta acgttcccta tgtcccctgg   7380
tatttattcc tgcttgagcg gcaatacgtc ggcctgtatg tactcaaaga ccgaaggcgc   7440
acttactaca ccatacatga ctatcaaagg ttcagtcatc gccaactgca agatgacaac   7500
atgtagatgt gtaaaccccc cgggtatcat atcgcaaaac tatggagaag ccgtgtctct   7560
aatagataaa caatcatgca atgttttatc cttaggcggg ataactttaa ggctcagtgg   7620
ggaattcgat gtaacttatc agaagaatat ctcaatacaa gattctcaag taataataac   7680
aggcaatctt gatatctcaa ctgagcttgg gaatgtcaac aactcgatca gtaatgcttt   7740
gaataagtta gaggaaagca acagaaaact agacaaagtc aatgtcaaac tgactagcac   7800
atctgctctc attacctata tcgttttgac tatcatatct cttgtttttg gtatacttag   7860
cctgattcta gcatgctacc taatgtacaa gcaaaaggcg caacaaaaga ccttattatg   7920
gcttgggaat aatactctag atcagatgag agccactaca aaaatgtgaa cacagatgag   7980
gaacgaaggt ttccctaata gtaatttgtg tgaaagttct ggtagtctgt cagttcagag   8040
agttaagaaa aaactaccgg ttgtagatga ccaaaggacg atatacgggt agaacggtaa   8100
gagaggccgc ccctcaattg cgagccaggc ttcacaacct ccgttctacc gcttcaccga   8160
caacagtcct caatcatgga ccgcgccgtt agccaagttg cgttagagaa tgatgaaaga   8220
gaggcaaaaa atacatggcg cttgatattc cggattgcaa tcttattctt aacagtagtg   8280
accttggcta tatctgtagc ctccctttta tatagcatgg gggctagcac acctagcgat   8340
cttgtaggca taccgactag gatttccagg gcagaagaaa agattacatc tacacttggt   8400
tccaatcaag atgtagtaga taggatatat aagcaagtgg cccttgagtc tccgttggca   8460
```

-continued

```
ttgttaaata ctgagaccac aattatgaac gcaataacat ctctctctta tcagattaat   8520
ggagctgcaa acaacagtgg gtggggggca cctatccatg acccagatta tatagggggg   8580
ataggcaaag aactcattgt agatgatgct agtgatgtca catcattcta tccctctgca   8640
tttcaagaac atctgaattt tatcccggcg cctactacag gatcaggttg cactcgaata   8700
ccctcatttg acatgagtgc tacccattac tgctacaccc ataatgtaat attgtctgga   8760
tgcagagatc actcacattc atatcagtat ttagcacttg gtgtgctccg gacatctgca   8820
acagggaggg tattcttttc tactctgcgt tccatcaacc tggacgacac ccaaaatcgg   8880
aagtcttgca gtgtgagtgc aactcccctg ggttgtgata tgctgtgctc gaaagtcacg   8940
gagacagagg aagaagatta taactcagct gtccctacgc ggatggtaca tgggaggtta   9000
gggttcgacg gccagtacca cgaaaaggac ctagatgtca caacattatt cggggactgg   9060
gtggccaact acccaggagt agggggtgga tcttttattg acagccgcgt atggttctca   9120
gtctacggag ggttaaaacc caattcaccc agtgacactg tacaggaagg gaaatatgtg   9180
atatacaagc gatacaatga cacatgccca gatgagcaag actaccagat tcgaatggcc   9240
aagtcttcgt ataagcctgg acggtttggt gggaaacgca tacagcaggc tatcttatct   9300
atcaaggtgt caacatcctt aggcgaagac ccggtactga ctgtaccgcc caacacagtc   9360
acactcatgg gggccgaagg cagaattctc acagtaggga catctcattt cttgtatcaa   9420
cgagggtcat catacttctc tcccgcgtta ttatatccta tgacagtcag caacaaaaca   9480
gccactcttc atagtcctta tacattcaat gccttcactc ggccaggtag tatcccttgc   9540
caggcttcag caagatgccc caactcgtgt gttactggag tctatacaga tccatatccc   9600
ctaatcttct atagaaacca caccttgcga ggggtattcg ggacaatgct tgatggtgta   9660
caagcaagac ttaaccctgc gtctgcagta ttcgatagca catcccgcag tcgcattact   9720
cgagtgagtt caagcagtac caaagcagca tacacaacat caacttgttt taaagtggtc   9780
aagactaata agacctattg tctcagcatt gctgaaatat ctaatactct cttcggagaa   9840
ttcagaatcg tcccgttact agttgagatc ctcaaagatg acggggttag agaagccagg   9900
tctggctagt tgagtcaatt ataaaggagt tggaaagatg gcattgtatc acctatcttc   9960
tgcgacatca agaatcaaac cgaatgccgg cgcgtgctcg aattccatgt tgccagttga  10020
ccacaatcag ccagtgctca tgcgatcaga ttaagccttg tcaatagtct cttgattaag  10080
aaaaaatgta agtggcaatg agatacaagg caaaacagct catggttaac aatacgggta  10140
ggacatggcg agctccggtc ctgaaagggc agagcatcag attatcctac cagagtcaca  10200
cctgtcttca ccattggtca agcacaaact actctattac tggaaattaa ctgggctacc  10260
gcttcctgat gaatgtgact tcgaccacct cattctcagc cgacaatgga aaaaaatact  10320
tgaatcggcc tctcctgata ctgagagaat gataaaactc ggaagggcag tacaccaaac  10380
tcttaaccac aattccagaa taaccggagt gctccacccc aggtgtttag aagaactggc  10440
taatattgag gtcccagatt caaccaacaa atttcggaag attgagaaga agatccaaat  10500
tcacaacacg agatatggag aactgttcac aaggctgtgt acgcatatag agaagaaact  10560
gctggggtca tcttggtcta acaatgtccc ccggtcagag gagttcagca gcattcgtac  10620
ggatccggca ttctggtttc actcaaaatg gtccacagcc aagtttgcat ggctccatat  10680
aaaacagatc cagaggcatc tgatggtggc agctaggaca aggtctgcgg ccaacaaatt  10740
ggtgatgcta acccataagg taggccaagt ctttgtcact cctgaacttg tcgttgtgac  10800
gcatacgaat gagaacaagt tcacatgtct tacccaggaa cttgtattga tgtatgcaga  10860
```

```
tatgatggag ggcagagata tggtcaacat aatatcaacc acggcggtgc atctcagaag  10920
cttatcagag aaaattgatg acattttgcg gttaatagac gctctggcaa aagacttggg  10980
taatcaagtc tacgatgttg tatcactaat ggagggattt gcatacggag ctgtccagct  11040
actcgagccg tcaggtacat ttgcaggaga tttcttcgca ttcaacctgc aggagcttaa  11100
agacattcta attggcctcc tccccaatga tatagcagaa tccgtgactc atgcaatcgc  11160
tactgtattc tctggtttag aacagaatca agcagctgag atgttgtgtc tgttgcgtct  11220
gtggggtcac ccactgcttg agtcccgtat tgcagcaaag gcagtcagga gccaaatgtg  11280
cgcaccgaaa atggtagact ttgatatgat ccttcaggta ctgtctttct tcaagggaac  11340
aatcatcaac gggtacagaa agaagaatgc aggtgtgtgg ccgcgagtca aagtggatac  11400
aatatatggg aaggtcattg ggcaactaca tgcagattca gcagagattt cacacgatat  11460
catgttgaga gagtataaga gtttatctgc acttgaattt gagccatgta tagaatatga  11520
ccctgtcacc aacctgagca tgttcctaaa agacaaggca atcgcacacc ccaacgataa  11580
ttggcttgcc tcgtttaggc ggaaccttct ctccgaagac cagaagaaac atgtaaaaga  11640
agcaacttcg actaatcgcc tcttgataga gtttttagag tcaaatgatt ttgatccata  11700
taaagagatg gaatatctga cgacccttga gtaccttaga gatgacaatg tggcagtatc  11760
atactcgctc aaggagaagg aagtgaaagt taatggacgg atcttcgcta agctgacaaa  11820
gaagttaagg aactgtcagg tgatggcgga agggatccta gccgatcaga ttgcaccttt  11880
ctttcaggga aatggagtca ttcaggatag catatccttg accaagagta tgctagcgat  11940
gagtcaactg tcttttaaca gcaataagaa acgtatcact gactgtaaag aaagagtatc  12000
ttcaaaccgc aatcatgatc cgaaaagcaa gaaccgtcgg agagttgcaa ccttcataac  12060
aactgacctg caaaagtact gtcttaattg gagatatcag acaatcaaat tgttcgctca  12120
tgccatcaat cagttgatgg gcctacctca cttcttcgaa tggattcacc taagactgat  12180
ggacactacg atgttcgtag gagacccttt caatcctcca agtgacccta ctgactgtga  12240
cctctcaaga gtccctaatg atgacatata tattgtcagt gccagagggg gtatcgaagg  12300
attatgccag aagctatgga caatgatctc aattgctgca atccaacttg ctgcagctag  12360
atcgcattgt cgtgttgcct gtatggtaca gggtgataat caagtaatag cagtaacgag  12420
agaggtaaga tcagacgact ctccggagat ggtgttgaca cagttgcatc aagccagtga  12480
taatttcttc aaggaattaa ttcatgtcaa tcatttgatt ggccataatt tgaaggatcg  12540
tgaaaccatc aggtcagaca cattcttcat atacagcaaa cgaatcttca aagatggagc  12600
aatcctcagt caagtcctca aaaattcatc taaattagtg ctagtgtcag gtgatctcag  12660
tgaaaacacc gtaatgtcct gtgccaacat tgcctctact gtagcacggc tatgcgagaa  12720
cgggcttccc aaagacttct gttactattt aaactatata atgagttgtg tgcagacata  12780
ctttgactct gagttctcca tcaccaacaa ttcgcacccc gatcttaatc agtcgtggat  12840
tgaggacatc tcttttgtgc actcatatgt tctgactcct gcccaattag gggactgag  12900
taaccttcaa tactcaaggc tctacactag aaatatcggt gacccgggga ctactgcttt  12960
tgcagagatc aagcgactag aagcagtggg attactgagt cctaacatta tgactaatat  13020
cttaactagg ccgcctggga atggagattg ggccagtctg tgcaacgacc catactcttt  13080
caattttgag actgttgcaa gcccaaatat tgttcttaag aaacatacgc aaagagtcct  13140
atttgaaact tgttcaaatc ccttattgtc tggagtgcac acagaggata atgaggcaga  13200
```

agagaaggca ttggctgaat tcttgcttaa tcaagaggtg attcatcccc gcgttgcgca 13260
tgccatcatg gaggcaagct ctgtaggtag gagaaagcaa attcaagggc ttgttgacac 13320
aacaaacacc gtaattaaga ttgcgcttac taggaggcca ttaggcatca agaggctgat 13380
gcggatagtc aattattcta gcatgcatgc aatgctgttt agagacgatg ttttttcctc 13440
cagtagatcc aaccacccct tagtctcttc taatatgtgt tctctgacac tggcagacta 13500
tgcacggaat agaagctggt cacctttgac gggaggcagg aaaatactgg gtgtatctaa 13560
tcctgatacg atagaactcg tagagggtga gattcttagt gtaagcggag ggtgtacaag 13620
atgtgacagc ggagatgaac aatttacttg gttccatctt ccaagcaata tagaattgac 13680
cgatgacacc agcaagaatc ctccgatgag ggtaccatat ctcgggtcaa agacacagga 13740
gaggagagct gcctcacttg caaaaatagc tcatatgtcg ccacatgtaa aggctgccct 13800
aagggcatca tccgtgttga tctgggctta tggggataat gaagtaaatt ggactgctgc 13860
tcttacgatt gcaaaatctc ggtgtaatgt aaacttagag tatcttcggt tactgtcccc 13920
tttacccacg gctgggaatc ttcaacatag actagatgat ggtataactc agatgacatt 13980
cacccctgca tctctctaca gggtgtcacc ttacattcac atatccaatg attctcaaag 14040
gctgttcact gaagaaggag tcaaagaggg gaatgtggtt taccaacaga tcatgctctt 14100
gggtttatct ctaatcgaat cgatctttcc aatgacaaca accaggacat atgatgagat 14160
cacactgcac ctacatagta aatttagttg ctgtatcaga gaagcacctg ttgcggttcc 14220
tttcgagcta cttggggtgg taccggaact gaggacagtg acctcaaata agtttatgta 14280
tgatcctagc cctgtatcgg agggagactt tgcgagactt gacttagcta tcttcaagag 14340
ttatgagctt aatctggagt catatcccac gatagagcta atgaacattc tttcaatatc 14400
cagcgggaag ttgattggcc agtctgtggt ttcttatgat gaagatacct ccataaagaa 14460
tgacgccata atagtgtatg acaataccccg aaattggatc agtgaagctc agaattcaga 14520
tgtggtccgc ctatttgaat atgcagcact tgaagtgctc ctcgactgtt cttaccaact 14580
ctattacctg agagtaagag gcctggacaa tattgtctta tatatgggtg atttatacaa 14640
gaatatgcca ggaattctac tttccaacat tgcagctaca atatctcatc ccgtcattca 14700
ttcaaggtta catgcagtgg gcctggtcaa ccatgacgga tcacaccaac ttgcagatac 14760
ggattttatc gaaatgtctg caaaactatt agtatcttgc acccgacgtg tgatctccgg 14820
cttatattca ggaaataagt atgatctgct gttcccatct gtcttagatg ataacctgaa 14880
tgagaagatg cttcagctga tatcccggtt atgctgtctg tacacggtac tctttgctac 14940
aacaagagaa atcccgaaaa taagaggctt aactgcagaa gagaaatgtt caatactcac 15000
tgagtattta ctgtcggatg ctgtgaaacc attacttagc cccgatcaag tgagctctat 15060
catgtctcct aacataatta cattcccagc taatctgtac tacatgtctc ggaagagcct 15120
caatttgatc agggaaaggg aggacaggga tactatcctg gcgttgttgt tcccccaaga 15180
gccattatta gagttccctt ctgtgcaaga tattggtgct cgagtgaaag atccattcac 15240
ccgacaacct gcggcatttt tgcaagagtt agatttgagt gctccagcaa ggtatgacgc 15300
attcacactt agtcagattc atcctgaact cacatctcca aatccggagg aagactactt 15360
agtacgatac ttgttcagag ggatagggac tgcatcttcc tcttggtata aggcatctca 15420
tctcctttct gtacccgagg taagatgtgc aagacacggg aactccttat acttagctga 15480
agggagcgga gccatcatga gtcttctcga actgcatgta ccacatgaaa ctatctatta 15540
caatacgctc ttttcaaatg agatgaaccc cccgcaacga catttcgggc cgaccccaac 15600

```
tcagtttttg aattcggttg tttataggaa tctacaggcg gaggtaacat gcaaagatgg  15660
atttgtccaa gagttccgtc cattatggag agaaaataca gaggaaagcg acctgacctc  15720
agataaagta gtggggtata ttacatctgc agtgccctac agatctgtat cattgctgca  15780
ttgtgacatt gaaattcctc cagggtccaa tcaaagctta ctagatcaac tagctatcaa  15840
tttatctctg attgccatgc attctgtaag ggagggcggg gtagtaatca tcaaagtgtt  15900
gtatgcaatg ggatactact ttcatctact catgaacttg tttgctccgt gttccacaaa  15960
aggatatatt ctctctaatg gttatgcatg tcgaggagat atggagtgtt acctggtatt  16020
tgtcatgggt tacctgggcg ggcctacatt tgtacatgag gtggtgagga tggcgaaaac  16080
tctggtgcag cggcacggta cgcttttgtc taaatcagat gagatcacac tgaccaggtt  16140
attcacctca cagcggcagc gtgtgacaga catcctatcc agtcctttac caagattaat  16200
aaagtacttg aggaagaata ttgacactgc gctgattgaa gccgggggac agcccgtccg  16260
tccattctgt gcggagagtc tggtgagcac gctagcgaac ataactcaga taacccagat  16320
catcgctagt cacattgaca cagttatccg gtctgtgata tatatggaag ctgagggtga  16380
tctcgctgac acagtatttc tatttacccc ttacaatctc tctactgacg ggaaaaagag  16440
gacatcactt aaacagtgca cgagacagat cctagaggtt acaatactag gtcttagagt  16500
cgaaaatctc aataaaatag gcgatataat cagcctagtg cttaaaggca tgatctccat  16560
ggaggacctt atcccactaa ggacatactt gaagcatagt acctgcccta aatatttgaa  16620
ggctgtccta ggtattacca aactcaaaga aatgtttaca gacacttctg tactgtactt  16680
gactcgtgct caacaaaaat tctacatgaa aactataggc aatgcagtca aaggatatta  16740
cagtaactgt gactcttaac gaaaatcaca tattaatagg ctcctttttt ggccaattgt  16800
attcttgttg atttaatcat attatgttag aaaaaagttg aaccctgact ccttaggact  16860
cgaattcgaa ctcaaataaa tgtcttaaaa aaaggttgcg cacaattatt cttgagtgta  16920
gtctcgtcat tcaccaaatc tttgtttggt                                  16950
```

<210> SEQ ID NO 13
<211> LENGTH: 16950
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 13

```
accaaacaga gaatccgtga gttacgataa aaggcgaagg agcaattgaa gtcgcacggg     60
tagaaggtgt gaatctcgag tgcgagcccg aagcacaaac tcgagaaagc cttctgccaa    120
catgtcttcc gtatttgatg agtacgaaca gctcctcgcg gctcagactc gccccaatgg    180
agctcatgga gggggagaaa aagggagtac cttaaaagta gacgtcccgg tattcactct    240
taacagtgat gacccagaag atagatggag ctttgtggta ttctgcctcc ggattgctgt    300
tagcgaagat gccaacaaac cactcaggca aggtgctctc atatctcttt tatgctccca    360
ctcacaggta atgaggaacc atgttgccct tgcagggaaa cagaatgaag ccacattggc    420
cgtgcttgag attgatggct ttgccaacgg cacgccccag ttcaacaata ggagtggagt    480
gtctgaagag agagcacaga gatttgcgat gatagcagga tctctccctc gggcatgcag    540
caacggaacc ccgttcgtca cagccggggc cgaagatgat gcaccagaag acatcaccga    600
taccctggag aggatcctct ctatccaggc tcaagtatgg gtcacagtag caaaagccat    660
```

-continued

```
gactgcgtat gagactgcag atgagtcgga aacaaggcga atcaataagt atatgcagca    720
aggcagggtc caaaagaaat acatcctcta ccccgtatgc aggagcacaa tccaactcac    780
gatcagacag tctcttgcag tccgcatctt tttggttagc gagctcaaga gaggccgcaa    840
cacggcaggt ggtacctcta cttattataa cctggtaggg gacgtagact catacatcag    900
gaataccggg cttactgcat tcttcttgac actcaagtac ggaatcaaca ccaagacatc    960
agcccttgca cttagtagcc tctcaggcga catccagaag atgaagcagc tcatgcgttt   1020
gtatcggatg aaaggagata atgcgccgta catgacatta cttggtgata gtgaccagat   1080
gagctttgcg cctgccgagt atgcacaact ttactccttt gccatgggta tggcatcagt   1140
cctagataaa ggtactggga aataccaatt tgccagggac tttatgagca catcattctg   1200
gagacttgga gtagagtacg ctcaggctca gggaagtagc attaacgagg atatggctgc   1260
cgagctaaag ctaaccccag cagcaaggag gggcctggca gctgctgccc aacgggtctc   1320
cgaggagacc agcagcatag acatgcctac tcaacaagtc ggagtcctca ctgggcttag   1380
cgaggggggg tcccaagctc tacaaggcgg atcgaataga tcgcaagggc aaccagaagc   1440
cggggatggg gagacccaat tcctggatct gatgagagcg gtagcaaata gcatgaggga   1500
ggcgccaaac tctgcacagg gcactcccca atcggggcct cccccaactc ctgggccatc   1560
ccaagataac gacaccgact gggggtattg atggacaaaa cccagcctgc ttccacaaaa   1620
acatcccaat gccctcaccc gtagtcgacc cctcgatttg cggctctata tgaccacacc   1680
ctcaaacaaa catcccctc tttcctccct cccccctgctg tacaactacg tacgccctag   1740
ataccacagg cacaatgcgg ctcactaaca atcaaaacag agccgaggga attagaaaaa   1800
agtacgggta gaagagggat attcagagat cagggcaagt ctcccgagtc tctgctctct   1860
cctctacctg atagaccagg acaaacatgg ccacctttac agatgcagag atcgacgagc   1920
tatttgagac aagtggaact gtcattgaca acataattac agcccagggt aaaccagcag   1980
agactgttgg aaggagtgca atcccacaag gcaagaccaa ggtgctgagc gcagcatggg   2040
agaagcatgg gagcatccag ccaccggcca gtcaagacaa ccccgatcga caggacagat   2100
ctgacaaaca accatccaca cccgagcaaa cgaccccgca tgacagcccg ccggccacat   2160
ccgccgacca gccccccacc caggccacag acgaagccgt cgacacacag ctcaggaccg   2220
gagcaagcaa ctctctgctg ttgatgcttg acaagctcag caataaatcg tccaatgcta   2280
aaaagggccc atggtcgagc cccaagaggg ggaatcacca acgtccgact caacagcagg   2340
ggagtcaacc cagtcgcgga aacagtcagg aaagaccgca gaaccaagtc aaggccgccc   2400
ctggaaacca gggcacagac gtgaacacag catatcatgg acaatgggag gagtcacaac   2460
tatcagctgg tgcaacccct catgctctcc gatcaaggca gagccaagac aataccccttg   2520
tatctgcgga tcatgtccag ccacctgtag actttgtgca agcgatgatg tctatgatgg   2580
aggcgatatc acagagagta agtaaggttg actatcagct agatcttgtc ttgaaacaga   2640
catcctccat ccctatgatg cggtccgaaa tccaacagct gaaaacatct gttgcagtca   2700
tggaagccaa cttgggaatg atgaagattc tggatcccgg ttgtgccaac atttcatctc   2760
tgagtgatct acgggcagtt gcccgatctc acccggtttt agtttcaggc cctggagacc   2820
cctctcccta tgtgacacaa ggaggcgaaa tggcacttaa taaactttcg caaccagtgc   2880
cacatccatc tgaattgatt aaacccgcca ctgcatgcgg gcctgatata ggagtggaaa   2940
aggacactgt ccgtgcattg atcatgtcac gcccaatgca cccgagttct tcagccaagc   3000
```

-continued

```
tcctaagcaa gttagatgca gccgggtcga tcgaggaaat caggaaaatc aagcgccttg   3060
ctctaaatgg ctaattacta ctgccacacg tagcgggtcc ctgtccactc ggcatcacac   3120
ggaatctgca ccgagttccc ccccgcggtt agaaaaaaata cgggtagaac cgccaccatg   3180
gccaccaccg ccatgcgcat gatcatcagc atcatcttca tcagcaccta cgtgacccac   3240
atcaccctgt gccagaacat caccgaggag ttctaccaga gcacctgcag cgccgtgagt   3300
cgcggctacc tgagcgccct gcgcaccggc tggtacacca gcgtggtgac catcgagctg   3360
agcaagatcc agaagaacgt gtgcaacagc accgacagca aggtgaagct gatcaagcag   3420
gagctggagc gctacaacaa cgccgtggtg gagctgcaga gcctgatgca gaacgagccc   3480
gccagcttca gccgcgccaa gcgcggcatc cccgagctga tccactacac ccgcaacagc   3540
accaagaagt tctacggcct gatgggcaag aagcgcaagc gccgcttcct gggcttcctg   3600
ctgggcatcg gcagcgccat cgccagcggc gtggccgtga gcaaggtgct gcacctggag   3660
ggcgaggtga acaagatcaa gaacgccctg ctgagcacca acaaggccgt ggtgagcctg   3720
agcaacggcg tgagcgtgct gaccagcaag gtgctggacc tgaagaacta catcgacaag   3780
gagctgctgc ccaaggtgaa caaccacgac tgccgcatca gcaagatcga gaccgtgatc   3840
gagttccagc agaagaacaa ccgcctgctg gagatcgccc gcgagttcag cgtgaacgcc   3900
ggcatcacca ccccccctgag cacctacatg ctgaccaaca gcgagctgct gagcctgatc   3960
aacgacatgc ccatcaccaa cgaccagaag aagctgatga gcagcaacgt gcagatcgtg   4020
cgccagcaga gctacagcat catgagcgtg gtgaaggagg aggtgatcgc ctacgtggtg   4080
cagctgccca tctacggcgt gatcgacacc ccctgctgga agctgcacac cagccccctg   4140
tgcaccaccg acaacaagga gggcagcaac atctgcctga cccgcaccga tcgcggctgg   4200
tactgcgaca acgccggcag cgtgagcttc ttcccccaga ccgagacctg caaggtgcag   4260
agcaaccgcg tgttctgcga caccatgaac agcctgaccc tgcccaccga cgtgaacctg   4320
tgcaacaccg acatcttcaa caccaagtac gactgcaaga tcatgaccag caagaccgac   4380
atcagcagca gcgtgatcac cagcatcggc gccatcgtga gctgctacgg caagaccaag   4440
tgcaccgcca gcaacaagaa tcgcggcatc atcaagacct tcagcaacgg ctgcgactac   4500
gtgagcaaca agggcgtgga caccgtgagc gtgggcaaca ccctgtacta cgtgaacaag   4560
ctggagggca aggccctgta catcaagggc gagcccatca tcaactacta cgacccccctg   4620
gtgttcccca gcgacgagtt cgacgccagc atcgcccagg tgaacgccaa gatcaaccag   4680
agcctggcct tcatccgccg cagcgacgag ctgctgcaca gcgtggacgt gggcaagagc   4740
accaccaacg tggtgatcac caccatcatc atcgtgatcg tggtggtgat cctgatgctg   4800
atcgccgtgg gcctgctgtt ctactgcaag accaagagca cccccatcat gctgggcaag   4860
gaccagctga gcggcatcaa caacctgagc ttcagcaagt aacccccccgc ggacccaagg   4920
tccaactctc caagcggcaa tcctctctcg cttcctcagc cccactgaat gatcgcgtaa   4980
ccgtaattaa tctagctaca tttaagatta agaaaaaaata cgggtagaat tggagtgccc   5040
caattgtgcc aagatggact catctaggac aattgggctg tactttgatt ctgcccattc   5100
ttctagcaac ctgttagcat ttccgatcgt cctacaagac acaggagatg ggaagaagca   5160
aatcgccccg caatatagga tccagcgcct tgacttgtgg actgatagta aggaggactc   5220
agtattcatc accacctatg gattcatctt tcaagttggg aatgaagaag ccaccgtcgg   5280
catgatcgat gataaaccca agcgcgagtt actttccgct gcgatgctct gcctaggaag   5340
cgtcccaaat accggagacc ttattgagct ggcaagggcc tgtctcacta tgatagtcac   5400
```

```
atgcaagaag agtgcaacta atactgagag aatggttttc tcagtagtgc aggcacccca   5460
agtgctgcaa agctgtaggg ttgtggcaaa caaatactca tcagtgaatg cagtcaagca   5520
cgtgaaagcg ccagagaaga ttcccgggag tggaacccta gaatacaagg tgaactttgt   5580
ctccttgact gtggtaccga agagggatgt ctacaagatc ccagctgcag tattgaaggt   5640
ttctggctcg agtctgtaca atcttgcgct caatgtcact attaatgtgg aggtagaccc   5700
gaggagtcct ttggttaaat ctctgtctaa gtctgacagc ggatactatg ctaacctctt   5760
cttgcatatt ggacttatga ccactgtaga taggaagggg aagaaagtga catttgacaa   5820
gctggaaaag aaaataagga gccttgatct atctgtcggg ctcagtgatg tgctcgggcc   5880
ttccgtgttg gtaaaagcaa gaggtgcacg gactaagctt ttggcacctt tcttctctag   5940
cagtgggaca gcctgctatc ccatagcaaa tgcttctcct caggtggcca agatactctg   6000
gagtcaaacc gcgtgcctgc ggagcgttaa aatcattatc caagcaggta cccaacgcgc   6060
tgtcgcagtg accgccgacc acgaggttac ctctactaag ctggagaagg ggcacaccct   6120
tgccaaatac aatcctttta agaaataagc tgcgtctctg agattgcgct ccgcccactc   6180
acccagatca tcatgacaca aaaaactaat ctgtcttgat tatttacagt tagtttacct   6240
gtctatcaag ttagaaaaaa cacgggtaga agattctgga tcccggttgg cgccctccag   6300
gtgcaagatg ggctccagac cttctaccaa gaacccagca cctatgatgc tgactatccg   6360
ggttgcgctg gtactgagtt gcatctgtcc ggcaaactcc attgatggca ggcctcttgc   6420
agctgcagga attgtggtta caggagacaa agccgtcaac atatacacct catcccagac   6480
aggatcaatc atagttaagc tcctcccgaa tctgcccaag gataaggagg catgtgcgaa   6540
agccccttg gatgcataca acaggacatt gaccactttg ctcacccccc ttggtgactc   6600
tatccgtagg atacaagagt ctgtgactac atctggaggg gggagacagg ggcgccttat   6660
aggcgccatt attggcggtg tggctcttgg ggttgcaact gccgcacaaa taacagcggc   6720
cgcagctctg atacaagcca aacaaaatgc tgccaacatc ctccgactta aagagagcat   6780
tgccgcaacc aatgaggctg tgcatgaggt cactgacgga ttatcgcaac tagcagtggc   6840
agttgggaag atgcagcagt ttgttaatga ccaatttaat aaaacagctc aggaattaga   6900
ctgcatcaaa attgcacagc aagttggtgt agagctcaac ctgtacctaa ccgaattgac   6960
tacagtattc ggaccacaaa tcacttcacc tgctttaaac aagctgacta ttcaggcact   7020
ttacaatcta gctggtggaa atatggatta cttattgact aagttaggtg tagggaacaa   7080
tcaactcagc tcattaatcg gtagcggctt aatcaccggt aaccctattc tatacgactc   7140
acagactcaa ctcttgggta tacaggtaac tctaccttca gtcgggaacc taaataatat   7200
gcgtgccacc tacttggaaa ccttatccgt aagcacaacc aggggatttg cctcggcact   7260
tgtcccaaaa gtggtgacac aggtcggttc tgtgatagaa gaacttgaca cctcatactg   7320
tatagaaact gacttagatt tatattgtac aagaatagta acgttcccta tgtcccctgg   7380
tatttattcc tgcttgagcg gcaatacgtc ggcctgtatg tactcaaaga ccgaaggcgc   7440
acttactaca ccatacatga ctatcaaagg ttcagtcatc gccaactgca agatgacaac   7500
atgtagatgt gtaaaccccc cgggtatcat atcgcaaaac tatggagaag ccgtgtctct   7560
aatagataaa caatcatgca atgttttatc cttaggcggg ataactttaa ggctcagtgg   7620
ggaattcgat gtaacttatc agaagaatat ctcaatacaa gattctcaag taataataac   7680
aggcaatctt gatatctcaa ctgagcttgg gaatgtcaac aactcgatca gtaatgcttt   7740
```

```
gaataagtta gaggaaagca acagaaaact agacaaagtc aatgtcaaac tgactagcac   7800
atctgctctc attacctata tcgttttgac tatcatatct cttgtttttg gtatacttag   7860
cctgattcta gcatgctacc taatgtacaa gcaaaaggcg caacaaaaga ccttattatg   7920
gcttgggaat aatactctag atcagatgag agccactaca aaaatgtgaa cacagatgag   7980
gaacgaaggt ttccctaata gtaatttgtg tgaaagttct ggtagtctgt cagttcagag   8040
agttaagaaa aaactaccgg ttgtagatga ccaaaggacg atatacgggt agaacggtaa   8100
gagaggccgc ccctcaattg cgagccaggc ttcacaacct ccgttctacc gcttcaccga   8160
caacagtcct caatcatgga ccgcgccgtt agccaagttg cgttagagaa tgatgaaaga   8220
gaggcaaaaa atacatggcg cttgatattc cggattgcaa tcttattctt aacagtagtg   8280
accttggcta tatctgtagc ctccctttta tatagcatgg gggctagcac acctagcgat   8340
cttgtaggca taccgactag gatttccagg gcagaagaaa agattacatc tacacttggt   8400
tccaatcaag atgtagtaga taggatatat aagcaagtgg cccttgagtc tccgttggca   8460
ttgttaaata ctgagaccac aattatgaac gcaataacat ctctctctta tcagattaat   8520
ggagctgcaa acaacagtgg gtggggggca cctatccatg acccagatta tatagggggg   8580
ataggcaaag aactcattgt agatgatgct agtgatgtca catcattcta tccctctgca   8640
tttcaagaac atctgaattt tatcccggcg cctactacag gatcaggttg cactcgaata   8700
ccctcatttg acatgagtgc tacccattac tgctacaccc ataatgtaat attgtctgga   8760
tgcagagatc actcacattc atatcagtat ttagcacttg gtgtgctccg gacatctgca   8820
acagggaggg tattcttttc tactctgcgt tccatcaacc tggacgacac ccaaaatcgg   8880
aagtcttgca gtgtgagtgc aactcccctg ggttgtgata tgctgtgctc gaaagtcacg   8940
gagacagagg aagaagatta taactcagct gtccctacgc ggatggtaca tgggaggtta   9000
gggttcgacg gccagtacca cgaaaaggac ctagatgtca caacattatt cggggactgg   9060
gtggccaact acccaggagt agggggtgga tcttttattg acagccgcgt atggttctca   9120
gtctacggag ggttaaaacc caattcaccc agtgacactg tacaggaagg gaaatatgtg   9180
atatacaagc gatacaatga cacatgccca gatgagcaag actaccagat tcgaatggcc   9240
aagtcttcgt ataagcctgg acggtttggt gggaaacgca tacagcaggc tatcttatct   9300
atcaaggtgt caacatcctt aggcgaagac ccggtactga ctgtaccgcc caacacagtc   9360
acactcatgg gggccgaagg cagaattctc acagtaggga catctcattt cttgtatcaa   9420
cgagggtcat catacttctc tcccgcgtta ttatatccta tgacagtcag caacaaaaca   9480
gccactcttc atagtcctta tacattcaat gccttcactc ggccaggtag tatcccttgc   9540
caggcttcag caagatgccc caactcgtgt gttactggag tctatacaga tccatatccc   9600
ctaatcttct atagaaacca caccttgcga ggggtattcg ggacaatgct tgatggtgta   9660
caagcaagac ttaaccctgc gtctgcagta ttcgatagca catcccgcag tcgcattact   9720
cgagtgagtt caagcagtac caaagcagca tacacaacat caacttgttt taaagtggtc   9780
aagactaata agacctattg tctcagcatt gctgaaatat ctaatactct cttcggagaa   9840
ttcagaatcg tcccgttact agttgagatc ctcaaagatg acggggttag agaagccagg   9900
tctggctagt tgagtcaatt ataaaggagt tggaaagatg gcattgtatc acctatcttc   9960
tgcgacatca agaatcaaac cgaatgccgg cgcgtgctcg aattccatgt tgccagttga  10020
ccacaatcag ccagtgctca tgcgatcaga ttaagccttg tcaatagtct cttgattaag  10080
aaaaaatgta agtggcaatg agatacaagg caaaacagct catggttaac aatacgggta  10140
```

```
ggacatggcg agctccggtc ctgaaagggc agagcatcag attatcctac cagagtcaca  10200
cctgtcttca ccattggtca agcacaaact actctattac tggaaattaa ctgggctacc  10260
gcttcctgat gaatgtgact tcgaccacct cattctcagc cgacaatgga aaaaaatact  10320
tgaatcggcc tctcctgata ctgagagaat gataaaactc ggaagggcag tacaccaaac  10380
tcttaaccac aattccagaa taaccggagt gctccacccc aggtgtttag aagaactggc  10440
taatattgag gtcccagatt caaccaacaa atttcggaag attgagaaga agatccaaat  10500
tcacaacacg agatatggag aactgttcac aaggctgtgt acgcatatag agaagaaact  10560
gctggggtca tcttggtcta acaatgtccc ccggtcagag gagttcagca gcattcgtac  10620
ggatccggca ttctggtttc actcaaaatg gtccacagcc aagtttgcat ggctccatat  10680
aaaacagatc cagaggcatc tgatggtggc agctaggaca aggtctgcgg ccaacaaatt  10740
ggtgatgcta acccataagg taggccaagt ctttgtcact cctgaacttg tcgttgtgac  10800
gcatacgaat gagaacaagt tcacatgtct tacccaggaa cttgtattga tgtatgcaga  10860
tatgatggag ggcagagata tggtcaacat aatatcaacc acggcggtgc atctcagaag  10920
cttatcagag aaaattgatg acattttgcg gttaatagac gctctggcaa aagacttggg  10980
taatcaagtc tacgatgttg tatcactaat ggagggattt gcatacggag ctgtccagct  11040
actcgagccg tcaggtacat ttgcaggaga tttcttcgca ttcaacctgc aggagcttaa  11100
agacattcta attggcctcc tccccaatga tatagcagaa tccgtgactc atgcaatcgc  11160
tactgtattc tctggtttag aacagaatca agcagctgag atgttgtgtc tgttgcgtct  11220
gtggggtcac ccactgcttg agtcccgtat tgcagcaaag gcagtcagga gccaaatgtg  11280
cgcaccgaaa atggtagact ttgatatgat ccttcaggta ctgtctttct tcaagggaac  11340
aatcatcaac gggtacagaa agaagaatgc aggtgtgtgg ccgcgagtca aagtggatac  11400
aatatatggg aaggtcattg ggcaactaca tgcagattca gcagagattt cacacgatat  11460
catgttgaga gagtataaga gtttatctgc acttgaattt gagccatgta tagaatatga  11520
ccctgtcacc aacctgagca tgttcctaaa agacaaggca atcgcacacc ccaacgataa  11580
ttggcttgcc tcgtttaggc ggaaccttct ctccgaagac cagaagaaac atgtaaaaga  11640
agcaacttcg actaatcgcc tcttgataga gtttttagag tcaaatgatt ttgatccata  11700
taaagagatg gaatatctga cgacccttga gtaccttaga gatgacaatg tggcagtatc  11760
atactcgctc aaggagaagg aagtgaaagt taatggacgg atcttcgcta agctgacaaa  11820
gaagttaagg aactgtcagg tgatggcgga agggatccta gccgatcaga ttgcaccttt  11880
ctttcaggga aatggagtca ttcaggatag catatccttg accaagagta tgctagcgat  11940
gagtcaactg tcttttaaca gcaataagaa acgtatcact gactgtaaag aaagagtatc  12000
ttcaaaccgc aatcatgatc cgaaaagcaa gaaccgtcgg agagttgcaa ccttcataac  12060
aactgacctg caaaagtact gtcttaattg gagatatcag acaatcaaat tgttcgctca  12120
tgccatcaat cagttgatgg gcctacctca cttcttcgaa tggattcacc taagactgat  12180
ggacactacg atgttcgtag gagacccttt caatcctcca agtgacccta ctgactgtga  12240
cctctcaaga gtccctaatg atgacatata tattgtcagt gccagagggg gtatcgaagg  12300
attatgccag aagctatgga caatgatctc aattgctgca atccaacttg ctgcagctag  12360
atcgcattgt cgtgttgcct gtatggtaca gggtgataat caagtaatag cagtaacgag  12420
agaggtaaga tcagacgact ctccggagat ggtgttgaca cagttgcatc aagccagtga  12480
```

```
taatttcttc aaggaattaa ttcatgtcaa tcatttgatt ggccataatt tgaaggatcg  12540
tgaaaccatc aggtcagaca cattcttcat atacagcaaa cgaatcttca aagatggagc  12600
aatcctcagt caagtcctca aaaattcatc taaattagtg ctagtgtcag gtgatctcag  12660
tgaaaacacc gtaatgtcct gtgccaacat tgcctctact gtagcacggc tatgcgagaa  12720
cgggcttccc aaagacttct gttactattt aaactatata atgagttgtg tgcagacata  12780
ctttgactct gagttctcca tcaccaacaa ttcgcacccc gatcttaatc agtcgtggat  12840
tgaggacatc tcttttgtgc actcatatgt tctgactcct gcccaattag gggactgag  12900
taaccttcaa tactcaaggc tctacactag aaatatcggt gacccgggga ctactgcttt  12960
tgcagagatc aagcgactag aagcagtggg attactgagt cctaacatta tgactaatat  13020
cttaactagg ccgcctggga atggagattg ggccagtctg tgcaacgacc catactcttt  13080
caattttgag actgttgcaa gcccaaatat tgttcttaag aaacatacgc aaagagtcct  13140
atttgaaact tgttcaaatc ccttattgtc tggagtgcac acagaggata atgaggcaga  13200
agagaaggca ttggctgaat tcttgcttaa tcaagaggtg attcatcccc gcgttgcgca  13260
tgccatcatg gaggcaagct ctgtaggtag gagaaagcaa attcaagggc ttgttgacac  13320
aacaaacacc gtaattaaga ttgcgcttac taggaggcca ttaggcatca agaggctgat  13380
gcggatagtc aattattcta gcatgcatgc aatgctgttt agagacgatg tttttcctc  13440
cagtagatcc aaccacccct tagtctcttc taatatgtgt tctctgacac tggcagacta  13500
tgcacggaat agaagctggt cacctttgac gggaggcagg aaaatactgg gtgtatctaa  13560
tcctgatacg atagaactcg tagagggtga gattcttagt gtaagcggag ggtgtacaag  13620
atgtgacagc ggagatgaac aatttacttg gttccatctt ccaagcaata tagaattgac  13680
cgatgacacc agcaagaatc ctccgatgag ggtaccatat ctcgggtcaa agacacagga  13740
gaggagagct gcctcacttg caaaaatagc tcatatgtcg ccacatgtaa aggctgccct  13800
aagggcatca tccgtgttga tctgggctta tggggataat gaagtaaatt ggactgctgc  13860
tcttacgatt gcaaaatctc ggtgtaatgt aaacttagag tatcttcggt tactgtcccc  13920
tttacccacg gctgggaatc ttcaacatag actagatgat ggtataactc agatgacatt  13980
cacccctgca tctctctaca gggtgtcacc ttacattcac atatccaatg attctcaaag  14040
gctgttcact gaagaaggag tcaaagaggg gaatgtggtt taccaacaga tcatgctctt  14100
gggtttatct ctaatcgaat cgatctttcc aatgacaaca accaggacat atgatgagat  14160
cacactgcac ctacatagta aatttagttg ctgtatcaga gaagcacctg ttgcggttcc  14220
tttcgagcta cttggggtgg taccggaact gaggacagtg acctcaaata agtttatgta  14280
tgatcctagc cctgtatcgg agggagactt tgcgagactt gacttagcta tcttcaagag  14340
ttatgagctt aatctggagt catatcccac gatagagcta atgaacattc tttcaatatc  14400
cagcgggaag ttgattggcc agtctgtggt ttcttatgat gaagatacct ccataaagaa  14460
tgacgccata atagtgtatg acaatacccg aaattggatc agtgaagctc agaattcaga  14520
tgtggtccgc ctatttgaat atgcagcact tgaagtgctc ctcgactgtt cttaccaact  14580
ctattacctg agagtaagag gcctggacaa tattgtctta tatatgggtg atttatacaa  14640
gaatatgcca ggaattctac tttccaacat tgcagctaca atatctcatc ccgtcattca  14700
ttcaaggtta catgcagtgg gcctggtcaa ccatgacgga tcacaccaac ttgcagatac  14760
ggattttatc gaaatgtctg caaaactatt agtatcttgc acccgacgtg tgatctccgg  14820
cttatattca ggaaataagt atgatctgct gttcccatct gtcttagatg ataacctgaa  14880
```

-continued

```
tgagaagatg cttcagctga tatcccggtt atgctgtctg tacacggtac tctttgctac  14940
aacaagagaa atcccgaaaa taagaggctt aactgcagaa gagaaatgtt caatactcac  15000
tgagtattta ctgtcggatg ctgtgaaacc attacttagc cccgatcaag tgagctctat  15060
catgtctcct aacataatta cattcccagc taatctgtac tacatgtctc ggaagagcct  15120
caatttgatc agggaaaggg aggacaggga tactatcctg gcgttgttgt tcccccaaga  15180
gccattatta gagttccctt ctgtgcaaga tattggtgct cgagtgaaag atccattcac  15240
ccgacaacct gcggcatttt tgcaagagtt agatttgagt gctccagcaa ggtatgacgc  15300
attcacactt agtcagattc atcctgaact cacatctcca aatccggagg aagactactt  15360
agtacgatac ttgttcagag ggatagggac tgcatcttcc tcttggtata aggcatctca  15420
tctcctttct gtacccgagg taagatgtgc aagacacggg aactccttat acttagctga  15480
agggagcgga gccatcatga gtcttctcga actgcatgta ccacatgaaa ctatctatta  15540
caatacgctc ttttcaaatg agatgaaccc cccgcaacga catttcgggc cgaccccaac  15600
tcagtttttg aattcggttg tttataggaa tctacaggcg gaggtaacat gcaaagatgg  15660
atttgtccaa gagttccgtc cattatggag agaaaataca gaggaaagcg acctgacctc  15720
agataaagta gtggggtata ttacatctgc agtgccctac agatctgtat cattgctgca  15780
ttgtgacatt gaaattcctc cagggtccaa tcaaagctta ctagatcaac tagctatcaa  15840
tttatctctg attgccatgc attctgtaag ggagggcggg gtagtaatca tcaaagtgtt  15900
gtatgcaatg ggatactact ttcatctact catgaacttg tttgctccgt gttccacaaa  15960
aggatatatt ctctctaatg gttatgcatg tcgaggagat atggagtgtt acctggtatt  16020
tgtcatgggt tacctgggcg ggcctacatt tgtacatgag gtggtgagga tggcgaaaac  16080
tctggtgcag cggcacggta cgcttttgtc taaatcagat gagatcacac tgaccaggtt  16140
attcacctca cagcggcagc gtgtgacaga catcctatcc agtcctttac caagattaat  16200
aaagtacttg aggaagaata ttgacactgc gctgattgaa gccgggggac agcccgtccg  16260
tccattctgt gcggagagtc tggtgagcac gctagcgaac ataactcaga taacccagat  16320
catcgctagt cacattgaca cagttatccg gtctgtgata tatatggaag ctgagggtga  16380
tctcgctgac acagtatttc tatttacccc ttacaatctc tctactgacg ggaaaaagag  16440
gacatcactt aaacagtgca cgagacagat cctagaggtt acaatactag gtcttagagt  16500
cgaaaatctc aataaaatag gcgatataat cagcctagtg cttaaaggca tgatctccat  16560
ggaggacctt atcccactaa ggacatactt gaagcatagt acctgcccta aatatttgaa  16620
ggctgtccta ggtattacca aactcaaaga aatgtttaca gacacttctg tactgtactt  16680
gactcgtgct caacaaaaat tctacatgaa aactataggc aatgcagtca aaggatatta  16740
cagtaactgt gactcttaac gaaaatcaca tattaatagg ctcctttttt ggccaattgt  16800
attcttgttg atttaatcat attatgttag aaaaaagttg aaccctgact ccttaggact  16860
cgaattcgaa ctcaaataaa tgtcttaaaa aaaggttgcg cacaattatt cttgagtgta  16920
gtctcgtcat tcaccaaatc tttgtttggt                                  16950
```

<210> SEQ ID NO 14
<211> LENGTH: 1740
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 14
atggccacca ccgccatgcg catgatcatc agcatcatct tcatcagcac ctacgtgacc 60
cacatcaccc tgtgccagaa catcaccgag gagttctacc agagcacctg cagcgccgtg 120
agtcgcggct acctgagcgc cctgcgcacc ggctggtaca ccagcgtggt gaccatcgag 180
ctgagcaaga tccagaagaa cgtgtgcaac agcaccgaca gcaaggtgaa gctgatcaag 240
caggagctgg agcgctacaa caacgccgtg gtggagctgc agagcctgat gcagaacgag 300
cccgccagct tcagccgcgc caagcgcggc atccccgagc tgatccacta cacccgcaac 360
agcaccaaga agttctacgg cctgatgggc aagaagcgca agcgccgctt cctgggcttc 420
ctgctgggca tcggcagcgc catcgccagc ggcgtggccg tgagcaaggt gctgcacctg 480
gagggcgagg tgaacaagat caagaacgcc ctgctgagca ccaacaaggc cgtggtgagc 540
ctgagcaacg gcgtgagcgt gctgaccagc aaggtgctgg acctgaagaa ctacatcgac 600
aaggagctgc tgcccaaggt gaacaaccac gactgccgca tcagcaagat cgagaccgtg 660
atcgagttcc agcagaagaa caaccgcctg ctggagatcg cccgcgagtt cagcgtgaac 720
gccggcatca ccacccccct gagcacctac atgctgacca acagcgagct gctgagcctg 780
atcaacgaca tgcccatcac caacgaccag aagaagctga tgagcagcaa cgtgcagatc 840
gtgcgccagc agagctacag catcatgagc gtggtgaagg aggaggtgat cgcctacgtg 900
gtgcagctgc ccatctacgg cgtgatcgac accccctgct ggaagctgca caccagcccc 960
ctgtgcacca ccgacaacaa ggagggcagc aacatctgcc tgacccgcac cgatcgcggc 1020
tggtactgcg acaacgccgg cagcgtgagc ttcttccccc agaccgagac ctgcaaggtg 1080
cagagcaacc gcgtgttctg cgacaccatg aacagcctga ccctgcccac cgacgtgaac 1140
ctgtgcaaca ccgacatctt caacaccaag tacgactgca agatcatgac cagcaagacc 1200
gacatcagca gcagcgtgat caccagcatc ggcgccatcg tgagctgcta cggcaagacc 1260
aagtgcaccg ccagcaacaa gaatcgcggc atcatcaaga ccttcagcaa cggctgcgac 1320
tacgtgagca acaagggcgt ggacaccgtg agcgtgggca acaccctgta ctacgtgaac 1380
aagctggagg gcaaggccct gtacatcaag ggcgagccca tcatcaacta ctacgacccc 1440
ctggtgttcc ccagcgacga gttcgacgcc agcatcgccc aggtgaacgc caagatcaac 1500
cagagcctgg ccttcatccg ccgcagcgac gagctgctgc acagcgtgga cgtgggcaag 1560
agcaccacca acgttaacct cattacctat atcgttttga ctatcatatc tcttgttttt 1620
ggtatactta gcctgattct agcatgctac ctaatgtaca agcaaaaggc gcaacaaaag 1680
accttattat ggcttgggaa taataccta gatcagatga gagccactac aaaaatgtga 1740

<210> SEQ ID NO 15
<211> LENGTH: 545
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 15

Met Ser Trp Lys Val Val Ile Ile Phe Ser Leu Leu Ile Thr Pro Gln
1 5 10 15

His Gly Leu Lys Glu Ser Tyr Leu Glu Glu Ser Cys Ser Thr Ile Thr
20 25 30

Glu Gly Tyr Leu Ser Val Leu Arg Thr Gly Trp Tyr Thr Asn Val Phe

```
        35                  40                  45

Thr Leu Glu Val Gly Asp Val Glu Asn Leu Thr Cys Ser Asp Gly Pro
    50                  55                  60

Ser Leu Ile Lys Thr Glu Leu Asp Leu Thr Lys Ser Ala Leu Arg Glu
65                  70                  75                  80

Leu Lys Thr Val Ser Ala Asp Gln Leu Ala Arg Glu Glu Gln Ile Glu
                85                  90                  95

Asn Pro Arg Gln Ser Arg Phe Val Leu Gly Ala Ile Ala Leu Gly Val
            100                 105                 110

Ala Thr Ala Ala Ala Val Thr Ala Gly Val Ala Ile Ala Lys Thr Ile
        115                 120                 125

Arg Leu Glu Ser Glu Val Thr Ala Ile Lys Asn Ala Leu Lys Thr Thr
    130                 135                 140

Asn Glu Ala Val Ser Thr Leu Gly Asn Gly Val Arg Val Leu Ala Thr
145                 150                 155                 160

Ala Val Arg Glu Leu Lys Asp Phe Val Ser Lys Asn Leu Thr Arg Ala
                165                 170                 175

Ile Asn Lys Asn Lys Cys Asp Ile Asp Asp Leu Lys Met Ala Val Ser
            180                 185                 190

Phe Ser Gln Phe Asn Arg Arg Phe Leu Asn Val Val Arg Gln Phe Ser
        195                 200                 205

Asp Asn Ala Gly Ile Thr Pro Ala Ile Ser Leu Asp Leu Met Thr Asp
    210                 215                 220

Ala Glu Leu Ala Arg Ala Val Ser Asn Met Pro Thr Ser Ala Gly Gln
225                 230                 235                 240

Ile Lys Leu Met Leu Glu Asn Arg Ala Met Val Arg Arg Lys Gly Phe
                245                 250                 255

Gly Ile Leu Ile Gly Val Tyr Gly Ser Ser Val Ile Tyr Met Val Gln
            260                 265                 270

Leu Pro Ile Phe Gly Val Ile Asp Thr Pro Cys Trp Ile Val Lys Ala
        275                 280                 285

Ala Pro Ser Cys Ser Glu Lys Lys Gly Asn Tyr Ala Cys Leu Leu Arg
    290                 295                 300

Glu Asp Gln Gly Trp Tyr Cys Gln Asn Ala Gly Ser Thr Val Tyr Tyr
305                 310                 315                 320

Pro Asn Glu Lys Asp Cys Glu Thr Arg Gly Asp His Val Phe Cys Asp
                325                 330                 335

Thr Ala Ala Gly Ile Asn Val Ala Glu Gln Ser Lys Glu Cys Asn Ile
            340                 345                 350

Asn Ile Ser Thr Thr Asn Tyr Pro Cys Lys Val Ser Thr Gly Arg His
        355                 360                 365

Pro Ile Ser Met Val Ala Leu Ser Pro Leu Gly Ala Leu Val Ala Cys
    370                 375                 380

Tyr Lys Gly Val Ser Cys Ser Ile Gly Ser Asn Arg Val Gly Ile Ile
385                 390                 395                 400

Lys Gln Leu Asn Lys Gly Cys Ser Tyr Ile Thr Asn Gln Asp Ala Asp
                405                 410                 415

Thr Val Thr Ile Asp Asn Thr Val Tyr Gln Leu Ser Lys Val Glu Gly
            420                 425                 430

Glu Gln His Val Ile Lys Gly Arg Pro Val Ser Ser Ser Phe Asp Pro
        435                 440                 445

Ile Lys Phe Pro Glu Asp Gln Phe Asn Val Ala Leu Asp Gln Val Phe
    450                 455                 460
```

```
Glu Ser Ile Glu Asn Ser Gln Ala Leu Val Asp Gln Ser Asn Arg Ile
465                 470                 475                 480

Leu Ser Ser Ala Glu Lys Gly Asn Thr Gly Val Asn Leu Ile Thr Tyr
                485                 490                 495

Ile Val Leu Thr Ile Ile Ser Leu Val Phe Gly Ile Leu Ser Leu Ile
            500                 505                 510

Leu Ala Cys Tyr Leu Met Tyr Lys Gln Lys Ala Gln Gln Lys Thr Leu
        515                 520                 525

Leu Trp Leu Gly Asn Asn Thr Leu Asp Gln Met Arg Ala Thr Thr Lys
    530                 535                 540

Met
545


<210> SEQ ID NO 16
<211> LENGTH: 1620
<212> TYPE: DNA
<213> ORGANISM: Human metapneumovirus

<400> SEQUENCE: 16

atgtcttgga aagtggtgat catttttca ttgctaataa cacctcaaca cggtcttaaa     60

gagagctacc tagaagaatc atgtagcact ataactgagg gatatcttag tgttctgagg    120

acaggttggt ataccaacgt tttacatta gaggtgggtg atgtagaaaa ccttacatgt    180

tctgatggac ctagcctaat aaaaacagaa ttagatctga ccaaaagtgc actaagagag    240

ctcaaaacag tctctgctga ccaattggca agagaggaac aaattgagaa tcccagacaa    300

tctaggtttg ttctaggagc aatagcactc ggtgttgcaa cagcagctgc agtcacagca    360

ggtgttgcaa ttgccaaaac catccggctt gagagtgaag tcacagcaat taagaatgcc    420

ctcaaaacga ccaatgaagc agtatctaca ttggggaatg gagttcgagt gttggcaact    480

gcagtgagag agctgaaaga ctttgtgagc aagaatttaa ctcgtgcaat caacaaaaac    540

aagtgcgaca ttgatgacct aaaaatggcc gttagcttca gtcaattcaa cagaaggttt    600

ctaaatgttg tgcggcaatt ttcagacaat gctggaataa caccagcaat atctttggac    660

ttaatgacag atgctgaact agccagggcc gtttctaaca tgccgacatc tgcaggacaa    720

ataaaattga tgttggagaa ccgcgcgatg gtgcgaagaa aggggttcgg aatcctgata    780

ggggtctacg ggagctctgt aatttacatg gtgcagctgc caatctttgg cgttatagac    840

acgccttgct ggatagtaaa agcagcccct tcttgttccg aaaaaaaggg aaactatgct    900

tgcctcttaa gagaagacca agggtggtat tgtcagaatg cagggtcaac tgtttactac    960

ccaaatgaga aagactgtga aacaagagga gaccatgtct tttgcgacac agcagcagga   1020

attaatgttg ctgagcaatc aaaggagtgc aacatcaaca tatccactac aaattaccca   1080

tgcaaagtca gcacaggaag acatcctatc agtatggttg cactgtctcc tcttggggct   1140

ctggttgctt gctacaaagg agtaagctgt tccattggca gcaacagagt agggatcatc   1200

aagcagctga acaaaggttg ctcctatata accaaccaag atgcagacac agtgacaata   1260

gacaacactg tatatcagct aagcaaagtt gagggtgaac agcatgttat aaaaggcaga   1320

ccagtgtcaa gcagctttga tccaatcaag tttcctgaag atcaattcaa tgttgcactt   1380

gaccaagttt ttgagagcat tgaaaacagc caggccttgg tagatcaatc aaacagaatc   1440

ctaagcagtg cagagaaagg gaatactggc ttcatcattg taataattct aattgctgtc   1500

cttggctcta gcatgatcct agtgagcatc ttcattataa tcaagaaaac aaagaaacca   1560
```

acgggagcac ctccagagct gagtggtgtc acaaacaatg gcttcatacc acacagttag 1620

<210> SEQ ID NO 17
<211> LENGTH: 539
<212> TYPE: PRT
<213> ORGANISM: Human metapneumovirus

<400> SEQUENCE: 17

```
Met Ser Trp Lys Val Val Ile Ile Phe Ser Leu Leu Ile Thr Pro Gln
1               5                   10                  15

His Gly Leu Lys Glu Ser Tyr Leu Glu Glu Ser Cys Ser Thr Ile Thr
            20                  25                  30

Glu Gly Tyr Leu Ser Val Leu Arg Thr Gly Trp Tyr Thr Asn Val Phe
        35                  40                  45

Thr Leu Glu Val Gly Asp Val Glu Asn Leu Thr Cys Ser Asp Gly Pro
    50                  55                  60

Ser Leu Ile Lys Thr Glu Leu Asp Leu Thr Lys Ser Ala Leu Arg Glu
65                  70                  75                  80

Leu Lys Thr Val Ser Ala Asp Gln Leu Ala Arg Glu Glu Gln Ile Glu
                85                  90                  95

Asn Pro Arg Gln Ser Arg Phe Val Leu Gly Ala Ile Ala Leu Gly Val
            100                 105                 110

Ala Thr Ala Ala Ala Val Thr Ala Gly Val Ala Ile Ala Lys Thr Ile
        115                 120                 125

Arg Leu Glu Ser Glu Val Thr Ala Ile Lys Asn Ala Leu Lys Thr Thr
    130                 135                 140

Asn Glu Ala Val Ser Thr Leu Gly Asn Gly Val Arg Val Leu Ala Thr
145                 150                 155                 160

Ala Val Arg Glu Leu Lys Asp Phe Val Ser Lys Asn Leu Thr Arg Ala
                165                 170                 175

Ile Asn Lys Asn Lys Cys Asp Ile Asp Asp Leu Lys Met Ala Val Ser
            180                 185                 190

Phe Ser Gln Phe Asn Arg Arg Phe Leu Asn Val Val Arg Gln Phe Ser
        195                 200                 205

Asp Asn Ala Gly Ile Thr Pro Ala Ile Ser Leu Asp Leu Met Thr Asp
    210                 215                 220

Ala Glu Leu Ala Arg Ala Val Ser Asn Met Pro Thr Ser Ala Gly Gln
225                 230                 235                 240

Ile Lys Leu Met Leu Glu Asn Arg Ala Met Val Arg Arg Lys Gly Phe
                245                 250                 255

Gly Ile Leu Ile Gly Val Tyr Gly Ser Ser Val Ile Tyr Met Val Gln
            260                 265                 270

Leu Pro Ile Phe Gly Val Ile Asp Thr Pro Cys Trp Ile Val Lys Ala
        275                 280                 285

Ala Pro Ser Cys Ser Glu Lys Lys Gly Asn Tyr Ala Cys Leu Leu Arg
    290                 295                 300

Glu Asp Gln Gly Trp Tyr Cys Gln Asn Ala Gly Ser Thr Val Tyr Tyr
305                 310                 315                 320

Pro Asn Glu Lys Asp Cys Glu Thr Arg Gly Asp His Val Phe Cys Asp
                325                 330                 335

Thr Ala Ala Gly Ile Asn Val Ala Glu Gln Ser Lys Glu Cys Asn Ile
            340                 345                 350

Asn Ile Ser Thr Thr Asn Tyr Pro Cys Lys Val Ser Thr Gly Arg His
        355                 360                 365
```

-continued

```
Pro Ile Ser Met Val Ala Leu Ser Pro Leu Gly Ala Leu Val Ala Cys
    370                 375                 380

Tyr Lys Gly Val Ser Cys Ser Ile Gly Ser Asn Arg Val Gly Ile Ile
385                 390                 395                 400

Lys Gln Leu Asn Lys Gly Cys Ser Tyr Ile Thr Asn Gln Asp Ala Asp
                405                 410                 415

Thr Val Thr Ile Asp Asn Thr Val Tyr Gln Leu Ser Lys Val Glu Gly
            420                 425                 430

Glu Gln His Val Ile Lys Gly Arg Pro Val Ser Ser Ser Phe Asp Pro
        435                 440                 445

Ile Lys Phe Pro Glu Asp Gln Phe Asn Val Ala Leu Asp Gln Val Phe
    450                 455                 460

Glu Ser Ile Glu Asn Ser Gln Ala Leu Val Asp Gln Ser Asn Arg Ile
465                 470                 475                 480

Leu Ser Ser Ala Glu Lys Gly Asn Thr Gly Phe Ile Ile Val Ile Ile
                485                 490                 495

Leu Ile Ala Val Leu Gly Ser Ser Met Ile Leu Val Ser Ile Phe Ile
            500                 505                 510

Ile Ile Lys Lys Thr Lys Lys Pro Thr Gly Ala Pro Pro Glu Leu Ser
        515                 520                 525

Gly Val Thr Asn Asn Gly Phe Ile Pro His Ser
    530                 535
```

<210> SEQ ID NO 18
<211> LENGTH: 1620
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 18

```
atgagctgga aggtggtgat catcttcagc ctgctgatca ccccccagca cggcctgaag     60

gagagctacc tggaggagag ctgcagcacc atcaccgagg gctacctgag cgtgctgaga    120

accggctggt acaccaacgt gttcaccctg gaggtgggcg acgtggagaa cctgacctgc    180

agcgacggcc ccagcctgat caagaccgag ctggacctga ccaagagcgc cctgagagag    240

ctgaagaccg tgagcgccga ccagctggcc agagaggagc agatcgagaa ccccagacag    300

agcagattcg tgctgggcgc catcgccctg ggcgtggcca ccgccgccgc cgtgaccgcc    360

ggcgtggcca tcgccaagac catcagactg gagagcgagg tgaccgccat caagaacgcc    420

ctgaagacca ccaacgaggc cgtgagcacc ctgggcaacg gcgtgagagt gctggccacc    480

gccgtgagag agctgaagga cttcgtgagc aagaacctga ccagagccat caacaagaac    540

aagtgcgaca tcgacgacct gaagatggcc gtgagcttca gccagttcaa cagaagattc    600

ctgaacgtgg tgagacagtt cagcgacaac gccggcatca cccccgccat cagcctggac    660

ctgatgaccg acgccgagct ggccagagcc gtgagcaaca tgcccaccag cgccggccag    720

atcaagctga tgctggagaa cagagccatg gtgagaagaa agggcttcgg catcctgatc    780

ggcgtgtacg gcagcagcgt gatctacatg gtgcagctgc ccatcttcgg cgtgatcgac    840

accccctgct ggatcgtgaa ggccgccccc agctgcagcg agaagaaggg caactacgcc    900

tgcctgctga gagaggacca gggctggtac tgccagaacg ccggcagcac cgtgtactac    960

cccaacgaga aggactgcga gaccagaggc gaccacgtgt tctgcgacac cgccgccggc   1020

atcaacgtgg ccgagcagag caaggagtgc aacatcaaca tcagcaccac caactacccc   1080
```

```
tgcaaggtga gcaccggcag acaccccatc agcatggtgg ccctgagccc cctgggcgcc   1140

ctggtggcct gctacaaggg cgtgagctgc agcatcggca gcaacagagt gggcatcatc   1200

aagcagctga acaagggctg cagctacatc accaaccagg acgccgacac cgtgaccatc   1260

gacaacaccg tgtaccagct gagcaaggtg gagggcgagc agcacgtgat caagggcaga   1320

cccgtgagca gcagcttcga ccccatcaag ttccccgagg accagttcaa cgtggccctg   1380

gaccaggtgt tcgagagcat cgagaacagc caggccctgg tggaccagag caacagaatc   1440

ctgagcagcg ccgagaaggg caacaccggc ttcatcatcg tgatcatcct gatcgccgtg   1500

ctgggcagca gcatgatcct ggtgagcatc ttcatcatca tcaagaagac caagaagccc   1560

accggcgccc cccccgagct gagcggcgtg accaacaacg gcttcatccc ccacagctga   1620
```

<210> SEQ ID NO 19
<211> LENGTH: 1638
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 19

```
atgagctgga aggtggtgat catcttcagc ctgctgatca ccccccagca cggcctgaag     60

gagagctacc tggaggagag ctgcagcacc atcaccgagg gctacctgag cgtgctgaga    120

accggctggt acaccaacgt gttcaccctg gaggtgggcg acgtggagaa cctgacctgc    180

agcgacggcc ccagcctgat caagaccgag ctggacctga ccaagagcgc cctgagagag    240

ctgaagaccg tgagcgccga ccagctggcc agagaggagc agatcgagaa ccccagacag    300

agcagattcg tgctgggcgc catcgccctg ggcgtggcca ccgccgccgc cgtgaccgcc    360

ggcgtggcca tcgccaagac catcagactg gagagcgagg tgaccgccat caagaacgcc    420

ctgaagacca ccaacgaggc cgtgagcacc ctgggcaacg gcgtgagagt gctggccacc    480

gccgtgagag agctgaagga cttcgtgagc aagaacctga ccagagccat caacaagaac    540

aagtgcgaca tcgacgacct gaagatggcc gtgagcttca gccagttcaa cagaagattc    600

ctgaacgtgg tgagacagtt cagcgacaac gccggcatca cccccgccat cagcctggac    660

ctgatgaccg acgccgagct ggccagagcc gtgagcaaca tgcccaccag cgccggccag    720

atcaagctga tgctggagaa cagagccatg gtgagaagaa agggcttcgg catcctgatc    780

ggcgtgtacg gcagcagcgt gatctacatg gtgcagctgc ccatcttcgg cgtgatcgac    840

acccccctgct ggatcgtgaa ggccgccccc agctgcagcg agaagaaggg caactacgcc    900

tgcctgctga gagaggacca gggctggtac tgccagaacg ccggcagcac cgtgtactac    960

cccaacgaga aggactgcga gaccagaggc gaccacgtgt tctgcgacac cgccgccggc   1020

atcaacgtgg ccgagcagag caaggagtgc aacatcaaca tcagcaccac caactacccc   1080

tgcaaggtga gcaccggcag acaccccatc agcatggtgg ccctgagccc cctgggcgcc   1140

ctggtggcct gctacaaggg cgtgagctgc agcatcggca gcaacagagt gggcatcatc   1200

aagcagctga acaagggctg cagctacatc accaaccagg acgccgacac cgtgaccatc   1260

gacaacaccg tgtaccagct gagcaaggtg gagggcgagc agcacgtgat caagggcaga   1320

cccgtgagca gcagcttcga ccccatcaag ttccccgagg accagttcaa cgtggccctg   1380

gaccaggtgt tcgagagcat cgagaacagc caggccctgg tggaccagag caacagaatc   1440

ctgagcagcg ccgagaaggg caacaccggc gttaacctca ttacctatat cgttttgact   1500
```

atcatatctc ttgtttttgg tatacttagc ctgattctag catgctacct aatgtacaag 1560
caaaaggcgc aacaaaagac cttattatgg cttgggaata ataccctaga tcagatgaga 1620
gccactacaa aaatgtga 1638

<210> SEQ ID NO 20
<211> LENGTH: 16842
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 20
accaaacaga gaatccgtga gttacgataa aaggcgaagg agcaattgaa gtcgcacggg 60
tagaaggtgt gaatctcgag tgcgagcccg aagcacaaac tcgagaaagc cttctgccaa 120
catgtcttcc gtatttgatg agtacgaaca gctcctcgcg gctcagactc gccccaatgg 180
agctcatgga gggggagaaa aagggagtac cttaaaagta gacgtcccgg tattcactct 240
taacagtgat gacccagaag atagatggag ctttgtggta ttctgcctcc ggattgctgt 300
tagcgaagat gccaacaaac cactcaggca aggtgctctc atatctcttt tatgctccca 360
ctcacaggta atgaggaacc atgttgccct tgcagggaaa cagaatgaag ccacattggc 420
cgtgcttgag attgatggct ttgccaacgg cacgccccag ttcaacaata ggagtggagt 480
gtctgaagag agagcacaga gatttgcgat gatagcagga tctctccctc gggcatgcag 540
caacggaacc ccgttcgtca cagccggggc cgaagatgat gcaccagaag acatcaccga 600
taccctggag aggatcctct ctatccaggc tcaagtatgg gtcacagtag caaaagccat 660
gactgcgtat gagactgcag atgagtcgga aacaaggcga atcaataagt atatgcagca 720
aggcagggtc caaaagaaat acatcctcta ccccgtatgc aggagcacaa tccaactcac 780
gatcagacag tctcttgcag tccgcatctt tttggttagc gagctcaaga gaggccgcaa 840
cacggcaggt ggtacctcta cttattataa cctggtaggg gacgtagact catacatcag 900
gaataccggg cttactgcat tcttcttgac actcaagtac ggaatcaaca ccaagacatc 960
agcccttgca cttagtagcc tctcaggcga catccagaag atgaagcagc tcatgcgttt 1020
gtatcggatg aaaggagata atgcgccgta catgacatta cttggtgata gtgaccagat 1080
gagctttgcg cctgccgagt atgcacaact ttactccttt gccatgggta tggcatcagt 1140
cctagataaa ggtactggga aataccaatt tgccagggac tttatgagca catcattctg 1200
gagacttgga gtagagtacg ctcaggctca gggaagtagc attaacgagg atatggctgc 1260
cgagctaaag ctaaccccag cagcaaggag gggcctggca gctgctgccc aacgggtctc 1320
cgaggagacc agcagcatag acatgcctac tcaacaagtc ggagtcctca ctgggcttag 1380
cgaggggggg tcccaagctc tacaaggcgg atcgaataga tcgcaagggc aaccagaagc 1440
cggggatggg gagacccaat tcctggatct gatgagagcg gtagcaaata gcatgaggga 1500
ggcgccaaac tctgcacagg gcactcccca atcggggcct cccccaactc ctgggccatc 1560
ccaagataac gacaccgact gggggtattg atggacaaaa cccagcctgc ttccacaaaa 1620
acatcccaat gccctcaccc gtagtcgacc cctcgatttg cggctctata tgaccacacc 1680
ctcaaacaaa catccccctc tttcctccct cccccctgctg tacaactacg tacgccctag 1740
ataccacagg cacaatgcgg ctcactaaca atcaaaacag agccgaggga attagaaaaa 1800
agtacgggta gaagagggat attcagagat cagggcaagt ctcccgagtc tctgctctct 1860

```
cctctacctg atagaccagg acaaacatgg ccacctttac agatgcagag atcgacgagc   1920

tatttgagac aagtggaact gtcattgaca acataattac agcccagggt aaaccagcag   1980

agactgttgg aaggagtgca atcccacaag gcaagaccaa ggtgctgagc gcagcatggg   2040

agaagcatgg gagcatccag ccaccggcca gtcaagacaa ccccgatcga caggacagat   2100

ctgacaaaca accatccaca cccgagcaaa cgaccccgca tgacagcccg ccggccacat   2160

ccgccgacca gccccccacc caggccacag acgaagccgt cgacacacag ctcaggaccg   2220

gagcaagcaa ctctctgctg ttgatgcttg acaagctcag caataaatcg tccaatgcta   2280

aaaagggccc atggtcgagc ccccaagagg ggaatcacca acgtccgact caacagcagg   2340

ggagtcaacc cagtcgcgga aacagtcagg aaagaccgca gaaccaagtc aaggccgccc   2400

ctggaaacca gggcacagac gtgaacacag catatcatgg acaatgggag gagtcacaac   2460

tatcagctgg tgcaacccct catgctctcc gatcaaggca gagccaagac aatacccttg   2520

tatctgcgga tcatgtccag ccacctgtag actttgtgca agcgatgatg tctatgatgg   2580

aggcgatatc acagagagta agtaaggttg actatcagct agatcttgtc ttgaaacaga   2640

catcctccat ccctatgatg cggtccgaaa tccaacagct gaaaacatct gttgcagtca   2700

tggaagccaa cttgggaatg atgaagattc tggatcccgg ttgtgccaac atttcatctc   2760

tgagtgatct acgggcagtt gcccgatctc accggttttt agtttcaggc cctggagacc   2820

cctctcccta tgtgacacaa ggaggcgaaa tggcacttaa taaactttcg caaccagtgc   2880

cacatccatc tgaattgatt aaacccgcca ctgcatgcgg gcctgatata ggagtggaaa   2940

aggacactgt ccgtgcattg atcatgtcac gcccaatgca cccgagttct tcagccaagc   3000

tcctaagcaa gttagatgca gccgggtcga tcgaggaaat caggaaaatc aagcgccttg   3060

ctctaaatgg ctaattacta ctgccacacg tagcgggtcc ctgtccactc ggcatcacac   3120

ggaatctgca ccgagttccc ccccgcggtt agaaaaaata cgggtagaac cgccaccatg   3180

tcttggaaag tggtgatcat tttttcattg ctaataacac ctcaacacgg tcttaaagag   3240

agctacctag aagaatcatg tagcactata actgagggat atcttagtgt tctgaggaca   3300

ggttggtata ccaacgtttt tacattagag gtgggtgatg tagaaaacct tacatgttct   3360

gatggaccta gcctaataaa aacagaatta gatctgacca aaagtgcact aagagagctc   3420

aaaacagtct ctgctgacca attggcaaga gaggaacaaa ttgagaatcc cagacaatct   3480

aggtttgttc taggagcaat agcactcggt gttgcaacag cagctgcagt cacagcaggt   3540

gttgcaattg ccaaaaccat ccggcttgag agtgaagtca cagcaattaa gaatgccctc   3600

aaaacgacca atgaagcagt atctacattg gggaatggag ttcgagtgtt ggcaactgca   3660

gtgagagagc tgaaagactt tgtgagcaag aatttaactc gtgcaatcaa caaaaacaag   3720

tgcgacattg atgacctaaa aatggccgtt agcttcagtc aattcaacag aaggtttcta   3780

aatgttgtgc ggcaattttc agacaatgct ggaataacac cagcaatatc tttggactta   3840

atgacagatg ctgaactagc cagggccgtt tctaacatgc cgacatctgc aggacaaata   3900

aaattgatgt tggagaaccg cgcgatggtg cgaagaaagg ggttcggaat cctgataggg   3960

gtctacggga gctctgtaat ttacatggtg cagctgccaa tctttggcgt tatagacacg   4020

ccttgctgga tagtaaaagc agccccttct tgttccgaaa aaagggaaa ctatgcttgc   4080

ctcttaagag aagaccaagg gtggtattgt cagaatgcag ggtcaactgt ttactaccca   4140

aatgagaaag actgtgaaac aagaggagac catgtctttt gcgacacagc agcaggaatt   4200
```

-continued

```
aatgttgctg agcaatcaaa ggagtgcaac atcaacatat ccactacaaa ttacccatgc   4260
aaagtcagca caggaagaca tcctatcagt atggttgcac tgtctcctct tggggctctg   4320
gttgcttgct acaaaggagt aagctgttcc attggcagca acagagtagg gatcatcaag   4380
cagctgaaca aaggttgctc ctatataacc aaccaagatg cagacacagt gacaatagac   4440
aacactgtat atcagctaag caaagttgag ggtgaacagc atgttataaa aggcagacca   4500
gtgtcaagca gctttgatcc aatcaagttt cctgaagatc aattcaatgt tgcacttgac   4560
caagtttttg agagcattga aaacagccag gccttggtag atcaatcaaa cagaatccta   4620
agcagtgcag agaaagggaa tactggcttc atcattgtaa taattctaat tgctgtcctt   4680
ggctctagca tgatcctagt gagcatcttc attataatca agaaaacaaa gaaaccaacg   4740
ggagcacctc cagagctgag tggtgtcaca aacaatggct tcataccaca cagttaggcc   4800
gcggacccaa ggtccaactc tccaagcggc aatcctctct cgcttcctca gccccactga   4860
atgatcgcgt aaccgtaatt aatctagcta catttaagat taagaaaaaa tacgggtaga   4920
attggagtgc cccaattgtg ccaagatgga ctcatctagg acaattgggc tgtactttga   4980
ttctgcccat tcttctagca acctgttagc atttccgatc gtcctacaag acacaggaga   5040
tgggaagaag caaatcgccc cgcaatatag gatccagcgc cttgacttgt ggactgatag   5100
taaggaggac tcagtattca tcaccaccta tggattcatc tttcaagttg ggaatgaaga   5160
agccaccgtc ggcatgatcg atgataaacc caagcgcgag ttactttccg ctgcgatgct   5220
ctgcctagga agcgtcccaa ataccggaga ccttattgag ctggcaaggg cctgtctcac   5280
tatgatagtc acatgcaaga agagtgcaac taatactgag agaatggttt tctcagtagt   5340
gcaggcaccc caagtgctgc aaagctgtag ggttgtggca aacaaatact catcagtgaa   5400
tgcagtcaag cacgtgaaag cgccagagaa gattcccggg agtggaaccc tagaatacaa   5460
ggtgaacttt gtctccttga ctgtggtacc gaagagggat gtctacaaga tcccagctgc   5520
agtattgaag gtttctggct cgagtctgta caatcttgcg ctcaatgtca ctattaatgt   5580
ggaggtagac ccgaggagtc ctttggttaa atctctgtct aagtctgaca gcggatacta   5640
tgctaacctc ttcttgcata ttggacttat gaccactgta gataggaagg ggaagaaagt   5700
gacatttgac aagctggaaa agaaaataag gagccttgat ctatctgtcg ggctcagtga   5760
tgtgctcggg ccttccgtgt tggtaaaagc aagaggtgca cggactaagc ttttggcacc   5820
tttcttctct agcagtggga cagcctgcta tcccatagca aatgcttctc ctcaggtggc   5880
caagatactc tggagtcaaa ccgcgtgcct gcggagcgtt aaaatcatta tccaagcagg   5940
tacccaacgc gctgtcgcag tgaccgccga ccacgaggtt acctctacta agctggagaa   6000
ggggcacacc cttgccaaat acaatccttt taagaaataa gctgcgtctc tgagattgcg   6060
ctccgcccac tcacccagat catcatgaca caaaaaacta atctgtcttg attatttaca   6120
gttagtttac ctgtctatca agttagaaaa aacacgggta gaagattctg gatcccggtt   6180
ggcgccctcc aggtgcaaga tgggctccag accttctacc aagaacccag cacctatgat   6240
gctgactatc cgggttgcgc tggtactgag ttgcatctgt ccggcaaact ccattgatgg   6300
caggcctctt gcagctgcag gaattgtggt tacaggagac aaagccgtca acatatacac   6360
ctcatcccag acaggatcaa tcatagttaa gctcctcccg aatctgccca aggataagga   6420
ggcatgtgcg aaagccccct tggatgcata caacaggaca ttgaccactt tgctcacccc   6480
ccttggtgac tctatccgta ggatacaaga gtctgtgact acatctggag gggggagaca   6540
ggggcgcctt ataggcgcca ttattggcgg tgtggctctt ggggttgcaa ctgccgcaca   6600
```

-continued

```
aataacagcg gccgcagctc tgatacaagc caaacaaaat gctgccaaca tcctccgact   6660
taaagagagc attgccgcaa ccaatgaggc tgtgcatgag gtcactgacg gattatcgca   6720
actagcagtg gcagttggga agatgcagca gtttgttaat gaccaattta ataaaacagc   6780
tcaggaatta gactgcatca aaattgcaca gcaagttggt gtagagctca acctgtacct   6840
aaccgaattg actacagtat tcggaccaca aatcacttca cctgctttaa acaagctgac   6900
tattcaggca ctttacaatc tagctggtgg aaatatggat tacttattga ctaagttagg   6960
tgtagggaac aatcaactca gctcattaat cggtagcggc ttaatcaccg gtaaccctat   7020
tctatacgac tcacagactc aactcttggg tatacaggta actctacctt cagtcgggaa   7080
cctaaataat atgcgtgcca cctacttgga aaccttatcc gtaagcacaa ccaggggatt   7140
tgcctcggca cttgtcccaa aagtggtgac acaggtcggt tctgtgatag aagaacttga   7200
cacctcatac tgtatagaaa ctgacttaga tttatattgt acaagaatag taacgttccc   7260
tatgtcccct ggtatttatt cctgcttgag cggcaatacg tcggcctgta tgtactcaaa   7320
gaccgaaggc gcacttacta caccatacat gactatcaaa ggttcagtca tcgccaactg   7380
caagatgaca acatgtagat gtgtaaaccc cccgggtatc atatcgcaaa actatggaga   7440
agccgtgtct ctaatagata aacaatcatg caatgtttta tccttaggcg ggataacttt   7500
aaggctcagt ggggaattcg atgtaactta tcagaagaat atctcaatac aagattctca   7560
agtaataata acaggcaatc ttgatatctc aactgagctt gggaatgtca acaactcgat   7620
cagtaatgct ttgaataagt tagaggaaag caacagaaaa ctagacaaag tcaatgtcaa   7680
actgactagc acatctgctc tcattaccta tatcgttttg actatcatat ctcttgtttt   7740
tggtatactt agcctgattc tagcatgcta cctaatgtac aagcaaaagg cgcaacaaaa   7800
gaccttatta tggcttggga ataatactct agatcagatg agagccacta caaaaatgtg   7860
aacacagatg aggaacgaag gtttccctaa tagtaatttg tgtgaaagtt ctggtagtct   7920
gtcagttcag agagttaaga aaaaactacc ggttgtagat gaccaaagga cgatatacgg   7980
gtagaacggt aagagaggcc gcccctcaat tgcgagccag gcttcacaac ctccgttcta   8040
ccgcttcacc gacaacagtc ctcaatcatg gaccgcgccg ttagccaagt tgcgttagag   8100
aatgatgaaa gagaggcaaa aaatacatgg cgcttgatat tccggattgc aatcttattc   8160
ttaacagtag tgaccttggc tatatctgta gcctcccttt tatatagcat gggggctagc   8220
acacctagcg atcttgtagg cataccgact aggatttcca gggcagaaga aaagattaca   8280
tctacacttg gttccaatca agatgtagta gataggatat ataagcaagt ggcccttgag   8340
tctccgttgg cattgttaaa tactgagacc acaattatga acgcaataac atctctctct   8400
tatcagatta atggagctgc aaacaacagt gggtgggggg cacctatcca tgacccagat   8460
tatatagggg ggataggcaa agaactcatt gtagatgatg ctagtgatgt cacatcattc   8520
tatccctctg catttcaaga acatctgaat tttatcccgg cgcctactac aggatcaggt   8580
tgcactcgaa taccctcatt tgacatgagt gctacccatt actgctacac ccataatgta   8640
atattgtctg gatgcagaga tcactcacat tcatatcagt atttagcact tggtgtgctc   8700
cggacatctg caacagggag ggtattcttt tctactctgc gttccatcaa cctggacgac   8760
acccaaaatc ggaagtcttg cagtgtgagt gcaactcccc tgggttgtga tatgctgtgc   8820
tcgaaagtca cggagacaga ggaagaagat tataactcag ctgtccctac gcggatggta   8880
catgggaggt tagggttcga cggccagtac cacgaaaagg acctagatgt cacaacatta   8940
```

-continued

```
ttcggggact gggtggccaa ctacccagga gtagggggtg gatcttttat tgacagccgc   9000
gtatggttct cagtctacgg agggttaaaa cccaattcac ccagtgacac tgtacaggaa   9060
gggaaatatg tgatatacaa gcgatacaat gacacatgcc cagatgagca agactaccag   9120
attcgaatgg ccaagtcttc gtataagcct ggacggtttg gtgggaaacg catacagcag   9180
gctatcttat ctatcaaggt gtcaacatcc ttaggcgaag acccggtact gactgtaccg   9240
cccaacacag tcacactcat gggggccgaa ggcagaattc tcacagtagg gacatctcat   9300
ttcttgtatc aacgagggtc atcatacttc tctcccgcgt tattatatcc tatgacagtc   9360
agcaacaaaa cagccactct tcatagtcct tatacattca atgccttcac tcggccaggt   9420
agtatccctt gccaggcttc agcaagatgc cccaactcgt gtgttactgg agtctataca   9480
gatccatatc ccctaatctt ctatagaaac cacaccttgc gaggggtatt cgggacaatg   9540
cttgatggtg tacaagcaag acttaaccct gcgtctgcag tattcgatag cacatcccgc   9600
agtcgcatta ctcgagtgag ttcaagcagt accaaagcag catacacaac atcaacttgt   9660
tttaaagtgg tcaagactaa taagacctat tgtctcagca ttgctgaaat atctaatact   9720
ctcttcggag aattcagaat cgtcccgtta ctagttgaga tcctcaaaga tgacggggtt   9780
agagaagcca ggtctggcta gttgagtcaa ttataaagga gttggaaaga tggcattgta   9840
tcacctatct tctgcgacat caagaatcaa accgaatgcc ggcgcgtgct cgaattccat   9900
gttgccagtt gaccacaatc agccagtgct catgcgatca gattaagcct tgtcaatagt   9960
ctcttgatta agaaaaaatg taagtggcaa tgagatacaa ggcaaaacag ctcatggtta  10020
acaatacggg taggacatgg cgagctccgg tcctgaaagg gcagagcatc agattatcct  10080
accagagtca cacctgtctt caccattggt caagcacaaa ctactctatt actggaaatt  10140
aactgggcta ccgcttcctg atgaatgtga cttcgaccac ctcattctca gccgacaatg  10200
gaaaaaaata cttgaatcgg cctctcctga tactgagaga atgataaaac tcggaagggc  10260
agtacaccaa actcttaacc acaattccag aataaccgga gtgctccacc ccaggtgttt  10320
agaagaactg gctaatattg aggtcccaga ttcaaccaac aaatttcgga agattgagaa  10380
gaagatccaa attcacaaca cgagatatgg agaactgttc acaaggctgt gtacgcatat  10440
agagaagaaa ctgctggggt catcttggtc taacaatgtc ccccggtcag aggagttcag  10500
cagcattcgt acggatccgg cattctggtt tcactcaaaa tggtccacag ccaagtttgc  10560
atggctccat ataaaacaga tccagaggca tctgatggtg gcagctagga caaggtctgc  10620
ggccaacaaa ttggtgatgc taacccataa ggtaggccaa gtctttgtca ctcctgaact  10680
tgtcgttgtg acgcatacga atgagaacaa gttcacatgt cttacccagg aacttgtatt  10740
gatgtatgca gatatgatgg agggcagaga tatggtcaac ataatatcaa ccacggcggt  10800
gcatctcaga agcttatcag agaaaattga tgacattttg cggttaatag acgctctggc  10860
aaaagacttg ggtaatcaag tctacgatgt tgtatcacta atggagggat ttgcatacgg  10920
agctgtccag ctactcgagc cgtcaggtac atttgcagga gatttcttcg cattcaacct  10980
gcaggagctt aaagacattc taattggcct cctccccaat gatatagcag aatccgtgac  11040
tcatgcaatc gctactgtat tctctggttt agaacagaat caagcagctg agatgttgtg  11100
tctgttgcgt ctgtggggtc acccactgct tgagtcccgt attgcagcaa aggcagtcag  11160
gagccaaatg tgcgcaccga aaatggtaga ctttgatatg atccttcagg tactgtcttt  11220
cttcaaggga acaatcatca acgggtacag aaagaagaat gcaggtgtgt ggccgcgagt  11280
caaagtggat acaatatatg ggaaggtcat tgggcaacta catgcagatt cagcagagat  11340
```

ttcacacgat atcatgttga gagagtataa gagtttatct gcacttgaat ttgagccatg 11400
tatagaatat gaccctgtca ccaacctgag catgttccta aaagacaagg caatcgcaca 11460
ccccaacgat aattggcttg cctcgtttag gcggaacctt ctctccgaag accagaagaa 11520
acatgtaaaa gaagcaactt cgactaatcg cctcttgata gagtttttag agtcaaatga 11580
ttttgatcca tataaagaga tggaatatct gacgaccctt gagtacctta gagatgacaa 11640
tgtggcagta tcatactcgc tcaaggagaa ggaagtgaaa gttaatggac ggatcttcgc 11700
taagctgaca aagaagttaa ggaactgtca ggtgatggcg gaagggatcc tagccgatca 11760
gattgcacct ttctttcagg gaaatggagt cattcaggat agcatatcct tgaccaagag 11820
tatgctagcg atgagtcaac tgtcttttaa cagcaataag aaacgtatca ctgactgtaa 11880
agaaagagta tcttcaaacc gcaatcatga tccgaaaagc aagaaccgtc ggagagttgc 11940
aaccttcata acaactgacc tgcaaaagta ctgtcttaat tggagatatc agacaatcaa 12000
attgttcgct catgccatca atcagttgat gggcctacct cacttcttcg aatggattca 12060
cctaagactg atggacacta cgatgttcgt aggagaccct ttcaatcctc caagtgaccc 12120
tactgactgt gacctctcaa gagtccctaa tgatgacata tatattgtca gtgccagagg 12180
gggtatcgaa ggattatgcc agaagctatg gacaatgatc tcaattgctg caatccaact 12240
tgctgcagct agatcgcatt gtcgtgttgc ctgtatggta cagggtgata atcaagtaat 12300
agcagtaacg agagaggtaa gatcagacga ctctccggag atggtgttga cacagttgca 12360
tcaagccagt gataatttct tcaaggaatt aattcatgtc aatcatttga ttggccataa 12420
tttgaaggat cgtgaaacca tcaggtcaga cacattcttc atatacagca aacgaatctt 12480
caaagatgga gcaatcctca gtcaagtcct caaaaattca tctaaattag tgctagtgtc 12540
aggtgatctc agtgaaaaca ccgtaatgtc ctgtgccaac attgcctcta ctgtagcacg 12600
gctatgcgag aacgggcttc ccaaagactt ctgttactat ttaaactata taatgagttg 12660
tgtgcagaca tactttgact ctgagttctc catcaccaac aattcgcacc ccgatcttaa 12720
tcagtcgtgg attgaggaca tctcttttgt gcactcatat gttctgactc ctgcccaatt 12780
agggggactg agtaaccttc aatactcaag gctctacact agaaatatcg gtgacccggg 12840
gactactgct tttgcagaga tcaagcgact agaagcagtg ggattactga gtcctaacat 12900
tatgactaat atcttaacta ggccgcctgg gaatggagat tgggccagtc tgtgcaacga 12960
cccatactct ttcaattttg agactgttgc aagcccaaat attgttctta agaaacatac 13020
gcaaagagtc ctatttgaaa cttgttcaaa tcccttattg tctggagtgc acacagagga 13080
taatgaggca gaagagaagg cattggctga attcttgctt aatcaagagg tgattcatcc 13140
ccgcgttgcg catgccatca tggaggcaag ctctgtaggt aggagaaagc aaattcaagg 13200
gcttgttgac acaacaaaca ccgtaattaa gattgcgctt actaggaggc cattaggcat 13260
caagaggctg atgcggatag tcaattattc tagcatgcat gcaatgctgt ttagagacga 13320
tgttttttcc tccagtagat ccaaccaccc cttagtctct tctaatatgt gttctctgac 13380
actggcagac tatgcacgga atagaagctg gtcacctttg acgggaggca ggaaaatact 13440
gggtgtatct aatcctgata cgatagaact cgtagagggt gagattctta gtgtaagcgg 13500
agggtgtaca agatgtgaca gcggagatga acaatttact tggttccatc ttccaagcaa 13560
tatagaattg accgatgaca ccagcaagaa tcctccgatg agggtaccat atctcgggtc 13620
aaagacacag gagaggagag ctgcctcact tgcaaaaata gctcatatgt cgccacatgt 13680

-continued

```
aaaggctgcc ctaagggcat catccgtgtt gatctgggct tatggggata atgaagtaaa  13740
ttggactgct gctcttacga ttgcaaaatc tcggtgtaat gtaaacttag agtatcttcg  13800
gttactgtcc cctttaccca cggctgggaa tcttcaacat agactagatg atggtataac  13860
tcagatgaca ttcacccctg catctctcta cagggtgtca ccttacattc acatatccaa  13920
tgattctcaa aggctgttca ctgaagaagg agtcaaagag gggaatgtgg tttaccaaca  13980
gatcatgctc ttgggtttat ctctaatcga atcgatcttt ccaatgacaa caaccaggac  14040
atatgatgag atcacactgc acctacatag taaatttagt tgctgtatca gagaagcacc  14100
tgttgcggtt cctttcgagc tacttggggt ggtaccggaa ctgaggacag tgacctcaaa  14160
taagtttatg tatgatccta gccctgtatc ggagggagac tttgcgagac ttgacttagc  14220
tatcttcaag agttatgagc ttaatctgga gtcatatccc acgatagagc taatgaacat  14280
tctttcaata tccagcggga agttgattgg ccagtctgtg gtttcttatg atgaagatac  14340
ctccataaag aatgacgcca taatagtgta tgacaatacc cgaaattgga tcagtgaagc  14400
tcagaattca gatgtggtcc gcctatttga atatgcagca cttgaagtgc tcctcgactg  14460
ttcttaccaa ctctattacc tgagagtaag aggcctggac aatattgtct tatatatggg  14520
tgatttatac aagaatatgc caggaattct actttccaac attgcagcta caatatctca  14580
tcccgtcatt cattcaaggt tacatgcagt gggcctggtc aaccatgacg gatcacacca  14640
acttgcagat acggatttta tcgaaatgtc tgcaaaacta ttagtatctt gcacccgacg  14700
tgtgatctcc ggcttatatt caggaaataa gtatgatctg ctgttcccat ctgtcttaga  14760
tgataacctg aatgagaaga tgcttcagct gatatcccgg ttatgctgtc tgtacacggt  14820
actctttgct acaacaagag aaatcccgaa aataagaggc ttaactgcag aagagaaatg  14880
ttcaatactc actgagtatt tactgtcgga tgctgtgaaa ccattactta gccccgatca  14940
agtgagctct atcatgtctc ctaacataat tacattccca gctaatctgt actacatgtc  15000
tcggaagagc ctcaatttga tcagggaaag ggaggacagg gatactatcc tggcgttgtt  15060
gttcccccaa gagccattat tagagttccc ttctgtgcaa gatattggtg ctcgagtgaa  15120
agatccattc acccgacaac ctgcggcatt tttgcaagag ttagatttga gtgctccagc  15180
aaggtatgac gcattcacac ttagtcagat tcatcctgaa ctcacatctc caaatccgga  15240
ggaagactac ttagtacgat acttgttcag agggataggg actgcatctt cctcttggta  15300
taaggcatct catctccttt ctgtacccga ggtaagatgt gcaagacacg ggaactcctt  15360
atacttagct gaagggagcg gagccatcat gagtcttctc gaactgcatg taccacatga  15420
aactatctat tacaatacgc tcttttcaaa tgagatgaac cccccgcaac gacatttcgg  15480
gccgacccca actcagtttt tgaattcggt tgtttatagg aatctacagg cggaggtaac  15540
atgcaaagat ggatttgtcc aagagttccg tccattatgg agagaaaata cagaggaaag  15600
cgacctgacc tcagataaag tagtggggta tattacatct gcagtgccct acagatctgt  15660
atcattgctg cattgtgaca ttgaaattcc tccagggtcc aatcaaagct tactagatca  15720
actagctatc aatttatctc tgattgccat gcattctgta agggagggcg gggtagtaat  15780
catcaaagtg ttgtatgcaa tgggatacta ctttcatcta ctcatgaact tgtttgctcc  15840
gtgttccaca aaaggatata ttctctctaa tggttatgca tgtcgaggag atatggagtg  15900
ttacctggta tttgtcatgg gttacctggg cgggcctaca tttgtacatg aggtggtgag  15960
gatggcgaaa actctggtgc agcggcacgg tacgcttttg tctaaatcag atgagatcac  16020
actgaccagg ttattcacct cacagcggca gcgtgtgaca gacatcctat ccagtccttt  16080
```

accaagatta ataaagtact tgaggaagaa tattgacact gcgctgattg aagccggggg 16140
acagcccgtc cgtccattct gtgcggagag tctggtgagc acgctagcga acataactca 16200
gataacccag atcatcgcta gtcacattga cacagttatc cggtctgtga tatatatgga 16260
agctgagggt gatctcgctg acacagtatt tctatttacc ccttacaatc tctctactga 16320
cgggaaaaag aggacatcac ttaaacagtg cacgagacag atcctagagg ttacaatact 16380
aggtcttaga gtcgaaaatc tcaataaaat aggcgatata atcagcctag tgcttaaagg 16440
catgatctcc atggaggacc ttatcccact aaggacatac ttgaagcata gtacctgccc 16500
taaatatttg aaggctgtcc taggtattac caaactcaaa gaaatgttta cagacacttc 16560
tgtactgtac ttgactcgtg ctcaacaaaa attctacatg aaaactatag gcaatgcagt 16620
caaaggatat tacagtaact gtgactctta acgaaaatca catattaata ggctcctttt 16680
ttggccaatt gtattcttgt tgatttaatc atattatgtt agaaaaaagt tgaaccctga 16740
ctccttagga ctcgaattcg aactcaaata aatgtcttaa aaaaaggttg cgcacaatta 16800
ttcttgagtg tagtctcgtc attcaccaaa tctttgtttg gt 16842

<210> SEQ ID NO 21
<211> LENGTH: 16842
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 21
accaaacaga gaatccgtga gttacgataa aaggcgaagg agcaattgaa gtcgcacggg 60
tagaaggtgt gaatctcgag tgcgagcccg aagcacaaac tcgagaaagc cttctgccaa 120
catgtcttcc gtatttgatg agtacgaaca gctcctcgcg gctcagactc gccccaatgg 180
agctcatgga gggggagaaa aagggagtac cttaaaagta gacgtcccgg tattcactct 240
taacagtgat gacccagaag atagatggag ctttgtggta ttctgcctcc ggattgctgt 300
tagcgaagat gccaacaaac cactcaggca aggtgctctc atatctcttt tatgctccca 360
ctcacaggta atgaggaacc atgttgccct tgcagggaaa cagaatgaag ccacattggc 420
cgtgcttgag attgatggct ttgccaacgg cacgccccag ttcaacaata ggagtggagt 480
gtctgaagag agagcacaga gatttgcgat gatagcagga tctctccctc gggcatgcag 540
caacggaacc ccgttcgtca cagccggggc cgaagatgat gcaccagaag acatcaccga 600
taccctggag aggatcctct ctatccaggc tcaagtatgg gtcacagtag caaaagccat 660
gactgcgtat gagactgcag atgagtcgga aacaaggcga atcaataagt atatgcagca 720
aggcagggtc caaaagaaat acatcctcta ccccgtatgc aggagcacaa tccaactcac 780
gatcagacag tctcttgcag tccgcatctt tttggttagc gagctcaaga gaggccgcaa 840
cacggcaggt ggtacctcta cttattataa cctggtaggg gacgtagact catacatcag 900
gaataccggg cttactgcat tcttcttgac actcaagtac ggaatcaaca ccaagacatc 960
agcccttgca cttagtagcc tctcaggcga catccagaag atgaagcagc tcatgcgttt 1020
gtatcggatg aaaggagata atgcgccgta catgacatta cttggtgata gtgaccagat 1080
gagctttgcg cctgccgagt atgcacaact ttactccttt gccatgggta tggcatcagt 1140
cctagataaa ggtactggga aataccaatt tgccagggac tttatgagca catcattctg 1200
gagacttgga gtagagtacg ctcaggctca gggaagtagc attaacgagg atatggctgc 1260

-continued

```
cgagctaaag ctaaccccag cagcaaggag gggcctggca gctgctgccc aacgggtctc   1320
cgaggagacc agcagcatag acatgcctac tcaacaagtc ggagtcctca ctgggcttag   1380
cgaggggggg tcccaagctc tacaaggcgg atcgaataga tcgcaagggc aaccagaagc   1440
cggggatggg gagacccaat tcctggatct gatgagagcg gtagcaaata gcatgaggga   1500
ggcgccaaac tctgcacagg gcactcccca atcggggcct cccccaactc ctgggccatc   1560
ccaagataac gacaccgact gggggtattg atggacaaaa cccagcctgc ttccacaaaa   1620
acatcccaat gccctcaccc gtagtcgacc cctcgatttg cggctctata tgaccacacc   1680
ctcaaacaaa catccccctc tttcctccct cccccctgctg tacaactacg tacgccctag   1740
ataccacagg cacaatgcgg ctcactaaca atcaaaacag agccgaggga attagaaaaa   1800
agtacgggta gaagagggat attcagagat cagggcaagt ctcccgagtc tctgctctct   1860
cctctacctg atagaccagg acaaacatgg ccacctttac agatgcagag atcgacgagc   1920
tatttgagac aagtggaact gtcattgaca acataattac agcccagggt aaaccagcag   1980
agactgttgg aaggagtgca atcccacaag gcaagaccaa ggtgctgagc gcagcatggg   2040
agaagcatgg gagcatccag ccaccggcca gtcaagacaa ccccgatcga caggacagat   2100
ctgacaaaca accatccaca cccgagcaaa cgaccccgca tgacagcccg ccggccacat   2160
ccgccgacca gccccccacc caggccacag acgaagccgt cgacacacag ctcaggaccg   2220
gagcaagcaa ctctctgctg ttgatgcttg acaagctcag caataaatcg tccaatgcta   2280
aaaagggccc atggtcgagc cccaagaggg ggaatcacca acgtccgact caacagcagg   2340
ggagtcaacc cagtcgcgga aacagtcagg aaagaccgca gaaccaagtc aaggccgccc   2400
ctggaaacca gggcacagac gtgaacacag catatcatgg acaatgggag gagtcacaac   2460
tatcagctgg tgcaacccct catgctctcc gatcaaggca gagccaagac aatacccttg   2520
tatctgcgga tcatgtccag ccacctgtag actttgtgca agcgatgatg tctatgatgg   2580
aggcgatatc acagagagta agtaaggttg actatcagct agatcttgtc ttgaaacaga   2640
catcctccat ccctatgatg cggtccgaaa tccaacagct gaaaacatct gttgcagtca   2700
tggaagccaa cttgggaatg atgaagattc tggatcccgg ttgtgccaac atttcatctc   2760
tgagtgatct acgggcagtt gcccgatctc acccggtttt agtttcaggc cctggagacc   2820
cctctcccta tgtgacacaa ggaggcgaaa tggcacttaa taaactttcg caaccagtgc   2880
cacatccatc tgaattgatt aaacccgcca ctgcatgcgg gcctgatata ggagtggaaa   2940
aggacactgt ccgtgcattg atcatgtcac gcccaatgca cccgagttct tcagccaagc   3000
tcctaagcaa gttagatgca gccgggtcga tcgaggaaat caggaaaatc aagcgccttg   3060
ctctaaatgg ctaattacta ctgccacacg tagcgggtcc ctgtccactc ggcatcacac   3120
ggaatctgca ccgagttccc ccccgcggtt agaaaaaaata cgggtagaac cgccaccatg   3180
agctggaagg tggtgatcat cttcagcctg ctgatcaccc cccagcacgg cctgaaggag   3240
agctacctgg aggagagctg cagcaccatc accgagggct acctgagcgt gctgagaacc   3300
ggctggtaca ccaacgtgtt caccctggag gtgggcgacg tggagaacct gacctgcagc   3360
gacggcccca gcctgatcaa gaccgagctg gacctgacca agagcgccct gagagagctg   3420
aagaccgtga gcgccgacca gctggccaga gaggagcaga tcgagaaccc cagacagagc   3480
agattcgtgc tgggcgccat cgccctgggc gtggccaccg ccgccgccgt gaccgccggc   3540
gtggccatcg ccaagaccat cagactggag agcgaggtga ccgccatcaa gaacgccctg   3600
```

-continued

```
aagaccacca acgaggccgt gagcaccctg ggcaacggcg tgagagtgct ggccaccgcc   3660
gtgagagagc tgaaggactt cgtgagcaag aacctgacca gagccatcaa caagaacaag   3720
tgcgacatcg acgacctgaa gatggccgtg agcttcagcc agttcaacag aagattcctg   3780
aacgtggtga gacagttcag cgacaacgcc ggcatcaccc ccgccatcag cctggacctg   3840
atgaccgacg ccgagctggc cagagccgtg agcaacatgc ccaccagcgc cggccagatc   3900
aagctgatgc tggagaacag agccatggtg agaagaaagg gcttcggcat cctgatcggc   3960
gtgtacggca gcagcgtgat ctacatggtg cagctgccca tcttcggcgt gatcgacacc   4020
ccctgctgga tcgtgaaggc cgcccccagc tgcagcgaga agaagggcaa ctacgcctgc   4080
ctgctgagag aggaccaggg ctggtactgc cagaacgccg gcagcaccgt gtactacccc   4140
aacgagaagg actgcgagac cagaggcgac cacgtgttct gcgacaccgc cgccggcatc   4200
aacgtggccg agcagagcaa ggagtgcaac atcaacatca gcaccaccaa ctacccctgc   4260
aaggtgagca ccggcagaca ccccatcagc atggtggccc tgagccccct gggcgccctg   4320
gtggcctgct acaagggcgt gagctgcagc atcggcagca acagagtggg catcatcaag   4380
cagctgaaca agggctgcag ctacatcacc aaccaggacg ccgacaccgt gaccatcgac   4440
aacaccgtgt accagctgag caaggtggag ggcgagcagc acgtgatcaa gggcagaccc   4500
gtgagcagca gcttcgaccc catcaagttc cccgaggacc agttcaacgt ggccctggac   4560
caggtgttcg agagcatcga gaacagccag gccctggtgg accagagcaa cagaatcctg   4620
agcagcgccg agaagggcaa caccggcttc atcatcgtga tcatcctgat cgccgtgctg   4680
ggcagcagca tgatcctggt gagcatcttc atcatcatca agaagaccaa gaagcccacc   4740
ggcgcccccc ccgagctgag cggcgtgacc aacaacggct tcatccccca cagctgagcc   4800
gcggacccaa ggtccaactc tccaagcggc aatcctctct cgcttcctca gccccactga   4860
atgatcgcgt aaccgtaatt aatctagcta catttaagat taagaaaaaa tacgggtaga   4920
attggagtgc cccaattgtg ccaagatgga ctcatctagg acaattgggc tgtactttga   4980
ttctgcccat tcttctagca acctgttagc atttccgatc gtcctacaag acacaggaga   5040
tgggaagaag caaatcgccc cgcaatatag gatccagcgc cttgacttgt ggactgatag   5100
taaggaggac tcagtattca tcaccaccta tggattcatc tttcaagttg ggaatgaaga   5160
agccaccgtc ggcatgatcg atgataaacc caagcgcgag ttactttccg ctgcgatgct   5220
ctgcctagga agcgtcccaa ataccggaga ccttattgag ctggcaaggg cctgtctcac   5280
tatgatagtc acatgcaaga agagtgcaac taatactgag agaatggttt tctcagtagt   5340
gcaggcaccc caagtgctgc aaagctgtag ggttgtggca aacaaatact catcagtgaa   5400
tgcagtcaag cacgtgaaag cgccagagaa gattcccggg agtggaaccc tagaatacaa   5460
ggtgaacttt gtctccttga ctgtggtacc gaagagggat gtctacaaga tcccagctgc   5520
agtattgaag gtttctggct cgagtctgta caatcttgcg ctcaatgtca ctattaatgt   5580
ggaggtagac ccgaggagtc ctttggttaa atctctgtct aagtctgaca gcggatacta   5640
tgctaacctc ttcttgcata ttggacttat gaccactgta gataggaagg ggaagaaagt   5700
gacatttgac aagctggaaa agaaaataag gagccttgat ctatctgtcg ggctcagtga   5760
tgtgctcggg ccttccgtgt tggtaaaagc aagaggtgca cggactaagc ttttggcacc   5820
tttcttctct agcagtggga cagcctgcta tcccatagca aatgcttctc ctcaggtggc   5880
caagatactc tggagtcaaa ccgcgtgcct gcggagcgtt aaaatcatta tccaagcagg   5940
tacccaacgc gctgtcgcag tgaccgccga ccacgaggtt acctctacta agctggagaa   6000
```

```
ggggcacacc cttgccaaat acaatccttt taagaaataa gctgcgtctc tgagattgcg   6060
ctccgcccac tcacccagat catcatgaca caaaaaacta atctgtcttg attatttaca   6120
gttagtttac ctgtctatca agttagaaaa aacacgggta gaagattctg gatcccggtt   6180
ggcgccctcc aggtgcaaga tgggctccag accttctacc aagaacccag cacctatgat   6240
gctgactatc cgggttgcgc tggtactgag ttgcatctgt ccggcaaact ccattgatgg   6300
caggcctctt gcagctgcag gaattgtggt tacaggagac aaagccgtca acatatacac   6360
ctcatcccag acaggatcaa tcatagttaa gctcctcccg aatctgccca aggataagga   6420
ggcatgtgcg aaagccccct tggatgcata caacaggaca ttgaccactt tgctcacccc   6480
ccttggtgac tctatccgta ggatacaaga gtctgtgact acatctggag gggggagaca   6540
ggggcgcctt ataggcgcca ttattggcgg tgtggctctt ggggttgcaa ctgccgcaca   6600
aataacagcg gccgcagctc tgatacaagc caaacaaaat gctgccaaca tcctccgact   6660
taaagagagc attgccgcaa ccaatgaggc tgtgcatgag gtcactgacg gattatcgca   6720
actagcagtg gcagttggga agatgcagca gtttgttaat gaccaattta ataaaacagc   6780
tcaggaatta gactgcatca aaattgcaca gcaagttggt gtagagctca acctgtacct   6840
aaccgaattg actacagtat tcggaccaca aatcacttca cctgctttaa acaagctgac   6900
tattcaggca ctttacaatc tagctggtgg aaatatggat tacttattga ctaagttagg   6960
tgtagggaac aatcaactca gctcattaat cggtagcggc ttaatcaccg gtaaccctat   7020
tctatacgac tcacagactc aactcttggg tatacaggta actctacctt cagtcgggaa   7080
cctaaataat atgcgtgcca cctacttgga aaccttatcc gtaagcacaa ccaggggatt   7140
tgcctcggca cttgtcccaa aagtggtgac acaggtcggt tctgtgatag aagaacttga   7200
cacctcatac tgtatagaaa ctgacttaga tttatattgt acaagaatag taacgttccc   7260
tatgtcccct ggtatttatt cctgcttgag cggcaatacg tcggcctgta tgtactcaaa   7320
gaccgaaggc gcacttacta caccatacat gactatcaaa ggttcagtca tcgccaactg   7380
caagatgaca acatgtagat gtgtaaaccc cccgggtatc atatcgcaaa actatggaga   7440
agccgtgtct ctaatagata aacaatcatg caatgtttta tccttaggcg ggataacttt   7500
aaggctcagt ggggaattcg atgtaactta tcagaagaat atctcaatac aagattctca   7560
agtaataata acaggcaatc ttgatatctc aactgagctt gggaatgtca acaactcgat   7620
cagtaatgct ttgaataagt tagaggaaag caacagaaaa ctagacaaag tcaatgtcaa   7680
actgactagc acatctgctc tcattaccta tatcgttttg actatcatat ctcttgtttt   7740
tggtatactt agcctgattc tagcatgcta cctaatgtac aagcaaaagg cgcaacaaaa   7800
gaccttatta tggcttggga ataatactct agatcagatg agagccacta caaaaatgtg   7860
aacacagatg aggaacgaag gtttccctaa tagtaatttg tgtgaaagtt ctggtagtct   7920
gtcagttcag agagttaaga aaaaactacc ggttgtagat gaccaaagga cgatatacgg   7980
gtagaacggt aagagaggcc gcccctcaat tgcgagccag gcttcacaac ctccgttcta   8040
ccgcttcacc gacaacagtc ctcaatcatg gaccgcgccg ttagccaagt tgcgttagag   8100
aatgatgaaa gagaggcaaa aaatacatgg cgcttgatat tccggattgc aatcttattc   8160
ttaacagtag tgaccttggc tatatctgta gcctcccttt tatatagcat gggggctagc   8220
acacctagcg atcttgtagg cataccgact aggatttcca gggcagaaga aaagattaca   8280
tctacacttg gttccaatca agatgtagta gataggatat ataagcaagt ggcccttgag   8340
```

-continued

```
tctccgttgg cattgttaaa tactgagacc acaattatga acgcaataac atctctctct   8400
tatcagatta atggagctgc aaacaacagt gggtgggggg cacctatcca tgacccagat   8460
tatatagggg ggataggcaa agaactcatt gtagatgatg ctagtgatgt cacatcattc   8520
tatccctctg catttcaaga acatctgaat tttatcccgg cgcctactac aggatcaggt   8580
tgcactcgaa taccctcatt tgacatgagt gctacccatt actgctacac ccataatgta   8640
atattgtctg gatgcagaga tcactcacat tcatatcagt atttagcact tggtgtgctc   8700
cggacatctg caacagggag ggtattcttt tctactctgc gttccatcaa cctggacgac   8760
acccaaaatc ggaagtcttg cagtgtgagt gcaactcccc tgggttgtga tatgctgtgc   8820
tcgaaagtca cggagacaga ggaagaagat tataactcag ctgtccctac gcggatggta   8880
catgggaggt tagggttcga cggccagtac cacgaaaagg acctagatgt cacaacatta   8940
ttcggggact gggtggccaa ctacccagga gtagggggtg gatcttttat tgacagccgc   9000
gtatggttct cagtctacgg agggttaaaa cccaattcac ccagtgacac tgtacaggaa   9060
gggaaatatg tgatatacaa gcgatacaat gacacatgcc cagatgagca agactaccag   9120
attcgaatgg ccaagtcttc gtataagcct ggacggtttg gtgggaaacg catacagcag   9180
gctatcttat ctatcaaggt gtcaacatcc ttaggcgaag acccggtact gactgtaccg   9240
cccaacacag tcacactcat gggggccgaa ggcagaattc tcacagtagg gacatctcat   9300
ttcttgtatc aacgagggtc atcatacttc tctcccgcgt tattatatcc tatgacagtc   9360
agcaacaaaa cagccactct tcatagtcct tatacattca atgccttcac tcggccaggt   9420
agtatccctt gccaggcttc agcaagatgc cccaactcgt gtgttactgg agtctataca   9480
gatccatatc ccctaatctt ctatagaaac cacaccttgc gaggggtatt cgggacaatg   9540
cttgatggtg tacaagcaag acttaaccct gcgtctgcag tattcgatag cacatcccgc   9600
agtcgcatta ctcgagtgag ttcaagcagt accaaagcag catacacaac atcaacttgt   9660
tttaaagtgg tcaagactaa taagacctat tgtctcagca ttgctgaaat atctaatact   9720
ctcttcggag aattcagaat cgtcccgtta ctagttgaga tcctcaaaga tgacggggtt   9780
agagaagcca ggtctggcta gttgagtcaa ttataaagga gttggaaaga tggcattgta   9840
tcacctatct tctgcgacat caagaatcaa accgaatgcc ggcgcgtgct cgaattccat   9900
gttgccagtt gaccacaatc agccagtgct catgcgatca gattaagcct tgtcaatagt   9960
ctcttgatta agaaaaaatg taagtggcaa tgagatacaa ggcaaaacag ctcatggtta  10020
acaatacggg taggacatgg cgagctccgg tcctgaaagg gcagagcatc agattatcct  10080
accagagtca cacctgtctt caccattggt caagcacaaa ctactctatt actggaaatt  10140
aactgggcta ccgcttcctg atgaatgtga cttcgaccac ctcattctca gccgacaatg  10200
gaaaaaaata cttgaatcgg cctctcctga tactgagaga atgataaaac tcggaagggc  10260
agtacaccaa actcttaacc acaattccag aataaccgga gtgctccacc ccaggtgttt  10320
agaagaactg gctaatattg aggtcccaga ttcaaccaac aaatttcgga agattgagaa  10380
gaagatccaa attcacaaca cgagatatgg agaactgttc acaaggctgt gtacgcatat  10440
agagaagaaa ctgctggggt catcttggtc taacaatgtc ccccggtcag aggagttcag  10500
cagcattcgt acggatccgg cattctggtt tcactcaaaa tggtccacag ccaagtttgc  10560
atggctccat ataaaacaga tccagaggca tctgatggtg gcagctagga caaggtctgc  10620
ggccaacaaa ttggtgatgc taacccataa ggtaggccaa gtctttgtca ctcctgaact  10680
tgtcgttgtg acgcatacga atgagaacaa gttcacatgt cttacccagg aacttgtatt  10740
```

gatgtatgca gatatgatgg agggcagaga tatggtcaac ataatatcaa ccacggcggt 10800
gcatctcaga agcttatcag agaaaattga tgacattttg cggttaatag acgctctggc 10860
aaaagacttg ggtaatcaag tctacgatgt tgtatcacta atggagggat ttgcatacgg 10920
agctgtccag ctactcgagc cgtcaggtac atttgcagga gatttcttcg cattcaacct 10980
gcaggagctt aaagacattc taattggcct cctccccaat gatatagcag aatccgtgac 11040
tcatgcaatc gctactgtat tctctggttt agaacagaat caagcagctg agatgttgtg 11100
tctgttgcgt ctgtggggtc acccactgct tgagtcccgt attgcagcaa aggcagtcag 11160
gagccaaatg tgcgcaccga aaatggtaga ctttgatatg atccttcagg tactgtcttt 11220
cttcaaggga acaatcatca acgggtacag aaagaagaat gcaggtgtgt ggccgcgagt 11280
caaagtggat acaatatatg ggaaggtcat tgggcaacta catgcagatt cagcagagat 11340
ttcacacgat atcatgttga gagagtataa gagtttatct gcacttgaat ttgagccatg 11400
tatagaatat gaccctgtca ccaacctgag catgttccta aaagacaagg caatcgcaca 11460
ccccaacgat aattggcttg cctcgtttag gcggaacctt ctctccgaag accagaagaa 11520
acatgtaaaa gaagcaactt cgactaatcg cctcttgata gagtttttag agtcaaatga 11580
ttttgatcca tataaagaga tggaatatct gacgaccctt gagtacctta gagatgacaa 11640
tgtggcagta tcatactcgc tcaaggagaa ggaagtgaaa gttaatggac ggatcttcgc 11700
taagctgaca aagaagttaa ggaactgtca ggtgatggcg gaagggatcc tagccgatca 11760
gattgcacct ttctttcagg gaaatggagt cattcaggat agcatatcct tgaccaagag 11820
tatgctagcg atgagtcaac tgtcttttaa cagcaataag aaacgtatca ctgactgtaa 11880
agaaagagta tcttcaaacc gcaatcatga tccgaaaagc aagaaccgtc ggagagttgc 11940
aaccttcata acaactgacc tgcaaaagta ctgtcttaat tggagatatc agacaatcaa 12000
attgttcgct catgccatca atcagttgat gggcctacct cacttcttcg aatggattca 12060
cctaagactg atggacacta cgatgttcgt aggagaccct ttcaatcctc caagtgaccc 12120
tactgactgt gacctctcaa gagtccctaa tgatgacata tatattgtca gtgccagagg 12180
gggtatcgaa ggattatgcc agaagctatg gacaatgatc tcaattgctg caatccaact 12240
tgctgcagct agatcgcatt gtcgtgttgc ctgtatggta cagggtgata atcaagtaat 12300
agcagtaacg agagaggtaa gatcagacga ctctccggag atggtgttga cacagttgca 12360
tcaagccagt gataatttct tcaaggaatt aattcatgtc aatcatttga ttggccataa 12420
tttgaaggat cgtgaaacca tcaggtcaga cacattcttc atatacagca aacgaatctt 12480
caaagatgga gcaatcctca gtcaagtcct caaaaattca tctaaattag tgctagtgtc 12540
aggtgatctc agtgaaaaca ccgtaatgtc ctgtgccaac attgcctcta ctgtagcacg 12600
gctatgcgag aacgggcttc ccaaagactt ctgttactat ttaaactata taatgagttg 12660
tgtgcagaca tactttgact ctgagttctc catcaccaac aattcgcacc ccgatcttaa 12720
tcagtcgtgg attgaggaca tctcttttgt gcactcatat gttctgactc ctgcccaatt 12780
agggggactg agtaaccttc aatactcaag gctctacact agaaatatcg gtgacccggg 12840
gactactgct tttgcagaga tcaagcgact agaagcagtg ggattactga gtcctaacat 12900
tatgactaat atcttaacta ggccgcctgg gaatggagat tgggccagtc tgtgcaacga 12960
cccatactct ttcaatttg agactgttgc aagcccaaat attgttctta agaaacatac 13020
gcaaagagtc ctatttgaaa cttgttcaaa tcccttattg tctggagtgc acacagagga 13080

-continued

```
taatgaggca gaagagaagg cattggctga attcttgctt aatcaagagg tgattcatcc  13140
ccgcgttgcg catgccatca tggaggcaag ctctgtaggt aggagaaagc aaattcaagg  13200
gcttgttgac acaacaaaca ccgtaattaa gattgcgctt actaggaggc cattaggcat  13260
caagaggctg atgcggatag tcaattattc tagcatgcat gcaatgctgt ttagagacga  13320
tgtttttttcc tccagtagat ccaaccaccc cttagtctct tctaatatgt gttctctgac  13380
actggcagac tatgcacgga atagaagctg gtcacctttg acgggaggca ggaaaatact  13440
gggtgtatct aatcctgata cgatagaact cgtagagggt gagattctta gtgtaagcgg  13500
agggtgtaca agatgtgaca gcggagatga acaatttact tggttccatc ttccaagcaa  13560
tatagaattg accgatgaca ccagcaagaa tcctccgatg agggtaccat atctcgggtc  13620
aaagacacag gagaggagag ctgcctcact tgcaaaaata gctcatatgt cgccacatgt  13680
aaaggctgcc ctaagggcat catccgtgtt gatctgggct tatggggata atgaagtaaa  13740
ttggactgct gctcttacga ttgcaaaatc tcggtgtaat gtaaacttag agtatcttcg  13800
gttactgtcc cctttaccca cggctgggaa tcttcaacat agactagatg atggtataac  13860
tcagatgaca ttcacccctg catctctcta cagggtgtca ccttacattc acatatccaa  13920
tgattctcaa aggctgttca ctgaagaagg agtcaaagag gggaatgtgg tttaccaaca  13980
gatcatgctc ttgggtttat ctctaatcga atcgatcttt ccaatgacaa caaccaggac  14040
atatgatgag atcacactgc acctacatag taaatttagt tgctgtatca gagaagcacc  14100
tgttgcggtt cctttcgagc tacttggggt ggtaccggaa ctgaggacag tgacctcaaa  14160
taagtttatg tatgatccta gccctgtatc ggagggagac tttgcgagac ttgacttagc  14220
tatcttcaag agttatgagc ttaatctgga gtcatatccc acgatagagc taatgaacat  14280
tctttcaata tccagcggga agttgattgg ccagtctgtg gtttcttatg atgaagatac  14340
ctccataaag aatgacgcca taatagtgta tgacaatacc cgaaattgga tcagtgaagc  14400
tcagaattca gatgtggtcc gcctatttga atatgcagca cttgaagtgc tcctcgactg  14460
ttcttaccaa ctctattacc tgagagtaag aggcctggac aatattgtct tatatatggg  14520
tgatttatac aagaatatgc caggaattct actttccaac attgcagcta caatatctca  14580
tcccgtcatt cattcaaggt tacatgcagt gggcctggtc aaccatgacg gatcacacca  14640
acttgcagat acggatttta tcgaaatgtc tgcaaaacta ttagtatctt gcacccgacg  14700
tgtgatctcc ggcttatatt caggaaataa gtatgatctg ctgttcccat ctgtcttaga  14760
tgataacctg aatgagaaga tgcttcagct gatatcccgg ttatgctgtc tgtacacggt  14820
actctttgct acaacaagag aaatcccgaa aataagaggc ttaactgcag aagagaaatg  14880
ttcaatactc actgagtatt tactgtcgga tgctgtgaaa ccattactta gccccgatca  14940
agtgagctct atcatgtctc ctaacataat tacattccca gctaatctgt actacatgtc  15000
tcggaagagc ctcaatttga tcagggaaag ggaggacagg gatactatcc tggcgttgtt  15060
gttcccccaa gagccattat tagagttccc ttctgtgcaa gatattggtg ctcgagtgaa  15120
agatccattc acccgacaac ctgcggcatt tttgcaagag ttagatttga gtgctccagc  15180
aaggtatgac gcattcacac ttagtcagat tcatcctgaa ctcacatctc caaatccgga  15240
ggaagactac ttagtacgat acttgttcag agggataggg actgcatctt cctcttggta  15300
taaggcatct catctccttt ctgtacccga ggtaagatgt gcaagacacg ggaactcctt  15360
atacttagct gaagggagcg gagccatcat gagtcttctc gaactgcatg taccacatga  15420
aactatctat tacaatacgc tcttttcaaa tgagatgaac cccccgcaac gacatttcgg  15480
```

```
gccgacccca actcagtttt tgaattcggt tgtttatagg aatctacagg cggaggtaac  15540
atgcaaagat ggatttgtcc aagagttccg tccattatgg agagaaaata cagaggaaag  15600
cgacctgacc tcagataaag tagtggggta tattacatct gcagtgccct acagatctgt  15660
atcattgctg cattgtgaca ttgaaattcc tccagggtcc aatcaaagct tactagatca  15720
actagctatc aatttatctc tgattgccat gcattctgta agggagggcg gggtagtaat  15780
catcaaagtg ttgtatgcaa tgggatacta ctttcatcta ctcatgaact tgtttgctcc  15840
gtgttccaca aaaggatata ttctctctaa tggttatgca tgtcgaggag atatggagtg  15900
ttacctggta tttgtcatgg gttacctggg cgggcctaca tttgtacatg aggtggtgag  15960
gatggcgaaa actctggtgc agcggcacgg tacgcttttg tctaaatcag atgagatcac  16020
actgaccagg ttattcacct cacagcggca gcgtgtgaca gacatcctat ccagtccttt  16080
accaagatta ataaagtact tgaggaagaa tattgacact gcgctgattg aagccggggg  16140
acagcccgtc cgtccattct gtgcggagag tctggtgagc acgctagcga acataactca  16200
gataacccag atcatcgcta gtcacattga cacagttatc cggtctgtga tatatatgga  16260
agctgagggt gatctcgctg acacagtatt tctatttacc ccttacaatc tctctactga  16320
cgggaaaaag aggacatcac ttaaacagtg cacgagacag atcctagagg ttacaatact  16380
aggtcttaga gtcgaaaatc tcaataaaat aggcgatata atcagcctag tgcttaaagg  16440
catgatctcc atggaggacc ttatcccact aaggacatac ttgaagcata gtacctgccc  16500
taaatatttg aaggctgtcc taggtattac caaactcaaa gaaatgttta cagacacttc  16560
tgtactgtac ttgactcgtg ctcaacaaaa attctacatg aaaactatag gcaatgcagt  16620
caaaggatat tacagtaact gtgactctta acgaaaatca catattaata ggctcctttt  16680
ttggccaatt gtattcttgt tgatttaatc atattatgtt agaaaaaagt tgaaccctga  16740
ctccttagga ctcgaattcg aactcaaata aatgtcttaa aaaaaggttg cgcacaatta  16800
ttcttgagtg tagtctcgtc attcaccaaa tctttgtttg gt                    16842
```

<210> SEQ ID NO 22
<211> LENGTH: 16974
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 22

```
accaaacaga gaatccgtga gttacgataa aaggcgaagg agcaattgaa gtcgcacggg     60
tagaaggtgt gaatctcgag tgcgagcccg aagcacaaac tcgagaaagc cttctgccaa    120
catgtcttcc gtatttgatg agtacgaaca gctcctcgcg gctcagactc gccccaatgg    180
agctcatgga gggggagaaa aagggagtac cttaaaagta gacgtcccgg tattcactct    240
taacagtgat gacccagaag atagatggag ctttgtggta ttctgcctcc ggattgctgt    300
tagcgaagat gccaacaaac cactcaggca aggtgctctc atatctcttt tatgctccca    360
ctcacaggta atgaggaacc atgttgccct tgcagggaaa cagaatgaag ccacattggc    420
cgtgcttgag attgatggct ttgccaacgg cacgccccag ttcaacaata ggagtggagt    480
gtctgaagag agagcacaga gatttgcgat gatagcagga tctctccctc gggcatgcag    540
caacggaacc ccgttcgtca cagccggggc cgaagatgat gcaccagaag acatcaccga    600
taccctggag aggatcctct ctatccaggc tcaagtatgg gtcacagtag caaaagccat    660
```

-continued

```
gactgcgtat gagactgcag atgagtcgga aacaaggcga atcaataagt atatgcagca    720
aggcagggtc caaaagaaat acatcctcta ccccgtatgc aggagcacaa tccaactcac    780
gatcagacag tctcttgcag tccgcatctt tttggttagc gagctcaaga gaggccgcaa    840
cacggcaggt ggtacctcta cttattataa cctggtaggg gacgtagact catacatcag    900
gaataccggg cttactgcat tcttcttgac actcaagtac ggaatcaaca ccaagacatc    960
agcccttgca cttagtagcc tctcaggcga catccagaag atgaagcagc tcatgcgttt   1020
gtatcggatg aaaggagata atgcgccgta catgacatta cttggtgata gtgaccagat   1080
gagctttgcg cctgccgagt atgcacaact ttactccttt gccatgggta tggcatcagt   1140
cctagataaa ggtactggga aataccaatt tgccagggac tttatgagca catcattctg   1200
gagacttgga gtagagtacg ctcaggctca gggaagtagc attaacgagg atatggctgc   1260
cgagctaaag ctaaccccag cagcaaggag gggcctggca gctgctgccc aacgggtctc   1320
cgaggagacc agcagcatag acatgcctac tcaacaagtc ggagtcctca ctgggcttag   1380
cgaggggggg tcccaagctc tacaaggcgg atcgaataga tcgcaagggc aaccagaagc   1440
cggggatggg gagacccaat tcctggatct gatgagagcg gtagcaaata gcatgaggga   1500
ggcgccaaac tctgcacagg gcactcccca atcggggcct cccccaactc ctgggccatc   1560
ccaagataac gacaccgact gggggtattg atggacaaaa cccagcctgc ttccacaaaa   1620
acatcccaat gccctcaccc gtagtcgacc cctcgatttg cggctctata tgaccacacc   1680
ctcaaacaaa catcccccctc tttcctccct cccccctgctg tacaactacg tacgccctag   1740
ataccacagg cacaatgcgg ctcactaaca atcaaaacag agccgaggga attagaaaaa   1800
agtacgggta gaagagggat attcagagat cagggcaagt ctcccgagtc tctgctctct   1860
cctctacctg atagaccagg acaaacatgg ccacctttac agatgcagag atcgacgagc   1920
tatttgagac aagtggaact gtcattgaca acataattac agcccagggt aaaccagcag   1980
agactgttgg aaggagtgca atcccacaag gcaagaccaa ggtgctgagc gcagcatggg   2040
agaagcatgg gagcatccag ccaccggcca gtcaagacaa ccccgatcga caggacagat   2100
ctgacaaaca accatccaca cccgagcaaa cgaccccgca tgacagcccg ccggccacat   2160
ccgccgacca gccccccacc caggccacag acgaagccgt cgacacacag ctcaggaccg   2220
gagcaagcaa ctctctgctg ttgatgcttg acaagctcag caataaatcg tccaatgcta   2280
aaaagggccc atggtcgagc cccaagaggg ggaatcacca acgtccgact caacagcagg   2340
ggagtcaacc cagtcgcgga aacagtcagg aaagaccgca gaaccaagtc aaggccgccc   2400
ctggaaacca gggcacagac gtgaacacag catatcatgg acaatgggag gagtcacaac   2460
tatcagctgg tgcaacccct catgctctcc gatcaaggca gagccaagac aatacccttg   2520
tatctgcgga tcatgtccag ccacctgtag actttgtgca agcgatgatg tctatgatgg   2580
aggcgatatc acagagagta agtaaggttg actatcagct agatcttgtc ttgaaacaga   2640
catcctccat ccctatgatg cggtccgaaa tccaacagct gaaaacatct gttgcagtca   2700
tggaagccaa cttgggaatg atgaagattc tggatcccgg ttgtgccaac atttcatctc   2760
tgagtgatct acgggcagtt gcccgatctc acccggtttt agtttcaggc cctggagacc   2820
cctctcccta tgtgacacaa ggaggcgaaa tggcacttaa taaactttcg caaccagtgc   2880
cacatccatc tgaattgatt aaacccgcca ctgcatgcgg gcctgatata ggagtggaaa   2940
aggacactgt ccgtgcattg atcatgtcac gcccaatgca cccgagttct tcagccaagc   3000
```

tcctaagcaa gttagatgca gccgggtcga tcgaggaaat caggaaaatc aagcgccttg 3060
ctctaaatgg ctaattacta ctgccacacg tagcgggtcc ctgtccactc ggcatcacac 3120
ggaatctgca ccgagttccc ccccgcggac ccaaggtcca actctccaag cggcaatcct 3180
ctctcgcttc ctcagcccca ctgaatgatc gcgtaaccgt aattaatcta gctacattta 3240
agattaagaa aaaatacggg tagaattgga gtgccccact agttttgcca ccatgtcttg 3300
gaaagtggtg atcatttttt cattgctaat aacacctcaa cacggtctta aagagagcta 3360
cctagaagaa tcatgtagca ctataactga gggatatctt agtgttctga ggacaggttg 3420
gtataccaac gtttttacat tagaggtggg tgatgtagaa aaccttacat gttctgatgg 3480
acctagccta ataaaaacag aattagatct gaccaaaagt gcactaagag agctcaaaac 3540
agtctctgct gaccaattgg caagagagga acaaattgag aatcccagac aatctaggtt 3600
tgttctagga gcaatagcac tcggtgttgc aacagcagct gcagtcacag caggtgttgc 3660
aattgccaaa accatccggc ttgagagtga agtcacagca attaagaatg ccctcaaaac 3720
gaccaatgaa gcagtatcta cattggggaa tggagttcga gtgttggcaa ctgcagtgag 3780
agagctgaaa gactttgtga gcaagaattt aactcgtgca atcaacaaaa acaagtgcga 3840
cattgatgac ctaaaaatgg ccgttagctt cagtcaattc aacagaaggt ttctaaatgt 3900
tgtgcggcaa ttttcagaca atgctggaat aacaccagca atatctttgg acttaatgac 3960
agatgctgaa ctagccaggg ccgtttctaa catgccgaca tctgcaggac aaataaaatt 4020
gatgttggag aaccgcgcga tggtgcgaag aaaggggttc ggaatcctga taggggtcta 4080
cgggagctct gtaatttaca tggtgcagct gccaatcttt ggcgttatag acacgccttg 4140
ctggatagta aaagcagccc cttcttgttc cgaaaaaaag ggaaactatg cttgcctctt 4200
aagagaagac caagggtggt attgtcagaa tgcagggtca actgtttact acccaaatga 4260
gaaagactgt gaaacaagag gagaccatgt cttttgcgac acagcagcag gaattaatgt 4320
tgctgagcaa tcaaaggagt gcaacatcaa catatccact acaaattacc catgcaaagt 4380
cagcacagga agacatccta tcagtatggt tgcactgtct cctcttgggg ctctggttgc 4440
ttgctacaaa ggagtaagct gttccattgg cagcaacaga gtagggatca tcaagcagct 4500
gaacaaaggt tgctcctata taaccaacca agatgcagac acagtgacaa tagacaacac 4560
tgtatatcag ctaagcaaag ttgagggtga acagcatgtt ataaaaggca gaccagtgtc 4620
aagcagcttt gatccaatca agtttcctga agatcaattc aatgttgcac ttgaccaagt 4680
ttttgagagc attgaaaaca gccaggcctt ggtagatcaa tcaaacagaa tcctaagcag 4740
tgcagagaaa gggaatactg gcgttaacct cattacctat atcgttttga ctatcatatc 4800
tcttgttttt ggtatactta gcctgattct agcatgctac ctaatgtaca agcaaaaggc 4860
gcaacaaaag accttattat ggcttgggaa taatacccta gatcagatga gagccactac 4920
aaaaatgtga ccgcggaccc aaggtccaac tctccaagcg gcaatcctct ctcgcttcct 4980
cagccccact gaatgatcgc gtaaccgtaa ttaatctagc tacatttaag attaagaaaa 5040
aatacgggta gaattggagt gccccaattg tgccaagatg gactcatcta ggacaattgg 5100
gctgtacttt gattctgccc attcttctag caacctgtta gcatttccga tcgtcctaca 5160
agacacagga gatgggaaga agcaaatcgc cccgcaatat aggatccagc gccttgactt 5220
gtggactgat agtaaggagg actcagtatt catcaccacc tatggattca tctttcaagt 5280
tgggaatgaa gaagccaccg tcggcatgat cgatgataaa cccaagcgcg agttactttc 5340
cgctgcgatg ctctgcctag gaagcgtccc aaataccgga gaccttattg agctggcaag 5400

```
ggcctgtctc actatgatag tcacatgcaa gaagagtgca actaatactg agagaatggt   5460
tttctcagta gtgcaggcac cccaagtgct gcaaagctgt agggttgtgg caaacaaata   5520
ctcatcagtg aatgcagtca agcacgtgaa agcgccagag aagattcccg ggagtggaac   5580
cctagaatac aaggtgaact ttgtctcctt gactgtggta ccgaagaggg atgtctacaa   5640
gatcccagct gcagtattga aggtttctgg ctcgagtctg tacaatcttg cgctcaatgt   5700
cactattaat gtggaggtag acccgaggag tcctttggtt aaatctctgt ctaagtctga   5760
cagcggatac tatgctaacc tcttcttgca tattggactt atgaccactg tagataggaa   5820
ggggaagaaa gtgacatttg acaagctgga aaagaaaata aggagccttg atctatctgt   5880
cgggctcagt gatgtgctcg ggccttccgt gttggtaaaa gcaagaggtg cacggactaa   5940
gcttttggca cctttcttct ctagcagtgg gacagcctgc tatcccatag caaatgcttc   6000
tcctcaggtg gccaagatac tctggagtca aaccgcgtgc ctgcggagcg ttaaaatcat   6060
tatccaagca ggtacccaac gcgctgtcgc agtgaccgcc gaccacgagg ttacctctac   6120
taagctggag aaggggcaca cccttgccaa atacaatcct tttaagaaat aagctgcgtc   6180
tctgagattg cgctccgccc actcacccag atcatcatga cacaaaaaac taatctgtct   6240
tgattattta cagttagttt acctgtctat caagttagaa aaaacacggg tagaagattc   6300
tggatcccgg ttggcgccct ccaggtgcaa gatgggctcc agaccttcta ccaagaaccc   6360
agcacctatg atgctgacta tccgggttgc gctggtactg agttgcatct gtccggcaaa   6420
ctccattgat ggcaggcctc ttgcagctgc aggaattgtg gttacaggag acaaagccgt   6480
caacatatac acctcatccc agacaggatc aatcatagtt aagctcctcc cgaatctgcc   6540
caaggataag gaggcatgtg cgaaagcccc cttggatgca tacaacagga cattgaccac   6600
tttgctcacc ccccttggtg actctatccg taggatacaa gagtctgtga ctacatctgg   6660
agggggggaga cagggggcgcc ttataggcgc cattattggc ggtgtggctc ttggggttgc   6720
aactgccgca caaataacag cggccgcagc tctgatacaa gccaaacaaa atgctgccaa   6780
catcctccga cttaaagaga gcattgccgc aaccaatgag gctgtgcatg aggtcactga   6840
cggattatcg caactagcag tggcagttgg gaagatgcag cagtttgtta atgaccaatt   6900
taataaaaca gctcaggaat tagactgcat caaaattgca cagcaagttg gtgtagagct   6960
caacctgtac ctaaccgaat tgactacagt attcggacca caaatcactt cacctgcttt   7020
aaacaagctg actattcagg cactttacaa tctagctggt ggaaatatgg attacttatt   7080
gactaagtta ggtgtaggga acaatcaact cagctcatta atcggtagcg gcttaatcac   7140
cggtaaccct attctatacg actcacagac tcaactcttg ggtatacagg taactctacc   7200
ttcagtcggg aacctaaata atatgcgtgc cacctacttg gaaaccttat ccgtaagcac   7260
aaccagggga tttgcctcgg cacttgtccc aaaagtggtg acacaggtcg gttctgtgat   7320
agaagaactt gacacctcat actgtataga aactgactta gatttatatt gtacaagaat   7380
agtaacgttc cctatgtccc ctggtattta ttcctgcttg agcggcaata cgtcggcctg   7440
tatgtactca aagaccgaag gcgcacttac tacaccatac atgactatca aaggttcagt   7500
catcgccaac tgcaagatga caacatgtag atgtgtaaac cccccgggta tcatatcgca   7560
aaactatgga gaagccgtgt ctctaataga taaacaatca tgcaatgttt tatccttagg   7620
cgggataact ttaaggctca gtggggaatt cgatgtaact tatcagaaga atatctcaat   7680
acaagattct caagtaataa taacaggcaa tcttgatatc tcaactgagc ttgggaatgt   7740
```

-continued

```
caacaactcg atcagtaatg ctttgaataa gttagaggaa agcaacagaa aactagacaa   7800
agtcaatgtc aaactgacta gcacatctgc tctcattacc tatatcgttt tgactatcat   7860
atctcttgtt tttggtatac ttagcctgat tctagcatgc tacctaatgt acaagcaaaa   7920
ggcgcaacaa aagaccttat tatggcttgg gaataatact ctagatcaga tgagagccac   7980
tacaaaaatg tgaacacaga tgaggaacga aggtttccct aatagtaatt tgtgtgaaag   8040
ttctggtagt ctgtcagttc agagagttaa gaaaaaacta ccggttgtag atgaccaaag   8100
gacgatatac gggtagaacg gtaagagagg ccgcccctca attgcgagcc aggcttcaca   8160
acctccgttc taccgcttca ccgacaacag tcctcaatca tggaccgcgc cgttagccaa   8220
gttgcgttag agaatgatga aagagaggca aaaaatacat ggcgcttgat attccggatt   8280
gcaatcttat tcttaacagt agtgaccttg gctatatctg tagcctccct tttatatagc   8340
atgggggcta gcacacctag cgatcttgta ggcataccga ctaggatttc cagggcagaa   8400
gaaaagatta catctacact tggttccaat caagatgtag tagataggat atataagcaa   8460
gtggcccttg agtctccgtt ggcattgtta aatactgaga ccacaattat gaacgcaata   8520
acatctctct cttatcagat taatggagct gcaaacaaca gtgggtgggg ggcacctatc   8580
catgacccag attatatagg ggggataggc aaagaactca ttgtagatga tgctagtgat   8640
gtcacatcat tctatccctc tgcatttcaa gaacatctga attttatccc ggcgcctact   8700
acaggatcag gttgcactcg aataccctca tttgacatga gtgctaccca ttactgctac   8760
acccataatg taatattgtc tggatgcaga gatcactcac attcatatca gtatttagca   8820
cttggtgtgc tccggacatc tgcaacaggg agggtattct tttctactct gcgttccatc   8880
aacctggacg acacccaaaa tcggaagtct tgcagtgtga gtgcaactcc cctgggttgt   8940
gatatgctgt gctcgaaagt cacggagaca gaggaagaag attataactc agctgtccct   9000
acgcggatgg tacatgggag gttagggttc gacggccagt accacgaaaa ggacctagat   9060
gtcacaacat tattcgggga ctgggtggcc aactacccag gagtaggggg tggatctttt   9120
attgacagcc gcgtatggtt ctcagtctac ggagggttaa aacccaattc acccagtgac   9180
actgtacagg aagggaaata tgtgatatac aagcgataca atgacacatg cccagatgag   9240
caagactacc agattcgaat ggccaagtct tcgtataagc ctggacggtt tggtgggaaa   9300
cgcatacagc aggctatctt atctatcaag gtgtcaacat ccttaggcga agacccggta   9360
ctgactgtac cgcccaacac agtcacactc atgggggccg aaggcagaat tctcacagta   9420
gggacatctc atttcttgta tcaacgaggg tcatcatact tctctcccgc gttattatat   9480
cctatgacag tcagcaacaa aacagccact cttcatagtc cttatacatt caatgccttc   9540
actcggccag gtagtatccc ttgccaggct tcagcaagat gccccaactc gtgtgttact   9600
ggagtctata cagatccata tcccctaatc ttctatagaa accacacctt gcgaggggta   9660
ttcgggacaa tgcttgatgg tgtacaagca agacttaacc ctgcgtctgc agtattcgat   9720
agcacatccc gcagtcgcat tactcgagtg agttcaagca gtaccaaagc agcatacaca   9780
acatcaactt gttttaaagt ggtcaagact aataagacct attgtctcag cattgctgaa   9840
atatctaata ctctcttcgg agaattcaga atcgtcccgt tactagttga gatcctcaaa   9900
gatgacgggg ttagagaagc caggtctggc tagttgagtc aattataaag gagttggaaa   9960
gatggcattg tatcacctat cttctgcgac atcaagaatc aaaccgaatg ccggcgcgtg  10020
ctcgaattcc atgttgccag ttgaccacaa tcagccagtg ctcatgcgat cagattaagc  10080
cttgtcaata gtctcttgat taagaaaaaa tgtaagtggc aatgagatac aaggcaaaac  10140
```

```
agctcatggt taacaatacg ggtaggacat ggcgagctcc ggtcctgaaa gggcagagca  10200
tcagattatc ctaccagagt cacacctgtc ttcaccattg gtcaagcaca aactactcta  10260
ttactggaaa ttaactgggc taccgcttcc tgatgaatgt gacttcgacc acctcattct  10320
cagccgacaa tggaaaaaaa tacttgaatc ggcctctcct gatactgaga gaatgataaa  10380
actcggaagg gcagtacacc aaactcttaa ccacaattcc agaataaccg gagtgctcca  10440
ccccaggtgt ttagaagaac tggctaatat tgaggtccca gattcaacca acaaatttcg  10500
gaagattgag aagaagatcc aaattcacaa cacgagatat ggagaactgt tcacaaggct  10560
gtgtacgcat atagagaaga aactgctggg gtcatcttgg tctaacaatg tcccccggtc  10620
agaggagttc agcagcattc gtacggatcc ggcattctgg tttcactcaa aatggtccac  10680
agccaagttt gcatggctcc atataaaaca gatccagagg catctgatgg tggcagctag  10740
gacaaggtct gcggccaaca aattggtgat gctaacccat aaggtaggcc aagtctttgt  10800
cactcctgaa cttgtcgttg tgacgcatac gaatgagaac aagttcacat gtcttaccca  10860
ggaacttgta ttgatgtatg cagatatgat ggagggcaga gatatggtca acataatatc  10920
aaccacggcg gtgcatctca gaagcttatc agagaaaatt gatgacattt tgcggttaat  10980
agacgctctg gcaaaagact tgggtaatca agtctacgat gttgtatcac taatggaggg  11040
atttgcatac ggagctgtcc agctactcga gccgtcaggt acatttgcag gagatttctt  11100
cgcattcaac ctgcaggagc ttaaagacat tctaattggc ctcctcccca atgatatagc  11160
agaatccgtg actcatgcaa tcgctactgt attctctggt ttagaacaga atcaagcagc  11220
tgagatgttg tgtctgttgc gtctgtgggg tcacccactg cttgagtccc gtattgcagc  11280
aaaggcagtc aggagccaaa tgtgcgcacc gaaaatggta gactttgata tgatccttca  11340
ggtactgtct ttcttcaagg gaacaatcat caacgggtac agaaagaaga atgcaggtgt  11400
gtggccgcga gtcaaagtgg atacaatata tgggaaggtc attgggcaac tacatgcaga  11460
ttcagcagag atttcacacg atatcatgtt gagagagtat aagagtttat ctgcacttga  11520
atttgagcca tgtatagaat atgaccctgt caccaacctg agcatgttcc taaaagacaa  11580
ggcaatcgca caccccaacg ataattggct tgcctcgttt aggcggaacc ttctctccga  11640
agaccagaag aaacatgtaa aagaagcaac ttcgactaat cgcctcttga tagagttttt  11700
agagtcaaat gattttgatc catataaaga gatggaatat ctgacgaccc ttgagtacct  11760
tagagatgac aatgtggcag tatcatactc gctcaaggag aaggaagtga aagttaatgg  11820
acggatcttc gctaagctga caaagaagtt aaggaactgt caggtgatgg cggaagggat  11880
cctagccgat cagattgcac ctttctttca gggaaatgga gtcattcagg atagcatatc  11940
cttgaccaag agtatgctag cgatgagtca actgtctttt aacagcaata agaaacgtat  12000
cactgactgt aaagaaagag tatcttcaaa ccgcaatcat gatccgaaaa gcaagaaccg  12060
tcggagagtt gcaaccttca taacaactga cctgcaaaag tactgtctta attggagata  12120
tcagacaatc aaattgttcg ctcatgccat caatcagttg atgggcctac ctcacttctt  12180
cgaatggatt cacctaagac tgatggacac tacgatgttc gtaggagacc ctttcaatcc  12240
tccaagtgac cctactgact gtgacctctc aagagtccct aatgatgaca tatatattgt  12300
cagtgccaga gggggtatcg aaggattatg ccagaagcta tggacaatga tctcaattgc  12360
tgcaatccaa cttgctgcag ctagatcgca ttgtcgtgtt gcctgtatgg tacagggtga  12420
taatcaagta atagcagtaa cgagagaggt aagatcagac gactctccgg agatggtgtt  12480
```

gacacagttg catcaagcca gtgataattt cttcaaggaa ttaattcatg tcaatcattt 12540
gattggccat aatttgaagg atcgtgaaac catcaggtca gacacattct tcatatacag 12600
caaacgaatc ttcaaagatg gagcaatcct cagtcaagtc ctcaaaaatt catctaaatt 12660
agtgctagtg tcaggtgatc tcagtgaaaa caccgtaatg tcctgtgcca acattgcctc 12720
tactgtagca cggctatgcg agaacgggct tcccaaagac ttctgttact atttaaacta 12780
tataatgagt tgtgtgcaga catactttga ctctgagttc tccatcacca acaattcgca 12840
ccccgatctt aatcagtcgt ggattgagga catctctttt gtgcactcat atgttctgac 12900
tcctgcccaa ttagggggac tgagtaacct tcaatactca aggctctaca ctagaaatat 12960
cggtgacccg gggactactg cttttgcaga gatcaagcga ctagaagcag tgggattact 13020
gagtcctaac attatgacta atatcttaac taggccgcct gggaatggag attgggccag 13080
tctgtgcaac gacccatact ctttcaattt tgagactgtt gcaagcccaa atattgttct 13140
taagaaacat acgcaaagag tcctatttga aacttgttca aatcccttat tgtctggagt 13200
gcacacagag gataatgagg cagaagagaa ggcattggct gaattcttgc ttaatcaaga 13260
ggtgattcat ccccgcgttg cgcatgccat catggaggca agctctgtag gtaggagaaa 13320
gcaaattcaa gggcttgttg acacaacaaa caccgtaatt aagattgcgc ttactaggag 13380
gccattaggc atcaagaggc tgatgcggat agtcaattat tctagcatgc atgcaatgct 13440
gtttagagac gatgtttttt cctccagtag atccaaccac cccttagtct cttctaatat 13500
gtgttctctg acactggcag actatgcacg gaatagaagc tggtcacctt tgacgggagg 13560
caggaaaata ctgggtgtat ctaatcctga tacgatagaa ctcgtagagg gtgagattct 13620
tagtgtaagc ggagggtgta caagatgtga cagcggagat gaacaattta cttggttcca 13680
tcttccaagc aatatagaat tgaccgatga caccagcaag aatcctccga tgagggtacc 13740
atatctcggg tcaaagacac aggagaggag agctgcctca cttgcaaaaa tagctcatat 13800
gtcgccacat gtaaaggctg ccctaagggc atcatccgtg ttgatctggg cttatgggga 13860
taatgaagta aattggactg ctgctcttac gattgcaaaa tctcggtgta atgtaaactt 13920
agagtatctt cggttactgt ccccttttacc cacggctggg aatcttcaac atagactaga 13980
tgatggtata actcagatga cattcacccc tgcatctctc tacagggtgt caccttacat 14040
tcacatatcc aatgattctc aaaggctgtt cactgaagaa ggagtcaaag aggggaatgt 14100
ggtttaccaa cagatcatgc tcttgggttt atctctaatc gaatcgatct ttccaatgac 14160
aacaaccagg acatatgatg agatcacact gcacctacat agtaaattta gttgctgtat 14220
cagagaagca cctgttgcgg ttcctttcga gctacttggg gtggtaccgg aactgaggac 14280
agtgacctca aataagttta tgtatgatcc tagccctgta tcggagggag actttgcgag 14340
acttgactta gctatcttca agagttatga gcttaatctg gagtcatatc ccacgataga 14400
gctaatgaac attctttcaa tatccagcgg gaagttgatt ggccagtctg tggtttctta 14460
tgatgaagat acctccataa agaatgacgc cataatagtg tatgacaata cccgaaattg 14520
gatcagtgaa gctcagaatt cagatgtggt ccgcctattt gaatatgcag cacttgaagt 14580
gctcctcgac tgttcttacc aactctatta cctgagagta agaggcctgg acaatattgt 14640
cttatatatg ggtgatttat acaagaatat gccaggaatt ctactttcca acattgcagc 14700
tacaatatct catcccgtca ttcattcaag gttacatgca gtgggcctgg tcaaccatga 14760
cggatcacac caacttgcag atacggattt tatcgaaatg tctgcaaaac tattagtatc 14820
ttgcacccga cgtgtgatct ccggcttata ttcaggaaat aagtatgatc tgctgttccc 14880

-continued

```
atctgtctta gatgataacc tgaatgagaa gatgcttcag ctgatatccc ggttatgctg  14940

tctgtacacg gtactctttg ctacaacaag agaaatcccg aaaataagag gcttaactgc  15000

agaagagaaa tgttcaatac tcactgagta tttactgtcg gatgctgtga aaccattact  15060

tagccccgat caagtgagct ctatcatgtc tcctaacata attacattcc cagctaatct  15120

gtactacatg tctcggaaga gcctcaattt gatcagggaa agggaggaca gggatactat  15180

cctggcgttg ttgttccccc aagagccatt attagagttc ccttctgtgc aagatattgg  15240

tgctcgagtg aaagatccat tcacccgaca acctgcggca tttttgcaag agttagattt  15300

gagtgctcca gcaaggtatg acgcattcac acttagtcag attcatcctg aactcacatc  15360

tccaaatccg gaggaagact acttagtacg atacttgttc agagggatag ggactgcatc  15420

ttcctcttgg tataaggcat ctcatctcct ttctgtaccc gaggtaagat gtgcaagaca  15480

cgggaactcc ttatacttag ctgaagggag cggagccatc atgagtcttc tcgaactgca  15540

tgtaccacat gaaactatct attacaatac gctcttttca aatgagatga acccccccgca  15600

acgacatttc gggccgaccc caactcagtt tttgaattcg gttgtttata ggaatctaca  15660

ggcggaggta acatgcaaag atggatttgt ccaagagttc cgtccattat ggagagaaaa  15720

tacagaggaa agcgacctga cctcagataa agtagtgggg tatattacat ctgcagtgcc  15780

ctacagatct gtatcattgc tgcattgtga cattgaaatt cctccagggt ccaatcaaag  15840

cttactagat caactagcta tcaatttatc tctgattgcc atgcattctg taagggaggg  15900

cggggtagta atcatcaaag tgttgtatgc aatgggatac tactttcatc tactcatgaa  15960

cttgtttgct ccgtgttcca caaaaggata tattctctct aatggttatg catgtcgagg  16020

agatatggag tgttacctgg tatttgtcat gggttacctg ggcgggccta catttgtaca  16080

tgaggtggtg aggatggcga aaactctggt gcagcggcac ggtacgcttt tgtctaaatc  16140

agatgagatc acactgacca ggttattcac ctcacagcgg cagcgtgtga cagacatcct  16200

atccagtcct ttaccaagat taataaagta cttgaggaag aatattgaca ctgcgctgat  16260

tgaagccggg ggacagcccg tccgtccatt ctgtgcggag agtctggtga gcacgctagc  16320

gaacataact cagataaccc agatcatcgc tagtcacatt gacacagtta tccggtctgt  16380

gatatatatg gaagctgagg gtgatctcgc tgacacagta tttctattta ccccttacaa  16440

tctctctact gacgggaaaa agaggacatc acttaaacag tgcacgagac agatcctaga  16500

ggttacaata ctaggtctta gagtcgaaaa tctcaataaa ataggcgata taatcagcct  16560

agtgcttaaa ggcatgatct ccatggagga ccttatccca ctaaggacat acttgaagca  16620

tagtacctgc cctaaatatt tgaaggctgt cctaggtatt accaaactca aagaaatgtt  16680

tacagacact tctgtactgt acttgactcg tgctcaacaa aaattctaca tgaaaactat  16740

aggcaatgca gtcaaaggat attacagtaa ctgtgactct taacgaaaat cacatattaa  16800

taggctcctt ttttggccaa ttgtattctt gttgatttaa tcatattatg ttagaaaaaa  16860

gttgaaccct gactccttag gactcgaatt cgaactcaaa taaatgtctt aaaaaaaggt  16920

tgcgcacaat tattcttgag tgtagtctcg tcattcacca aatctttgtt tggt        16974
```

<210> SEQ ID NO 23
<211> LENGTH: 25
<212> TYPE: PRT
<213> ORGANISM: Human respiratory syncytial virus

<400> SEQUENCE: 23

-continued

Met Glu Leu Leu Ile Leu Lys Ala Asn Ala Ile Thr Thr Ile Leu Thr
1 5 10 15

Ala Val Thr Phe Cys Phe Ala Ser Gly
20 25

<210> SEQ ID NO 24
<211> LENGTH: 18
<212> TYPE: PRT
<213> ORGANISM: Human metapneumovirus

<400> SEQUENCE: 24

Met Ser Trp Lys Val Val Ile Ile Phe Ser Leu Leu Ile Thr Pro Gln
1 5 10 15

His Gly

<210> SEQ ID NO 25
<211> LENGTH: 1725
<212> TYPE: DNA
<213> ORGANISM: Human respiratory syncytial virus

<400> SEQUENCE: 25
atggagttgc caatcctcaa aacaaatgct attaccacaa tccttgctgc agtcacactc 60
tgttttgctt ccagtcaaaa catcactgaa gaattttatc aatcaacatg cagtgcagtt 120
agcaaaggct atcttagtgc tctaagaact ggttggtata ctagtgttat aactatagaa 180
ttaagtaata tcaaggaaaa taagtgtaat ggtacagacg ctaaggtaaa attaataaaa 240
caagaattag ataaatataa aaatgctgta acagaattgc agttgctcat gcaaagcaca 300
ccagcagcca acagtcgagc cagaagagaa ctaccaagat ttatgaatta tacactcaac 360
aataccaaaa acaccaatgt aacattaagt aagaaaagga aaagaagatt tcttggattt 420
ttgttaggtg ttggatctgc aatcgccagt ggcattgccg tatccaaggt cctgcaccta 480
gaaggggaag tgaacaaaat caaaagtgct ctactatcca caaacaaggc tgtagtcagc 540
ttatctaatg gagtcagtgt cttaaccagc aaggtgttag acctcaaaaa ctatatagat 600
aaacagttgt tacctattgt taacaagcaa agctgcagca tatcaaacat tgaaactgtg 660
atagagttcc aacaaaagaa caacagacta ctagagatta ccagagaatt tagtgttaat 720
gcaggtgtaa ctacacctgt aagcacttat atgttaacta atagtgagtt attatcatta 780
atcaatgata tgcctataac aaatgatcag aaaaagttaa tgtccagcaa tgttcaaata 840
gttagacagc aaagttactc tatcatgtca ataataaaag aggaagtctt agcatatgta 900
gtacaattac cactatatgg tgtaatagat actccttgtt ggaaactaca cacatcccct 960
ctatgtacaa ccaacacaaa ggaaggatcc aacatctgct taacaagaac cgacagagga 1020
tggtactgtg acaatgcagg atcagtatcc tttttcccac aagctgaaac atgtaaagtt 1080
caatcgaatc gggtgttttg tgacacaatg aacagtttaa cattaccaag tgaggtaaat 1140
ctctgcaaca ttgacatatt caaccccaaa tatgattgca aaattatgac ttcaaaaaca 1200
gatgtaagca gctccgttat cacatctcta ggagccattg tgtcatgcta tggcaaaacc 1260
aaatgtacag catccaataa aaatcgtggg atcataaaga cattctctaa cgggtgtgat 1320
tatgtatcaa ataagggggt ggatactgtg tctgtaggta atacattata ttatgtaaat 1380
aagcaagaag gcaaaagtct ctatgtaaaa ggtgaaccaa taataaattt ctatgatcca 1440
ttagtgttcc cctctgatga atttgatgca tcaatatctc aagtcaatga gaaaattaat 1500
cagagtctag catttatccg taaatcagat gaattattac ataatgtaaa tgctggtaaa 1560
tccaccacaa atatcatgat aactaccata attatagtaa ttatagtaat attgttagca 1620
ttaattgcag ttggactgct tctatactgc aaggccagaa gcacaccagt cacattaagt 1680
aaggatcaac tgagtggtat aaataacatt gcatttagta actga 1725

<210> SEQ ID NO 26
<211> LENGTH: 1722
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 26
atggagctgc ccatcctgaa gaccaacgcc atcaccacca tcctggccgc cgtgaccctg 60
tgcttcgcca gcagccagaa catcaccgag gagttctacc agagcacctg cagcgccgtg 120
agcaagggct acctgagcgc cctgagaacc ggctggtaca ccagcgtgat caccatcgag 180
ctgagcaaca tcaaggagaa caagtgcaac ggcaccgacg ccaaggtgaa gctgatcaag 240
caggagctgg acaagtacaa gaacgccgtg accgagctgc agctgctgat gcagagcacc 300
cccgccgcca acagcagagc cagaagagag ctgcccagat tcatgaacta caccctgaac 360
aacaccaaga acaccaacgt gaccctgagc aagaagagaa agagaagatt cctgggcttc 420
ctgctgggcg tgggcagcgc catcgccagc ggcatcgccg tgagcaaggt gctgcacctg 480
gagggcgagg tgaacaagat caagagcgcc ctgctgagca ccaacaaggc cgtggtgagc 540
ctgagcaacg gcgtgagcgt gctgaccagc aaggtgctgg acctgaagaa ctacatcgac 600
aagcagctgc tgcccatcgt gaacaagcag agctgcagca tcagcaacat cgagaccgtg 660
atcgagttcc agcagaagaa caacagactg ctggagatca ccagagagtt cagcgtgaac 720
gccggcgtga ccacccccgt gagcacctac atgctgacca acagcgagct gctgagcctg 780
atcaacgaca tgcccatcac caacgaccag aagaagctga tgagcagcaa cgtgcagatc 840
gtgagacagc agagctacag catcatgagc atcatcaagg aggaggtgct ggcctacgtg 900
gtgcagctgc ccctgtacgg cgtgatcgac accccctgct ggaagctgca caccagcccc 960
ctgtgcacca ccaacaccaa ggagggcagc aacatctgcc tgaccagaac cgacagaggc 1020
tggtactgcg acaacgccgg cagcgtgagc ttcttccccc aggccgagac ctgcaaggtg 1080
cagagcaaca gagtgttctg cgacaccatg aacagcctga ccctgcccag cgaggtgaac 1140
ctgtgcaaca tcgacatctt caaccccaag tacgactgca agatcatgac cagcaagacc 1200
gacgtgagca gcagcgtgat caccagcctg ggcgccatcg tgagctgcta cggcaagacc 1260
aagtgcaccg ccagcaacaa gaacagaggc atcatcaaga ccttcagcaa cggctgcgac 1320
tacgtgagca acaagggcgt ggacaccgtg agcgtgggca acaccctgta ctacgtgaac 1380
aagcaggagg gcaagagcct gtacgtgaag ggcgagccca tcatcaactt ctacgacccc 1440
ctggtgttcc ccagcgacga gttcgacgcc agcatcagcc aggtgaacga gaagatcaac 1500
cagagcctgg ccttcatcag aaagagcgac gagctgctgc acaacgtgaa cgccggcaag 1560
agcaccacca acatcatgat caccaccatc atcatcgtga tcatcgtgat cctgctggcc 1620
ctgatcgccg tgggcctgct gctgtactgc aaggccagaa gcacccccgt gaccctgagc 1680
aaggaccagc tgagcggcat caacaacatc gccttcagca ac 1722

<210> SEQ ID NO 27
<211> LENGTH: 1725
<212> TYPE: DNA

<213> ORGANISM: Human respiratory syncytial virus

<400> SEQUENCE: 27
atggagttgc tgatccatag atcaagtgta atcttcctaa ctcttgctat taacgcattg 60
tacctcacct caagtcagaa cataactgag gagttttacc aatcgacatg tagtgcagtt 120
agcagaggtt actttagtgc tttaagaaca ggttggtata ctagtgtcat aacaatagaa 180
ttaagtaata taaaagaaac caaatgcaat ggaactgaca ctaaagtaaa acttataaaa 240
caagaattag ataagtataa gaatgcagta acagaattac agttacttat gcaaaacata 300
ccagctgcca acaaccgagc cagaagagaa gcaccacagt atatgaacta cacaatcaat 360
accactaaaa acctaaatgt atcaataagc aagaagagga aacgaagatt tctgggcttc 420
ttgttaggtg taggatctgc aatagcaagt ggcatagctg tatccaaagt tctacacctt 480
gaaggagaag tgaacaagat caaaaatgct ttgctgtcta caaacaaagc tgtagtcagt 540
ctatcaaatg ggtcagtgt tttaaccagc aaagtgttag atctcaagaa ttatataaac 600
aaccaattat tacctatagt aaatcaacag agttgtcgca tctccaacat tgaaacagtt 660
atagaattcc agcagaagaa cagcagattg ttggaaatca ccagagaatt tagtgtcaat 720
gcaggtgtaa cgacaccttt aagcacttac atgttaacaa acagtgagtt gctatcatta 780
atcaatgata tgcctataac aaatgatcag aagaaattaa tgtcaagcaa tgttcagata 840
gtaaggcaac aaagttattc tatcatgtct ataataaagg aagaagtcct cgcatatgtt 900
gtacagctac ctatctatgg tgtaatagat acaccttgct ggaaattaca cacatcacct 960
ctgtgcacca ccaacatcaa ggaaggttca aatatttgtt taacaaggac tgatagagga 1020
tggtactgtg ataatgcagg atcagtatcc ttctttccac aggctgacac ttgtaaagta 1080
cagtccaatc gagtattttg tgacactatg aacagtttga cattaccaag tgaagtcagc 1140
ctttgtaaca ctgacatatt caattccaag tatgattgca aaattatgac atcaaaaaca 1200
gacataagca gctcagtaat tacttctcta ggagctatag tgtcatgcta tggtaaaact 1260
aaatgcactg catccaacaa aaatcgtgga attataaaga cattttctaa tggttgtgat 1320
tatgtgtcaa acaaaggagt agatactgta tcagtgggca acactttata ctatgtcaac 1380
aagctggaag gcaaaaacct ttatgtaaaa ggggaaccta taataaatta ctatgaccct 1440
ctagtgtttc cttctgatga gtttgatgca tcaatatctc aagtcaatga aaaaattaat 1500
caaagtttag cttttattcg tagatccgat gaattattac ataatgtaaa tactggaaaa 1560
tctactacaa atattatgat aactgtaatt attatagtaa tcattgtagt attgttatca 1620
ttaatagcta ttggtttact gttgtattgc aaagccaaaa acacaccagt tacactaagc 1680
aaagaccaac taagtggaat caataatatt gcattcagca aatag 1725

<210> SEQ ID NO 28
<211> LENGTH: 1722
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 28
atggagctgc tgatccacag aagcagcgtg atcttcctga ccctggccat caacgccctg 60
tacctgacca gcagccagaa catcaccgag gagttctacc agagcacctg cagcgccgtg 120
agcagaggct acttcagcgc cctgagaacc ggctggtaca ccagcgtgat caccatcgag 180
ctgagcaaca tcaaggagac caagtgcaac ggcaccgaca ccaaggtgaa gctgatcaag 240
caggagctgg acaagtacaa gaacgccgtg accgagctgc agctgctgat gcagaacatc 300
cccgccgcca acaacagagc cagaagagag gccccccagt acatgaacta caccatcaac 360
accaccaaga acctgaacgt gagcatcagc aagaagagaa agagaagatt cctgggcttc 420
ctgctgggcg tgggcagcgc catcgccagc ggcatcgccg tgagcaaggt gctgcacctg 480
gagggcgagg tgaacaagat caagaacgcc ctgctgagca ccaacaaggc cgtggtgagc 540
ctgagcaacg gcgtgagcgt gctgaccagc aaggtgctgg acctgaagaa ctacatcaac 600
aaccagctgc tgcccatcgt gaaccagcag agctgcagaa tcagcaacat cgagaccgtg 660
atcgagttcc agcagaagaa cagcagactg ctggagatca ccagagagtt cagcgtgaac 720
gccggcgtga ccacccccct gagcacctac atgctgacca acagcgagct gctgagcctg 780
atcaacgaca tgcccatcac caacgaccag aagaagctga tgagcagcaa cgtgcagatc 840
gtgagacagc agagctacag catcatgagc atcatcaagg aggaggtgct ggcctacgtg 900
gtgcagctgc ccatctacgg cgtgatcgac accccctgct ggaagctgca caccagcccc 960
ctgtgcacca ccaacatcaa ggagggcagc aacatctgcc tgaccagaac cgacagaggc 1020
tggtactgcg acaacgccgg cagcgtgagc ttcttccccc aggccgacac ctgcaaggtg 1080
cagagcaaca gagtgttctg cgacaccatg aacagcctga ccctgcccag cgaggtgagc 1140
ctgtgcaaca ccgacatctt caacagcaag tacgactgca agatcatgac cagcaagacc 1200
gacatcagca gcagcgtgat caccagcctg ggcgccatcg tgagctgcta cggcaagacc 1260
aagtgcaccg ccagcaacaa gaacagaggc atcatcaaga ccttcagcaa cggctgcgac 1320
tacgtgagca acaagggcgt ggacaccgtg agcgtgggca acaccctgta ctacgtgaac 1380
aagctggagg gcaagaacct gtacgtgaag ggcgagccca tcatcaacta ctacgacccc 1440
ctggtgttcc ccagcgacga gttcgacgcc agcatcagcc aggtgaacga gaagatcaac 1500
cagagcctgg ccttcatcag aagaagcgac gagctgctgc acaacgtgaa caccggcaag 1560
agcaccacca acatcatgat caccgtgatc atcatcgtga tcatcgtggt gctgctgagc 1620
ctgatcgcca tcggcctgct gctgtactgc aaggccaaga acaccccccgt gaccctgagc 1680 aaggaccagc tgagcggcat caacaacatc gccttcagca ag 1722

<210> SEQ ID NO 29
<211> LENGTH: 1725
<212> TYPE: DNA
<213> ORGANISM: Human respiratory syncytial virus

<400> SEQUENCE: 29
atggagttgc caatcctcaa agcaaatgct attaccacaa tccttgctgc agtcacactc 60
tgttttgctt ccagtcaaaa catcactgaa gaattttatc aatcaacatg cagtgcagtt 120
agcaaaggct atcttagtgc tctaagaact ggttggtata ctagtgttat aactatagaa 180
ttaagtaata tcaaggaaaa taagtgtaat ggaacagatg ctaaggtaaa attgataaaa 240
caagaattag ataaatacaa aaatgctgta acagaattgc agttgctcat gcaaagcaca 300
ccagcagcca acaatcgagc cagaagggaa ttaccaagat ttatgaatta tacactcaac 360
aatactgaaa acaccaatgt aacattaagc aagaaaagga aaagaagatt tcttggcttt 420
ttgttaggtg ttggatctgc aatcgccagt ggcattgccg tatccaaggt cctgcaccta 480
gaaggggaag tgaacaaaat caaaagtgct ctactatcca caaacaaggc tgtagtcagc 540
ttatcaaatg gagtcagtgt cttaaccagc aaagtgttag atctcaaaaa ctatatagat 600

```
aaacagttgt tacctattgt gaacaagcaa agctgcagca tatcaaacat tgaaactgta    660
atagagttcc aacaaaagaa caacagacta ctagagatta ccagagaatt tagtgttaat    720
gcaggtgtaa ctacacctgt aagcacttat atgttaacta atagtgaatt attatcatta    780
atcaatgata tgcctataac aaatgatcag aaaaagttaa tgtccaacaa tgttcaaata    840
gttagacagc aaagttactc tatcatgtcc ataataaaag aggaagtctt agcatatgta    900
gtacaattac cactatatgg tgtaatagat acaccttgtt ggaaactgca cacatcccct    960
ctatgtacaa ccaacacaaa ggaagggtcc aacatctgct taacaagaac cgacagagga   1020
tggtactgtg acaatgcagg atcagtatct ttcttcccac aagccgaaac atgtaaagtt   1080
caatcgaatc gggtattttg tgacacaatg aacagtttaa cattaccaag tgaggtaagt   1140
ctctgcaacg ttgacatatt caaccccaaa tatgattgca aaattatgac ttcaaaaaca   1200
gatgtaagca gctccgttat cacatctctg ggagccattg tgtcatgcta tggcaaaacc   1260
aaatgtacag catccaataa aaatcgtggg atcataaaga cattttctaa cgggtgtgat   1320
tatgtatcaa ataagggggt ggatactgtg tctgtaggta atacattata ttatgtaaat   1380
aagcaagaag gcaaaaatct ctatgtaaaa ggtgaaccaa taataaattt ctatgaccca   1440
ttagtgttcc cctctgatga atttgatgca tcaatatctc aagtcaatga gaagattaac   1500
cagagtctag catttattcg taaatcagat gaattattac ataatgtaaa tgctgttaaa   1560
tccactacaa atatcatgat aactactata attatagtga ttatagtaat attgttatca   1620
ttaattgtag ttggactgct tctatactgc aaggccagaa gcacaccagt cacactaagt   1680
aaggatcaac tgagtggtat aaataatatt gcatttagta gctga                   1725
```

<210> SEQ ID NO 30
<211> LENGTH: 1722
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 30

```
atggagctgc ccatcctgaa ggccaacgcc atcaccacca tcctggccgc cgtgaccctg     60
tgcttcgcca gcagccagaa catcaccgag gagttctacc agagcacctg cagcgccgtg    120
agcaagggct acctgagcgc cctgagaacc ggctggtaca ccagcgtgat caccatcgag    180
ctgagcaaca tcaaggagaa caagtgcaac ggcaccgacg ccaaggtgaa gctgatcaag    240
caggagctgg acaagtacaa gaacgccgtg accgagctgc agctgctgat gcagagcacc    300
cccgccgcca acaacagagc cagaagagag ctgcccagat tcatgaacta caccctgaac    360
aacaccgaga acaccaacgt gaccctgagc aagaagagaa agagaagatt cctgggcttc    420
ctgctgggcg tgggcagcgc catcgccagc ggcatcgccg tgagcaaggt gctgcacctg    480
gagggcgagg tgaacaagat caagagcgcc ctgctgagca ccaacaaggc cgtggtgagc    540
ctgagcaacg gcgtgagcgt gctgaccagc aaggtgctgg acctgaagaa ctacatcgac    600
aagcagctgc tgcccatcgt gaacaagcag agctgcagca tcagcaacat cgagaccgtg    660
atcgagttcc agcagaagaa caacagactg ctggagatca ccagagagtt cagcgtgaac    720
gccggcgtga ccaccccccgt gagcacctac atgctgacca acagcgagct gctgagcctg    780
atcaacgaca tgcccatcac caacgaccag aagaagctga tgagcaacaa cgtgcagatc    840
gtgagacagc agagctacag catcatgagc atcatcaagg aggaggtgct ggcctacgtg    900
```

gtgcagctgc ccctgtacgg cgtgatcgac accccctgct ggaagctgca caccagcccc 960
ctgtgcacca ccaacaccaa ggagggcagc aacatctgcc tgaccagaac cgacagaggc 1020
tggtactgcg acaacgccgg cagcgtgagc ttcttccccc aggccgagac ctgcaaggtg 1080
cagagcaaca gagtgttctg cgacaccatg aacagcctga ccctgcccag cgaggtgagc 1140
ctgtgcaacg tggacatctt caaccccaag tacgactgca agatcatgac cagcaagacc 1200
gacgtgagca gcagcgtgat caccagcctg ggcgccatcg tgagctgcta cggcaagacc 1260
aagtgcaccg ccagcaacaa gaacagaggc atcatcaaga ccttcagcaa cggctgcgac 1320
tacgtgagca acaagggcgt ggacaccgtg agcgtgggca acaccctgta ctacgtgaac 1380
aagcaggagg gcaagaacct gtacgtgaag ggcgagccca tcatcaactt ctacgacccc 1440
ctggtgttcc ccagcgacga gttcgacgcc agcatcagcc aggtgaacga gaagatcaac 1500
cagagcctgg ccttcatcag aaagagcgac gagctgctgc acaacgtgaa cgccgtgaag 1560
agcaccacca acatcatgat caccaccatc atcatcgtga tcatcgtgat cctgctgagc 1620
ctgatcgtgg tgggcctgct gctgtactgc aaggccagaa gcacccccgt gaccctgagc 1680
aaggaccagc tgagcggcat caacaacatc gccttcagca gc 1722

<210> SEQ ID NO 31
<211> LENGTH: 1740
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 31
atggcgacaa cagccatgag gatgatcatc agcattatct tcatctctac ctatgtgaca 60
catatcactt tatgccaaaa cataacagaa gaattttatc aatcaacatg cagtgcagtt 120
agtagaggtt accttagtgc attaagaact ggatggtata caagtgtggt aacaatagag 180
ttgagcaaaa tacaaaaaaa tgtgtgtaat agtactgatt caaaagtgaa attaataaag 240
caagaactag aaagatacaa caatgcagta gtggaattgc agtcacttat gcaaaatgaa 300
ccggcctcct tcagtagagc aaaaagaggg ataccagagt tgatacatta tacaagaaac 360
tctacaaaaa agttttatgg gctaatgggc aagaagagaa aaaggagatt tttaggattc 420
ttgctaggta ttggatctgc tattgcaagt ggtgtagcag tgtccaaagt actacacctg 480
gagggagagg tgaataaaat taaaaatgca ctgctatcca caaataaagc agtagttagt 540
ctatccaatg gagttagtgt ccttactagc aaagtacttg atctaaagaa ctatatagac 600
aaagagcttc tacctaaagt taacaatcat gattgtagga tatccaaaat agaaactgtg 660
atagaattcc aacaaaaaaa caatagattg ttagaaattg ctagggaatt tagtgtaaat 720
gctggtatta ccacacctct cagtacatac atgttgacca atagtgaatt actatcacta 780
attaatgata tgcctataac gaatgaccaa aaaaagctaa tgtcaagtaa tgttcaaata 840
gtcaggcaac agagttattc cattatgtca gtggtcaaag aagaagtcat agcttatgtt 900
gtacaattgc ctatttatgg agttatagac accccctgtt ggaaactaca cacctctccg 960
ttatgcacca ctgataataa agaagggtca aacatctgct taactaggac agatcgtggg 1020
tggtattgtg acaatgcagg ctctgtgtct tttttcccac agacagagac atgtaaggta 1080
caatcaaata gagtgttctg tgacacaatg aacagtttaa ctctgcctac tgacgttaac 1140
ttatgcaaca ctgacatatt caatacaaag tatgactgta aaataatgac atctaaaact 1200

```
gacataagta gctctgtgat aacttcaatt ggagctattg tatcatgcta tgggaagaca   1260
aaatgtacag cttctaataa aaatcgtgga atcataaaga ctttttccaa tgggtgtgat   1320
tatgtatcaa acaaaggagt agatactgta tctgttggta acacactata ttatgtaaat   1380
aagctagagg ggaaagcact ctatataaag ggtgaaccaa ttattaatta ctatgatcca   1440
ctagtgtttc cttctgatga gtttgatgca tcaattgccc aagtaaacgc aaaaataaac   1500
caaagcctgg ccttcatacg tcgatctgat gagttacttc acagtgtaga tgtaggaaaa   1560
tccaccacaa atgttaacct cattacctat atcgttttga ctatcatatc tcttgttttt   1620
ggtatactta gcctgattct agcatgctac ctaatgtaca agcaaaaggc gcaacaaaag   1680
accttattat ggcttgggaa taataccctq gatcagatga gagccactac aaaaatgtga   1740
```

<210> SEQ ID NO 32
<211> LENGTH: 1638
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 32

```
atgtcttgga aagtggtgat catttttttca ttgctaataa cacctcaaca cggtcttaaa     60
gagagctacc tagaagaatc atgtagcact ataactgagg gatatcttag tgttctgagg    120
acaggttggt ataccaacgt tttacatta gaggtgggtg atgtagaaaa ccttacatgt    180
tctgatggac ctagcctaat aaaaacagaa ttagatctga ccaaaagtgc actaagagag    240
ctcaaaacag tctctgctga ccaattggca agagaggaac aaattgagaa tcccagacaa    300
tctaggtttg ttctaggagc aatagcactc ggtgttgcaa cagcagctgc agtcacagca    360
ggtgttgcaa ttgccaaaac catccggctt gagagtgaag tcacagcaat taagaatgcc    420
ctcaaaacga ccaatgaagc agtatctaca ttggggaatg gagttcgagt gttggcaact    480
gcagtgagag agctgaaaga ctttgtgagc aagaatttaa ctcgtgcaat caacaaaaac    540
aagtgcgaca ttgatgacct aaaaatggcc gttagcttca gtcaattcaa cagaaggttt    600
ctaaatgttg tgcggcaatt ttcagacaat gctggaataa caccagcaat atctttggac    660
ttaatgacag atgctgaact agccagggcc gtttctaaca tgccgacatc tgcaggacaa    720
ataaaattga tgttggagaa ccgcgcgatg gtgcgaagaa aggggttcgg aatcctgata    780
ggggtctacg ggagctctgt aatttacatg gtgcagctgc caatctttgg cgttatagac    840
acgccttgct ggatagtaaa agcagcccct tcttgttccg aaaaaaaggg aaactatgct    900
tgcctcttaa gagaagacca agggtggtat tgtcagaatg cagggtcaac tgtttactac    960
ccaaatgaga aagactgtga aacaagagga gaccatgtct tttgcgacac agcagcagga   1020
attaatgttg ctgagcaatc aaaggagtgc aacatcaaca tatccactac aaattaccca   1080
tgcaaagtca gcacaggaag acatcctatc agtatggttg cactgtctcc tcttggggct   1140
ctggttgctt gctacaaagg agtaagctgt tccattggca gcaacagagt agggatcatc   1200
aagcagctga acaaaggttg ctcctatata accaaccaag atgcagacac agtgacaata   1260
gacaacactg tatatcagct aagcaaagtt gagggtgaac agcatgttat aaaaggcaga   1320
ccagtgtcaa gcagctttga tccaatcaag tttcctgaag atcaattcaa tgttgcactt   1380
gaccaagttt ttgagagcat tgaaaacagc caggccttgg tagatcaatc aaacagaatc   1440
ctaagcagtg cagagaaagg gaatactggc gttaacctca ttacctatat cgttttgact   1500
```

atcatatctc ttgtttttgg tatacttagc ctgattctag catgctacct aatgtacaag 1560
caaaaggcgc aacaaaagac cttattatgg cttgggaata ataccctaga tcagatgaga 1620
gccactacaa aaatgtga 1638

<210> SEQ ID NO 33
<211> LENGTH: 579
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 33

Met Ala Thr Thr Ala Met Arg Met Ile Ile Ser Ile Ile Phe Ile Ser
1 5 10 15

Thr Tyr Val Thr His Ile Thr Leu Cys Gln Asn Ile Thr Glu Glu Phe
20 25 30

Tyr Gln Ser Thr Cys Ser Ala Val Ser Arg Gly Tyr Leu Ser Ala Leu
35 40 45

Arg Thr Gly Trp Tyr Thr Ser Val Val Thr Ile Glu Leu Ser Lys Ile
50 55 60

Gln Lys Asn Val Cys Asn Ser Thr Asp Ser Lys Val Lys Leu Ile Lys
65 70 75 80

Gln Glu Leu Glu Arg Tyr Asn Asn Ala Val Val Glu Leu Gln Ser Leu
85 90 95

Met Gln Asn Glu Pro Ala Ser Phe Ser Arg Ala Lys Arg Gly Ile Pro
100 105 110

Glu Leu Ile His Tyr Thr Arg Asn Ser Thr Lys Lys Phe Tyr Gly Leu
115 120 125

Met Gly Lys Lys Arg Lys Arg Arg Phe Leu Gly Phe Leu Leu Gly Ile
130 135 140

Gly Ser Ala Ile Ala Ser Gly Val Ala Val Ser Lys Val Leu His Leu
145 150 155 160

Glu Gly Glu Val Asn Lys Ile Lys Asn Ala Leu Leu Ser Thr Asn Lys
165 170 175

Ala Val Val Ser Leu Ser Asn Gly Val Ser Val Leu Thr Ser Lys Val
180 185 190

Leu Asp Leu Lys Asn Tyr Ile Asp Lys Glu Leu Leu Pro Lys Val Asn
195 200 205

Asn His Asp Cys Arg Ile Ser Lys Ile Glu Thr Val Ile Glu Phe Gln
210 215 220

Gln Lys Asn Asn Arg Leu Leu Glu Ile Ala Arg Glu Phe Ser Val Asn
225 230 235 240

Ala Gly Ile Thr Thr Pro Leu Ser Thr Tyr Met Leu Thr Asn Ser Glu
245 250 255

Leu Leu Ser Leu Ile Asn Asp Met Pro Ile Thr Asn Asp Gln Lys Lys
260 265 270

Leu Met Ser Ser Asn Val Gln Ile Val Arg Gln Gln Ser Tyr Ser Ile
275 280 285

Met Ser Val Val Lys Glu Glu Val Ile Ala Tyr Val Val Gln Leu Pro
290 295 300

Ile Tyr Gly Val Ile Asp Thr Pro Cys Trp Lys Leu His Thr Ser Pro
305 310 315 320

Leu Cys Thr Thr Asp Asn Lys Glu Gly Ser Asn Ile Cys Leu Thr Arg

```
                325                 330                 335

Thr Asp Arg Gly Trp Tyr Cys Asp Asn Ala Gly Ser Val Ser Phe Phe
            340                 345                 350

Pro Gln Thr Glu Thr Cys Lys Val Gln Ser Asn Arg Val Phe Cys Asp
        355                 360                 365

Thr Met Asn Ser Leu Thr Leu Pro Thr Asp Val Asn Leu Cys Asn Thr
    370                 375                 380

Asp Ile Phe Asn Thr Lys Tyr Asp Cys Lys Ile Met Thr Ser Lys Thr
385                 390                 395                 400

Asp Ile Ser Ser Ser Val Ile Thr Ser Ile Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Leu Glu Gly
    450                 455                 460

Lys Ala Leu Tyr Ile Lys Gly Glu Pro Ile Ile Asn Tyr Tyr Asp Pro
465                 470                 475                 480

Leu Val Phe Pro Ser Asp Glu Phe Asp Ala Ser Ile Ala Gln Val Asn
                485                 490                 495

Ala Lys Ile Asn Gln Ser Leu Ala Phe Ile Arg Arg Ser Asp Glu Leu
            500                 505                 510

Leu His Ser Val Asp Val Gly Lys Ser Thr Thr Asn Val Asn Leu Ile
        515                 520                 525

Thr Tyr Ile Val Leu Thr Ile Ile Ser Leu Val Phe Gly Ile Leu Ser
    530                 535                 540

Leu Ile Leu Ala Cys Tyr Leu Met Tyr Lys Gln Lys Ala Gln Gln Lys
545                 550                 555                 560

Thr Leu Leu Trp Leu Gly Asn Asn Thr Leu Asp Gln Met Arg Ala Thr
                565                 570                 575

Thr Lys Met


<210> SEQ ID NO 34
<211> LENGTH: 1644
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 34

atgagctgga aggtggtgat catcttcagc ctgctgatca ccccccagca cggcctgaag      60

gagagctacc tggaggagag ctgcagcacc atcaccgagg gctacctgag cgtgctgaga     120

accggctggt acaccaacgt gttcaccctg gaggtgggcg acgtggagaa cctgacctgc     180

gccgacggcc ccagcctgat caagaccgag ctggacctga ccaagagcgc cctgagagag     240

ctgaagaccg tgagcgccga ccagctggcc agagaggagc agatcgagaa ccccagacag     300

agcagattcg tgctgggcgc catcgccctg ggcgtggcca ccgccgccgc cgtgaccgcc     360

ggcgtggcca tcgccaagac catcagactg gagagcgagg tgaccgccat caagaacgcc     420

ctgaagaaga ccaacgaggc cgtgagcacc ctgggcaacg gcgtgagagt gctggccacc     480

gccgtgagag agctgaagga cttcgtgagc aagaacctga ccagagccat caacaagaac     540

aagtgcgaca tcgacgacct gaagatggcc gtgagcttca gccagttcaa cagaagattc     600
```

ctgaacgtgg tgagacagtt cagcgacaac gccggcatca cccccgccat cagcctggac 660
ctgatgaccg acgccgagct ggccagagcc gtgagcaaca tgcccaccag cgccggccag 720
atcaagctga tgctggagaa cagagccatg gtgagaagaa agggcttcgg catcctgatc 780
ggcgtgtacg gcagcagcgt gatctacatg gtgcagctgc ccatcttcgg cgtgatcgac 840
accccctgct ggatcgtgaa ggccgccccc agctgcagcg agaagaaggg caactacgcc 900
tgcctgctga gagaggacca gggctggtac tgccagaacg ccggcagcac cgtgtactac 960
cccaacgaga aggactgcga gaccagaggc gaccacgtgt tctgcgacac cgccgccggc 1020
atcaacgtgg ccgagcagag caaggagtgc aacatcaaca tcagcaccac caactacccc 1080
tgcaaggtga gcaccggcag acaccccatc agcatggtgg ccctgagccc cctgggcgcc 1140
ctggtggcct gctacaaggg cgtgagctgc agcatcggca gcaacagagt gggcatcatc 1200
aagcagctga acaagggctg cagctacatc accaaccagg acgccgacac cgtgaccatc 1260
gacaacaccg tgtaccagct gagcaaggtg gagggcgagc agcacgtgat caagggcaga 1320
cccgtgagca gcagcttcga ccccgtgaag ttccccgagg accagttcaa cgtggccctg 1380
gaccaggtgt tcgagaacat cgagaacagc caggccctgg tggaccagag caacagaatc 1440
ctgagcagcg ccgagaaggg caacaccggc gttaacctca ttacctatat cgttttgact 1500
atcatatctc ttgtttttgg tatacttagc ctgattctag catgctacct aatgtacaag 1560
caaaaggcgc aacaaaagac cttattatgg cttgggaata ataccctaga tcagatgaga 1620
gccactacaa aaatgtgacc gcgg 1644

<210> SEQ ID NO 35
<211> LENGTH: 1644
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 35
atgagctgga aggtgatgat catcatcagc ctgctgatca ccccccagca cggcctgaag 60
gagagctacc tggaggagag ctgcagcacc atcaccgagg gctacctgag cgtgctgaga 120
accggctggt acaccaacgt gttcaccctg gaggtgggcg acgtggagaa cctgacctgc 180
accgacggcc ccagcctgat caagaccgag ctggacctga ccaagagcgc cctgagagag 240
ctgaagaccg tgagcgccga ccagctggcc agagaggagc agatcgagaa ccccagacag 300
agcagattcg tgctgggcgc catcgccctg ggcgtggcca ccgccgccgc cgtgaccgcc 360
ggcatcgcca tcgccaagac catcagactg gagagcgagg tgaacgccat caagggcgcc 420
ctgaagcaga ccaacgaggc cgtgagcacc ctgggcaacg gcgtgagagt gctggccacc 480
gccgtgagag agctgaagga gttcgtgagc aagaacctga ccagcgccat caacagaaac 540
aagtgcgaca tcgccgacct gaagatggcc gtgagcttca gccagttcaa cagaagattc 600
ctgaacgtgg tgagacagtt cagcgacaac gccggcatca cccccgccat cagcctggac 660
ctgatgaccg acgccgagct ggccagagcc gtgagctaca tgcccaccag cgccggccag 720
atcaagctga tgctggagaa cagagccatg gtgagaagaa agggcttcgg catcctgatc 780
ggcgtgtacg gcagcagcgt gatctacatg gtgcagctgc ccatcttcgg cgtgatcgac 840
accccctgct ggatcatcaa ggccgccccc agctgcagcg agaagaacgg caactacgcc 900
tgcctgctga gagaggacca gggctggtac tgcaagaacg ccggcagcac cgtgtactac 960

```
cccaacgaga aggactgcga gaccagaggc gaccacgtgt tctgcgacac cgccgccggc    1020

atcaacgtgg ccgagcagag cagagagtgc aacatcaaca tcagcaccac caactacccc    1080

tgcaaggtga gcaccggcag acaccccatc agcatggtgg ccctgagccc cctgggcgcc    1140

ctggtggcct gctacaaggg cgtgagctgc agcatcggca gcaacagagt gggcatcatc    1200

aagcagctgc ccaagggctg cagctacatc accaaccagg acgccgacac cgtgaccatc    1260

gacaacaccg tgtaccagct gagcaaggtg gagggcgagc agcacgtgat caagggcaga    1320

cccgtgagca gcagcttcga ccccatcaga ttccccgagg accagttcaa cgtggccctg    1380

gaccaggtgt tcgagagcat cgagaacagc caggccctgg tggagcagag caacaagatc    1440

ctgaacagcg ccgagaaggg caacaccggc gttaacctca ttacctatat cgttttgact    1500

atcatatctc ttgtttttgg tatacttagc ctgattctag catgctacct aatgtacaag    1560

caaaaggcgc aacaaaagac cttattatgg cttgggaata ataccctaga tcagatgaga    1620

gccactacaa aaatgtgacc gcgg                                           1644
```

<210> SEQ ID NO 36
<211> LENGTH: 1644
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 36

```
atgagctgga aggtggtgat catcttcagc ctgctgatca ccccccagca cggcctgaag     60

gagagctacc tggaggagag ctgcagcacc atcaccgagg gctacctgag cgtgctgaga    120

accggctggt acaccaacgt gttcaccctg gaggtgggcg acgtggagaa cctgacctgc    180

agcgacggcc ccagcctgat caagaccgag ctggacctga ccaagagcgc cctgagagag    240

ctgaagaccg tgagcgccga ccagctggcc agagaggagc agatcgagaa ccccagacag    300

agcagattcg tgctgggcgc catcgccctg ggcgtggcca ccgccgccgc cgtgaccgcc    360

ggcgtggcca tcgccaagac catcagactg gagagcgagg tgaccgccat caagaacgcc    420

ctgaagacca ccaacgaggc cgtgagcacc ctgggcaacg gcgtgagagt gctggccacc    480

gccgtgagag agctgaagga cttcgtgagc aagaacctga ccagagccat caacaagaac    540

aagtgcgaca tcgacgacct gaagatggcc gtgagcttca gccagttcaa cagaagattc    600

ctgaacgtgg tgagacagtt cagcgacaac gccggcatca cccccgccat cagcctggac    660

ctgatgaccg acgccgagct ggccagagcc gtgagcaaca tgcccaccag cgccggccag    720

atcaagctga tgctggagaa cagagccatg gtgagaagaa agggcttcgg catcctgatc    780

ggcgtgtacg gcagcagcgt gatctacatg gtgcagctgc ccatcttcgg cgtgatcgac    840

accccctgct ggatcgtgaa ggccgccccc agctgcagcg agaagaaggg caactacgcc    900

tgcctgctga gagaggacca gggctggtac tgccagaacg ccggcagcac cgtgtactac    960

cccaacgaga aggactgcga gaccagaggc gaccacgtgt tctgcgacac cgccgccggc   1020

atcaacgtgg ccgagcagag caaggagtgc aacatcaaca tcagcaccac caactacccc   1080

tgcaaggtga gcaccggcag acaccccatc agcatggtgg ccctgagccc cctgggcgcc   1140

ctggtggcct gctacaaggg cgtgagctgc agcatcggca gcaacagagt gggcatcatc   1200

aagcagctga caagggctg cagctacatc accaaccagg acgccgacac cgtgaccatc   1260

gacaacaccg tgtaccagct gagcaaggtg gagggcgagc agcacgtgat caagggcaga   1320
```

cccgtgagca gcagcttcga ccccatcaag ttccccgagg accagttcaa cgtggccctg 1380
gaccaggtgt tcgagaacat cgagaacagc caggccctgg tggaccagag caacagaatc 1440
ctgagcagcg ccgagaaggg caacaccggc gttaacctca ttacctatat cgttttgact 1500
atcatatctc ttgtttttgg tatacttagc ctgattctag catgctacct aatgtacaag 1560
caaaaggcgc aacaaaagac cttattatgg cttgggaata ataccctaga tcagatgaga 1620
gccactacaa aaatgtgacc gcgg 1644

<210> SEQ ID NO 37
<211> LENGTH: 16979
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 37
accaaacaga gaatccgtga gttacgataa aaggcgaagg agcaattgaa gtcgcacggg 60
tagaaggtgt gaatctcgag tgcgagcccg aagcacaaac tcgagaaagc cttctgccaa 120
catgtcttcc gtatttgatg agtacgaaca gctcctcgcg gctcagactc gccccaatgg 180
agctcatgga gggggagaaa aagggagtac cttaaaagta gacgtcccgg tattcactct 240
taacagtgat gacccagaag atagatggag ctttgtggta ttctgcctcc ggattgctgt 300
tagcgaagat gccaacaaac cactcaggca aggtgctctc atatctcttt tatgctccca 360
ctcacaggta atgaggaacc atgttgccct tgcagggaaa cagaatgaag ccacattggc 420
cgtgcttgag attgatggct ttgccaacgg cacgccccag ttcaacaata ggagtggagt 480
gtctgaagag agagcacaga gatttgcgat gatagcagga tctctccctc gggcatgcag 540
caacggaacc ccgttcgtca cagccggggc cgaagatgat gcaccagaag acatcaccga 600
taccctggag aggatcctct ctatccaggc tcaagtatgg gtcacagtag caaaagccat 660
gactgcgtat gagactgcag atgagtcgga aacaaggcga atcaataagt atatgcagca 720
aggcagggtc caaaagaaat acatcctcta ccccgtatgc aggagcacaa tccaactcac 780
gatcagacag tctcttgcag tccgcatctt tttggttagc gagctcaaga gaggccgcaa 840
cacggcaggt ggtacctcta cttattataa cctggtaggg gacgtagact catacatcag 900
gaataccggg cttactgcat tcttcttgac actcaagtac ggaatcaaca ccaagacatc 960
agcccttgca cttagtagcc tctcaggcga catccagaag atgaagcagc tcatgcgttt 1020
gtatcggatg aaaggagata atgcgccgta catgacatta cttggtgata gtgaccagat 1080
gagctttgcg cctgccgagt atgcacaact ttactccttt gccatgggta tggcatcagt 1140
cctagataaa ggtactggga aataccaatt tgccagggac tttatgagca catcattctg 1200
gagacttgga gtagagtacg ctcaggctca gggaagtagc attaacgagg atatggctgc 1260
cgagctaaag ctaaccccag cagcaaggag ggcctggca gctgctgccc aacgggtctc 1320
cgaggagacc agcagcatag acatgcctac tcaacaagtc ggagtcctca ctgggcttag 1380
cgaggggggg tcccaagctc tacaaggcgg atcgaataga tcgcaagggc aaccagaagc 1440
cggggatggg gagacccaat tcctggatct gatgagagcg gtagcaaata gcatgaggga 1500
ggcgccaaac tctgcacagg gcactcccca atcggggcct cccccaactc ctgggccatc 1560
ccaagataac gacaccgact gggggtattg atggacaaaa cccagcctgc ttccacaaaa 1620
acatcccaat gccctcaccc gtagtcgacc cctcgatttg cggctctata tgaccacacc 1680

```
ctcaaacaaa catccccctc tttcctccct ccccctgctg tacaactacg tacgccctag   1740
ataccacagg cacaatgcgg ctcactaaca atcaaaacag agccgaggga attagaaaaa   1800
agtacgggta gaagagggat attcagagat cagggcaagt ctcccgagtc tctgctctct   1860
cctctacctg atagaccagg acaaacatgg ccacctttac agatgcagag atcgacgagc   1920
tatttgagac aagtggaact gtcattgaca acataattac agcccagggt aaaccagcag   1980
agactgttgg aaggagtgca atcccacaag gcaagaccaa ggtgctgagc gcagcatggg   2040
agaagcatgg gagcatccag ccaccggcca gtcaagacaa ccccgatcga caggacagat   2100
ctgacaaaca accatccaca cccgagcaaa cgaccccgca tgacagcccg ccggccacat   2160
ccgccgacca gcccccccacc caggccacag acgaagccgt cgacacacag ctcaggaccg   2220
gagcaagcaa ctctctgctg ttgatgcttg acaagctcag caataaatcg tccaatgcta   2280
aaaagggccc atggtcgagc cccaagaggg ggaatcacca acgtccgact caacagcagg   2340
ggagtcaacc cagtcgcgga aacagtcagg aaagaccgca gaaccaagtc aaggccgccc   2400
ctggaaacca gggcacagac gtgaacacag catatcatgg acaatgggag gagtcacaac   2460
tatcagctgg tgcaaccccct catgctctcc gatcaaggca gagccaagac aatacccttg   2520
tatctgcgga tcatgtccag ccacctgtag actttgtgca agcgatgatg tctatgatgg   2580
aggcgatatc acagagagta agtaaggttg actatcagct agatcttgtc ttgaaacaga   2640
catcctccat ccctatgatg cggtccgaaa tccaacagct gaaaacatct gttgcagtca   2700
tggaagccaa cttgggaatg atgaagattc tggatcccgg ttgtgccaac atttcatctc   2760
tgagtgatct acgggcagtt gcccgatctc acccggtttt agtttcaggc cctggagacc   2820
cctctcccta tgtgacacaa ggaggcgaaa tggcacttaa taaactttcg caaccagtgc   2880
cacatccatc tgaattgatt aaacccgcca ctgcatgcgg gcctgatata ggagtggaaa   2940
aggacactgt ccgtgcattg atcatgtcac gcccaatgca cccgagttct tcagccaagc   3000
tcctaagcaa gttagatgca gccgggtcga tcgaggaaat caggaaaatc aagcgccttg   3060
ctctaaatgg ctaattacta ctgccacacg tagcgggtcc ctgtccactc ggcatcacac   3120
ggaatctgca ccgagttccc ccccgcggtt agaaaaaata cgggtagaac cgccaccatg   3180
gccaccaccg ccatgcgcat gatcatcagc atcatcttca tcagcaccta cgtgacccac   3240
atcaccctgt gccagaacat caccgaggag ttctaccaga gcacctgcag cgccgtgagt   3300
cgcggctacc tgagcgccct gcgcaccggc tggtacacca gcgtggtgac catcgagctg   3360
agcaagatcc agaagaacgt gtgcaacagc accgacagca aggtgaagct gatcaagcag   3420
gagctggagc gctacaacaa cgccgtggtg gagctgcaga gcctgatgca gaacgagccc   3480
gccagcttca gccgcgccaa gcgcggcatc cccgagctga tccactacac ccgcaacagc   3540
accaagaagt tctacggcct gatgggcaag aagcgcaagc gccgcttcct gggcttcctg   3600
ctgggcatcg gcagcgccat cgccagcggc gtggccgtga gcaaggtgct gcacctggag   3660
ggcgaggtga acaagatcaa gaacgccctg ctgagcacca acaaggccgt ggtgagcctg   3720
agcaacggcg tgagcgtgct gaccagcaag gtgctggacc tgaagaacta catcgacaag   3780
gagctgctgc ccaaggtgaa caaccacgac tgccgcatca gcaagatcga gaccgtgatc   3840
gagttccagc agaagaacaa ccgcctgctg gagatcgccc gcgagttcag cgtgaacgcc   3900
ggcatcacca cccccctgag cacctacatg ctgaccaaca gcgagctgct gagcctgatc   3960
aacgacatgc ccatcaccaa cgaccagaag aagctgatga gcagcaacgt gcagatcgtg   4020
```

-continued cgccagcaga gctacagcat catgagcgtg gtgaaggagg aggtgatcgc ctacgtggtg 4080
cagctgccca tctacggcgt gatcgacacc ccctgctgga agctgcacac cagccccctg 4140
tgcaccaccg acaacaagga gggcagcaac atctgcctga cccgcaccga tcgcggctgg 4200
tactgcgaca acgccggcag cgtgagcttc ttcccccaga ccgagacctg caaggtgcag 4260
agcaaccgcg tgttctgcga caccatgaac agcctgaccc tgcccaccga cgtgaacctg 4320
tgcaacaccg acatcttcaa caccaagtac gactgcaaga tcatgaccag caagaccgac 4380
atcagcagca gcgtgatcac cagcatcggc gccatcgtga gctgctacgg caagaccaag 4440
tgcaccgcca gcaacaagaa tcgcggcatc atcaagacct tcagcaacgg ctgcgactac 4500
gtgagcaaca agggcgtgga caccgtgagc gtgggcaaca ccctgtacta cgtgaacaag 4560
ctggagggca aggccctgta catcaagggc gagcccatca tcaactacta cgaccccctg 4620
gtgttcccca gcgacgagtt cgacgccagc atcgcccagg tgaacgccaa gatcaaccag 4680
agcctggcct tcatccgccg cagcgacgag ctgctgcaca gcgtggacgt gggcaagagc 4740
accaccaacg ttaacctcat tacctatatc gttttgacta tcatatctct tgtttttggt 4800
atacttagcc tgattctagc atgctaccta atgtacaagc aaaaggcgca acaaaagacc 4860
ttattatggc ttgggaataa taccctagat cagatgagag ccactacaaa aatgtgagct 4920
tcagcaagta accccccgcg gacccaaggt ccaactctcc aagcggcaat cctctctcgc 4980
ttcctcagcc ccactgaatg atcgcgtaac cgtaattaat ctagctacat ttaagattaa 5040
gaaaaaatac gggtagaatt ggagtgcccc aattgtgcca agatggactc atctaggaca 5100
attgggctgt actttgattc tgcccattct tctagcaacc tgttagcatt tccgatcgtc 5160
ctacaagaca caggagatgg gaagaagcaa atcgccccgc aatataggat ccagcgcctt 5220
gacttgtgga ctgatagtaa ggaggactca gtattcatca ccacctatgg attcatcttt 5280
caagttggga atgaagaagc caccgtcggc atgatcgatg ataaacccaa gcgcgagtta 5340
ctttccgctg cgatgctctg cctaggaagc gtcccaaata ccggagacct tattgagctg 5400
gcaagggcct gtctcactat gatagtcaca tgcaagaaga gtgcaactaa tactgagaga 5460
atggttttct cagtagtgca ggcaccccaa gtgctgcaaa gctgtagggt tgtggcaaac 5520
aaatactcat cagtgaatgc agtcaagcac gtgaaagcgc cagagaagat tcccgggagt 5580
ggaaccctag aatacaaggt gaactttgtc tccttgactg tggtaccgaa gagggatgtc 5640
tacaagatcc cagctgcagt attgaaggtt tctggctcga gtctgtacaa tcttgcgctc 5700
aatgtcacta ttaatgtgga ggtagacccg aggagtcctt tggttaaatc tctgtctaag 5760
tctgacagcg gatactatgc taacctcttc ttgcatattg gacttatgac cactgtagat 5820
aggaagggga agaaagtgac atttgacaag ctggaaaaga aaataaggag ccttgatcta 5880
tctgtcgggc tcagtgatgt gctcgggcct tccgtgttgg taaaagcaag aggtgcacgg 5940
actaagcttt tggcaccttt cttctctagc agtgggacag cctgctatcc catagcaaat 6000
gcttctcctc aggtggccaa gatactctgg agtcaaaccg cgtgcctgcg gagcgttaaa 6060
atcattatcc aagcaggtac ccaacgcgct gtcgcagtga ccgccgacca cgaggttacc 6120
tctactaagc tggagaaggg gcacaccctt gccaaataca atccttttaa gaaataagct 6180
gcgtctctga gattgcgctc cgcccactca cccagatcat catgacacaa aaaactaatc 6240
tgtcttgatt atttacagtt agtttacctg tctatcaagt tagaaaaaac acgggtagaa 6300
gattctggat cccggttggc gccctccagg tgcaagatgg gctccagacc ttctaccaag 6360
aacccagcac ctatgatgct gactatccgg gttgcgctgg tactgagttg catctgtccg 6420

-continued

```
gcaaactcca ttgatggcag gcctcttgca gctgcaggaa ttgtggttac aggagacaaa   6480
gccgtcaaca tatacacctc atcccagaca ggatcaatca tagttaagct cctcccgaat   6540
ctgcccaagg ataaggaggc atgtgcgaaa gccccccttgg atgcatacaa caggacattg   6600
accactttgc tcacccccct tggtgactct atccgtagga tacaagagtc tgtgactaca   6660
tctggagggg ggagacaggg gcgccttata ggcgccatta ttggcggtgt ggctcttggg   6720
gttgcaactg ccgcacaaat aacagcggcc gcagctctga tacaagccaa acaaaatgct   6780
gccaacatcc tccgacttaa agagagcatt gccgcaacca atgaggctgt gcatgaggtc   6840
actgacggat tatcgcaact agcagtggca gttgggaaga tgcagcagtt tgttaatgac   6900
caatttaata aaacagctca ggaattagac tgcatcaaaa ttgcacagca agttggtgta   6960
gagctcaacc tgtacctaac cgaattgact acagtattcg gaccacaaat cacttcacct   7020
gctttaaaca agctgactat tcaggcactt tacaatctag ctggtggaaa tatggattac   7080
ttattgacta agttaggtgt agggaacaat caactcagct cattaatcgg tagcggctta   7140
atcaccggta accctattct atacgactca cagactcaac tcttgggtat acaggtaact   7200
ctaccttcag tcgggaacct aaataatatg cgtgccacct acttggaaac cttatccgta   7260
agcacaacca ggggatttgc ctcggcactt gtcccaaaag tggtgacaca ggtcggttct   7320
gtgatagaag aacttgacac ctcatactgt atagaaactg acttagattt atattgtaca   7380
agaatagtaa cgttccctat gtcccctggt atttattcct gcttgagcgg caatacgtcg   7440
gcctgtatgt actcaaagac cgaaggcgca cttactacac catacatgac tatcaaaggt   7500
tcagtcatcg ccaactgcaa gatgacaaca tgtagatgtg taaacccccc gggtatcata   7560
tcgcaaaact atggagaagc cgtgtctcta atagataaac aatcatgcaa tgttttatcc   7620
ttaggcggga taactttaag gctcagtggg gaattcgatg taacttatca gaagaatatc   7680
tcaatacaag attctcaagt aataataaca ggcaatcttg atatctcaac tgagcttggg   7740
aatgtcaaca actcgatcag taatgctttg aataagttag aggaaagcaa cagaaaacta   7800
gacaaagtca atgtcaaact gactagcaca tctgctctca ttacctatat cgttttgact   7860
atcatatctc ttgtttttgg tatacttagc ctgattctag catgctacct aatgtacaag   7920
caaaaggcgc aacaaaagac cttattatgg cttgggaata atactctaga tcagatgaga   7980
gccactacaa aaatgtgaac acagatgagg aacgaaggtt tccctaatag taatttgtgt   8040
gaaagttctg gtagtctgtc agttcagaga gttaagaaaa aactaccggt tgtagatgac   8100
caaaggacga tatacgggta gaacggtaag agaggccgcc cctcaattgc gagccaggct   8160
tcacaacctc cgttctaccg cttcaccgac aacagtcctc aatcatggac cgcgccgtta   8220
gccaagttgc gttagagaat gatgaaagag aggcaaaaaa tacatggcgc ttgatattcc   8280
ggattgcaat cttattctta acagtagtga ccttggctat atctgtagcc tccctttat    8340
atagcatggg ggctagcaca cctagcgatc ttgtaggcat accgactagg atttccaggg   8400
cagaagaaaa gattacatct acacttggtt ccaatcaaga tgtagtagat aggatatata   8460
agcaagtggc ccttgagtct ccgttggcat tgttaaatac tgagaccaca attatgaacg   8520
caataacatc tctctcttat cagattaatg gagctgcaaa caacagtggg tggggggcac   8580
ctatccatga cccagattat atagggggga taggcaaaga actcattgta gatgatgcta   8640
gtgatgtcac atcattctat ccctctgcat ttcaagaaca tctgaatttt atcccggcgc   8700
ctactacagg atcaggttgc actcgaatac cctcatttga catgagtgct acccattact   8760
```

```
gctacaccca taatgtaata ttgtctggat gcagagatca ctcacattca tatcagtatt   8820
tagcacttgg tgtgctccgg acatctgcaa cagggagggt attcttttct actctgcgtt   8880
ccatcaacct ggacgacacc caaaatcgga agtcttgcag tgtgagtgca actcccctgg   8940
gttgtgatat gctgtgctcg aaagtcacgg agacagagga agaagattat aactcagctg   9000
tccctacgcg gatggtacat gggaggttag ggttcgacgg ccagtaccac gaaaaggacc   9060
tagatgtcac aacattattc ggggactggg tggccaacta cccaggagta gggggtggat   9120
cttttattga cagccgcgta tggttctcag tctacggagg gttaaaaccc aattcaccca   9180
gtgacactgt acaggaaggg aaatatgtga tatacaagcg atacaatgac acatgcccag   9240
atgagcaaga ctaccagatt cgaatggcca agtcttcgta taagcctgga cggtttggtg   9300
ggaaacgcat acagcaggct atcttatcta tcaaggtgtc aacatcctta ggcgaagacc   9360
cggtactgac tgtaccgccc aacacagtca cactcatggg ggccgaaggc agaattctca   9420
cagtagggac atctcatttc ttgtatcaac gagggtcatc atacttctct cccgcgttat   9480
tatatcctat gacagtcagc aacaaaacag ccactcttca tagtccttat acattcaatg   9540
ccttcactcg gccaggtagt atcccttgcc aggcttcagc aagatgcccc aactcgtgtg   9600
ttactggagt ctatacagat ccatatcccc taatcttcta tagaaaccac accttgcgag   9660
gggtattcgg gacaatgctt gatggtgtac aagcaagact taaccctgcg tctgcagtat   9720
tcgatagcac atcccgcagt cgcattactc gagtgagttc aagcagtacc aaagcagcat   9780
acacaacatc aacttgtttt aaagtggtca agactaataa gacctattgt ctcagcattg   9840
ctgaaatatc taatactctc ttcggagaat tcagaatcgt cccgttacta gttgagatcc   9900
tcaaagatga cggggttaga gaagccaggt ctggctagtt gagtcaatta taaaggagtt   9960
ggaaagatgg cattgtatca cctatcttct gcgacatcaa gaatcaaacc gaatgccggc  10020
gcgtgctcga attccatgtt gccagttgac cacaatcagc cagtgctcat gcgatcagat  10080
taagccttgt caatagtctc ttgattaaga aaaaatgtaa gtggcaatga gatacaaggc  10140
aaaacagctc atggttaaca atacgggtag gacatggcga gctccggtcc tgaaagggca  10200
gagcatcaga ttatcctacc agagtcacac ctgtcttcac cattggtcaa gcacaaacta  10260
ctctattact ggaaattaac tgggctaccg cttcctgatg aatgtgactt cgaccacctc  10320
attctcagcc gacaatggaa aaaaatactt gaatcggcct ctcctgatac tgagagaatg  10380
ataaaactcg gaagggcagt acaccaaact cttaaccaca attccagaat aaccggagtg  10440
ctccacccca ggtgtttaga agaactggct aatattgagg tcccagattc aaccaacaaa  10500
tttcggaaga ttgagaagaa gatccaaatt cacaacacga gatatggaga actgttcaca  10560
aggctgtgta cgcatataga gaagaaactg ctggggtcat cttggtctaa caatgtcccc  10620
cggtcagagg agttcagcag cattcgtacg gatccggcat tctggtttca ctcaaaatgg  10680
tccacagcca agtttgcatg gctccatata aaacagatcc agaggcatct gatggtggca  10740
gctaggacaa ggtctgcggc caacaaattg gtgatgctaa cccataaggt aggccaagtc  10800
tttgtcactc ctgaacttgt cgttgtgacg catacgaatg agaacaagtt cacatgtctt  10860
acccaggaac ttgtattgat gtatgcagat atgatggagg gcagagatat ggtcaacata  10920
atatcaacca cggcggtgca tctcagaagc ttatcagaga aaattgatga cattttgcgg  10980
ttaatagacg ctctggcaaa agacttgggt aatcaagtct acgatgttgt atcactaatg  11040
gagggatttg catacggagc tgtccagcta ctcgagccgt caggtacatt tgcaggagat  11100
ttcttcgcat tcaacctgca ggagcttaaa gacattctaa ttggcctcct ccccaatgat  11160
```

-continued

```
atagcagaat ccgtgactca tgcaatcgct actgtattct ctggtttaga acagaatcaa  11220
gcagctgaga tgttgtgtct gttgcgtctg tggggtcacc cactgcttga gtcccgtatt  11280
gcagcaaagg cagtcaggag ccaaatgtgc gcaccgaaaa tggtagactt tgatatgatc  11340
cttcaggtac tgtctttctt caagggaaca atcatcaacg ggtacagaaa gaagaatgca  11400
ggtgtgtggc cgcgagtcaa agtggataca atatatggga aggtcattgg gcaactacat  11460
gcagattcag cagagatttc acacgatatc atgttgagag agtataagag tttatctgca  11520
cttgaatttg agccatgtat agaatatgac cctgtcacca acctgagcat gttcctaaaa  11580
gacaaggcaa tcgcacaccc caacgataat tggcttgcct cgtttaggcg gaaccttctc  11640
tccgaagacc agaagaaaca tgtaaaagaa gcaacttcga ctaatcgcct cttgatagag  11700
tttttagagt caaatgattt tgatccatat aaagagatgg aatatctgac gacccttgag  11760
taccttagag atgacaatgt ggcagtatca tactcgctca aggagaagga agtgaaagtt  11820
aatggacgga tcttcgctaa gctgacaaag aagttaagga actgtcaggt gatggcggaa  11880
gggatcctag ccgatcagat tgcacctttc tttcagggaa atggagtcat tcaggatagc  11940
atatccttga ccaagagtat gctagcgatg agtcaactgt cttttaacag caataagaaa  12000
cgtatcactg actgtaaaga aagagtatct tcaaaccgca atcatgatcc gaaaagcaag  12060
aaccgtcgga gagttgcaac cttcataaca actgacctgc aaaagtactg tcttaattgg  12120
agatatcaga caatcaaatt gttcgctcat gccatcaatc agttgatggg cctacctcac  12180
ttcttcgaat ggattcacct aagactgatg gacactacga tgttcgtagg agaccctttc  12240
aatcctccaa gtgaccctac tgactgtgac ctctcaagag tccctaatga tgacatatat  12300
attgtcagtg ccagaggggg tatcgaagga ttatgccaga agctatggac aatgatctca  12360
attgctgcaa tccaacttgc tgcagctaga tcgcattgtc gtgttgcctg tatggtacag  12420
ggtgataatc aagtaatagc agtaacgaga gaggtaagat cagacgactc tccggagatg  12480
gtgttgacac agttgcatca agccagtgat aatttcttca aggaattaat tcatgtcaat  12540
catttgattg gccataattt gaaggatcgt gaaaccatca ggtcagacac attcttcata  12600
tacagcaaac gaatcttcaa agatggagca atcctcagtc aagtcctcaa aaattcatct  12660
aaattagtgc tagtgtcagg tgatctcagt gaaaacaccg taatgtcctg tgccaacatt  12720
gcctctactg tagcacggct atgcgagaac gggcttccca aagacttctg ttactattta  12780
aactatataa tgagttgtgt gcagacatac tttgactctg agttctccat caccaacaat  12840
tcgcaccccg atcttaatca gtcgtggatt gaggacatct cttttgtgca ctcatatgtt  12900
ctgactcctg cccaattagg gggactgagt aaccttcaat actcaaggct ctacactaga  12960
aatatcggtg acccggggac tactgctttt gcagagatca agcgactaga agcagtggga  13020
ttactgagtc ctaacattat gactaatatc ttaactaggc cgcctgggaa tggagattgg  13080
gccagtctgt gcaacgaccc atactctttc aattttgaga ctgttgcaag cccaaatatt  13140
gttcttaaga aacatacgca aagagtccta tttgaaactt gttcaaatcc cttattgtct  13200
ggagtgcaca cagaggataa tgaggcagaa gagaaggcat tggctgaatt cttgcttaat  13260
caagaggtga ttcatccccg cgttgcgcat gccatcatgg aggcaagctc tgtaggtagg  13320
agaaagcaaa ttcaagggct tgttgacaca acaaacaccg taattaagat tgcgcttact  13380
aggaggccat taggcatcaa gaggctgatg cggatagtca attattctag catgcatgca  13440
atgctgttta gagacgatgt tttttcctcc agtagatcca accacccctt agtctcttct  13500
```

-continued

```
aatatgtgtt ctctgacact ggcagactat gcacggaata gaagctggtc acctttgacg  13560
ggaggcagga aaatactggg tgtatctaat cctgatacga tagaactcgt agagggtgag  13620
attcttagtg taagcggagg gtgtacaaga tgtgacagcg gagatgaaca atttacttgg  13680
ttccatcttc caagcaatat agaattgacc gatgacacca gcaagaatcc tccgatgagg  13740
gtaccatatc tcgggtcaaa gacacaggag aggagagctg cctcacttgc aaaaatagct  13800
catatgtcgc cacatgtaaa ggctgcccta agggcatcat ccgtgttgat ctgggcttat  13860
ggggataatg aagtaaattg gactgctgct cttacgattg caaaatctcg gtgtaatgta  13920
aacttagagt atcttcggtt actgtcccct ttacccacgg ctgggaatct tcaacataga  13980
ctagatgatg gtataactca gatgacattc acccctgcat ctctctacag ggtgtcacct  14040
tacattcaca tatccaatga ttctcaaagg ctgttcactg aagaaggagt caaagagggg  14100
aatgtggttt accaacagat catgctcttg ggtttatctc taatcgaatc gatctttcca  14160
atgacaacaa ccaggacata tgatgagatc acactgcacc tacatagtaa atttagttgc  14220
tgtatcagag aagcacctgt tgcggttcct ttcgagctac ttggggtggt accggaactg  14280
aggacagtga cctcaaataa gtttatgtat gatcctagcc ctgtatcgga gggagacttt  14340
gcgagacttg acttagctat cttcaagagt tatgagctta atctggagtc atatcccacg  14400
atagagctaa tgaacattct ttcaatatcc agcgggaagt tgattggcca gtctgtggtt  14460
tcttatgatg aagatacctc cataaagaat gacgccataa tagtgtatga caatacccga  14520
aattggatca gtgaagctca gaattcagat gtggtccgcc tatttgaata tgcagcactt  14580
gaagtgctcc tcgactgttc ttaccaactc tattacctga gagtaagagg cctggacaat  14640
attgtcttat atatgggtga tttatacaag aatatgccag gaattctact ttccaacatt  14700
gcagctacaa tatctcatcc cgtcattcat tcaaggttac atgcagtggg cctggtcaac  14760
catgacggat cacaccaact tgcagatacg gattttatcg aaatgtctgc aaaactatta  14820
gtatcttgca cccgacgtgt gatctccggc ttatattcag gaaataagta tgatctgctg  14880
ttcccatctg tcttagatga taacctgaat gagaagatgc ttcagctgat atcccggtta  14940
tgctgtctgt acacggtact ctttgctaca acaagagaaa tcccgaaaat aagaggctta  15000
actgcagaag agaaatgttc aatactcact gagtatttac tgtcggatgc tgtgaaacca  15060
ttacttagcc ccgatcaagt gagctctatc atgtctccta acataattac attcccagct  15120
aatctgtact acatgtctcg gaagagcctc aatttgatca gggaaaggga ggacagggat  15180
actatcctgg cgttgttgtt cccccaagag ccattattag agttcccttc tgtgcaagat  15240
attggtgctc gagtgaaaga tccattcacc cgacaacctg cggcattttt gcaagagtta  15300
gatttgagtg ctccagcaag gtatgacgca ttcacactta gtcagattca tcctgaactc  15360
acatctccaa atccggagga agactactta gtacgatact tgttcagagg gatagggact  15420
gcatcttcct cttggtataa ggcatctcat ctcctttctg tacccgaggt aagatgtgca  15480
agacacggga actccttata cttagctgaa gggagcggag ccatcatgag tcttctcgaa  15540
ctgcatgtac cacatgaaac tatctattac aatacgctct tttcaaatga gatgaacccc  15600
ccgcaacgac atttcgggcc gaccccaact cagtttttga attcggttgt ttataggaat  15660
ctacaggcgg aggtaacatg caaagatgga tttgtccaag agttccgtcc attatggaga  15720
gaaaatacag aggaaagcga cctgacctca gataaagtag tggggtatat tacatctgca  15780
gtgccctaca gatctgtatc attgctgcat tgtgacattg aaattcctcc agggtccaat  15840
caaagcttac tagatcaact agctatcaat ttatctctga ttgccatgca ttctgtaagg  15900
```

```
gagggcgggg tagtaatcat caaagtgttg tatgcaatgg gatactactt tcatctactc  15960
atgaacttgt ttgctccgtg ttccacaaaa ggatatattc tctctaatgg ttatgcatgt  16020
cgaggagata tggagtgtta cctggtattt gtcatgggtt acctgggcgg gcctacattt  16080
gtacatgagg tggtgaggat ggcgaaaact ctggtgcagc ggcacggtac gcttttgtct  16140
aaatcagatg agatcacact gaccaggtta ttcacctcac agcggcagcg tgtgacagac  16200
atcctatcca gtcctttacc aagattaata aagtacttga ggaagaatat tgacactgcg  16260
ctgattgaag ccgggggaca gcccgtccgt ccattctgtg cggagagtct ggtgagcacg  16320
ctagcgaaca taactcagat aacccagatc atcgctagtc acattgacac agttatccgg  16380
tctgtgatat atatggaagc tgagggtgat ctcgctgaca cagtatttct atttacccct  16440
tacaatctct ctactgacgg gaaaaagagg acatcactta aacagtgcac gagacagatc  16500
ctagaggtta caatactagg tcttagagtc gaaaatctca ataaaatagg cgatataatc  16560
agcctagtgc ttaaaggcat gatctccatg gaggacctta tcccactaag gacatacttg  16620
aagcatagta cctgccctaa atatttgaag gctgtcctag gtattaccaa actcaaagaa  16680
atgtttacag acacttctgt actgtacttg actcgtgctc aacaaaaatt ctacatgaaa  16740
actataggca atgcagtcaa aggatattac agtaactgtg actcttaacg aaaatcacat  16800
attaataggc tcctttttg gccaattgta ttcttgttga tttaatcata ttatgttaga  16860
aaaaagttga accctgactc cttaggactc gaattcgaac tcaaataaat gtcttaaaaa  16920
aaggttgcgc acaattattc ttgagtgtag tctcgtcatt caccaaatct ttgtttggt   16979
```

```
<210> SEQ ID NO 38
<211> LENGTH: 1749
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 38
```

```
atggccacca ccgccatgag aatgatcatc agcatcatct tcatcagcac ctacgtgacc     60
cacatcaccc tgtgccagaa catcaccgag gagttctacc agagcacctg cagcgccgtg    120
agcagaggct acctgagcgc cctgagaacc ggctggtaca ccagcgtggt gaccatcgag    180
ctgagcaaga tccagaagaa cgtgtgcaag agcaccgaca gcaaggtgaa gctgatcaag    240
caggagctgg agagatacaa caacgccgtg gtggagctgc agagcctgat gcagaacgag    300
cccgccagct tcagcagagc caagagaggc atccccgagc tgatccacta caccagaaac    360
agcaccaaga agttctacgg cctgatgggc aagaagagaa agagaagatt cctgggcttc    420
ctgctgggca tcggcagcgc cgtggccagc ggcgtggccg tgagcaaggt gctgcacctg    480
gagggcgagg tgaacaagat caagaacgcc ctgctgagca ccaacaaggc cgtggtgagc    540
ctgagcaacg gcgtgagcgt gctgaccagc aaggtgctgg acctgaagaa ctacatcgac    600
aaggagctgc tgccccaggt gaacaaccac gactgcagaa tcagcaacat cgagaccgtg    660
atcgagttcc agcagaagaa caacagactg ctggagatcg ccagagagtt cagcgtgaac    720
gccggcatca ccaccccccct gagcacctac atgctgacca acagcgagct gctgagcctg    780
atcaacgaca tgcccatcac caacgaccag aagaagctga tgagcagcaa cgtgcagatc    840
gtgagacagc agagctacag catcatgagc gtggtgaagg aggaggtgat cgcctacgtg    900
gtgcagctgc ccatctacgg cgtgatcgac acccccctgct ggaagctgca caccagcccc    960
```

ctgtgcacca ccgacaacaa ggagggcagc aacatctgcc tgaccagaac cgacagaggc 1020
tggtactgcg acaacgccgg cagcgtgagc ttcttccccc agaccgagac ctgcaaggtg 1080
cagagcaaca gagtgttctg cgacaccatg aacagcctga ccctgcccac cgacgtgaac 1140
ctgtgcaaca ccgacatctt caacaccaag tacgactgca agatcatgac cagcaagacc 1200
gacatcagca gcagcgtgat caccagcatc ggcgccatcg tgagctgcta cggcaagacc 1260
aagtgcaccg ccagcaacaa gaacagaggc atcatcaaga ccttcagcaa cggctgcgac 1320
tacgtgagca acaagggcgt ggacaccgtg agcgtgggca acaccctgta ctacgtgaac 1380
aagctggagg gcaaggccct gtacatcaag ggcgagccca tcatcaacta ctacgacccc 1440
ctggtgttcc ccagcgacga gttcgacgcc agcatcgccc aggtgaacgc caagatcaac 1500
cagagcctgg ccttcatcag aagaagcgac gagctgctgc acagcgtgga cgtgggcaag 1560
agcaccacca acgtggttaa cctcattacc tatatcgttt tgactatcat atctcttgtt 1620
tttggtatac ttagcctgat tctagcatgc tacctaatgt acaagcaaaa ggcgcaacaa 1680
aagaccttat tatggcttgg gaataatacc ctagatcaga tgagagccac tacaaaaatg 1740
tgaccgcgg 1749

<210> SEQ ID NO 39
<211> LENGTH: 1749
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 39
atggccacca ccgccatgac catgatcatc agcatcatct tcatcagcac ctacgtgacc 60
cacatcaccc tgtgccagaa catcaccgag gagttctacc agagcacctg cagcgccgtg 120
agcagaggct acctgagcgc cctgagaacc ggctggtaca ccagcgtggt gaccatcgag 180
ctgagcaaga tccagaagaa cgtgtgcaag agcaccgaca gcaaggtgaa gctgatcaag 240
caggagctgg agagatacaa caacgccgtg gtggagctgc agagcctgat gcagaacgag 300
cccgccagct tcagcagagc caagagaagc atccccgagc tgatccacta caccagaaac 360
agcaccaaga agttctacgg cctgatgggc aagaagagaa agagaagatt cctgggcttc 420
ctgctgggca tcggcagcgc catcgccagc ggcgtggccg tgagcaaggt gctgcacctg 480
gagggcgagg tgaacaagat caagaacgcc ctgctgagca ccaacaaggc cgtggtgagc 540
ctgagcaacg gcgtgagcgt gctgaccagc aaggtgctgg acctgaagaa ctacatcgac 600
aaggagctgc tgcccaaggt gaacaaccac gactgcagaa tcagcaacat cgccaccgtg 660
atcgagttcc agcagaagaa caacagactg ctggagatcg ccagagagtt cagcgtgaac 720
gccggcatca ccacccccct gagcacctac atgctgacca acagcgagct gctgagcctg 780
atcaacgaca tgcccatcac caacgaccag aagaagctga tgagcagcaa cgtgcagatc 840
gtgagacagc agagctacag catcatgagc gtggtgaagg aggaggtgat cgcctacgtg 900
gtgcagctgc ccatctacgg cgtgatcgac acccccctgct ggaagctgca caccagcccc 960
ctgtgcacca ccgacaacaa ggagggcagc aacatctgcc tgaccagaac cgacagaggc 1020
tggtactgcg acaacgccgg cagcgtgagc ttcttccccc aggccgagac ctgcaaggtg 1080
cagagcaaca gagtgttctg cgacaccatg aacagcctga ccctgcccac cgacgtgaac 1140
ctgtgcaaca ccgacatctt caacaccaag tacgactgca agatcatgac cagcaagacc 1200

```
gacatcagca gcagcgtgat caccagcatc ggcgccatcg tgagctgcta cggcaagacc   1260
aagtgcaccg ccagcaacaa gaacagaggc atcatcaaga ccttcagcaa cggctgcgac   1320
tacgtgagca acaagggcgt ggacaccgtg agcgtgggca acaccctgta ctacgtgaac   1380
aagctggagg gcaaggccct gtacatcaag ggcgagccca tcatcaacta ctacgacccc   1440
ctggtgttcc ccagcgacga gttcgacgcc agcatcgccc aggtgaacgc caagatcaac   1500
cagagcctgg ccttcatcag aagaagcgac gagctgctgc acagcgtgga cgtgggcaag   1560
agcaccacca acgtggttaa cctcattacc tatatcgttt tgactatcat atctcttgtt   1620
tttggtatac ttagcctgat tctagcatgc tacctaatgt acaagcaaaa ggcgcaacaa   1680
aagaccttat tatggcttgg gaataatacc ctagatcaga tgagagccac tacaaaaatg   1740
tgaccgcgg                                                            1749
```

<210> SEQ ID NO 40
<211> LENGTH: 1725
<212> TYPE: DNA
<213> ORGANISM: Bovine respiratory syncytial virus

<400> SEQUENCE: 40

```
atggcgacaa cagccatgag gatgatcatc agcattatct tcatctctac ctatgtgaca     60
catatcactt tatgccaaaa cataacagaa gaattttatc aatcaacatg cagtgcagtt    120
agtagaggtt accttagtgc attaagaact ggatggtata caagtgtggt aacaatagag    180
ttgagcaaaa tacaaaaaaa tgtgtgtaaa agtactgatt caaaagtgaa attaataaag    240
caagaactag aaagatacaa caatgcagta gtggaattgc agtcacttat gcaaaatgaa    300
ccggcctcct tcagtagagc aaaaagaggg ataccagagt tgatacatta tacaagaaac    360
tctacaaaaa agttttatgg gctaatgggc aagaagagaa aaaggagatt tttaggattc    420
ttgctaggta ttggatctgc tgttgcaagt ggtgtagcag tgtccaaagt actacacctg    480
gagggagagg tgaataaaat taaaaatgca ctgctatcca caaataaagc agtagttagt    540
ctatccaatg gagttagtgt ccttactagc aaagtacttg atctaaagaa ctatatagac    600
aaagagcttc tacctcaagt taacaatcat gattgtagga tatccaacat agaaactgtg    660
atagaattcc aacaaaaaaa caatagattg ttagaaattg ctagggaatt tagtgtaaat    720
gctggtatta ccacacctct cagtacatac atgttgacca atagtgaatt actatcacta    780
attaatgata tgcctataac gaatgaccaa aaaaagctaa tgtcaagtaa tgttcaaata    840
gtcaggcaac agagttattc cattatgtca gtggtcaaag aagaagtcat agcttatgtt    900
gtacaattgc ctatttatgg agttatagac accccctgtt ggaaactaca cacctctccg    960
ttatgcacca ctgataataa agaagggtca aacatctgct taactaggac agatcgtggg   1020
tggtattgtg acaatgcagg ctctgtgtct tttttcccac agacagagac atgtaaggta   1080
caatcaaata gagtgttctg tgacacaatg aacagtttaa ctctgcctac tgacgttaac   1140
ttatgcaaca ctgacatatt caatacaaag tatgactgta aaataatgac atctaaaact   1200
gacataagta gctctgtgat aacttcaatt ggagctattg tatcatgcta tgggaagaca   1260
aaatgtacag cttctaataa aaatcgtgga atcataaaga ctttttccaa tgggtgtgat   1320
tatgtatcaa acaaaggagt agatactgta tctgttggta acacactata ttatgtaaat   1380
aagctagagg ggaaagcact ctatataaag ggtgaaccaa ttattaatta ctatgatcca   1440
ctagtgtttc cttctgatga gtttgatgca tcaattgccc aagtaaacgc aaaaataaac   1500
```

```
caaagcctgg ccttcatacg tcgatctgat gagttacttc acagtgtaga tgtaggaaaa   1560

tccaccacaa atgtagtaat tactactatt atcatagtga tagttgtagt gatattaatg   1620

ttaatagctg taggattact gttttactgt aagaccaaga gtactcctat catgttaggg   1680

aaggatcagc tcagtggtat caacaatctt tcctttagta aatga                   1725
```

```
<210> SEQ ID NO 41
<211> LENGTH: 1722
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 41

atggccacca ccgccatgag aatgatcatc agcatcatct tcatcagcac ctacgtgacc     60

cacatcaccc tgtgccagaa catcaccgag gagttctacc agagcacctg cagcgccgtg    120

agcagaggct acctgagcgc cctgagaacc ggctggtaca ccagcgtggt gaccatcgag    180

ctgagcaaga tccagaagaa cgtgtgcaag agcaccgaca gcaaggtgaa gctgatcaag    240

caggagctgg agagatacaa caacgccgtg gtggagctgc agagcctgat gcagaacgag    300

cccgccagct tcagcagagc caagagaggc atccccgagc tgatccacta caccagaaac    360

agcaccaaga agttctacgg cctgatgggc aagaagagaa agagaagatt cctgggcttc    420

ctgctgggca tcggcagcgc cgtggccagc ggcgtggccg tgagcaaggt gctgcacctg    480

gagggcgagg tgaacaagat caagaacgcc ctgctgagca ccaacaaggc cgtggtgagc    540

ctgagcaacg gcgtgagcgt gctgaccagc aaggtgctgg acctgaagaa ctacatcgac    600

aaggagctgc tgccccaggt gaacaaccac gactgcagaa tcagcaacat cgagaccgtg    660

atcgagttcc agcagaagaa caacagactg ctggagatcg ccagagagtt cagcgtgaac    720

gccggcatca ccacccccct gagcacctac atgctgacca acagcgagct gctgagcctg    780

atcaacgaca tgcccatcac caacgaccag aagaagctga tgagcagcaa cgtgcagatc    840

gtgagacagc agagctacag catcatgagc gtggtgaagg aggaggtgat cgcctacgtg    900

gtgcagctgc ccatctacgg cgtgatcgac accccctgct ggaagctgca caccagcccc    960

ctgtgcacca ccgacaacaa ggagggcagc aacatctgcc tgaccagaac cgacagaggc   1020

tggtactgcg acaacgccgg cagcgtgagc ttcttccccc agaccgagac ctgcaaggtg   1080

cagagcaaca gagtgttctg cgacaccatg aacagcctga ccctgcccac cgacgtgaac   1140

ctgtgcaaca ccgacatctt caacaccaag tacgactgca agatcatgac cagcaagacc   1200

gacatcagca gcagcgtgat caccagcatc ggcgccatcg tgagctgcta cggcaagacc   1260

aagtgcaccg ccagcaacaa gaacagaggc atcatcaaga ccttcagcaa cggctgcgac   1320

tacgtgagca acaagggcgt ggacaccgtg agcgtgggca acaccctgta ctacgtgaac   1380

aagctggagg gcaaggccct gtacatcaag ggcgagccca tcatcaacta ctacgacccc   1440

ctggtgttcc ccagcgacga gttcgacgcc agcatcgccc aggtgaacgc caagatcaac   1500

cagagcctgg ccttcatcag aagaagcgac gagctgctgc acagcgtgga cgtgggcaag   1560

agcaccacca acgtggtgat caccaccatc atcatcgtga tcgtggtggt gatcctgatg   1620

ctgatcgccg tgggcctgct gttctactgc aagaccaaga gcacccccat catgctgggc   1680

aaggaccagc tgagcggcat caacaacctg agcttcagca ag                      1722


<210> SEQ ID NO 42
```

<211> LENGTH: 1725
<212> TYPE: DNA
<213> ORGANISM: Bovine respiratory syncytial virus

<400> SEQUENCE: 42
atggcgacaa cagccatgac gatgatcatc agcattatct tcatctctac ctatgtgaca 60
catatcactt tatgccaaaa cataacagaa gaattttatc aatcaacatg cagtgcagtt 120
agtagaggtt accttagtgc attaagaact ggatggtata caagtgtggt aacaatagag 180
ttgagcaaaa tacaaaaaaa tgtgtgtaaa agtactgatt cgaaagtgaa attaataaag 240
caagaactag aaagatacaa caatgcagta gtggaattgc agtcacttat gcaaaatgaa 300
ccggcctcct tcagtagagc aaaaagaagt ataccagagt tgatacatta tacaagaaac 360
tctacaaaaa agttttatgg gctaatgggc aagaagagaa aaaggagatt tttaggattc 420
ttactaggta ttggatctgc tattgcaagt ggtgtagcag tgtccaaagt actacacctg 480
gagggagagg tgaataaaat taaaaatgca ctgctatcca caaacaaagc agtagttagt 540
ctatccaatg gagttagtgt ccttactagc aaagtacttg atctaaagaa ctatatagac 600
aaagagcttc tacctaaagt taacaatcat gattgtagga tatccaacat agcaactgtg 660
atagaattcc aacaaaaaaa caatagattg ttagaaattg ctagggaatt tagtgtaaat 720
gctggtatta ccacacccct cagtacatac atgttgacca atagtgaatt actatcacta 780
attaatgata tgcctataac gaatgaccaa aaaaagctaa tgtcaagtaa tgttcaaata 840
gtcaggcaac agagttattc cattatgtca gtggtcaaag aagaggtcat agcttatgtt 900
gtacaattgc ctatttatgg agttatagac acccccctgtt ggaaactaca cacttctcca 960
ttatgcacca ctgataataa agaagggtca aacatctgct taactaggac agatcgtggg 1020
tggtattgtg acaatgcagg ctctgtatct tttttcccac aggcagagac gtgtaaggta 1080
caatcaaata gagtgttctg tgacacaatg aacagtttaa ctctgcctac tgatgttaac 1140
ttatgcaaca ctgacatatt caatacaaag tatgactgta aaataatgac atctaaaact 1200
gacataagta gctctgtaat aacttcaatt ggagctattg tatcatgcta tgggaagaca 1260
aaatgtacag cttctaataa aaatcgtgga atcataaaga ctttttccaa tgggtgtgat 1320
tatgtatcaa acaaaggagt tgatactgta tctgttggta acacactata ttatgtaaat 1380
aagctagagg ggaaagcact ctatataaag ggtgaaccaa ttattaatta ctatgatcca 1440
ctagtgtttc cttctgatga gtttgatgca tcaattgccc aagtaaacgc aaaaataaac 1500
caaagcctgg ctttcatacg tcgatctgat gagttacttc acagtgtaga tgtaggaaaa 1560
tccaccacaa atgtagtaat tactactatt atcatagtga tagttgtagt gatattaatg 1620
ttaatagctg taggattact gttttactgt aagaccagga gtactcctat catgttaggg 1680
aaggatcagc ttagtggtat caacaatctt tcctttagta aatga 1725

<210> SEQ ID NO 43
<211> LENGTH: 1722
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 43
atggccacca ccgccatgac catgatcatc agcatcatct tcatcagcac ctacgtgacc 60
cacatcaccc tgtgccagaa catcaccgag gagttctacc agagcacctg cagcgccgtg 120

```
agcagaggct acctgagcgc cctgagaacc ggctggtaca ccagcgtggt gaccatcgag    180

ctgagcaaga tccagaagaa cgtgtgcaag agcaccgaca gcaaggtgaa gctgatcaag    240

caggagctgg agagatacaa caacgccgtg gtggagctgc agagcctgat gcagaacgag    300

cccgccagct tcagcagagc caagagaagc atccccgagc tgatccacta caccagaaac    360

agcaccaaga agttctacgg cctgatgggc aagaagagaa agagaagatt cctgggcttc    420

ctgctgggca tcggcagcgc catcgccagc ggcgtggccg tgagcaaggt gctgcacctg    480

gagggcgagg tgaacaagat caagaacgcc ctgctgagca ccaacaaggc cgtggtgagc    540

ctgagcaacg gcgtgagcgt gctgaccagc aaggtgctgg acctgaagaa ctacatcgac    600

aaggagctgc tgcccaaggt gaacaaccac gactgcagaa tcagcaacat cgccaccgtg    660

atcgagttcc agcagaagaa caacagactg ctggagatcg ccagagagtt cagcgtgaac    720

gccggcatca ccacccccct gagcacctac atgctgacca acagcgagct gctgagcctg    780

atcaacgaca tgcccatcac caacgaccag aagaagctga tgagcagcaa cgtgcagatc    840

gtgagacagc agagctacag catcatgagc gtggtgaagg aggaggtgat cgcctacgtg    900

gtgcagctgc ccatctacgg cgtgatcgac acccccctgct ggaagctgca caccagcccc    960

ctgtgcacca ccgacaacaa ggagggcagc aacatctgcc tgaccagaac cgacagaggc   1020

tggtactgcg acaacgccgg cagcgtgagc ttcttccccc aggccgagac ctgcaaggtg   1080

cagagcaaca gagtgttctg cgacaccatg aacagcctga ccctgcccac cgacgtgaac   1140

ctgtgcaaca ccgacatctt caacaccaag tacgactgca agatcatgac cagcaagacc   1200

gacatcagca gcagcgtgat caccagcatc ggcgccatcg tgagctgcta cggcaagacc   1260

aagtgcaccg ccagcaacaa gaacagaggc atcatcaaga ccttcagcaa cggctgcgac   1320

tacgtgagca acaagggcgt ggacaccgtg agcgtgggca acaccctgta ctacgtgaac   1380

aagctggagg gcaaggccct gtacatcaag ggcgagccca tcatcaacta ctacgacccc   1440

ctggtgttcc ccagcgacga gttcgacgcc agcatcgccc aggtgaacgc caagatcaac   1500

cagagcctgg ccttcatcag aagaagcgac gagctgctgc acagcgtgga cgtgggcaag   1560

agcaccacca acgtggtgat caccaccatc atcatcgtga tcgtggtggt gatcctgatg   1620

ctgatcgccg tgggcctgct gttctactgc aagaccagaa gcacccccat catgctgggc   1680

aaggaccagc tgagcggcat caacaacctg agcttcagca ag                      1722
```

<210> SEQ ID NO 44
<211> LENGTH: 1752
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 44

```
atggagctgc ccatcctgaa gaccaacgcc atcaccacca tcctggccgc cgtgaccctg     60

tgcttcgcca gcagccagaa catcaccgag gagttctacc agagcacctg cagcgccgtg    120

agcaagggct acctgagcgc cctgagaacc ggctggtaca ccagcgtgat caccatcgag    180

ctgagcaaca tcaaggagaa caagtgcaac ggcaccgacg ccaaggtgaa gctgatcaag    240

caggagctgg acaagtacaa gaacgccgtg accgagctgc agctgctgat gcagagcacc    300

cccgccgcca acagcagagc cagaagagag ctgcccagat tcatgaacta caccctgaac    360

aacaccaaga acaccaacgt gaccctgagc aagaagagaa agagaagatt cctgggcttc    420
```

ctgctgggcg tgggcagcgc catcgccagc ggcatcgccg tgagcaaggt gctgcacctg 480
gagggcgagg tgaacaagat caagagcgcc ctgctgagca ccaacaaggc cgtggtgagc 540
ctgagcaacg gcgtgagcgt gctgaccagc aaggtgctgg acctgaagaa ctacatcgac 600
aagcagctgc tgcccatcgt gaacaagcag agctgcagca tcagcaacat cgagaccgtg 660
atcgagttcc agcagaagaa caacagactg ctggagatca ccagagagtt cagcgtgaac 720
gccggcgtga ccacccccgt gagcacctac atgctgacca acagcgagct gctgagcctg 780
atcaacgaca tgcccatcac caacgaccag aagaagctga tgagcagcaa cgtgcagatc 840
gtgagacagc agagctacag catcatgagc atcatcaagg aggaggtgct ggcctacgtg 900
gtgcagctgc ccctgtacgg cgtgatcgac accccctgct ggaagctgca caccagcccc 960
ctgtgcacca ccaacaccaa ggagggcagc aacatctgcc tgaccagaac cgacagaggc 1020
tggtactgcg acaacgccgg cagcgtgagc ttcttccccc aggccgagac ctgcaaggtg 1080
cagagcaaca gagtgttctg cgacaccatg aacagcctga ccctgcccag cgaggtgaac 1140
ctgtgcaaca tcgacatctt caaccccaag tacgactgca agatcatgac cagcaagacc 1200
gacgtgagca gcagcgtgat caccagcctg ggcgccatcg tgagctgcta cggcaagacc 1260
aagtgcaccg ccagcaacaa gaacagaggc atcatcaaga ccttcagcaa cggctgcgac 1320
tacgtgagca acaagggcgt ggacaccgtg agcgtgggca acaccctgta ctacgtgaac 1380
aagcaggagg gcaagagcct gtacgtgaag ggcgagccca tcatcaactt ctacgacccc 1440
ctggtgttcc ccagcgacga gttcgacgcc agcatcagcc aggtgaacga gaagatcaac 1500
cagagcctgg ccttcatcag aaagagcgac gagctgctgc acaacgtgaa cgccggcaag 1560
agcaccacca acatcatggt taacctcatt acctatatcg ttttgactat catatctctt 1620
gtttttggta tacttagcct gattctagca tgctacctaa tgtacaagca aaaggcgcaa 1680
caaaagacct tattatggct tgggaataat accctagatc agatgagagc cactacaaaa 1740
atgtgaccgc gg 1752

<210> SEQ ID NO 45
<211> LENGTH: 1752
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 45
atggagctgc tgatccacag aagcagcgtg atcttcctga ccctggccat caacgccctg 60
tacctgacca gcagccagaa catcaccgag gagttctacc agagcacctg cagcgccgtg 120
agcagaggct acttcagcgc cctgagaacc ggctggtaca ccagcgtgat caccatcgag 180
ctgagcaaca tcaaggagac caagtgcaac ggcaccgaca ccaaggtgaa gctgatcaag 240
caggagctgg acaagtacaa gaacgccgtg accgagctgc agctgctgat gcagaacatc 300
cccgccgcca acaacagagc cagaagagag gccccccagt acatgaacta caccatcaac 360
accaccaaga acctgaacgt gagcatcagc aagaagagaa agagaagatt cctgggcttc 420
ctgctgggcg tgggcagcgc catcgccagc ggcatcgccg tgagcaaggt gctgcacctg 480
gagggcgagg tgaacaagat caagaacgcc ctgctgagca ccaacaaggc cgtggtgagc 540
ctgagcaacg gcgtgagcgt gctgaccagc aaggtgctgg acctgaagaa ctacatcaac 600
aaccagctgc tgcccatcgt gaaccagcag agctgcagaa tcagcaacat cgagaccgtg 660

```
atcgagttcc agcagaagaa cagcagactg ctggagatca ccagagagtt cagcgtgaac    720

gccggcgtga ccaccccccct gagcacctac atgctgacca acagcgagct gctgagcctg    780

atcaacgaca tgcccatcac caacgaccag aagaagctga tgagcagcaa cgtgcagatc    840

gtgagacagc agagctacag catcatgagc atcatcaagg aggaggtgct ggcctacgtg    900

gtgcagctgc ccatctacgg cgtgatcgac accccctgct ggaagctgca caccagcccc    960

ctgtgcacca ccaacatcaa ggagggcagc aacatctgcc tgaccagaac cgacagaggc   1020

tggtactgcg acaacgccgg cagcgtgagc ttcttccccc aggccgacac ctgcaaggtg   1080

cagagcaaca gagtgttctg cgacaccatg aacagcctga ccctgcccag cgaggtgagc   1140

ctgtgcaaca ccgacatctt caacagcaag tacgactgca agatcatgac cagcaagacc   1200

gacatcagca gcagcgtgat caccagcctg ggcgccatcg tgagctgcta cggcaagacc   1260

aagtgcaccg ccagcaacaa gaacagaggc atcatcaaga ccttcagcaa cggctgcgac   1320

tacgtgagca acaagggcgt ggacaccgtg agcgtgggca acaccctgta ctacgtgaac   1380

aagctggagg gcaagaacct gtacgtgaag ggcgagccca tcatcaacta ctacgacccc   1440

ctggtgttcc ccagcgacga gttcgacgcc agcatcagcc aggtgaacga gaagatcaac   1500

cagagcctgg ccttcatcag aagaagcgac gagctgctgc acaacgtgaa caccggcaag   1560

agcaccacca acatcatggt taacctcatt acctatatcg ttttgactat catatctctt   1620

gtttttggta tacttagcct gattctagca tgctacctaa tgtacaagca aaaggcgcaa   1680

caaaagacct tattatggct tgggaataat accctagatc agatgagagc cactacaaaa   1740

atgtgaccgc gg                                                       1752
```

<210> SEQ ID NO 46
<211> LENGTH: 1752
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 46

```
atggagctgc ccatcctgaa ggccaacgcc atcaccacca tcctggccgc cgtgaccctg     60

tgcttcgcca gcagccagaa catcaccgag gagttctacc agagcacctg cagcgccgtg    120

agcaagggct acctgagcgc cctgagaacc ggctggtaca ccagcgtgat caccatcgag    180

ctgagcaaca tcaaggagaa caagtgcaac ggcaccgacg ccaaggtgaa gctgatcaag    240

caggagctgg acaagtacaa gaacgccgtg accgagctgc agctgctgat gcagagcacc    300

cccgccgcca acaacagagc cagaagagag ctgcccagat tcatgaacta caccctgaac    360

aacaccgaga acaccaacgt gaccctgagc aagaagagaa agagaagatt cctgggcttc    420

ctgctgggcg tgggcagcgc catcgccagc ggcatcgccg tgagcaaggt gctgcacctg    480

gagggcgagg tgaacaagat caagagcgcc ctgctgagca ccaacaaggc cgtggtgagc    540

ctgagcaacg gcgtgagcgt gctgaccagc aaggtgctgg acctgaagaa ctacatcgac    600

aagcagctgc tgcccatcgt gaacaagcag agctgcagca tcagcaacat cgagaccgtg    660

atcgagttcc agcagaagaa caacagactg ctggagatca ccagagagtt cagcgtgaac    720

gccggcgtga ccacccccgt gagcacctac atgctgacca acagcgagct gctgagcctg    780

atcaacgaca tgcccatcac caacgaccag aagaagctga tgagcaacaa cgtgcagatc    840

gtgagacagc agagctacag catcatgagc atcatcaagg aggaggtgct ggcctacgtg    900
```

gtgcagctgc ccctgtacgg cgtgatcgac acccccctgct ggaagctgca caccagcccc 960
ctgtgcacca ccaacaccaa ggagggcagc aacatctgcc tgaccagaac cgacagaggc 1020
tggtactgcg acaacgccgg cagcgtgagc ttcttccccc aggccgagac ctgcaaggtg 1080
cagagcaaca gagtgttctg cgacaccatg aacagcctga ccctgcccag cgaggtgagc 1140
ctgtgcaacg tggacatctt caaccccaag tacgactgca agatcatgac cagcaagacc 1200
gacgtgagca gcagcgtgat caccagcctg ggcgccatcg tgagctgcta cggcaagacc 1260
aagtgcaccg ccagcaacaa gaacagaggc atcatcaaga ccttcagcaa cggctgcgac 1320
tacgtgagca acaagggcgt ggacaccgtg agcgtgggca acaccctgta ctacgtgaac 1380
aagcaggagg gcaagaacct gtacgtgaag ggcgagccca tcatcaactt ctacgacccc 1440
ctggtgttcc ccagcgacga gttcgacgcc agcatcagcc aggtgaacga gaagatcaac 1500
cagagcctgg ccttcatcag aaagagcgac gagctgctgc acaacgtgaa cgccgtgaag 1560
agcaccacca acatcatggt taacctcatt acctatatcg ttttgactat catatctctt 1620
gtttttggta tacttagcct gattctagca tgctacctaa tgtacaagca aaaggcgcaa 1680
caaaagacct tattatggct tgggaataat accctagatc agatgagagc cactacaaaa 1740
atgtgaccgc gg 1752

<210> SEQ ID NO 47
<211> LENGTH: 15186
<212> TYPE: DNA
<213> ORGANISM: Newcastle disease virus

<400> SEQUENCE: 47
accaaacaga gaatccgtga gttacgataa aaggcgaagg agcaattgaa gtcgcacggg 60
tagaaggtgt gaatctcgag tgcgagcccg aagcacaaac tcgagaaagc cttctgccaa 120
catgtcttcc gtatttgatg agtacgaaca gctcctcgcg gctcagactc gccccaatgg 180
agctcatgga gggggagaaa aagggagtac cttaaaagta gacgtcccgg tattcactct 240
taacagtgat gacccagaag atagatggag ctttgtggta ttctgcctcc ggattgctgt 300
tagcgaagat gccaacaaac cactcaggca aggtgctctc atatctcttt tatgctccca 360
ctcacaggta atgaggaacc atgttgccct tgcagggaaa cagaatgaag ccacattggc 420
cgtgcttgag attgatggct ttgccaacgg cacgccccag ttcaacaata ggagtggagt 480
gtctgaagag agagcacaga gatttgcgat gatagcagga tctctccctc gggcatgcag 540
caacggaacc ccgttcgtca cagccggggc cgaagatgat gcaccagaag acatcaccga 600
taccctggag aggatcctct ctatccaggc tcaagtatgg gtcacagtag caaaagccat 660
gactgcgtat gagactgcag atgagtcgga aacaaggcga atcaataagt atatgcagca 720
aggcagggtc caaaagaaat acatcctcta ccccgtatgc aggagcacaa tccaactcac 780
gatcagacag tctcttgcag tccgcatctt tttggttagc gagctcaaga gaggccgcaa 840
cacggcaggt ggtacctcta cttattataa cctggtaggg gacgtagact catacatcag 900
gaataccggg cttactgcat tcttcttgac actcaagtac ggaatcaaca ccaagacatc 960
agcccttgca cttagtagcc tctcaggcga catccagaag atgaagcagc tcatgcgttt 1020
gtatcggatg aaaggagata atgcgccgta catgacatta cttggtgata gtgaccagat 1080
gagctttgcg cctgccgagt atgcacaact ttactccttt gccatgggta tggcatcagt 1140
cctagataaa ggtactggga aataccaatt tgccagggac tttatgagca catcattctg 1200
gagacttgga gtagagtacg ctcaggctca gggaagtagc attaacgagg atatggctgc 1260

```
cgagctaaag ctaaccccag cagcaaggag gggcctggca gctgctgccc aacgggtctc   1320
cgaggagacc agcagcatag acatgcctac tcaacaagtc ggagtcctca ctgggcttag   1380
cgaggggggg tcccaagctc tacaaggcgg atcgaataga tcgcaagggc aaccagaagc   1440
cggggatggg gagacccaat tcctggatct gatgagagcg gtagcaaata gcatgaggga   1500
ggcgccaaac tctgcacagg gcactcccca atcggggcct cccccaactc ctgggccatc   1560
ccaagataac gacaccgact gggggtattg atggacaaaa cccagcctgc ttccacaaaa   1620
acatcccaat gccctcaccc gtagtcgacc cctcgatttg cggctctata tgaccacacc   1680
ctcaaacaaa catcccctc tttcctccct ccccctgctg tacaactacg tacgccctag   1740
ataccacagg cacaatgcgg ctcactaaca atcaaaacag agccgaggga attagaaaaa   1800
agtacgggta gaagagggat attcagagat cagggcaagt ctcccgagtc tctgctctct   1860
cctctacctg atagaccagg acaaacatgg ccacctttac agatgcagag atcgacgagc   1920
tatttgagac aagtggaact gtcattgaca acataattac agcccagggt aaaccagcag   1980
agactgttgg aaggagtgca atcccacaag gcaagaccaa ggtgctgagc gcagcatggg   2040
agaagcatgg gagcatccag ccaccggcca gtcaagacaa ccccgatcga caggacagat   2100
ctgacaaaca accatccaca cccgagcaaa cgaccccgca tgacagcccg ccggccacat   2160
ccgccgacca gccccccacc caggccacag acgaagccgt cgacacacag ctcaggaccg   2220
gagcaagcaa ctctctgctg ttgatgcttg acaagctcag caataaatcg tccaatgcta   2280
aaaagggccc atggtcgagc cccaagaggg ggaatcacca acgtccgact caacagcagg   2340
ggagtcaacc cagtcgcgga aacagtcagg aaagaccgca gaaccaagtc aaggccgccc   2400
ctggaaacca gggcacagac gtgaacacag catatcatgg acaatgggag gagtcacaac   2460
tatcagctgg tgcaacccct catgctctcc gatcaaggca gagccaagac aatacccttg   2520
tatctgcgga tcatgtccag ccacctgtag actttgtgca agcgatgatg tctatgatgg   2580
aggcgatatc acagagagta agtaaggttg actatcagct agatcttgtc ttgaaacaga   2640
catcctccat ccctatgatg cggtccgaaa tccaacagct gaaaacatct gttgcagtca   2700
tggaagccaa cttgggaatg atgaagattc tggatcccgg ttgtgccaac atttcatctc   2760
tgagtgatct acgggcagtt gcccgatctc acccggtttt agtttcaggc cctggagacc   2820
cctctcccta tgtgacacaa ggaggcgaaa tggcacttaa taaactttcg caaccagtgc   2880
cacatccatc tgaattgatt aaacccgcca ctgcatgcgg gcctgatata ggagtggaaa   2940
aggacactgt ccgtgcattg atcatgtcac gcccaatgca cccgagttct tcagccaagc   3000
tcctaagcaa gttagatgca gccgggtcga tcgaggaaat caggaaaatc aagcgccttg   3060
ctctaaatgg ctaattacta ctgccacacg tagcgggtcc ctgtccactc ggcatcacac   3120
ggaatctgca ccgagttccc ccccgcggac ccaaggtcca actctccaag cggcaatcct   3180
ctctcgcttc ctcagcccca ctgaatgatc gcgtaaccgt aattaatcta gctacattta   3240
agattaagaa aaaatacggg tagaattgga gtgccccaat tgtgccaaga tggactcatc   3300
taggacaatt gggctgtact ttgattctgc ccattcttct agcaacctgt tagcatttcc   3360
gatcgtccta caagacacag gagatgggaa gaagcaaatc gccccgcaat ataggatcca   3420
gcgccttgac ttgtggactg atagtaagga ggactcagta ttcatcacca cctatggatt   3480
catctttcaa gttgggaatg aagaagccac cgtcggcatg atcgatgata aacccaagcg   3540
cgagttactt tccgctgcga tgctctgcct aggaagcgtc ccaaataccg gagaccttat   3600
```

```
tgagctggca agggcctgtc tcactatgat agtcacatgc aagaagagtg caactaatac   3660
tgagagaatg gttttctcag tagtgcaggc accccaagtg ctgcaaagct gtagggttgt   3720
ggcaaacaaa tactcatcag tgaatgcagt caagcacgtg aaagcgccag agaagattcc   3780
cgggagtgga accctagaat acaaggtgaa ctttgtctcc ttgactgtgg taccgaagag   3840
ggatgtctac aagatcccag ctgcagtatt gaaggtttct ggctcgagtc tgtacaatct   3900
tgcgctcaat gtcactatta atgtggaggt agacccgagg agtcctttgg ttaaatctct   3960
gtctaagtct gacagcggat actatgctaa cctcttcttg catattggac ttatgaccac   4020
tgtagatagg aaggggaaga aagtgacatt tgacaagctg gaaaagaaaa taaggagcct   4080
tgatctatct gtcgggctca gtgatgtgct cgggccttcc gtgttggtaa aagcaagagg   4140
tgcacggact aagcttttgg cacctttctt ctctagcagt gggacagcct gctatcccat   4200
agcaaatgct tctcctcagg tggccaagat actctggagt caaaccgcgt gcctgcggag   4260
cgttaaaatc attatccaag caggtaccca acgcgctgtc gcagtgaccg ccgaccacga   4320
ggttacctct actaagctgg agaaggggca cacccttgcc aaatacaatc cttttaagaa   4380
ataagctgcg tctctgagat tgcgctccgc ccactcaccc agatcatcat gacacaaaaa   4440
actaatctgt cttgattatt tacagttagt ttacctgtct atcaagttag aaaaaacacg   4500
ggtagaagat tctggatccc ggttggcgcc ctccaggtgc aagatgggct ccagaccttc   4560
taccaagaac ccagcaccta tgatgctgac tatccgggtt gcgctggtac tgagttgcat   4620
ctgtccggca aactccattg atggcaggcc tcttgcagct gcaggaattg tggttacagg   4680
agacaaagcc gtcaacatat acacctcatc ccagacagga tcaatcatag ttaagctcct   4740
cccgaatctg cccaaggata aggaggcatg tgcgaaagcc cccttggatg catacaacag   4800
gacattgacc actttgctca ccccccttgg tgactctatc cgtaggatac aagagtctgt   4860
gactacatct ggagggggga gacaggggcg ccttataggc gccattattg gcggtgtggc   4920
tcttggggtt gcaactgccg cacaaataac agcggccgca gctctgatac aagccaaaca   4980
aaatgctgcc aacatcctcc gacttaaaga gagcattgcc gcaaccaatg aggctgtgca   5040
tgaggtcact gacggattat cgcaactagc agtggcagtt gggaagatgc agcagtttgt   5100
taatgaccaa tttaataaaa cagctcagga attagactgc atcaaaattg cacagcaagt   5160
tggtgtagag ctcaacctgt acctaaccga attgactaca gtattcggac cacaaatcac   5220
ttcacctgct ttaaacaagc tgactattca ggcactttac aatctagctg gtggaaatat   5280
ggattactta ttgactaagt taggtgtagg gaacaatcaa ctcagctcat taatcggtag   5340
cggcttaatc accggtaacc ctattctata cgactcacag actcaactct tgggtataca   5400
ggtaactcta ccttcagtcg ggaacctaaa taatatgcgt gccacctact tggaaacctt   5460
atccgtaagc acaaccaggg gatttgcctc ggcacttgtc ccaaaagtgg tgacacaggt   5520
cggttctgtg atagaagaac ttgacacctc atactgtata gaaactgact tagatttata   5580
ttgtacaaga atagtaacgt tccctatgtc ccctggtatt tattcctgct tgagcggcaa   5640
tacgtcggcc tgtatgtact caaagaccga aggcgcactt actacaccat acatgactat   5700
caaaggttca gtcatcgcca actgcaagat gacaacatgt agatgtgtaa accccccggg   5760
tatcatatcg caaaactatg gagaagccgt gtctctaata gataaacaat catgcaatgt   5820
tttatcctta ggcgggataa ctttaaggct cagtggggaa ttcgatgtaa cttatcagaa   5880
gaatatctca atacaagatt ctcaagtaat aataacaggc aatcttgata tctcaactga   5940
gcttgggaat gtcaacaact cgatcagtaa tgctttgaat aagttagagg aaagcaacag   6000
```

aaaactagac aaagtcaatg tcaaactgac tagcacatct gctctcatta cctatatcgt 6060
tttgactatc atatctcttg tttttggtat acttagcctg attctagcat gctacctaat 6120
gtacaagcaa aaggcgcaac aaaagacctt attatggctt gggaataata ctctagatca 6180
gatgagagcc actacaaaaa tgtgaacaca gatgaggaac gaaggtttcc ctaatagtaa 6240
tttgtgtgaa agttctggta gtctgtcagt tcagagagtt aagaaaaaac taccggttgt 6300
agatgaccaa aggacgatat acgggtagaa cggtaagaga ggccgcccct caattgcgag 6360
ccaggcttca caacctccgt tctaccgctt caccgacaac agtcctcaat catggaccgc 6420
gccgttagcc aagttgcgtt agagaatgat gaaagagagg caaaaaatac atggcgcttg 6480
atattccgga ttgcaatctt attcttaaca gtagtgacct tggctatatc tgtagcctcc 6540
cttttatata gcatgggggc tagcacacct agcgatcttg taggcatacc gactaggatt 6600
tccagggcag aagaaaagat tacatctaca cttggttcca atcaagatgt agtagatagg 6660
atatataagc aagtggccct tgagtctccg ttggcattgt taaatactga gaccacaatt 6720
atgaacgcaa taacatctct ctcttatcag attaatggag ctgcaaacaa cagtgggtgg 6780
ggggcaccta tccatgaccc agattatata ggggggatag gcaaagaact cattgtagat 6840
gatgctagtg atgtcacatc attctatccc tctgcatttc aagaacatct gaattttatc 6900
ccggcgccta ctacaggatc aggttgcact cgaataccct catttgacat gagtgctacc 6960
cattactgct acacccataa tgtaatattg tctggatgca gagatcactc acattcatat 7020
cagtatttag cacttggtgt gctccggaca tctgcaacag ggagggtatt cttttctact 7080
ctgcgttcca tcaacctgga cgacacccaa aatcggaagt cttgcagtgt gagtgcaact 7140
cccctgggtt gtgatatgct gtgctcgaaa gtcacggaga cagaggaaga agattataac 7200
tcagctgtcc ctacgcggat ggtacatggg aggttagggt tcgacggcca gtaccacgaa 7260
aaggacctag atgtcacaac attattcggg gactgggtgg ccaactaccc aggagtaggg 7320
ggtggatctt ttattgacag ccgcgtatgg ttctcagtct acggagggtt aaaacccaat 7380
tcacccagtg acactgtaca ggaagggaaa tatgtgatat acaagcgata caatgacaca 7440
tgcccagatg agcaagacta ccagattcga atggccaagt cttcgtataa gcctggacgg 7500
tttggtggga aacgcataca gcaggctatc ttatctatca aggtgtcaac atccttaggc 7560
gaagacccgg tactgactgt accgcccaac acagtcacac tcatgggggc cgaaggcaga 7620
attctcacag tagggacatc tcatttcttg tatcaacgag ggtcatcata cttctctccc 7680
gcgttattat atcctatgac agtcagcaac aaaacagcca ctcttcatag tccttataca 7740
ttcaatgcct tcactcggcc aggtagtatc ccttgccagg cttcagcaag atgccccaac 7800
tcgtgtgtta ctggagtcta tacagatcca tatcccctaa tcttctatag aaaccacacc 7860
ttgcgagggg tattcgggac aatgcttgat ggtgtacaag caagacttaa ccctgcgtct 7920
gcagtattcg atagcacatc ccgcagtcgc attactcgag tgagttcaag cagtaccaaa 7980
gcagcataca caacatcaac ttgttttaaa gtggtcaaga ctaataagac ctattgtctc 8040
agcattgctg aaatatctaa tactctcttc ggagaattca gaatcgtccc gttactagtt 8100
gagatcctca aagatgacgg ggttagagaa gccaggtctg gctagttgag tcaattataa 8160
aggagttgga aagatggcat tgtatcacct atcttctgcg acatcaagaa tcaaaccgaa 8220
tgccggcgcg tgctcgaatt ccatgttgcc agttgaccac aatcagccag tgctcatgcg 8280
atcagattaa gccttgtcaa tagtctcttg attaagaaaa aatgtaagtg gcaatgagat 8340

-continued acaaggcaaa acagctcatg gttaacaata cgggtaggac atggcgagct ccggtcctga 8400
aagggcagag catcagatta tcctaccaga gtcacacctg tcttcaccat tggtcaagca 8460
caaactactc tattactgga aattaactgg gctaccgctt cctgatgaat gtgacttcga 8520
ccacctcatt ctcagccgac aatggaaaaa aatacttgaa tcggcctctc ctgatactga 8580
gagaatgata aaactcggaa gggcagtaca ccaaactctt aaccacaatt ccagaataac 8640
cggagtgctc caccccaggt gtttagaaga actggctaat attgaggtcc cagattcaac 8700
caacaaattt cggaagattg agaagaagat ccaaattcac aacacgagat atggagaact 8760
gttcacaagg ctgtgtacgc atatagagaa gaaactgctg gggtcatctt ggtctaacaa 8820
tgtcccccgg tcagaggagt tcagcagcat tcgtacggat ccggcattct ggtttcactc 8880
aaaatggtcc acagccaagt ttgcatggct ccatataaaa cagatccaga ggcatctgat 8940
ggtggcagct aggacaaggt ctgcggccaa caaattggtg atgctaaccc ataaggtagg 9000
ccaagtcttt gtcactcctg aacttgtcgt tgtgacgcat acgaatgaga acaagttcac 9060
atgtcttacc caggaacttg tattgatgta tgcagatatg atggagggca gagatatggt 9120
caacataata tcaaccacgg cggtgcatct cagaagctta tcagagaaaa ttgatgacat 9180
tttgcggtta atagacgctc tggcaaaaga cttgggtaat caagtctacg atgttgtatc 9240
actaatggag ggatttgcat acggagctgt ccagctactc gagccgtcag gtacatttgc 9300
aggagatttc ttcgcattca acctgcagga gcttaaagac attctaattg gcctcctccc 9360
caatgatata gcagaatccg tgactcatgc aatcgctact gtattctctg gtttagaaca 9420
gaatcaagca gctgagatgt tgtgtctgtt gcgtctgtgg ggtcacccac tgcttgagtc 9480
ccgtattgca gcaaaggcag tcaggagcca aatgtgcgca ccgaaaatgg tagactttga 9540
tatgatcctt caggtactgt ctttcttcaa gggaacaatc atcaacgggt acagaaagaa 9600
gaatgcaggt gtgtggccgc gagtcaaagt ggatacaata tatgggaagg tcattgggca 9660
actacatgca gattcagcag agatttcaca cgatatcatg ttgagagagt ataagagttt 9720
atctgcactt gaatttgagc catgtataga atatgaccct gtcaccaacc tgagcatgtt 9780
cctaaaagac aaggcaatcg cacaccccaa cgataattgg cttgcctcgt ttaggcggaa 9840
ccttctctcc gaagaccaga agaaacatgt aaaagaagca acttcgacta atcgcctctt 9900
gatagagttt ttagagtcaa atgattttga tccatataaa gagatggaat atctgacgac 9960
ccttgagtac cttagagatg acaatgtggc agtatcatac tcgctcaagg agaaggaagt 10020
gaaagttaat ggacggatct tcgctaagct gacaaagaag ttaaggaact gtcaggtgat 10080
ggcggaaggg atcctagccg atcagattgc acctttcttt cagggaaatg gagtcattca 10140
ggatagcata tccttgacca agagtatgct agcgatgagt caactgtctt ttaacagcaa 10200
taagaaacgt atcactgact gtaaagaaag agtatcttca aaccgcaatc atgatccgaa 10260
aagcaagaac cgtcggagag ttgcaacctt cataacaact gacctgcaaa agtactgtct 10320
taattggaga tatcagacaa tcaaattgtt cgctcatgcc atcaatcagt tgatgggcct 10380
acctcacttc ttcgaatgga ttcacctaag actgatggac actacgatgt tcgtaggaga 10440
ccctttcaat cctccaagtg accctactga ctgtgacctc tcaagagtcc ctaatgatga 10500
catatatatt gtcagtgcca gagggggtat cgaaggatta tgccagaagc tatggacaat 10560
gatctcaatt gctgcaatcc aacttgctgc agctagatcg cattgtcgtg ttgcctgtat 10620
ggtacagggt gataatcaag taatagcagt aacgagagag gtaagatcag acgactctcc 10680
ggagatggtg ttgacacagt tgcatcaagc cagtgataat ttcttcaagg aattaattca 10740
tgtcaatcat ttgattggcc ataatttgaa ggatcgtgaa accatcaggt cagacacatt 10800
cttcatatac agcaaacgaa tcttcaaaga tggagcaatc ctcagtcaag tcctcaaaaa 10860
ttcatctaaa ttagtgctag tgtcaggtga tctcagtgaa aacaccgtaa tgtcctgtgc 10920
caacattgcc tctactgtag cacggctatg cgagaacggg cttcccaaag acttctgtta 10980
ctatttaaac tatataatga gttgtgtgca gacatacttt gactctgagt tctccatcac 11040
caacaattcg caccccgatc ttaatcagtc gtggattgag gacatctctt ttgtgcactc 11100
atatgttctg actcctgccc aattaggggg actgagtaac cttcaatact caaggctcta 11160
cactagaaat atcggtgacc cggggactac tgcttttgca gagatcaagc gactagaagc 11220
agtgggatta ctgagtccta acattatgac taatatctta actaggccgc ctgggaatgg 11280
agattgggcc agtctgtgca acgacccata ctctttcaat tttgagactg ttgcaagccc 11340
aaatattgtt cttaagaaac atacgcaaag agtcctattt gaaacttgtt caaatccctt 11400
attgtctgga gtgcacacag aggataatga ggcagaagag aaggcattgg ctgaattctt 11460
gcttaatcaa gaggtgattc atccccgcgt tgcgcatgcc atcatggagg caagctctgt 11520
aggtaggaga aagcaaattc aagggcttgt tgacacaaca aacaccgtaa ttaagattgc 11580
gcttactagg aggccattag gcatcaagag gctgatgcgg atagtcaatt attctagcat 11640
gcatgcaatg ctgtttagag acgatgtttt ttcctccagt agatccaacc accccttagt 11700
ctcttctaat atgtgttctc tgacactggc agactatgca cggaatagaa gctggtcacc 11760
tttgacggga ggcaggaaaa tactgggtgt atctaatcct gatacgatag aactcgtaga 11820
gggtgagatt cttagtgtaa gcggagggtg tacaagatgt gacagcggag atgaacaatt 11880
tacttggttc catcttccaa gcaatataga attgaccgat gacaccagca agaatcctcc 11940
gatgagggta ccatatctcg ggtcaaagac acaggagagg agagctgcct cacttgcaaa 12000
aatagctcat atgtcgccac atgtaaaggc tgccctaagg gcatcatccg tgttgatctg 12060
ggcttatggg gataatgaag taaattggac tgctgctctt acgattgcaa aatctcggtg 12120
taatgtaaac ttagagtatc ttcggttact gtccccttta cccacggctg ggaatcttca 12180
acatagacta gatgatggta taactcagat gacattcacc cctgcatctc tctacagggt 12240
gtcaccttac attcacatat ccaatgattc tcaaaggctg ttcactgaag aaggagtcaa 12300
agaggggaat gtggtttacc aacagatcat gctcttgggt ttatctctaa tcgaatcgat 12360
ctttccaatg acaacaacca ggacatatga tgagatcaca ctgcacctac atagtaaatt 12420
tagttgctgt atcagagaag cacctgttgc ggttcctttc gagctacttg ggtggtacc 12480
ggaactgagg acagtgacct caaataagtt tatgtatgat cctagccctg tatcggaggg 12540
agactttgcg agacttgact tagctatctt caagagttat gagcttaatc tggagtcata 12600
tcccacgata gagctaatga acattctttc aatatccagc gggaagttga ttggccagtc 12660
tgtggtttct tatgatgaag atacctccat aaagaatgac gccataatag tgtatgacaa 12720
tacccgaaat tggatcagtg aagctcagaa ttcagatgtg gtccgcctat ttgaatatgc 12780
agcacttgaa gtgctcctcg actgttctta ccaactctat tacctgagag taagaggcct 12840
ggacaatatt gtcttatata tgggtgattt atacaagaat atgccaggaa ttctactttc 12900
caacattgca gctacaatat ctcatcccgt cattcattca aggttacatg cagtgggcct 12960
ggtcaaccat gacggatcac accaacttgc agatacggat tttatcgaaa tgtctgcaaa 13020
actattagta tcttgcaccc gacgtgtgat ctccggctta tattcaggaa ataagtatga 13080

```
tctgctgttc ccatctgtct tagatgataa cctgaatgag aagatgcttc agctgatatc  13140
ccggttatgc tgtctgtaca cggtactctt tgctacaaca agagaaatcc cgaaaataag  13200
aggcttaact gcagaagaga aatgttcaat actcactgag tatttactgt cggatgctgt  13260
gaaaccatta cttagccccg atcaagtgag ctctatcatg tctcctaaca taattacatt  13320
cccagctaat ctgtactaca tgtctcggaa gagcctcaat ttgatcaggg aaagggagga  13380
cagggatact atcctggcgt tgttgttccc ccaagagcca ttattagagt tcccttctgt  13440
gcaagatatt ggtgctcgag tgaaagatcc attcacccga caacctgcgg catttttgca  13500
agagttagat ttgagtgctc cagcaaggta tgacgcattc acacttagtc agattcatcc  13560
tgaactcaca tctccaaatc cggaggaaga ctacttagta cgatacttgt tcagagggat  13620
agggactgca tcttcctctt ggtataaggc atctcatctc ctttctgtac ccgaggtaag  13680
atgtgcaaga cacgggaact ccttatactt agctgaaggg agcggagcca tcatgagtct  13740
tctcgaactg catgtaccac atgaaactat ctattacaat acgctctttt caaatgagat  13800
gaacccccg caacgacatt tcgggccgac cccaactcag tttttgaatt cggttgttta  13860
taggaatcta caggcggagg taacatgcaa agatggattt gtccaagagt tccgtccatt  13920
atggagagaa aatacagagg aaagcgacct gacctcagat aaagtagtgg ggtatattac  13980
atctgcagtg ccctacagat ctgtatcatt gctgcattgt gacattgaaa ttcctccagg  14040
gtccaatcaa agcttactag atcaactagc tatcaattta tctctgattg ccatgcattc  14100
tgtaagggag ggcggggtag taatcatcaa agtgttgtat gcaatgggat actactttca  14160
tctactcatg aacttgtttg ctccgtgttc cacaaaagga tatattctct ctaatggtta  14220
tgcatgtcga ggagatatgg agtgttacct ggtatttgtc atgggttacc tgggcgggcc  14280
tacatttgta catgaggtgg tgaggatggc gaaaactctg gtgcagcggc acggtacgct  14340
tttgtctaaa tcagatgaga tcacactgac caggttattc acctcacagc ggcagcgtgt  14400
gacagacatc ctatccagtc ctttaccaag attaataaag tacttgagga agaatattga  14460
cactgcgctg attgaagccg ggggacagcc cgtccgtcca ttctgtgcgg agagtctggt  14520
gagcacgcta gcgaacataa ctcagataac ccagatcatc gctagtcaca ttgacacagt  14580
tatccggtct gtgatatata tggaagctga gggtgatctc gctgacacag tatttctatt  14640
taccccttac aatctctcta ctgacgggaa aaagaggaca tcacttaaac agtgcacgag  14700
acagatccta gaggttacaa tactaggtct tagagtcgaa aatctcaata aaataggcga  14760
tataatcagc ctagtgctta aaggcatgat ctccatggag gaccttatcc cactaaggac  14820
atacttgaag catagtacct gccctaaata tttgaaggct gtcctaggta ttaccaaact  14880
caaagaaatg tttacagaca cttctgtact gtacttgact cgtgctcaac aaaaattcta  14940
catgaaaact ataggcaatg cagtcaaagg atattacagt aactgtgact cttaacgaaa  15000
atcacatatt aataggctcc ttttttggcc aattgtattc ttgttgattt aatcatatta  15060
tgttagaaaa aagttgaacc ctgactcctt aggactcgaa ttcgaactca aataaatgtc  15120
ttaaaaaaag gttgcgcaca attattcttg agtgtagtct cgtcattcac caaatctttg  15180
tttggt                                                               15186
```

<210> SEQ ID NO 48
<211> LENGTH: 15186
<212> TYPE: DNA
<213> ORGANISM: Newcastle disease virus

<400> SEQUENCE: 48

-continued

```
accaaacaga gaatccgtaa gttacgataa aaggcgaagg agcaattgaa gtcgcacggg     60
tagaaggtgt gaatctcgag tgcgagcccg aagcacaaac tcgaggaagc cttctgccaa    120
catgtcttcc gtattcgacg agtacgaaca gctcctcgcg gctcagactc gccccaatgg    180
agctcatgga ggggggaga aagggagtac cttaaaagta gacgtcccgg tattcactct    240
taacagtgat gacccagaag ataggtggag ctttgtggta ttctgcctcc ggattgctgt    300
tagcgaagat gccaacaaac cactcaggca aggtgctctc atatctcttt tatgctccca    360
ctcacaggta atgaggaacc atgttgccct tgcagggaaa cagaatgaag ccacattggc    420
cgtgcttgag attgatggct ttgccaacgg cacgccccag ttcaacaata ggagtggagt    480
gtctgaagag agagcacaga gatttgcgat gatagcagga tctctccctc gggcatgcag    540
caacggcacc ccgttcgtca cagccggggc tgaagatgat gcaccagaag acatcaccga    600
taccctggag aggatcctct ctatccaggc tcaagtatgg gtcacagtag caaaagccat    660
gactgcgtat gagactgcag atgagtcgga aacaaggcga atcaataagt atatgcagca    720
aggcagggtc caaaagaaat acatcctcta ccccgtatgc aggagcacaa tccaactcac    780
gatcagacag tctcttgcag tccgcatctt tttggttagc gagctcaaga gaggccgcaa    840
cacggcaggt ggtacctcta cttattataa cctagtaggg gacgtagact catatatcag    900
gaataccggg cttactgcat tcttcttgac actcaagtac ggaatcaaca ccaagacatc    960
agcccttgca cttagtagcc tctcaggcga catccagaag atgaagcagc tcatgcgttt   1020
gtatcggatg aaaggagata atgcgccgta catgacatta cttggtgata gtgaccagat   1080
gagctttgcg cctgccgagt atgcacaact ttactccttt gccatgggta tggcatcagt   1140
cctagataaa ggtactggga aataccaatt tgccagggac tttatgagca catcattctg   1200
gagacttgga gtagagtacg ctcaggctca gggaagtagc attaacgagg atatggctgc   1260
cgagctaaag ctaaccccgg cagcaaggag gggcctggca gctgctgccc aacgagtctc   1320
cgaggtgacc agcagcatag acatgcctac tcaacaagtc ggagtcctca ctgggcttag   1380
cgaggggga tcccaagccc tacaaggcgg atcgaataga tcgcaagggc aaccagaagc   1440
cggggatggg gagacccaat tcctggatct gatgagagcg gtagcaaata gcatgaggga   1500
ggcgccaaac tctgcacagg gcactcccca atcggggcct cccccaactc ctgggccatc   1560
ccaagataac gacaccgact gggggtattg attgacaaaa cccagcctgc ttctacaaga   1620
acatcccaat gctctcaccc gtagtcgacc cctcgatttg cggctctata tgaccacacc   1680
ctcaaacaaa catcccctc tttcctccct cccctgctg tacaactccg cacgccctag   1740
ataccacagg cacaccgcgg ctcactaaca atcaaaacag agccgaggga attagaaaaa   1800
agtacgggta gaagagggat attcagagat cagggcaagt ctcccgagtc tctgctctct   1860
cctctacctg atagaccagg acaaacatgg ccacctttac agatgcagag atcgacgagc   1920
tatttgagac aagtggaact gtcattgaca acataattac agcccagggt aaaccagcag   1980
agactgttgg aaggagtgca atcccacagg gcaagaccaa ggtgctgagc gcagcatggg   2040
agaagcatgg gagcatccag ccaccggcca gtcaagacaa cctcgatcga caggacagat   2100
ctgacaaaca accatccaca cccgagcaaa cgaccccgca cgacagcccg ccggccacat   2160
ccgctgacca gcccccacc caggccacag acgaagccgt cgacacacag ctcaggaccg   2220
gagcaagcaa ctctctgctg ttgatgcttg acaagctcag caataaatcg tccaatgcta   2280
aaaagggccc atggtcgagc cccaagaggg ggaatcacca acgtccgact caacagcagg   2340
```

```
ggagtcaacc cagtcgcgga aacagccagg aaagactgca gaaccaagtc aaggccgccc   2400
ctggaaacca gggcacagac gtgaacacag catatcatgg acaatgggag gagtcacaac   2460
tatcagctgg tgcaacccct catgctctcc gatcaaggca gagccaagac aataccctg    2520
tatctgcgga tcatgtccag ccacctgtag actttgtgca agcgatgatg tctatgatgg   2580
gggcgatatc acagagagta agtaaggttg actatcagct agatcttgtc ttgaaacaga   2640
catcctccat ccctatgatg cggtccgaaa tccaacagct gaaaacatct gttgcagtca   2700
tggaagccaa cttgggaatg atgaagattc tggatcccgg ttgtgccaac atttcatctc   2760
tgagtgatct acgggcagtt gcccgatctc acccggtttt agtttcaggc cctggagacc   2820
catctcccta tgtgatacaa ggaggcgaaa tggcacttaa taaactttcg caaccagtgc   2880
cacatccatc tgaattgatt aaacccgcca ctgcatgcgg gcctgatata ggagtggaga   2940
gggacactgt ccgtgcattg atcatgtcac gcccaatgca cccgagttct tcagccaagc   3000
tcctaagcaa gttagatgca gccgggtcga tcgaggaaat caggaaaatc aagcgccttg   3060
ctctaaatgg ctaattacta ctgccacacg tagcgggtcc ctgtccactc ggcatcacac   3120
ggaatctgca ccgagttccc ccccgcagac ccaaggtcca actctagaag cggcaatcct   3180
ctctcgcttc ctcagcccca ctgaatgatc gcgtaaccgt aattaatcta gctacattaa   3240
ggattaagaa aaaatacggg tagaattgga gtgccccaat tgtgccaaga tggactcatc   3300
taggacaatt gggctgtact ttgattctgc ccattcttct agcaacctgt tagcatttcc   3360
gatcgtccta caagacacag gagatgggaa gaagcaaatc gccccgcaat ataggatcca   3420
gcgccttgac tcgtggactg atagtaagga agactcagta ttcatcacca cctatggatt   3480
catctttcaa gttgggaatg aggaagccac tgtcggcatg atcgatgata aacccaagcg   3540
cgagttactt tccgctgcga tgctctgcct aggaagcgtc ccaaataccg gagaccttgt   3600
tgagctggca agggcctgtc tcactatgat ggtcacatgc aagaagagtg caactaatac   3660
tgagagaatg gttttctcag tagtgcaggc accccaagtg ctgcaaagct gtagggttgt   3720
ggcaaataaa tactcatcag tgaatgcagt caagcacgtg aaagcgccag agaagatccc   3780
cgggagtgga accctagaat acaaggtgaa ctttgtctcc ttgactgtgg taccgaagaa   3840
ggatgtctac aagatcccag ctgcagtatt gaagatttct ggctcgagtc tgtacaatct   3900
tgcgctcaat gtcactatta atgtggaggt agacccgagg agtcctttgg ttaaatctct   3960
gtctaagtct gacagcggat actatgctaa cctcttcttg catattggac ttatgaccac   4020
cgtagatagg aaggggaaga aagtgacatt tgacaagctg gaaaagaaaa taaggagcct   4080
tgatctatct gtcgggctca gtgatgtgct cgggccttcc gtgttggtaa aagcaagagg   4140
tgcacggact aagcttttgg caccttctt ctctagcagt gggacagcct gctatcccat    4200
agcaaatgct tctcctcagg tggccaagat actctggagt caaaccgcgt gcctgcggag   4260
cgttaaaatc attatccaag caggtaccca acgcgctgtc gcagtgaccg ctgaccacga   4320
ggttacctct actaagctgg agaaggggca cacccttgcc aaatacaatc cttttaagaa   4380
ataagctgcg tctctgagat tgcgctccgc ccactcaccc agatcatcat gacacaaaaa   4440
actaatctgt cttgattatt tacagttagt ttacctgtcc atcaagttag aaaaaacacg   4500
ggtagaagat tctggatccc ggttggcgcc ctccaggtgc aggatgggct ccagaccttc   4560
taccaagaac ccagcaccta tgatgctgac tatccgggtc gcgctggtac tgagttgcat   4620
ctgcccggca aactccattg atggcaggcc tcttgcagct gcaggaattg tggttacagg   4680
agacaaagca gtcaacatat acacctcatc ccagacagga tcaatcatag ttaagctcct   4740
```

```
cccgaatctg cccaaggata aggaggcatg tgcgaaagcc cccttggatg catacaacag   4800
gacattgacc actttgctca ccccccttgg tgactctatc cgtaggatac aagagtctgt   4860
gactacatct ggaggggga gacaggggcg ccttataggc gccattattg gcggtgtggc   4920
tcttggggtt gcaactgccg cacaaataac agcggccgca gctctgatac aagccaaaca   4980
aaatgctgcc aacatcctcc gacttaaaga gagcattgcc gcaaccaatg aggctgtgca   5040
tgaggtcact gacggattat cgcaactagc agtggcagtt gggaagatgc agcagtttgt   5100
taatgaccaa tttaataaaa cagctcagga attagactgc atcaaaattg cacagcaagt   5160
tggtgtagag ctcaacctgt acctaaccga attgactaca gtattcggac cacaaatcac   5220
ttcacctgcc ttaaacaagc tgactattca ggcactttac aatctagctg gtgggaatat   5280
ggattactta ttgactaagt taggtatagg gaacaatcaa ctcagctcat taatcggtag   5340
cggcttaatc accggtaacc ctattctata cgactcacag actcaactct tgggtataca   5400
ggtaactcta ccttcagtcg ggaacctaaa taatatgcgt gccacctact tggaaacctt   5460
atccgtaagc acaaccaggg gatttgcctc ggcacttgtc ccaaaagtgg tgacacaggt   5520
cggttctgtg atagaagaac ttgacacctc atactgtata gaaactgact tagatttata   5580
ttgtacaaga atagtaacgt tccctatgtc ccctggtatt tactcctgct tgagcggcaa   5640
tacatcggcc tgtatgtact caaagaccga aggcgcactt actacaccat atatgactat   5700
caaaggctca gtcatcgcta actgcaagat gacaacatgt agatgtgtaa acccccccggg   5760
tatcatatcg caaaactatg gagaagccgt gtctctaata gataaacaat catgcaatgt   5820
tttatcctta ggcgggataa ctttaaggct cagtggggaa ttcgatgtaa cttatcagaa   5880
gaatatctca atacaagatt ctcaagtaat aataacaggc aatcttgata tctcaactga   5940
gcttgggaat gtcaacaact cgatcagtaa tgctttgaat aagttagagg aaagcaacag   6000
aaaactagac aaagtcaatg tcaaactgac cagcacatct gctctcatta cctatatcgt   6060
tttgactatc atatctcttg tttttggtat acttagcctg attctagcat gctacctaat   6120
gtacaagcaa aaggcgcaac aaaagacctt attatggctt gggaataata ccctagatca   6180
gatgagagcc actacaaaaa tgtgaacaca gatgaggaac gaaggtttcc ctaatagtaa   6240
tttgtgtgaa agttctggta gtctgtcagt tcggagagtt aagaaaaaac taccggttgt   6300
agatgaccaa aggacgatat acgggtagaa cggtaagaga ggccgcccct caattgcgag   6360
ccagacttca caacctccgt tctaccgctt caccgacaac agtcctcaat catggaccgc   6420
gccgttagcc aagttgcgtt agagaatgat gaaagagagg caaaaaatac atggcgcttg   6480
atattccgga ttgcaatctt attcttaaca gtagtgacct tggctatatc tgtagcctcc   6540
cttttatata gcatgggggc tagcacacct agcgatcttg taggcatacc gactaggatt   6600
tccagggcag aagaaaagat tacatctaca cttggttcca atcaagatgt agtagatagg   6660
atatataagc aagtggccct tgagtctcca ttggcattgt taaatactga gaccacaatt   6720
atgaacgcaa taacatctct ctcttatcag attaatggag ctgcaaacaa cagcgggtgg   6780
ggggcaccta ttcatgaccc agattatata gggggggatag gcaaagaact cattgtagat   6840
gatgctagtg atgtcacatc attctatccc tctgcatttc aagaacatct gaattttatc   6900
ccggcgccta ctacaggatc aggttgcact cgaataccct catttgacat gagtgctacc   6960
cattactgct acacccataa tgtaatattg tctggatgca gagatcactc acactcacat   7020
cagtatttag cacttggtgt gctccggaca tctgcaacag ggagggtatt cttttctact   7080
```

-continued

```
ctgcgttcca tcaacctgga cgacacccaa aatcggaagt cttgcagtgt gagtgcaact   7140
cccctgggtt gtgatatgct gtgctcgaaa gccacggaga cagaggaaga agattataac   7200
tcagctgtcc ctacgcggat ggtacatggg aggttagggt tcgacggcca atatcacgaa   7260
aaggacctag atgtcacaac attattcggg gactgggtgg ccaactaccc aggagtaggg   7320
ggtggatctt ttattgacag ccgcgtatgg ttctcagtct acggagggtt aaaacccaat   7380
acacccagtg acactgtaca ggaagggaaa tatgtgatat acaagcgata caatgacaca   7440
tgcccagatg agcaagacta ccagattcga atggccaagt cttcgtataa gcctggacgg   7500
tttggtggga aacgcataca gcaggctatc ttatctatca aagtgtcaac atccttaggc   7560
gaagacccgg tactgactgt accgcccaac acagtcacac tcatgggggc cgaaggcaga   7620
attctcacag tagggacatc ccatttcttg tatcagcgag ggtcatcata cttctctccc   7680
gcgttattat atcctatgac agtcagcgac aaaacagcca ctcttcatag tccttataca   7740
ttcaatgcct tcactcggcc aggtagtatc ccttgccagg cttcagcaag atgccccaac   7800
tcgtgtgtta ctggagtcta tacagatcca tatcccctaa tcttctatag aaaccacacc   7860
ttgcgagggg tattcgggac aatgcttgat ggtgaacaag caagacttaa ccctgcgtct   7920
gcagtattcg atagcacatc ccgcagtcgc ataactcgag tgagttcaag cagcatcaaa   7980
gcagcataca caacatcaac ttgttttaaa gtggtcaaga ccaataagac ctattgtctc   8040
agcattgctg aaatatctaa tactctcttc ggagaattca gaatcgtccc gttactagtt   8100
gagatcctca aagatgacgg ggttagagaa gccaggtctg gctagttgag tcaactatga   8160
aagagttgga aagatggcat tgtatcacct atcttctgcg acatcaagaa tcaaaccgaa   8220
tgccggcgcg tgctcgaatt ccatgtcgcc agttgaccac aatcagccag tgctcatgcg   8280
atcagattaa gccttgtcaa tagtctcttg attaagaaaa aatgtaagtg gcaatgagat   8340
acaaggcaaa acagctcacg gtaaataata cgggtaggac atggcgagct ccggtcctga   8400
aagggcagag catcagatta tcctaccaga gtcacacctg tcttcaccat tggtcaagca   8460
caaactactc tattattgga aattaactgg gctaccgctt cctgatgaat gtgacttcga   8520
ccacctcatt ctcagccgac aatggaaaaa aatacttgaa tcggcctctc ctgatactga   8580
gagaatgata aaactcggaa gggcagtaca ccaaactctt aaccacaatt ccagaataac   8640
cggagtactc caccccaggt gtttagaaga actggctaat attgaggtcc ctgattcaac   8700
caacaaattt cggaagattg agaagaagat ccaaattcac aacacgagat atggagaact   8760
gttcacaagg ctgtgtacgc atatagagaa gaaactgctg ggtcatcttg gtctaacaa    8820
tgtcccccgg tcagaggagt tcagcagcat tcgtacggat ccggcattct ggtttcactc   8880
aaaatggtcc acagccaagt ttgcatggct ccatataaaa cagatccaga ggcatctgat   8940
tgtggcagct aggacaaggt ctgcggccaa caaattggtg atgctaaccc ataaggtagg   9000
ccaagtcttt gtcactcctg aacttgttgt tgtgacgcat acgaatgaga acaagttcac   9060
atgtcttacc caggaacttg tattgatgta tgcagatatg atggagggca gagatatggt   9120
caacataata tcaaccacgg cggtgcatct cagaagctta tcagagaaaa ttgatgacat   9180
tttgcggtta atagacgctc tggcaaaaga cttgggtaat caagtctacg atgttgtatc   9240
actaatggag ggatttgcat acggagctgt ccagctactc gagccgtcag gtacatttgc   9300
gggagatttc ttcgcattca acctgcagga gcttaaagac attctaattg gcctcctccc   9360
caatgatata gcagaatccg tgactcatgc aatcgctact gtattctctg gtttagaaca   9420
gaatcaagca gctgagatgt tgtgcctgtt gcgtctgtgg ggtcacccac tgcttgagtc   9480
```

```
ccgtattgca gcaaaggcag tcaggagcca aatgtgcgca ccgaaaatgg tagactttga   9540
tatgatcctt caggtactgt ctttcttcaa gggaacaatc atcaacggat acagaaagaa   9600
gaatgcaggt gtgtggccgc gagtcaaagt ggatacaata tatgggaagg tcattgggca   9660
actacatgca gattcagcag agatttcaca cgatatcatg ttgagagagt ataagagttt   9720
atctgcactt gaatttgagc catgtataga atacgaccct gtcactaacc tgagcatgtt   9780
cctaaaagac aaggcaatcg cacaccccaa cgataattgg cttgcctcgt ttaggcggaa   9840
ccttctctcc gaagaccaga agaaacatgt aaaggaagcg acttcgacta accgcctctt   9900
gatagagttt ttagagtcaa atgattttga tccatataaa gagatggaat atctgacgac   9960
ccttgagtac cttagagatg acaatgtggc agtatcatac tcgctcaaag agaaggaagt  10020
gaaagttaat ggacggatct tcgctaagct gacaaagaag ttaaggaact gtcaggtgat  10080
ggcggaaggg atcctagccg atcagattgc acctttcttt cagggaaatg gagtcattca  10140
ggatagcata tccttgacca agagtatgct agcgatgagt caactgtctt ttaacagcaa  10200
taagaaacgt atcactgact gtaaagaaag agtatgttca aaccgcaatc atgatccgaa  10260
aagcaagaac cgtcggagag ttgcaacctt cataacaact gacctgcaaa agtactgtct  10320
taattggaga tatcagacga tcaaattgtt cgctcatgcc atcaatcagt tgatgggcct  10380
acctcatttc ttcgagtgga ttcacctaag actgatggac actacgatgt tcgtaggaga  10440
ccctttcaat cctccaagtg accctactga ctgtgacctc tcaagagtcc ctaatgatga  10500
catatatatt gtcagtgcca gagggggtat cgaaggatta tgccagaagc tatggacaat  10560
gatctcaatt gctgcaatcc aacttgctgc agctagatcg cattgtcgtg ttgcctgtat  10620
ggtacagggt gataatcaag taatagcagt aacgagagag gtaagatcag atgactctcc  10680
ggagatggtg ttgacacagt tgcatcaagc cagtgataat ttcttcaagg aattaatcca  10740
tgtcaatcat ttgattggcc ataatttgaa ggatcgtgaa accatcaggt cagacacatt  10800
cttcatatac agcaaacgaa tcttcaaaga tggagcaatc ctcagtcaag tcctcaaaaa  10860
ttcatctaaa ttagtgctag tgtcaggtga tctcagtgaa aacaccgtaa tgtcctgtgc  10920
caacattgcc tctactgtag cacggctatg cgagaacggg cttcccaaag acttctgtta  10980
ctatttaaac tatataatga gttgtgtgca gacatacttt gactctgagt tctccatcac  11040
caacaattcg caccccgatc ttaatcagtc gtggattgag gacatctctt ttgtgcactc  11100
atatgttctg actcctgccc aattaggggg actgagtaac cttcaatact caaggctcta  11160
cactagaaat atcggtgacc cggggactac tgcttttgca gagatcaagc gactagaagc  11220
agtgggacta ctgagtccta acattaggac taatatctta actaggccgc ctgggaatgg  11280
agattgggcc agtctgtgca acgacccata ctctttcaat tttgagactg ttgcaagccc  11340
aaacattgtt cttaagaaac atacgcaaag agtcctattt gaaacttgtt caaatccctt  11400
attgtctgga gtgcacacag aggataatga ggcagaagag aaggcattgg ctgaattctt  11460
gcttaatcaa gaggtgattc atccccgcgt tgcgcatgcc atcatggagg caagctctgt  11520
aggtaggaga aagcaaattc aagggcttgt tgacacaaca aacactgtaa ttaagattgc  11580
gcttactagg aggccattag gcatcaagag gctgatgcgg atagtcaatt attctagcat  11640
gcatgcaatg ctgtttagag acgatgtttt ttcctctagt agatccaacc accccttagt  11700
ctcttctaat atgtgttctc tgacactggc agactatgca cggaatagaa gctggtcacc  11760
tttgacggga ggcaggaaaa tactgggtgt atctaatcct gatacgatag aactcgtaga  11820
```

```
gggtgagatt cttagtgtaa gcggagggtg tacaagatgt gacagcggag atgaacaatt  11880
tacttggttc catcttccaa gcaatataga attgaccgat gacaccagca agaatcctcc  11940
gatgagggta ccatatctcg ggtcaaagac acaggagagg agagctgcct cacttgcgaa  12000
aatagctcat atgtcgccac atgtgaaggc tgccctaagg gcatcatccg tgttgatctg  12060
ggcttatggg gataatgaag taaattggac tgctgctctt acgattgcaa aatctcggtg  12120
taatgtaaac ttagagtatc ttcggttact gtccccttta cccacggctg ggaatcttca  12180
acatagacta gatgatggta taactcagat gacattcacc cctgcatctc tctacagggt  12240
gtcaccttac attcacatat ccaatgattc tcaaaggctg ttcactgaag aaggagtcaa  12300
agaggggaat gtggtttacc aacagatcat gctcttgggt ttatctctaa tcgaatcgat  12360
ctttccaatg acaacaacca gaacatatga tgagatcaca ctgcacctac atagtaaatt  12420
tagttgctgt atcagggaag cacctgttgc ggttcctttc gagctacttg ggtggcacc  12480
ggaactgagg acagtgacct caaataagtt tatgtatgat cctagccctg tatcggaggg  12540
agactttgcg agacttgact tagctatctt caagagttat gagcttaatc tggagtcata  12600
tcccacgata gagctaatga acattctttc aatatccagc gggaagttga ttggccagtc  12660
tgtggtttct tatgatgaag atacctccat aaagaatgat gccataatag tgtatgacaa  12720
tacccgaaat tggatcagtg aagctcagaa ttcagatgtg gtccgcctat ttgaatatgc  12780
agcacttgaa gtgctcctcg actgttctta ccaactctat tacctgagag taagagacct  12840
agacaatatt gtcttatata tgggtgattt atacaagaat atgccaggaa ttctactttc  12900
caacattgca gctacaatat ctcatcctgt cattcattca aggttacatg cagtgggcct  12960
ggtcaaccat gacggatcac accaacttgc agatacggat tttatcgaaa tgtctgcaaa  13020
actgttagta tcttgcaccc gacgtgtgat ctccggctta tattcaggaa ataagtatga  13080
tctgctgttc ccatctgtct tagatgataa cctgaatgag aagatgcttc agctgatatc  13140
ccggttatgc tgtctgtaca cggtactctt tgctacaaca agagaaatcc cgaaaataag  13200
aggcttaact gcagaagaga aatgttcaat actcactgag tatttactgt cggatgctgt  13260
gaaaccatta cttagccccg atcaagtgag ctctatcatg tctcctaaca taattacatt  13320
cccagctaat ctgtactaca tgtctcggaa gagcctcaat ttgatcaggg aaagggagga  13380
cagggatact atcctggcgt tgttgttccc ccaagagcca ttattagagt tcccttctgt  13440
gcaagatatt ggtgctcgag tgaaagatcc attcacccga caacctgcgg catttttgca  13500
agagttagat ttgagtgctc cagcaaggta tgacgcattc acacttagtc agattcatcc  13560
tgaactcaca tctccaaatc cggaggaaga ctacttagta cgatacttgt tcagagggat  13620
agggactgca tcttcctctt ggtataaggc atcccatctc ctttctgtac ccgaggtaag  13680
atgtgcaaga cacgggaact ccttatactt ggctgaagga agcggagcca tcatgagtct  13740
tcttgaactg catgtaccac atgaaactat ctattacaat acgctctttt caaatgagat  13800
gaacccccg caacgacatt tcgggccgac ccccaactcag tttttgaatt cggttgttta  13860
taggaatcta caggcggagg taacatgcaa ggatggattt gtccaagagt tccgtccatt  13920
atggagagaa aatacagagg aaagtgacct gacctcagat aaagcagtgg ggtatattac  13980
atctgcagta ccctacagat ctgtatcatt gctgcattgt gacattgaaa ttcctccagg  14040
gtccaatcaa agcttactag atcaactagc tatcaattta tctctgattg ccatgcattc  14100
tgtaagggag ggcggggtag taatcatcaa agtgttgtat gcaatgggat actactttca  14160
tctactcatg aacttgtttg ctccgtgttc cacaaaagga tatattctct ctaatggtta  14220
```

```
tgcatgtcga ggggatatgg agtgttacct ggtatttgtc atgggttacc tgggcgggcc  14280

tacatttgta catgaggtgg tgaggatggc aaaaactctg gtgcagcggc acggtacgct  14340

tttgtctaaa tcagatgaga tcacactgac caggttattc acctcacagc ggcagcgtgt  14400

gacagacatc ctatccagtc ctttaccaag attaataaag tacttgagga agaatattga  14460

cactgcgctg attgaagccg ggggacagcc cgtccgtcca ttctgtgcgg agagtctggt  14520

gagcacgcta gcgaacataa ctcagataac ccagatcatc gctagtcaca ttgacacagt  14580

catccggtct gtgatatata tggaagctga gggtgatctc gctgacacag tatttctatt  14640

taccccttac aatctctcta ctgacgggaa aaagaggaca tcacttaaac agtgcacgag  14700

acagatccta gaggttacaa tactaggtct tagagtcgaa aatctcaata aaataggcga  14760

tataatcagc ctagtgctta aaggcatgat ctccatggag gaccttatcc cactaaggac  14820

atacttgaag catagtacct gccctaaata tttgaaggct gtcctaggta ttaccaaact  14880

caaagaaatg tttacagaca cttctgtact gtacttgact cgtgctcaac aaaaattcta  14940

catgaaaact ataggcaatg cagtcaaagg atattacagt aactgtgact cctaacgaaa  15000

atcacatatt aataggctcc ttttttggcc aattgtattc ttgttgattt aattatatta  15060

tgttagaaaa aagttgaact ctgactcctt aggactcgaa ttcgaactca aataaatgtc  15120

tttaaaaaag gttgcgcaca attattcttg agtgtagtct cgtcattcac caaatctttg  15180

tttggt                                                             15186


<210> SEQ ID NO 49
<211> LENGTH: 574
<212> TYPE: PRT
<213> ORGANISM: Human respiratory syncytial virus

<400> SEQUENCE: 49

Met Glu Leu Pro Ile Leu Lys Ala Asn Ala Ile Thr Thr Ile Leu Ala
1               5                   10                  15

Ala Val Thr Leu Cys Phe Ala Ser Ser Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Ala Asn Asn Arg Ala Arg Arg Glu Leu Pro
            100                 105                 110

Arg Phe Met Asn Tyr Thr Leu Asn Asn Thr Glu Asn Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Ile Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190
```

-continued

```
Leu Asp Leu Lys Asn Tyr Ile Asp Lys Gln Leu Leu Pro Ile Val Asn
        195                 200                 205

Lys Gln Ser Cys Ser Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Ser Leu Cys Asn Val
    370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Gln Glu Gly
    450                 455                 460

Lys Asn Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu His Asn Val Asn Ala Val Lys Ser Thr Thr Asn Ile Met Ile Thr
        515                 520                 525

Thr Ile Ile Ile Val Ile Ile Val Ile Leu Leu Ser Leu Ile Val Val
    530                 535                 540

Gly Leu Leu Leu Tyr Cys Lys Ala Arg Ser Thr Pro Val Thr Leu Ser
545                 550                 555                 560

Lys Asp Gln Leu Ser Gly Ile Asn Asn Ile Ala Phe Ser Ser
                565                 570
```

<210> SEQ ID NO 50
<211> LENGTH: 574
<212> TYPE: PRT
<213> ORGANISM: Human respiratory syncytial virus

<400> SEQUENCE: 50

```
Met Glu Leu Pro Ile Leu Lys Thr Asn Ala Ile Thr Thr Ile Leu Ala
1               5                   10                  15

Ala Val Thr Leu Cys Phe Ala Ser Ser Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Ala Asn Ser Arg Ala Arg Arg Glu Leu Pro
            100                 105                 110

Arg Phe Met Asn Tyr Thr Leu Asn Asn Thr Lys Asn Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Ile Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Ser Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Ile
    370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415
```

```
Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Gln Glu Gly
    450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu His Asn Val Asn Ala Gly Lys Ser Thr Thr Asn Ile Met Ile Thr
        515                 520                 525

Thr Ile Ile Ile Val Ile Ile Val Ile Leu Leu Ala Leu Ile Ala Val
    530                 535                 540

Gly Leu Leu Leu Tyr Cys Lys Ala Arg Ser Thr Pro Val Thr Leu Ser
545                 550                 555                 560

Lys Asp Gln Leu Ser Gly Ile Asn Asn Ile Ala Phe Ser Asn
                565                 570
```

<210> SEQ ID NO 51
<211> LENGTH: 1740
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 51

```
atggagttgc taatcctcaa agcaaatgca attaccacaa tcctcactgc agtcacattt     60

tgttttgctt ctggtcaaaa catcactgaa gaattttatc aatcaacatg cagtgcagtt    120

agcaaaggct atcttagtgc tctgagaact ggttggtata ccagtgttat aactatagaa    180

ttaagtaata tcaaggaaaa taagtgtaat ggaacagatg ctaaggtaaa attgataaaa    240

caagaattag ataaatataa aaatgctgta acagaattgc agttgctcat gcaaagcaca    300

ccagcaacaa acaatcgagc cagaagagaa ctaccaaggt ttatgaatta tacactcaac    360

aatgccaaaa aaaccaatgt aacattaagc aagaaaagga aaagaagatt tcttggtttt    420

ttgttaggtg ttggatctgc aatcgccagt ggcgttgctg tatctaaggt cctgcaccta    480

gaaggggaag tgaacaagat caaaagtgct ctactatcca caaacaaggc tgtagtcagc    540

ttatcaaatg gagttagtgt cttaaccagc aaagtgttag acctcaaaaa ctatatagat    600

aaacaattgt tacctattgt gaacaagcaa agctgcagca tatcaaatat agcaactgtg    660

atagagttcc aacaaaagaa caacagacta ctagagatta ccagggaatt tagtgttaat    720

gcaggtgtaa ctacacctgt aagcacttac atgttaacta atagtgaatt attgtcatta    780

atcaatgata tgcctataac aaatgatcag aaaaagttaa tgtccaacaa tgttcaaata    840

gttagacagc aaagttactc tatcatgtcc ataataaaag aggaagtctt agcatatgta    900

gtacaattac cactatatgg tgttatagat acaccctgtt ggaaactaca cacatcccct    960

ctatgtacaa ccaacacaaa agaagggtcc aacatctgtt taacaagaac tgacagagga   1020

tggtactgtg acaatgcagg atcagtatct ttcttcccac aagctgaaac atgtaaagtt   1080

caatcaaatc gagtattttg tgacacaatg aacagtttaa cattaccaag tgaagtaaat   1140
```

```
ctctgcaatg ttgacatatt caaccccaaa tatgattgta aaattatgac ttcaaaaaca   1200

gatgtaagca gctccgttat cacatctcta ggagccattg tgtcatgcta tggcaaaact   1260

aaatgtacag catccaataa aaatcgtgga atcataaaga cattttctaa cgggtgcgat   1320

tatgtatcaa ataaaggggt ggacactgtg tctgtaggta acacattata ttatgtaaat   1380

aagcaagaag gtaaaagtct ctatgtaaaa ggtgaaccaa taataaattt ctatgaccca   1440

ttagtattcc cctctgatga atttgatgca tcaatatctc aagtcaacga gaagattaac   1500

cagagcctag catttattcg taaatccgat gaattattac ataatgtaaa tgctggtaaa   1560

tccaccataa atgttaacct cattacctat atcgttttga ctatcatatc tcttgttttt   1620

ggtatactta gcctgattct agcatgctac ctaatgtaca agcaaaaggc gcaacaaaag   1680

accttattat ggcttgggaa taataccccta gatcagatga gagccactac aaaaatgtga   1740
```

<210> SEQ ID NO 52
<211> LENGTH: 1620
<212> TYPE: DNA
<213> ORGANISM: Human metapneumovirus

<400> SEQUENCE: 52

```
atgtcttgga aagtggtgat catttttttca ttgctaataa cacctcaaca cggtcttaaa     60

gagagctact tagaagaatc atgtagcact ataactgagg gatatctcag tgttctgagg    120

acaggttggt ataccaacgt ttttacatta gaagtgggtg atgtagaaaa cctcacatgt    180

gctgatggac ctagcctaat aaaaaacagaa ttagatctga ccaaaagtgc actaagagag    240

ctcaaaacag tttctgctga ccaattggca agagaggaac agattgagaa tcccagacaa    300

tctagatttg ttctaggagc aatagcactc ggtgttgcga cagcagctgc agttacagca    360

ggtgttgcaa ttgccaaaac tatccgactt gagagtgaag ttacagcaat taagaatgcc    420

cttaaaaaga ctaatgaagc agtgtctaca ttggggaatg gagttcgagt gttagcaact    480

gcagtgaggg aactgaaaga ttttgtgagc aagaatttaa ctcgtgcaat caacaaaaac    540

aagtgcgaca ttgatgacct aaaaatggct gttagcttca gtcaattcaa cagaaggttt    600

ctaaatgttg tgcggcaatt ttcagacaat gctggaataa caccagcaat atctttagac    660

ttaatgacag atgctgaact agccagggcc gtttccaaca tgccgacatc tgcaggacaa    720

ataaaattga tgttggaaaa ccgtgcaatg gtgcgaagga aggggttcgg aatcctgatc    780

ggggtctacg gagctccgt aatttacatg gtgcagctgc caatctttgg cgttatagac    840

acgccttgct ggatagtaaa agcagcccct tcttgttccg aaaaaaaggg aaactatgct    900

tgcctcttaa gagaagacca agggtggtat tgtcagaatg cagggtcaac tgtttactac    960

ccaaatgaga aggactgtga aacaagagga gaccatgtct tttgcgacac agcagcagga   1020

attaatgttg ctgagcaatc aaaggagtgc aacatcaata tatccaccac aaattacccg   1080

tgcaaagtca gcacaggaag gcatcccatc agtatggttg cactgtcccc tcttggggct   1140

ctggttgcct gttacaaggg agtaagctgt tccattggca gcaatagagt agggatcatc   1200

aagcagctga acaaaggttg ctcttatata accaaccaag atgcagacac agtgacaata   1260

gacaacactg tatatcagct gagcaaagtt gagggtgaac agcatgttat aaaaggcaga   1320

ccagtgtcaa gcagctttga tccagtcaag tttcctgaag atcaattcaa tgttgcactt   1380

gatcaagttt ttgaaaacat tgaaaacagc caggccttgg tagatcaatc aaacagaatc   1440

ctaagcagtg cagagaaagg gaacactggc ttcatcattg tgataattct aattgctgtc   1500

cttggctcta gcatgatcct ggtgagcgtc tttattataa tcaagaaaac aaagaaacca   1560
```

acaggagcac ctccagagct aagcggtgtc acaaacaatg gcttcatacc gcacagttag 1620

<210> SEQ ID NO 53
<211> LENGTH: 1620
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 53
atgagctgga aggtggtgat catcttcagc ctgctgatca ccccccagca cggcctgaag 60
gagagctacc tggaggagag ctgcagcacc atcaccgagg gctacctgag cgtgctgaga 120
accggctggt acaccaacgt gttcaccctg gaggtgggcg acgtggagaa cctgacctgc 180
gccgacggcc ccagcctgat caagaccgag ctggacctga ccaagagcgc cctgagagag 240
ctgaagaccg tgagcgccga ccagctggcc agagaggagc agatcgagaa ccccagacag 300
agcagattcg tgctgggcgc catcgccctg ggcgtggcca ccgccgccgc cgtgaccgcc 360
ggcgtggcca tcgccaagac catcagactg gagagcgagg tgaccgccat caagaacgcc 420
ctgaagaaga ccaacgaggc cgtgagcacc ctgggcaacg gcgtgagagt gctggccacc 480
gccgtgagag agctgaagga cttcgtgagc aagaacctga ccagagccat caacaagaac 540
aagtgcgaca tcgacgacct gaagatggcc gtgagcttca gccagttcaa cagaagattc 600
ctgaacgtgg tgagacagtt cagcgacaac gccggcatca cccccgccat cagcctggac 660
ctgatgaccg acgccgagct ggccagagcc gtgagcaaca tgcccaccag cgccggccag 720
atcaagctga tgctggagaa cagagccatg gtgagaagaa agggcttcgg catcctgatc 780
ggcgtgtacg gcagcagcgt gatctacatg gtgcagctgc ccatcttcgg cgtgatcgac 840
accccctgct ggatcgtgaa ggccgccccc agctgcagcg agaagaaggg caactacgcc 900
tgcctgctga gagaggacca gggctggtac tgccagaacg ccggcagcac cgtgtactac 960
cccaacgaga aggactgcga gaccagaggc gaccacgtgt tctgcgacac cgccgccggc 1020
atcaacgtgg ccgagcagag caaggagtgc aacatcaaca tcagcaccac caactacccc 1080
tgcaaggtga gcaccggcag acaccccatc agcatggtgg ccctgagccc cctgggcgcc 1140
ctggtggcct gctacaaggg cgtgagctgc agcatcggca gcaacagagt gggcatcatc 1200
aagcagctga acaagggctg cagctacatc accaaccagg acgccgacac cgtgaccatc 1260
gacaacaccg tgtaccagct gagcaaggtg gagggcgagc agcacgtgat caagggcaga 1320
cccgtgagca gcagcttcga ccccgtgaag ttccccgagg accagttcaa cgtggccctg 1380
gaccaggtgt tcgagaacat cgagaacagc caggccctgg tggaccagag caacagaatc 1440
ctgagcagcg ccgagaaggg caacaccggc ttcatcatcg tgatcatcct gatcgccgtg 1500
ctgggcagca gcatgatcct ggtgagcgtg ttcatcatca tcaagaagac caagaagccc 1560
accggcgccc cccccgagct gagcggcgtg accaacaacg gcttcatccc ccacagctga 1620

<210> SEQ ID NO 54
<211> LENGTH: 1620
<212> TYPE: DNA
<213> ORGANISM: Human metapneumovirus

<400> SEQUENCE: 54
atgtcttgga aagtgatgat catcatttcg ttactcataa caccccagca cgggctaaag 60
gagagttatt tggaagaatc atgcagtact ataactgagg gatacctcag tgttttaaga 120
acaggctggt acaccaatgt cttcacatta gaagttggtg atgttgaaaa tcttacatgt 180
actgatggac ctagcttaat caaaacagaa cttgacctaa caaaaagtgc tttaagggaa 240
ctcaaaacag tctctgctga tcagttagcg agagaggagc aaattgaaaa tcccagacaa 300
tcaagatttg tcctaggtgc aatagctctc ggagttgcta cagcagcagc agtcacagca 360
ggcattgcaa tagccaaaac cataaggctt gagagtgagg tgaatgcaat taaaggtgct 420
ctcaaacaaa ctaatgaagc agtatccaca ttaggaaatg gtgtgcgggt cctagccact 480
gcagtgagag agctaaaaga atttgtgagc aaaaatctga ctagtgcaat caacaggaac 540
aaatgtgaca ttgctgatct gaagatggct gtcagcttca gtcaattcaa cagaagattt 600
ctaaatgttg tgcggcagtt ttcagacaat gcagggataa caccagcaat atcattggac 660
ctaatgactg atgctgaatt ggccagagct gtatcataca tgccaacatc tgcaggacag 720
ataaaactga tgttggagaa ccgcgcaatg gtaaggagaa aaggatttgg aatcctaata 780
ggggtctacg gaagctctgt gatttacatg gttcaattgc cgatctttgg tgtcatagat 840
acaccttgtt ggataatcaa ggcagctccc tcttgctcag aaaaaaacgg gaattatgct 900
tgcctcctaa gagaggatca agggtggtat tgtaaaaatg caggatccac tgtttactac 960
ccaaacgaaa aagactgtga aacaagaggt gatcatgttt tttgtgacac agcagcaggg 1020
atcaatgttg ctgagcaatc aagagaatgc aacatcaaca tatctactac caactaccca 1080
tgcaaagtca gcacaggaag acaccctata agcatggttg cactatcacc tctcggtgct 1140
ttggtggctt gctataaagg ggtaagctgc tcgattggca gcaatcgggt tggaatcatc 1200
aaacaattac ctaaaggctg ctcatacata actaaccagg atgcagacac tgtaacaatt 1260
gacaataccg tgtatcaact aagcaaagtt gaaggtgaac agcatgtaat aaaagggaga 1320
ccagtttcaa gcagttttga cccaatcagg tttcctgagg atcagttcaa tgttgcactt 1380
gatcaagtct tcgaaagcat tgagaacagt caggcactgg tggaacagtc aaacaaaatt 1440
ctaaacagtg cagaaaaagg aaacactggc ttcattattg taataatttt ggttgctgtt 1500
cttggtttaa ccatgatttc agtgagcatc atcatcataa tcaagaaaac aaggaagccc 1560
acaggagcac ctccagagct gaatggtgtc accaacggcg gtttcatacc acatagttag 1620

<210> SEQ ID NO 55
<211> LENGTH: 1620
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 55
atgagctgga aggtgatgat catcatcagc ctgctgatca ccccccagca cggcctgaag 60
gagagctacc tggaggagag ctgcagcacc atcaccgagg gctacctgag cgtgctgaga 120
accggctggt acaccaacgt gttcaccctg gaggtgggcg acgtggagaa cctgacctgc 180
accgacggcc ccagcctgat caagaccgag ctggacctga ccaagagcgc cctgagagag 240
ctgaagaccg tgagcgccga ccagctggcc agagaggagc agatcgagaa ccccagacag 300
agcagattcg tgctgggcgc catcgccctg ggcgtggcca ccgccgccgc cgtgaccgcc 360
ggcatcgcca tcgccaagac catcagactg gagagcgagg tgaacgccat caagggcgcc 420
ctgaagcaga ccaacgaggc cgtgagcacc ctgggcaacg gcgtgagagt gctggccacc 480
gccgtgagag agctgaagga gttcgtgagc aagaacctga ccagcgccat caacagaaac 540

-continued aagtgcgaca tcgccgacct gaagatggcc gtgagcttca gccagttcaa cagaagattc 600
ctgaacgtgg tgagacagtt cagcgacaac gccggcatca cccccgccat cagcctggac 660
ctgatgaccg acgccgagct ggccagagcc gtgagctaca tgcccaccag cgccggccag 720
atcaagctga tgctggagaa cagagccatg gtgagaagaa agggcttcgg catcctgatc 780
ggcgtgtacg gcagcagcgt gatctacatg gtgcagctgc ccatcttcgg cgtgatcgac 840
accccctgct ggatcatcaa ggccgccccc agctgcagcg agaagaacgg caactacgcc 900
tgcctgctga gagaggacca gggctggtac tgcaagaacg ccggcagcac cgtgtactac 960
cccaacgaga aggactgcga gaccagaggc gaccacgtgt tctgcgacac cgccgccggc 1020
atcaacgtgg ccgagcagag cagagagtgc aacatcaaca tcagcaccac caactacccc 1080
tgcaaggtga gcaccggcag acaccccatc agcatggtgg ccctgagccc cctgggcgcc 1140
ctggtggcct gctacaaggg cgtgagctgc agcatcggca gcaacagagt gggcatcatc 1200
aagcagctgc ccaagggctg cagctacatc accaaccagg acgccgacac cgtgaccatc 1260
gacaacaccg tgtaccagct gagcaaggtg gagggcgagc agcacgtgat caagggcaga 1320
cccgtgagca gcagcttcga ccccatcaga ttccccgagg accagttcaa cgtggccctg 1380
gaccaggtgt tcgagagcat cgagaacagc caggccctgg tggagcagag caacaagatc 1440
ctgaacagcg ccgagaaggg caacaccggc ttcatcatcg tgatcatcct ggtggccgtg 1500
ctgggcctga ccatgatcag cgtgagcatc atcatcatca tcaagaagac cagaaagccc 1560
accggcgccc cccccgagct gaacggcgtg accaacggcg gcttcatccc ccacagctga 1620

<210> SEQ ID NO 56
<211> LENGTH: 1620
<212> TYPE: DNA
<213> ORGANISM: Human metapneumovirus

<400> SEQUENCE: 56
atgtcttgga aagtggtgat catttttttca ttgctaataa cacctcaaca cggtcttaaa 60
gaaagctacc tagaagaatc atgtagcact ataactgagg gatatcttag tgttctgagg 120
acaggttggt ataccaacgt ttttacatta gaggtgggtg atgtagaaaa ccttacatgt 180
tctgatggac ctagcctaat aaaaacagaa ttagatctga ccaaaagtgc actaagagag 240
ctcaaaacag tctctgctga ccaattggca agagaggaac aaattgagaa tcccagacaa 300
tctaggtttg ttctaggagc aatagcactc ggtgttgcaa cagcagctgc agtcacagca 360
ggtgttgcaa ttgccaaaac catccggctt gagagtgaag tcacagcaat taagaatgcc 420
ctcaaaacga ccaatgaagc agtatctaca ttggggaatg gagttcgagt gttagcaact 480
gcagtgagag agctgaaaga ctttgtgagc aagaatttaa cccgtgcaat caacaaaaac 540
aagtgtgaca ttgatgacct aaaaatggcc gttagcttca gtcaattcaa cagaaggttt 600
ctaaatgttg tgcggcaatt ttcagacaat gctggaataa caccagcaat atctctggac 660
ttaatgacag atgctgaact agccagggcc gtttctaaca tgccgacatc tgcaggacaa 720
ataaaattga tgttggagaa ccgtgcgatg gtgcgaagaa aggggttcgg aatcctgata 780
ggggtctacg ggagctccgt aatttacatg gtgcagctgc caatctttgg cgttatagac 840
acgccttgct ggatagtaaa agcagcccct tcttgttccg aaaaaaaggg aaactatgct 900
tgcctcttaa gagaagacca agggtggtat tgtcagaatg cagggtcaac tgtttactac 960
ccaaatgaga aagactgtga aacaagagga gaccatgtct tttgcgacac agcagcagga 1020
attaatgttg ctgagcaatc aaaggagtgc aacatcaaca tatccactac aaattaccca 1080
tgcaaagtca gcacaggaag acatcctatc agtatggttg cactgtctcc tcttggggct 1140
ctggttgctt gctacaaagg agtaagctgt tccattggca gcaacagagt agggatcatc 1200
aagcagctga acaaaggttg ctcctatata accaaccaag atgcagacac agtgacaata 1260
gacaacactg tatatcagct aagcaaagtt gagggtgaac agcatgttat aaaaggcaga 1320
ccagtgtcaa gcagctttga tccaatcaag tttcctgaag atcaattcaa tgttgcactt 1380
gaccaagttt ttgagaacat tgaaaacagc caggccttgg tagatcaatc aaacagaatc 1440
ctaagcagtg cagagaaagg gaacactggc ttcatcattg taataattct aattgctgtc 1500
cttggctcta gcatgatcct agtgagcatc ttcattataa tcaagaaaac aaagaaacca 1560
acgggagcac ctccagagct gagtggtgtc acaaacaatg gcttcatacc acacagttag 1620

<210> SEQ ID NO 57
<211> LENGTH: 1620
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 57
atgagctgga aggtggtgat catcttcagc ctgctgatca ccccccagca cggcctgaag 60
gagagctacc tggaggagag ctgcagcacc atcaccgagg gctacctgag cgtgctgaga 120
accggctggt acaccaacgt gttcaccctg gaggtgggcg acgtggagaa cctgacctgc 180
agcgacggcc ccagcctgat caagaccgag ctggacctga ccaagagcgc cctgagagag 240
ctgaagaccg tgagcgccga ccagctggcc agagaggagc agatcgagaa ccccagacag 300
agcagattcg tgctgggcgc catcgccctg ggcgtggcca ccgccgccgc cgtgaccgcc 360
ggcgtggcca tcgccaagac catcagactg gagagcgagg tgaccgccat caagaacgcc 420
ctgaagacca ccaacgaggc cgtgagcacc ctgggcaacg gcgtgagagt gctggccacc 480
gccgtgagag agctgaagga cttcgtgagc aagaacctga ccagagccat caacaagaac 540
aagtgcgaca tcgacgacct gaagatggcc gtgagcttca gccagttcaa cagaagattc 600
ctgaacgtgg tgagacagtt cagcgacaac gccggcatca cccccgccat cagcctggac 660
ctgatgaccg acgccgagct ggccagagcc gtgagcaaca tgcccaccag cgccggccag 720
atcaagctga tgctggagaa cagagccatg gtgagaagaa agggcttcgg catcctgatc 780
ggcgtgtacg gcagcagcgt gatctacatg gtgcagctgc ccatcttcgg cgtgatcgac 840
accccctgct ggatcgtgaa ggccgccccc agctgcagcg agaagaaggg caactacgcc 900
tgcctgctga gagaggacca gggctggtac tgccagaacg ccggcagcac cgtgtactac 960
cccaacgaga aggactgcga gaccagaggc gaccacgtgt tctgcgacac cgccgccggc 1020
atcaacgtgg ccgagcagag caaggagtgc aacatcaaca tcagcaccac caactacccc 1080
tgcaaggtga gcaccggcag acaccccatc agcatggtgg ccctgagccc cctgggcgcc 1140
ctggtggcct gctacaaggg cgtgagctgc agcatcggca gcaacagagt gggcatcatc 1200
aagcagctga acaagggctg cagctacatc accaaccagg acgccgacac cgtgaccatc 1260
gacaacaccg tgtaccagct gagcaaggtg gagggcgagc agcacgtgat caagggcaga 1320
cccgtgagca gcagcttcga ccccatcaag ttccccgagg accagttcaa cgtggccctg 1380
gaccaggtgt tcgagaacat cgagaacagc caggccctgg tggaccagag caacagaatc 1440

```
ctgagcagcg ccgagaaggg caacaccggc ttcatcatcg tgatcatcct gatcgccgtg   1500

ctgggcagca gcatgatcct ggtgagcatc ttcatcatca tcaagaagac caagaagccc   1560

accggcgccc cccccgagct gagcggcgtg accaacaacg gcttcatccc ccacagctga   1620


<210> SEQ ID NO 58
<211> LENGTH: 574
<212> TYPE: PRT
<213> ORGANISM: Human respiratory syncytial virus

<400> SEQUENCE: 58

Met Glu Leu Leu Ile His Arg Ser Ser Val Ile Phe Leu Thr Leu Ala
1               5                   10                  15

Ile Asn Ala Leu Tyr Leu Thr Ser Ser Gln Asn Ile Thr Glu Glu Phe
            20                  25                  30

Tyr Gln Ser Thr Cys Ser Ala Val Ser Arg Gly Tyr Phe Ser Ala Leu
        35                  40                  45

Arg Thr Gly Trp Tyr Thr Ser Val Ile Thr Ile Glu Leu Ser Asn Ile
    50                  55                  60

Lys Glu Thr Lys Cys Asn Gly Thr Asp Thr Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Asn Ile Pro Ala Ala Asn Asn Arg Ala Arg Arg Glu Ala Pro
            100                 105                 110

Gln Tyr Met Asn Tyr Thr Ile Asn Thr Thr Lys Asn Leu Asn Val Ser
        115                 120                 125

Ile Ser Lys Lys Arg Lys Arg Arg Phe Leu Gly Phe Leu Leu Gly Val
    130                 135                 140

Gly Ser Ala Ile Ala Ser Gly Ile Ala Val Ser Lys Val Leu His Leu
145                 150                 155                 160

Glu Gly Glu Val Asn Lys Ile Lys Asn Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asn Asn Gln Leu Leu Pro Ile Val Asn
        195                 200                 205

Gln Gln Ser Cys Arg Ile Ser Asn Ile Glu Thr Val Ile Glu Phe Gln
    210                 215                 220

Gln Lys Asn Ser Arg Leu Leu Glu Ile Thr Arg Glu Phe Ser Val Asn
225                 230                 235                 240

Ala Gly Val Thr Thr Pro Leu Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Ser Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Ile Tyr Gly Val Ile Asp Thr Pro Cys Trp Lys Leu His Thr Ser Pro
305                 310                 315                 320

Leu Cys Thr Thr Asn Ile Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350
```

Pro Gln Ala Asp Thr Cys Lys Val Gln Ser Asn Arg Val Phe Cys Asp
355 360 365

Thr Met Asn Ser Leu Thr Leu Pro Ser Glu Val Ser Leu Cys Asn Thr
370 375 380

Asp Ile Phe Asn Ser Lys Tyr Asp Cys Lys Ile Met Thr Ser Lys Thr
385 390 395 400

Asp Ile Ser Ser Ser Val Ile Thr Ser Leu Gly Ala Ile Val Ser Cys
405 410 415

Tyr Gly Lys Thr Lys Cys Thr Ala Ser Asn Lys Asn Arg Gly Ile Ile
420 425 430

Lys Thr Phe Ser Asn Gly Cys Asp Tyr Val Ser Asn Lys Gly Val Asp
435 440 445

Thr Val Ser Val Gly Asn Thr Leu Tyr Tyr Val Asn Lys Leu Glu Gly
450 455 460

Lys Asn Leu Tyr Val Lys Gly Glu Pro Ile Ile Asn Tyr Tyr Asp Pro
465 470 475 480

Leu Val Phe Pro Ser Asp Glu Phe Asp Ala Ser Ile Ser Gln Val Asn
485 490 495

Glu Lys Ile Asn Gln Ser Leu Ala Phe Ile Arg Arg Ser Asp Glu Leu
500 505 510

Leu His Asn Val Asn Thr Gly Lys Ser Thr Thr Asn Ile Met Ile Thr
515 520 525

Val Ile Ile Ile Val Ile Ile Val Val Leu Leu Ser Leu Ile Ala Ile
530 535 540

Gly Leu Leu Leu Tyr Cys Lys Ala Lys Asn Thr Pro Val Thr Leu Ser
545 550 555 560

Lys Asp Gln Leu Ser Gly Ile Asn Asn Ile Ala Phe Ser Lys
565 570

<210> SEQ ID NO 59
<211> LENGTH: 16979
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 59
accaaacaga gaatccgtga gttacgataa aaggcgaagg agcaattgaa gtcgcacggg 60
tagaaggtgt gaatctcgag tgcgagcccg aagcacaaac tcgagaaagc cttctgccaa 120
catgtcttcc gtatttgatg agtacgaaca gctcctcgcg gctcagactc gccccaatgg 180
agctcatgga gggggagaaa aagggagtac cttaaaagta gacgtcccgg tattcactct 240
taacagtgat gacccagaag atagatggag ctttgtggta ttctgcctcc ggattgctgt 300
tagcgaagat gccaacaaac cactcaggca aggtgctctc atatctcttt tatgctccca 360
ctcacaggta atgaggaacc atgttgccct tgcagggaaa cagaatgaag ccacattggc 420
cgtgcttgag attgatggct ttgccaacgg cacgccccag ttcaacaata ggagtggagt 480
gtctgaagag agagcacaga gatttgcgat gatagcagga tctctccctc gggcatgcag 540
caacggaacc ccgttcgtca cagccggggc cgaagatgat gcaccagaag acatcaccga 600
taccctggag aggatcctct ctatccaggc tcaagtatgg gtcacagtag caaaagccat 660
gactgcgtat gagactgcag atgagtcgga aacaaggcga atcaataagt atatgcagca 720
aggcagggtc caaaagaaat acatcctcta ccccgtatgc aggagcacaa tccaactcac 780

```
gatcagacag tctcttgcag tccgcatctt tttggttagc gagctcaaga gaggccgcaa    840
cacggcaggt ggtacctcta cttattataa cctggtaggg gacgtagact catacatcag    900
gaataccggg cttactgcat tcttcttgac actcaagtac ggaatcaaca ccaagacatc    960
agcccttgca cttagtagcc tctcaggcga catccagaag atgaagcagc tcatgcgttt   1020
gtatcggatg aaaggagata atgcgccgta catgacatta cttggtgata gtgaccagat   1080
gagctttgcg cctgccgagt atgcacaact ttactccttt gccatgggta tggcatcagt   1140
cctagataaa ggtactggga aataccaatt tgccagggac tttatgagca catcattctg   1200
gagacttgga gtagagtacg ctcaggctca gggaagtagc attaacgagg atatggctgc   1260
cgagctaaag ctaaccccag cagcaaggag gggcctggca gctgctgccc aacgggtctc   1320
cgaggagacc agcagcatag acatgcctac tcaacaagtc ggagtcctca ctgggcttag   1380
cgaggggggg tcccaagctc tacaaggcgg atcgaataga tcgcaagggc aaccagaagc   1440
cggggatggg gagacccaat tcctggatct gatgagagcg gtagcaaata gcatgaggga   1500
ggcgccaaac tctgcacagg gcactcccca atcggggcct cccccaactc ctgggccatc   1560
ccaagataac gacaccgact gggggtattg atggacaaaa cccagcctgc ttccacaaaa   1620
acatcccaat gccctcaccc gtagtcgacc cctcgatttg cggctctata tgaccacacc   1680
ctcaaacaaa catccccctc tttcctccct ccccctgctg tacaactacg tacgccctag   1740
ataccacagg cacaatgcgg ctcactaaca atcaaaacag agccgaggga attagaaaaa   1800
agtacgggta gaagagggat attcagagat cagggcaagt ctcccgagtc tctgctctct   1860
cctctacctg atagaccagg acaaacatgg ccacctttac agatgcagag atcgacgagc   1920
tatttgagac aagtggaact gtcattgaca acataattac agcccagggt aaaccagcag   1980
agactgttgg aaggagtgca atcccacaag gcaagaccaa ggtgctgagc gcagcatggg   2040
agaagcatgg gagcatccag ccaccggcca gtcaagacaa ccccgatcga caggacagat   2100
ctgacaaaca accatccaca cccgagcaaa cgaccccgca tgacagcccg ccggccacat   2160
ccgccgacca gccccccacc caggccacag acgaagccgt cgacacacag ctcaggaccg   2220
gagcaagcaa ctctctgctg ttgatgcttg acaagctcag caataaatcg tccaatgcta   2280
aaaagggccc atggtcgagc cccaagaggg ggaatcacca acgtccgact caacagcagg   2340
ggagtcaacc cagtcgcgga aacagtcagg aaagaccgca gaaccaagtc aaggccgccc   2400
ctggaaacca gggcacagac gtgaacacag catatcatgg acaatgggag gagtcacaac   2460
tatcagctgg tgcaacccct catgctctcc gatcaaggca gagccaagac aatacccttg   2520
tatctgcgga tcatgtccag ccacctgtag actttgtgca agcgatgatg tctatgatgg   2580
aggcgatatc acagagagta agtaaggttg actatcagct agatcttgtc ttgaaacaga   2640
catcctccat ccctatgatg cggtccgaaa tccaacagct gaaaacatct gttgcagtca   2700
tggaagccaa cttgggaatg atgaagattc tggatcccgg ttgtgccaac atttcatctc   2760
tgagtgatct acgggcagtt gcccgatctc acccggtttt agtttcaggc cctggagacc   2820
cctctcccta tgtgacacaa ggaggcgaaa tggcacttaa taaactttcg caaccagtgc   2880
cacatccatc tgaattgatt aaacccgcca ctgcatgcgg gcctgatata ggagtggaaa   2940
aggacactgt ccgtgcattg atcatgtcac gcccaatgca cccgagttct tcagccaagc   3000
tcctaagcaa gttagatgca gccgggtcga tcgaggaaat caggaaaatc aagcgccttg   3060
ctctaaatgg ctaattacta ctgccacacg tagcgggtcc ctgtccactc ggcatcacac   3120
```

-continued

```
ggaatctgca ccgagttccc ccccgcggtt agaaaaaata cgggtagaac cgccaccatg   3180
gcgacaacag ccatgaggat gatcatcagc attatcttca tctctaccta tgtgacacat   3240
atcactttat gccaaaacat aacagaagaa ttttatcaat caacatgcag tgcagttagt   3300
agaggttacc ttagtgcatt aagaactgga tggtatacaa gtgtggtaac aatagagttg   3360
agcaaaatac aaaaaaatgt gtgtaatagt actgattcaa aagtgaaatt aataaagcaa   3420
gaactagaaa gatacaacaa tgcagtagtg gaattgcagt cacttatgca aaatgaaccg   3480
gcctccttca gtagagcaaa aagagggata ccagagttga tacattatac aagaaactct   3540
acaaaaaagt tttatgggct aatgggcaag aagagaaaaa ggagattttt aggattcttg   3600
ctaggtattg gatctgctat tgcaagtggt gtagcagtgt ccaaagtact acacctggag   3660
ggagaggtga ataaaattaa aaatgcactg ctatccacaa ataaagcagt agttagtcta   3720
tccaatggag ttagtgtcct tactagcaaa gtacttgatc taaagaacta tatagacaaa   3780
gagcttctac ctaaagttaa caatcatgat tgtaggatat ccaaaataga aactgtgata   3840
gaattccaac aaaaaaacaa tagattgtta gaaattgcta gggaatttag tgtaaatgct   3900
ggtattacca cacctctcag tacatacatg ttgaccaata gtgaattact atcactaatt   3960
aatgatatgc ctataacgaa tgaccaaaaa aagctaatgt caagtaatgt tcaaatagtc   4020
aggcaacaga gttattccat tatgtcagtg gtcaaagaag aagtcatagc ttatgttgta   4080
caattgccta tttatggagt tatagacacc ccctgttgga aactacacac ctctccgtta   4140
tgcaccactg ataataaaga agggtcaaac atctgcttaa ctaggacaga tcgtgggtgg   4200
tattgtgaca atgcaggctc tgtgtctttt ttcccacaga cagagacatg taaggtacaa   4260
tcaaatagag tgttctgtga cacaatgaac agtttaactc tgcctactga cgttaactta   4320
tgcaacactg acatattcaa tacaaagtat gactgtaaaa taatgacatc taaaactgac   4380
ataagtagct ctgtgataac ttcaattgga gctattgtat catgctatgg gaagacaaaa   4440
tgtacagctt ctaataaaaa tcgtggaatc ataaagactt tttccaatgg gtgtgattat   4500
gtatcaaaca aaggagtaga tactgtatct gttggtaaca cactatatta tgtaaataag   4560
ctagagggga aagcactcta tataaagggt gaaccaatta ttaattacta tgatccacta   4620
gtgtttcctt ctgatgagtt tgatgcatca attgcccaag taaacgcaaa aataaaccaa   4680
agcctggcct tcatacgtcg atctgatgag ttacttcaca gtgtagatgt aggaaaatcc   4740
accacaaatg ttaacctcat tacctatatc gttttgacta tcatatctct tgtttttggt   4800
atacttagcc tgattctagc atgctaccta atgtacaagc aaaaggcgca acaaaagacc   4860
ttattatggc ttgggaataa taccctagat cagatgagag ccactacaaa aatgtgagct   4920
tcagcaagta accccccgcg gacccaaggt ccaactctcc aagcggcaat cctctctcgc   4980
ttcctcagcc ccactgaatg atcgcgtaac cgtaattaat ctagctacat ttaagattaa   5040
gaaaaaatac gggtagaatt ggagtgcccc aattgtgcca agatggactc atctaggaca   5100
attgggctgt actttgattc tgcccattct tctagcaacc tgttagcatt tccgatcgtc   5160
ctacaagaca caggagatgg gaagaagcaa atcgccccgc aatataggat ccagcgcctt   5220
gacttgtgga ctgatagtaa ggaggactca gtattcatca ccacctatgg attcatcttt   5280
caagttggga atgaagaagc caccgtcggc atgatcgatg ataaacccaa gcgcgagtta   5340
ctttccgctg cgatgctctg cctaggaagc gtcccaaata ccggagacct tattgagctg   5400
gcaagggcct gtctcactat gatagtcaca tgcaagaaga gtgcaactaa tactgagaga   5460
atggttttct cagtagtgca ggcaccccaa gtgctgcaaa gctgtagggt tgtggcaaac   5520
```

-continued

```
aaatactcat cagtgaatgc agtcaagcac gtgaaagcgc cagagaagat tcccgggagt   5580
ggaaccctag aatacaaggt gaactttgtc tccttgactg tggtaccgaa gagggatgtc   5640
tacaagatcc cagctgcagt attgaaggtt tctggctcga gtctgtacaa tcttgcgctc   5700
aatgtcacta ttaatgtgga ggtagacccg aggagtcctt tggttaaatc tctgtctaag   5760
tctgacagcg gatactatgc taacctcttc ttgcatattg gacttatgac cactgtagat   5820
aggaagggga agaaagtgac atttgacaag ctggaaaaga aaataaggag ccttgatcta   5880
tctgtcgggc tcagtgatgt gctcgggcct tccgtgttgg taaaagcaag aggtgcacgg   5940
actaagcttt tggcaccttt cttctctagc agtgggacag cctgctatcc catagcaaat   6000
gcttctcctc aggtggccaa gatactctgg agtcaaaccg cgtgcctgcg gagcgttaaa   6060
atcattatcc aagcaggtac ccaacgcgct gtcgcagtga ccgccgacca cgaggttacc   6120
tctactaagc tggagaaggg gcacaccctt gccaaataca atccttttaa gaaataagct   6180
gcgtctctga gattgcgctc cgcccactca cccagatcat catgacacaa aaaactaatc   6240
tgtcttgatt atttacagtt agtttacctg tctatcaagt tagaaaaaac acgggtagaa   6300
gattctggat cccggttggc gccctccagg tgcaagatgg gctccagacc ttctaccaag   6360
aacccagcac ctatgatgct gactatccgg gttgcgctgg tactgagttg catctgtccg   6420
gcaaactcca ttgatggcag gcctcttgca gctgcaggaa ttgtggttac aggagacaaa   6480
gccgtcaaca tatacacctc atcccagaca ggatcaatca tagttaagct cctcccgaat   6540
ctgcccaagg ataaggaggc atgtgcgaaa gccccttgg atgcatacaa caggacattg   6600
accactttgc tcacccccct tggtgactct atccgtagga tacaagagtc tgtgactaca   6660
tctggagggg ggagacaggg gcgccttata ggcgccatta ttggcggtgt ggctcttggg   6720
gttgcaactg ccgcacaaat aacagcggcc gcagctctga tacaagccaa acaaaatgct   6780
gccaacatcc tccgacttaa agagagcatt gccgcaacca atgaggctgt gcatgaggtc   6840
actgacggat tatcgcaact agcagtggca gttgggaaga tgcagcagtt tgttaatgac   6900
caatttaata aaacagctca ggaattagac tgcatcaaaa ttgcacagca agttggtgta   6960
gagctcaacc tgtacctaac cgaattgact acagtattcg gaccacaaat cacttcacct   7020
gctttaaaca agctgactat tcaggcactt tacaatctag ctggtggaaa tatggattac   7080
ttattgacta agttaggtgt agggaacaat caactcagct cattaatcgg tagcggctta   7140
atcaccggta accctattct atacgactca cagactcaac tcttgggtat acaggtaact   7200
ctaccttcag tcgggaacct aaataatatg cgtgccacct acttggaaac cttatccgta   7260
agcacaacca ggggatttgc ctcggcactt gtcccaaaag tggtgacaca ggtcggttct   7320
gtgatagaag aacttgacac ctcatactgt atagaaactg acttagattt atattgtaca   7380
agaatagtaa cgttccctat gtcccctggt atttattcct gcttgagcgg caatacgtcg   7440
gcctgtatgt actcaaagac cgaaggcgca cttactacac catacatgac tatcaaaggt   7500
tcagtcatcg ccaactgcaa gatgacaaca tgtagatgtg taaacccccc gggtatcata   7560
tcgcaaaact atggagaagc cgtgtctcta atagataaac aatcatgcaa tgttttatcc   7620
ttaggcggga taactttaag gctcagtggg gaattcgatg taacttatca gaagaatatc   7680
tcaatacaag attctcaagt aataataaca ggcaatcttg atatctcaac tgagcttggg   7740
aatgtcaaca actcgatcag taatgctttg aataagttag aggaaagcaa cagaaaacta   7800
gacaaagtca atgtcaaact gactagcaca tctgctctca ttacctatat cgttttgact   7860
```

-continued

```
atcatatctc ttgtttttgg tatacttagc ctgattctag catgctacct aatgtacaag   7920
caaaaggcgc aacaaaagac cttattatgg cttgggaata atactctaga tcagatgaga   7980
gccactacaa aaatgtgaac acagatgagg aacgaaggtt tccctaatag taatttgtgt   8040
gaaagttctg gtagtctgtc agttcagaga gttaagaaaa aactaccggt tgtagatgac   8100
caaaggacga tatacgggta gaacggtaag agaggccgcc cctcaattgc gagccaggct   8160
tcacaacctc cgttctaccg cttcaccgac aacagtcctc aatcatggac cgcgccgtta   8220
gccaagttgc gttagagaat gatgaaagag aggcaaaaaa tacatggcgc ttgatattcc   8280
ggattgcaat cttattctta acagtagtga ccttggctat atctgtagcc tccctttttat   8340
atagcatggg ggctagcaca cctagcgatc ttgtaggcat accgactagg atttccaggg   8400
cagaagaaaa gattacatct acacttggtt ccaatcaaga tgtagtagat aggatatata   8460
agcaagtggc ccttgagtct ccgttggcat tgttaaatac tgagaccaca attatgaacg   8520
caataacatc tctctcttat cagattaatg gagctgcaaa caacagtggg tggggggcac   8580
ctatccatga cccagattat atagggggga taggcaaaga actcattgta gatgatgcta   8640
gtgatgtcac atcattctat ccctctgcat ttcaagaaca tctgaatttt atcccggcgc   8700
ctactacagg atcaggttgc actcgaatac cctcatttga catgagtgct acccattact   8760
gctacaccca taatgtaata ttgtctggat gcagagatca ctcacattca tatcagtatt   8820
tagcacttgg tgtgctccgg acatctgcaa cagggagggt attcttttct actctgcgtt   8880
ccatcaacct ggacgacacc caaaatcgga agtcttgcag tgtgagtgca actcccctgg   8940
gttgtgatat gctgtgctcg aaagtcacgg agacagagga agaagattat aactcagctg   9000
tccctacgcg gatggtacat gggaggttag ggttcgacgg ccagtaccac gaaaaggacc   9060
tagatgtcac aacattattc ggggactggg tggccaacta cccaggagta gggggtggat   9120
cttttattga cagccgcgta tggttctcag tctacggagg gttaaaaccc aattcaccca   9180
gtgacactgt acaggaaggg aaatatgtga tatacaagcg atacaatgac acatgcccag   9240
atgagcaaga ctaccagatt cgaatggcca agtcttcgta taagcctgga cggtttggtg   9300
ggaaacgcat acagcaggct atcttatcta tcaaggtgtc aacatcctta ggcgaagacc   9360
cggtactgac tgtaccgccc aacacagtca cactcatggg ggccgaaggc agaattctca   9420
cagtagggac atctcatttc ttgtatcaac gagggtcatc atacttctct cccgcgttat   9480
tatatcctat gacagtcagc aacaaaacag ccactcttca tagtccttat acattcaatg   9540
ccttcactcg gccaggtagt atcccttgcc aggcttcagc aagatgcccc aactcgtgtg   9600
ttactggagt ctatacagat ccatatcccc taatcttcta tagaaaccac accttgcgag   9660
gggtattcgg gacaatgctt gatggtgtac aagcaagact taaccctgcg tctgcagtat   9720
tcgatagcac atcccgcagt cgcattactc gagtgagttc aagcagtacc aaagcagcat   9780
acacaacatc aacttgtttt aaagtggtca agactaataa gacctattgt ctcagcattg   9840
ctgaaatatc taatactctc ttcggagaat tcagaatcgt cccgttacta gttgagatcc   9900
tcaaagatga cggggttaga gaagccaggt ctggctagtt gagtcaatta taaaggagtt   9960
ggaaagatgg cattgtatca cctatcttct gcgacatcaa gaatcaaacc gaatgccggc  10020
gcgtgctcga attccatgtt gccagttgac cacaatcagc cagtgctcat gcgatcagat  10080
taagccttgt caatagtctc ttgattaaga aaaaatgtaa gtggcaatga gatacaaggc  10140
aaaacagctc atggttaaca atacgggtag gacatggcga gctccggtcc tgaaagggca  10200
gagcatcaga ttatcctacc agagtcacac ctgtcttcac cattggtcaa gcacaaacta  10260
```

```
ctctattact ggaaattaac tgggctaccg cttcctgatg aatgtgactt cgaccacctc  10320
attctcagcc gacaatggaa aaaaatactt gaatcggcct ctcctgatac tgagagaatg  10380
ataaaactcg gaagggcagt acaccaaact cttaaccaca attccagaat aaccggagtg  10440
ctccacccca ggtgtttaga agaactggct aatattgagg tcccagattc aaccaacaaa  10500
tttcggaaga ttgagaagaa gatccaaatt cacaacacga gatatggaga actgttcaca  10560
aggctgtgta cgcatataga gaagaaactg ctggggtcat cttggtctaa caatgtcccc  10620
cggtcagagg agttcagcag cattcgtacg gatccggcat tctggtttca ctcaaaatgg  10680
tccacagcca agtttgcatg gctccatata aaacagatcc agaggcatct gatggtggca  10740
gctaggacaa ggtctgcggc caacaaattg gtgatgctaa cccataaggt aggccaagtc  10800
tttgtcactc ctgaacttgt cgttgtgacg catacgaatg agaacaagtt cacatgtctt  10860
acccaggaac ttgtattgat gtatgcagat atgatggagg gcagagatat ggtcaacata  10920
atatcaacca cggcggtgca tctcagaagc ttatcagaga aaattgatga cattttgcgg  10980
ttaatagacg ctctggcaaa agacttgggt aatcaagtct acgatgttgt atcactaatg  11040
gagggatttg catacggagc tgtccagcta ctcgagccgt caggtacatt tgcaggagat  11100
ttcttcgcat tcaacctgca ggagcttaaa gacattctaa ttggcctcct ccccaatgat  11160
atagcagaat ccgtgactca tgcaatcgct actgtattct ctggtttaga acagaatcaa  11220
gcagctgaga tgttgtgtct gttgcgtctg tggggtcacc cactgcttga gtcccgtatt  11280
gcagcaaagg cagtcaggag ccaaatgtgc gcaccgaaaa tggtagactt tgatatgatc  11340
cttcaggtac tgtctttctt caagggaaca atcatcaacg ggtacagaaa gaagaatgca  11400
ggtgtgtggc cgcgagtcaa agtggataca atatatggga aggtcattgg gcaactacat  11460
gcagattcag cagagatttc acacgatatc atgttgagag agtataagag tttatctgca  11520
cttgaatttg agccatgtat agaatatgac cctgtcacca acctgagcat gttcctaaaa  11580
gacaaggcaa tcgcacaccc caacgataat tggcttgcct cgtttaggcg gaaccttctc  11640
tccgaagacc agaagaaaca tgtaaaagaa gcaacttcga ctaatcgcct cttgatagag  11700
tttttagagt caaatgattt tgatccatat aaagagatgg aatatctgac gacccttgag  11760
taccttagag atgacaatgt ggcagtatca tactcgctca aggagaagga agtgaaagtt  11820
aatggacgga tcttcgctaa gctgacaaag aagttaagga actgtcaggt gatggcggaa  11880
gggatcctag ccgatcagat tgcacctttc tttcagggaa atggagtcat tcaggatagc  11940
atatccttga ccaagagtat gctagcgatg agtcaactgt cttttaacag caataagaaa  12000
cgtatcactg actgtaaaga aagagtatct tcaaaccgca atcatgatcc gaaaagcaag  12060
aaccgtcgga gagttgcaac cttcataaca actgacctgc aaaagtactg tcttaattgg  12120
agatatcaga caatcaaatt gttcgctcat gccatcaatc agttgatggg cctacctcac  12180
ttcttcgaat ggattcacct aagactgatg gacactacga tgttcgtagg agaccctttc  12240
aatcctccaa gtgaccctac tgactgtgac ctctcaagag tccctaatga tgacatatat  12300
attgtcagtg ccagaggggg tatcgaagga ttatgccaga agctatggac aatgatctca  12360
attgctgcaa tccaacttgc tgcagctaga tcgcattgtc gtgttgcctg tatggtacag  12420
ggtgataatc aagtaatagc agtaacgaga gaggtaagat cagacgactc tccggagatg  12480
gtgttgacac agttgcatca agccagtgat aatttcttca aggaattaat tcatgtcaat  12540
catttgattg gccataattt gaaggatcgt gaaaccatca ggtcagacac attcttcata  12600
```

```
tacagcaaac gaatcttcaa agatggagca atcctcagtc aagtcctcaa aaattcatct  12660
aaattagtgc tagtgtcagg tgatctcagt gaaaacaccg taatgtcctg tgccaacatt  12720
gcctctactg tagcacggct atgcgagaac gggcttccca aagacttctg ttactattta  12780
aactatataa tgagttgtgt gcagacatac tttgactctg agttctccat caccaacaat  12840
tcgcaccccg atcttaatca gtcgtggatt gaggacatct cttttgtgca ctcatatgtt  12900
ctgactcctg cccaattagg gggactgagt aaccttcaat actcaaggct ctacactaga  12960
aatatcggtg acccggggac tactgctttt gcagagatca agcgactaga agcagtggga  13020
ttactgagtc ctaacattat gactaatatc ttaactaggc cgcctgggaa tggagattgg  13080
gccagtctgt gcaacgaccc atactctttc aattttgaga ctgttgcaag cccaaatatt  13140
gttcttaaga aacatacgca aagagtccta tttgaaactt gttcaaatcc cttattgtct  13200
ggagtgcaca cagaggataa tgaggcagaa gagaaggcat tggctgaatt cttgcttaat  13260
caagaggtga ttcatccccg cgttgcgcat gccatcatgg aggcaagctc tgtaggtagg  13320
agaaagcaaa ttcaagggct tgttgacaca acaaacaccg taattaagat tgcgcttact  13380
aggaggccat taggcatcaa gaggctgatg cggatagtca attattctag catgcatgca  13440
atgctgttta gagacgatgt tttttcctcc agtagatcca accacccctt agtctcttct  13500
aatatgtgtt ctctgacact ggcagactat gcacggaata gaagctggtc acctttgacg  13560
ggaggcagga aaatactggg tgtatctaat cctgatacga tagaactcgt agagggtgag  13620
attcttagtg taagcggagg gtgtacaaga tgtgacagcg gagatgaaca atttacttgg  13680
ttccatcttc caagcaatat agaattgacc gatgacacca gcaagaatcc tccgatgagg  13740
gtaccatatc tcgggtcaaa gacacaggag aggagagctg cctcacttgc aaaaatagct  13800
catatgtcgc cacatgtaaa ggctgcccta agggcatcat ccgtgttgat ctgggcttat  13860
ggggataatg aagtaaattg gactgctgct cttacgattg caaaatctcg gtgtaatgta  13920
aacttagagt atcttcggtt actgtcccct ttacccacgg ctgggaatct tcaacataga  13980
ctagatgatg gtataactca gatgacattc acccctgcat ctctctacag ggtgtcacct  14040
tacattcaca tatccaatga ttctcaaagg ctgttcactg aagaaggagt caaagagggg  14100
aatgtggttt accaacagat catgctcttg ggtttatctc taatcgaatc gatctttcca  14160
atgacaacaa ccaggacata tgatgagatc acactgcacc tacatagtaa atttagttgc  14220
tgtatcagag aagcacctgt tgcggttcct ttcgagctac ttggggtggt accggaactg  14280
aggacagtga cctcaaataa gtttatgtat gatcctagcc ctgtatcgga gggagacttt  14340
gcgagacttg acttagctat cttcaagagt tatgagctta atctggagtc atatcccacg  14400
atagagctaa tgaacattct ttcaatatcc agcgggaagt tgattggcca gtctgtggtt  14460
tcttatgatg aagatacctc cataaagaat gacgccataa tagtgtatga caatacccga  14520
aattggatca gtgaagctca gaattcagat gtggtccgcc tatttgaata tgcagcactt  14580
gaagtgctcc tcgactgttc ttaccaactc tattacctga gagtaagagg cctggacaat  14640
attgtcttat atatgggtga tttatacaag aatatgccag gaattctact ttccaacatt  14700
gcagctacaa tatctcatcc cgtcattcat tcaaggttac atgcagtggg cctggtcaac  14760
catgacggat cacaccaact tgcagatacg gattttatcg aaatgtctgc aaaactatta  14820
gtatcttgca cccgacgtgt gatctccggc ttatattcag gaaataagta tgatctgctg  14880
ttcccatctg tcttagatga taacctgaat gagaagatgc ttcagctgat atcccggtta  14940
tgctgtctgt acacggtact ctttgctaca acaagagaaa tcccgaaaat aagaggctta  15000
```

-continued

```
actgcagaag agaaatgttc aatactcact gagtatttac tgtcggatgc tgtgaaacca  15060
ttacttagcc ccgatcaagt gagctctatc atgtctccta acataattac attcccagct  15120
aatctgtact acatgtctcg gaagagcctc aatttgatca gggaaaggga ggacagggat  15180
actatcctgg cgttgttgtt cccccaagag ccattattag agttcccttc tgtgcaagat  15240
attggtgctc gagtgaaaga tccattcacc cgacaacctg cggcattttt gcaagagtta  15300
gatttgagtg ctccagcaag gtatgacgca ttcacactta gtcagattca tcctgaactc  15360
acatctccaa atccggagga agactactta gtacgatact tgttcagagg gatagggact  15420
gcatcttcct cttggtataa ggcatctcat ctcctttctg tacccgaggt aagatgtgca  15480
agacacggga actccttata cttagctgaa gggagcggag ccatcatgag tcttctcgaa  15540
ctgcatgtac cacatgaaac tatctattac aatacgctct tttcaaatga gatgaacccc  15600
ccgcaacgac atttcgggcc gaccccaact cagtttttga attcggttgt ttataggaat  15660
ctacaggcgg aggtaacatg caaagatgga tttgtccaag agttccgtcc attatggaga  15720
gaaaatacag aggaaagcga cctgacctca gataaagtag tggggtatat tacatctgca  15780
gtgccctaca gatctgtatc attgctgcat tgtgacattg aaattcctcc agggtccaat  15840
caaagcttac tagatcaact agctatcaat ttatctctga ttgccatgca ttctgtaagg  15900
gagggcgggg tagtaatcat caaagtgttg tatgcaatgg gatactactt tcatctactc  15960
atgaacttgt ttgctccgtg ttccacaaaa ggatatattc tctctaatgg ttatgcatgt  16020
cgaggagata tggagtgtta cctggtattt gtcatgggtt acctgggcgg gcctacattt  16080
gtacatgagg tggtgaggat ggcgaaaact ctggtgcagc ggcacggtac gcttttgtct  16140
aaatcagatg agatcacact gaccaggtta ttcacctcac agcggcagcg tgtgacagac  16200
atcctatcca gtcctttacc aagattaata aagtacttga ggaagaatat tgacactgcg  16260
ctgattgaag ccgggggaca gcccgtccgt ccattctgtg cggagagtct ggtgagcacg  16320
ctagcgaaca taactcagat aacccagatc atcgctagtc acattgacac agttatccgg  16380
tctgtgatat atatggaagc tgagggtgat ctcgctgaca cagtatttct atttacccct  16440
tacaatctct ctactgacgg gaaaaagagg acatcactta aacagtgcac gagacagatc  16500
ctagaggtta caatactagg tcttagagtc gaaaatctca ataaaatagg cgatataatc  16560
agcctagtgc ttaaaggcat gatctccatg gaggacctta tcccactaag gacatacttg  16620
aagcatagta cctgccctaa atatttgaag gctgtcctag gtattaccaa actcaaagaa  16680
atgtttacag acacttctgt actgtacttg actcgtgctc aacaaaaatt ctacatgaaa  16740
actataggca atgcagtcaa aggatattac agtaactgtg actcttaacg aaaatcacat  16800
attaataggc tcctttttg gccaattgta ttcttgttga tttaatcata ttatgttaga  16860
aaaaagttga accctgactc cttaggactc gaattcgaac tcaaataaat gtcttaaaaa  16920
aaggttgcgc acaattattc ttgagtgtag tctcgtcatt caccaaatct ttgtttggt   16979
```

```
<210> SEQ ID NO 60
<211> LENGTH: 25
<212> TYPE: PRT
<213> ORGANISM: Bovine respiratory syncytial virus

<400> SEQUENCE: 60

Met Ala Thr Thr Ala Met Arg Met Ile Ile Ser Ile Ile Phe Ile Ser
1               5                   10                  15

Thr Tyr Val Thr His Ile Thr Leu Cys
```

-continued

```
            20                  25


<210> SEQ ID NO 61
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 61

His His His His His His
1               5


<210> SEQ ID NO 62
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62

ctgtccactc ggcatcacac                                                  20


<210> SEQ ID NO 63
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63

ctagattaat tacggttacg c                                                21
```

RECOMBINANT NEWCASTLE DISEASE VIRUSES AND USES THEREOF FOR THE PREVENTION OF RSV DISEASE OR HUMAN METAPNEUMOVIRUS DISEASE

This application is a U.S. National Stage Application under 35 U.S.C. § 371 of International Patent Application No. PCT/US2019/046837, filed Aug. 16, 2019, which claims the benefit of U.S. Provisional Patent Application No. 62/765,242, filed Aug. 17, 2018, the disclosure of each of which is incorporated by reference herein in its entirety.

The instant application contains a Sequence Listing which has been submitted electronically in ASCII format and is hereby incorporated by reference in its entirety. Said ASCII copy, created on Jul. 31, 2019, is named 6923-280-228_SL.txt and is 375,809 bytes in size.

This invention was made with government support under grants 047226 and AI 088770 awarded by the National Institutes of Health. The government has certain rights in the invention.

1. INTRODUCTION

In one aspect, described herein are recombinant Newcastle disease virus ("NDV") comprising a packaged genome, wherein the packaged genome comprises a transgene encoding respiratory syncytial virus ("RSV") F protein. In a specific embodiment, described herein are recombinant NDV comprising a packaged genome, wherein the packaged genome comprises a transgene comprising a codon optimized nucleic acid sequence encoding RSV F protein. In a specific embodiment, described herein are recombinant NDV comprising a packaged genome, wherein the packaged genome comprises a transgene encoding a chimeric F protein, wherein the chimeric F protein comprises an RSV F protein ectodomain and NDV F protein transmembrane and cytoplasmic domains. In some embodiments, the ectodomain of the RSV F protein is encoded by a codon optimized nucleic acid sequence. Also described herein are compositions comprising such recombinant NDV and the use of such recombinant NDV to induce an immune response to RSV F protein. In another aspect, described herein are recombinant NDV comprising a packaged genome, wherein the packaged genome comprises a transgene encoding human metapneumovirus (hMPV) F protein. In a specific embodiment, described herein are recombinant NDV comprising a packaged genome, wherein the packaged genome comprises a transgene comprising a codon optimized nucleic acid sequence encoding hMPV F protein. In a specific embodiment, described herein are recombinant NDV comprising a packaged genome, wherein the packaged genome comprises a transgene encoding a chimeric F protein, wherein the chimeric F protein comprises an hMPV F protein ectodomain and NDV F protein transmembrane and cytoplasmic domains. In some embodiments, the ectodomain of the hMPV F protein is encoded by a codon optimized nucleic acid sequence. Also described herein are compositions comprising such recombinant NDV and the use of such recombinant NDV to induce an immune response to hMPV F protein.

2. BACKGROUND

2.1 RSV

Human respiratory syncytial virus (RSV), a negative sense RNA virus in the Pneumoviridae family (Afonso et al., 2016, Arch. Virol. 161: 2351-2360), is the major cause of bronchiolitis and pneumonia in infants (Hall C B, Long C E, Schnabel K C. Respiratory syncytial virus infections in previously healthy working adults. Clinical infectious diseases: an official publication of the Infectious Diseases Society of America. 2001; 33(6):792-6. Epub 2001/08/21. doi: 10.1086/322657. PubMed PMID: 11512084; Paramore L C, Ciuryla V, Ciesla G, Liu L. Economic impact of respiratory syncytial virus-related illness in the US: an analysis of national databases. PharmacoEconomics. 2004; 22(5):275-84. Epub 2004/04/06. PubMed PMID: 15061677). RSV outbreaks occur on an annual basis and essentially all persons are infected within the first two years of life. While RSV infection is limited to the upper respiratory tract in most healthy adults and children, severe, even fatal, RSV pneumonia occurs in young infants 2 to 4 months of age, transplant recipients and the elderly (Hall et al.). Secondary RSV infections, which are generally limited to the upper respiratory tract, present with mild, cold-like symptoms in healthy adults, but are commonly associated with otitis media in young children (Alper C M, Winther B, Mandel E M, Hendley J O, Doyle W J. Rate of concurrent otitis media in upper respiratory tract infections with specific viruses. Archives of otolaryngology—head & neck surgery. 2009; 135(1):17-21. Epub 2009/01/21. doi: 10.1001/archotol.135.1.17. PubMed PMID: 19153302; Hall C B, Walsh E E, Long C E, Schnabel K C. Immunity to and frequency of reinfection with respiratory syncytial virus. The Journal of infectious diseases. 1991; 163(4):693-8. Epub 1991/04/01. PubMed PMID: 2010624; Simoes E A, Carbonell-Estrany X. Impact of severe disease caused by respiratory syncytial virus in children living in developed countries. The Pediatric infectious disease journal. 2003; 22(2 Suppl):S13-8; discussion S8-20. Epub 2003/04/03. doi: 10.1097/01.inf.0000053881.47279.d9. PubMed PMID: 12671448). In addition, RSV has been associated with the development of asthma, and exacerbation of wheezing in asthmatic patients (Korppi M, Piippo-Savolainen E, Korhonen K, Remes S. Respiratory morbidity 20 years after RSV infection in infancy. Pediatric pulmonology. 2004; 38(2):155-60. Epub 2004/06/24. doi: 10.1002/ppul.20058. PubMed PMID: 15211700; Pelaia G, Vatrella A, Gallelli L, Renda T, Cazzola M, Maselli R, et al. Respiratory infections and asthma. Respiratory medicine. 2006; 100(5):775-84. Epub 2005/11/18. doi: 10.1016/j.rmed.2005.08.025. PubMed PMID: 16289785; Sigurs N, Bjarnason R, Sigurbergsson F, Kjellman B. Respiratory syncytial virus bronchiolitis in infancy is an important risk factor for asthma and allergy at age 7. American journal of respiratory and critical care medicine. 2000; 161(5):1501-7. Epub 2000/05/12. PubMed PMID: 10806145; Sigurs N, Gustafsson P M, Bjarnason R, Lundberg F, Schmidt S, Sigurbergsson F, et al. Severe respiratory syncytial virus bronchiolitis in infancy and asthma and allergy at age 13. American journal of respiratory and critical care medicine. 2005; 171(2):137-41. Epub 2004/11/02. doi: 10.1164/rccm.200406-7300C. PubMed PMID: 15516534).

Immunity to RSV is remarkably ineffective, allowing for repeated infection of immunocompetent children and adults (Buchman C A, Doyle W J, Pilcher O, Gentile D A, Skoner D P. Nasal and otologic effects of experimental respiratory syncytial virus infection in adults. American journal of otolaryngology. 2002; 23(2):70-5. Epub 2002/03/15. PubMed PMID: 1189397; Mills Jt, Van Kirk J E, Wright P F, Chanock R M. Experimental respiratory syncytial virus infection of adults. Possible mechanisms of resistance to infection and illness. Journal of immunology. 1971; 107(1): 123-30. Epub 1971/07/01. PubMed PMID: 5091954; Habibi M S, Jozwik A, Makris S, Dunning J, Paras A, DeVincenzo J P, et al. Impaired Antibody-mediated Protection and Defective IgA B-Cell Memory in Experimental Infection of Adults with Respiratory Syncytial Virus. American journal of respiratory and critical care medicine. 2015; 191(9):1040-9. doi: 10.1164/rccm.201412-22560C. PubMedPMID: 25730467; PubMed Central PMCID: PMCPMC4435460). Unlike other viral pathogens, serum antibody levels are very slow to rise following RSV infection, with a gradual accumulation of protective antibodies only after multiple re-infections (Wagner D K, Muelenaer P, Henderson F W, Snyder M H, Reimer C B, Walsh E E, et al. Serum immunoglobulin G antibody subclass response to respiratory syncytial virus F and G glycoproteins after first, second, and third infections. Journal of clinical microbiology. 1989; 27(3):589-92. Epub 1989/03/01. PubMed PMID: 2715331; PubMed Central PMCID: PMC267370; Welliver R C, Kaul T N, Putnam T I, Sun M, Riddlesberger K, Ogra P L. The antibody response to primary and secondary infection with respiratory syncytial virus: kinetics of class-specific responses. The Journal of pediatrics. 1980; 96(5):808-13. Epub 1980/05/01. PubMed PMID: 7365579). The inability of RSV to induce robust immunity following repeated natural infections likely underlies the difficulties encountered in attempts to design effective, attenuated vaccine strains (Crowe J E, Jr. Respiratory syncytial virus vaccine development. Vaccine. 2001; 20 Suppl 1:S32-7. Epub 2001/10/06. PubMed PMID: 11587807).

A recent study suggests that the ability of RSV to re-infect immunocompetent adults is correlated with a defect in B cell memory. Neutralizing serum and nasal antibody levels in experimentally infected healthy adult volunteers increased post-infection, but returned to baseline levels 6 months later (Habibi M S, Jozwik A, Makris S, Dunning J, Paras A, DeVincenzo J P, et al. Impaired Antibody-mediated Protection and Defective IgA B-Cell Memory in Experimental Infection of Adults with Respiratory Syncytial Virus. American journal of respiratory and critical care medicine. 2015; 191(9):1040-9. doi: 10.1164/rccm.201412-22560C. PubMed PMID: 25730467; PubMed Central PMCID: PMCPMC4435460). This differs markedly from the lifelong persistence of influenza specific IgG that follows this infection (Fujimoto C, Takeda N, Matsunaga A, Sawada A, Tanaka T, Kimoto T, et al. Induction and maintenance of anti-influenza antigen-specific nasal secretory IgA levels and serum IgG levels after influenza infection in adults. Influenza Other Respir Viruses. 2012; 6(6):396-403. doi: 10.1111/j.1750-2659.2011.00330.x. PubMed PMID: 22226319; PubMed Central PMCID: PMCPMC4941696). Thus, it is important that any RSV vaccine candidate induce both systemic and mucosal RSV-specific antibodies, but do so in a manner that induces a B cell memory response superior to that induced by RSV infection.

While an effective RSV vaccine has been eagerly sought, no licensed vaccine yet exists. RSV vaccine development has focused primarily on live-attenuation, a strategy with demonstrated safety in infants, the target population for most RSV vaccines. Unfortunately, live-attenuated RSV vaccines evaluated clinically to date have been poorly immunogenic, an outcome that could be predicted from the poor immune response to natural RSV infection (Gomez M, Mufson M A, Dubovsky F, Knightly C, Zeng W, Losonsky G. Phase-I study MEDI-534, of a live, attenuated intranasal vaccine against respiratory syncytial virus and parainfluenza-3 virus in seropositive children. The Pediatric infectious disease journal. 2009; 28(7):655-8. Epub 2009/06/02. doi: 10.1097/INF.0b013e318199c3b1. PubMed PMID: 19483659; Wright P F, Belshe R B, Kim H W, Van Voris L P, Chanock R M. Administration of a highly attenuated, live respiratory syncytial virus vaccine to adults and children. Infection and immunity. 1982; 37(1):397-400. Epub 1982/07/01. PubMed PMID: 7107009; PubMed Central PMCID: PMC347542; Wright P F, Shinozaki T, Fleet W, Sell S H, Thompson J, Karzon D T. Evaluation of a live, attenuated respiratory syncytial virus vaccine in infants. The Journal of pediatrics. 1976; 88(6):931-6. Epub 1976/06/01. PubMed PMID: 178852). Disappointing immunogenicity of live-attenuated RSV vaccines has led investigators to diversify RSV vaccine strategies (reviewed in Mazur N I, Martinon-Torres F, Baraldi E, Fauroux B, Greenough A, Heikkinen T, et al. Lower respiratory tract infection caused by respiratory syncytial virus: current management and new therapeutics. Lancet Respir Med. 2015; 3(11):888-900. doi: 10.1016/52213-2600(15)00255-6. PubMed PMID: 26411809).

An important goal of pre-clinical vaccine evaluation is to establish the safety profile of a vaccine candidate. This is particularly true for RSV vaccine candidates given the history of the 1960's vaccine trial in which enhanced pathology following natural RSV infection of infants that had previously received a formalin-inactivated RSV vaccine (FI-RSV) (Kim H W, Canchola J G, Brandt C D, Pyles G, Chanock R M, Jensen K, et al. Respiratory syncytial virus disease in infants despite prior administration of antigenic inactivated vaccine. American journal of epidemiology. 1969; 89(4):422-34. Epub 1969/04/01. PubMed PMID: 4305198). It has been suggested that this vaccine-enhanced disease may have been related to the presence of non-neutralizing antibody, allowing virus replication and simultaneous immune complex deposition in the lung (Polack F P, Teng M N, Collins P L, Prince G A, Exner M, Regele H, et al. A role for immune complexes in enhanced respiratory syncytial virus disease. The Journal of experimental medicine. 2002; 196(6):859-65. PubMed PMID: 12235218; PubMed Central PMCID: PMCPMC2194058). FI-RSV has been shown to generate primarily non-neutralizing antibody in mice, and RSV challenge of mice receiving the FI-RSV vaccine resulted in immune complex mediated pathology (Id.). It is therefore important to demonstrate the induction of long-lasting, virus-specific adaptive immunity by any vaccine candidate, but also to verify the absence of disease-promoting immune responses.

2.2 HMPV

Human metapneumovirus (hMPV) is a nonsegmented negative strand RNA virus in the Pneumovirinae family that also includes human respiratory syncytial virus (RSV) (Afonso et al., 2016, Arch. Virol. 161: 2351-2360). hMPV was first isolated in the Netherlands in 2001 (van den Hoogen B G, de Jong J C, Groen J, Kuiken T, de Groot R, Fouchier R A, Osterhaus A D. 2001. "A newly discovered human pneumovirus isolated from young children with respiratory tract disease." Nat Med 7:719-724) and has subsequently been identified worldwide as second to RSV in causing respiratory disease and hospitalization in infants, with also a significant impact in young kids together with RSV and influenza viruses (Esper F, Boucher D, Weibel C, Martinello R A, Kahn J S. 2003. Human metapneumovirus infection in the United States: clinical manifestations associated with a newly emerging respiratory infection in children. Pediatrics 111:1407-1410). In fact, hMPV was found to be a major pathogen associated with hospitalization of children and with the same severity of illness as RSV but in a slightly older population (Akhras N, Weinberg J B, Newton D. 2010. Human metapneumovirus and respiratory syncytial virus: subtle differences but comparable severity.

Infect Dis Rep 2:e12). Both RSV and hMPV are an important cause of severe respiratory disease in immunocompromised patients. No vaccines are available at this moment for these two important human respiratory pathogens. Thus, a need exists for a safe and effective vaccine for RSV and hMPV.

2.3 NDV

Newcastle disease virus (NDV) is a member of the Avulavirus genus in the Paramyxoviridae family, which has been shown to infect a number of avian species (Alexander, DJ (1988). Newcastle disease, Newcastle disease virus—an avian paramyxovirus. Kluwer Academic Publishers: Dordrecht, The Netherlands. pp 1-22). NDV possesses a single-stranded RNA genome in negative sense and does not undergo recombination with the host genome or with other viruses (Alexander, DJ (1988). Newcastle disease, Newcastle disease virus—an avian paramyxovirus. Kluwer Academic Publishers: Dordrecht, The Netherlands. pp 1-22). The genomic RNA contains genes in the order of 3'-NP-P-M-F-HN-L-5', described in further detail below. Two additional proteins, V and W, are produced by NDV from the P gene by alternative mRNAs that are generated by RNA editing. The genomic RNA also contains a leader sequence at the 3' end.

The structural elements of the virion include the virus envelope which is a lipid bilayer derived from the cell plasma membrane. The glycoprotein, hemagglutinin-neuraminidase (HN) protrudes from the envelope allowing the virus to contain both hemagglutinin (e.g., receptor binding/fusogenic) and neuraminidase activities. The fusion glycoprotein (F), which also interacts with the viral membrane, is first produced as an inactive precursor, then cleaved post-translationally to produce two disulfide linked polypeptides. The active F protein is involved in penetration of NDV into host cells by facilitating fusion of the viral envelope with the host cell plasma membrane. The matrix protein (M), is involved with viral assembly, and interacts with both the viral membrane as well as the nucleocapsid proteins.

The main protein subunit of the nucleocapsid is the nucleocapsid protein (NP) which confers helical symmetry on the capsid. In association with the nucleocapsid are the P and L proteins. The phosphoprotein (P), which is subject to phosphorylation, is thought to play a regulatory role in transcription, and may also be involved in methylation, phosphorylation and polyadenylation. The L gene, which encodes an RNA-dependent RNA polymerase, is required for viral RNA synthesis together with the P protein. The L protein, which takes up nearly half of the coding capacity of the viral genome is the largest of the viral proteins, and plays an important role in both transcription and replication. The V protein has been shown to inhibit interferon-alpha and to contribute to the virulence of NDV (Huang et al. (2003). Newcastle disease virus V protein is associated with viral pathogenesis and functions as an Alpha Interferon Antagonist. *Journal of Virology* 77: 8676-8685).

3. SUMMARY

In one aspect, presented herein are recombinant Newcastle disease virus ("NDV") comprising a packaged genome, wherein the packaged genome comprises a transgene encoding a respiratory syncytial virus ("RSV") F protein. The RSV F protein may be an RSV F protein of a human or bovine strain of RSV. In a specific embodiment, the transgene encodes the human RSV F protein comprising the amino acid sequence set forth in SEQ ID NO: 6 or the bovine RSV F protein comprising the amino acid sequence set forth in SEQ ID NO: 10. Due to the degeneracy of the nucleic acid code, multiple different nucleic acid sequences may encode for the same human RSV F protein or the same bovine RSV F protein. In one embodiment, described herein is a recombinant NDV comprising a packaged genome comprising a transgene encoding a human RSV F protein, wherein the transgene comprises an RNA sequence corresponding to the negative sense of the cDNA sequence of SEQ ID NO:1. In another embodiment described herein is a recombinant NDV comprising a packaged genome comprising a transgene encoding a human RSV F protein comprising the amino acid sequence set forth in SEQ ID NO:49, 50 or 58. In another embodiment described herein is a recombinant NDV comprising a packaged genome comprising a transgene encoding a human RSV F protein, wherein the transgene comprises an RNA sequence corresponding to the negative sense of the cDNA sequence of SEQ ID NO: 25, 27 or 29. In another embodiment, described herein is a recombinant NDV comprising a packaged genome comprising a transgene encoding a bovine RSV F protein, wherein the transgene comprises an RNA sequence corresponding to the negative sense of the cDNA sequence of SEQ ID NO:9. In another embodiment, described herein is a recombinant NDV comprising a packaged genome comprising a transgene encoding a bovine RSV F protein, wherein the transgene comprises an RNA sequence corresponding to the negative sense of the cDNA sequence of SEQ ID NO:40 or 42. In a preferred embodiment, a transgene comprises a codon optimized version of a nucleic acid sequence encoding an RSV F protein (e.g., a human or bovine RSV F protein). In a specific embodiment, the RSV F protein is expressed by cells infected with the recombinant NDV.

In a specific embodiment, described herein are recombinant NDV comprising a packaged genome, wherein the packaged genome comprises a transgene comprising a codon optimized nucleic acid sequence encoding a human RSV F protein. Specific examples of codon optimized nucleic acid sequences encoding a human RSV F protein include SEQ ID NO: 2, 26, 28 or 30. In a preferred embodiment, described herein is a recombinant NDV comprising a packaged genome comprising a transgene encoding a human RSV F protein, wherein the transgene comprises an RNA sequence corresponding to the negative sense of the cDNA sequence of SEQ ID NO:2. In a specific embodiment, the human RSV F protein is expressed by cells infected with the recombinant NDV.

In a specific embodiment, described herein are recombinant NDV comprising a packaged genome, wherein the packaged genome comprises a transgene comprising a codon optimized nucleic acid sequence encoding a bovine RSV F protein. Specific examples of codon optimized nucleic acid sequences encoding a bovine RSV F protein include SEQ ID NO: 11, 41, or 43. In a preferred embodiment, described herein is a recombinant NDV comprising a packaged genome comprising a transgene encoding a bovine RSV F protein, wherein the transgene comprises an RNA sequence corresponding to the negative sense of the cDNA sequence of SEQ ID NO:11. In a specific embodiment, the bovine RSV F protein is expressed by cells infected with the recombinant NDV.

In another embodiment, described herein are recombinant NDV comprising a packaged genome, wherein the packaged genome comprises a transgene encoding a chimeric F protein, wherein the chimeric F protein comprises an RSV F protein ectodomain and NDV F protein transmembrane and cytoplasmic domains. In other words, the NDV F protein transmembrane and cytoplasmic domains replace the RSV F protein transmembrane and cytoplasmic domains so that the chimeric F protein does not include the RSV F protein transmembrane and cytoplasmic domains. The RSV F protein may be an RSV F protein of a human or bovine strain of RSV. In a specific embodiment, the transgene encodes a chimeric F protein comprising the amino acid sequence set forth in SEQ ID NO: 7 or 33. In another embodiment, described herein are recombinant NDV comprising a packaged genome, wherein the packaged genome comprises a transgene encoding a chimeric F protein, wherein the chimeric F protein comprises a human RSV F protein ectodomain and NDV F protein transmembrane and cytoplasmic domains, and wherein the transgene comprises an RNA sequence corresponding to the negative sense of the cDNA sequence of SEQ ID NO:51. In another embodiment, described herein are recombinant NDV comprising a packaged genome, wherein the packaged genome comprises a transgene encoding a chimeric F protein, wherein the chimeric F protein comprises a bovine RSV F protein ectodomain and NDV F protein transmembrane and cytoplasmic domains, and wherein the transgene comprises an RNA sequence corresponding to the negative sense of the cDNA sequence of SEQ ID NO: 31. In a preferred embodiment, a transgene comprises a codon optimized version of a nucleic acid sequence encoding the RSV F protein ectodomain (e.g., a human or bovine RSV F protein ectodomain). In a specific embodiment, the RSV F protein is expressed by cells infected with the recombinant NDV. In another specific embodiment, the chimeric F protein is expressed by cells infected with the recombinant NDV and the chimeric F protein is incorporated into the NDV virion.

In a specific embodiment, described herein are recombinant NDV comprising a packaged genome, wherein the packaged genome comprises a transgene encoding a chimeric F protein, wherein the chimeric F protein comprises a human RSV F protein ectodomain and NDV F protein transmembrane and cytoplasmic domains, and wherein the ectodomain of the RSV F protein is encoded by a codon optimized nucleic acid sequence. Specific examples of nucleic acid sequences encoding a chimeric F protein, wherein the chimeric F protein comprises a human RSV F protein ectodomain and NDV F protein transmembrane and cytoplasmic domains, and wherein the ectodomain of the RSV F protein is encoded by a codon optimized nucleic acid sequence, include SEQ ID NO:4, 44, 45 or 46. In a preferred embodiment, described herein is a recombinant NDV comprising a packaged genome, wherein the packaged genome comprises a transgene encoding a chimeric F protein, wherein the chimeric F protein comprises a human RSV F protein ectodomain and NDV F protein transmembrane and cytoplasmic domains, and wherein the transgene comprises an RNA sequence corresponding to the negative sense of the cDNA sequence of SEQ ID NO:4. In a specific embodiment, the chimeric F protein is expressed by cells infected with the recombinant NDV. In another specific embodiment, the chimeric F protein is expressed by cells infected with the recombinant NDV and the chimeric F protein is incorporated into the NDV virion.

In a specific embodiment, described herein are recombinant NDV comprising a packaged genome, wherein the packaged genome comprises a transgene encoding a chimeric F protein, wherein the chimeric F protein comprises a bovine RSV F protein ectodomain and NDV F protein transmembrane and cytoplasmic domains, and wherein the ectodomain of the RSV F protein is encoded by a codon optimized nucleic acid sequence. Specific examples of nucleic acid sequences encoding a chimeric F protein, wherein the chimeric F protein comprises a bovine RSV F protein ectodomain and NDV F protein transmembrane and cytoplasmic domains, and wherein the ectodomain of the RSV F protein is encoded by a codon optimized nucleic acid sequence, include SEQ ID NO:14, 38 or 39. In a preferred embodiment, described herein is a recombinant NDV comprising a packaged genome, wherein the packaged genome comprises a transgene encoding a chimeric F protein, wherein the chimeric F protein comprises a bovine RSV F protein ectodomain and NDV F protein transmembrane and cytoplasmic domains, and wherein the transgene comprises an RNA sequence corresponding to the negative sense of the cDNA sequence of SEQ ID NO:14. In a specific embodiment, the chimeric F protein is expressed by cells infected with the recombinant NDV. In another specific embodiment, the chimeric F protein is expressed by cells infected with the recombinant NDV and the chimeric F protein is incorporated into the NDV virion.

The recombinant NDV may have the backbone of any NDV type or strain, including, but not limited to, naturally-occurring strains, variants or mutants, mutagenized viruses, reassortants or genetically engineered viruses, or any combination thereof. The NDV that serves as the backbone for genetic engineering of the recombinant NDV may be a lentogenic strain, a mesogenic strain, or a velogenic strain. In a specific embodiment, the recombinant NDV comprises an NDV backbone which is lentogenic. In another specific embodiment, the recombinant NDV comprises an NDV backbone of the NDV LaSota strain. See, .e.g., SEQ ID NO: 47 for a cDNA sequence of the genomic sequence of NDV LaSota strain. In another specific embodiment, the recombinant NDV comprises an NDV backbone of the NDV Hitchner B1 strain. See, e.g., SEQ ID NO: 48 for a cDNA sequence of the genomic sequence of NDV Hitchner strain. In another specific embodiment, the recombinant NDV comprises an NDV backbone of a lentogenic strain other than the NDV Hitchner B1 strain. In another specific embodiment, the recombinant NDV comprises an NDV backbone of the NDV Fuller strain. In another specific embodiment, the recombinant NDV comprises an NDV backbone of the NDV Ulster strain.

The transgene encoding a RSV F protein or a chimeric F protein may be incorporated into the genome of any NDV type or strain. In a specific embodiment, the transgene is incorporated into the genome of a lentogenic NDV. In another specific embodiment, the transgene is incorporated in the genome of NDV strain LaSota. See, e.g., SEQ ID NO: 47 for a cDNA sequence of the genomic sequence of NDV LaSota strain. Other examples of NDV strains into which the transgene may be incorporated are the NDV Fuller, the NDV Ulster strain or the NDV Hitchner B1 strain. In a specific embodiment, the transgene may be incorporated into the genomic sequence of NDV Hitchner B1 strain. See, e.g., SEQ ID NO:48 for a cDNA sequence of the genomic sequence of NDV Hitchner B1 strain. In a specific embodiment, the transgene may be incorporated into the genome of a lentogenic strain other than the NDV Hitchner B1 strain. The transgene may be incorporated into the NDV genome between two transcription units (e.g., between NDV P and M genes).

In a specific embodiment, a transgene encoding a human RSV F protein is incorporated into the genome of any NDV type or strain (e.g., NDV LaSota strain). For example, a transgene encoding the human RSV F protein set forth in SEQ ID NO:6 may be incorporated into the genome of any NDV type or strain (e.g., NDV LaSota strain). In a specific embodiment, such a transgene comprises an RNA sequence corresponding to the negative sense of the cDNA sequence set forth in SEQ ID NO:1. However, given the degeneracy of the nucleic acid code, there are a number of different nucleic acid sequences that may encode the same human RSV F protein. In certain embodiments, a transgene encoding the human RSV F protein set forth in SEQ ID NO:49, 50 or 58 may be incorporated into the genome of any NDV type or strain (e.g., NDV LaSota strain). In some embodiments, a transgene encoding the human RSV F protein comprises the amino acid sequence encoded by the nucleic acid sequence comprising the sequence of SEQ ID NO:25, 27 or 29. In a specific embodiment, transgene encoding a human RSV F protein is codon optimized. For example, the human RSV F protein is encoded by the codon optimized nucleic acid sequence set forth in SEQ ID NO: 2, 26, 28 or 30. The transgene encoding a human RSV F protein may be incorporated between any two NDV transcription units (e.g., between NDV P and M genes). In a specific embodiment, a recombinant NDV described herein comprises a packaged genome, wherein the packaged genome corresponds to a negative sense RNA sequence transcribed from the cDNA sequence set forth in SEQ ID NO: 3. In certain embodiment, the genome of the recombinant NDV does not comprise a heterologous sequence encoding a heterologous protein other than the human RSV F protein. In some embodiments, the genome of the recombinant NDV does not comprise a transgene other than a transgene encoding a human RSV F protein. In certain embodiments, the genome of the recombinant NDV comprises a transgene encoding a human RSV F protein and a transgene encoding an hMPV F protein or a chimeric F protein, wherein the chimeric F protein comprises an hMPV F protein ectodomain and NDV F protein transmembrane and cytoplasmic domains. In such embodiments, the genome of the recombinant NDV may not comprise any additional transgenes.

In a specific embodiment, a transgene encoding a bovine RSV F protein is incorporated into the genome of any NDV type or strain (e.g., NDV LaSota strain). For example, a transgene encoding the bovine RSV F protein comprising the amino acid sequence set forth in SEQ ID NO:10 may be incorporated into the genome of any NDV type or strain (e.g., NDV LaSota strain). In a specific embodiment, such a transgene comprises an RNA sequence corresponding to the negative sense of the cDNA sequence set forth in SEQ ID NO:9. However, given the degeneracy of the nucleic acid code, there are a number of different nucleic acid sequences that may encode the same bovine RSV F protein. In some embodiments, a transgene encoding the bovine RSV F protein comprises the amino acid sequence encoded by the nucleic acid sequence comprising the sequence of SEQ ID NO:40 or 42. In a specific embodiment, transgene encoding a bovine RSV F protein is codon optimized. For example, the bovine RSV F protein is encoded by the codon optimized nucleic acid sequence set forth in SEQ ID NO: 11, 41 or 43. The transgene encoding a bovine RSV F protein may be incorporated between any two NDV transcription units (e.g., between NDV P and M genes). In a specific embodiment, a recombinant NDV described herein comprises a packaged genome, wherein the packaged genome is an RNA sequence corresponding to the negative sense of the cDNA sequence set forth in SEQ ID NO: 12 or 13. In certain embodiment, the genome of the recombinant NDV does not comprise a heterologous sequence encoding a heterologous protein other than the bovine RSV F protein. In some embodiments, the genome of the recombinant NDV does not comprise a transgene other than a transgene encoding a bovine RSV F protein.

In a specific embodiment, a transgene encoding a chimeric F protein is incorporated into the genome of any NDV type or strain (e.g., NDV LaSota strain), wherein the chimeric F protein comprises the ectodomain of an RSV F protein (e.g., a human or bovine RSV F protein) and NDV F protein transmembrane and cytoplasmic domains. For example, a transgene encoding the chimeric F protein comprising the amino acid sequence set forth in SEQ ID NO:7 may be incorporated into the genome of any NDV type or strain (e.g., NDV LaSota strain). In a specific embodiment, such a transgene comprises an RNA sequence corresponding to the negative sense of the cDNA sequence set forth in SEQ ID NO: 51. However, given the degeneracy of the nucleic acid code, there are a number of different nucleic acid sequences that may encode the same chimeric F protein. In a specific embodiment, the nucleic acid sequence encoding a human RSV F protein ectodomain is codon optimized. For example, the nucleic acid sequence of one or more of the domains of the chimeric F protein may be codon optimized (e.g. the ectodomain of the chimeric F protein may be encoded by a codon optimized nucleic acid sequence, such as set forth in SEQ ID NO: 4, 44, 45, or 46. The transgene encoding a chimeric F protein may be incorporated between any two NDV transcription units (e.g., between NDV P and M genes). In a specific embodiment, a recombinant NDV described herein comprises a packaged genome, wherein the packaged genome corresponds to a negative sense RNA sequence transcribed from a cDNA sequence comprising the sequence set forth in SEQ ID NO: 5. In certain embodiments, the genome of the recombinant NDV does not comprise a heterologous sequence encoding a heterologous protein other than the chimeric F protein. In some embodiments, the genome of the recombinant NDV does not comprise a transgene other than a transgene encoding a chimeric F protein. In certain embodiments, the genome of the recombinant NDV comprises a transgene encoding a first chimeric F protein and a transgene encoding an hMPV F protein or a second chimeric F protein, wherein the first chimeric F protein comprises a human RSV F protein ectodomain and NDV F protein transmembrane and cytoplasmic domains and the second chimeric F protein comprises an hMPV F protein ectodomain and NDV F protein transmembrane and cytoplasmic domains. In such embodiments, the genome of the recombinant NDV may not comprise any additional transgenes.

In a specific embodiment, a transgene encoding a chimeric F protein is incorporated into the genome of any NDV type or strain (e.g., NDV LaSota strain), wherein the chimeric F protein comprises the ectodomain of an RSV F protein (e.g., a human or bovine RSV F protein) and NDV F protein transmembrane and cytoplasmic domains. For example, a transgene encoding the chimeric F protein comprising the amino acid sequence set forth in SEQ ID NO:33 may be incorporated into the genome of any NDV type or strain (e.g., NDV LaSota strain). In a specific embodiment, such a transgene comprises an RNA sequence corresponding to the negative sense of the cDNA sequence set forth in SEQ ID NO: 31. However, given the degeneracy of the nucleic acid code, there are a number of different nucleic acid sequences that may encode the same chimeric F protein. In a specific embodiment, the nucleic acid sequence encoding a bovine RSV F protein ectodomain is codon optimized. For example, the nucleic acid sequence of one or more of the domains of the chimeric F protein may be codon optimized (e.g. the ectodomain of the chimeric F protein may be encoded by a codon optimized nucleic acid sequence, such as set forth in SEQ ID NO: 14, 38, or 39. The transgene encoding a chimeric F protein may be incorporated between any two NDV transcription units (e.g., between NDV P and M genes). In certain embodiment, the genome of the recombinant NDV does not comprise a heterologous sequence encoding a heterologous protein other than the chimeric F protein. In some embodiments, the genome of the recombinant NDV does not comprise a transgene other than a transgene encoding a chimeric F protein. In certain embodiments, the genome of the recombinant NDV comprises a transgene encoding a first chimeric F protein and a transgene encoding an hMPV F protein or a second chimeric F protein, wherein the first chimeric F protein comprises a bovine RSV F protein ectodomain and NDV F protein transmembrane and cytoplasmic domains and the second chimeric F protein comprises an hMPV F protein ectodomain and NDV F protein transmembrane and cytoplasmic domains. In such embodiments, the genome of the recombinant NDV may not comprise any additional transgenes.

The recombinant NDV and uses thereof described herein are based, in part, on the robust, long-lived antigen-specific humoral immunity induced by the recombinant NDV and the prevention of RSV infection of the lower airway and the largely eliminated RSV replication in the upper airway in animals. In addition, the recombinant NDV and uses thereof described herein are based, in part, on the demonstration of vaccine efficacy in previously-infected, seropositive animals. Further, the recombinant NDV and uses thereof described herein are based, in part, on the decreased inflammation induced by the recombinant NDV with the NDV LaSota strain backbone and the enhanced RSV F protein expression resulting from the use of a codon optimized nucleic acid sequence encoding RSV F protein or a nucleic acid sequence encoding a chimeric F protein.

In another aspect, presented herein are methods for inducing an immune response to a RSV F protein comprising administering to a subject (e.g., a human subject) a recombinant NDV, wherein the recombinant NDV comprises a packaged genome comprising a transgene encoding a human RSV F protein. In one embodiment, the human RSV F protein comprises the amino acid sequence set forth in SEQ ID NO: 6, 49, 50 or 58. Due to the degeneracy of the nucleic acid code, a number of different nucleic acid sequences may encode for the same human RSV F protein. For example, the human RSV F protein may be encoded a sequence comprising the amino acid sequence set forth SEQ ID NO:1, 25, 27 or 29. Alternatively, the nucleic acid sequence encoding the human RSV F protein may be codon optimized, such as set forth in SEQ ID NO: 2, 26, 28 or 30. In some embodiments, the human RSV F protein is encoded by a sequence comprising the nucleic acid sequence set forth in SEQ ID NO:1, 2, 25, 26, 27, 28, 29, or 30. In a specific embodiment, presented herein are methods for inducing an immune response to a RSV F protein comprising administering to a subject (e.g., a human subject) a recombinant NDV, wherein the recombinant NDV comprises a packaged genome comprising a transgene, and wherein the transgene comprises a codon optimized nucleic acid sequence encoding a human RSV F protein. In a specific embodiment, the human RSV F protein is expressed by cells infected with the recombinant NDV. In another specific embodiment, the recombinant NDV is administered to a subject intranasally. In another specific embodiment, the subject is a human infant. In another specific embodiment, the subject is a human infant six months old or older. In another specific embodiment, the subject is a human toddler. In another specific embodiment, the subject is a human child. In another specific embodiment, the subject is a human adult. In another specific embodiment, the subject is an elderly human. In another specific embodiment, the subject is seropositive for antibodies to RSV (e.g., the subject is seropositive for antibodies to RSV F protein or RSV G protein).

In another aspect, presented herein are methods for inducing an immune response to a RSV F protein comprising administering to a subject (e.g., a bovine subject) a recombinant NDV, wherein the recombinant NDV comprises a packaged genome comprising a transgene encoding a bovine RSV F protein. In one embodiment, the bovine RSV F protein comprises the amino acid sequence set forth in SEQ ID NO: 10. Due to the degeneracy of the nucleic acid code, a number of different nucleic acid sequences may encode for the same bovine RSV F protein. For example, the bovine RSV F protein may be encoded by SEQ ID NO:9. Alternatively, the nucleic acid sequence encoding the bovine RSV F protein may be codon optimized, such as set forth in SEQ ID NO: 11. In some embodiments, the bovine RSV F protein is encoded by a sequence comprising the nucleic acid sequence set forth in SEQ ID NO:9, 11, 40, 41, 42, or 43. In a specific embodiment, presented herein are methods for inducing an immune response to a RSV F protein comprising administering to a subject (e.g., a bovine subject) a recombinant NDV, wherein the recombinant NDV comprises a packaged genome comprising a transgene, and wherein the transgene comprises a codon optimized nucleic acid sequence encoding a bovine RSV F protein. In a specific embodiment, the bovine RSV F protein is expressed by cells infected with the recombinant NDV. In another specific embodiment, the recombinant NDV is administered to a subject intranasally. In another specific embodiment, the subject is seropositive for antibodies to RSV (e.g., the subject is seropositive for antibodies to RSV F protein or RSV G protein).

In another aspect, presented herein are methods for inducing an immune response to a RSV F protein comprising administering to a subject (e.g., a human subject) a recombinant NDV, wherein the recombinant NDV comprises a packaged genome comprising a transgene encoding a chimeric F protein, wherein the chimeric F protein comprises a human RSV F protein ectodomain and NDV F protein transmembrane and cytoplasmic domains. In one embodiment, the chimeric F protein comprises the amino acid sequence set forth in SEQ ID NO: 7. Due to the degeneracy of the nucleic acid code, a number of different nucleic acid sequences may encode for the same chimeric F protein. For example, the chimeric F protein may be encoded by SEQ ID NO:51. Alternatively, the nucleic acid sequence encoding one or more domains of the chimeric F protein may be codon optimized (e.g., the nucleic acid sequence encoding the RSV F protein ectodomain may be codon optimized, such as set forth in SEQ ID NO:4, 44, 45, or 46). In a specific embodiment, presented herein are methods for inducing an immune response to a RSV F protein comprising administering to a subject (e.g., a human subject) a recombinant NDV, wherein the recombinant NDV comprises a packaged genome comprising a transgene encoding a chimeric F protein, wherein the chimeric F protein comprise a human RSV F protein ectodomain and NDV F protein transmembrane and cytoplasmic domains, and wherein the transgene comprises a codon optimized nucleic acid sequence encoding the RSV F protein ectodomain. In a specific embodiment, the chimeric F protein is expressed by cells infected with the recombinant NDV. In another specific embodiment, the recombinant NDV is administered to a subject intranasally. In another specific embodiment, the subject is a human infant. In another specific embodiment, the subject is a human infant six months old or older. In another specific embodiment, the subject is a human toddler. In another specific embodiment, the subject is a human child. In another specific embodiment, the subject is a human adult. In another specific embodiment, the subject is an elderly human. In another specific embodiment, the subject is seropositive for antibodies to RSV (e.g., the subject is seropositive for antibodies to RSV F protein or RSV G protein).

In another aspect, presented herein are methods for inducing an immune response to a RSV F protein comprising administering to a subject (e.g., a bovine subject) a recombinant NDV, wherein the recombinant NDV comprises a packaged genome comprising a transgene encoding a chimeric F protein, wherein the chimeric F protein comprises a bovine RSV F protein ectodomain and NDV F protein transmembrane and cytoplasmic domains. In one embodiment, the chimeric F protein comprises the amino acid sequence set forth in SEQ ID NO:33. Due to the degeneracy of the nucleic acid code, a number of different nucleic acid sequences may encode for the same chimeric F protein. For example, the chimeric F protein may be encoded by SEQ ID NO:31. Alternatively, the nucleic acid sequence encoding one or more domains of the chimeric F protein may be codon optimized (e.g., the nucleic acid sequence encoding the RSV F protein ectodomain may be codon optimized, such as set forth in SEQ ID NO:14, 38, or 39). In a specific embodiment, presented herein are methods for inducing an immune response to a RSV F protein comprising administering to a subject (e.g., a bovine subject) a recombinant NDV, wherein the recombinant NDV comprises a packaged genome comprising a transgene encoding a chimeric F protein, wherein the chimeric F protein comprise a bovine RSV F protein ectodomain and NDV F protein transmembrane and cytoplasmic domains, and wherein the transgene comprises a codon optimized nucleic acid sequence encoding the RSV F protein ectodomain. In a specific embodiment, the chimeric F protein is expressed by cells infected with the recombinant NDV. In another specific embodiment, the recombinant NDV is administered to a subject intranasally. In another specific embodiment, the subject is seropositive for antibodies to RSV (e.g., the subject is seropositive for antibodies to RSV F protein or RSV G protein).

In another aspect, presented herein are methods for immunizing against RSV comprising administering to a subject (e.g., a human subject) a recombinant NDV, wherein the recombinant NDV comprises a packaged genome comprising a transgene encoding a human RSV F protein. In one embodiment, the human RSV F protein comprises the amino acid sequence set forth in SEQ ID NO: 6, 49, 50 or 58. Due to the degeneracy of the nucleic acid code, a number of different nucleic acid sequences may encode for the same human RSV F protein. For example, the human RSV F protein may be encoded by SEQ ID NO:1, 25, 27 or 29. Alternatively, the nucleic acid sequence encoding the human RSV F protein may be codon optimized, such as set forth in SEQ ID NO:2, 26, 28, or 30. In some embodiments, the human RSV F protein is encoded by a nucleic acid sequence comprising the sequence of SEQ ID NO: 1, 2, 25, 26, 27. 28, 29, or 30. In a specific embodiment, presented herein are methods for immunizing against RSV comprising administering to a subject (e.g., a human subject) a recombinant NDV, wherein the recombinant NDV comprises a packaged genome comprising a transgene, and wherein the transgene comprises a codon optimized nucleic acid sequence encoding a human RSV F protein. In a specific embodiment, the human RSV F protein is expressed by cells infected with the recombinant NDV. In another specific embodiment, the recombinant NDV is administered to a subject intranasally. In another specific embodiment, the subject is a human infant. In another specific embodiment, the subject is a human infant six months old or older. In another specific embodiment, the subject is a human toddler. In another specific embodiment, the subject is a human child. In another specific embodiment, the subject is a human adult. In another specific embodiment, the subject is an elderly human. In another specific embodiment, the subject is seropositive for antibodies to RSV (e.g., the subject is seropositive for antibodies to RSV F protein or RSV G protein).

In another aspect, presented herein are methods for immunizing against RSV comprising administering to a subject (e.g., a bovine subject) a recombinant NDV, wherein the recombinant NDV comprises a packaged genome comprising a transgene encoding a bovine RSV F protein. In one embodiment, the bovine RSV F protein comprises the amino acid sequence set forth in SEQ ID NO: 10. Due to the degeneracy of the nucleic acid code, a number of different nucleic acid sequences may encode for the same bovine RSV F protein. For example, the bovine RSV F protein may be encoded by SEQ ID NO:9. Alternatively, the nucleic acid sequence encoding the bovine RSV F protein may be codon optimized, such as set forth in SEQ ID NO: 11. In some embodiments, the bovine RSV F protein is encoded by a sequence comprising the nucleic acid sequence set forth in SEQ ID NO:9, 11, 40, 41, 42 or 43. In a specific embodiment, presented herein are methods for immunizing against RSV comprising administering to a subject (e.g., a bovine subject) a recombinant NDV, wherein the recombinant NDV comprises a packaged genome comprising a transgene, and wherein the transgene comprises a codon optimized nucleic acid sequence encoding a bovine RSV F protein. In a specific embodiment, the bovine RSV F protein is expressed by cells infected with the recombinant NDV. In another specific embodiment, the recombinant NDV is administered to a subject intranasally. In another specific embodiment, the subject is seropositive for antibodies to RSV (e.g., the subject is seropositive for antibodies to RSV F protein or RSV G protein).

In another aspect, presented herein are methods for immunizing against RSV comprising administering to a subject (e.g., a human subject) a recombinant NDV, wherein the recombinant NDV comprises a packaged genome comprising a transgene encoding a chimeric F protein, wherein the chimeric F protein comprises a human RSV F protein ectodomain and NDV F protein transmembrane and cytoplasmic domains. In one embodiment, the chimeric F protein comprises the amino acid sequence set forth in SEQ ID NO:7. Due to the degeneracy of the nucleic acid code, a number of different nucleic acid sequences may encode for the same chimeric F protein. For example, the chimeric F protein may be encoded by SEQ ID NO:51. Alternatively, the nucleic acid sequence encoding one or more domains of the chimeric F protein may be codon optimized (e.g., the nucleic acid sequence encoding the RSV F protein ectodomain may be codon optimized, such as set forth in SEQ ID NO:4, 44, 45, or 46). In a specific embodiment, presented herein are methods for immunizing against RSV comprising administering to a subject (e.g., a human subject) a recombinant NDV, wherein the recombinant NDV comprises a packaged genome comprising a transgene encoding a chimeric F protein, wherein the chimeric F protein comprise a human RSV F protein ectodomain and NDV F protein transmembrane and cytoplasmic domains, and wherein the transgene comprises a codon optimized nucleic acid sequence encoding the RSV F protein ectodomain. In a specific embodiment, the chimeric F protein is expressed by cells infected with the recombinant NDV. In another specific embodiment, the recombinant NDV is administered to a subject intranasally. In another specific embodiment, the subject is a human infant. In another specific embodiment, the subject is a human infant six months old or older. In another specific embodiment, the subject is a human toddler. In another specific embodiment, the subject is a human child. In another specific embodiment, the subject is a human adult. In another specific embodiment, the subject is an elderly human. In another specific embodiment, the subject is seropositive for antibodies to RSV (e.g., the subject is seropositive for antibodies to RSV F protein or RSV G protein).

In another aspect, presented herein are methods for immunizing against RSV comprising administering to a subject (e.g., a bovine subject) a recombinant NDV, wherein the recombinant NDV comprises a packaged genome comprising a transgene encoding a chimeric F protein, wherein the chimeric F protein comprises a bovine RSV F protein ectodomain and NDV F protein transmembrane and cytoplasmic domains. In one embodiment, the chimeric F protein comprises the amino acid sequence set forth in SEQ ID NO:33. Due to the degeneracy of the nucleic acid code, a number of different nucleic acid sequences may encode for the same chimeric F protein. For example, the chimeric F protein may be encoded by SEQ ID NO:31. Alternatively, the nucleic acid sequence encoding one or more domains of the chimeric F protein may be codon optimized (e.g., the nucleic acid sequence encoding the RSV F protein ectodomain may be codon optimized, such as set forth in SEQ ID NO:14, 38, or 39). In a specific embodiment, presented herein are methods for immunizing against RSV comprising administering to a subject (e.g., a bovine subject) a recombinant NDV, wherein the recombinant NDV comprises a packaged genome comprising a transgene encoding a chimeric F protein, wherein the chimeric F protein comprise a bovine RSV F protein ectodomain and NDV F protein transmembrane and cytoplasmic domains, and wherein the transgene comprises a codon optimized nucleic acid sequence encoding the RSV F protein ectodomain. In a specific embodiment, the chimeric F protein is expressed by cells infected with the recombinant NDV. In another specific embodiment, the recombinant NDV is administered to a subject intranasally. In another specific embodiment, the subject is seropositive for antibodies to RSV (e.g., the subject is seropositive for antibodies to RSV F protein or RSV G protein).

In another aspect, presented herein are methods for the prevention of RSV disease comprising administering to a subject (e.g., a human subject) a recombinant NDV, wherein the recombinant NDV comprises a packaged genome comprising a transgene encoding a human RSV F protein. In one embodiment, the human RSV F protein comprises the amino acid sequence set forth in SEQ ID NO: 6, 49, 50 or 58. Due to the degeneracy of the nucleic acid code, a number of different nucleic acid sequences may encode for the same human RSV F protein. For example, the human RSV F protein may be encoded by SEQ ID NO:1, 25, 27 or 29. Alternatively, the nucleic acid sequence encoding the human RSV F protein may be codon optimized, such as set forth in SEQ ID NO: 2, 26, 28 or 30. In some embodiments, the human RSV F protein is encoded by a nucleic acid sequence comprising the sequence of SEQ ID NO: 1, 2, 25, 26, 27. 28, 29, or 30. In a specific embodiment, presented herein are methods for the prevention of RSV disease comprising administering to a subject (e.g., a human subject) a recombinant NDV, wherein the recombinant NDV comprises a packaged genome comprising a transgene, and wherein the transgene comprises a codon optimized nucleic acid sequence encoding a human RSV F protein. In a specific embodiment, the human RSV F protein is expressed by cells infected with the recombinant NDV. In another specific embodiment, the recombinant NDV is administered to a subject intranasally. In another specific embodiment, the subject is a human infant. In another specific embodiment, the subject is a human infant six months old or older. In another specific embodiment, the subject is a human toddler. In another specific embodiment, the subject is a human child. In another specific embodiment, the subject is a human adult. In another specific embodiment, the subject is an elderly human. In another specific embodiment, the subject is seropositive for antibodies to RSV (e.g., the subject is seropositive for antibodies to RSV F protein or RSV G protein).

In another aspect, presented herein are methods for the prevention of RSV disease comprising administering to a subject (e.g., a bovine subject) a recombinant NDV, wherein the recombinant NDV comprises a packaged genome comprising a transgene encoding a bovine RSV F protein. In one embodiment, the bovine RSV F protein comprises the amino acid sequence set forth in SEQ ID NO: 10. Due to the degeneracy of the nucleic acid code, a number of different nucleic acid sequences may encode for the same bovine RSV F protein. For example, the bovine RSV F protein may be encoded by SEQ ID NO:9. Alternatively, the nucleic acid sequence encoding the bovine RSV F protein may be codon optimized, such as set forth in SEQ ID NO: 11. In some embodiments, the bovine RSV F protein is encoded by a nucleic acid sequence comprising the sequence of SEQ ID NO: 9, 11, 40, 41, 42, or 43. In a specific embodiment, presented herein are methods for the prevention of RSV disease comprising administering to a subject (e.g., a bovine subject) a recombinant NDV, wherein the recombinant NDV comprises a packaged genome comprising a transgene, and wherein the transgene comprises a codon optimized nucleic acid sequence encoding a bovine RSV F protein. In a specific embodiment, the bovine RSV F protein is expressed by cells infected with the recombinant NDV. In another specific embodiment, the recombinant NDV is administered to a subject intranasally. In another specific embodiment, the subject is seropositive for antibodies to RSV (e.g., the subject is seropositive for antibodies to RSV F protein or RSV G protein).

In another aspect, presented herein are methods for the prevention of RSV disease comprising administering to a subject (e.g., a human subject) a recombinant NDV, wherein the recombinant NDV comprises a packaged genome comprising a transgene encoding a chimeric F protein, wherein the chimeric F protein comprises a human RSV F protein ectodomain and NDV F protein transmembrane and cytoplasmic domains. In one embodiment, the chimeric F protein comprises the amino acid sequence set forth in SEQ ID NO: 7. Due to the degeneracy of the nucleic acid code, a number of different nucleic acid sequences may encode for the same chimeric F protein. For example, the chimeric F protein may be encoded by SEQ ID NO:51. Alternatively, the nucleic acid sequence encoding one or more domains of the chimeric F protein may be codon optimized (e.g., the nucleic acid sequence encoding the RSV F protein ectodomain may be codon optimized, such as set forth in SEQ ID NO: 4, 44, 45, or 46). In a specific embodiment, presented herein are methods for the prevention of RSV disease comprising administering to a subject (e.g., a human subject) a recombinant NDV, wherein the recombinant NDV comprises a packaged genome comprising a transgene encoding a chimeric F protein, wherein the chimeric F protein comprise a human RSV F protein ectodomain and NDV F protein transmembrane and cytoplasmic domains, and wherein the transgene comprises a codon optimized nucleic acid sequence encoding the RSV F protein ectodomain. In a specific embodiment, the chimeric F protein is expressed by cells infected with the recombinant NDV. In another specific embodiment, the recombinant NDV is administered to a subject intranasally. In another specific embodiment, the subject is a human infant. In another specific embodiment, the subject is a human infant six months old or older. In another specific embodiment, the subject is a human toddler. In another specific embodiment, the subject is a human child. In another specific embodiment, the subject is a human adult. In another specific embodiment, the subject is an elderly human. In another specific embodiment, the subject is seropositive for antibodies to RSV (e.g., the subject is seropositive for antibodies to RSV F protein or RSV G protein).

In another aspect, presented herein are methods for the prevention of RSV disease comprising administering to a subject (e.g., a bovine subject) a recombinant NDV, wherein the recombinant NDV comprises a packaged genome comprising a transgene encoding a chimeric F protein, wherein the chimeric F protein comprises a bovine RSV F protein ectodomain and NDV F protein transmembrane and cytoplasmic domains. In one embodiment, the chimeric F protein comprises the amino acid sequence set forth in SEQ ID NO:33. Due to the degeneracy of the nucleic acid code, a number of different nucleic acid sequences may encode for the same chimeric F protein. For example, the chimeric F protein may be encoded by SEQ ID NO:31. Alternatively, the nucleic acid sequence encoding one or more domains of the chimeric F protein may be codon optimized (e.g., the nucleic acid sequence encoding the RSV F protein ectodomain may be codon optimized, such as set forth in SEQ ID NO:14, 38, or 39). In a specific embodiment, presented herein are methods for the prevention of RSV disease comprising administering to a subject (e.g., a bovine subject) a recombinant NDV, wherein the recombinant NDV comprises a packaged genome comprising a transgene encoding a chimeric F protein, wherein the chimeric F protein comprise a bovine RSV F protein ectodomain and NDV F protein transmembrane and cytoplasmic domains, and wherein the transgene comprises a codon optimized nucleic acid sequence encoding the RSV F protein ectodomain. In a specific embodiment, the chimeric F protein is expressed by cells infected with the recombinant NDV. In another specific embodiment, the recombinant NDV is administered to a subject intranasally. In another specific embodiment, the subject is seropositive for antibodies to RSV (e.g., the subject is seropositive for antibodies to RSV F protein or RSV G protein).

The recombinant NDV described herein may be administered to a subject in combination with one or more other therapies. The recombinant NDV and one or more other therapies may be administered by the same or different routes of administration to the subject. In a specific embodiment, the recombinant NDV is administered to a subject intranasally. See, e.g., Sections 5.15.1, and 6, infra for information regarding recombinant NDV, Section 5.5.4 for information regarding other therapies, Section 5.4, infra, for information regarding compositions and routes of administration, and Sections 5.5.1 and 66, infra, for information regarding methods of immunizing against RSV.

In another embodiment, presented herein is a recombinant NDV or composition thereof for inducing an immune response to an RSV F protein. In another embodiment, presented herein is a recombinant NDV or composition thereof for immunizing a subject (e.g., a human or bovine subject) against RSV. In another embodiment, presented herein is a recombinant NDV or composition thereof for the prevention of an RSV disease. See, e.g., Sections 5.1, and 6, infra for information regarding recombinant NDV, Section 5.5.4, for information regarding other therapies, Section 5.4, infra, for information regarding compositions and routes of administration, and Sections 5.5.1 and 6, infra, for information regarding methods of immunizing against RSV.

In another aspect, presented herein are recombinant NDV comprising a packaged genome, wherein the packaged genome comprises a transgene encoding a human metapneumovirus ("hMPV") F protein. The hMPV F protein may be an hMPV F protein of any strain of hMPV. In a specific embodiment, the transgene encodes the hMPV F protein set forth in SEQ ID NO:17. Due to the degeneracy of the nucleic acid code, multiple different nucleic acid sequences may encode for the same hMPV F protein. In one embodiment, described herein is a recombinant NDV comprising a packaged genome comprising a transgene encoding a hMPV F protein, wherein the transgene comprises an RNA sequence corresponding to the negative sense of the cDNA sequence of SEQ ID NO:16. In some embodiments, the hMPV F protein is encoded by a nucleic acid sequence comprising the sequence of SEQ ID NO:16, 52, 54, or 56. In a preferred embodiment, a transgene comprises a codon optimized version of a nucleic acid sequence encoding an hMPV F protein. In a specific embodiment, the hMPV F protein is expressed by cells infected with the recombinant NDV.

In a specific embodiment, described herein are recombinant NDV comprising a packaged genome, wherein the packaged genome comprises a transgene comprising a codon optimized nucleic acid sequence encoding a hMPV F protein. Specific examples of codon optimized nucleic acid sequences encoding a hMPV F protein include those set forth in SEQ ID NO:18, 53, 55, or 57. In a specific embodiment, described herein is a recombinant NDV comprising a packaged genome comprising a transgene encoding a human RSV F protein, wherein the transgene comprises an RNA sequence corresponding to the negative sense of the cDNA sequence of SEQ ID NO:18. In a specific embodiment, the human RSV F protein is expressed by cells infected with the recombinant NDV.

In another embodiment, described herein are recombinant NDV comprising a packaged genome, wherein the packaged genome comprises a transgene encoding a chimeric F protein, wherein the chimeric F protein comprises an hMPV F protein ectodomain and NDV F protein transmembrane and cytoplasmic domains. In other words, the NDV F protein transmembrane and cytoplasmic domains replace the hMPV F protein transmembrane and cytoplasmic domains so that the chimeric F protein does not include the hMPV F protein transmembrane and cytoplasmic domains. The hMPV F protein may be an hMPV F protein of any of hMPV. In another embodiment, described herein are recombinant NDV comprising a packaged genome, wherein the packaged genome comprises a transgene encoding a chimeric F protein, wherein the chimeric F protein comprises a hMPV F protein ectodomain and NDV F protein transmembrane and cytoplasmic domains, and wherein the transgene comprises an RNA sequence corresponding to the negative sense of the cDNA sequence of SEQ ID NO:32. In a preferred embodiment, a transgene comprises a codon optimized version of a nucleic acid sequence encoding the hMPV F protein ectodomain. In a specific embodiment, the hMPV F protein is expressed by cells infected with the recombinant NDV.

In a specific embodiment, described herein are recombinant NDV comprising a packaged genome, wherein the packaged genome comprises a transgene encoding a chimeric F protein, wherein the chimeric F protein comprises a hMPV F protein ectodomain and NDV F protein transmembrane and cytoplasmic domains, and wherein the ectodomain of the hMPV F protein is encoded by a codon optimized nucleic acid sequence. Specific examples of nucleic acid sequences encoding a chimeric F protein, wherein the chimeric F protein comprises a hMPV F protein ectodomain and NDV F protein transmembrane and cytoplasmic domains, and wherein the ectodomain of the hMPV F protein is encoded by a codon optimized nucleic acid sequence, include SEQ ID NO:19, 34, 35, or 36. In a specific embodiment, described herein is a recombinant NDV comprising a packaged genome, wherein the packaged genome comprises a transgene encoding a chimeric F protein, wherein the chimeric F protein comprises a hMPV F protein ectodomain and NDV F protein transmembrane and cytoplasmic domains, and wherein the transgene comprises an RNA sequence corresponding to the negative sense of the cDNA sequence of SEQ ID NO:19. In a specific embodiment, the chimeric F protein is expressed by cells infected with the recombinant NDV. In another specific embodiment, the chimeric F protein is expressed by cells infected with the recombinant NDV and the chimeric F protein is incorporated into the NDV virion.

The recombinant NDV may have the backbone of any NDV type or strain, including, but not limited to, naturally-occurring strains, variants or mutants, mutagenized viruses, reassortants, genetically engineered viruses, or any combination thereof. The NDV that serves as the backbone for genetic engineering of the recombinant NDV may be a lentogenic strain, a mesogenic strain, or a velogenic strain. In a specific embodiment, the recombinant NDV comprises an NDV backbone which is lentogenic. In another specific embodiment, the recombinant NDV comprises an NDV backbone of the NDV LaSota strain. In another specific embodiment, the recombinant NDV comprises an NDV backbone of the NDV Hitchner B1 strain. In another specific embodiment, the recombinant NDV comprises an NDV backbone of a lentogenic strain other than the NDV Hitchner B1 strain. In another specific embodiment, the recombinant NDV comprises an NDV backbone of the NDV Fuller strain. In another specific embodiment, the recombinant NDV comprises an NDV backbone of the NDV Ulster strain.

The transgene encoding a hMPV F protein or a chimeric F protein may be incorporated into the genome of any NDV type or strain. In a specific embodiment, the transgene is incorporated into the genome of a lentogenic NDV. In another specific embodiment, the transgene is incorporated in the genome of NDV strain LaSota. Other examples of NDV strains into which the transgene may be incorporated are the NDV Fuller, the NDV Ulster strain or the NDV Hitchner B1 strain. The transgene may be incorporated into the NDV genome between two transcription units (e.g., between NDV P and M genes).

In a specific embodiment, a transgene encoding a hMPV F protein is incorporated into the genome of any NDV type or strain (e.g., NDV LaSota strain). For example, a transgene encoding the hMPV F protein comprising the amino acid sequence set forth in SEQ ID NO:17 may be incorporated into the genome of any NDV type or strain (e.g., NDV LaSota strain). In a specific embodiment, such a transgene comprises an RNA sequence corresponding to the negative sense of the cDNA sequence set forth in SEQ ID NO:16. However, given the degeneracy of the nucleic acid code, there are a number of different nucleic acid sequences that may encode the same hMPV F protein. In a specific embodiment, transgene encoding a hMPV F protein is codon optimized. For example, the hMPV F protein is encoded by the codon optimized nucleic acid sequence set forth in SEQ ID NO: 18. In some embodiments, the hMPV F protein is encoded by a nucleic acid sequence comprising the sequence of SEQ ID NO: 16, 18, 52, 53, 54, 55, 56, or 57. The transgene encoding a hMPV F protein may be incorporated between any two NDV transcription units (e.g., between NDV P and M genes). In a specific embodiment, a recombinant NDV described herein comprises a packaged genome, wherein the packaged genome corresponds to a negative sense RNA sequence transcribed from the cDNA sequence set forth in SEQ ID NO: 20 or 21. In certain embodiment, the genome of the recombinant NDV does not comprise a heterologous sequence encoding a heterologous protein other than the hMPV F protein. In some embodiments, the genome of the recombinant NDV does not comprise a transgene other than a transgene encoding a hMPV F protein.

In a specific embodiment, a transgene encoding a chimeric F protein is incorporated into the genome of any NDV type or strain, wherein the chimeric F protein comprises the ectodomain of an hMPV F protein and NDV F protein transmembrane and cytoplasmic domains. For example, a transgene encoding the chimeric F protein comprising the amino acid sequence set forth in SEQ ID NO:15 may be incorporated into the genome of any NDV type or strain. In a specific embodiment, such a transgene comprises an RNA sequence corresponding to the negative sense of the cDNA sequence set forth in SEQ ID NO:32. However, given the degeneracy of the nucleic acid code, there are a number of different nucleic acid sequences that may encode the same chimeric F protein. In a specific embodiment, the nucleic acid sequence encoding the ectodomain of the hMPV F protein is codon optimized. For example, the chimeric F protein may be encoded by the codon optimized nucleic acid sequence, such as set forth in SEQ ID NO: 19, 34, 35, or 36. The nucleotide sequence comprising the nucleic acid sequence encoding a chimeric F protein may be incorporated between any two NDV transcription units (e.g., between NDV P and M genes). In a specific embodiment, a recombinant NDV described herein comprises a packaged genome, wherein the packaged genome corresponds to a negative sense RNA sequence transcribed from the cDNA sequence set forth in SEQ ID NO:22. In certain embodiment, the genome of the recombinant NDV does not comprise a heterologous sequence encoding a heterologous protein other than the chimeric F protein. In some embodiments, the genome of the recombinant NDV does not comprise a transgene other than a transgene encoding a chimeric F protein.

In another aspect, presented herein are methods for inducing an immune response to an hMPV F protein comprising administering to a subject (e.g., a human subject) a recombinant NDV, wherein the recombinant NDV comprises a packaged genome comprising a transgene encoding a hMPV F protein. In one embodiment, the hMPV F protein comprises the amino acid sequence set forth in SEQ ID NO: 17. Due to the degeneracy of the nucleic acid code, a number of different nucleic acid sequences may encode for the same hMPV F protein. For example, the hMPV F protein may be encoded by SEQ ID NO:16. Alternatively, the nucleic acid sequence encoding the hMPV F protein may be codon optimized, such as set forth in SEQ ID NO: 18. In some embodiments, the hMPV F protein is encoded by a nucleic acid sequence comprising the sequence of SEQ ID NO: 16, 18, 52, 53, 54, 55, 56 or 57. In a specific embodiment, presented herein are methods for inducing an immune response to an hMPV F protein comprising administering to a subject (e.g., a human subject) a recombinant NDV, wherein the recombinant NDV comprises a packaged genome comprising a transgene, and wherein the transgene comprises a codon optimized nucleic acid sequence encoding an hMPV F protein. In a specific embodiment, the hMPV F protein is expressed by cells infected with the recombinant NDV. In another specific embodiment, the recombinant NDV is administered to a subject intranasally. In another specific embodiment, the subject is a human infant. In another specific embodiment, the subject is a human toddler. In another specific embodiment, the subject is a human child. In another specific embodiment, the subject is a human adult. In another specific embodiment, the subject is an elderly human. In another specific embodiment, the subject is seropositive for antibodies to hMPV.

In another aspect, presented herein are methods for inducing an immune response to an hMPV F protein comprising administering to a subject (e.g., a human subject) a recombinant NDV, wherein the recombinant NDV comprises a packaged genome comprising a transgene encoding a chimeric F protein, wherein the chimeric F protein comprises an hMPV F protein ectodomain and NDV F protein transmembrane and cytoplasmic domains. In one embodiment, the chimeric F protein comprises the amino acid sequence set forth in SEQ ID NO:15. Due to the degeneracy of the nucleic acid code, a number of different nucleic acid sequences may encode for the same chimeric F protein. For example, the chimeric F protein may be encoded by SEQ ID NO:32. Alternatively, the nucleic acid sequence encoding one or more domains of the chimeric F protein may be codon optimized (e.g., the nucleic acid sequence encoding the hMPV F protein ectodomain may be codon optimized, such as set forth in SEQ ID NO: 19, 34, 35 or 36). In a specific embodiment, presented herein are methods for inducing an immune response to an hMPV F protein comprising administering to a subject (e.g., a human subject) a recombinant NDV, wherein the recombinant NDV comprises a packaged genome comprising a transgene encoding a chimeric F protein, wherein the chimeric F protein comprise an hMPV RSV F protein ectodomain and NDV F protein transmembrane and cytoplasmic domains, and wherein the transgene comprises a codon optimized nucleic acid sequence encoding the hMPV F protein ectodomain. In a specific embodiment, the chimeric F protein is expressed by cells infected with the recombinant NDV. In another specific embodiment, the recombinant NDV is administered to a subject intranasally. In another specific embodiment, the subject is a human infant. In another specific embodiment, the subject is a human toddler. In another specific embodiment, the subject is a human child. In another specific embodiment, the subject is a human adult. In another specific embodiment, the subject is an elderly human. In another specific embodiment, the subject is seropositive for antibodies to hMPV.

In another aspect, presented herein are methods for immunizing against hMPV comprising administering to a subject (e.g., a human subject) a recombinant NDV, wherein the recombinant NDV comprises a packaged genome comprising a transgene encoding a hMPV F protein. In one embodiment, the hMPV F protein comprises the amino acid sequence set forth in SEQ ID NO: 17. Due to the degeneracy of the nucleic acid code, a number of different nucleic acid sequences may encode for the same hMPV F protein. For example, the hMPV F protein may be encoded by SEQ ID NO:16. Alternatively, the nucleic acid sequence encoding the hMPV F protein may be codon optimized, such as set forth in SEQ ID NO: 18. In some embodiments, the hMPV F protein is encoded by a nucleic acid sequence comprising the sequence of SEQ ID NO: 16, 18, 52, 53, 54, 55, 56 or 57. In a specific embodiment, presented herein are methods for immunizing against hMPV comprising administering to a subject (e.g., a human subject) a recombinant NDV, wherein the recombinant NDV comprises a packaged genome comprising a transgene, and wherein the transgene comprises a codon optimized nucleic acid sequence encoding an hMPV F protein. In a specific embodiment, the hMPV F protein is expressed by cells infected with the recombinant NDV. In another specific embodiment, the recombinant NDV is administered to a subject intranasally. In another specific embodiment, the subject is a human infant. In another specific embodiment, the subject is a human toddler. In another specific embodiment, the subject is a human child. In another specific embodiment, the subject is a human adult. In another specific embodiment, the subject is an elderly human. In another specific embodiment, the subject is seropositive for antibodies to hMPV.

In another aspect, presented herein are methods for immunizing against hMPV comprising administering to a subject (e.g., a human subject) a recombinant NDV, wherein the recombinant NDV comprises a packaged genome comprising a transgene encoding a chimeric F protein, wherein the chimeric F protein comprises an hMPV F protein ectodomain and NDV F protein transmembrane and cytoplasmic domains. In one embodiment, the chimeric F protein comprises the amino acid sequence set forth in SEQ ID NO:15. Due to the degeneracy of the nucleic acid code, a number of different nucleic acid sequences may encode for the same chimeric F protein. For example, the chimeric F protein may be encoded by SEQ ID NO:32. Alternatively, the nucleic acid sequence encoding one or more domains of the chimeric F protein may be codon optimized (e.g., the nucleic acid sequence encoding the hMPV F protein ectodomain may be codon optimized, such as set forth in SEQ ID NO: 19, 34, 35, or 36). In a specific embodiment, presented herein are methods for immunizing against hMPV comprising administering to a subject (e.g., a human subject) a recombinant NDV, wherein the recombinant NDV comprises a packaged genome comprising a transgene encoding a chimeric F protein, wherein the chimeric F protein comprise an hMPV RSV F protein ectodomain and NDV F protein transmembrane and cytoplasmic domains, and wherein the transgene comprises a codon optimized nucleic acid sequence encoding the hMPV F protein ectodomain. In a specific embodiment, the chimeric F protein is expressed by cells infected with the recombinant NDV. In another specific embodiment, the chimeric F protein is expressed by cells infected with the recombinant NDV and the chimeric F protein is incorporated into the NDV virion. In another specific embodiment, the recombinant NDV is administered to a subject intranasally. In another specific embodiment, the subject is a human infant. In another specific embodiment, the subject is a human toddler. In another specific embodiment, the subject is a human child. In another specific embodiment, the subject is a human adult. In another specific embodiment, the subject is an elderly human. In another specific embodiment, the subject is seropositive for antibodies to hMPV.

In another aspect, presented herein are methods for the prevention of hMPV disease comprising administering to a subject (e.g., a human subject) a recombinant NDV, wherein the recombinant NDV comprises a packaged genome comprising a transgene encoding a hMPV F protein. In one embodiment, the hMPV F protein comprises the amino acid sequence set forth in SEQ ID NO: 17. Due to the degeneracy of the nucleic acid code, a number of different nucleic acid sequences may encode for the same hMPV F protein. For example, the hMPV F protein may be encoded by SEQ ID NO:16. Alternatively, the nucleic acid sequence encoding the hMPV F protein may be codon optimized, such as set forth in SEQ ID NO: 18. In some embodiments, the hMPV F protein is encoded by a nucleic acid sequence comprising the sequence of SEQ ID NO: 16, 18, 52, 53, 54, 55, 56 or 57. In a specific embodiment, presented herein are methods for the prevention of hMPV disease comprising administering to a subject (e.g., a human subject) a recombinant NDV, wherein the recombinant NDV comprises a packaged genome comprising a transgene, and wherein the transgene comprises a codon optimized nucleic acid sequence encoding an hMPV F protein. In a specific embodiment, the hMPV F protein is expressed by cells infected with the recombinant NDV. In another specific embodiment, the recombinant NDV is administered to a subject intranasally. In another specific embodiment, the subject is a human infant. In another specific embodiment, the subject is a human toddler. In another specific embodiment, the subject is a human child. In another specific embodiment, the subject is a human adult. In another specific embodiment, the subject is an elderly human. In another specific embodiment, the subject is seropositive for antibodies to hMPV.

In another aspect, presented herein are methods for the prevention of hMPV disease comprising administering to a subject (e.g., a human subject) a recombinant NDV, wherein the recombinant NDV comprises a packaged genome comprising a transgene encoding a chimeric F protein, wherein the chimeric F protein comprises an hMPV F protein ectodomain and NDV F protein transmembrane and cytoplasmic domains. In one embodiment, the chimeric F protein comprises the amino acid sequence set forth in SEQ ID NO:15. Due to the degeneracy of the nucleic acid code, a number of different nucleic acid sequences may encode for the same chimeric F protein. For example, the chimeric F protein may be encoded by SEQ ID NO:32. Alternatively, the nucleic acid sequence encoding one or more domains of the chimeric F protein may be codon optimized (e.g., the nucleic acid sequence encoding the hMPV F protein ectodomain may be codon optimized, such as set forth in SEQ ID NO: 19, 34, 35, or 36). In a specific embodiment, presented herein are methods for the prevention of hMPV disease comprising administering to a subject (e.g., a human subject) a recombinant NDV, wherein the recombinant NDV comprises a packaged genome comprising a transgene encoding a chimeric F protein, wherein the chimeric F protein comprise an hMPV RSV F protein ectodomain and NDV F protein transmembrane and cytoplasmic domains, and wherein the transgene comprises a codon optimized nucleic acid sequence encoding the hMPV F protein ectodomain. In a specific embodiment, the chimeric F protein is expressed by cells infected with the recombinant NDV. In another specific embodiment, the chimeric F protein is expressed by cells infected with the recombinant NDV and the chimeric F protein is incorporated into the NDV virion. In another specific embodiment, the recombinant NDV is administered to a subject intranasally. In another specific embodiment, the subject is a human infant. In another specific embodiment, the subject is a human toddler. In another specific embodiment, the subject is a human child. In another specific embodiment, the subject is a human adult. In another specific embodiment, the subject is an elderly human. In another specific embodiment, the subject is seropositive for antibodies to hMPV.

The recombinant NDV described herein may be administered to a subject in combination with one or more other therapies. The recombinant NDV and one or more other therapies may be administered by the same or different routes of administration to the subject. In a specific embodiment, the recombinant NDV is administered to a subject intranasally. See, e.g., Sections 5.15.1, and 6, infra for information regarding recombinant NDV, Section 5.5.4 for information regarding other therapies, Section 5.4, infra, for information regarding compositions and routes of administration, and Sections 5.5.2 5.5.1 and 6, infra, for information regarding methods of immunizing against hMPV.

In another embodiment, presented herein is a recombinant NDV or composition thereof for inducing an immune response to an hMPV F protein. In another embodiment, presented herein is a recombinant NDV or composition thereof for immunizing a subject (e.g., a human subject) against hMPV. In another embodiment, presented herein is a recombinant NDV or composition thereof for the prevention of an hMPV disease. See, e.g., Sections 5.1, and 6, infra for information regarding recombinant NDV, Section 5.5.4 for information regarding other therapies, Section 5.4, infra, for information regarding compositions and routes of administration, and Sections 5.5.2 and 6, infra, for information regarding methods of immunizing against hMPV.

In another aspect, presented herein are pharmaceutical compositions (e.g., immunogenic compositions) comprising a recombinant NDV described herein, in admixture with a pharmaceutically acceptable carrier. In a specific embodiment, a pharmaceutical composition (e.g., an immunogenic composition) comprises a recombinant NDV described herein as the sole active ingredient, in admixture with a pharmaceutically acceptable carrier. In another specific embodiment, a pharmaceutical composition (e.g., an immunogenic composition) comprises two different recombinant NDVs described herein, in admixture with a pharmaceutically acceptable carrier. See, e.g., Section 5.4, infra, for examples of pharmaceutical compositions. The pharmaceutical compositions may be used to induce an immune response to an RSV F protein or hMPV F protein, immunize against RSV or hMPV, or prevent RSV disease or hMPV disease.

3.1 Terminology

As used herein, the term “about” or “approximately” when used in conjunction with a number refers to any number within 1, 5 or 10% of the referenced number.

As used herein, the terms “antibody” and “antibodies” refer to molecules that contain an antigen binding site, e.g., immunoglobulins. Antibodies include, but are not limited to, monoclonal antibodies, bispecific antibodies, multispecific antibodies, human antibodies, humanized antibodies, synthetic antibodies, chimeric antibodies, polyclonal antibodies, single domain antibodies, camelized antibodies, single-chain Fvs (scFv), single chain antibodies, Fab fragments, F(ab') fragments, disulfide-linked bispecific Fvs (sdFv), intrabodies, and anti-idiotypic (anti-Id) antibodies (including, e.g., anti-Id and anti-anti-Id antibodies to antibodies), and epitope-binding fragments of any of the above. In particular, antibodies include immunoglobulin molecules and immunologically active fragments of immunoglobulin molecules. Immunoglobulin molecules can be of any type (e.g., IgG, IgE, IgM, IgD, IgA and IgY), class (e.g., IgG1, IgG2, IgG3, IgG4, IgA1 and IgA2) or subclass.

As used herein, the term “heterologous” in the context of NDV refers to an entity not found in nature to be associated with (e.g., encoded by, expressed by the genome of, or both) a naturally occurring NDV. In a specific embodiment, a heterologous sequence encodes a protein that is not found associated with naturally occurring NDV.

As used herein, the term “elderly human” refers to a human 65 years or older.

As used herein, the term “human adult” refers to a human that is 18 years or older.

As used herein, the term “human child” refers to a human that is 1 year to 18 years old.

As used herein, the term “human toddler” refers to a human that is 1 year to 3 years old.

As used herein, the term “human infant” refers to a newborn to 1 year old year human.

“Human Metapneumovirus F protein” and “hMPV F protein” refer to any Human Metapneumovirus F protein known to those of skill in the art. The hMPV F protein is synthesized as a F0 inactive precursor. The F0 inactive precursor requires cleavage during intracellular maturation. The hMPV F is cleaved to form F1 and F2. The hMPV F protein exists in two conformations, prefusion and post-fusion. GenBank™ accession number AY145301.1 and KJ627437.1, provide exemplary nucleic acid sequences encoding hMPV F protein. In a preferred embodiment, an hMPV F protein is encoded by a nucleic acid sequence provided in Section 5.1.4, 5.1.5 or 6, e.g., SEQ ID NOs: 16, 18, 52, 53, 54, 55, 56, or 57. GenBank™ accession numbers AAN52915.1, AHV79975.1, AGJ74035.1, and AGZ48845.1 provide exemplary hMPV F protein amino acid sequences. In a preferred embodiment, an hMPV F protein comprises an amino acid sequence provided in Section 5.1.4 or 6, e.g., SEQ ID NOs: 17. As used herein, the terms “hMPV F protein” and “human metapneumovirus F protein” encompass hMPV F polypeptides that are modified by post-translational processing such as signal peptide cleavage, disulfide bond formation, glycosylation (e.g., N-linked glycosylation), protease cleavage and lipid modification (e.g. S-palmitoylation). In some embodiments, the hMPV F protein includes a signal sequence. In other embodiments, hMPV F protein does not include a signal sequence. The signal sequence can be the naturally occurring signal peptide sequence or a variant thereof. The hMPV F protein signal sequence is typically 18 amino acids in length. See, e.g., SEQ ID NO:24 for an exemplary hMPV protein signal sequence. In some embodiments, the signal peptide is an hMPV F protein signal peptide. In some embodiments, the signal peptide is heterologous to an hMPV F protein signal peptide.

As used herein, the phrases “IFN deficient systems” or “IFN-deficient substrates” refer to systems, e.g., cells, cell lines and animals, such as mice, chickens, turkeys, rabbits, rats, horses etc., which do not produce one, two or more types of IFN, or do not produce any type of IFN, or produce low levels of one, two or more types of IFN, or produce low levels of any IFN (i.e., a reduction in any IFN expression of 5-10%, 10-20%, 20-30%, 30-40%, 40-50%, 50-60%, 60-70%, 70-80%, 80-90% or more when compared to IFN-competent systems under the same conditions), do not respond or respond less efficiently to one, two or more types of IFN, or do not respond to any type of IFN, have a delayed response to one, two or more types of IFN, are deficient in the activity of antiviral genes induced by one, two or more types of IFN, or induced by any type of IFN, or any combination thereof.

As used herein, the phrase “multiplicity of infection” or “MOI” is the average number of virus per infected cell. The MOI is determined by dividing the number of virus added (ml added x Pfu/ml) by the number of cells added (Pfu added/cells).

“RSV F protein” and “respiratory syncytial virus F protein” refer to any respiratory syncytial F protein known to those of skill in the art. The RSV F protein typically exists as a homotrimer. The RSV F protein is synthesized as a F0 inactive precursor which is heavily N-glycosylated. The F0 inactive precursor requires cleavage during intracellular maturation by a furin-like proteases. The RSV F contains two furin sites, and cleavage by furin-like proteases leads to three polypeptides: F2, p27 and F1, with the latter containing a hydrophobic fusion peptide at its N terminus. The RSV F protein exists in two conformations, prefusion and post-fusion. The RSV F protein may be human RSV F protein or bovine F protein. GenBank™ accession numbers KJ155694.1, KU950686.1, KJ672481.1, KP119747, and AF035006.1 provide exemplary nucleic acid sequences encoding human RSV F protein. In a preferred embodiment, a human RSV F protein may be encoded by the nucleic acid sequence provided in Section 5.1.2, 5.1.3. or 6, e.g., SEQ ID NOs: 1, 2, 25, 26, 27, 28, 29 or 30. GenBank™ accession numbers AHL84194.1, AMT79817.1, AHX57603.1, AIY70220.1 and AAC14902.1 provide exemplary human RSV F protein amino acid sequences. In a preferred embodiment, a human RSV F protein comprises the amino sequence provided in Section 5.1.2 or 6, e.g., SEQ ID NO: 6, 49, 50 or 58. GenBank™ accession numbers AF295543.1, AF092942.1, and Y17970.1 provide exemplary nucleic acid sequences encoding bovine RSV F protein. In a specific embodiment, a bovine RSV F protein is encoded by a nucleic acid sequence comprising the nucleic acid sequence of SEQ ID NO:9, 11, 39, 40, 41, 42 or 43. GenBank™ accession numbers AAL49399.1, NP_048055.1, AAC96308.1, and CAA76980.1 provide exemplary bovine RSV F protein amino acid sequences. In another embodiment, a bovine RSV F protein comprises the amino acid sequence provided in Section 5.1.2 or 6, e.g., SEQ ID NO: 10. As used herein, the terms “RSV F protein” and “respiratory syncytial virus F protein” encompass RSV F polypeptides that are modified by post-translational processing such as signal peptide cleavage, disulfide bond formation, glycosylation (e.g., N-linked glycosylation), protease cleavage and lipid modification (e.g. S-palmitoylation). In some embodiments, the RSV F protein includes a signal sequence. In other embodiments, RSV F protein does not include a signal sequence. The signal sequence can be the naturally occurring signal peptide sequence or a variant thereof. The RSV F protein signal sequence is typically 25 amino acids in length. See, e.g., SEQ ID NO:23 or 60 for an exemplary human RSV F protein signal sequence and bovine RSV F protein signal sequence, respectively. In some embodiments, the signal peptide is an RSV F protein signal peptide. In some embodiments, the signal peptide is heterologous to an RSV F protein signal peptide.

As used herein, the terms “subject” or “patient” are used interchangeably. As used herein, the terms “subject” and “subjects” refers to an animal. In some embodiments, the subject is a mammal including a non-primate (e.g., a camel, donkey, zebra, bovine, horse, horse, cat, dog, rat, and mouse) and a primate (e.g., a monkey, chimpanzee, and a human). In some embodiments, the subject is a non-human mammal.

In certain embodiments, the subject is a pet (e.g., dog or cat) or farm animal (e.g., a horse, pig or cow). In specific embodiments, the subject is a human. In other specific embodiments, the subject is a bovine. In certain embodiments, the mammal (e.g., human) is 4 to 6 months old, 6 to 12 months old, 1 to 5 years old, 5 to 10 years old, 10 to 15 years old, 15 to 20 years old, 20 to 25 years old, 25 to 30 years old, 30 to 35 years old, 35 to 40 years old, 40 to 45 years old, 45 to 50 years old, 50 to 55 years old, 55 to 60 years old, 60 to 65 years old, 65 to 70 years old, 70 to 75 years old, 75 to 80 years old, 80 to 85 years old, 85 to 90 years old, 90 to 95 years old or 95 to 100 years old. In specific embodiments, the subject is an animal that is not avian.

As used herein, the term "in combination" in the context of the administration of (a) therapy(ies) to a subject, refers to the use of more than one therapy. The use of the term "in combination" does not restrict the order in which therapies are administered to a subject. A first therapy can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy to a subject. For example, a recombinant NDV described herein may be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of another therapy.

As used herein, the terms "therapies" and "therapy" can refer to any protocol(s), method(s), agent(s) or a combination thereof that can be used in the treatment or prevention of RSV disease or hMPV disease, or vaccination. In certain embodiments, the term "therapy" refers to a recombinant NDV described herein. In other embodiments, the term "therapy" refers to an agent that is not a recombinant NDV described herein.

As used herein, the term "wild-type" in the context of nucleotide and amino acid sequences of viruses refers to the nucleotide and amino acid sequences of viral strains found in nature. In particular, the sequences described as wild-type herein are sequences that have been reported in public databases as sequences from natural viral isolates.

4. BRIEF DESCRIPTION OF THE FIGURES

Figure 1G:
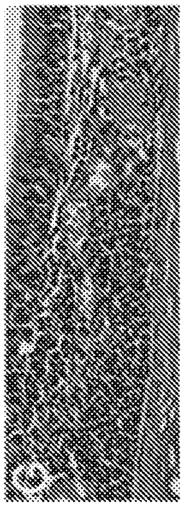
Figure 1D:
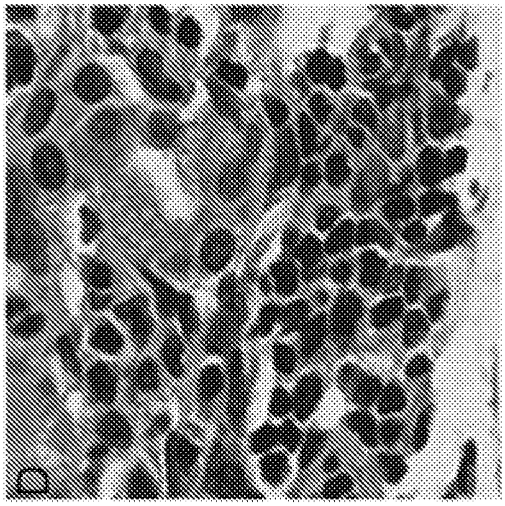
Figure 1H:
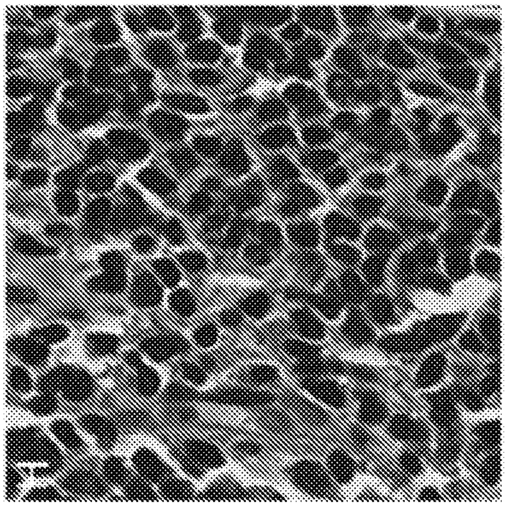
Figures 1I, 1J, 1K, 1L, 1M, 1N:
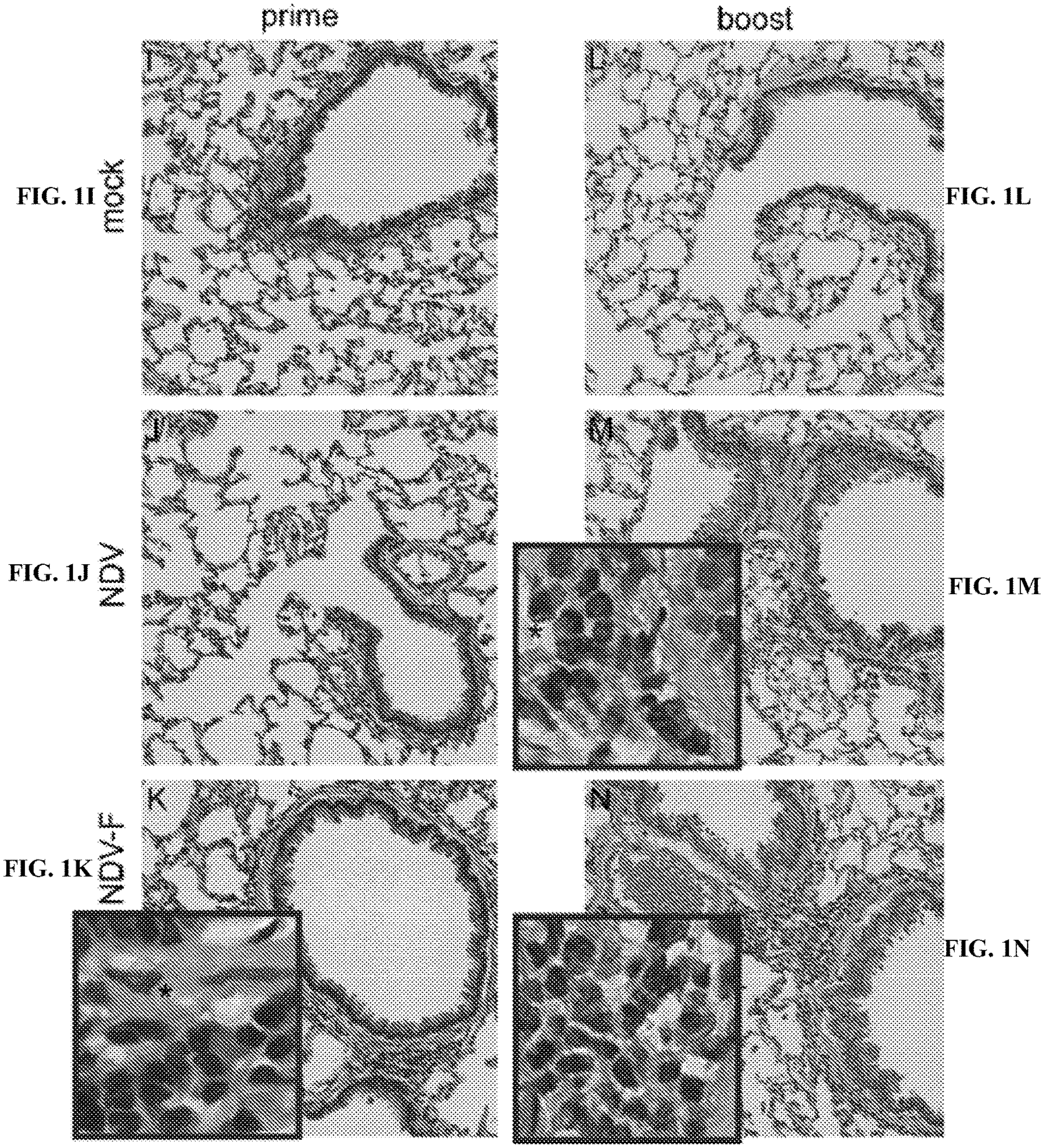

FIGS. 1A-1N. Inflammation following NDV-F vaccination and boost. Cohorts of cotton rats were sacrificed 28 days after the priming intranasal immunization, or 1 month after a second, boosting dose given on day 28. Mock-immunized animals were given allantoic fluid alone, or the NDV vaccine vector. Representative sections from the nasal cavity and lung after a single priming dose (FIGS. 1A-1D, and FIGS. 1I-1K), or after both a priming and a boosting dose (FIGS. 1E-1H and FIGS. 1L-1N), are pictured. A lymphohistiocytic submucosal infiltrate is present in the nasal cavity (FIGS. 1C and 1D), and surrounding bronchioles (FIG. 1K), after priming with NDV-F, with increased cellularity 1 month following the boosting dose (FIGS. 1G, 3H, and 3N). A minimal peribronchiolar infiltrate is detected only after priming and boosting with the NDV vector. Rare eosinophils are indicated (*). Images were captured at 100× or 400× (insets) magnification.

Figures 2A, 2B, 2C, 2D, 2E, 2F:
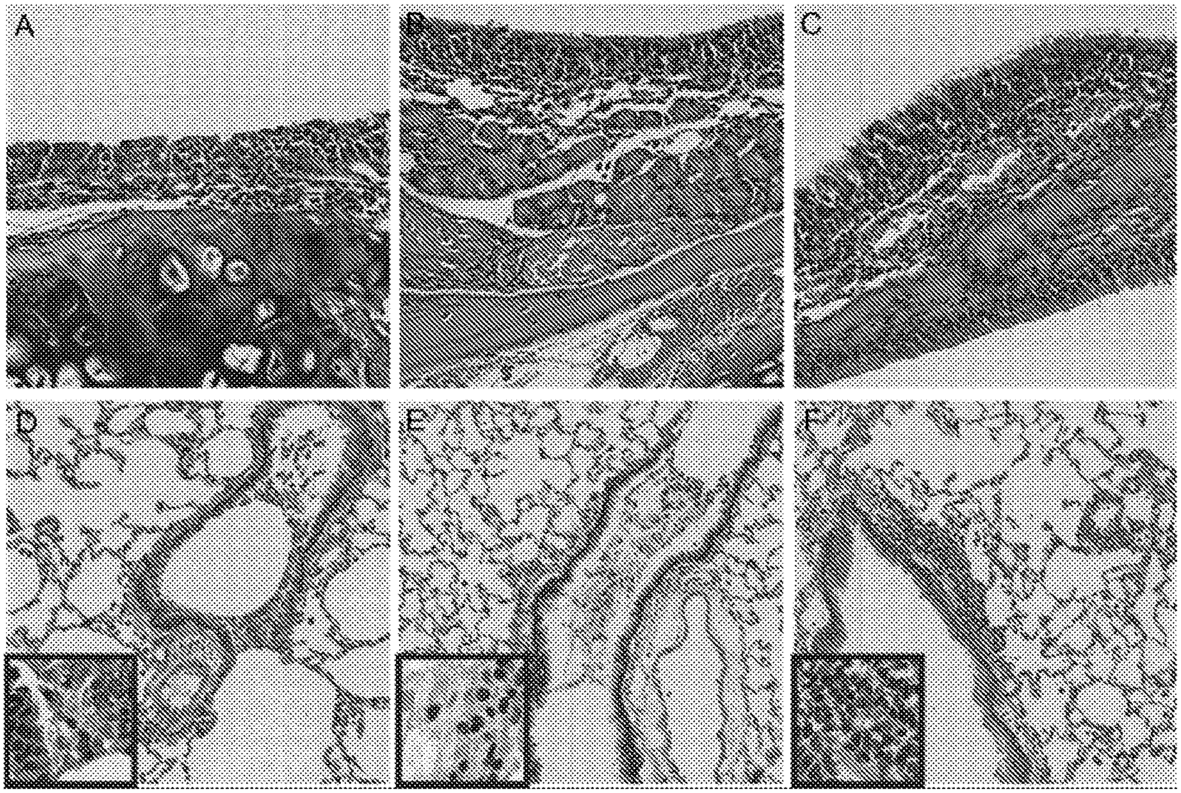

FIGS. 2A-2F. Histology of the nasal cavity and lung following primary RSV challenge. Nasal cavity (FIGS. 2A-2C) and lung (FIGS. 2D-2F) were collected 4 days after primary RSV challenge from animals that had been previously mock-vaccinated, or given a priming and boosting dose of NDV-F. Respiratory mucosa in the noses of infected animals was disrupted by lymphoplasmacytic infiltrates (FIGS. 2A and 2B), whereas, the nasal cavities of NDV-F vaccinated animals (FIG. 2C) were similar to those observed following vaccination alone (FIG. 1). RSV infection of the lung induced mild peribronchiolar infiltrates of lymphocytes, plasma cells and rare eosinophils and mucus production, with plugging of small airways (FIGS. 2D and 2E). RSV challenge of NDV-F vaccinated animals resulted in lymphoplasmacytic peribronchial infiltrates (FIG. 2F), but without obstruction of small airways by mucus and necrotic cells. Images were taken at 100× (FIGS. 2D-2E), 200× (FIGS. 2A-2C) or 400× (insets) magnification.

FIGS. 3A-3G. Viral burden following primary RSV challenge. Nasal cavity and lung were collected 4 days after primary RSV challenge from controls and animals that had been previously vaccinated. RSV immunohistochemistry revealed marked to complete reduction in antigen-positive cells in nasal cavity (FIGS. 3A-3C) and lung (FIGS. 3D-3F) collected from NDV-F immunized animals compared to controls. Virus was detected by plaque assay (FIG. 3G) only in samples collected from animals mock-immunized with allantoic fluid or vector alone. Images were taken at 200× (FIGS. 3A-3C), 100× (FIGS. 3D-3F) or 400× (insets) magnification.

Figure 4A:
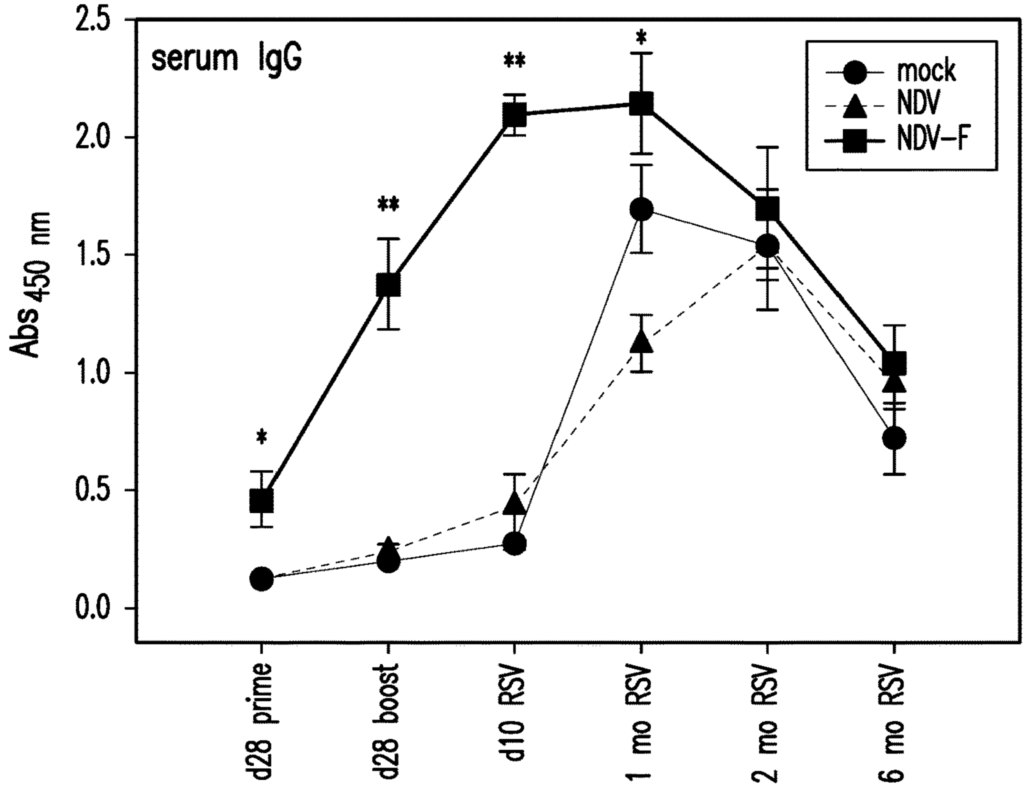
Figure 4B:
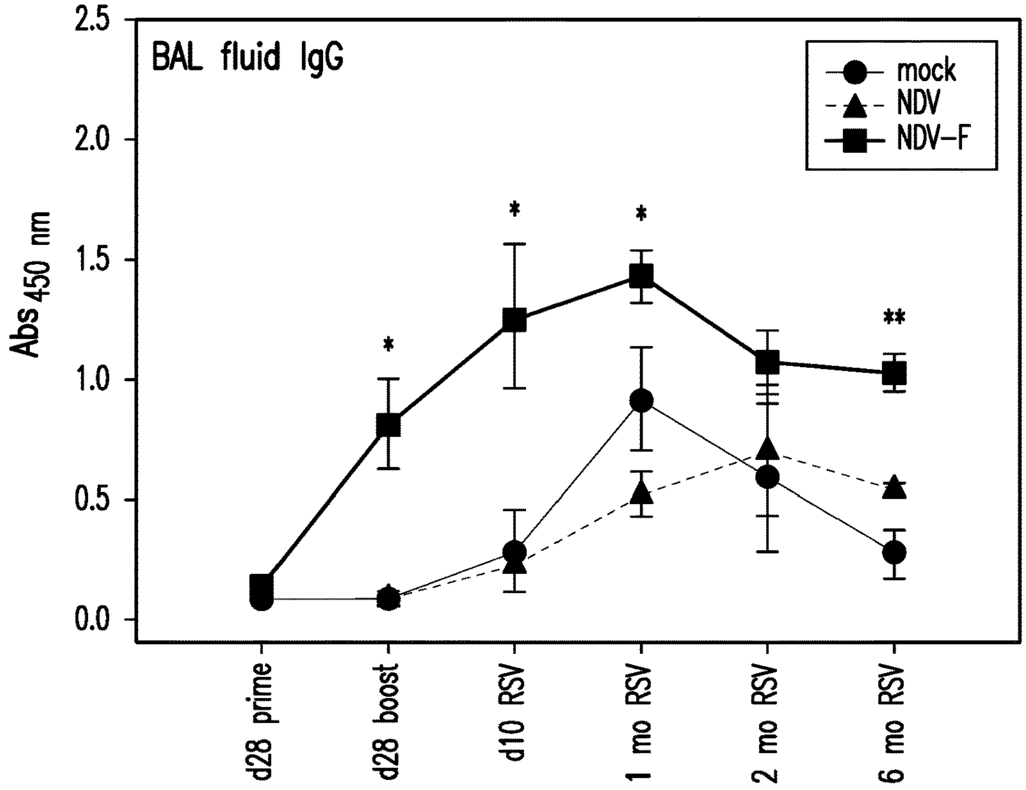
Figure 4C:
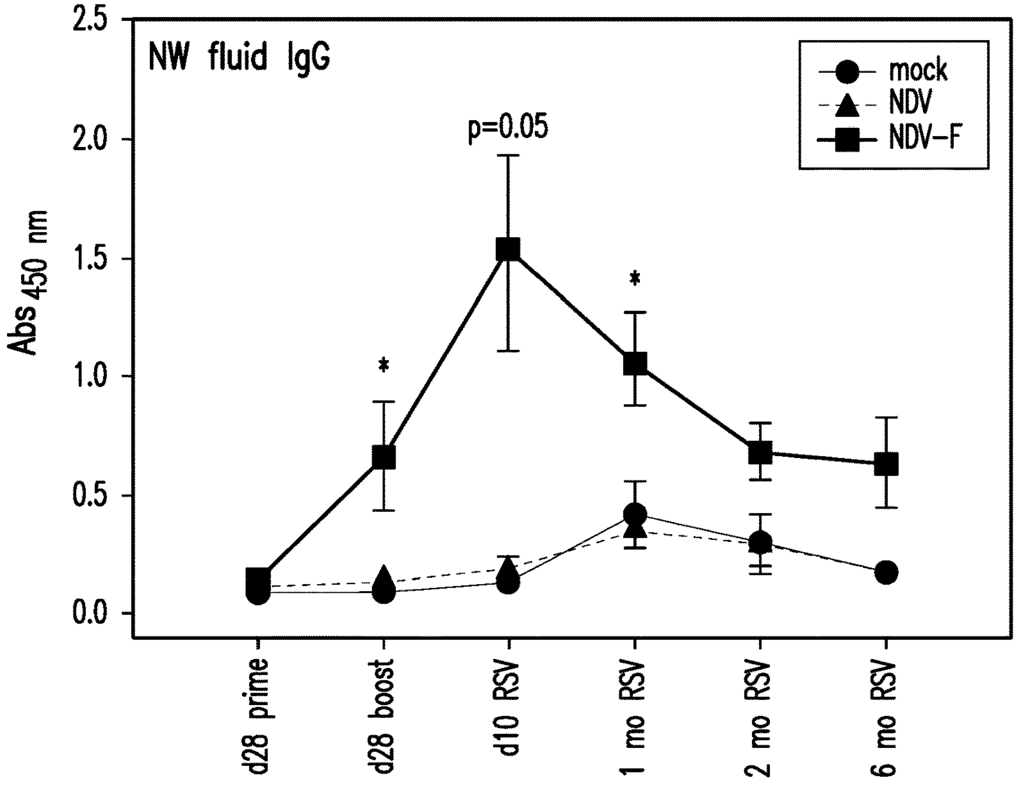
Figure 4D:
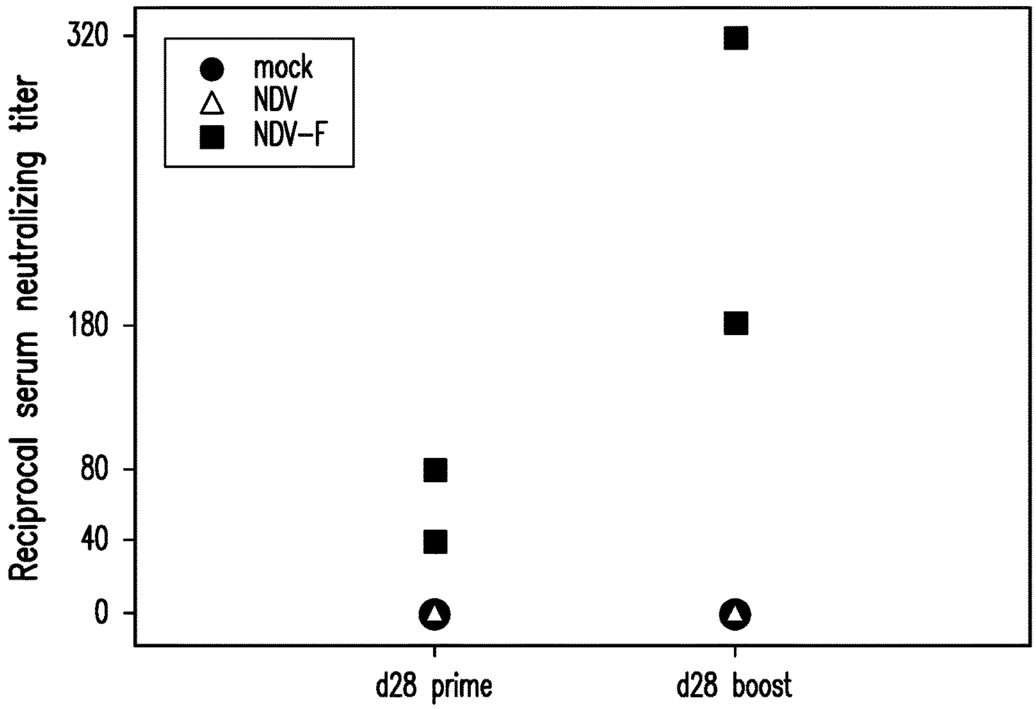
Figure 4E:
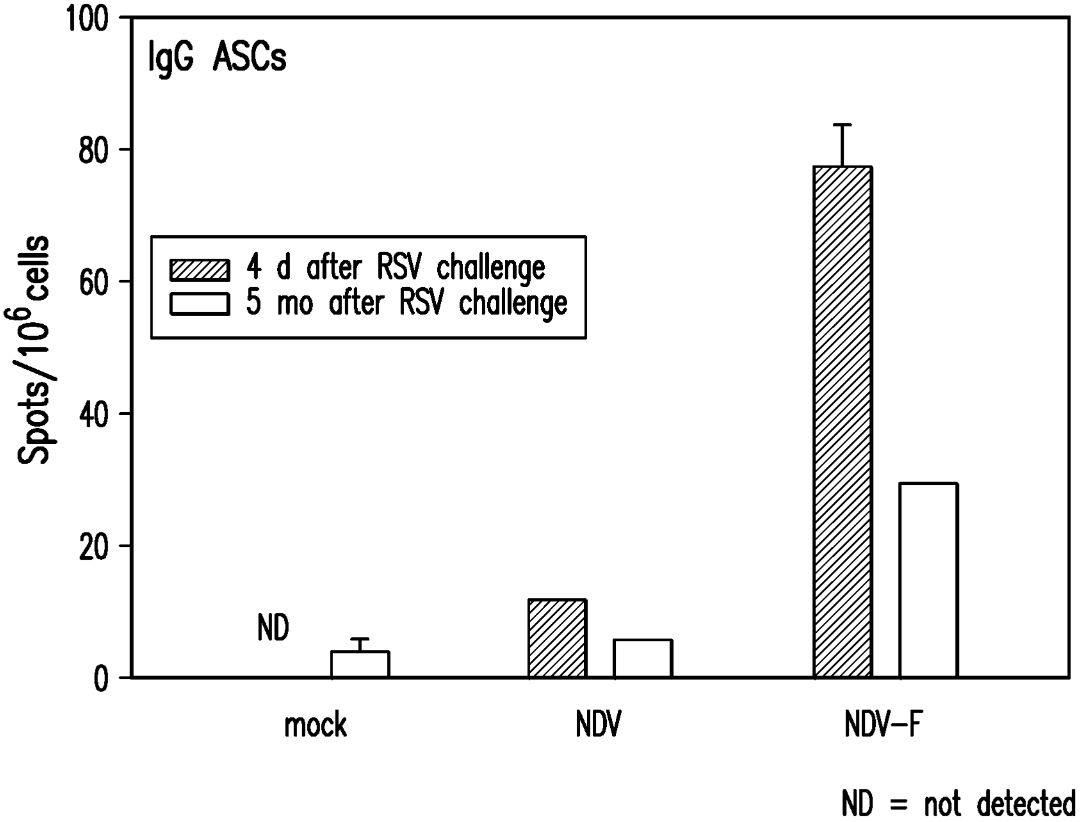

FIGS. 4A-4E. Humoral immune responses to vaccination and RSV challenge. Serum, BAL fluid and NW fluid were collected at multiple time points after vaccination and RSV challenge and F-specific IgG levels were determined by ELISA (FIGS. 4A-4C). Virus neutralization assay (FIG. 4D) revealed that F-specific antibodies induced by NDV-F vaccination were neutralizing. Cervical lymph nodes (CLNs) were collected 4 days and 5 months after RSV challenge of vaccinated animals and F-specific IgG secreting cells (ASCs) were enumerated by ELISpot (FIG. 4E).

Figure 5A:
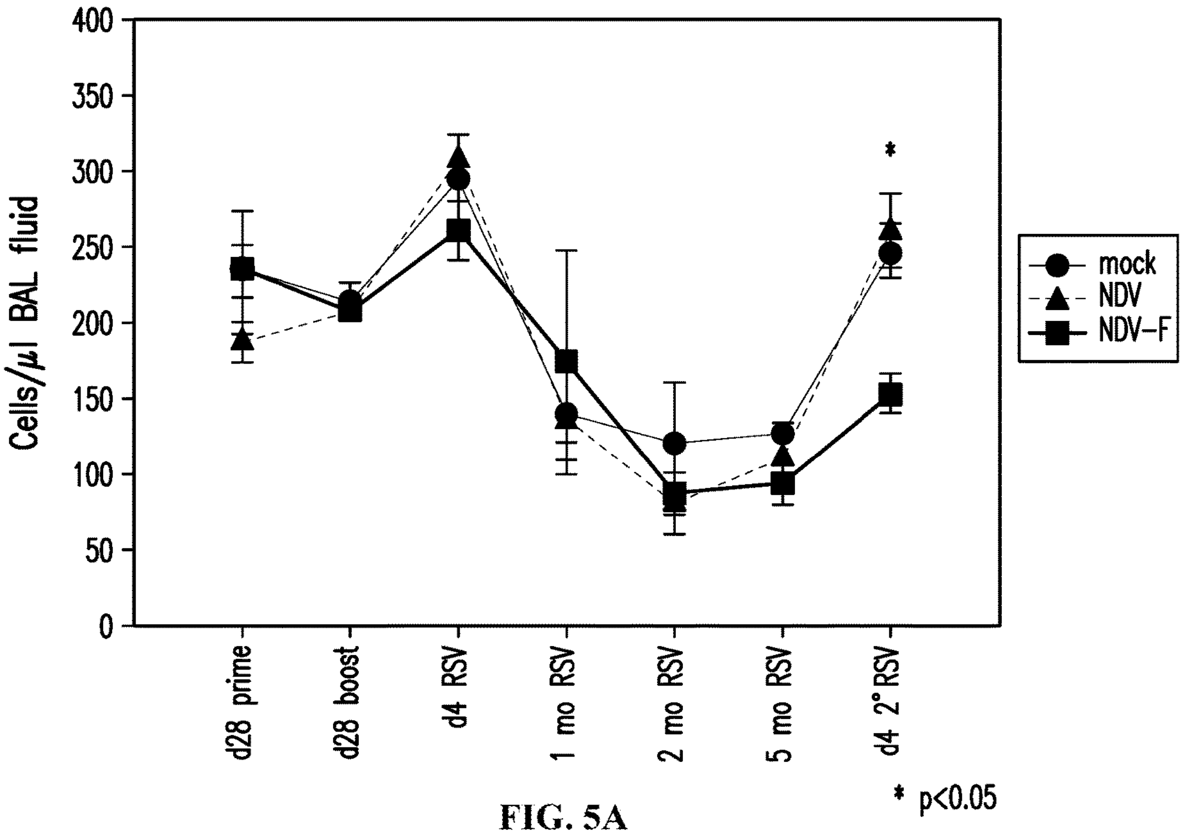
Figure 5B:
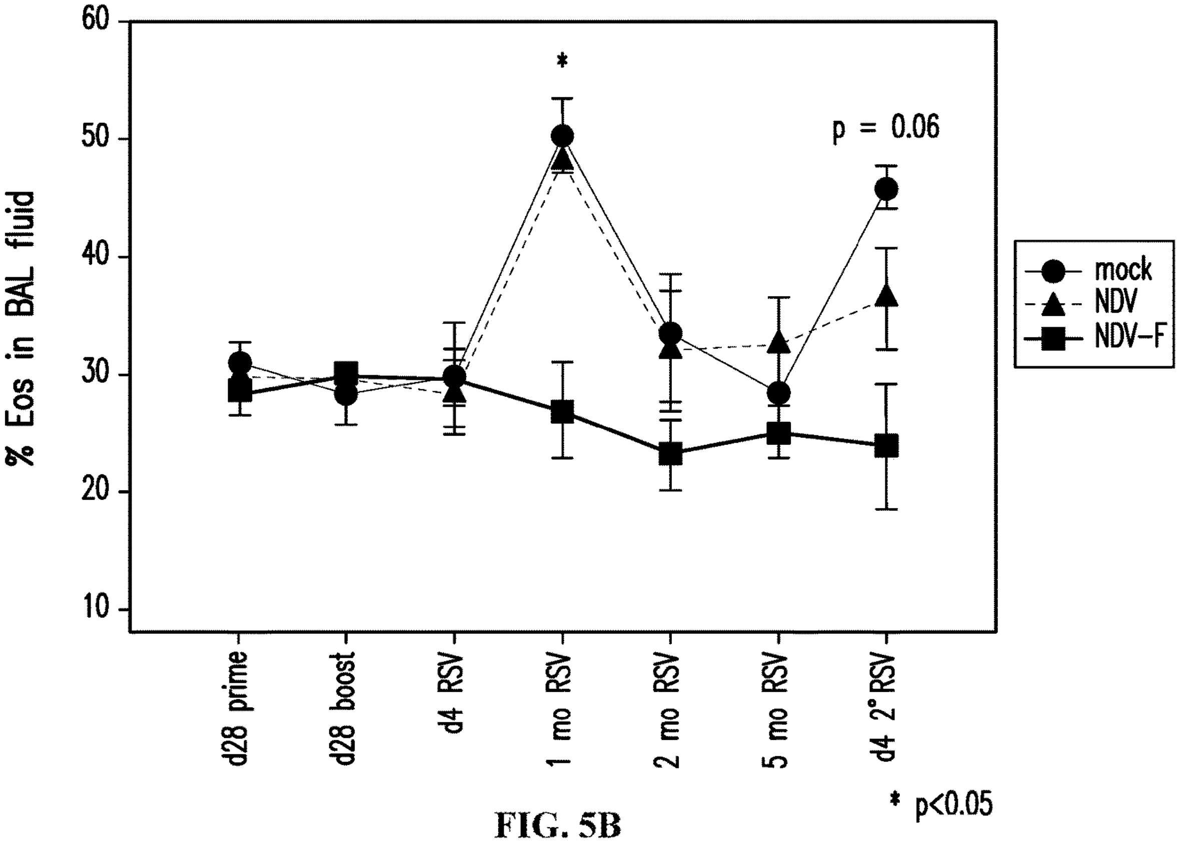

FIGS. 5A-5B. BAL fluid cellularity following vaccination and RSV challenge. BAL fluid was collected at multiple time points after vaccination and RSV challenge. Cellularity (FIG. 5A) of BAL fluid collected from animals in all cohorts increased slightly, but not significantly, in response to primary RSV challenge then decreased gradually over time. Cellularity increased in BAL fluid collected from mock and NDV, but not NDV-F, vaccinated animals in response to secondary RSV challenge. The percentage of eosinophils (FIG. 5B) in BAL fluid collected from mock and NDV, but not NDV-F vaccinated animals, increased in response to primary and secondary RSV challenge. BAL fluid cellularity and eosinophil percentage were not affected by vaccination alone. * $p<0.05$ FIG. 6. Immunization of RSV-immune animals. Cotton rats were infected with RSV on day 0. Two months post infection, 20/40 animals were primed with NDV-F, and boosted with a second dose 28 days later. At 4 months and 9 months post infection serum samples were taken from cohorts of immunized and control animals (N=5). At the 9 month time point, all animals were given a second challenge of RSV, and sacrificed day 2 and day 4 post re-infection.

Figure 7B:
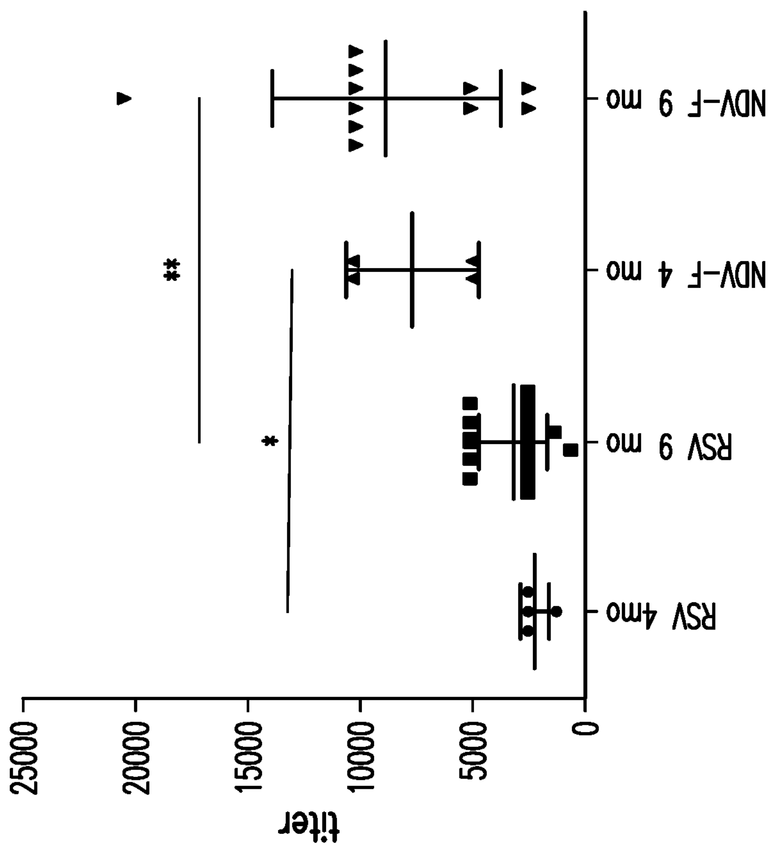
Figure 7A:
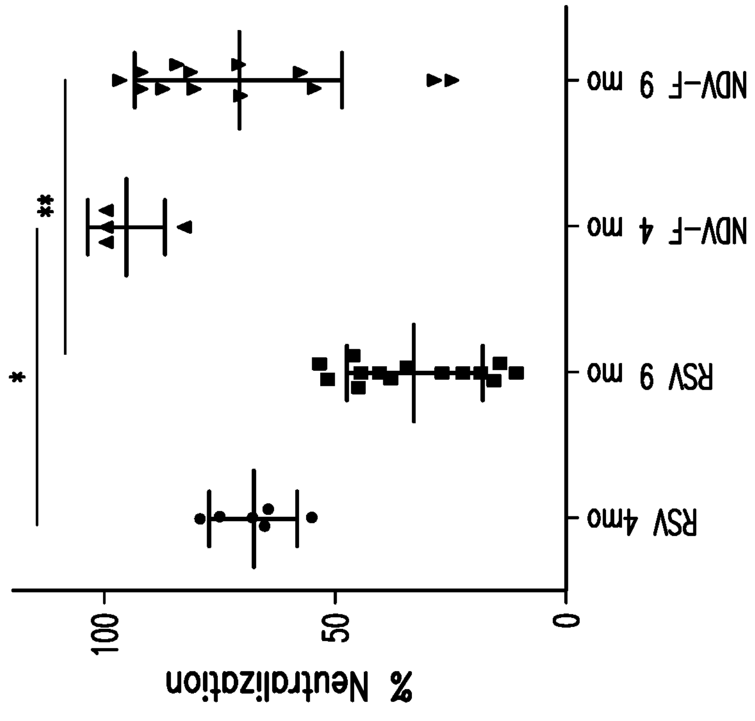

FIGS. 7A-7B. Serum antibody titers following post-infection immunization. Serum was harvested from cotton rats 4 or 9 months following primary RSV infection. (FIG. 7A) Levels of neutralizing antibody were determined by incubation of a 1/800 dilution of each serum with rgRSV, which was then used to inoculate A549 cells. Percentage of GFP-expressing cells was used to calculate % neutralization. * p=0.0027; ** p<0.0001. (FIG. 7B) Levels of RSV F specific antibody in each sample were determined by ELISA. *p=0.0114; ** p=0.0004. Levels of neutralizing and RSV F specific antibody were significantly higher in the NDV-F vaccinated animals at 4 and 9 months post primary infection as determined by the unpaired t test.

Figure 8:
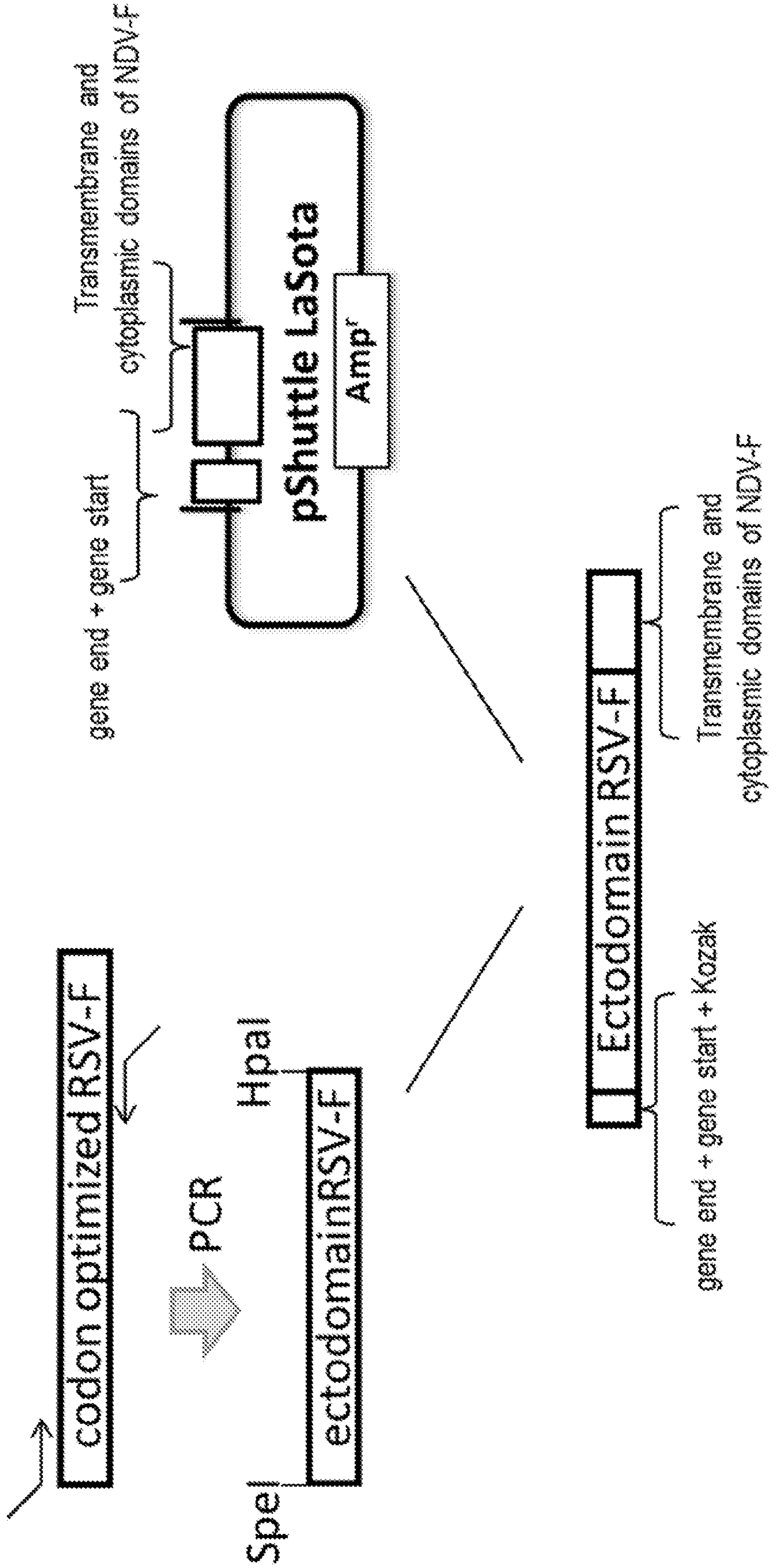
Figure 13:
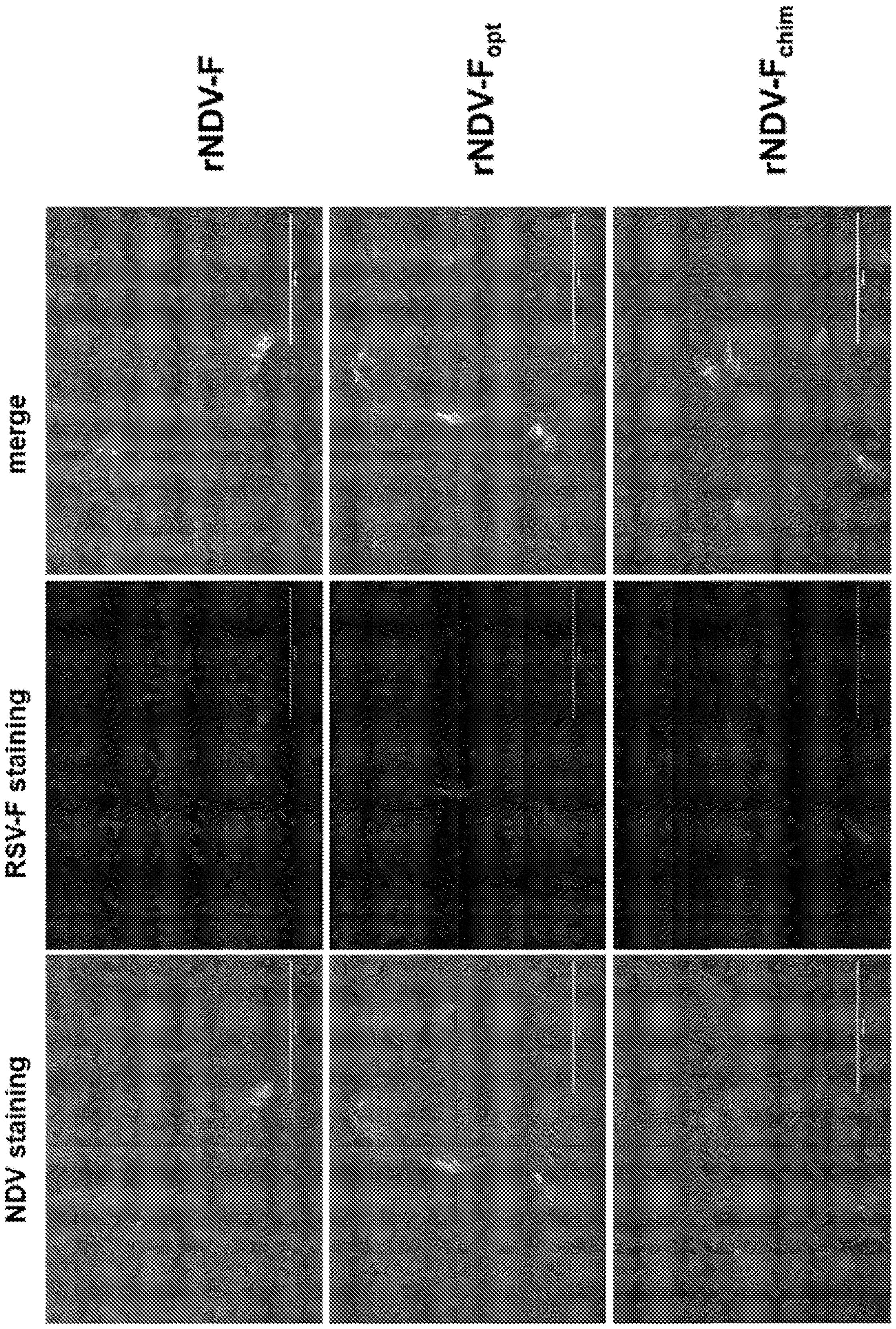

FIG. 8. Cloning of the chimeric F protein with the ectodomain of the human RSV F and the transmembrane and cytoplasmic domains of the NDV F (not to scale). After rescue all the recombinant NDVs were amplified by inoculation in 8-10 old embryonated chicken eggs and characterized by RT-PCR and immunofluorescence (FIG. 13).

Figure 9:
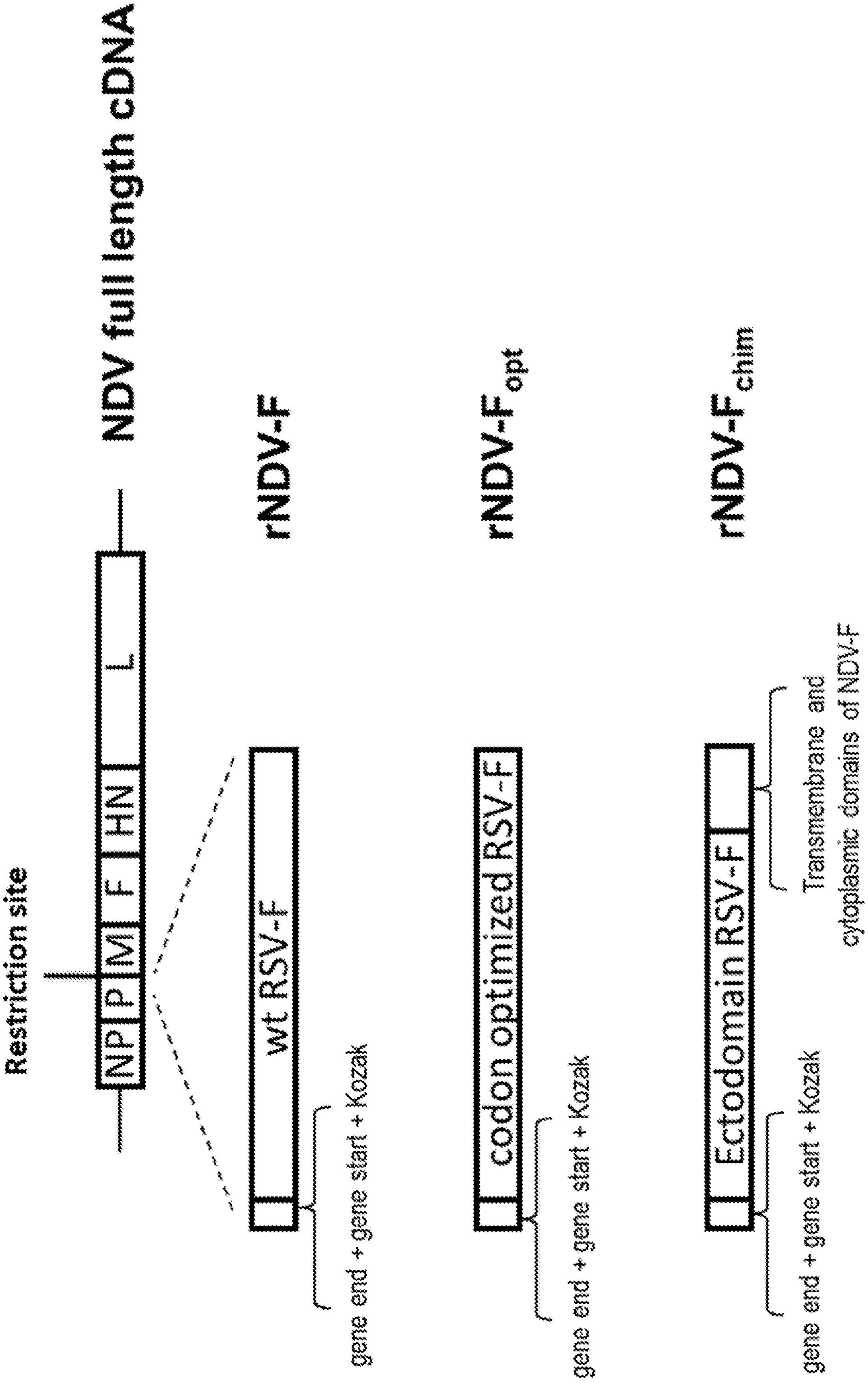

FIG. 9. A schematic representation of the different rNDV-F, rNDV-$F_{opt}$, rNDV-$F_{chim}$ are shown.

Figure 10:
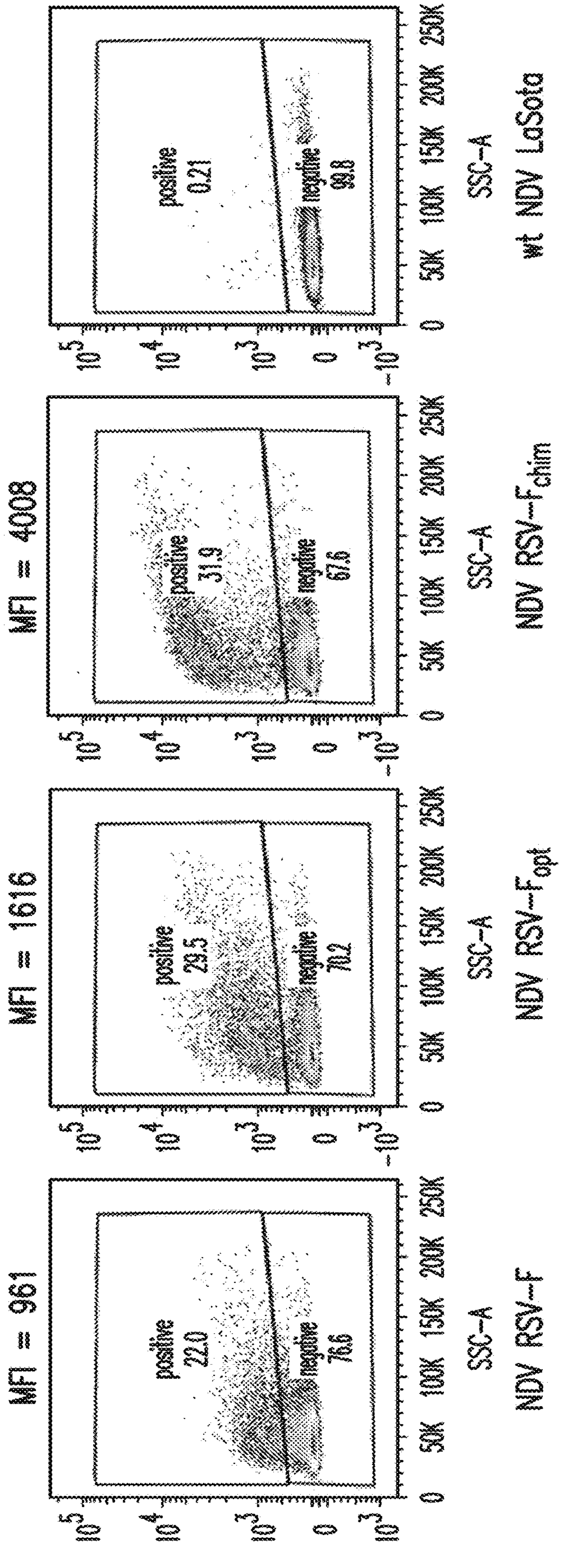

FIG. 10. Vero cells were infected with each construct, or the LaSota NDV virus vector for 24 hours, then stained with the Synagis® antibody to detect RSV F expression by flow cytometry. Mean Fluorescence Intensity (MFI) of the positive gated cells is shown.

Figure 11:
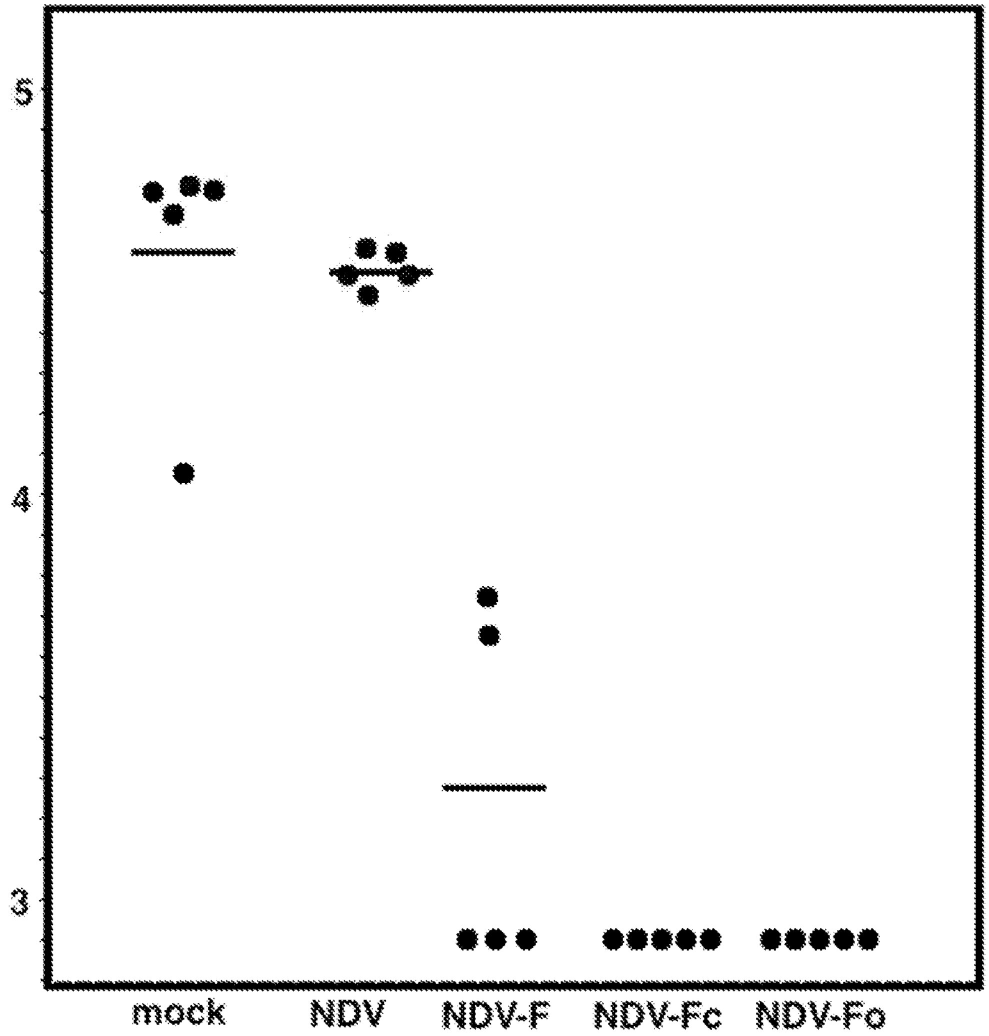

FIG. 11. The number of plaque forming units of RSV detected in lung homogenates obtained from cotton rats mock treated or given priming and boosting doses of NDV, rNDV-F, rNDV-$F_{opt}$, or rNDV-$F_{chim}$ following RSV challenge.

Figure 12A:
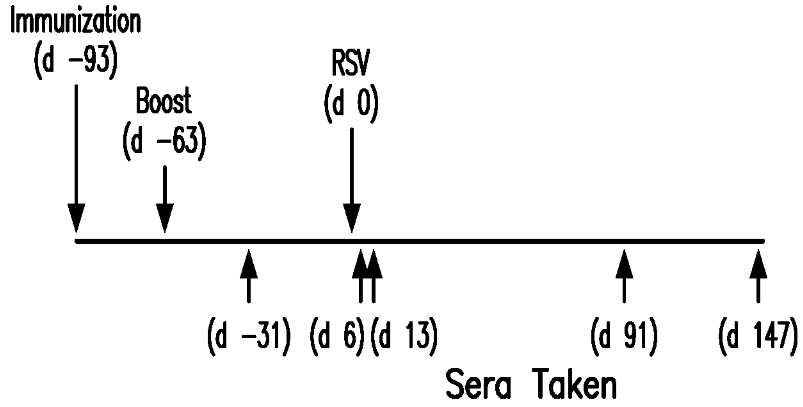
Figure 12B:
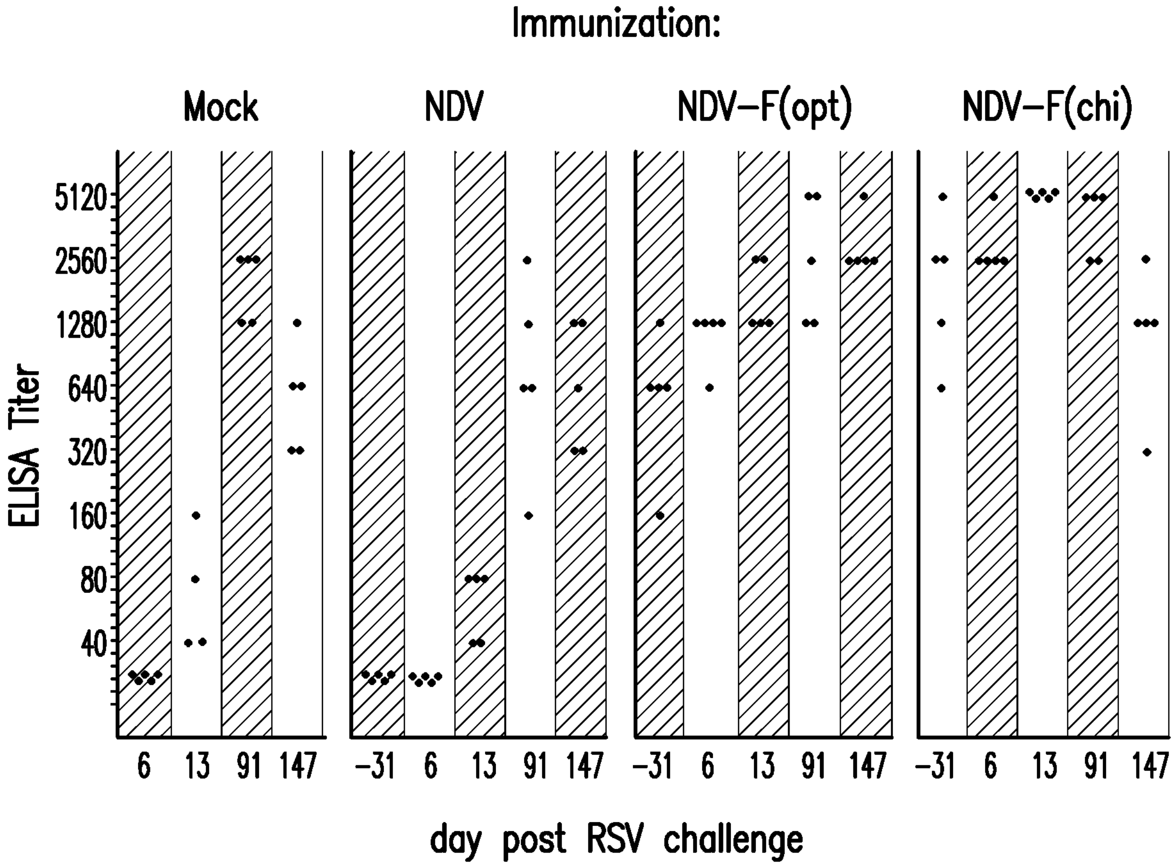

FIGS. 12A-12B. FIG. 12A shows the relationship of serum sampling to immunization and challenge. FIG. 12B shows antibody titers from individual cotton rats measured with an RSV F protein specific ELISA.

FIG. 13. Detection of the RSV F protein and NDV HN protein expressed by the different recombinant NDVs by double immunofluorescent microscopy.

Figure 14:
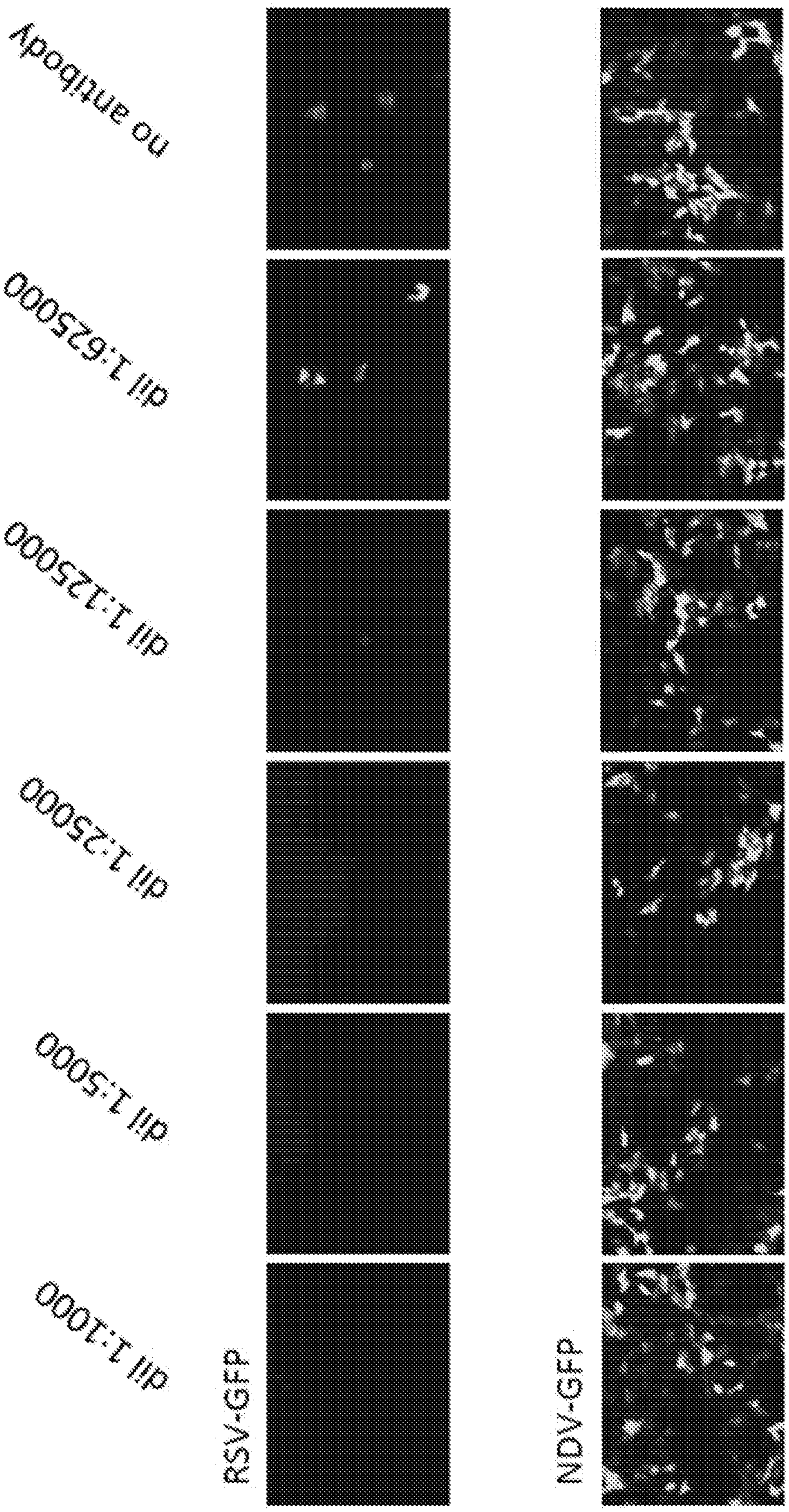

FIG. 14. Detection of virus in cells treated with different concentrations of Synagis® followed by infection with GFP expressing viruses (RSV-GFP and NDV-GFP). Representative microscopic fields were photographed to prepare the figure.

Figure 15:
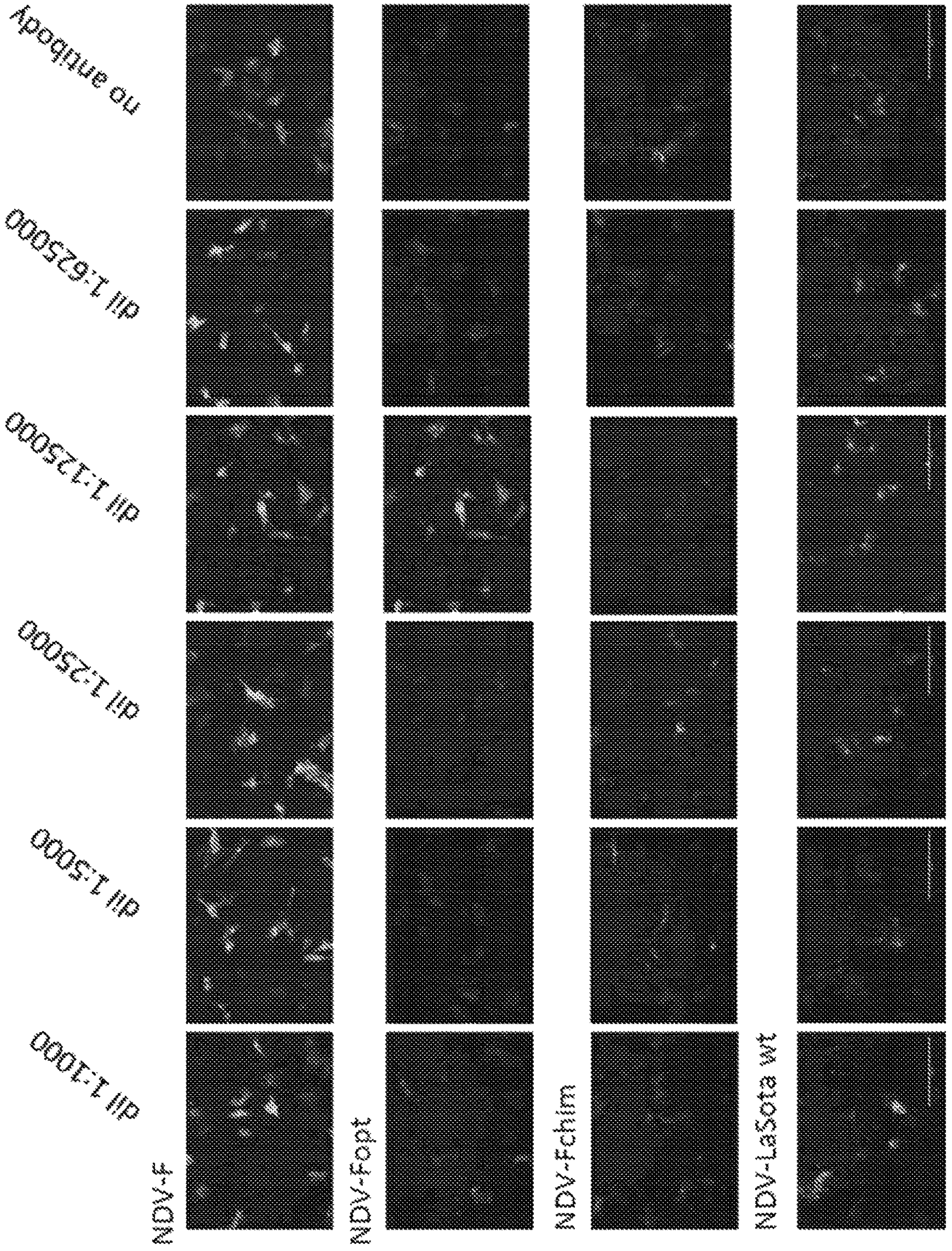

FIG. 15. Detection of NDV in cells treated with different concentrations of Synagis® followed by infection with NDV, rNDV-F, rNDV-Fopt, or rNDV-Fchim. Representative microscopic fields were photographed to prepare the figure.

FIGS. 16A-16C. An alignment comparing the wild-type nucleic acid sequence encoding human RSV F protein (SEQ ID NO:1) to the codon optimized nucleic acid sequence encoding human RSV F protein (SEQ ID NO:2).

FIGS. 17A-17C. An alignment comparing the wild-type nucleic acid sequence encoding bovine RSV F protein (SEQ ID NO:9) to the codon optimized nucleic acid sequence encoding bovine RSV F protein (SEQ ID NO:11).

Figure 18:
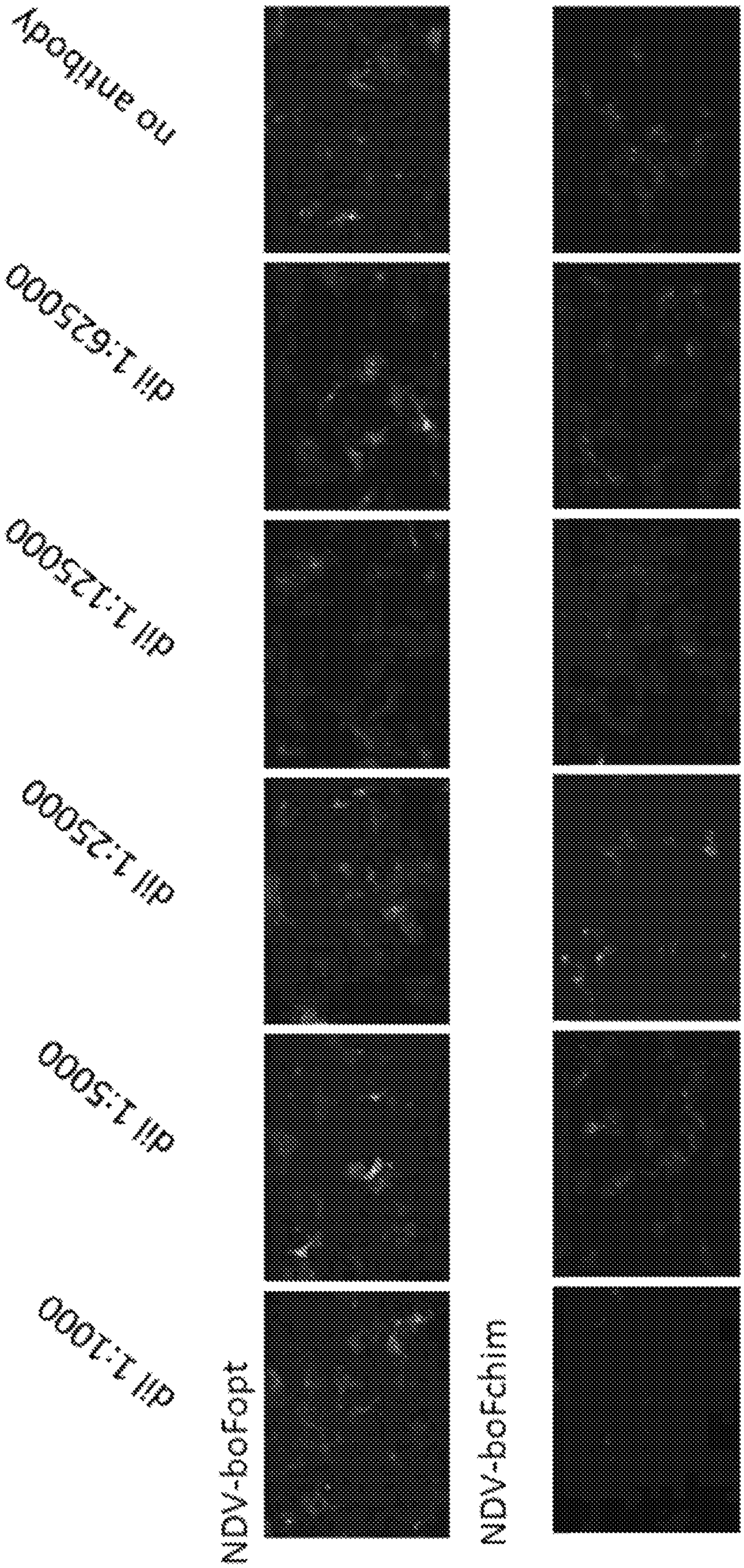

FIG. 18. Detection of NDV in cells treated with different concentrations of Synagis® followed by infection with rNDV-bovine RSV $F_{opt}$ or rNDV-bovine RSV$F_{chim}$. Representative microscopic fields were photographed to prepare the figure.

FIGS. 19A-19C. An alignment comparing the wild-type nucleic acid sequence encoding human metapneumovirus F protein (SEQ ID NO:16) to the codon optimized nucleic acid sequence encoding human metapneumovirus F protein (SEQ ID NO:18).

5. DETAILED DESCRIPTION

In one aspect, described herein are recombinant Newcastle disease viruses ("NDVs") comprising a packaged genome, wherein the packaged genome comprises a transgene encoding a respiratory syncytial virus ("RSV") F protein or human metapneumovirus ('hMPV") F protein. In another aspect, described herein are recombinant NDVs comprising a packaged genome, wherein the packaged genome comprises a transgene encoding a chimeric F protein, wherein the chimeric F protein comprises (i) an RSV F protein ectodomain and NDV F protein transmembrane and cytoplasmic domains; or (ii) an hMPV F protein ectodomain and NDV F protein transmembrane and cytoplasmic domains. In another aspect, described herein are compositions (e.g., immunogenic compositions) comprising a recombinant NDV described herein. In another aspect, the recombinant NDVs and compositions thereof are useful for inducing an immune response to RSV F protein or hMPV F protein, immunizing against RSV or hMPV, or the prevention of RSV disease or hMPV disease.

5.1 Recombinant Newcastle Disease Virus

5.1.1 NDV

Any NDV type or strain may be serve as the "backbone" that is engineered to encode a transgene described herein, including, but not limited to, naturally-occurring strains, variants or mutants, mutagenized viruses, reassortants and/or genetically engineered viruses. In a specific embodiment, the nucleotide sequence is incorporated into the genome of a lentogenic NDV. In another specific embodiment, the nucleotide sequence is incorporated in the genome of NDV strain LaSota. Other examples of NDV strains into which the nucleotide sequence may be incorporated are the NDV Fuller, the NDV Ulster strain or the NDV Hitchner B1 strain. In some embodiments, a lentogenic strain other than NDV Hitchner B1 strain is used as the backbone into which a nucleotide sequence may be incorporated. The nucleotide sequence may be incorporated into the NDV genome between two transcription units (e.g., between the M and P transcription units or between the HN and L transcription units).

In a specific embodiment, the NDV that is engineered to encode a transgene described herein is a naturally-occurring strain. In certain embodiments, the NDV that is engineered to encode a transgene described herein is a lytic strain. In other embodiments, the NDV that is engineered to encode a transgene described herein is a non-lytic strain. In certain embodiments, the NDV that is engineered to encode a transgene described herein is lentogenic strain. In some embodiments, the NDV that is engineered to encode a transgene described herein is a mesogenic strain. In other embodiments, the NDV that is engineered to encode a transgene described herein is a velogenic strain. Specific examples of NDV strains include, but are not limited to, the 73-T strain, NDV HUJ strain, Ulster strain (see, e.g., GenBank No. U25837), Fuller strain, MTH-68 strain, Italien strain (see, e.g., GenBank No. EU293914), Hickman strain (see, e.g., Genbank No. AF309418), PV701 strain, Hitchner B1 strain (see, e.g., GenBank No. AF309418 or NC_002617), La Sota strain (see, e.g., GenBank Nos. AY845400, AF07761.1 and JF950510.1 and GI No. 56799463), YG97 strain (see, e.g., GenBank Nos. AY351959 or AY390310), MET95 strain (see, e.g., GenBank No. AY143159), Roakin strain (see, e.g., GenBank No. AF124443), and F48E9 strain (see, e.g., GenBank Nos. AF163440 and U25837). In a specific embodiment, the NDV that is engineered to encode a transgene described herein is the Hitchner B1 strain. In another embodiment, the NDV that is engineered to encode a transgene described herein is a B1 strain as identified by GenBank No. AF309418 or NC_002617. In a specific embodiment, the nucleotide sequence of the Hitchner B1 genome comprises an RNA sequence corresponding to the negative sense of the cDNA sequence set forth in SEQ ID NO:48. In another specific embodiment, the NDV that is engineered to encode a transgene described herein is the La Sota strain. In another embodiment, the NDV that is engineered to encode a transgene described herein is a LaSota strain as identified by GenBank Nos. AY845400, AF07761.1 or JF950510.1. In a specific embodiment, the nucleotide sequence of the La Sota genome comprises an RNA sequence corresponding to the negative sense of the cDNA sequence set forth in SEQ ID NO:47. One skilled in the art will understand that the NDV genomic RNA sequence is an RNA sequence corresponding to the negative sense of a cDNA sequence encoding the NDV genome. Thus, any program that converts a nucleotide sequence to its reverse complement sequence may be utilized to convert a cDNA sequence encoding an NDV genome into the genomic RNA sequence (see, e.g., Bioinformatics.org and DNAStar). Accordingly, the nucleotide sequences provided in Tables 1-6, infra, may be readily converted to the negative-sense RNA sequence of the NDV genome by one of skill in the art.

In specific embodiments, the NDV that is engineered to encode a transgene described herein is not pathogenic in birds as assessed by a technique known to one of skill. In certain specific embodiments, the NDV that is engineered to encode a transgene described herein is not pathogenic as assessed by intracranial injection of 1-day-old chicks with the virus, and disease development and death as scored for 8 days. In some embodiments, the NDV that is engineered to encode a transgene described herein has an intracranial pathogenicity index of less than 0.7, less than 0.6, less than 0.5, less than 0.4, less than 0.3, less than 0.2 or less than 0.1. In certain embodiments, the NDV that is engineered to encode a transgene described herein has an intracranial pathogenicity index of zero. See, e.g., OIE Terrestrial Manual 2012, Chapter 2.3.14, entitled "Newcastle Disease (Infection With Newcastle Disease Virus) for a description of this assay, which is incorporated herein by reference in its entirety.

In certain embodiments, the NDV that is engineered to encode a transgene described herein is a mesogenic strain that has been genetically engineered so as not be a considered pathogenic in birds as assessed by techniques known to one skilled in the art. In certain embodiments, the NDV that is engineered to encode a transgene described herein is a velogenic strain that has been genetically engineered so as not be a considered pathogenic in birds as assessed by techniques known to one skilled in the art.

In preferred embodiments, the NDV that is engineered to encode a transgene described herein is non-pathogenic in humans or bovine. In preferred embodiments, the NDV that is engineered to encode a transgene described herein is non-pathogenic in humans, bovines and avians. In certain embodiments, the NDV that is engineered to encode a transgene described herein is attenuated such that the NDV remains, at least partially, infectious and can replicate in vivo, but only generate low titers resulting in subclinical levels of infection that are non-pathogenic (see, e.g., Khattar et al., 2009, J. Virol. 83:7779-7782). Such attenuated NDVs may be especially suited for embodiments wherein the virus is administered to a subject in order to act as an immunogen, e.g., a live vaccine. The viruses may be attenuated by any method known in the art. In a specific embodiment, the NDV genome comprises sequences necessary for infection and replication of the attenuated virus such that progeny is produced and the infection level is subclinical.

5.1.2 RSV F Protein/Chimeric F Protein with the RSV F Protein Ectodomain

In a specific embodiment, a transgene encoding a human RSV F protein is incorporated into the genome of any NDV type or strain. (e.g., NDV LaSota strain) See, e.g., Section 5.1.1., supra, for types and strains of NDV that may be used. The transgene encoding any RSV F protein may inserted into any NDV type or strain (e.g., NDV LaSota strain). The RSV F protein may be an RSV F protein of a human or bovine strain of RSV. In a specific embodiment, a transgene encoding a human RSV F protein is incorporated into the genome of any NDV type or strain (e.g., NDV LaSota strain). See, e.g., Section 5.8 3.1 for exemplary sequences for human RSV F protein and exemplary nucleic acid sequences encoding human RSV F protein. One of skill in the art would be able to use such sequence information to produce a transgene for incorporation into the genome of any NDV type or strain. For example, a transgene encoding the human RSV F protein comprising the amino acid sequence set forth in SEQ ID NO:6, 49, 50 or 58 may be incorporated into the genome of any NDV type or strain. In a specific embodiment, such a transgene comprises an RNA sequence corresponding to the negative sense of the cDNA sequence set forth in SEQ ID NO:1, 25, 27 or 29. However, given the degeneracy of the nucleic acid code, there are a number of different nucleic acid sequences that may encode the same human RSV F protein. In a specific embodiment, a transgene encoding a human RSV F protein is codon optimized. See, e.g., Section 5.1.6, infra, for a discussion regarding codon optimization. For example, the human RSV F protein may be encoded by a codon optimized nucleic acid sequence, such as set forth in SEQ ID NO: 2, 26, 28 or 30. In some embodiments, the transgene encoding a human RSV F protein comprises the amino acid sequence encoded by the nucleic acid sequence comprising the sequence set forth in SEQ ID NO:1, 2, 25, 26, 27, 28, 29, or 30. The transgene encoding a human RSV F protein may be incorporated between any two NDV transcription units (e.g., between the NDV P and M transcription units, or between the HN and L transcription units).

In a specific embodiment, a transgene encoding a bovine RSV F protein is incorporated into the genome of any NDV type or strain (e.g., NDV LaSota strain). See, e.g., Section 5.8 3.1 for exemplary sequences for bovine RSV F protein and exemplary nucleic acid sequences encoding bovine RSV F protein. One of skill in the art would be able to use such sequence information to produce a transgene for incorporation into the genome of any NDV type or strain. For example, a transgene encoding the bovine RSV F protein comprising the amino acid sequence set forth in SEQ ID NO:10 may be incorporated into the genome of any NDV type or strain (e.g., NDV LaSota strain). In a specific embodiment, a transgene encoding the bovine RSV F protein comprises an RNA sequence corresponding to the negative sense of the cDNA sequence set forth in SEQ ID NO:9, 40 or 42. However, given the degeneracy of the nucleic acid code, there are a number of different nucleic acid sequences that may encode the same bovine RSV F protein. In a specific embodiment, a transgene encoding a bovine RSV F protein is codon optimized. For example, the bovine RSV F protein may be encoded by the codon optimized nucleic acid sequence set forth in SEQ ID NO: 11, 41 or 43. In some embodiments, the transgene encoding a bovine RSV F protein comprises the amino acid sequence encoded by the nucleic acid sequence comprising the sequence set forth in SEQ ID NO:9, 11, 40, 41, 42, or 43. The transgene encoding a bovine RSV F protein may be incorporated between any two NDV transcription units (e.g., between NDV P and M genes).

In another embodiment, described herein are transgenes encoding a chimeric F protein, wherein the chimeric F protein comprises an RSV F protein ectodomain and NDV F protein transmembrane and cytoplasmic domains. In other words, the NDV F protein transmembrane and cytoplasmic domains replace the RSV F protein transmembrane and cytoplasmic domains so that the chimeric F protein does not include the RSV F protein transmembrane and cytoplasmic domains. The RSV F protein may be an RSV F protein of a human or bovine strain of RSV. The ectodomain, transmembrane and cytoplasmic domains of the RSV F protein and NDV F protein may be determined using techniques known to one of skill in the art. For example, published information, GenBank or websites such as VIPR virus pathogen website, DTU Bioinformatics domain website or programs available to determine the transmembrane domain may be used to determined the ectodomain, transmembrane and cytoplasmic domains of the RSV F protein and NDV F protein. See, e.g., the tables infra with the transmembrane and cytoplasmic domains indicated. In specific embodiment, described herein is a transgene encoding a chimeric F protein, wherein the chimeric F protein comprises a human RSV F protein ectodomain and NDV F protein transmembrane and cytoplasmic domains, and wherein the transgene comprises an RNA sequence corresponding to the negative sense of the cDNA sequence of SEQ ID NO: 51. In another embodiment, described herein is a transgene encoding a chimeric F protein, wherein the chimeric F protein comprises a bovine RSV F protein ectodomain and NDV F protein transmembrane and cytoplasmic domains, and wherein the transgene comprises the an RNA sequence corresponding to the negative sense of the cDNA sequence of SEQ ID NO: 31. In a preferred embodiment, a transgene comprises a codon optimized version of a nucleic acid sequence encoding the RSV F protein ectodomain (e.g., a human or bovine RSV F protein ectodomain). In a specific embodiment, a transgene encoding a chimeric F protein is incorporated into the genome of any NDV type or strain (e.g., NDV LaSota strain). See, e.g., Section 5.1.1, supra, for types and strains of NDV that may be used. The transgene encoding a chimeric F protein may be incorporated between any two NDV transcription units (e.g., between the NDV P and M transcription units, or between the HN and L transcription units).

In a specific embodiment, described herein is a transgene encoding a chimeric F protein, wherein the chimeric F protein comprises a human RSV F protein ectodomain and NDV F protein transmembrane and cytoplasmic domains, and wherein the ectodomain of the RSV F protein is encoded by a codon optimized nucleic acid sequence. Specific examples of nucleic acid sequences encoding a chimeric F protein, wherein the chimeric F protein comprises a human RSV F protein ectodomain and NDV F protein transmembrane and cytoplasmic domains, and wherein the ectodomain of the RSV F protein is encoded by a codon optimized nucleic acid sequence, include SEQ ID NO:4, 44, 45, or 46. In a preferred embodiment, described herein is a transgene encoding a chimeric F protein, wherein the chimeric F protein comprises a human RSV F protein ectodomain and NDV F protein transmembrane and cytoplasmic domains, and wherein the transgene comprises an RNA sequence corresponding to the negative sense of the cDNA sequence of SEQ ID NO:4. In a specific embodiment, a transgene encoding a chimeric F protein is incorporated into the genome of any NDV type or strain. See, e.g., Section 5.1.1, supra, for types and strains of NDV that may be used. The transgene encoding a chimeric F protein may be incorporated between any two NDV transcription units (e.g., between the NDV P and M transcription units, or between the HN and L transcription units).

In a specific embodiment, described herein is a transgene encoding a chimeric F protein, wherein the chimeric F protein comprises a bovine RSV F protein ectodomain and NDV F protein transmembrane and cytoplasmic domains, and wherein the ectodomain of the RSV F protein is encoded by a codon optimized nucleic acid sequence. Specific examples of nucleic acid sequences encoding a chimeric F protein, wherein the chimeric F protein comprises a bovine RSV F protein ectodomain and NDV F protein transmembrane and cytoplasmic domains, and wherein the ectodomain of the RSV F protein is encoded by a codon optimized nucleic acid sequence, include SEQ ID NO:14, 38, or 39. In a preferred embodiment, described herein is a transgene encoding a chimeric F protein, wherein the chimeric F protein comprises a bovine RSV F protein ectodomain and NDV F protein transmembrane and cytoplasmic domains, and wherein the transgene comprises an RNA sequence corresponding to the negative sense of the cDNA sequence of SEQ ID NO:14 or 31. In a specific embodiment, a transgene encoding a chimeric F protein is incorporated into the genome of any NDV type or strain. See, e.g., Section 5.1.1, supra, for types and strains of NDV that may be used. The transgene encoding a chimeric F protein may be incorporated between any two NDV transcription units (e.g., between the NDV P and M transcription units, or between the HN and L transcription units).

In a specific embodiments, a transgene encoding a human RSV F protein or a chimeric F protein is encoded by a nucleic acid sequence comprising a nucleic acid sequence set forth in SEQ ID NO:1, 2, 4, 25, 26, 27, 28, 29, 30, 44, 45, 46, or 51, or an RNA sequence corresponding to the negative sense thereof. In specific embodiments, a transgene encoding a bovine RSV F protein or chimeric F protein is encoded by a nucleic acid sequence comprising a nucleic acid sequence set forth in SEQ ID NO: 9, 11, 14, 31, 38, 39, 40, 41, 42, or 43, or an RNA sequence corresponding to the negative sense thereof. See, e.g., Tables 1 and 3 for nucleic acid and amino acid sequences of RSV F. Also, see, e.g., Section 5.8 for exemplary human or bovine RSV F proteins, or chimeric F proteins.

In a specific embodiment, a transgene encoding an RSV F protein or a chimeric F protein is as described in Section 6, infra.

In certain embodiments, a transgene encoding an RSV F protein or a chimeric F protein comprises NDV regulatory signals (e.g., gene end, intergenic, and gene start sequences) and Kozak sequences. In some embodiments, a transgene encoding an RSV F protein or a chimeric F protein comprises NDV regulatory signals (e.g., gene end, intergenic, and gene start sequences), Kozak sequences and restriction sites to facilitate cloning. See, e.g., FIG. 8. In certain embodiments, a transgene encoding an RSV F protein or a chimeric F protein comprises NDV regulatory signals (gene end, intergenic and gene start sequences), Kozak sequences, restriction sites to facilitate cloning, and additional nucleotides in the non-coding region to ensure compliance with the rule of six. In a preferred embodiment, the transgene complies with the rule of six.

5.1.3 Recombinant NDV Encoding an RSV F Protein or a Chimeric F Protein with an RSV Ectodomain In one aspect, presented herein are recombinant Newcastle disease virus ("NDV") comprising a packaged genome, wherein the packaged genome comprises a transgene encoding a respiratory syncytial virus ("RSV") F protein. The RSV F protein may be an RSV F protein of a human or bovine strain of RSV. See, e.g., Section 5.1.2 and 6 for transgenes encoding a human or bovine RSV F protein which the packaged genome may comprise. In a specific embodiment, the transgene encodes the human RSV F protein comprising the amino sequence set forth in SEQ ID NO: 6, 49, 50 or 58, or the bovine RSV F protein set forth in SEQ ID NO: 10. Due to the degeneracy of the nucleic acid code, multiple different nucleic acid sequences may encode for the same human RSV F protein or the same bovine RSV F protein. In one embodiment, described herein is a recombinant NDV comprising a packaged genome comprising a transgene encoding a human RSV F protein, wherein the transgene comprises an RNA sequence corresponding to the negative sense of the cDNA sequence of SEQ ID NO:1, 25, 27 or 29. In another embodiment, described herein is a recombinant NDV comprising a packaged genome comprising a transgene encoding a bovine RSV F protein, wherein the transgene comprises an RNA sequence corresponding to the negative sense of the cDNA sequence of SEQ ID NO:9, 40 or 42. In a preferred embodiment, a transgene comprises a codon optimized version of a nucleic acid sequence encoding an RSV F protein (e.g., a human or bovine RSV F protein). In a specific embodiment, the RSV F protein is expressed by cells infected with the recombinant NDV. In some embodiments, RSV F protein is detected in the virion of recombinant NDV.

In a specific embodiment, described herein are recombinant NDV comprising a packaged genome, wherein the packaged genome comprises a transgene comprising a codon optimized nucleic acid sequence encoding a human RSV F protein. Specific examples of codon optimized nucleic acid sequences encoding a human RSV F protein include those in SEQ ID Nos:2, 26, 28, or 30. In a preferred embodiment, described herein is a recombinant NDV comprising a packaged genome comprising a transgene encoding a human RSV F protein, wherein the transgene comprises the an RNA sequence corresponding to the negative sense of the cDNA sequence of SEQ ID NO:2. In a specific embodiment, the human RSV F protein is expressed by cells infected with the recombinant NDV. In some embodiments, RSV F protein is detected in the virion of recombinant NDV.

In a specific embodiment, described herein are recombinant NDV comprising a packaged genome, wherein the packaged genome comprises a transgene comprising a codon optimized nucleic acid sequence encoding a bovine RSV F protein. Specific examples of codon optimized nucleic acid sequences encoding a bovine RSV F protein include those in SEQ ID Nos: 11, 41, or 43. In a preferred embodiment, described herein is a recombinant NDV comprising a packaged genome comprising a transgene encoding a bovine RSV F protein, wherein the transgene comprises an RNA sequence corresponding to the negative sense of the cDNA sequence of SEQ ID NO:11. In a specific embodiment, the bovine RSV F protein is expressed by cells infected with the recombinant NDV. In some embodiments, RSV F protein is detected in the virion of recombinant NDV.

In another embodiment, described herein are recombinant NDV comprising a packaged genome, wherein the packaged genome comprises a transgene encoding a chimeric F protein, wherein the chimeric F protein comprises an RSV F protein ectodomain and NDV F protein transmembrane and cytoplasmic domains. In other words, the NDV F protein transmembrane and cytoplasmic domains replace the RSV F protein transmembrane and cytoplasmic domains so that the chimeric F protein does not include the RSV F protein transmembrane and cytoplasmic domains. In a specific embodiment, the NDV F protein transmembrane and cytoplasmic domains are from the same strain of NDV as the NDV backbone. For example, if the NDV backbone is NDV LaSota, then the transmembrane and cytoplasmic domains of the chimeric F protein are NDV LaSota transmembrane and cytoplasmic domains. The RSV F protein may be an RSV F protein of a human or bovine strain of RSV. See, e.g., Section 5.1.2 and 6 for transgenes encoding a chimeric F protein which the packaged genome may comprise. In another embodiment, described herein are recombinant NDV comprising a packaged genome, wherein the packaged genome comprises a transgene encoding a chimeric F protein, wherein the chimeric F protein comprises a human RSV F protein ectodomain and NDV F protein transmembrane and cytoplasmic domains, and wherein the transgene comprises an RNA sequence corresponding to the negative sense of the cDNA sequence of SEQ ID NO:51. In another embodiment, described herein are recombinant NDV comprising a packaged genome, wherein the packaged genome comprises a transgene encoding a chimeric F protein, wherein the chimeric F protein comprises a bovine RSV F protein ectodomain and NDV F protein transmembrane and cytoplasmic domains, and wherein the transgene comprises an RNA sequence corresponding to the negative sense of the cDNA sequence of SEQ ID NO:31. In a preferred embodiment, a transgene comprises a codon optimized version of a nucleic acid sequence encoding the RSV F protein ectodomain (e.g., a human or bovine RSV F protein ectodomain). In a specific embodiment, the RSV F protein is expressed by cells infected with the recombinant NDV. In another specific embodiment, the RSV F protein is expressed by cells infected with the recombinant NDV and the chimeric F protein is incorporated into the NDV virion.

In a specific embodiment, described herein are recombinant NDV comprising a packaged genome, wherein the packaged genome comprises a transgene encoding a chimeric F protein, wherein the chimeric F protein comprises a human RSV F protein ectodomain and NDV F protein transmembrane and cytoplasmic domains, and wherein the ectodomain of the RSV F protein is encoded by a codon optimized nucleic acid sequence. Specific examples of nucleic acid sequences encoding a chimeric F protein, wherein the chimeric F protein comprises a human RSV F protein ectodomain and NDV F protein transmembrane and cytoplasmic domains, and wherein the ectodomain of the RSV F protein is encoded by a codon optimized nucleic acid sequence, include SEQ ID NO:4, 44, 45, and 46. In a preferred embodiment, described herein is a recombinant NDV comprising a packaged genome, wherein the packaged genome comprises a transgene encoding a chimeric F protein, wherein the chimeric F protein comprises a human RSV F protein ectodomain and NDV F protein transmembrane and cytoplasmic domains, and wherein the transgene comprises an RNA sequence corresponding to the negative sense of the cDNA sequence of SEQ ID NO:4. In a specific embodiment, the chimeric F protein is expressed by cells infected with the recombinant NDV. In another specific embodiment, the chimeric F protein is expressed by cells infected with the recombinant NDV and the chimeric F protein is incorporated into the virion of the NDV. In another specific embodiment, the RSV F protein is expressed by cells infected with the recombinant NDV and the chimeric F protein is incorporated into the NDV virion.

In a specific embodiment, described herein are recombinant NDV comprising a packaged genome, wherein the packaged genome comprises a transgene encoding a chimeric F protein, wherein the chimeric F protein comprises a bovine RSV F protein ectodomain and NDV F protein transmembrane and cytoplasmic domains, and wherein the ectodomain of the RSV F protein is encoded by a codon optimized nucleic acid sequence. Specific examples of nucleic acid sequences encoding a chimeric F protein, wherein the chimeric F protein comprises a bovine RSV F protein ectodomain and NDV F protein transmembrane and cytoplasmic domains, and wherein the ectodomain of the RSV F protein is encoded by a codon optimized nucleic acid sequence, include SEQ ID NO:14, 38, or 39. In a preferred embodiment, described herein is a recombinant NDV comprising a packaged genome, wherein the packaged genome comprises a transgene encoding a chimeric F protein, wherein the chimeric F protein comprises a bovine RSV F protein ectodomain and NDV F protein transmembrane and cytoplasmic domains, and wherein the transgene comprises an RNA sequence corresponding to the negative sense of the cDNA sequence of SEQ ID NO:14. In a specific embodiment, the chimeric F protein is expressed by cells infected with the recombinant NDV. In another specific embodiment, the chimeric F protein is expressed by cells infected with the recombinant NDV and the chimeric F protein is incorporated into the virion of the NDV.

In a specific embodiments, a recombinant NDV comprises a packaged genome, wherein the packaged genome comprises a transgene encoding a RSV F protein or a chimeric F protein, wherein the RSV F protein or chimeric F protein is encoded by a nucleic acid sequence comprising a nucleic acid sequence set forth in SEQ ID NO:1, 2, 4, 25, 26, 27, 28, 29, 30, 44, 45, 46, or 51, or an RNA sequence corresponding to the negative sense thereof. In specific embodiments, recombinant NDV comprises a packaged genome, wherein the packaged genome comprises a transgene encoding a RSV F protein or a chimeric F protein, wherein the RSV F protein or chimeric F protein is encoded by a nucleic acid sequence comprising a nucleic acid sequence set forth in SEQ ID NO: 9, 11, 14, 31, 38, 39, 40, 41, 42, or 43, or an RNA sequence corresponding to the negative sense thereof.

In a specific embodiment, a recombinant NDV is as described in Section 6, infra.

In a specific embodiment, a recombinant NDV described herein comprises a packaged genome, wherein the packaged genome corresponds to a negative sense RNA transcribed from a cDNA sequence comprising (or consisting of) the sequence set forth in SEQ ID NO: 3. In certain embodiment, the genome of the recombinant NDV does not comprise a heterologous sequence encoding a heterologous protein other than the human RSV F protein. In some embodiments, the genome of the recombinant NDV does not comprise a transgene other than a transgene encoding a human RSV F protein described herein. In certain embodiments, a recombinant NDV described herein comprises a packaged genome, wherein the genome comprises the genes found in NDV and a transgene encoding a human RSV F protein. In other words, the recombinant NDV encodes for both NDV F protein and the human RSV F protein. In certain embodiments, a recombinant NDV described herein comprises a packaged genome, wherein the genome comprises the genes found in NDV, a transgene encoding a human RSV F protein, and a transgene encoding an hMPV F protein or a chimeric F protein described herein, e.g., in Section 5.1.4, but does not include other transgenes, wherein the chimeric F protein comprises the ectodomain of hMPV F protein and the transmembrane and cytoplasmic domains of NDV F protein. In some embodiments, a recombinant NDV described herein comprises a packaged genome, wherein the genome comprises the genes found in NDV and a transgene encoding a human RSV F protein but does not include any other transgenes.

In a specific embodiment, a recombinant NDV described herein comprises a packaged genome, wherein the packaged genome corresponds to a negative sense RNA of a cDNA sequence comprising (or consisting of) the sequence set forth in SEQ ID NO: 12 or 13. In certain embodiment, the genome of the recombinant NDV does not comprise a heterologous sequence encoding a heterologous protein other than the bovine RSV F protein. In some embodiments, the genome of the recombinant NDV does not comprise a transgene other than a transgene encoding a bovine RSV F protein described herein. In certain embodiments, a recombinant NDV described herein comprises a packaged genome, wherein the genome comprises the genes found in NDV and a transgene encoding a bovine RSV F protein. In other words, the recombinant NDV encodes for both NDV F protein and the bovine RSV F protein. In certain embodiments, a recombinant NDV described herein comprises a packaged genome, wherein the genome comprises the genes found in NDV, a transgene encoding a bovine RSV F protein, and a transgene encoding an hMPV F protein or a chimeric F protein described herein, e.g., in Section 5.1.4, but does not include other transgenes, wherein the chimeric F protein comprises the ectodomain of hMPV F protein and the transmembrane and cytoplasmic domains of NDV F protein. In some embodiments, a recombinant NDV described herein comprises a packaged genome, wherein the genome comprises the genes found in NDV and a transgene encoding a bovine RSV F protein but does not include any other transgenes.

In a specific embodiment, a recombinant NDV described herein comprises a packaged genome, wherein the packaged genome corresponds to a negative sense RNA sequence of a cDNA sequence comprising (or consisting of) the sequence set forth in SEQ ID NO: 5, 37 or 59. In some embodiments, the packaged genome of NDV encodes a chimeric F protein, wherein the chimeric F protein comprises the human or bovine RSV F protein ectodomain and NDV F protein transmembrane and cytoplasmic domains. In certain embodiment, the genome of the recombinant NDV does not comprise a heterologous sequence encoding a heterologous protein other than the chimeric F protein. In some embodiments, the genome of the recombinant NDV does not comprise a transgene other than a transgene encoding a chimeric F protein described herein. In certain embodiments, a recombinant NDV described herein comprises a packaged genome, wherein the genome comprises the genes found in NDV and a transgene encoding a chimeric F protein. In other words, the recombinant NDV encodes for both NDV F protein and the chimeric F protein. In some embodiment, the genome of a recombinant NDV described herein comprises a transgene encoding a chimeric F protein and the genes found in NDV except for the gene encoding NDV F protein. In other words, the NDV encodes the chimeric F protein but not the NDV F protein. In certain embodiments, a recombinant NDV described herein comprises a packaged genome, wherein the genome comprises the genes found in NDV, a transgene encoding first chimeric F protein, and a transgene encoding an hMPV F protein or a second chimeric F protein described herein, e.g., in Section 5.1.4, but does not include other transgenes, wherein the first chimeric F protein comprises the ectodomain of human RSV F protein or bovine RSV F protein and the transmembrane and cytoplasmic domains of NDV F protein, and wherein the second chimeric F protein comprises the ectodomain of hMPV F protein and the transmembrane and cytoplasmic domains of NDV F protein. In some embodiments, a recombinant NDV described herein comprises a packaged genome, wherein the genome comprises the genes found in NDV and a transgene encoding a chimeric F protein but does not include other transgenes.

5.1.4 Human Metapneumovirus (hMPV) F Protein

In a specific embodiment, a transgene encoding a hMPV F protein is incorporated into the genome of any NDV type or strain. See, e.g., Section 5.1.1, supra, for types and strains of NDV that may be used. The transgene encoding any hMPV F protein may inserted into any NDV type or strain (e.g., NDV LaSota strain). The hMPV F protein may be an hMPV F protein of any strain of hMPV. See, e.g., Section 5.8 for exemplary sequences for hMPV F protein and exemplary nucleic acid sequences encoding hMPV F protein. One of skill in the art would be able to use such sequence information to produce a transgene for incorporation into the genome of any NDV type or strain. For example, a transgene encoding the hMPV F protein comprising the amino acid sequence set forth in SEQ ID NO:17 may be incorporated into the genome of any NDV type or strain. In a specific embodiment, such a transgene comprises an RNA sequence corresponding to the negative sense of the cDNA sequence set forth in SEQ ID NO:16, 52, 54, or 56. However, given the degeneracy of the nucleic acid code, there are a number of different nucleic acid sequences that may encode the same hMPV F protein. In a specific embodiment, a transgene encoding an hMPV F protein is codon optimized. See, e.g., Section 5.1.6, infra, for a discussion regarding codon optimization. For example, the hMPV F protein is encoded by the codon optimized nucleic acid sequence, such as set forth in SEQ ID NO: 18, 53, 55, or 57. In some embodiments, the transgene encoding an hMPV F protein comprises the amino acid sequence encoded by the nucleic acid sequence comprising the sequence set forth in SEQ ID NO:16, 18, 52, 53, 54, 55, 56 or 57. In certain embodiments, the hMPV F protein is encoded by a transgene comprising the an RNA sequence corresponding to the negative sense of the cDNA sequence set forth in SEQ ID NO:16, 18, 52, 53, 54, 55, 56 or 57. The transgene encoding a hMPV F protein may be incorporated between any two NDV transcription units (e.g., between the NDV P and M transcription units, or between the HN and L transcription units).

In another embodiment, described herein are transgenes encoding a chimeric F protein, wherein the chimeric F protein comprises an hMPV F protein ectodomain and NDV F protein transmembrane and cytoplasmic domains. In other words, the NDV F protein transmembrane and cytoplasmic domains replace the hMPV F protein transmembrane and cytoplasmic domains so that the chimeric F protein does not include the hMPV F protein transmembrane and cytoplasmic domains. The hMPV F protein may be an hMPV F protein of any strain of hMPV. The ectodomain, transmembrane and cytoplasmic domains of the hMPV F protein and NDV F protein may be determined using techniques known to one of skill in the art. For example, published information, GenBank or websites such as VIPR virus pathogen website, DTU Bioinformatics domain website, or programs available to determine the transmembrane domain may be used to determined the ectodomain, transmembrane and cytoplasmic domains of the hMPV F protein and NDV F protein. See, e.g., the tables below indicating the transmembrane and cytoplasmic domains. In specific embodiment, described herein is a transgene encoding a chimeric F protein, wherein the chimeric F protein comprises a hMPV F protein ectodomain and NDV F protein transmembrane and cytoplasmic domains, and wherein the transgene comprises an RNA sequence corresponding to the negative sense of the cDNA sequence of SEQ ID NO:32. In a preferred embodiment, a transgene comprises a codon optimized version of a nucleic acid sequence encoding the hMPV F protein ectodomain. In specific embodiment, described herein is a transgene encoding a chimeric F protein, wherein the chimeric F protein comprises a hMPV F protein ectodomain and NDV F protein transmembrane and cytoplasmic domains, and wherein the transgene comprises an RNA sequence corresponding to the negative sense of the cDNA sequence of SEQ ID NO:19, 34, 35, or 36. In a specific embodiment, a transgene encoding a chimeric F protein is incorporated into the genome of any NDV type or strain. See, e.g., Section 5.1.1, supra, for types and strains of NDV that may be used. The transgene encoding a chimeric F protein may be incorporated between any two NDV transcription units (e.g., between the NDV P and M transcription units, or between the HN and L transcription units).

In a specific embodiment, described herein is a transgene encoding a chimeric F protein, wherein the chimeric F protein comprises a hMPV F protein ectodomain and NDV F protein transmembrane and cytoplasmic domains, and wherein the ectodomain of the hMPV F protein is encoded by a codon optimized nucleic acid sequence. Specific examples of nucleic acid sequences encoding a chimeric F protein, wherein the chimeric F protein comprises a human hMPV F protein ectodomain and NDV F protein transmembrane and cytoplasmic domains, and wherein the ectodomain of the hMPV F protein is encoded by a codon optimized nucleic acid sequence, include SEQ ID NO:19, 34, 35, and 36. In a preferred embodiment, described herein is a transgene encoding a chimeric F protein, wherein the chimeric F protein comprises a hMPV F protein ectodomain and NDV F protein transmembrane and cytoplasmic domains, and wherein the transgene comprises an RNA sequence corresponding to the negative sense of the cDNA sequence of SEQ ID NO:19. In a specific embodiment, a transgene encoding a chimeric F protein is incorporated into the genome of any NDV type or strain. See, e.g., Section 5.1.1, supra, for types and strains of NDV that may be used. The transgene encoding a chimeric F protein may be incorporated between any two NDV transcription units (e.g., between the NDV P and M transcription units, or between the HN and L transcription units).

In specific embodiments, a transgene encoding an hMPV F protein or a chimeric F protein is encoded by a nucleic acid sequence comprising a nucleic acid sequence set forth in SEQ ID NO:16, 18, 19, 32, 34, 35, 36, 52, 53, 54, 55, 56, or 57, or an RNA sequence corresponding to the negative sense thereof. See, e.g., Section 5.8 for exemplary hMPV F protein or chimeric F proteins.

In a specific embodiment, a transgene encoding an hMPV F protein or a chimeric F protein is as described in Section 6, infra.

In certain embodiments, a transgene encoding an hMPV F protein or a chimeric F protein comprises NDV regulatory signals (e.g., gene end, intergenic, and gene start sequences) and Kozak sequences. In some embodiments, a transgene encoding an hMPV F protein or a chimeric F protein comprises NDV regulatory signals (e.g., gene end, intergenic, and gene start sequences), Kozak sequences and restriction sites to facilitate cloning. In certain embodiments, a transgene encoding an hMPV F protein or a chimeric F protein comprises NDV regulatory signals (gene end, intergenic and gene start sequences), Kozak sequences, restriction sites to facilitate cloning, and additional nucleotides in the non-coding region to ensure compliance with the rule of six. In a preferred embodiment, the transgene complies with the rule of six.

5.1.5 Recombinant NDV Encoding a hMPV F Protein or a Chimeric F Protein with an hMPV Ectodomain In one aspect, presented herein are recombinant Newcastle disease virus ("NDV") comprising a packaged genome, wherein the packaged genome comprises a transgene encoding a human metapneumovirus ("hMPV") F protein. See, e.g., Section 5.1.4 and 6 for transgenes encoding an hMPV F protein which the packaged genome may comprise. The hMPV F protein may be an hMPV F protein of any strain of hMPV. In a specific embodiment, the transgene encodes the hMPV F protein comprising the sequence set forth in SEQ ID NO: 17. Due to the degeneracy of the nucleic acid code, multiple different nucleic acid sequences may encode for the same hMPV F protein. Specific examples of nucleic acid sequences encoding a hMPV F protein include those set forth in SEQ ID NOs:16, 52, 54 and 56. In one embodiment, described herein is a recombinant NDV comprising a packaged genome comprising a transgene encoding a hMPV F protein, wherein the transgene comprises an RNA sequence corresponding to the negative sense of the cDNA sequence of SEQ ID NO:16. In a preferred embodiment, a transgene comprises a codon optimized version of a nucleic acid sequence encoding an hMPV F protein. In a specific embodiment, the hMPV F protein is expressed by cells infected with the recombinant NDV.

In a specific embodiment, described herein are recombinant NDV comprising a packaged genome, wherein the packaged genome comprises a transgene comprising a codon optimized nucleic acid sequence encoding a hMPV F protein. Specific examples of codon optimized nucleic acid sequences encoding a hMPV F protein include those set forth in SEQ ID Nos:18, 53, 55 and 57. In a specific embodiment, described herein is a recombinant NDV comprising a packaged genome comprising a transgene encoding a hMPV F protein, wherein the transgene comprises an RNA sequence corresponding to the negative sense of the cDNA sequence of SEQ ID NO:18. In a specific embodiment, the hMPV F protein is expressed by cells infected with the recombinant NDV.

In another embodiment, described herein are recombinant NDV comprising a packaged genome, wherein the packaged genome comprises a transgene encoding a chimeric F protein, wherein the chimeric F protein comprises an hMPV F protein ectodomain and NDV F protein transmembrane and cytoplasmic domains. In other words, the NDV F protein transmembrane and cytoplasmic domains replace the hMPV F protein transmembrane and cytoplasmic domains so that the chimeric F protein does not include the hMPV F protein transmembrane and cytoplasmic domains. The chimeric hMPV F protein may comprise the amino acid sequence of SEQ ID NO:15. In a specific embodiment, the NDV F protein transmembrane and cytoplasmic domains are from the strain of NDV as the NDV backbone. The hMPV F protein may be an hMPV F protein of any strain of hMPV. See, e.g., Section 5.1.4 and 6 for transgenes encoding a chimeric F protein which the packaged genome may comprise. In another embodiment, described herein are recombinant NDV comprising a packaged genome, wherein the packaged genome comprises a transgene encoding a chimeric F protein, wherein the chimeric F protein comprises a hMPV F protein ectodomain and NDV F protein transmembrane and cytoplasmic domains, and wherein the transgene comprises an RNA sequence corresponding to the negative sense of the cDNA sequence of SEQ ID NO:32. In a preferred embodiment, a transgene comprises a codon optimized version of a nucleic acid sequence encoding the hMPV F protein ectodomain. In a specific embodiment, the hMPV F protein is expressed by cells infected with the recombinant NDV. In some embodiments, hMPV F protein is detected in the NDV virion.

In a specific embodiment, described herein are recombinant NDV comprising a packaged genome, wherein the packaged genome comprises a transgene comprising a codon optimized nucleic acid sequence encoding a hMPV F protein. Specific examples of codon optimized nucleic acid sequences encoding a hMPV F protein include those set forth in SEQ ID NOs: 19, 34, 35 and 36. In a specific embodiment, described herein is a recombinant NDV comprising a packaged genome comprising a transgene encoding a hMPV F protein, wherein the transgene comprises an RNA sequence corresponding to the negative sense of the cDNA sequence of SEQ ID NO:19. In a specific embodiment, the hMPV F protein is expressed by cells infected with the recombinant NDV. In some embodiments, hMPV F protein is detected in the NDV virion.

In a specific embodiment, a recombinant NDV described herein comprises a packaged genome, wherein the packaged genome corresponds to a negative sense RNA of the cDNA sequence comprising (or consisting of) the sequence set forth in SEQ ID NO: 20 or 21. In certain embodiment, the genome of the recombinant NDV does not comprise a heterologous sequence encoding a heterologous protein other than the hMPV F protein. In some embodiments, the genome of the recombinant NDV does not comprise a transgene other than a transgene encoding a hMPV F protein described herein. In certain embodiments, a recombinant NDV described herein comprises a packaged genome, wherein the genome comprises the genes found in NDV and a transgene encoding an hMPV F protein. In other words, the recombinant NDV encodes for both NDV F protein and the hMPV F protein. In certain embodiments, a recombinant NDV described herein comprises a packaged genome, wherein the genome comprises the genes found in NDV, a transgene encoding an hMPV F protein, and a transgene encoding a human RSV F protein or a second chimeric F protein described herein, e.g., in Section 5.1.2, but does not include other transgenes, wherein the first chimeric F protein comprises the ectodomain of human RSV F protein and the transmembrane and cytoplasmic domains of NDV F protein. In some embodiments, a recombinant NDV described herein comprises a packaged genome, wherein the genome comprises the genes found in NDV and a transgene encoding an hMPV F protein but does not include other transgenes.

In a specific embodiment, a recombinant NDV described herein comprises a packaged genome, wherein the packaged genome corresponds to a negative sense RNA of the cDNA sequence comprising (or consisting of) the sequence set forth in SEQ ID NO: 22. In a specific embodiment, a recombinant NDV is as described in Section 6, infra. In certain embodiment, the genome of the recombinant NDV does not comprise a heterologous sequence encoding a heterologous protein other than the chimeric F protein. In some embodiments, the genome of the recombinant NDV does not comprise a transgene other than a transgene encoding a chimeric F protein described herein. In certain embodiments, a recombinant NDV described herein comprises a packaged genome, wherein the genome comprises the genes found in NDV and a transgene encoding a chimeric F protein. In other words, the recombinant NDV encodes for both NDV F protein and the chimeric F protein. In some embodiments, the genome of a recombinant NDV described herein comprises a transgene encoding the chimeric F protein and the genes of NDV except the gene encoding NDV F protein. In other words, the recombinant NDV encodes the chimeric F protein but not the NDV F protein. In certain embodiments, a recombinant NDV described herein comprises a packaged genome, wherein the genome comprises the genes found in NDV, a transgene encoding a first chimeric F protein, and a transgene encoding a human RSV F protein or a second chimeric F protein described herein, e.g., in Section 5.1.2, but does not include other transgenes, wherein the first chimeric F protein comprises the ectodomain of hMPV F protein and the transmembrane and cytoplasmic domains of NDV F protein, and wherein the second chimeric F protein comprises the ectodomain of human RSV F protein and the transmembrane and cytoplasmic domains of NDV F protein. In some embodiments, a recombinant NDV described herein comprises a packaged genome, wherein the genome comprises the genes found in NDV and a transgene encoding a chimeric F protein but does not include other transgenes.

5.1.6 Codon Optimization

Any codon optimization technique known to one of skill in the art may be used to codon optimize a nucleic acid sequence encoding an RSV F protein or a domain thereof (e.g., the ectodomain thereof). Similarly, any codon optimization technique may be used to codon optimize a nucleic acid sequence encoding an hMPV F protein or a domain thereof (e.g., the ectodomain thereof). Methods of codon optimization are known in the art, e.g., the OptimumGene™ (GenScript®) protocol and Genewiz® protocol, which are incorporated by reference herein in its entirety. See also U.S. Pat. No. 8,326,547 for methods for codon optimization, which is incorporated herein by reference in its entirety.

As an exemplary method for codon optimization, each codon in the open frame of the nucleic acid sequence encoding an RSV F protein or a domain thereof (e.g., the ectodomain thereof), or an hMPV F protein or a domain thereof (e.g., the ectodomain thereof) is replaced by the codon most frequently used in mammalian proteins. This may be done using a web-based program (Encorbio) that uses the Codon Usage Database, maintained by the Department of Plant Gene Research in Kazusa, Japan. This nucleic acid sequence optimized for mammalian expression may be inspected for: (1) the presence of stretches of 5xA or more that may act as transcription terminators; (2) the presence of restriction sites that may interfere with subcloning; (3) compliance with the rule of six. Following inspection, (1) stretches of 5xA or more that may act as transcription terminators may be replaced by synonymous mutations; (2) restriction sites that may interfere with subcloning may be replaced by synonymous mutations; (3) NDV regulatory signals (gene end, intergenic and gene start sequences), and Kozak sequences for optimal protein expression may be added; and (4) nucleotides may be added in the non-coding region to ensure compliance with the rule of six. Synonymous mutations are typically nucleotide changes that do not change the amino acid encoded. For example, in the case of a stretch of 6 As (AAAAAA), which sequence encodes Lys-Lys, a synonymous sequence would be AAGAAG, which sequence also encodes Lys-Lys.

In a specific embodiment, codon optimization reduces the AU content of the nucleic acid sequences encoding an RSV F protein (e.g., a human or bovine RSV-F protein) or a domain thereof (e.g., the ectodomain thereof), or a human MPV-F or a domain thereof (e.g., the ectodomain thereof). FIGS. 16A-16C is an alignment comparing the wild-type nucleic acid sequence encoding a wild-type human RSV F protein to the codon optimized nucleic acid sequence encoding human RSV F protein. FIGS. 17A-17C is an alignment comparing the wild-type nucleic acid sequence encoding a bovine RSV F protein to the codon optimized nucleic acid sequence encoding bovine RSV F protein. FIGS. 19A-19C is an alignment comparing the wild-type nucleic acid sequence encoding a wild-type hMPV F protein to the codon optimized nucleic acid sequence encoding hMPV F protein.

In a specific embodiment, the codon optimized nucleic acid sequence encoding human RSV F protein has a 10%, 15%, 20%, 25% or more drop in the AU content relative to the wild-type nucleic acid sequence encoding human RSV F protein. In another specific embodiment, the codon optimized nucleic acid sequence encoding human RSV F protein has a 10% to 25%, 10% to 30%, 15% to 25% 15% to 30%, or 20% to 30% drop in the AU content relative to the wild-type nucleic acid sequence encoding human RSV F protein. The open reading frame of the wild-type nucleic acid sequence encoding human RSV F protein set forth in SEQ ID NO:1 has a 65.16% A+U, whereas the codon optimized nucleic acid sequence set forth in SEQ ID NO:2 has a 39.43% A+U. In a specific embodiment, the codon optimized nucleic acid sequence encoding bovine RSV F protein has a 10%, 15%, 20%, 25% or more drop in the AU content relative to the wild-type nucleic acid sequence encoding bovine RSV F protein. In another specific embodiment, the codon optimized nucleic acid sequence encoding bovine RSV F protein has a 10% to 25%, 10% to 30%, 15% to 25% 15% to 30%, or 20% to 30% drop in the AU content relative to the wild-type nucleic acid sequence encoding bovine RSV F protein. The open reading frame of the wild-type nucleic acid sequence encoding bovine RSV F protein set forth in SEQ ID NO:9 has a 64.4% A+U, whereas the codon optimized nucleic acid sequence set forth in SEQ ID NO:11 has a 39.66% A+U. In a specific embodiment, the codon optimized nucleic acid sequence encoding hMPV F protein has a 10%, 15%, 20%, 25% or more drop in the AU content relative to the wild-type nucleic acid sequence encoding hMPV F protein. In another specific embodiment, the codon optimized nucleic acid sequence encoding hMPV F protein has a 10% to 25%, 10% to 30%, 15% to 25% 15% to 30%, or 20% to 30% drop in the AU content relative to the wild-type nucleic acid sequence encoding hMPV F protein. The open reading frame of the wild-type nucleic acid sequence encoding hMPV F protein set forth in SEQ ID NO:16 has a 56.86% A+U, whereas the codon optimized nucleic acid sequence set forth in SEQ ID NO:18 has a 37.9% A+U.

5.2 Construction of NDVs

The recombinant NDVs described herein (see, e.g., Sections 5.1 and 6) can be generated using the reverse genetics technique. The reverse genetics technique involves the preparation of synthetic recombinant viral RNAs that contain the non-coding regions of the negative-strand, viral RNA which are essential for the recognition by viral polymerases and for packaging signals necessary to generate a mature virion. The recombinant RNAs are synthesized from a recombinant DNA template and reconstituted in vitro with purified viral polymerase complex to form recombinant ribonucleoproteins (RNPs) which can be used to transfect cells. A more efficient transfection is achieved if the viral polymerase proteins are present during transcription of the synthetic RNAs either in vitro or in vivo. The synthetic recombinant RNPs can be rescued into infectious virus particles. The foregoing techniques are described in U.S. Pat. No. 5,166,057 issued Nov. 24, 1992; in U.S. Pat. No. 5,854,037 issued Dec. 29, 1998; in U.S. Pat. No. 6,146,642 issued Nov. 14, 2000; in European Patent Publication EP 0702085A1, published Feb. 20, 1996; in U.S. patent application Ser. No. 09/152,845; in International Patent Publications PCT WO97/12032 published Apr. 3, 1997; WO96/34625 published Nov. 7, 1996; in European Patent Publication EP A780475; WO 99/02657 published Jan. 21, 1999; WO 98/53078 published Nov. 26, 1998; WO 98/02530 published Jan. 22, 1998; WO 99/15672 published Apr. 1, 1999; WO 98/13501 published Apr. 2, 1998; WO 97/06270 published Feb. 20, 1997; and EPO 780 475A1 published Jun. 25, 1997, each of which is incorporated by reference herein in its entirety.

The helper-free plasmid technology can also be utilized to engineer a NDV described herein. Briefly, a complete cDNA of a NDV (e.g., the Hitchner B1 strain or LaSota strain) is constructed, inserted into a plasmid vector and engineered to contain a unique restriction site between two transcription units (e.g., the NDV P and M genes; or the NDV HN and L genes). A nucleotide sequence encoding a heterologous amino acid sequence (e.g., a transgene or other sequence described herein such as, e.g., a nucleotide sequence encoding an RSV F protein, a chimeric F protein, hMPV F protein) may be inserted into the viral genome at the unique restriction site. Alternatively, a nucleotide sequence encoding a heterologous amino acid sequence (e.g., a transgene or other sequence described herein such as, e.g., a nucleotide sequence encoding an RSV F protein, a chimeric F protein, hMPV F protein) may be engineered into a NDV transcription unit so long as the insertion does not affect the ability of the virus to infect and replicate. The single segment is positioned between a T7 promoter and the hepatitis delta virus ribozyme to produce an exact negative or positive transcript from the T7 polymerase. The plasmid vector and expression vectors comprising the necessary viral proteins are transfected into cells leading to production of recombinant viral particles (see, e.g., International Publication No. WO 01/04333; U.S. Pat. Nos. 7,442,379, 6,146,642, 6,649,372, 6,544,785 and 7,384,774; Swayne et al. (2003). Avian Dis. 47:1047-1050; and Swayne et al. (2001). J. Virol. 11868-11873, each of which is incorporated by reference in its entirety).

Bicistronic techniques to produce multiple proteins from a single mRNA are known to one of skill in the art. Bicistronic techniques allow the engineering of coding sequences of multiple proteins into a single mRNA through the use of IRES sequences. IRES sequences direct the internal recruitment of ribosomes to the RNA molecule and allow downstream translation in a cap independent manner. Briefly, a coding region of one protein is inserted downstream of the ORF of a second protein. The insertion is flanked by an IRES and any untranslated signal sequences necessary for proper expression and/or function. The insertion must not disrupt the open reading frame, polyadenylation or transcriptional promoters of the second protein (see, e.g., Garcia-Sastre et al., 1994, J. Virol. 68:6254-6261 and Garcia-Sastre et al., 1994 Dev. Biol. Stand. 82:237-246, each of which are incorporated by reference herein in their entirety).

Methods for cloning recombinant NDV to encode a transgene and express a heterologous protein encoded by the transgene (e.g., a transgene encoding an RSV F protein, a chimeric F protein, hMPV F protein) are known to one skilled in the art, such as, e.g., insertion of the transgene into a restriction site that has been engineered into the NDV genome, inclusion an appropriate signals in the transgene for recognition by the NDV RNA-dependent-RNA polymerase (e.g., sequences upstream of the open reading frame of the transgene that allow for the NDV polymerase to recognize the end of the previous gene and the beginning of the transgene, which may be, e.g., spaced by a single nucleotide intergenic sequence), inclusion of a valid Kozak sequence (e.g., to improve eukaryotic ribosomal translation); incorporation of a transgene that satisfies the "rule of six" for NDV cloning; and inclusion of silent mutations to remove extraneous gene end and/or gene start sequences within the transgene. Regarding the rule of six, one skilled in the art will understand that efficient replication of NDV (and more generally, most members of the paramyxoviridae family) is dependent on the genome length being a multiple of six, known as the "rule of six" (see, e.g., Calain, P. & Roux, L. The rule of six, a basic feature of efficient replication of Sendai virus defective interfering RNA. J. Virol. 67, 4822-4830 (1993)). Thus, when constructing a recombinant NDV described herein, care should be taken to satisfy the "Rule of Six" for NDV cloning. Methods known to one skilled in the art to satisfy the Rule of Six for NDV cloning may be used, such as, e.g., addition of nucleotides downstream of the transgene. See, e.g., Ayllon et al., Rescue of Recombinant Newcastle Disease Virus from cDNA. J. Vis. Exp. (80), e50830, doi:10.3791/50830 (2013) for a discussion of methods for cloning and rescuing of NDV (e.g., recombinant NDV), which is incorporated by reference herein in its entirety.

In a specific embodiment, an NDV described herein (see, e.g., Sections 5.1 and 6) may be generated according to a method described in Section 6, infra.

In a specific embodiment, a recombinant NDV comprising a packaged genome comprising a transgene encoding RSV F protein described herein comprises a LaSota strain backbone. In a specific embodiment, the genomic sequence of the La Sota strain backbone (i.e., without the transgene) is as set forth in SEQ ID NO:47.

In a specific embodiment, a recombinant NDV comprising a packaged genome comprising a transgene encoding hMPV F protein described herein comprises a LaSota strain backbone. In a specific embodiment, the genomic sequence of the La Sota strain backbone (i.e., without the transgene) is as set forth in SEQ ID NO:47.

In a specific embodiment, a recombinant NDV comprising a packaged genome comprising a transgene encoding a chimeric F protein described herein comprises a LaSota strain backbone. In a specific embodiment, the genomic sequence of the La Sota strain backbone (i.e., without the transgene) is as set forth in SEQ ID NO:47.

5.3 Propagation of NDVs

The recombinant NDVs described herein (e.g., Sections 5.1 and 6) can be propagated in any substrate that allows the virus to grow to titers that permit the uses of the viruses described herein. In one embodiment, the substrate allows the recombinant NDVs described herein to grow to titers comparable to those determined for the corresponding wild-type viruses.

The recombinant NDVs described herein (e.g., Sections 5.1 and 6) may be grown in cells (e.g., avian cells, chicken cells, etc.) that are susceptible to infection by the viruses, embryonated eggs (e.g., chicken eggs or quail eggs) or animals (e.g., birds). Such methods are well-known to those skilled in the art. In a specific embodiment, the recombinant NDVs described herein may be propagated in cancer cells, e.g., carcinoma cells (e.g., breast cancer cells and prostate cancer cells), sarcoma cells, leukemia cells, lymphoma cells, and germ cell tumor cells (e.g., testicular cancer cells and ovarian cancer cells). In another specific embodiment, the recombinant NDVs described herein may be propagated in cell lines, e.g., cancer cell lines such as HeLa cells, MCF7 cells, THP-1 cells, U87 cells, DU145 cells, Lncap cells, and T47D cells. In certain embodiments, the cells or cell lines (e.g., cancer cells or cancer cell lines) are obtained, derived, or obtained and derived from a human(s). In another embodiment, the recombinant NDVs described herein are propagated in interferon deficient systems or interferon (IFN) deficient substrates, such as, e.g., IFN deficient cells (e.g., IFN deficient cell lines) or IFN deficient embryonated eggs. In another embodiment, the recombinant NDVs described herein are propagated in chicken cells or embryonated chicken eggs. Representative chicken cells include, but are not limited to, chicken embryo fibroblasts and chicken embryo kidney cells. In a specific embodiment, the recombinant NDVs described herein are propagated in Vero cells. In another specific embodiment, the recombinant NDVs described herein are propagated in chicken eggs or quail eggs. In certain embodiments, a recombinant NDV virus described herein is first propagated in embryonated eggs and then propagated in cells (e.g., a cell line).

The recombinant NDVs described herein may be propagated in embryonated eggs, e.g., from 6 to 14 days old, 6 to 12 days old, 6 to 10 days old, 6 to 9 days old, 6 to 8 days old, 8 to 10 day old, or 10 to 12 days old. In a specific embodiment, 10 day old embryonated chicken eggs are used to propagate the recombinant NDVs described herein. Young or immature embryonated eggs can be used to propagate the recombinant NDVs described herein. Immature embryonated eggs encompass eggs which are less than ten day old eggs, e.g., eggs 6 to 9 days old or 6 to 8 days old that are IFN-deficient. Immature embryonated eggs also encompass eggs which artificially mimic immature eggs up to, but less than ten day old, as a result of alterations to the growth conditions, e.g., changes in incubation temperatures; treating with drugs; or any other alteration which results in an egg with a retarded development, such that the IFN system is not fully developed as compared with ten to twelve day old eggs. The recombinant NDVs described herein can be propagated in different locations of the embryonated egg, e.g., the allantoic cavity. For a detailed discussion on the growth and propagation viruses, see, e.g., U.S. Pat. Nos. 6,852,522 and 7,494,808, both of which are hereby incorporated by reference in their entireties.

For virus isolation, the recombinant NDVs described herein can be removed from embryonated eggs or cell culture and separated from cellular components, typically by well known clarification procedures, e.g., such as centrifugation, depth filtration, and microfiltration, and may be further purified as desired using procedures well known to those skilled in the art, e.g., tangential flow filtration (TFF), density gradient centrifugation, differential extraction, or chromatography.

In a specific embodiment, virus isolation from allantoic fluid of an infected egg (e.g., a chicken egg) begins with harvesting allantoic fluid, which is clarified using a filtration system to remove cells and other large debris, specifically, comprising a membrane having a net positive charge such that there is a measurable reduction in host cell DNA. The clarified bulk is subsequently processed by tangential flow filtration. The concentrated clarified bulk is then diafiltered against four diavolumes of high salt buffer, followed by four diavolumes of low salt formulation buffer and subsequently concentrated approximately 10-fold. Accordingly, residual egg proteins, e.g., primarily ovalbumin, and residual DNA are reduced to acceptable levels, and the buffer is exchanged to a buffer compatible with formulation of the recombinant NDV for a composition to be administered to a subject. The resulting product is then sterile filtered through a filter, e.g., a 0.2 μm filter, dispensed into appropriate sterile storage containers, frozen, and stored at −70 degrees Celsius.

In a specific embodiment, a recombinant NDV described herein (see, e.g., Sections 5.1 and 6) is propagated, isolated, and/or purified according to a method described in Section 6. In a specific embodiment, a recombinant NDV described herein (see, e.g., Sections 5.1 and 6) is either propagated, isolated, or purified, or any two or all of the foregoing, using a method described in Section 6.

In a specific embodiment, provided herein is a cell (e.g., a cell line) or embryonated egg (e.g., a chicken embryonated egg) comprising a recombinant NDV described herein. In another specific embodiment, provided herein is a method for propagating a recombinant NDV described herein, the method comprising culturing a cell (e.g., a cell line) or embryonated egg (e.g., a chicken embryonated egg) infected with the recombinant NDV. In some embodiments, the method may further comprise isolating or purifying the recombinant NDV from the cell or embryonated egg. In a specific embodiment, provided herein is a method for propagating a recombinant NDV described herein, the method comprising (a) culturing a cell (e.g., a cell line) or embryonated egg infected with a recombinant NDV described herein; and (b) isolating the recombinant NDV from the cell or embyronated egg. The cell or embyronated egg may be one described herein or known to one of skill in the art. In some embodiments, the cell or embyronated egg is IFN deficient.

In a specific embodiment, provided herein is a method for producing a pharmaceutical composition (e.g., an immunogenic composition) comprising a recombinant NDV described herein, the method comprising (a) propagating a recombinant NDV described herein a cell (e.g., a cell line) or embyronated egg; and (b) isolating the recombinant NDV from the cell or embyronated egg. The method may further comprise adding the recombinant NDV to a container along with a pharmaceutically acceptable carrier.

5.4 Compositions and Routes of Administration

Provided herein are compositions comprising a recombinant NDV described herein (e.g., Section 5.1 or 6). In a specific embodiment, the compositions are pharmaceutical compositions, such as immunogenic compositions (e.g., vaccine compositions). In a specific embodiment, provided herein are immunogenic compositions comprising a recombinant NDV described herein (e.g., Section 5.1 or 6). The compositions may be used in methods of inducing an immune response to RSV F protein or hMPV F protein. The compositions may be used in methods for immunizing against RSV or hMPV. The compositions may be used in methods for preventing an RSV disease or hMPV disease.

In one embodiments, a pharmaceutical composition comprises a recombinant NDV described herein (e.g., Section 5.1 or 6), in an admixture with a pharmaceutically acceptable carrier. In some embodiments, the pharmaceutical composition further comprises one or more additional prophylactic or therapeutic agents, such as described in Section 5.5.4, infra. In a specific embodiment, a pharmaceutical composition comprises an effective amount of a recombinant NDV described herein (e.g., Section 5.1 or 6), and optionally one or more additional prophylactic or therapeutic agents, in a pharmaceutically acceptable carrier. In some embodiments, the recombinant NDV (e.g., Sections 5.1 or 6) is the only active ingredient included in the pharmaceutical composition. In specific embodiments, two or more recombinant NDV are included in the pharmaceutical composition. In a particular embodiment, the pharmaceutical composition is an immunogenic composition.

In a specific embodiment, a pharmaceutical composition comprises a first recombinant NDV and a second recombinant NDV, in an admixture with a pharmaceutically acceptable carrier, wherein the first recombinant NDV comprises a packaged genome comprising a first transgene, wherein the first transgene encodes a human RSV F protein, and wherein the second recombinant NDV comprises a packaged genome comprising a second transgene, wherein the second transgene encodes an hMPV F protein. In another specific embodiment, a pharmaceutical composition comprises a first recombinant NDV and a second recombinant NDV, in an admixture with a pharmaceutically acceptable carrier, wherein the first recombinant NDV comprises a packaged genome comprising a first transgene, wherein the first transgene encodes a human RSV F protein, wherein the second recombinant NDV comprises a packaged genome comprising a second transgene, and wherein the second transgene encodes a chimeric F protein comprising an hMPV F protein ectodomain and NDV F protein transmembrane and cytoplasmic domains. In another specific embodiment, a pharmaceutical composition comprises a first recombinant NDV and a second recombinant NDV, in an admixture with a pharmaceutically acceptable carrier, wherein the first recombinant NDV comprises a packaged genome comprising a first transgene, wherein the first transgene encodes an hMPV F protein, wherein the second recombinant NDV comprises a packaged genome comprising a second transgene, and wherein the second transgene encodes a chimeric F protein comprising a human RSV F protein ectodomain and NDV F protein transmembrane and cytoplasmic domains. In another specific embodiment, a pharmaceutical composition comprises a first recombinant NDV and a second recombinant NDV, in an admixture with a pharmaceutically acceptable carrier, wherein the first recombinant NDV comprises a packaged genome comprising a first transgene, wherein the first transgene encodes a first chimeric F protein comprising an hMPV F protein ectodomain and NDV F protein transmembrane and cytoplasmic domains, wherein the second recombinant NDV comprises a packaged genome comprising a second transgene, and wherein the second transgene encodes a second chimeric F protein comprising a human RSV F protein ectodomain and NDV F protein transmembrane and cytoplasmic domains. See, e.g., Section 5.1 or 6 for nucleic acid sequences encoding such transgenes. In a particular embodiment, the pharmaceutical composition is an immunogenic composition.

In a specific embodiment, the recombinant NDV included in a pharmaceutical composition described herein is a live virus. In particular, embodiment, the recombinant NDV included in a pharmaceutical composition described herein is an attenuated live virus. In some embodiments, the recombinant NDV included in a pharmaceutical composition described herein is inactivated. In particular embodiments, the RSV F protein or hMPV F protein of the inactivated recombinant NDV is in the pre-fusion conformation.

The pharmaceutical compositions provided herein can be in any form that allows for the composition to be administered to a subject. In a specific embodiment, the pharmaceutical compositions are suitable for veterinary administration, human administration, or both. As used herein, the term "pharmaceutically acceptable" means approved by a regulatory agency of the Federal or a state government or listed in the U.S. Pharmacopeia or other generally recognized pharmacopeiae for use in animals, and more particularly in humans. The term "carrier" refers to a diluent, adjuvant, excipient, or vehicle with which the pharmaceutical composition is administered. Saline solutions and aqueous dextrose and glycerol solutions can also be employed as liquid carriers, particularly for injectable solutions. Suitable excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Examples of suitable pharmaceutical carriers are described in "Remington's Pharmaceutical Sciences" by E. W. Martin. The formulation should suit the mode of administration.

In a specific embodiment, the pharmaceutical compositions are formulated to be suitable for the intended route of administration to a subject. For example, the pharmaceutical composition may be formulated to be suitable for parenteral, intravenous, intraarterial, intrapleural, inhalation, intranasal, intraperitoneal, oral, intradermal, colorectal, intraperitoneal, intracranial, and intratumoral administration. In one embodiment, the pharmaceutical composition may be formulated for intravenous, intraarterial, oral, intraperitoneal, intranasal, intratracheal, intrapleural, intracranial, subcutaneous, intramuscular, topical, pulmonary, or intratumoral administration. In a specific embodiment, the pharmaceutical composition may be formulated for intranasal administration.

In a specific embodiment, the pharmaceutical composition comprising a recombinant NDV described herein (see, e.g., Sections 5.1 or 6) is formulated to be suitable for intranasal administration to the subject (e.g., human subject or bovine subject). In a specific embodiment, the pharmaceutical composition comprising a recombinant NDV, wherein the recombinant NDV comprises a packaged genome comprising a transgene encoding an RSV F protein, is formulated to be suitable for intranasal administration to the subject (e.g., human subject). In another specific embodiment, the pharmaceutical composition comprising a recombinant NDV is formulated to be suitable for intranasal administration to the subject (e.g., human subject), wherein the recombinant NDV comprises a packaged genome comprising a transgene encoding a chimeric F protein, and wherein the chimeric F protein comprises an RSV F protein ectodomain and transmembrane and cytoplasmic domains of an NDV F protein. In a particular embodiment, the pharmaceutical composition is an immunogenic composition.

In a specific embodiment, the pharmaceutical composition comprising a recombinant NDV comprising a packaged genome comprising a transgene encoding an hMPV F protein is formulated to be suitable for intranasal administration to the subject (e.g., human subject). In another specific embodiment, the pharmaceutical composition comprising a recombinant NDV is formulated to be suitable for intranasal administration to the subject (e.g., human subject), wherein the recombinant NDV comprises a packaged genome comprising a transgene encoding a chimeric F protein, and wherein the chimeric F protein comprises an hMPV F protein ectodomain and transmembrane and cytoplasmic domains of an NDV F protein. In a particular embodiment, the pharmaceutical composition is an immunogenic composition.

5.5 Prophylactic Uses of a Recombinant NDV 5.5.1 Prevention of RSV Disease

In another aspect, presented herein are methods for inducing an immune response in a subject (e.g., a human subject) comprising administering the subject (e.g., a human subject) a recombinant NDV, wherein the recombinant NDV comprises a packaged genome comprising a transgene encoding a human RSV F protein. See, e.g., Section 5.1.2 and 6 for transgenes encoding a human RSV F protein which the packaged genome may comprise. See also Sections 5.1.3 and 6 for examples of recombinant NDV that may be used in the methods. In a specific embodiment, the transgene comprises a codon optimized nucleic acid sequence encoding the human RSV F protein. In another aspect, presented herein are methods for inducing an immune response in a subject (e.g., a human subject) comprising administering the subject (e.g., a human subject) a recombinant NDV, wherein the recombinant NDV comprises a packaged genome comprising a transgene encoding a chimeric F protein, wherein the chimeric F protein comprises the ectodomain of human RSV F protein and the transmembrane and cytoplasmic domains of NDV F protein. See, e.g., Section 5.1.2 and 6 for transgenes encoding a chimeric RSV F protein which the packaged genome may comprise. See also Sections 5.1.3 and 6 for examples of recombinant NDV that may be used in the methods. In a specific embodiment, the ectodomain of the human RSV F protein is encoded by a codon optimized nucleic acid sequence.

In another aspect, presented herein are methods for inducing an immune response to a RSV F protein comprising administering to a subject (e.g., a human subject) a recombinant NDV, wherein the recombinant NDV comprises a packaged genome comprising a transgene encoding a human RSV F protein. See, e.g., Section 5.1.2 and 6 for transgenes encoding a chimeric RSV F protein which the packaged genome may comprise. See also Sections 5.1.3 and 6 for examples of recombinant NDV that may be used in the methods. In one embodiment, the human RSV F protein comprises the amino acid sequence set forth in SEQ ID NO: 6, 49, 50 or 58. Due to the degeneracy of the nucleic acid code, a number of different nucleic acid sequences may encode for the same human RSV F protein. For example, the human RSV F protein may be encoded by SEQ ID NO:1, 25, 27 or 29. Alternatively, the nucleic acid sequence encoding the human RSV F protein may be codon optimized, such as set forth in SEQ ID NO: 2, 26, 28, or 30. Specific examples of transgenes encoding a human RSV F protein include transgenes comprising an RNA sequence corresponding to the negative sense of the cDNA sequence set forth in SEQ ID Nos: 1, 2, 25, 26, 27, 28, 29, and 30. In a specific embodiment, presented herein are methods for inducing an immune response to a RSV F protein comprising administering to a subject (e.g., a human subject) a recombinant NDV, wherein the recombinant NDV comprises a packaged genome comprising a transgene, and wherein the transgene comprises a codon optimized nucleic acid sequence encoding a human RSV F protein. In a specific embodiment, the human RSV F protein is expressed by cells infected with the recombinant NDV. The recombinant NDV may be administered to a subject by any route of administration. In another specific embodiment, the recombinant NDV is administered to a subject intranasally. In some embodiments, the recombinant NDV is administered to a subject intramuscularly.

In another aspect, presented herein are methods for inducing an immune response to a RSV F protein comprising administering to a subject (e.g., a human subject) a recombinant NDV, wherein the recombinant NDV comprises a packaged genome comprising a transgene encoding a chimeric F protein, wherein the chimeric F protein comprises a human RSV F protein ectodomain and NDV F protein transmembrane and cytoplasmic domains. See, e.g., Section 5.1.2 and 6 for transgenes encoding a human RSV F protein which the packaged genome may comprise. See also Sections 5.1.3 and 6 for examples of recombinant NDV that may be used in the methods. In one embodiment, the chimeric F protein comprises the amino acid sequence set forth in SEQ ID NO:7. Due to the degeneracy of the nucleic acid code, a number of different nucleic acid sequences may encode for the same chimeric F protein. For example, the chimeric F protein may be encoded by SEQ ID NO:51. Alternatively, the nucleic acid sequence encoding one or more domains of the chimeric F protein may be codon optimized (e.g., the nucleic acid sequence encoding the RSV F protein ectodomain may be codon optimized, such as set forth in SEQ ID NO: 4, 44, 45, and 46). In a specific embodiment, the codon optimized sequence comprises the nucleic acid sequence of SEQ ID NO:4. In a specific embodiment, presented herein are methods for inducing an immune response to a RSV F protein comprising administering to a subject (e.g., a human subject) a recombinant NDV, wherein the recombinant NDV comprises a packaged genome comprising a transgene encoding a chimeric F protein, wherein the chimeric F protein comprise a human RSV F protein ectodomain and NDV F protein transmembrane and cytoplasmic domains, and wherein the transgene comprises a codon optimized nucleic acid sequence encoding the RSV F protein ectodomain. In a specific embodiment, the chimeric F protein is expressed by cells infected with the recombinant NDV. The recombinant NDV may be administered to a subject by any route of administration. In another specific embodiment, the recombinant NDV is administered to a subject intranasally. In some embodiments, the recombinant NDV is administered to a subject intramuscularly.

In another aspect, presented herein are methods for immunizing against RSV comprising administering to a subject (e.g., a human subject) a recombinant NDV, wherein the recombinant NDV comprises a packaged genome comprising a transgene encoding a human RSV F protein. See, e.g., Section 5.1.2 and 6 for transgenes encoding a human RSV F protein which the packaged genome may comprise. See also Sections 5.1.3 and 6 for examples of recombinant NDV that may be used in the methods. In one embodiment, the human RSV F protein comprises the amino acid sequence set forth in SEQ ID NO: 6, 49, 50 or 58. Due to the degeneracy of the nucleic acid code, a number of different nucleic acid sequences may encode for the same human RSV F protein. For example, the human RSV F protein may be encoded by SEQ ID NO:1, 25, 27 or 29. Alternatively, the nucleic acid sequence encoding the human RSV F protein may be codon optimized, such as set forth in SEQ ID NO: 2, 26, 28, or 30. In a specific embodiment, the codon optimized nucleic acid sequence comprises the nucleic acid sequence of SEQ ID NO:2. Specific examples of transgenes encoding a human RSV F protein include transgenes comprising an RNA sequence corresponding to the negative sense of the cDNA sequence set forth in SEQ ID Nos: 1, 2, 25, 26, 27, 28, 29, and 30. In a specific embodiment, presented herein are methods for immunizing against RSV comprising administering to a subject (e.g., a human subject) a recombinant NDV, wherein the recombinant NDV comprises a packaged genome comprising a transgene, and wherein the transgene comprises a codon optimized nucleic acid sequence encoding a human RSV F protein. In a specific embodiment, the human RSV F protein is expressed by cells infected with the recombinant NDV. The recombinant NDV may be administered to a subject by any route of administration. In another specific embodiment, the recombinant NDV is administered to a subject intranasally. In some embodiments, the recombinant NDV is administered to a subject intramuscularly.

In another aspect, presented herein are methods for immunizing against RSV comprising administering to a subject (e.g., a human subject) a recombinant NDV, wherein the recombinant NDV comprises a packaged genome comprising a transgene encoding a chimeric F protein, wherein the chimeric F protein comprises a human RSV F protein ectodomain and NDV F protein transmembrane and cytoplasmic domains. See, e.g., Section 5.1.2 and 6 for transgenes encoding a chimeric F protein which the packaged genome may comprise. See also Sections 5.1.3 and 6 for examples of recombinant NDV that may be used in the methods. In one embodiment, the chimeric F protein comprises the amino acid sequence set forth in SEQ ID NO: 7. Due to the degeneracy of the nucleic acid code, a number of different nucleic acid sequences may encode for the same chimeric F protein. For example, the chimeric F protein may be encoded by SEQ ID NO:51. Alternatively, the nucleic acid sequence encoding one or more domains of the chimeric F protein may be codon optimized (e.g., the nucleic acid sequence encoding the RSV F protein ectodomain may be codon optimized, such as set forth in SEQ ID NO: 4, 44, 45, or 46). In a specific embodiment, the codon optimized nucleic acid sequence comprises the nucleic acid sequence of SEQ ID NO:4. In a specific embodiment, presented herein are methods for immunizing against RSV comprising administering to a subject (e.g., a human subject) a recombinant NDV, wherein the recombinant NDV comprises a packaged genome comprising a transgene encoding a chimeric F protein, wherein the chimeric F protein comprise a human RSV F protein ectodomain and NDV F protein transmembrane and cytoplasmic domains, and wherein the transgene comprises a codon optimized nucleic acid sequence encoding the RSV F protein ectodomain. In a specific embodiment, the chimeric F protein is expressed by cells infected with the recombinant NDV. The recombinant NDV may be administered to a subject by any route of administration. In another specific embodiment, the recombinant NDV is administered to a subject intranasally. In some embodiments, the recombinant NDV is administered to a subject intramuscularly.

In another aspect, presented herein are methods for the prevention of RSV disease comprising administering to a subject (e.g., a human subject) a recombinant NDV, wherein the recombinant NDV comprises a packaged genome comprising a transgene encoding a human RSV F protein. See, e.g., Section 5.1.2 and 6 for transgenes encoding a human RSV F protein which the packaged genome may comprise. See also Sections 5.1.3 and 6 for examples of recombinant NDV that may be used in the methods. In one embodiment, the human RSV F protein comprises the amino acid sequence set forth in SEQ ID NO: 6, 49, 50 or 58. Due to the degeneracy of the nucleic acid code, a number of different nucleic acid sequences may encode for the same human RSV F protein. For example, the human RSV F protein may be encoded by SEQ ID NO:1, 25, 27 or 29. Alternatively, the nucleic acid sequence encoding the human RSV F protein may be codon optimized, such as set forth in SEQ ID NO: 2, 26, 28, or 30. Specific examples of transgenes encoding a human RSV F protein include transgenes comprising an RNA sequence corresponding to the negative sense of the cDNA sequence set forth in SEQ ID NOs: 1, 2, 25, 26, 27, 28, 29, and 30. In a specific embodiment, presented herein are methods for the prevention of RSV disease comprising administering to a subject (e.g., a human subject) a recombinant NDV, wherein the recombinant NDV comprises a packaged genome comprising a transgene, and wherein the transgene comprises a codon optimized nucleic acid sequence encoding a human RSV F protein. In a specific embodiment, the human RSV F protein is expressed by cells infected with the recombinant NDV. The recombinant NDV may be administered to a subject by any route of administration. In another specific embodiment, the recombinant NDV is administered to a subject intranasally. In some embodiments, the recombinant NDV is administered to a subject intramuscularly.

In another aspect, presented herein are methods for the prevention of RSV disease comprising administering to a subject (e.g., a human subject) a recombinant NDV, wherein the recombinant NDV comprises a packaged genome comprising a transgene encoding a chimeric F protein, wherein the chimeric F protein comprises a human RSV F protein ectodomain and NDV F protein transmembrane and cytoplasmic domains. See, e.g., Section 5.1.2 and 6 for transgenes encoding a chimeric F protein which the packaged genome may comprise. See also Sections 5.1.3 and 6 for examples of recombinant NDV that may be used in the methods. In one embodiment, the chimeric F protein comprises the amino acid sequence set forth in SEQ ID NO: 7. Due to the degeneracy of the nucleic acid code, a number of different nucleic acid sequences may encode for the same chimeric F protein. For example, the chimeric F protein may be encoded by SEQ ID NO:51. Alternatively, the nucleic acid sequence encoding one or more domains of the chimeric F protein may be codon optimized (e.g., the nucleic acid sequence encoding the RSV F protein ectodomain may be codon optimized, such as set forth in SEQ ID NO: 4, 44, 45, or 46). In a specific embodiment, the codon optimized nucleic acid sequence comprises the nucleic acid sequence of SEQ ID NO:4. In a specific embodiment, presented herein are methods for the prevention of RSV disease comprising administering to a subject (e.g., a human subject) a recombinant NDV, wherein the recombinant NDV comprises a packaged genome comprising a transgene encoding a chimeric F protein, wherein the chimeric F protein comprise a human RSV F protein ectodomain and NDV F protein transmembrane and cytoplasmic domains, and wherein the transgene comprises a codon optimized nucleic acid sequence encoding the RSV F protein ectodomain. In a specific embodiment, the chimeric F protein is expressed by cells infected with the recombinant NDV. The recombinant NDV may be administered to a subject by any route of administration. In another specific embodiment, the recombinant NDV is administered to a subject intranasally. In some embodiments, the recombinant NDV is administered to a subject intramuscularly.

In another aspect, presented herein are methods for immunizing against RSV in a subject (e.g., a bovine subject) comprising administering the subject (e.g., a bovine subject) a recombinant NDV, wherein the recombinant NDV comprises a packaged genome comprising a transgene encoding a bovine RSV F protein. See, e.g., Section 5.1.2 and 6 for transgenes encoding a bovine RSV F protein which the packaged genome may comprise. See also Sections 5.1.3 and 6 for examples of recombinant NDV that may be used in the methods. In a specific embodiment, the transgene comprises a codon optimized nucleic acid sequence encoding the bovine RSV protein. In another aspect, presented herein are methods for inducing an immune response in a subject (e.g., a bovine subject) comprising administering the subject (e.g., a bovine subject) a recombinant NDV, wherein the recombinant NDV comprises a packaged genome comprising a transgene encoding a chimeric F protein, wherein the chimeric F protein comprises the ectodomain of bovine RSV F protein and the transmembrane and cytoplasmic domains of NDV F protein. See, e.g., Section 5.1.2 and 6 for transgenes encoding a chimeric F protein which the packaged genome may comprise. See also Sections 5.1.3 and 6 for examples of recombinant NDV that may be used in the methods. In a specific embodiment, the ectodomain of the bovine RSV F protein is encoded by a codon optimized nucleic acid sequence.

In another aspect, presented herein are methods for inducing an immune response to a RSV F protein comprising administering to a subject (e.g., a bovine subject) a recombinant NDV, wherein the recombinant NDV comprises a packaged genome comprising a transgene encoding a bovine RSV F protein. See, e.g., Section 5.1.2 and 6 for transgenes encoding a bovine RSV F protein which the packaged genome may comprise. See also Sections 5.1.3 and 6 for examples of recombinant NDV that may be used in the methods. In one embodiment, the bovine RSV F protein comprises the amino acid sequence set forth in SEQ ID NO: 10. Due to the degeneracy of the nucleic acid code, a number of different nucleic acid sequences may encode for the same bovine RSV F protein. For example, the bovine RSV F protein may be encoded by SEQ ID NO:9. Alternatively, the nucleic acid sequence encoding the bovine RSV F protein may be codon optimized, such as set forth in SEQ ID NO: 11. Specific examples of transgenes encoding a bovine RSV F protein include transgenes comprising an RNA sequence corresponding to the negative sense of the cDNA sequence set forth in SEQ ID NOs: 9, 11, 40, 41, 42, and 43. In a specific embodiment, presented herein are methods for inducing an immune response to a RSV F protein comprising administering to a subject (e.g., a bovine subject) a recombinant NDV, wherein the recombinant NDV comprises a packaged genome comprising a transgene, and wherein the transgene comprises a codon optimized nucleic acid sequence encoding a bovine RSV F protein. In a specific embodiment, the bovine RSV F protein is expressed by cells infected with the recombinant NDV. The recombinant NDV may be administered to a subject by any route of administration. In another specific embodiment, the recombinant NDV is administered to a subject intranasally. In some embodiments, the recombinant NDV is administered to a subject intramuscularly.

In another aspect, presented herein are methods for inducing an immune response to a RSV F protein comprising administering to a subject (e.g., a bovine subject) a recombinant NDV, wherein the recombinant NDV comprises a packaged genome comprising a transgene encoding a chimeric F protein, wherein the chimeric F protein comprises a bovine RSV F protein ectodomain and NDV F protein transmembrane and cytoplasmic domains. See, e.g., Section 5.1.2 and 6 for transgenes encoding a chimeric F protein which the packaged genome may comprise. See also Sections 5.1.3 and 6 for examples of recombinant NDV that may be used in the methods. In one embodiment, the chimeric F protein comprises the amino acid sequence set forth in SEQ ID NO:33. Due to the degeneracy of the nucleic acid code, a number of different nucleic acid sequences may encode for the same chimeric F protein. For example, the chimeric F protein may be encoded by SEQ ID NO:33. Alternatively, the nucleic acid sequence encoding one or more domains of the chimeric F protein may be codon optimized (e.g., the nucleic acid sequence encoding the RSV F protein ectodomain may be codon optimized, such as set forth in SEQ ID NO:14, 38 or 39). In a specific embodiment, the codon optimized nucleic acid sequence comprises the nucleic acid sequence of SEQ ID NO:14. In a specific embodiment, presented herein are methods for inducing an immune response to a RSV F protein comprising administering to a subject (e.g., a bovine subject) a recombinant NDV, wherein the recombinant NDV comprises a packaged genome comprising a transgene encoding a chimeric F protein, wherein the chimeric F protein comprise a bovine RSV F protein ectodomain and NDV F protein transmembrane and cytoplasmic domains, and wherein the transgene comprises a codon optimized nucleic acid sequence encoding the RSV F protein ectodomain. In a specific embodiment, the chimeric F protein is expressed by cells infected with the recombinant NDV. The recombinant NDV may be administered to a subject by any route of administration. In another specific embodiment, the recombinant NDV is administered to a subject intranasally. In some embodiments, the recombinant NDV is administered to a subject intramuscularly.

In another aspect, presented herein are methods for immunizing against RSV comprising administering to a subject (e.g., a bovine subject) a recombinant NDV, wherein the recombinant NDV comprises a packaged genome comprising a transgene encoding a bovine RSV F protein. See, e.g., Section 5.1.2 and 6 for transgenes encoding a bovine RSV F protein which the packaged genome may comprise. See also Sections 5.1.3 and 6 for examples of recombinant NDV that may be used in the methods. In one embodiment, the bovine RSV F protein comprises the amino acid sequence set forth in SEQ ID NO: 10. Due to the degeneracy of the nucleic acid code, a number of different nucleic acid sequences may encode for the same bovine RSV F protein. For example, the bovine RSV F protein may be encoded by SEQ ID NO:9. Alternatively, the nucleic acid sequence encoding the bovine RSV F protein may be codon optimized, such as set forth in SEQ ID NO: 11. Specific examples of transgenes encoding a bovine RSV F protein include transgenes comprising an RNA sequence corresponding to the negative sense of the cDNA sequence set forth in SEQ ID NOs: 9, 11, 40, 41, 42, and 43. In a specific embodiment, presented herein are methods for immunizing against RSV comprising administering to a subject (e.g., a bovine subject) a recombinant NDV, wherein the recombinant NDV comprises a packaged genome comprising a transgene, and wherein the transgene comprises a codon optimized nucleic acid sequence encoding a bovine RSV F protein. In a specific embodiment, the bovine RSV F protein is expressed by cells infected with the recombinant NDV. The recombinant NDV may be administered to a subject by any route of administration. In another specific embodiment, the recombinant NDV is administered to a subject intranasally. In some embodiments, the recombinant NDV is administered to a subject intramuscularly.

In another aspect, presented herein are methods for immunizing against RSV comprising administering to a subject (e.g., a bovine subject) a recombinant NDV, wherein the recombinant NDV comprises a packaged genome comprising a transgene encoding a chimeric F protein, wherein the chimeric F protein comprises a bovine RSV F protein ectodomain and NDV F protein transmembrane and cytoplasmic domains. See, e.g., Section 5.1.2 and 6 for transgenes encoding a chimeric F protein which the packaged genome may comprise. See also Sections 5.1.3 and 6 for examples of recombinant NDV that may be used in the methods. In one embodiment, the chimeric F protein comprises the amino acid sequence set forth in SEQ ID NO:33. Due to the degeneracy of the nucleic acid code, a number of different nucleic acid sequences may encode for the same chimeric F protein. For example, the chimeric F protein may be encoded by SEQ ID NO:31. Alternatively, the nucleic acid sequence encoding one or more domains of the chimeric F protein may be codon optimized (e.g., the nucleic acid sequence encoding the RSV F protein ectodomain may be codon optimized, such as set forth in SEQ ID NO:14, 38, or 39). In a specific embodiment, the codon optimized nucleic acid sequence comprises the nucleic acid sequence of SEQ ID NO:14. In a specific embodiment, presented herein are methods for immunizing against RSV comprising administering to a subject (e.g., a bovine subject) a recombinant NDV, wherein the recombinant NDV comprises a packaged genome comprising a transgene encoding a chimeric F protein, wherein the chimeric F protein comprise a bovine RSV F protein ectodomain and NDV F protein transmembrane and cytoplasmic domains, and wherein the transgene comprises a codon optimized nucleic acid sequence encoding the RSV F protein ectodomain. In a specific embodiment, the chimeric F protein is expressed by cells infected with the recombinant NDV. The recombinant NDV may be administered to a subject by any route of administration. In another specific embodiment, the recombinant NDV is administered to a subject intranasally. In some embodiments, the recombinant NDV is administered to a subject intramuscularly.

In another aspect, presented herein are methods for the prevention of RSV disease comprising administering to a subject (e.g., a bovine subject) a recombinant NDV, wherein the recombinant NDV comprises a packaged genome comprising a transgene encoding a bovine RSV F protein. See, e.g., Section 5.1.2 and 6 for transgenes encoding a bovine RSV F protein which the packaged genome may comprise. See also Sections 5.1.3 and 6 for examples of recombinant NDV that may be used in the methods. In one embodiment, the bovine RSV F protein comprises the amino acid sequence set forth in SEQ ID NO: 10. Due to the degeneracy of the nucleic acid code, a number of different nucleic acid sequences may encode for the same bovine RSV F protein. For example, the bovine RSV F protein may be encoded by SEQ ID NO:9. Alternatively, the nucleic acid sequence encoding the bovine RSV F protein may be codon optimized, such as set forth in SEQ ID NO: 11. Specific examples of transgenes encoding a bovine RSV F protein include transgenes comprising an RNA sequence corresponding to the negative sense of the cDNA sequence set forth in SEQ ID NOs: 9, 11, 40, 41, 42, and 43. In a specific embodiment, presented herein are methods for the prevention of RSV disease comprising administering to a subject (e.g., a bovine subject) a recombinant NDV, wherein the recombinant NDV comprises a packaged genome comprising a transgene, and wherein the transgene comprises a codon optimized nucleic acid sequence encoding a bovine RSV F protein. In a specific embodiment, the bovine RSV F protein is expressed by cells infected with the recombinant NDV. The recombinant NDV may be administered to a subject by any route of administration. In another specific embodiment, the recombinant NDV is administered to a subject intranasally. In some embodiments, the recombinant NDV is administered to a subject intramuscularly.

In another aspect, presented herein are methods for the prevention of RSV disease comprising administering to a subject (e.g., a bovine subject) a recombinant NDV, wherein the recombinant NDV comprises a packaged genome comprising a transgene encoding a chimeric F protein, wherein the chimeric F protein comprises a bovine RSV F protein ectodomain and NDV F protein transmembrane and cytoplasmic domains. See, e.g., Section 5.1.2 and 6 for transgenes encoding a chimeric F protein which the packaged genome may comprise. See also Sections 5.1.3 and 6 for examples of recombinant NDV that may be used in the methods. In one embodiment, the chimeric F protein comprises the amino acid sequence set forth in SEQ ID NO:33. Due to the degeneracy of the nucleic acid code, a number of different nucleic acid sequences may encode for the same chimeric F protein. For example, the chimeric F protein may be encoded by SEQ ID NO:33. Alternatively, the nucleic acid sequence encoding one or more domains of the chimeric F protein may be codon optimized (e.g., the nucleic acid sequence encoding the RSV F protein ectodomain may be codon optimized, such as set forth in SEQ ID NO:14, 38 or 39). In a specific embodiment, the codon optimized nucleic acid sequence comprises the nucleic acid sequence of SEQ ID NO:14. In a specific embodiment, presented herein are methods for the prevention of RSV disease comprising administering to a subject (e.g., a bovine subject) a recombinant NDV, wherein the recombinant NDV comprises a packaged genome comprising a transgene encoding a chimeric F protein, wherein the chimeric F protein comprise a bovine RSV F protein ectodomain and NDV F protein transmembrane and cytoplasmic domains, and wherein the transgene comprises a codon optimized nucleic acid sequence encoding the RSV F protein ectodomain. In a specific embodiment, the chimeric F protein is expressed by cells infected with the recombinant NDV. The recombinant NDV may be administered to a subject by any route of administration. In another specific embodiment, the recombinant NDV is administered to a subject intranasally. In some embodiments, the recombinant NDV is administered to a subject intramuscularly.

In another embodiment, presented herein is a recombinant NDV or composition thereof for inducing an immune response to an RSV F protein. In another embodiment, presented herein is a recombinant NDV or composition thereof for immunizing a subject (e.g., a human or bovine subject) against RSV. In another embodiment, presented herein is a recombinant NDV or composition thereof for the prevention of an RSV disease. See, e.g., Sections 5.1, and 6, infra for information regarding recombinant NDV, Section 5.5.4 for information regarding other therapies, and Section 5.4, infra, for information regarding compositions and routes of administration.

The recombinant NDV described herein may be administered to a subject in combination with one or more other therapies. The recombinant NDV and one or more other therapies may be administered by the same or different routes of administration to the subject. In a specific embodiment, the recombinant NDV is administered to a subject intranasally. See, e.g., Sections 5.1, and 6, infra for information regarding recombinant NDV, Section 5.5.4 for information regarding other therapies, and Section 5.4, infra, for information regarding compositions and routes of administration.

The recombinant NDV and one or more additional therapies may be administered concurrently or sequentially to the subject. In certain embodiments, the recombinant NDV and one or more additional therapies are administered in the same composition. In other embodiments, the recombinant NDV and one or more additional therapies are administered in different compositions. The recombinant NDV and one or more other therapies may be administered by the same or different routes of administration to the subject. Any route known to one of skill in the art or described herein may used to administer the recombinant NDV and one or more other therapies. In a specific embodiment, the recombinant NDV is administered intranasally and the one or more other therapies is administered intravenously.

In some embodiments, a recombinant NDV described herein or a composition thereof, or a combination therapy described herein is administered to a patient to prevent the onset of one, two or more symptoms of an RSV disease (such a patient may be at risk of developing an RSV infection). In a specific embodiment, the administration of a recombinant NDV described herein or a composition thereof, or a combination therapy described herein to a subject prevents the onset or development of one, two or more symptoms of RSV disease, reduces the severity of one, two or more symptoms of RSV disease, or prevents the onset or development of one, two or more symptoms of RSV disease and reduces the severity of one, two or more symptoms of RSV disease. Symptoms of RSV disease include congested or runny nose, cough, fever, sore throat, headache, wheezing, rapid or shallow breathing or difficulty breathing, bluish color the skin due to lack of oxygen, lack of appetite, lethargy and irritability.

In a specific embodiment, the administration of a recombinant NDV described herein or a composition thereof, or a combination therapy described herein to a subject prevents the spread of RSV infection. In another specific embodiment, the administration of a recombinant NDV described herein or a composition thereof, or a combination therapy described herein to a subject prevents hospitalization. In another specific embodiment, the administration of a recombinant NDV described herein or a composition thereof, or a combination therapy described herein to a subject prevents pneumonia caused by RSV infection. In another specific embodiment, the administration of a recombinant NDV described herein or a composition thereof, or a combination therapy described herein to a subject prevents otitis media caused by RSV infection. In another specific embodiment, the administration of a recombinant NDV described herein or a composition thereof, or a combination therapy described herein to a subject prevents bronchiolitis caused by RSV infection. In another specific embodiment, the administration of a recombinant NDV described herein or a composition thereof, or a combination therapy described herein to a subject prevents recurring RSV infections. In another specific embodiment, the administration of a recombinant NDV described herein or a composition thereof, or a combination therapy described herein to a subject reduces the likelihood of asthma linked to RSV infection.

In another specific embodiment, the administration of a recombinant NDV described herein or a composition thereof, or a combination therapy described herein induces antibodies to RSV F protein. In another specific embodiment, the administration of a recombinant NDV described herein or a composition thereof, or a combination therapy described herein induces both mucosal and systemic antibodies to RSV F protein (e.g., neutralizing antibodies). In another specific embodiment, the administration of a recombinant NDV described herein or a composition thereof, or a combination therapy described herein to a subject induces neutralizing antibody to RSV F protein. In another specific embodiment, the administration of a recombinant NDV described herein or a composition thereof, or a combination therapy described herein to a subject induces robust, long-lived (e.g., 6 months, 1 year, 2 years, 3 years or more), antigen-specific humoral immunity. In another specific embodiment, the administration of a recombinant NDV described herein or a composition thereof, or a combination therapy described herein does not induce a disease-promoting immune response. In another specific embodiment, the administration of a recombinant NDV described herein or a composition thereof induces no or a low level of inflammation. In a particular embodiment, the administration of a recombinant NDV described herein induces no inflammation in the lung or nasal cavity as assessed by the lack of evidence of inflammatory infiltrates. In another embodiment, the administration of a recombinant NDV described herein induces a small amount of inflammation in the lung or nasal cavity that is not clinically significant. In another specific embodiment, the administration of a recombinant NDV described herein or a composition thereof, or a combination therapy described herein to a subject induces an IFN response. In another specific embodiment, the administration of a recombinant NDV described herein or a composition thereof, or a combination therapy described herein to a subject prevents RSV infection of the lower airway and inhibits RSV replication in the upper airway.

In a specific embodiment, the administration of a recombinant NDV described herein or a composition thereof, or a combination therapy described herein to a subject results one, two, three or more, or all of the effects reported in Section 6 (e.g., Section 6.1, 6.2, or 6.4). In a specific embodiment, a method of preventing RSV disease or immunizing against RSV involves a protocol similar to or the same as that described in Section 6, infra.

In some embodiments, a recombinant NDV described herein or a composition thereof, or a combination therapy described herein is administered to a subject suffering from an RSV disease. In other embodiments, an NDV (e.g., a recombinant NDV) described herein or a composition thereof, or a combination therapy described herein is administered to a subject predisposed or susceptible to an RSV disease. In some embodiments, an NDV (e.g., a recombinant NDV) or a composition thereof, or a combination therapy described herein is administered to a subject seronegative for RSV antibodies (e.g., antibodies to RSV F protein, RSV G protein, or both). In some embodiments, an NDV (e.g., a recombinant NDV) or a composition thereof, or a combination therapy described herein is administered to a subject seropositive for RSV antibodies (e.g., antibodies to RSV F protein, RSV G protein, or both). In certain embodiments, the subject is assessed for anti-RSV antibodies prior to administration of a recombinant NDV described herein or a composition thereof, or a combination therapy described herein. In other embodiments, the subject is not assessed for anti-RSV antibodies prior to administration of a recombinant NDV described herein or a composition thereof, or a combination therapy described herein.

In certain embodiments, a recombinant NDV described herein or a composition thereof, or a combination therapy described herein is administered to a human that is 0 to 6 months old, 2 to 4 months old, 4 to 6 months old, 6 to 12 months old, 6 to 18 months old, 18 to 36 months old, 1 to 5 years old, 5 to 10 years old, 10 to 15 years old, 15 to 20 years old, 20 to 25 years old, 25 to 30 years old, 30 to 35 years old, 35 to 40 years old, 40 to 45 years old, 45 to 50 years old, 50 to 55 years old, 55 to 60 years old, 60 to 65 years old, 65 to 70 years old, 70 to 75 years old, 75 to 80 years old, 80 to 85 years old, 85 to 90 years old, 90 to 95 years old or 95 to 100 years old. In some embodiments, a recombinant NDV described herein or a composition thereof, or a combination therapy described herein is administered to a human infant. In another specific embodiment, the subject is a human infant six months old or older. In other embodiments, a recombinant NDV described herein or a composition thereof, or a combination therapy described herein is administered to a human toddler. In other embodiments, a recombinant NDV described herein or a composition thereof, or a combination therapy described herein is administered to a human child. In other embodiments, a recombinant NDV described herein or a composition thereof, or a combination therapy described herein is administered to a human adult. In yet other embodiments, a recombinant NDV described herein or a composition thereof, or a combination therapy described herein is administered to an elderly human.

In a specific embodiment, a recombinant NDV described herein or a composition thereof, or a combination therapy described herein is administered a subject (e.g., a human subject) in close contact with an individual with increased risk of an RSV or disease resulting from RSV infection (e.g., immunocompromised or immunosuppressed individuals). In some embodiments, a recombinant NDV described herein or a composition thereof, or a combination therapy described herein is administered a subject (e.g., a human subject) who is pregnant. In other embodiments, a recombinant NDV described herein or a composition thereof, or a combination therapy described herein is administered a subject (e.g., a human subject) who may or will be pregnant during the RSV season (e.g., generally, October to April (with peak RSV in December through February) in the Northern hemisphere). In specific embodiments, a recombinant NDV described herein or a composition thereof, or a combination therapy described herein is administered a subject (e.g., a human subject) who is a woman who has given birth 1, 2, 3, 4, 5, 6, 7, or 8 weeks earlier. In specific embodiments, a recombinant NDV described herein or a composition thereof, or a combination therapy described herein is administered a subject (e.g., a human subject) who is a parent (e.g., a mother or father) of children under the age of 18 years old.

In particular embodiments, a recombinant NDV described herein or a composition thereof, or a combination therapy described herein is administered a subject (e.g., a human subject) with a condition that increases susceptibility to RSV complications or for which RSV increases complications associated with the condition. Examples of conditions that increase susceptibility to RSV complications or for which RSV increases complications associated with the condition include conditions that affect the lung, such as cystic fibrosis, chronic obstructive pulmonary disease (COPD), emphysema, asthma, or bacterial infections (e.g., infections caused by *Haemophilus influenzae, Streptococcus pneumoniae, Legionella pneumophila*, and *Chlamydia* trachomatus); cardiovascular disease (e.g., congenital heart disease, congestive heart failure, and coronary artery disease); endocrine disorders (e.g., diabetes); and neurological and neuron-developmental conditions (e.g., disorders of the brain, the spinal cord, the peripheral nerve, and muscle (such as cerebral palsy, epilepsy (seizure disorders), stroke, intellectual disability (e.g., mental retardation), muscular dystrophy, and spinal cord injury)).

In some embodiments, a recombinant NDV described herein or a composition thereof, or a combination therapy described herein is administered a subject (e.g., a human subject) that resides in a group home, such as a nursing home. In some embodiments, a recombinant NDV described herein or a composition thereof, or a combination therapy described herein is administered a subject (e.g., a human subject) that works in, or spends a significant amount of time in, a group home, e.g., a nursing home. In some embodiments, a recombinant NDV described herein or a composition thereof, or a combination therapy described herein is administered a subject (e.g., a human subject) that is a health care worker (e.g., a doctor or nurse). In some embodiments, a recombinant NDV described herein or a composition thereof, or a combination therapy described herein is administered a subject (e.g., a human subject) that is a smoker.

In some embodiments, a recombinant NDV described herein or a composition thereof, or a combination therapy described herein is administered to (1) a subject (e.g., a human subject) who can transmit RSV to those at high risk for complications, such as, e.g., members of households with high-risk subjects, including households that include or will include human infants (e.g., infants younger than 6 months), (2) a subject coming into contact with human infants (e.g., infants less than 6 months of age), (3) a subject who is or will come into contact with subjects who live in nursing homes or other long-term care facilities, or (4) a subject who is or will come into contact with subjects with long-term disorders of the lungs, heart, or circulation; (5) subjects with metabolic diseases (e.g., diabetes) or subjects with weakened immune systems (including immunosuppression caused by medications, malignancies such as cancer, organ transplant, or HIV infection).; or (6) any combination of 1-5

In certain embodiments, a recombinant NDV described herein or a composition thereof, or a combination therapy described herein is administered to a calf. In some embodiments, a recombinant NDV described herein or a composition thereof, or a combination therapy described herein is administered to a cow. In certain embodiments, a recombinant NDV described herein or a composition thereof, or a combination therapy described herein is administered to a cow undergoing or about to undergo transportation with other cattle.

In certain embodiments a recombinant NDV described herein or a composition thereof, or a combination therapy described herein is administered to a subject in an immunocompromised state or immunosuppressed state or at risk for becoming immunocompromised or immunosuppressed. In certain embodiments, a recombinant NDV described herein or a composition thereof, or a combination therapy described herein is administered to a subject that has or is at risk of getting RSV disease. For example, a recombinant NDV described herein or a composition thereof, or a combination therapy described herein is administered to a subject with COPD, cystic fibrosis or asthma. In some embodiments, a recombinant NDV described herein or a composition thereof is administered to a patient that is a transplant recipient.

5.5.2 Prevention of Human Metapneumovirus Disease

In another aspect, presented herein are methods for inducing an immune response in a subject (e.g., a human subject) comprising administering the subject (e.g., a human subject) a recombinant NDV, wherein the recombinant NDV comprises a packaged genome comprising a transgene encoding a hMPV F protein. See, e.g., Section 5.1.4 and 6 for transgenes encoding an hMPV F protein which the packaged genome may comprise. See also Sections 5.1.5 and 6 for examples of recombinant NDV that may be used in the methods. In a specific embodiment, the transgene comprises a codon optimized nucleic acid sequence encoding the hMPV F protein. In another aspect, presented herein are methods for inducing an immune response in a subject (e.g., a human subject) comprising administering the subject (e.g., a human subject) a recombinant NDV, wherein the recombinant NDV comprises a packaged genome comprising a transgene encoding a chimeric F protein, wherein the chimeric F protein comprises the ectodomain of hMPV F protein and the transmembrane and cytoplasmic domains of NDV F protein. In a specific embodiment, the ectodomain of the hMPV F protein is encoded by a codon optimized nucleic acid sequence.

In another aspect, presented herein are methods for inducing an immune response to an hMPV F protein comprising administering to a subject (e.g., a human subject) a recombinant NDV, wherein the recombinant NDV comprises a packaged genome comprising a transgene encoding a hMPV F protein. See, e.g., Section 5.1.4 and 6 for transgenes encoding an hMPV F protein which the packaged genome may comprise. See also Sections 5.1.5 and 6 for examples of recombinant NDV that may be used in the methods. In one embodiment, the hMPV F protein comprises the amino acid sequence set forth in SEQ ID NO: 17. Due to the degeneracy of the nucleic acid code, a number of different nucleic acid sequences may encode for the same hMPV F protein. In some embodiments, the hMPV F protein may be encoded by SEQ ID NO:16, 52, 54 or 56. Alternatively, the nucleic acid sequence encoding the hMPV F protein may be codon optimized, such as set forth in SEQ ID NO: 18, 53, 55 or 57. Specific examples of transgenes encoding an hMPV F protein include transgenes comprising RNA sequence corresponding to the negative sense of the cDNA sequence set forth in SEQ ID NOs:16, 18, 52, 53, 54, 55, and 57. In a specific embodiment, presented herein are methods for inducing an immune response to an hMPV F protein comprising administering to a subject (e.g., a human subject) a recombinant NDV, wherein the recombinant NDV comprises a packaged genome comprising a transgene, and wherein the transgene comprises a codon optimized nucleic acid sequence encoding an hMPV F protein. In a specific embodiment, the hMPV F protein is expressed by cells infected with the recombinant NDV. The recombinant NDV may be administered to a subject by any route of administration. In another specific embodiment, the recombinant NDV is administered to a subject intranasally. In some embodiments, the recombinant NDV is administered to a subject intramuscularly.

In another aspect, presented herein are methods for inducing an immune response to an hMPV F protein comprising administering to a subject (e.g., a human subject) a recombinant NDV, wherein the recombinant NDV comprises a packaged genome comprising a transgene encoding a chimeric F protein, wherein the chimeric F protein comprises an hMPV F protein ectodomain and NDV F protein transmembrane and cytoplasmic domains. See, e.g., Section 5.1.4 and 6 for transgenes encoding a chimeric F protein which the packaged genome may comprise. See also Sections 5.1.5 and 6 for examples of recombinant NDV that may be used in the methods. In one embodiment, the chimeric F protein comprises the amino acid sequence set forth in SEQ ID NO:15. Due to the degeneracy of the nucleic acid code, a number of different nucleic acid sequences may encode for the same chimeric F protein. For example, the chimeric F protein may be encoded by SEQ ID NO:32. Alternatively, the nucleic acid sequence encoding one or more domains of the chimeric F protein may be codon optimized (e.g., the nucleic acid sequence encoding the hMPV F protein ectodomain may be codon optimized, such as set forth in SEQ ID NO: 19, 34, 35, and 36). In a specific embodiment, presented herein are methods for inducing an immune response to an hMPV F protein comprising administering to a subject (e.g., a human subject) a recombinant NDV, wherein the recombinant NDV comprises a packaged genome comprising a transgene encoding a chimeric F protein, wherein the chimeric F protein comprise an hMPV F protein ectodomain and NDV F protein transmembrane and cytoplasmic domains, and wherein the transgene comprises a codon optimized nucleic acid sequence encoding the hMPV F protein ectodomain. In a specific embodiment, the chimeric F protein is expressed by cells infected with the recombinant NDV. The recombinant NDV may be administered to a subject by any route of administration. In another specific embodiment, the recombinant NDV is administered to a subject intranasally. In some embodiments, the recombinant NDV is administered to a subject intramuscularly.

In another aspect, presented herein are methods for immunizing against hMPV comprising administering to a subject (e.g., a human subject) a recombinant NDV, wherein the recombinant NDV comprises a packaged genome comprising a transgene encoding a hMPV F protein. See, e.g., Section 5.1.4 and 6 for transgenes encoding an hMPV F protein which the packaged genome may comprise. See also Sections 5.1.5 and 6 for examples of recombinant NDV that may be used in the methods. In one embodiment, the hMPV F protein comprises the amino acid sequence set forth in SEQ ID NO: 17. Due to the degeneracy of the nucleic acid code, a number of different nucleic acid sequences may encode for the same hMPV F protein. In some embodiments, the hMPV F protein may be encoded by SEQ ID NO:16, 52, 54 or 56. Alternatively, the nucleic acid sequence encoding the hMPV F protein may be codon optimized, such as set forth in SEQ ID NO: 18, 53, 55, or 57. Specific examples of transgenes encoding an hMPV F protein include transgenes comprising an RNA sequence corresponding to the negative sense of the cDNA sequence set forth in SEQ ID NOs:16, 18, 52, 53, 54, 55, and 57. In a specific embodiment, presented herein are methods for immunizing against hMPV comprising administering to a subject (e.g., a human subject) a recombinant NDV, wherein the recombinant NDV comprises a packaged genome comprising a transgene, and wherein the transgene comprises a codon optimized nucleic acid sequence encoding an hMPV F protein. In a specific embodiment, the hMPV F protein is expressed by cells infected with the recombinant NDV. The recombinant NDV may be administered to a subject by any route of administration. In another specific embodiment, the recombinant NDV is administered to a subject intranasally. In some embodiments, the recombinant NDV is administered to a subject intramuscularly.

In another aspect, presented herein are methods for immunizing against hMPV comprising administering to a subject (e.g., a human subject) a recombinant NDV, wherein the recombinant NDV comprises a packaged genome comprising a transgene encoding a chimeric F protein, wherein the chimeric F protein comprises an hMPV F protein ectodomain and NDV F protein transmembrane and cytoplasmic domains. See, e.g., Section 5.1.4 and 6 for transgenes encoding a chimeric F protein which the packaged genome may comprise. See also Sections 5.1.5 and 6 for examples of recombinant NDV that may be used in the methods. In one embodiment, the chimeric F protein comprises the amino acid sequence set forth in SEQ ID NO:15. Due to the degeneracy of the nucleic acid code, a number of different nucleic acid sequences may encode for the same chimeric F protein. For example, the chimeric F protein may be encoded by SEQ ID NO:32. Alternatively, the nucleic acid sequence encoding one or more domains of the chimeric F protein may be codon optimized (e.g., the nucleic acid sequence encoding the hMPV F protein ectodomain may be codon optimized, such as set forth in SEQ ID NO: 19, 34, 35, and 36). In a specific embodiment, presented herein are methods for immunizing against hMPV comprising administering to a subject (e.g., a human subject) a recombinant NDV, wherein the recombinant NDV comprises a packaged genome comprising a transgene encoding a chimeric F protein, wherein the chimeric F protein comprise an hMPV F protein ectodomain and NDV F protein transmembrane and cytoplasmic domains, and wherein the transgene comprises a codon optimized nucleic acid sequence encoding the hMPV F protein ectodomain. In a specific embodiment, the chimeric F protein is expressed by cells infected with the recombinant NDV. The recombinant NDV may be administered to a subject by any route of administration. In another specific embodiment, the recombinant NDV is administered to a subject intranasally. In some embodiments, the recombinant NDV is administered to a subject intramuscularly.

In another aspect, presented herein are methods for the prevention of hMPV disease comprising administering to a subject (e.g., a human subject) a recombinant NDV, wherein the recombinant NDV comprises a packaged genome comprising a transgene encoding a hMPV F protein. See, e.g., Section 5.1.4 and 6 for transgenes encoding an hMPV F protein which the packaged genome may comprise. See also Sections 5.1.5 and 6 for examples of recombinant NDV that may be used in the methods. In one embodiment, the hMPV F protein comprises the amino acid sequence set forth in SEQ ID NO: 17. Due to the degeneracy of the nucleic acid code, a number of different nucleic acid sequences may encode for the same hMPV F protein. In some embodiments, the hMPV F protein may be encoded by SEQ ID NO:16, 52, 54 or 56. Alternatively, the nucleic acid sequence encoding the hMPV F protein may be codon optimized, such as set forth in SEQ ID NO: 18, 53, 55 or 57. Specific examples of transgenes encoding an hMPV F protein include transgenes comprising an RNA sequence corresponding to the negative sense of the cDNA sequence set forth in SEQ ID NOs:16, 18, 52, 53, 54, 55, and 57. In a specific embodiment, presented herein are methods for the prevention of hMPV disease comprising administering to a subject (e.g., a human subject) a recombinant NDV, wherein the recombinant NDV comprises a packaged genome comprising a transgene, and wherein the transgene comprises a codon optimized nucleic acid sequence encoding an hMPV F protein. In a specific embodiment, the hMPV F protein is expressed by cells infected with the recombinant NDV. The recombinant NDV may be administered to a subject by any route of administration. In another specific embodiment, the recombinant NDV is administered to a subject intranasally. In some embodiments, the recombinant NDV is administered to a subject intramuscularly.

In another aspect, presented herein are methods for the prevention of hMPV disease comprising administering to a subject (e.g., a human subject) a recombinant NDV, wherein the recombinant NDV comprises a packaged genome comprising a transgene encoding a chimeric F protein, wherein the chimeric F protein comprises an hMPV F protein ectodomain and NDV F protein transmembrane and cytoplasmic domains. See, e.g., Section 5.1.4 and 6 for transgenes encoding a chimeric F protein which the packaged genome may comprise. See also Sections 5.1.5 and 6 for examples of recombinant NDV that may be used in the methods. In one embodiment, the chimeric F protein comprises the amino acid sequence set forth in SEQ ID NO:15. Due to the degeneracy of the nucleic acid code, a number of different nucleic acid sequences may encode for the same chimeric F protein. For example, the chimeric F protein may be encoded by SEQ ID NO:32. Alternatively, the nucleic acid sequence encoding one or more domains of the chimeric F protein may be codon optimized (e.g., the nucleic acid sequence encoding the hMPV F protein ectodomain may be codon optimized, such as set forth in SEQ ID NO: 19, 34, 35, and 36). In a specific embodiment, presented herein are methods for the prevention of hMPV disease comprising administering to a subject (e.g., a human subject) a recombinant NDV, wherein the recombinant NDV comprises a packaged genome comprising a transgene encoding a chimeric F protein, wherein the chimeric F protein comprise an hMPV F protein ectodomain and NDV F protein transmembrane and cytoplasmic domains, and wherein the transgene comprises a codon optimized nucleic acid sequence encoding the hMPV F protein ectodomain. In a specific embodiment, the chimeric F protein is expressed by cells infected with the recombinant NDV. The recombinant NDV may be administered to a subject by any route of administration. In another specific embodiment, the recombinant NDV is administered to a subject intranasally. In some embodiments, the recombinant NDV is administered to a subject intramuscularly. In another embodiment, presented herein is a recombinant NDV or composition thereof for inducing an immune response to an hMPV F protein. In another embodiment, presented herein is a recombinant NDV or composition thereof for immunizing a subject (e.g., a human subject) against hMPV. In another embodiment, presented herein is a recombinant NDV or composition thereof for the prevention of an hMPV disease. See, e.g., Sections 5.1, and 6, infra for information regarding recombinant NDV, Section 5.5.4 for information regarding other therapies, and Section 5.4, infra, for information regarding compositions and routes of administration.

The recombinant NDV described herein may be administered to a subject in combination with one or more other therapies. The recombinant NDV and one or more other therapies may be administered by the same or different routes of administration to the subject. In a specific embodiment, the recombinant NDV is administered to a subject intranasally. See, e.g., Sections 5.1, and 6, infra for information regarding recombinant NDV, Section 5.5.4 for information regarding other therapies, and Section 5.4, infra, for information regarding compositions and routes of administration.

In some embodiments, a recombinant NDV described herein or a composition thereof, or a combination therapy described herein is administered to a patient to prevent the onset of one, two or more symptoms of an hMPV disease (e.g., such a patient is at risk of developing an hMPV infection). In a specific embodiment, the administration of a recombinant NDV described herein or a composition thereof, or a combination therapy described herein to a subject prevents the onset or development of one, two or more symptoms of hMPV disease, reduces the severity of one, two or more symptoms of hMPV disease, or prevents the onset or development of one, two or more symptoms of hMPV disease and reduces the severity of one, two or more symptoms of hMPV disease. Symptoms of hMPV disease include nasal congestion, runny nose, fever, cough, sore throat, wheezing, difficulty breathing, lack of appetite, lethargy and irritability.

In a specific embodiment, the administration of a recombinant NDV described herein or a composition thereof, or a combination therapy described herein to a subject prevents the spread of hMPV infection. In another specific embodiment, the administration of a recombinant NDV described herein or a composition thereof, or a combination therapy described herein to a subject prevents hospitalization. In another specific embodiment, the administration of a recombinant NDV described herein or a composition thereof, or a combination therapy described herein to a subject prevents pneumonia caused by hMPV infection. In another specific embodiment, the administration of a recombinant NDV described herein or a composition thereof, or a combination therapy described herein to a subject reduces the likelihood of asthma linked to hMPV infection.

In another specific embodiment, the administration of a recombinant NDV described herein or a composition thereof, or a combination therapy described herein induces antibodies to hMPV F protein. In another specific embodiment, the administration of a recombinant NDV described herein or a composition thereof, or a combination therapy described herein induces both mucosal and systemic antibodies to hMPV F protein (e.g., neutralizing antibodies). In another specific embodiment, the administration of a recombinant NDV described herein or a composition thereof, or a combination therapy described herein to a subject induces neutralizing antibody to hMPV F protein. In another specific embodiment, the administration of a recombinant NDV described herein or a composition thereof, or a combination therapy described herein does not induce a disease-promoting immune response. In another specific embodiment, the administration of a recombinant NDV described herein or a composition thereof induces no or a low level of inflammation. In a particular embodiment, the administration of a recombinant NDV described herein induces no inflammation in the lung or nasal cavity as assessed by the lack of evidence of inflammatory infiltrates. In another embodiment, the administration of a recombinant NDV described herein induces a small amount of inflammation in the lung or nasal cavity that is not clinically significant. In another specific embodiment, the administration of a recombinant NDV described herein or a composition thereof, or a combination therapy described herein to a subject induces robust, long-lived (e.g., 6 months, 1 year, 2 years, 3 years or more), antigen-specific humoral immunity. In another specific embodiment, the administration of a recombinant NDV described herein or a composition thereof, or a combination therapy described herein to a subject induces an IFN response. In another specific embodiment, the administration of a recombinant NDV described herein or a composition thereof, or a combination therapy described herein to a subject prevents hMPV infection of the lower airway and inhibits hMPV replication in the upper airway.

In some embodiments, a recombinant NDV described herein or a composition thereof, or a combination therapy described herein is administered to a subject suffering from an hMPV disease. In other embodiments, an NDV (e.g., a recombinant NDV) described herein or a composition thereof, or a combination therapy described herein is administered to a subject predisposed or susceptible to an hMPV disease. In some embodiments, an NDV (e.g., a recombinant NDV) or a composition thereof, or a combination therapy described herein is administered to a subject seronegative for hMPV antibodies (e.g., antibodies to hMPV F protein, hMPV G protein or both). In some embodiments, an NDV (e.g., a recombinant NDV) or a composition thereof, or a combination therapy described herein is administered to a subject seropositive for hMPV antibodies (e.g., antibodies to hMPV F protein, hMPV G protein, both). In certain embodiments, the subject is assessed for anti-hMPV antibodies prior to administration of a recombinant NDV described herein or a composition thereof, or a combination therapy described herein. In other embodiments, the subject is not assessed for anti-hMPV antibodies prior to administration of a recombinant NDV described herein or a composition thereof, or a combination therapy described herein.

In certain embodiments, a recombinant NDV described herein or a composition thereof, or a combination therapy described herein is administered to a human that is 0 to 6 months old, 2 to 4 months old, 4 to 6 months old, 6 to 12 months old, 6 to 18 months old, 18 to 36 months old, 1 to 5 years old, 5 to 10 years old, 10 to 15 years old, 15 to 20 years old, 20 to 25 years old, 25 to 30 years old, 30 to 35 years old, 35 to 40 years old, 40 to 45 years old, 45 to 50 years old, 50 to 55 years old, 55 to 60 years old, 60 to 65 years old, 65 to 70 years old, 70 to 75 years old, 75 to 80 years old, 80 to 85 years old, 85 to 90 years old, 90 to 95 years old or 95 to 100 years old. In some embodiments, a recombinant NDV described herein or a composition thereof, or a combination therapy described herein is administered to a human infant. In another specific embodiment, the subject is a human infant six months old or older. In other embodiments, a recombinant NDV described herein or a composition thereof, or a combination therapy described herein is administered to a human toddler. In other embodiments, a recombinant NDV described herein or a composition thereof, or a combination therapy described herein is administered to a human child. In other embodiments, a recombinant NDV described herein or a composition thereof, or a combination therapy described herein is administered to a human adult. In yet other embodiments, a recombinant NDV described herein or a composition thereof, or a combination therapy described herein is administered to an elderly human.

In a specific embodiment, a recombinant NDV described herein or a composition thereof, or a combination therapy described herein is administered a subject (e.g., a human subject) in close contact with an individual with increased risk of an hMPV infection or disease resulting from hMPV infection (e.g., immunocompromised or immunosuppressed individuals). In some embodiments, a recombinant NDV described herein or a composition thereof, or a combination therapy described herein is administered a subject (e.g., a human subject) who is pregnant. In other embodiments, a recombinant NDV described herein or a composition thereof, or a combination therapy described herein is administered a subject (e.g., a human subject) who may or will be pregnant during the hMPV season (e.g., generally, November to July in the Northern hemisphere). In specific embodiments, a recombinant NDV described herein or a composition thereof, or a combination therapy described herein is administered a subject (e.g., a human subject) who is a woman who has given birth 1, 2, 3, 4, 5, 6, 7, or 8 weeks earlier. In specific embodiments, a recombinant NDV described herein or a composition thereof, or a combination therapy described herein is administered a subject (e.g., a human subject) who is a parent (e.g., a mother or father) of children under the age of 18 years old.

In particular embodiments, a recombinant NDV described herein or a composition thereof, or a combination therapy described herein is administered a subject (e.g., a human subject) with a condition that increases susceptibility to hMPV complications or for which hMPV increases complications associated with the condition. Examples of conditions that increase susceptibility to hMPV complications or for which hMPV increases complications associated with the condition include conditions that affect the lung, such as cystic fibrosis, chronic obstructive pulmonary disease (COPD), emphysema, asthma, or bacterial infections (e.g., infections caused by *Haemophilus influenzae, Streptococcus*

*pneumoniae, Legionella pneumophila*, and *Chlamydia* trachomatus); cardiovascular disease (e.g., congenital heart disease, congestive heart failure, and coronary artery disease); endocrine disorders (e.g., diabetes); and neurological and neuron-developmental conditions (e.g., disorders of the brain, the spinal cord, the peripheral nerve, and muscle (such as cerebral palsy, epilepsy (seizure disorders), stroke, intellectual disability (e.g., mental retardation), muscular dystrophy, and spinal cord injury)).

In some embodiments, a recombinant NDV described herein or a composition thereof, or a combination therapy described herein is administered a subject (e.g., a human subject) that resides in a group home, such as a nursing home. In some embodiments, a recombinant NDV described herein or a composition thereof, or a combination therapy described herein is administered a subject (e.g., a human subject) that works in, or spends a significant amount of time in, a group home, e.g., a nursing home. In some embodiments, a recombinant NDV described herein or a composition thereof, or a combination therapy described herein is administered a subject (e.g., a human subject) that is a health care worker (e.g., a doctor or nurse). In some embodiments, a recombinant NDV described herein or a composition thereof, or a combination therapy described herein is administered a subject (e.g., a human subject) that is a smoker.

In some embodiments, a recombinant NDV described herein or a composition thereof, or a combination therapy described herein is administered to (1) a subject (e.g., a human subject) who can transmit hMPV to those at high risk for complications, such as, e.g., members of households with high-risk subjects, including households that include or will include human infants (e.g., infants younger than 6 months), (2) a subject coming into contact with human infants (e.g., infants less than 6 months of age), (3) a subject who is or will come into contact with subjects who live in nursing homes or other long-term care facilities, (4) a subject who is or will come into contact with subjects with long-term disorders of the lungs, heart, or circulation; (5) subjects with metabolic diseases (e.g., diabetes) or subjects with weakened immune systems (including immunosuppression caused by medications, malignancies such as cancer, organ transplant, or HIV infection); or (6) any combination of 1-5.

In certain embodiments a recombinant NDV described herein or a composition thereof, or a combination therapy described herein is administered to a subject in an immunocompromised state or immunosuppressed state or at risk for becoming immunocompromised or immunosuppressed. In certain embodiments, a recombinant NDV described herein or a composition thereof, or a combination therapy described herein is administered to a subject that has or is at risk of getting hMPV disease. For example, a recombinant NDV described herein or a composition thereof, or a combination therapy described herein is administered to a subject with COPD, cystic fibrosis or asthma. In some embodiments, a recombinant NDV described herein or a composition thereof is administered to a patient that is a transplant recipient.

5.5.3 Dosage and Frequency

The amount of a recombinant NDV or a composition thereof, which will be effective in the prevention of RSV disease or hMPV disease, or immunization against RSV or hMPV will depend on the route of administration, the general health of the subject, etc. Standard clinical techniques, such as in vitro assays, may optionally be employed to help identify dosage ranges. However, suitable dosage ranges of a recombinant NDV for administration are generally about $10^4$ to about $10^{12}$, and can be administered to a subject once, twice, three, four or more times with intervals as often as needed. In certain embodiments, dosages similar to those currently being used in clinical trials for NDV are administered to a subject.

In certain embodiments, a recombinant NDV or a composition thereof is administered to a subject as a single dose followed by a second dose 1 to 6 weeks, 1 to 5 weeks, 1 to 4 weeks, 1 to 3 weeks, 1 to 2 weeks, 6 to 12 weeks, 3 to 6 months, 6 to 9 months, 6 to 12 months, or 6 to 9 months later. In accordance with these embodiments, booster inoculations may be administered to the subject at 3 to 6 month or 6 to 12 month intervals following the second inoculation.

In certain embodiments, administration of the same recombinant NDV or a composition thereof may be repeated and the administrations may be separated by at least 1 day, 2 days, 3 days, 5 days, 6 says, 7 days, 10 days, 14 days, 15 days, 21 days, 28 days, 30 days, 45 days, 2 months, 75 days, 3 months, or at least 6 months. In other embodiments, administration of the same recombinant NDV or a composition thereof may be repeated and the administrations may be separated by 1 to 14 days, 1 to 7 days, 7 to 14 days, 1 to 30 days, 15 to 30 days, 15 to 45 days, 15 to 75 days, 15 to 90 days, 1 to 3 months, 3 to 6 months, 3 to 12 months, or 6 to 12 months. In some embodiments, a first recombinant NDV or a composition thereof is administered to a subject followed by the administration of a second recombinant NDV or a composition thereof. In some embodiments, the first and second recombinant NDV are different from each other. For example, the first recombinant NDV may comprise a packaged genome comprising a transgene encoding an RSV F protein, and the second recombinant NDV may comprise a package genome comprising a transgene encoding a chimeric F protein, wherein the chimeric F protein comprises an RSV F protein ectodomain and NDV F protein transmembrane and cytoplasmic domains. In another example, the first recombinant NDV may comprise a packaged genome comprising a transgene encoding an hMPV F protein, and the second recombinant NDV may comprise a package genome comprising a transgene encoding a chimeric F protein, wherein the chimeric F protein comprises an hMPV F protein ectodomain and NDV F protein transmembrane and cytoplasmic domains. In certain embodiments, the first and second recombinant NDVs or compositions thereof may be separated by at least 1 day, 2 days, 3 days, 5 days, 6 days, 7 days, 10 days, 14 days, 15 days, 21 days, 28 days, 30 days, 45 days, 2 months, 75 days, 3 months, or at least 6 months. In other embodiments, the first and second recombinant NDVs or compositions thereof may be separated by 1 to 14 days, 1 to 7 days, 7 to 14 days, 1 to 30 days, 15 to 30 days, 15 to 45 days, 15 to 75 days, 15 to 90 days, 1 to 3 months, 3 to 6 months, 3 to 12 months, or 6 to 12 months.

In certain embodiments, a recombinant NDV or composition thereof is administered to a subject in combination with one or more additional therapies, such as a therapy described in Section 5.5.4, infra. The dosage of the other one or more additional therapies will depend upon various factors including, e.g., the therapy, the route of administration, the general health of the subject, etc. and should be decided according to the judgment of a medical practitioner. In specific embodiments, the dose of the other therapy is the dose and/or frequency of administration of the therapy recommended for the therapy for use as a single agent is used in accordance with the methods disclosed herein. Recommended doses for approved therapies can be found in the Physician's Desk Reference.

In certain embodiments, an recombinant NDV or composition thereof is administered to a subject concurrently with the administration of one or more additional therapies. In a specific embodiment, a first pharmaceutical composition comprising a first recombinant NDV is administered to a subject in combination with a second pharmaceutical composition comprising a second recombinant NDV, wherein the first recombinant NDV comprises a packaged genome comprising a first transgene, wherein the first transgene encodes a human RSV F protein, and wherein the second recombinant NDV comprises a packaged genome comprising a second transgene, wherein the second transgene encodes an hMPV F protein. In another specific embodiment, a first pharmaceutical composition comprising a first recombinant NDV is administered to a subject in combination with a second pharmaceutical composition comprising a second recombinant NDV, wherein the first recombinant NDV comprises a packaged genome comprising a first transgene, wherein the first transgene encodes a human RSV F protein, wherein the second recombinant NDV comprises a packaged genome comprising a second transgene, and wherein the second transgene encodes a chimeric F protein comprising an hMPV F protein ectodomain and NDV F protein transmembrane and cytoplasmic domains. In another specific embodiment, a first pharmaceutical composition comprising a first recombinant NDV is administered to a subject in combination with a second pharmaceutical composition comprising a second recombinant NDV, wherein the first recombinant NDV comprises a packaged genome comprising a first transgene, wherein the first transgene encodes an hMPV F protein, wherein the second recombinant NDV comprises a packaged genome comprising a second transgene, and wherein the second transgene encodes a chimeric F protein comprising a human RSV F protein ectodomain and NDV F protein transmembrane and cytoplasmic domains. In another specific embodiment, a first pharmaceutical composition comprising a first recombinant NDV is administered to a subject in combination with a second pharmaceutical composition comprising a second recombinant NDV, wherein the first recombinant NDV comprises a packaged genome comprising a first transgene, wherein the first transgene encodes a first chimeric F protein comprising an hMPV RSV F protein ectodomain and NDV F protein transmembrane and cytoplasmic domains, wherein the second recombinant NDV comprises a packaged genome comprising a second transgene, and wherein the second transgene encodes a second chimeric F protein comprising a human RSV F protein ectodomain and NDV F protein transmembrane and cytoplasmic domains. See, e.g., Section 5.1 or 6 for nucleic acid sequences encoding such transgenes. In certain embodiments, the first and second pharmaceutical compositions are administered concurrently to the subject, or within 1 minute, 2 minutes, 5 minutes, 10 minutes, 15 minutes, 20 minutes, 30 minutes, 45 minutes, 60 minutes, 1.5 hours, 2 hours, 3 hours, 4 hours, 5 hours, or 6 hours of each other. In certain embodiments, the first and second pharmaceutical compositions are administered to the subject within 12 hours, 1 day, 2 days, 3 days, 4 days, 5 days, 6 days, 7 days, 2 weeks, 3 weeks, 4 weeks, 5 weeks, 6 weeks, 7 weeks, 8 weeks or 12 weeks of each other. In certain embodiments, the first and second pharmaceutical compositions are administered to the subject within 3-6 months, 6-9 months, 6-12 months, or 3 months, 4 months, 6 months, 9 months, or 12 months of each other.

In certain embodiments, a first pharmaceutical composition is administered to a subject as a priming dose and after a certain period (e.g., 1 month, 2 months, 3 months, 4 months, 5 months, 6 months, or 1-6 months) a booster dose of a second pharmaceutical composition is administered. In some embodiments, the first pharmaceutical composition comprises a first recombinant NDV and a second recombinant NDV, wherein the first recombinant NDV comprises a packaged genome comprising a transgene encoding a human RSV F protein, and the second recombinant NDV comprises a package genome comprising a transgene encoding a chimeric F protein, wherein the chimeric F protein comprises an hMPV F protein ectodomain and NDV F protein transmembrane and cytoplasmic domains. In certain embodiments, the first pharmaceutical composition comprises a first recombinant NDV and a second recombinant NDV, wherein the first recombinant NDV comprises a packaged genome comprising a transgene encoding an hMPV F protein, and the second recombinant NDV comprises a package genome comprising a transgene encoding a chimeric F protein, wherein the chimeric F protein comprises a human RSV F protein ectodomain and NDV F protein transmembrane and cytoplasmic domains. In some embodiments, the first pharmaceutical composition comprises a first recombinant NDV and a second recombinant NDV, wherein the first recombinant NDV comprises a packaged genome comprising a transgene encoding a human RSV F protein, and the second recombinant NDV comprises a package genome comprising a transgene encoding an hMPV F protein. In certain embodiments, the first pharmaceutical composition comprises a first recombinant NDV and a second recombinant NDV, wherein the first recombinant NDV comprises a packaged genome comprising a transgene encoding a first chimeric F protein, and the second recombinant NDV comprises a package genome comprising a transgene encoding a second chimeric F protein, wherein the first chimeric F protein comprises a human RSV F protein ectodomain and NDV F protein transmembrane and cytoplasmic domains, and wherein the second chimeric F protein comprises an hMPV F protein ectodomain and NDV F protein transmembrane and cytoplasmic domains. In some embodiments, the second pharmaceutical composition comprises the same recombinant NDV as the first pharmaceutical composition. In another embodiments, the second pharmaceutical composition comprises the same recombinant NDV as the first pharmaceutical composition with the exception that the strain of NDV used as the backbone of the virus is different.

5.5.4 Additional Therapies

Additional therapies that can be used in a combination with a recombinant NDV described herein or a composition thereof include, but are not limited to, acetaminophen, ibuprofen, throat lozenges, cough suppressants, inhalers, antibiotics and oxygen. In a specific embodiment, the additional therapy is a second recombinant NDV described herein.

5.6 Biological Assays

In a specific embodiment, one, two or more of the assays described in Section 6 may be used to characterize a recombinant NDV described herein, or an F protein or a chimeric F protein.

5.6.1 In Vitro Viral Assays

Viral assays include those that indirectly measure viral replication (as determined, e.g., by plaque formation) or the production of viral proteins (as determined, e.g., by western blot analysis) or viral RNAs (as determined, e.g., by RT-PCR or northern blot analysis) in cultured cells in vitro using methods which are well known in the art.

Growth of the recombinant NDVs described herein can be assessed by any method known in the art or described herein (e.g., in cell culture (e.g., cultures of chicken embryonic kidney cells or cultures of chicken embryonic fibroblasts (CEF)) (see, e.g., Section 6). Viral titer may be determined by inoculating serial dilutions of a recombinant NDV described herein into cell cultures (e.g., CEF, MDCK, EFK-2 cells, Vero cells, primary human umbilical vein endothelial cells (HUVEC), H292 human epithelial cell line or HeLa cells), chick embryos, or live animals (e.g., avians). After incubation of the virus for a specified time, the virus is isolated using standard methods. Physical quantitation of the virus titer can be performed using PCR applied to viral supernatants (Quinn & Trevor, 1997; Morgan et al., 1990), hemagglutination assays, tissue culture infectious doses (TCID50) or egg infectious doses (EID50). An exemplary method of assessing viral titer is described in Section 6, below.

Incorporation of nucleotide sequences encoding a heterologous peptide or protein (e.g., a transgene into the genome of a recombinant NDV described herein can be assessed by any method known in the art or described herein (e.g., in cell culture, an animal model or viral culture in embryonated eggs)). For example, viral particles from cell culture of the allantoic fluid of embryonated eggs can be purified by centrifugation through a sucrose cushion and subsequently analyzed for protein expression by Western blotting using methods well known in the art. In a specific embodiment, a method described in Section 6, infra, is used to assess the incorporation of a transgene into the genome of a recombinant NDV.

Immunofluorescence-based approaches may also be used to detect virus and assess viral growth. Such approaches are well known to those of skill in the art, e.g., fluorescence microscopy and flow cytometry (see, e.g., Section 6, infra). Methods for flow cytometry, including fluorescence activated cell sorting (FACS), are available (see, e.g., Owens, et al. (1994) *Flow Cytometry Principles for Clinical Laboratory Practice*, John Wiley and Sons, Hoboken, NJ; Givan (2001) *Flow Cytometry, 2$^{nd}$* ed.; Wiley-Liss, Hoboken, NJ; Shapiro (2003) *Practical Flow Cytometry*, John Wiley and Sons, Hoboken, NJ). Fluorescent reagents suitable for modifying nucleic acids, including nucleic acid primers and probes, polypeptides, and antibodies, for use, e.g., as diagnostic reagents, are available (Molecular Probesy (2003) *Catalogue*, Molecular Probes, Inc., Eugene, OR; Sigma-Aldrich (2003) *Catalogue*, St. Louis, MO). See, e.g., the assays described in Section 6, infra.

Standard methods of histology of the immune system are described (see, e.g., Muller-Harmelink (ed.) (1986) *Human Thymus: Histopathology and Pathology*, Springer Verlag, New York, NY; Hiatt, et al. (2000) *Color Atlas of Histology*, Lippincott, Williams, and Wilkins, Phila, PA; Louis, et al. (2002) *Basic Histology: Text and Atlas*, McGraw-Hill, New York, NY). See also Section 6, infra, for histology and immunohistochemistry assays that may be used.

5.6.2 Interferon Assays

IFN induction and release by a recombinant NDV described herein may be determined using techniques known to one of skill in the art. For example, the amount of IFN induced in cells following infection with a recombinant NDV described herein may be determined using an immunoassay (e.g., an ELISA or Western blot assay) to measure IFN expression or to measure the expression of a protein whose expression is induced by IFN. Alternatively, the amount of IFN induced may be measured at the RNA level by assays, such as Northern blots and quantitative RT-PCR, known to one of skill in the art. In specific embodiments, the amount of IFN released may be measured using an ELISPOT assay. Further, the induction and release of cytokines and/or interferon-stimulated genes may be determined by, e.g., an immunoassay or ELISPOT assay at the protein level and/or quantitative RT-PCR or northern blots at the RNA level.

5.6.3 Activation Marker Assays and Immune Cell Infiltration Assay

Techniques for assessing the expression of T cell marker, B cell marker, activation marker, co-stimulatory molecule, ligand, or inhibitory molecule by immune cells are known to one of skill in the art. For example, the expression of T cell marker, B cell marker, an activation marker, co-stimulatory molecule, ligand, or inhibitory molecule by an immune cell can be assessed by flow cytometry. In a specific embodiment, an assay described in Section 6, infra, is used to assess infiltration of a type(s) of immune cell.

5.6.4 Toxicity Studies

In some embodiments, the recombinant NDVs described herein or compositions thereof, or combination therapies described herein are tested for cytotoxicity in mammalian, preferably human, cell lines. In certain embodiments, cytotoxicity is assessed in one or more of the following non-limiting examples of cell lines: U937, a human monocyte cell line; primary peripheral blood mononuclear cells (PBMC); Huh7, a human hepatoblastoma cell line; HL60 cells, HT1080, HEK 293T and 293H, MLPC cells, human embryonic kidney cell lines; human melanoma cell lines, such as SkMel2, SkMel-119 and SkMel-197; THP-1, monocytic cells; a HeLa cell line; and neuroblastoma cells lines, such as MC-IXC, SK-N-MC, SK-N-MC, SK-N-DZ, SH-SY5Y, and BE(2)-C. In some embodiments, the ToxLite assay is used to assess cytotoxicity.

Many assays well-known in the art can be used to assess viability of cells or cell lines following infection with a recombinant NDV described herein or composition thereof, and, thus, determine the cytotoxicity of the recombinant NDV or composition thereof. For example, cell proliferation can be assayed by measuring Bromodeoxyuridine (BrdU) incorporation, ($^3$H) thymidine incorporation, by direct cell count, or by detecting changes in transcription, translation or activity of known genes such as proto-oncogenes (e.g., fos, myc) or cell cycle markers (Rb, cdc2, cyclin A, D1, D2, D3, E, etc.). The levels of such protein and mRNA and activity can be determined by any method well known in the art. For example, protein can be quantitated by known immunodiagnostic methods such as ELISA, Western blotting or immunoprecipitation using antibodies, including commercially available antibodies. mRNA can be quantitated using methods that are well known and routine in the art, for example, using northern analysis, RNase protection, or polymerase chain reaction in connection with reverse transcription. Cell viability can be assessed by using trypan-blue staining or other cell death or viability markers known in the art. In a specific embodiment, the level of cellular ATP is measured to determined cell viability. In preferred embodiments, a recombinant NDV described herein or composition thereof does not kill healthy (i.e., non-cancerous) cells.

In specific embodiments, cell viability may be measured in three-day and seven-day periods using an assay standard in the art, such as the CellTiter-Glo Assay Kit (Promega) which measures levels of intracellular ATP. A reduction in cellular ATP is indicative of a cytotoxic effect. In another specific embodiment, cell viability can be measured in the neutral red uptake assay. In other embodiments, visual observation for morphological changes may include enlargement, granularity, cells with ragged edges, a filmy appearance, rounding, detachment from the surface of the well, or other changes.

The recombinant NDVs described herein or compositions thereof, or combination therapies can be tested for in vivo toxicity in animal models. For example, animal models, known in the art to test the effects of compounds on RSV infection or hMPV infection can also be used to determine the in vivo toxicity of the recombinant NDVs described herein or compositions thereof, or combination therapies. For example, animals are administered a range of pfu of a recombinant NDV described herein, and subsequently, the animals are monitored over time for various parameters, such as one, two or more of the following: lethality, weight loss or failure to gain weight, and levels of serum markers that may be indicative of tissue damage (e.g., creatine phosphokinase level as an indicator of general tissue damage, level of glutamic oxalic acid transaminase or pyruvic acid transaminase as indicators for possible liver damage). These in vivo assays may also be adapted to test the toxicity of various administration mode and regimen in addition to dosages.

The toxicity, efficacy or both of a recombinant NDV described herein or a composition thereof, or a combination therapy described herein can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Therapies that exhibit large therapeutic indices are preferred.

The data obtained from the cell culture assays and animal studies can be used in formulating a range of dosage of the therapies for use in subjects. The dosage of such agents lies preferably within a range of circulating concentrations that include the ED50 with little or no toxicity. The dosage may vary within this range depending upon the dosage form employed and the route of administration utilized. For any therapy described herein, the therapeutically effective dose can be estimated initially from cell culture assays.

5.6.5 Biological Activity Assays

The recombinant NDVs described herein or compositions thereof, or combination therapies described herein can be tested for biological activity using animal models for inhibiting RSV disease, hMPV disease, antibody response to the recombinant NDVs, etc. (see, e.g., Section 6). Such animal model systems include, but are not limited to, rats, mice, hamsters, cotton rats, chicken, cows, monkeys (e.g., African green monkey), pigs, dogs, rabbits, etc.

In a specific embodiment, the recombinant NDVs described herein or compositions thereof, or combination therapies described herein may be tested using animal models for the ability to induce a certain geometric mean titer of antibody(ies) that binds to the RSV F protein (e.g., human RSV F protein or bovine F protein) or hMPV F protein. In another specific embodiment, the recombinant NDVs described herein or compositions thereof, or combination therapies described herein may be tested using animal models for the ability to induce antibodies that have neutralizing activity against RSV F protein (e.g., human RSV F protein or bovine F protein) or hMPV F protein in a microneutralization assay. For example, the microneutralization assay described in Section 6, infra, may be used to assess neutralizing activity. In some embodiments, the recombinant NDVs described herein or compositions thereof, or combination therapies described herein may be tested using animal models for the ability to induce a certain geometric mean titer of antibody(ies) that binds to the RSV F protein (e.g., human RSV F protein or bovine F protein) or hMPV F protein and neutralizes RSV F protein (e.g., human RSV F protein or bovine F protein) or hMPV F protein in a microneutralizsation assay. In a specific embodiment, the recombinant NDVs described herein or compositions thereof, or combination therapies described herein may be tested using animal models for the ability to induce a certain fold increase in levels of antibody(ies) that binds to RSV F protein (e.g., human RSV F protein or bovine F protein) or hMPV F protein post-immunization with a recombinant NDV described herein or a composition thereof relative to the levels of such antibody pre-immunization. For example, a 3 fold, 4 fold, 5 fold, 6 fold, 7 fold, 8 fold or greater increase in levels of antibody(ies) that binds to RSV F protein (e.g., human RSV F protein or bovine F protein) or hMPV F protein post-immunization with a recombinant NDV described herein or a composition thereof relative to the levels of such antibody(ies) pre-immunization.

5.6.6 Expression of Transgene

Assays for testing the expression of RSV F protein, chimeric F protein, or hMPV F protein in cells infected with a recombinant NDV comprising a packaged genome comprising a transgene encoding RSV F protein, chimeric F protein, or hMPV F protein, respectively may be conducted using any assay known in the art, such as, e.g., western blot, immunofluorescence, and ELISA, or any assay described herein (see, e.g., Section 6).

In a specific aspect, ELISA is utilized to detect expression of RSV F protein, chimeric F protein, or hMPV F protein in cells infected with a recombinant NDV comprising a packaged genome comprising a transgene encoding of RSV F protein, chimeric F protein, or hMPV F protein. In a specific embodiment, RSV F protein is quantified using an ELISA such as described in Section 6, infra.

In one embodiment, RSV F protein or chimeric F protein encoded by a packaged genome of a recombinant NDV described herein is assayed for proper folding by testing its ability to bind specifically to an anti-RSV F protein antibody (e.g., Synagis®) using any assay for antibody-antigen interaction known in the art. In another embodiment, hMPV F protein or chimeric F protein encoded by a packaged genome of a recombinant NDV described herein is assayed for proper folding by testing its ability to bind specifically to an anti-hMPV F protein antibody using any assay for antibody-antigen interaction known in the art. In another embodiment, an RSV F protein, a chimeric F protein, or an hMPV F protein encoded by a packaged genome of a recombinant NDV described herein is assayed for proper folding by determination of the structure or conformation of the RSV F protein, chimeric F protein, or hMPV F protein, respectively using any method known in the art such as, e.g., NMR, X-ray crystallographic methods, or secondary structure prediction methods, e.g., circular dichroism. Additional assays assessing the conformation and antigenicity of RSV F protein, chimeric F protein, or hMPV F protein may include, e.g., immunofluorescence microscopy, flow cytometry, western blot, and ELISA may be used. In vivo immunization in animal models, such as cotton rats or mice, may also be used to assess the antigenicity of RSV F protein, chimeric F protein, or hMPV F protein.

Assays for testing the functionality of RSV F protein, chimeric F protein, or hMPV F protein in cells infected with a recombinant NDV comprising a packaged genome comprising a transgene encoding RSV F protein, chimeric F protein, or hMPV F protein, respectively, may be conducted using any assay known in the art. However, it is not necessary that the RSV F protein, chimeric F protein, or hMPV F protein of a recombinant NDV described herein maintain the ability of the F protein to fuse the virus envelope with the cell membrane.

5.7 Kits

In one aspect, provided herein is a pharmaceutical pack or kit comprising one or more containers filled with one or more of the ingredients of a composition (e.g., a pharmaceutical compositions) described herein. In a specific embodiment, provided herein is a pharmaceutical pack or kit comprising a container, wherein the container comprises a recombinant NDV comprising a packaged genome comprising a transgene encoding an RSV F protein (e.g., a human or bovine RSV F protein), or a pharmaceutical composition comprising the recombinant NDV. In another specific embodiment, provided herein is a pharmaceutical pack or kit comprising a container, wherein the container comprises a recombinant NDV comprising a packaged genome comprising a transgene encoding chimeric F protein, or a pharmaceutical composition comprising the recombinant NDV, wherein the chimeric F protein comprises an RSV F protein (e.g., a human or bovine RSV F protein) ectodomain and NDV F protein transmembrane and cytoplasmic domains. In a specific embodiment, provided herein is a pharmaceutical pack or kit comprising a container, wherein the container comprises a recombinant NDV comprising a packaged genome comprising a transgene encoding an hMPV F protein, or a pharmaceutical composition comprising the recombinant NDV. In another specific embodiment, provided herein is a pharmaceutical pack or kit comprising a container, wherein the container comprises a recombinant NDV comprising a packaged genome comprising a transgene encoding chimeric F protein, or a pharmaceutical composition comprising the recombinant NDV, wherein the chimeric F protein comprises an hMPV F protein ectodomain and NDV F protein transmembrane and cytoplasmic domains. Optionally associated with such container(s) can be a notice in the form prescribed by a governmental agency regulating the manufacture, use or sale of pharmaceuticals or biological products, which notice reflects approval by the agency of manufacture, use or sale for human administration.

5.8 Sequences

The sequences disclosed in this section may be used to produce the recombinant NDV described herein.

TABLE 1

Human RSV F Sequences

| Description | Sequence | SEQ ID NO. |
|---|---|---|
| Wild-type nucleic acid sequence encoding human RSV-F of A2 strain | atggagttgctaatcctcaaagcaaatgcaattaccacaatcctcactgcag<br>tcacattttgttttgcttctggtcaaaacatcactgaagaattttatcaatc<br>aacatgcagtgcagttagcaaaggctatcttagtgctctgagaactggttgg<br>tataccagtgttataactatagaattaagtaatatcaaggaaaataagtgta<br>atggaacagatgctaaggtaaaattgataaaacaagaattagataaatataa<br>aaatgctgtaacagaattgcagttgctcatgcaaagcacaccagcaacaaac<br>aatcgagccagaagagaactaccaaggtttatgaattatacactcaacaatg<br>ccaaaaaaaccaatgtaacattaagcaagaaaaggaaaagaagatttcttgg<br>tttttgttaggtgttggatctgcaatcgccagtggcgttgctgtatctaag<br>gtcctgcacctagaaggggaagtgaacaagatcaaaagtgctctactatcca<br>caaacaaggctgtagtcagcttatcaaatggagttagtgtcttaaccagcaa<br>agtgttagacctcaaaaactatatagataaacaattgttacctattgtgaac<br>aagcaaagctgcagcatatcaaatatagcaactgtgatagagttccaacaaa<br>agaacaacagactactagagattaccagggaatttagtgttaatgcaggtgt<br>aactacacctgtaagcacttacatgttaactaatagtgaattattgtcatta<br>atcaatgatatgcctataacaaatgatcagaaaaagttaatgtccaacaatg<br>ttcaaatagttagacagcaaagttactctatcatgtccataataaaagagga<br>agtcttagcatatgtagtacaattaccactatatggtgttatagatacaccc<br>tgttggaaactacacacatcccctctatgtacaaccaacacaaaagaagggt<br>ccaacatctgtttaacaagaactgacagaggatggtactgtgacaatgcagg<br>atcagtatctttcttcccacaagctgaaacatgtaaagttcaatcaaatcga<br>gtattttgtgacacaatgaacagtttaacattaccaagtgaagtaaatctct<br>gcaatgttgacatattcaaccccaaatatgattgtaaaattatgacttcaaa<br>aacagatgtaagcagctccgttatcacatctctaggagccattgtgtcatgc<br>tatggcaaaactaaatgtacagcatccaataaaaatcgtggaatcataaaga<br>cattttctaacgggtgcgattatgtatcaaataaaggggtggacactgtgtc<br>tgtaggtaacacattatattatgtaaataagcaagaaggtaaaagtctctat<br>gtaaaaggtgaaccaataataaatttctatgacccattagtattcccctctg<br>atgaatttgatgcatcaatatctcaagtcaacgagaagattaaccagagcct<br>agcatttattcgtaaatccgatgaattattacataatgtaaatgctggtaaa<br>tccaccataaatatcatgataactactataattatagtgattatagtaatat<br>tgttatcattaattgctgttggactgctcttatactgtaaggccagaagcac<br>accagtcacactaagcaaagatcaactgagtggtataaataatattgcattt<br>agtaactaa | 1 |
| Codon-optimized nucleic acid sequence encoding human RSV F of A2 strain (codon optimized version of SEQ ID NO:1) | ATGGAGCTGCTGATCCTGAAGGCCAACGCCATCACCAC<br>CATCCTGACCGCCGTGACCTTCTGCTTCGCCAGCGGCCA<br>GAACATCACCGAGGAGTTCTACCAGAGCACCTGCAGCG<br>CCGTGAGCAAGGGCTACCTGAGCGCCCTGCGCACCGGC<br>TGGTACACCAGCGTGATCACCATCGAGCTGAGCAACAT<br>CAAGGAGAACAAGTGCAACGGCACCGACGCCAAGGTG<br>AAGCTGATCAAGCAGGAGCTGGACAAGTACAAGAACG<br>CCGTGACCGAGCTGCAGCTGCTGATGCAGAGCACCCCC<br>GCCACCAACAACCGCGCCCGCCGCGAGCTGCCCCGCTT<br>CATGAACTACACCCTGAACAACGCCAAGAAGACCAACG<br>TGACCCTGAGCAAGAAGCGCAAGCGCCGCTTCCTGGGC<br>TTCCTGCTGGGCGTGGGCAGCGCCATCGCCAGCGGCGT | 2 |

TABLE 1-continued

| Human RSV F Sequences | | |
|---|---|---|
| Description | Sequence | SEQ ID NO. |
| | GGCCGTGAGCAAGGTGCTGCACCTGGAGGGCGAGGTGA<br>ACAAGATCAAGAGCGCCCTGCTGAGCACCAACAAGGCC<br>GTGGTGAGCCTGAGCAACGGCGTGAGCGTGCTGACCAG<br>CAAGGTGCTGGACCTGAAGAACTACATCGACAAGCAGC<br>TGCTGCCCATCGTGAACAAGCAGAGCTGCAGCATCAGC<br>AACATCGCCACCGTGATCGAGTTCCAGCAGAAGAACAA<br>CCGCCTGCTGGAGATCACCCGCGAGTTCAGCGTGAACG<br>CCGGCGTGACCACCCCCGTGAGCACCTACATGCTGACC<br>AACAGCGAGCTGCTGAGCCTGATCAACGACATGCCCAT<br>CACCAACGACCAGAAGAAGCTGATGAGCAACAACGTG<br>CAGATCGTGCGCCAGCAGAGCTACAGCATCATGAGCAT<br>CATCAAGGAGGAGGTGCTGGCCTACGTGGTGCAGCTGC<br>CCCTGTACGGCGTGATCGACACCCCCTGCTGGAAGCTG<br>CACACCAGCCCCCTGTGCACCACCAACACCAAGGAGGG<br>CAGCAACATCTGCCTGACCCGCACCGACAGGGGCTGGT<br>ACTGCGACAACGCCGGCAGCGTGAGCTTCTTCCCCCAG<br>GCCGAGACCTGCAAGGTGCAGAGCAACCGCGTGTTCTG<br>CGACACCATGAACAGCCTGACCCTGCCCAGCGAGGTGA<br>ACCTGTGCAACGTGGACATCTTCAACCCCAAGTACGAC<br>TGCAAGATCATGACCAGCAAGACCGACGTGAGCAGCAG<br>CGTGATCACCAGCCTGGGCGCCATCGTGAGCTGCTACG<br>GCAAGACCAAGTGCACCGCCAGCAACAAGAACAGGGG<br>CATCATCAAGACCTTCAGCAACGGCTGCGACTACGTGA<br>GCAACAAGGGCGTGGACACCGTGAGCGTGGGCAACAC<br>CCTGTACTACGTGAACAAGCAGGAGGGCAAGAGCCTGT<br>ACGTGAAGGGCGAGCCCATCATCAACTTCTACGACCCC<br>CTGGTGTTCCCCAGCGACGAGTTCGACGCCAGCATCAG<br>CCAGGTGAACGAGAAGATCAACCAGAGCCTGGCCTTCA<br>TCCGCAAGAGCGACGAGCTGCTGCACAACGTGAACGCC<br>GGCAAGAGCACCATCAACATCATGATCACCACCATCAT<br>CATCGTGATCATCGTGATCCTGCTGAGCCTGATCGCCGT<br>GGGCCTGCTGCTGTACTGCAAGGCCCGCAGCACCCCCG<br>TGACCCTGAGCAAGGACCAGCTGAGCGGCATCAACAAC<br>ATCGCCTTCAGCAACTAA | |
| cDNA of the full genome of NDV strain LaSota with the transgene comprising the codon-optimized nucleic acid sequence (SEQ ID NO: 2) encoding human RSV F protein of A2 strain inserted between the NDV P and M genes (The Sac II (CCGCGG) restriction sites used to insert the codon optimized human RSV F protein open reading frame into the genomic sequence are double underlined. The initiation and stop codons of the codon optimized human RSV F open reading frame are underlined. The open reading from of the codon optimized human RSV F is | accaaacagagaatccgtgagttacgataaaaggcgaaggagcaattg<br>aagtcgcacgggtagaaggtgtgaatctcgagtgcgagcccgaagcac<br>aaactcgagaaagccttctgccaacatgtcttccgtatttgatgagta<br>cgaacagctcctcgcggctcagactcgccccaatggagctcatggagg<br>gggagaaaaagggagtaccttaaaagtagacgtcccggtattcactct<br>taacagtgatgacccagaagatagatggagctttgtggtattctgcct<br>ccggattgctgttagcgaagatgccaacaaaccactcaggcaaggtgc<br>tctcatatctcttttatgctcccactcacaggtaatgaggaaccatgt<br>tgccCttgcagggaaacagaatgaagccacattggccgtgcttgagat<br>tgatggctttgccaacggcacgccccagttcaacaataggagtggagt<br>gtctgaagagagagcacagagatttgcgatgatagcaggatctctccc<br>tcgggcatgcagcaacggaaccccgttcgtcacagccggggcCgaaga<br>tgatgcaccagaagacatcaccgataccctggagaggatcctctctat<br>ccaggctcaagtatgggtcacagtagcaaaagccatgactgcgtatga<br>gactgcagatgagtcggaaacaaggcgaatcaataagtatatgcagca<br>aggcagggtccaaaagaaatacatcctctaccccgtatgcaggagcac<br>aatccaactcacgatcagacagtctcttgcagtccgcatctttttggt<br>tagcgagctcaagagaggccgcaacacggcaggtggtacctctactta<br>ttataacctggtaggggacgtagactcatacatcaggaataccgggct<br>tactgcattcttcttgacactcaagtacggaatcaacaccaagacatc<br>agcccttgcacttagtagcctctcaggcgacatccagaagatgaagca<br>gctcatgcgtttgtatcggatgaaaggagataatgcgccgtacatgac<br>attacttggtgatagtgaccagatgagctttgcgcctgccgagtatgc<br>acaactttactcctttgccatgggtatggcatcagtcctagataaagg<br>tactgggaaataccaatttgccagggactttatgagcacatcattctg<br>gagacttggagtagagtacgctcaggctcagggaagtagcattaacga<br>ggatatggctgccgagctaaagctaaccccagcagcaaGgaGgggcct<br>ggcagctgctgcccaacgggtctccgaGgaGaccagcagcataGacat<br>gcctactcaacaagtcggagtcctcactgggcttagcgagggggggtc<br>ccaagctctacaaggcggatcgaatagatcgcaagggcaaccagaagc<br>cggggatggggagacccaattcctggatctgatgagagcggtagcaaa<br>tagcatgagggaggcgccaaactctgcacagggcactccccaatcggg<br>gcctcccccaactcctgggccatcccaagataacgacaccgactgggg<br>gtattgatggacaaaacccagcctgcttccacaaaaacatcccaatgc<br>cctcacccgtagtcgacccctcgatttgcggctctatatgaccacacc<br>ctcaaacaaacatcccccctctttcctccctccccctgctgtacaactA<br>cgTacgccctagataccacaggcacaatgcggctcactaacaatcaaa<br>acagagccgagggaattagaaaaaagtacgggtagaagagggatattc<br>agagatcagggcaagtctcccgagtctctgctctctcctctacctgat<br>agaccaggacaaacatggccacctttacagatgcagagatcgacgagc | 3 |

TABLE 1-continued

| Human RSV F Sequences | | |
|---|---|---|
| Description | Sequence | SEQ ID NO. |
| in bold. | tatttgagacaagtggaactgtcattgacaacataattacagcccagg<br>gtaaaccagcagagactgttggaaggagtgcaatcccacaaggcaaga<br>ccaaggtgctgagcgcagcatgggagaagcatgggagcatccagccac<br>cggccagtcaagacaaccccgatcgacaggacagatctgacaaacaac<br>catccacacccgagcaaacgaccccgcatgacagcccgccggccacat<br>ccgccgaccagcccccccacccaggccacagacgaagccgtcgacacac<br>agCtcaggaccggagcaagcaactctctgctgttgatgcttgacaagc<br>tcagcaataaatcgtccaatgctaaaaagggcccatggtcgagccccc<br>aagaggggaatcaccaacgtccgactcaacagcaggggagtcaaccca<br>gtcgcggaaacagtcaggaaagaccgcagaaccaagtcaaggccgccc<br>ctggaaaccagggcacagacgtgaacacagcatatcatggacaatggg<br>aggagtcacaactatcagctggtgcaacccctcatgctctccgatcaa<br>ggcagagccaagacaatacccttgtatctgcggatcatgtccagccac<br>ctgtagactttgtgcaagcgatgatgtctatgatggaggcgatatcac<br>agagagtaagtaaggttgactatcagctagatcttgtcttgaaacaga<br>catcctccatccctatgatgcggtccgaaatccaacagctgaaaacat<br>ctgttgcagtcatggaagccaacttgggaatgatgaagattctggatc<br>ccggttgtgccaacatttcatctctgagtgatctacgggcagttgccc<br>gatctcacccggttttagtttcaggccctggagacccctctccctatg<br>tgacacaaggaggcgaaatggcacttaataaactttcgcaaccagtgc<br>cacatccatctgaattgattaaacccgccactgcatgcgggcctgata<br>taggagtggaaaaggacactgtccgtgcattgatcatgtcacgcccaa<br>tgcacccgagttcttcagccaagctcctaagcaagttagatgcagccg<br>ggtcgatcgaggaaatcaggaaaatcaagcgccttgctctaaatggct<br>aattactactgccacacgtagcgggtccctgtccactcggcatcacac<br>ggaatctgcaccgagttcccccccgcGgTTAGAAAAAATACGGGTAGA<br>ACCGCCACC**ATGGAGCTGCTGATCCTGAAGGCCAACGCCATCACCACC**<br>**ATCCTGACCGCCGTGACCTTCTGCTTCGCCAGCGGCCAGAACATCACC**<br>**GAGGAGTTCTACCAGAGCACCTGCAGCGCCGTGAGCAAGGGCTACCTG**<br>**AGCGCCCTGCGCACCGGCTGGTACACCAGCGTGATCACCATCGAGCTG**<br>**AGCAACATCAAGGAGAACAAGTGCAACGGCACCGACGCCAAGGTGAAG**<br>**CTGATCAAGCAGGAGCTGGACAAGTACAAGAACGCCGTGACCGAGCTG**<br>**CAGCTGCTGATGCAGAGCACCCCCGCCACCAACAACCGCGCCCGCCGC**<br>**GAGCTGCCCCGCTTCATGAACTACACCCTGAACAACGCCAAGAAGACC**<br>**AACGTGACCCTGAGCAAGAAGCGCAAGCGCCGCTTCCTGGGCTTCCTG**<br>**CTGGGCGTGGGCAGCGCCATCGCCAGCGGCGTGGCCGTGAGCAAGGTG**<br>**CTGCACCTGGAGGGCGAGGTGAACAAGATCAAGAGCGCCCTGCTGAGC**<br>**ACCAACAAGGCCGTGGTGAGCCTGAGCAACGGCGTGAGCGTGCTGACC**<br>**AGCAAGGTGCTGGACCTGAAGAACTACATCGACAAGCAGCTGCTGCCC**<br>**ATCGTGAACAAGCAGAGCTGCAGCATCAGCAACATCGCCACCGTGATC**<br>**GAGTTCCAGCAGAAGAACAACCGCCTGCTGGAGATCACCCGCGAGTTC**<br>**AGCGTGAACGCCGGCGTGACCACCCCCGTGAGCACCTACATGCTGACC**<br>**AACAGCGAGCTGCTGAGCCTGATCAACGACATGCCCATCACCAACGAC**<br>**CAGAAGAAGCTGATGAGCAACAACGTGCAGATCGTGCGCCAGCAGAGC**<br>**TACAGCATCATGAGCATCATCAAGGAGGAGGTGCTGGCCTACGTGGTG**<br>**CAGCTGCCCCTGTACGGCGTGATCGACACCCCCTGCTGGAAGCTGCAC**<br>**ACCAGCCCCCTGTGCACCACCAACACCAAGGAGGGCAGCAACATCTGC**<br>**CTGACCCGCACCGACaGgGGCTGGTACTGCGACAACGCCGGCAGCGTG**<br>**AGCTTCTTCCCCCAGGCCGAGACCTGCAAGGTGCAGAGCAACCGCGTG**<br>**TTCTGCGACACCATGAACAGCCTGACCCTGCCCAGCGAGGTGAACCTG**<br>**TGCAACGTGGACATCTTCAACCCCAAGTACGACTGCAAGATCATGACC**<br>**AGCAAGACCGACGTGAGCAGCAGCGTGATCACCAGCCTGGGCGCCATC**<br>**GTGAGCTGCTACGGCAAGACCAAGTGCACCGCCAGCAACAAGAACaGg**<br>**GGCATCATCAAGACCTTCAGCAACGGCTGCGACTACGTGAGCAACAAG**<br>**GGCGTGGACACCGTGAGCGTGGGCAACACCCTGTACTACGTGAACAAG**<br>**CAGGAGGGCAAGAGCCTGTACGTGAAGGGCGAGCCCATCATCAACTTC**<br>**TACGACCCCCTGGTGTTCCCCAGCGACGAGTTCGACGCCAGCATCAGC**<br>**CAGGTGAACGAGAAGATCAACCAGAGCCTGGCCTTCATCCGCAAGAGC**<br>**GACGAGCTGCTGCACAACGTGAACGCCGGCAAGAGCACCATCAACATC**<br>**ATGATCACCACCATCATCATCGTGATCATCGTGATCCTGCTGAGCCTG**<br>**ATCGCCGTGGGCCTGCTGCTGTACTGCAAGGCCCGCAGCACCCCCGTG**<br>**ACCCTGAGCAAGGACCAGCTGAGCGGCATCAACAACATCGCCTTCAGC**<br>**AACTAA**ccccccgcggacccaaggtccaactctccaagcggcaatcct<br>ctctcgcttcctcagccccactgaatgAtcgcgtaaccgtaattaatc<br>tagctacatttaagattaagaaaaaatacgggtagaattggagtgccc<br>caattgtgccaagatggactcatctaggacaattgggctgtactttga<br>ttctgcccattcttctagcaacctgttagcatttccgatcgtcctaca<br>agAcacaggagatgggaagaagcaaatcgccccgcaatataggatcca<br>gcgccttgacttgtggactgatagtaaggaggactcagtattcatcac<br>cacctatggattcatctttcaagttgggaatgaagaagccacCgtcgg<br>catgatcgatgataaacccaagcgcgagttactttccgctgcgatgct<br>ctgcctaggaagcgtcccaaataccggagaccttattgagctggcaag<br>ggcctgtctcactatgatagtcacatgcaagaagagtgcaactaatac<br>tgagagaatggttttctcagtagtgcaggcaccccaagtgctgcaaag<br>ctgtagggttgtggcaaacaaatactcatcagtgaatgcagtcaagca | |

TABLE 1-continued

Human RSV F Sequences

| Description | Sequence | SEQ ID NO. |
|---|---|---|
| | cgtgaaagcgccagagaagattcccgggagtggaaccctagaatacaa | |
| | ggtgaactttgtctccttgactgtggtaccgaagaGggatgtctacaa | |
| | gatcccagctgcagtattgaaggtttctggctcgagtctgtacaatct | |
| | tgcgctcaatgtcactattaatgtggaggtagacccgaggagtccttt | |
| | ggttaaatctCtgtctaagtctgacagcggatactatgctaacctctt | |
| | cttgcatattggacttatgaccacTgtagataggaaggggaagaaagt | |
| | gacatttgacaagctggaaaagaaaataaggagccttgatctatctgt | |
| | cgggctcagtgatgtgctcgggccttccgtgttggtaaaagcaagagg | |
| | tgcacggactaagcttttggcacctttcttctctagcagtgggacagc | |
| | ctgctatcccatagcaaatgcttctcctcaggtggccaagatactctg | |
| | gagtcaaaccgcgtgcctgcggagcgttaaaatcattatccaagcagg | |
| | tacccaacgcgctgtcgcagtgaccgccgaccacgaggttacctctac | |
| | taagctggagaaggggcacacccttgccaaatacaatccttttaagaa | |
| | ataagctgcgtctctgagattgcgctccgcccactcacccagatcatc | |
| | atgacacaaaaaactaatctgtcttgattatttacagttagtttacct | |
| | gtctatcaagttagaaaaaacacgggtagaagattctggatcccggtt | |
| | ggcgccctccaggtgcaagatgggctccagaccttctaccaagaaccc | |
| | agcacctatgatgctgactatccgggttgcgctggtactgagttgcat | |
| | ctgtccggcaaactccattgatggcaggcctcttgcagctgcaggaat | |
| | tgtggttacaggagacaaagccgtcaacatatacacctcatcccagac | |
| | aggatcaatcatagttaagctcctcccgaatctgcccaaggataagga | |
| | ggcatgtgcgaaagccccccttggatgcatacaacaggacattgaccac | |
| | tttgctcaccccccttggtgactctatccgtaggatacaagagtctgt | |
| | gactacatctggagggggagacaggggcgccttataggcgccattat | |
| | tggcggtgtggctcttggggttgcaactgccgcacaaataacagcggc | |
| | cgcagctctgatacaagccaaacaaaatgctgccaacatcctccgact | |
| | taaagagagcattgccgcaaccaatgaggctgtgcatgaggtcactga | |
| | cggattatcgcaactagcagtggcagttgggaagatgcagcagtttgt | |
| | taatgaccaatttaataaaacagctcaggaattagactgcatcaaaat | |
| | tgcacagcaagttggtgtagagctcaacctgtacctaaccgaattgac | |
| | tacagtattcggaccacaaatcacttcacctgctttaaacaagctgac | |
| | tattcaggcactttacaatctagctggtggaaatatggattacttatt | |
| | gactaagttaggtgtagggaacaatcaactcagctcattaatcggtag | |
| | cggcttaatcaccggtaaccctattctatacgactcacagactcaact | |
| | cttgggtatacaggtaactctaccttcagtcgggaacctaaataatat | |
| | gcgtgccacctacttggaaaccttatccgtaagcacaaccaggggatt | |
| | tgcctcggcacttgtcccAaaagtggtgacacaggtcggttctgtgat | |
| | agaagaacttgacacctcatactgtatagaaactgacttagatttata | |
| | ttgtacaagaatagtaacgttccctatgtcccctggtatttattcctg | |
| | cttgagcggcaatacgtcggcctgtatgtactcaaagaccgaaggcgc | |
| | acttactacaccatacatgactatcaaaggttcagtcatcgccaactg | |
| | caagatgacaacatgtagatgtgtaaaccccccgggtatcatatcgca | |
| | aaactatggagaagccgtgtctctaatagataaacaatcatgcaatgt | |
| | tttatccttaggcgggataactttaaggctcagtggggaattcgatgt | |
| | aacttatcagaagaatatctcaatacaagattctcaagtaataataac | |
| | aggcaatcttgatatctcaactgagcttgggaatgtcaacaactcgat | |
| | cagtaatgctttgaataagttagaggaaagcaacagaaaactagacaa | |
| | agtcaatgtcaaactgactagcacatctgctctcattacctatatcgt | |
| | tttgactatcatatctcttgtttttggtatacttagcctgattctagc | |
| | atgctacctaatgtacaagcaaaaggcgcaacaaaagaccttattatg | |
| | gcttgggaataatactctagatcagatgagagccactacaaaaatgtg | |
| | aacacagatgaggaacgaaggtttccctaatagtaatttgtgtgaaag | |
| | ttctggtagtctgtcagttcagagagttaagaaaaaactaccggttgt | |
| | agatgaccaaaggacgatatacgggtagaacggtaagagaggccgccc | |
| | ctcaattgcgagccaggcttcacaacctccgttctaccgcttcaccga | |
| | caacagtcctcaatcatggaccgcgccgttagccaagttgcgttagag | |
| | aatgatgaaagagaggcaaaaaatacatggcgcttgatattccggatt | |
| | gcaatcttattcttaacagtagtgaccttggctatatctgtagcctcc | |
| | cttttatatagcatgggggctagcacacctagcgatcttgtaggcata | |
| | ccgactaggatttccagggcagaagaaaagattacatctacacttggt | |
| | tccaatcaagatgtagtagataggatatataagcaagtggcccttgag | |
| | tctccgttggcattgttaaatactgagaccacaattatgaacgcaata | |
| | acatctctctcttatcagattaatggagctgcaaacaacagtgggtgg | |
| | ggggcacctatccatgacccagattatataggggggataggcaaagaa | |
| | ctcattgtagatgatgctagtgatgtcacatcattctatccctctgca | |
| | tttcaagaacatctgaattttatcccggcgcctactacaggatcaggt | |
| | tgcactcgaataccctcatttgacatgagtgctacccattactgctac | |
| | acccataatgtaatattgtctggatgcagagatcactcacattcatat | |
| | cagtatttagcacttggtgtgctccggacatctgcaacagggagggta | |
| | ttcttttctactctgcgttccatcaacctggacgacacccaaaatcgg | |
| | aagtcttgcagtgtgagtgcaactcccctgggttgtgatatgctgtgc | |
| | tcgaaagtcacggagacagaggaagaagattataactcagctgtccct | |
| | acgcggatggtacatgggaggttagggttcgacggccagtaccacgaa | |
| | aaggacctagatgtcacaacattattcggggactgggtggccaactac | |
| | ccaggagtagggggtggatcttttattgacagccgcgtatggttctca | |

TABLE 1-continued

Human RSV F Sequences

| Description | Sequence | SEQ ID NO. |
| --- | --- | --- |
| | gtctacggagggttaaaacccaattcacccagtgacactgtacaggaa<br>gggaaatatgtgatatacaagcgatacaatgacacatgcccagatgag<br>caagactaccagattcgaatggccaagtcttcgtataagcctggacgg<br>tttggtgggaaacgcatacagcaggctatcttatctatcaaggtgtca<br>acatccttaggcgaagacccggtactgactgtaccgcccaacacagtc<br>acactcatgggggccgaaggcagaattctcacagtagggacatctcat<br>ttcttgtatcaacgagggtcatcatacttctctcccgcgttattatat<br>cctatgacagtcagcaacaaaacagccactcttcatagtccttataca<br>ttcaatgccttcactcggccaggtagtatcccttgccaggcttcagca<br>agatgccccaactcgtgtgttactggagtctatacagatccatatccc<br>ctaatcttctatagaaaccacaccttgcgaggggtattcgggacaatg<br>cttgatggtgtacaagcaagacttaaccctgcgtctgcagtattcgat<br>agcacatcccgcagtcgcattactcgagtgagttcaagcagtaccaaa<br>gcagcatacacaacatcaacttgttttaaagtggtcaagactaataag<br>acctattgtctcagcattgctgaaatatctaatactctcttcggagaa<br>ttcagaatcgtcccgttactagttgagatcctcaaagatgacggggtt<br>agagaagccaggtctggctagttgagtcaattataaaggagttggaaa<br>gatggcattgtatcacctatcttctgcgacatcaagaatcaaaccgaa<br>tgccggcgcgtgctcgaattccatgttgccagttgaccacaatcagcc<br>agtgctcatgcgatcagattaagccttgtcaAtaGtctcttgattaag<br>aaaaaatgtaagtggcaatgagatacaaggcaaaacagctcatggtTa<br>aCaatacgggtaggacatggcgagctccggtcctgaaagggcagagca<br>tcagattatcctaccagagTcacacctgtcttcaccattggtcaagca<br>caaactactctattactggaaattaactgggctaccgcttcctgatga<br>atgtgacttcgaccacctcattctcagccgacaatggaaaaaaatact<br>tgaatcggcctctcctgatactgagagaatgataaaactcggaagggc<br>agtacaccaaactcttaaccacaattccagaataaccggagtgctcca<br>ccccaggtgtttagaaGaactggctaatattgaggtcccagattcaac<br>caacaaatttcggaagattgagaagaagatccaaattcacaacacgag<br>atatggagaactgttcacaaggctgtgtacgcatatagagaagaaact<br>gctggggtcatcttggtctaacaatgtcccccggtcagaggagttcag<br>cagcattcgtacggatccggcattctggtttcactcaaaatggtccac<br>agccaagtttgcatggctccatataaaacagatccagaggcatctgat<br>ggtggcagctaGgacaaggtctgcggccaacaaattggtgatgctaac<br>ccataaggtaggccaagtctttgtcactcctgaacttgtcgttgtgac<br>gcatacgaatgagaacaagttcacatgtcttacccaggaacttgtatt<br>gatgtatgcagatatgatggagggcagagatatggtcaacataatatc<br>aaccacggcggtgcatctcagaagcttatcagagaaaattgatgacat<br>tttgcggttaatagacgctctggcaaaagacttgggtaatcaagtcta<br>cgatgttgtatcactaatggagggatttgcatacggagctgtccagct<br>actcgagccgtcaggtacatttgcaggagatttcttcgcattcaacct<br>gcaggagcttaaagacattctaattggcctcctccccaatgatatagc<br>agaatccgtgactcatgcaatcgctactgtattctctggtttagaaca<br>gaatcaagcagctgagatgttgtgtctgttgcgtctgtggggtcaccc<br>actgcttgagtcccgtattgcagcaaaggcagtcaggagccaaatgtg<br>cgcaccgaaaatggtagactttgatatgatccttcaggtactgtcttt<br>cttcaagggaacaatcatcaacgggtacagaaagaagaatgcaggtgt<br>gtggccgcgagtcaaagtggatacaatatatgggaaggtcattgggca<br>actacatgcagattcagcagagatttcacacgatatcatgttgagaga<br>gtataagagtttatctgcacttgaatttgagccatgtatagaatatga<br>ccctgtcaccaacctgagcatgttcctaaaagacaaggcaatcgcaca<br>ccccaacgataattggcttgcctcgtttaggcggaaccttctctccga<br>agaccagaagaaacatgtaaaagaagcaacttcgactaatcgcctctt<br>gatagagtttttagagtcaaatgattttgatccatataaagagatgga<br>atatctgacgacccttgagtaccttagagatgacaatgtggcagtatc<br>atactcgctcaaggagaaggaagtgaaagttaatggacggatcttcgc<br>taagctgacaaagaagttaaggaactgtcaggtgatggcggaagggat<br>cctagccgatcagattgcacctttctttcagggaaatggagtcattca<br>ggatagcatatccttgaccaagagtatgctagcgatgagtcaactgtc<br>ttttaacagcaataagaaacgtatcactgactgtaaagaaagagtatc<br>ttcaaaccgcaatcatgatccgaaaagcaagaaccgtcggagagttgc<br>aaccttcataacaactgacctgcaaaagtactgtcttaattggagata<br>tcagacaatcaaattgttcgctcatgccatcaatcagttgatgggcct<br>acctcacttcttcgaatggattcacctaagactgatggacactacgat<br>gttcgtaggagaccctttcaatcctccaagtgaccctactgactgtga<br>cctctcaagagtccctaatgatgacatatatattgtcagtgccagagg<br>gggtatcgaaggattatgccagaagctatggacaatgatctcaattgc<br>tgcaatccaacttgctgcagctagatcgcattgtcgtgttgcctgtat<br>ggtacagggtgataatcaagtaatagcagtaacgagagaggtaagatc<br>agacgactctccggagatggtgttgacacagttgcatcaagccagtga<br>taatttcttcaaggaattaattcatgtcaatcatttgattggccataa<br>tttgaaggatcgtgaaaccatcaggtcagacacattcttcatatacag<br>caaacgaatcttcaaagatggagcaatcctcagtcaagtcctcaaaaa<br>ttcatctaaattagtgctagtgtcaggtgatctcagtgaaaacaccgt<br>aatgtcctgtgccaacattgcctctactgtagcacggctatgcgagaa | |

TABLE 1-continued

Human RSV F Sequences

| Description | Sequence | SEQ ID NO. |
|---|---|---|
| | cgggcttcccaaagacttctgttactatttaaactatataatgagttg<br>tgtgcagacatactttgactctgagttctccatcaccaacaattcgca<br>ccccgatcttaatcagtcgtggattgaggacatctcttttgtgcactc<br>atatgttctgactcctgcccaattagggggactgagtaaccttcaata<br>ctcaaggctctacactagaaatatcggtgacccggggactactgcttt<br>tgcagagatcaagcgactagaagcagtgggattactgagtcctaacat<br>tatgactaatatcttaactaggccgcctgggaatggagattgggccag<br>tctgtgcaacgacccatactctttcaattttgagactgttgcaagccc<br>aaatattgttcttaagaaacatacgcaaagagtcctatttgaaacttg<br>ttcaaatcccttattgtctggagtgcacacagaggataatgaggcaga<br>agagaaggcattggctgaattcttgcttaatcaagaggtgattcatcc<br>ccgcgttgcgcatgccatcatggaggcaagctctgtaggtaggagaaa<br>gcaaattcaagggcttgttgacacaacaaacaccgtaattaagattgc<br>gcttactaggaggccattaggcatcaagaggctgatgcggatagtcaa<br>ttattctagcatgcatgcaatgctgtttagagacgatgtttttttcctc<br>cagtagatccaaccaccccttagtctcttctaatatgtgttctctgac<br>actggcagactatgcacggaatagaagctggtcacctttgacgggagg<br>caggaaaatactgggtgtatctaatcctgatacgatagaactcgtaga<br>gggtgagattcttagtgtaagcggagggtgtacaagatgtgacagcgg<br>agatgaacaatttacttggttccatcttccaagcaatatagaattgac<br>cgatgacaccagcaagaatcctccgatgagggtaccatatctcgggtc<br>aaagacacaggagaggagagctgcctcacttgcaaaaatagctcatat<br>gtcgccacatgtaaaggctgccctaagggcatcatccgtgttgatctg<br>ggcttatggggataatgaagtaaattggactgctgctcttacgattgc<br>aaaatctcggtgtaatgtaaacttagagtatcttcggttactgtcccc<br>tttacccacggctgggaatcttcaacatagactagatgatggtataac<br>tcagatgacattcaccccctgcatctctctacaggGtgtcaccttacat<br>tcacatatccaatgattctcaaaggctgttcactgaagaaggagtcaa<br>agaggggaatgtggtttaccaacagatcatgctcttgggtttatctct<br>aatcgaatcgatctttccaatgacaacaaccaggacatatgatgagat<br>cacactgcacctacatagtaaatttagttgctgtatcagagaagcacc<br>tgttgcggttcctttcgagctacttggggtggtaccggaactgaggac<br>agtgacctcaaataagtttatgtatgatcctagccctgtatcggaggg<br>agactttgcgagacttgacttagctatcttcaagagttatgagcttaa<br>tctggagtcatatcccacgatagagctaatgaacattctttcaatatc<br>cagcgggaagttgattggccagtctgtggtttcttatgatgaagatac<br>ctccataaagaatgacgccataatagtgtatgacaatacccgaaattg<br>gatcagtgaagctcagaattcagatgtggtccgcctatttgaatatgc<br>agcacttgaagtgctcctcgactgttcttaccaactctattacctgag<br>agtaagaggcctGgacaatattgtcttatatatgggtgatttatacaa<br>gaatatgccaggaattctactttccaacattgcagctacaatatctca<br>tcccgtcattcattcaaggttacatgcagtgggcctggtcaaccatga<br>cggatcacaccaacttgcagatacggattttatcgaaatgtctgcaaa<br>actattagtatcttgcacccgacgtgtgatctccggcttatattcagg<br>aaataagtatgatctgctgttcccatctgtcttagatgataacctgaa<br>tgagaagatgcttcagctgatatcccggttatgctgtctgtacacggt<br>actctttgctacaacaagagaaatcccgaaaataagaggcttaactgc<br>agaagagaaatgttcaatactcactgagtatttactgtcggatgctgt<br>gaaaccattacttagccccgatcaagtgagctctatcatgtctcctaa<br>cataattacattcccagctaatctgtactacatgtctcggaagagcct<br>caatttgatcagggaaagggaggacagggatactatcctggcgttgtt<br>gttcccccaagagccattattagagttcccttctgtgcaagatattgg<br>tgctcgagtgaaagatccattcacccgacaacctgcggcatttttgca<br>agagttagatttgagtgctccagcaaggtatgacgcattcacacttag<br>tcagattcatcctgaactcacatctccaaatccggaggaagactactt<br>agtacgatacttgttcagagggatagggactgcatcttcctcttggta<br>taaggcatctcatctcctttctgtacccgaggtaagatgtgcaagaca<br>cgggaactccttatacttagctgaagggagcggagccatcatgagtct<br>tctcgaactgcatgtaccacatgaaactatctattacaatacgctctt<br>ttcaaatgagatgaacccccgcaacgacatttcggccgaccccaac<br>tcagtttttgaattcggttgtttataggaatctacaggcggaggtaac<br>atgcaaagatggatttgtccaagagttccgtccattatggagagaaaa<br>tacagaggaaagCgacctgacctcagataaagTagtggggtatattac<br>atctgcagtgccctacagatctgtatcattgctgcattgtgacattga<br>aattcctccagggtccaatcaaagcttactagatcaactagctatcaa<br>tttatctctgattgccatgcattctgtaagggagggcggggtagtaat<br>catcaaagtgttgtatgcaatgggatactactttcatctactcatgaa<br>cttgtttgctccgtgttccacaaaaggatatattctctctaatggtta<br>tgcatgtcgaggagatatggagtgttacctggtatttgtcatgggtta<br>cctgggcgggcctacatttgtacatgaggtggtgaggatggcGaaaac<br>tctggtgcagcggcacggtacgctTttgtctaaatcagatgagatcac<br>actgaccaggttattcacctcacagcggcagcgtgtgacagacatcct<br>atccagtcctttaccaagattaataaagtacttgaggaagaatattga<br>cactgcgctgattgaagccgggggacagcccgtccgtccattctgtgc<br>ggagagtctggtgagcacgctagcgaacataactcagataacccagat | |

TABLE 1-continued

| Human RSV F Sequences | | |
|---|---|---|
| Description | Sequence | SEQ ID NO. |
| | Catcgctagtcacattgacacagttatccggtctgtgatatatatgga<br>agctgagggtgatctcgctgacacagtatttctatttaccccttacaa<br>tctctctactgacgggaaaaagaggacatcacttaAacagtgcacgag<br>acagatcctagaggttacaatactaggtcttagagtcgaaaatctcaa<br>taaaataggcgatataatcagcctagtgcttaaaggcatgatctccat<br>ggaggaccttatcccactaaggacatacttgaagcatagtacctgccc<br>taaatatttgaaggctgtcctaggtattaccaaactcaaagaaatgtt<br>tacagacacttctgtaCtgtacttgactcgtgctcaacaaaaattcta<br>catgaaaactataggcaatgcagtcaaaggatattacagtaactgtga<br>ctcttaacgaaaatcacatattaataggctcctttttttggccaattgt<br>attcttgttgatttaatcatattatgttagaaaaaagttgaaccctga<br>ctccttaggactcgaattcgaactcaaataaatgtcttaaaaaaaggt<br>tgcgcacaattattcttgagtgtagtctcgtcattcaccaaatctttg<br>tttggt | |
| Nucleic acid sequence of chimeric F sequence, wherein the chimeric F protein comprises the human RSV F protein ectodomain of the RSV A2 strain fused to the transmembrane and cytoplasmic domains of the NDV LaSota strain. The nucleic acid sequence encoding the ectodomain of the human RSV F protein of the RSV A2 strain is codon-optimized. (The transmembrane and cytoplasmic domains of NDV F are underlined.) | ATGGAGCTGCTGATCCTGAAGGCCAACGCCATCACCAC<br>CATCCTGACCGCCGTGACCTTCTGCTTCGCCAGCGGCCA<br>GAACATCACCGAGGAGTTCTACCAGAGCACCTGCAGCG<br>CCGTGAGCAAGGGCTACCTGAGCGCCCTGCGCACCGGC<br>TGGTACACCAGCGTGATCACCATCGAGCTGAGCAACAT<br>CAAGGAGAACAAGTGCAACGGCACCGACGCCAAGGTG<br>AAGCTGATCAAGCAGGAGCTGGACAAGTACAAGAACG<br>CCGTGACCGAGCTGCAGCTGCTGATGCAGAGCACCCCC<br>GCCACCAACAACCGCGCCCGCCGCGAGCTGCCCCGCTT<br>CATGAACTACACCCTGAACAACGCCAAGAAGACCAACG<br>TGACCCTGAGCAAGAAGCGCAAGCGCCGCTTCCTGGGC<br>TTCCTGCTGGGCGTGGGCAGCGCCATCGCCAGCGGCGT<br>GGCCGTGAGCAAGGTGCTGCACCTGGAGGGCGAGGTGA<br>ACAAGATCAAGAGCGCCCTGCTGAGCACCAACAAGGCC<br>GTGGTGAGCCTGAGCAACGGCGTGAGCGTGCTGACCAG<br>CAAGGTGCTGGACCTGAAGAACTACATCGACAAGCAGC<br>TGCTGCCCATCGTGAACAAGCAGAGCTGCAGCATCAGC<br>AACATCGCCACCGTGATCGAGTTCCAGCAGAAGAACAA<br>CCGCCTGCTGGAGATCACCCGCGAGTTCAGCGTGAACG<br>CCGGCGTGACCACCCCCGTGAGCACCTACATGCTGACC<br>AACAGCGAGCTGCTGAGCCTGATCAACGACATGCCCAT<br>CACCAACGACCAGAAGAAGCTGATGAGCAACAACGTG<br>CAGATCGTGCGCCAGCAGAGCTACAGCATCATGAGCAT<br>CATCAAGGAGGAGGTGCTGGCCTACGTGGTGCAGCTGC<br>CCCTGTACGGCGTGATCGACACCCCCTGCTGGAAGCTG<br>CACACCAGCCCCCTGTGCACCACCAACACCAAGGAGGG<br>CAGCAACATCTGCCTGACCCGCACCGACAGGGGCTGGT<br>ACTGCGACAACGCCGGCAGCGTGAGCTTCTTCCCCCAG<br>GCCGAGACCTGCAAGGTGCAGAGCAACCGCGTGTTCTG<br>CGACACCATGAACAGCCTGACCCTGCCCAGCGAGGTGA<br>ACCTGTGCAACGTGGACATCTTCAACCCCAAGTACGAC<br>TGCAAGATCATGACCAGCAAGACCGACGTGAGCAGCAG<br>CGTGATCACCAGCCTGGGCGCCATCGTGAGCTGCTACG<br>GCAAGACCAAGTGCACCGCCAGCAACAAGAACAGGGG<br>CATCATCAAGACCTTCAGCAACGGCTGCGACTACGTGA<br>GCAACAAGGGCGTGGACACCGTGAGCGTGGGCAACAC<br>CCTGTACTACGTGAACAAGCAGGAGGGCAAGAGCCTGT<br>ACGTGAAGGGCGAGCCCATCATCAACTTCTACGACCCC<br>CTGGTGTTCCCCAGCGACGAGTTCGACGCCAGCATCAG<br>CCAGGTGAACGAGAAGATCAACCAGAGCCTGGCCTTCA<br>TCCGCAAGAGCGACGAGCTGCTGCACAACGTGAACGCC<br>GGCAAGAGCACCATCAACGTTAACCTCATTACCTATAT<br>CGTTTTGACTATCATATCTCTTGTTTTTGGTATACTTAGC<br>CTGATTCTAGCATGCTACCTAATGTACAAGCAAAAGGC<br>GCAACAAAAGACCTTATTATGGCTTGGGAATAATACCC<br>TAGATCAGATGAGAGCCACTACAAAAATGTGA | 4 |
| cDNA of genomic sequence of the NDV strain LaSota genome with the chimeric F sequence (SEQ ID NO:4) inserted (The Sac II (CCGCGG) restriction sites used to insert the | accaaacagagaatccgtgagttacgataaaaggcgaaggagca<br>attgaagtcgcacgggtagaaggtgtgaatctcgagtgcgagcc<br>cgaagcacaaactcgagaaagccttctgccaacatgtcttccgt<br>atttgatgagtacgaacagctcctcgcggctcagactcgcccca<br>atggagctcatggagggggagaaaaagggagtaccttaaaagta<br>gacgtcccggtattcactcttaacagtgatgacccagaagatag<br>atggagctttgtggtattctgcctccggattgctgttagcgaag<br>atgccaacaaaccactcaggcaaggtgctctcatatctcttta<br>tgctcccactcacaggtaatgaggaaccatgttgccCttgcagg<br>gaaacagaatgaagccacattggccgtgcttgagattgatggct<br>ttgccaacggcacgccccagttcaacaataggagtggagtgtct<br>gaagagagagcacagagatttgcgatgatagcaggatctctccc<br>tcgggcatgcagcaacggaaccccgttcgtcacagccggggcCg | 5 |

TABLE 1-continued

Human RSV F Sequences

| Description | Sequence | SEQ ID NO. |
|---|---|---|
| chimeric F open reading frame into the genomic sequence are shown by double underlining. The initiation and stop codons of the chimeric F open reading frame are underlined. The sequence coding for the RSV-F ectodomain is in bold. The sequence coding the transmembrane and cytoplasmic domains of the NDV F protein is in italics.) | aagatgatgcaccagaagacatcaccgataccctggagaggatc<br>ctctctatccaggctcaagtatgggtcacagtagcaaaagccat<br>gactgcgtatgagactgcagatgagtcggaaacaaggcgaatca<br>ataagtatatgcagcaaggcagggtccaaaagaaatacatcctc<br>taccccgtatgcaggagcacaatccaactcacgatcagacagtc<br>tcttgcagtccgcatctttttggttagcgagctcaagagaggcc<br>gcaacacggcaggtggtacctctacttattataacctggtaggg<br>gacgtagactcatacatcaggaataccgggcttactgcattctt<br>cttgacactcaagtacggaatcaacaccaagacatcagcccttg<br>cacttagtagcctctcaggcgacatccagaagatgaagcagctc<br>atgcgtttgtatcggatgaaaggagataatgcgccgtacatgac<br>attacttggtgatagtgaccagatgagctttgcgcctgccgagt<br>atgcacaactttactcctttgccatgggtatggcatcagtccta<br>gataaaggtactgggaaataccaatttgccagggactttatgag<br>cacatcattctggagacttggagtagagtacgctcaggctcagg<br>gaagtagcattaacgaggatatggctgccgagctaaagctaacc<br>ccagcagcaaGgaGgggcctggcagctgctgcccaacgggtctc<br>cgaGgaGaccagcagcataGacatgcctactcaacaagtcggag<br>tcctcactgggcttagcgagggggggtcccaagctctacaaggc<br>ggatcgaatagatcgcaagggcaaccagaagccggggatgggga<br>gacccaattcctggatctgatgagagcggtagcaaatagcatga<br>gggaggcgccaaactctgcacagggcactccccaatcggggcct<br>cccccaactcctgggccatcccaagataacgacaccgactgggg<br>gtattgatggacaaaacccagcctgcttccacaaaaacatccca<br>atgccctcacccgtagtcgacccctcgatttgcggctctatatg<br>accacaccctcaaacaaacatccccctctttcctccctcccccct<br>gctgtacaactAcgTacgccctagataccacaggcacaatgcgg<br>ctcactaacaatcaaaacagagccgagggaattagaaaaaagta<br>cgggtagaagagggatattcagagatcagggcaagtctcccgag<br>tctctgctctctcctctacctgatagaccaggacaaacatggcc<br>acctttacagatgcagagatcgacgagctatttgagacaagtgg<br>aactgtcattgacaacataattacagcccagggtaaaccagcag<br>agactgttggaaggagtgcaatcccacaaggcaagaccaaggtg<br>ctgagcgcagcatgggagaagcatgggagcatccagccaccggc<br>cagtcaagacaaccccgatcgacaggacagatctgacaaacaac<br>catccacacccgagcaaacgaccccgcatgacagcccgccggcc<br>acatccgccgaccagcccccccacccaggccacagacgaagccgt<br>cgacacacagCtcaggaccggagcaagcaactctctgctgttga<br>tgcttgacaagctcagcaataaatcgtccaatgctaaaaagggc<br>ccatggtcgagcccccaagaggggaatcaccaacgtccgactca<br>acagcaggggagtcaacccagtcgcggaaacagtcaggaaagac<br>cgcagaaccaagtcaaggccgcccctggaaaccagggcacagac<br>gtgaacacagcatatcatggacaatgggaggagtcacaactatc<br>agctggtgcaacccctcatgctctccgatcaaggcagagccaag<br>acaatacccttgtatctgcggatcatgtccagccacctgtagac<br>tttgtgcaagcgatgatgtctatgatggaggcgatatcacagag<br>agtaagtaaggttgactatcagctagatcttgtcttgaaacaga<br>catcctccatccctatgatgcggtccgaaatccaacagctgaaa<br>acatctgttgcagtcatggaagccaacttgggaatgatgaagat<br>tctggatcccggttgtgccaacatttcatctctgagtgatctac<br>gggcagttgcccgatctcacccggttttagtttcaggccctgga<br>gacccctctccctatgtgacacaaggaggcgaaatggcacttaa<br>taaactttcgcaaccagtgccacatccatctgaattgattaaac<br>ccgccactgcatgcgggcctgatataggagtggaaaaggacact<br>gtccgtgcattgatcatgtcacgcccaatgcacccgagttcttc<br>agccaagctcctaagcaagttagatgcagccgggtcgatcgagg<br>aaatcaggaaaatcaagcgccttgctctaaatggctaattacta<br>ctgccacacgtagcgggtccctgtccactcggcatcacacggaa<br>tctgcaccgagttcccccccgcGgacccaaggtccaactctcca<br>agcggcaatcctctctcgcttcctcagccccactgaatgAtcgc<br>gtaaccgtaattaatctagctacatttaagattaagaaaaaata<br>cgggtagaattggagtgccccaCtAgtgccaCC**ATGGAGCTGCT**<br>**GATCCTGAAGGCCAACGCCATCACCACCATCCTGACCGCCGTGA**<br>**CCTTCTGCTTCGCCAGCGGCCAGAACATCACCGAGGAGTTCTAC**<br>**CAGAGCACCTGCAGCGCCGTGAGCAAGGGCTACCTGAGCGCCCT**<br>**GCGCACCGGCTGGTACACCAGCGTGATCACCATCGAGCTGAGCA**<br>**ACATCAAGGAGAACAAGTGCAACGGCACCGACGCCAAGGTGAAG**<br>**CTGATCAAGCAGGAGCTGGACAAGTACAAGAACGCCGTGACCGA**<br>**GCTGCAGCTGCTGATGCAGAGCACCCCCGCCACCAACAACCGCG**<br>**CCCGCCGCGAGCTGCCCCGCTTCATGAACTACACCCTGAACAAC**<br>**GCCAAGAAGACCAACGTGACCCTGAGCAAGAAGCGCAAGCGCCG**<br>**CTTCCTGGGCTTCCTGCTGGGCGTGGGCAGCGCCATCGCCAGCG**<br>**GCGTGGCCGTGAGCAAGGTGCTGCACCTGGAGGGCGAGGTGAAC**<br>**AAGATCAAGAGCGCCCTGCTGAGCACCAACAAGGCCGTGGTGAG**<br>**CCTGAGCAACGGCGTGAGCGTGCTGACCAGCAAGGTGCTGGACC** | |

TABLE 1-continued

| Description | Sequence | SEQ ID NO. |
|---|---|---|
| | Human RSV F Sequences | |
| | **TGAAGAACTACATCGACAAGCAGCTGCTGCCCATCGTGAACAAG**<br>**CAGAGCTGCAGCATCAGCAACATCGCCACCGTGATCGAGTTCCA**<br>**GCAGAAGAACAACCGCCTGCTGGAGATCACCCGCGAGTTCAGCG**<br>**TGAACGCCGGCGTGACCACCCCCGTGAGCACCTACATGCTGACC**<br>**AACAGCGAGCTGCTGAGCCTGATCAACGACATGCCCATCACCAA**<br>**CGACCAGAAGAAGCTGATGAGCAACAACGTGCAGATCGTGCGCC**<br>**AGCAGAGCTACAGCATCATGAGCATCATCAAGGAGGAGGTGCTG**<br>**GCCTACGTGGTGCAGCTGCCCCTGTACGGCGTGATCGACACCCC**<br>**CTGCTGGAAGCTGCACACCAGCCCCCTGTGCACCACCAACACCA**<br>**AGGAGGGCAGCAACATCTGCCTGACCCGCACCGACaGgGGCTGG**<br>**TACTGCGACAACGCCGGCAGCGTGAGCTTCTTCCCCCAGGCCGA**<br>**GACCTGCAAGGTGCAGAGCAACCGCGTGTTCTGCGACACCATGA**<br>**ACAGCCTGACCCTGCCCAGCGAGGTGAACCTGTGCAACGTGGAC**<br>**ATCTTCAACCCCAAGTACGACTGCAAGATCATGACCAGCAAGAC**<br>**CGACGTGAGCAGCAGCGTGATCACCAGCCTGGGCGCCATCGTGA**<br>**GCTGCTACGGCAAGACCAAGTGCACCGCCAGCAACAAGAACaGg**<br>**GGCATCATCAAGACCTTCAGCAACGGCTGCGACTACGTGAGCAA**<br>**CAAGGGCGTGGACACCGTGAGCGTGGGCAACACCCTGTACTACG**<br>**TGAACAAGCAGGAGGGCAAGAGCCTGTACGTGAAGGGCGAGCCC**<br>**ATCATCAACTTCTACGACCCCCTGGTGTTCCCCAGCGACGAGTT**<br>**CGACGCCAGCATCAGCCAGGTGAACGAGAAGATCAACCAGAGCC**<br>**TGGCCTTCATCCGCAAGAGCGACGAGCTGCTGCACAACGTGAAC**<br>**GCCGGCAAGAGCACCATCAAC***GTTAACCTCATTACCTATATCGT*<br>*TTTGACTATCATATCTCTTGTTTTTGGTATACTTAGCCTGATTC*<br>*TAGCATGCTACCTAATGTACAAGCAAAAGGCGCAACAAAAGACC*<br>*TTATTATGGCTTGGGAATAATACCCTAGATCAGATGAGAGCCAC*<br>*TACAAAAATGTGA*ccgcggacccaaggtccaactctccaagcgg<br>caatcctctctcgcttcctcagccccactgaatgAtcgcgtaac<br>cgtaattaatctagctacatttaagattaagaaaaaatacgggt<br>agaattggagtgccccaattgtgccaagatggactcatctagga<br>caattgggctgtactttgattctgcccattcttctagcaacctg<br>ttagcatttccgatcgtcctacaagAcacaggagatgggaagaa<br>gcaaatcgccccgcaatataggatccagcgccttgacttgtgga<br>ctgatagtaaggaggactcagtattcatcaccacctatggattc<br>atctttcaagttgggaatgaagaagccacCgtcggcatgatcga<br>tgataaacccaagcgcgagttactttccgctgcgatgctctgcc<br>taggaagcgtcccaaataccggagaccttattgagctggcaagg<br>gcctgtctcactatgatagtcacatgcaagaagagtgcaactaa<br>tactgagagaatggttttctcagtagtgcaggcaccccaagtgc<br>tgcaaagctgtagggttgtggcaaacaaatactcatcagtgaat<br>gcagtcaagcacgtgaaagcgccagagaagattcccgggagtgg<br>aaccctagaatacaaggtgaactttgtctccttgactgtggtac<br>cgaagaGggatgtctacaagatcccagctgcagtattgaaggtt<br>tctggctcgagtctgtacaatcttgcgctcaatgtcactattaa<br>tgtggaggtagacccgaggagtcctttggttaaatctCtgtcta<br>agtctgacagcggatactatgctaacctcttcttgcatattgga<br>cttatgaccacTgtagataggaaggggaagaaagtgacatttga<br>caagctggaaaagaaaataaggagccttgatctatctgtcgggc<br>tcagtgatgtgctcgggccttccgtgttggtaaaagcaagaggt<br>gcacggactaagcttttggcacctttcttctctagcagtgggac<br>agcctgctatcccatagcaaatgcttctcctcaggtggccaaga<br>tactctggagtcaaaccgcgtgcctgcggagcgttaaaatcatt<br>atccaagcaggtacccaacgcgctgtcgcagtgaccgccgacca<br>cgaggttacctctactaagctggagaaggggcacacccttgcca<br>aatacaatccttttaagaaataagctgcgtctctgagattgcgc<br>tccgcccactcacccagatcatcatgacacaaaaaactaatctg<br>tcttgattatttacagttagtttacctgtctatcaagttagaaa<br>aaacacgggtagaagattctggatcccggttggcgccctccagg<br>tgcaagatgggctccagaccttctaccaagaacccagcacctat<br>gatgctgactatccgggttgcgctggtactgagttgcatctgtc<br>cggcaaactccattgatggcaggcctcttgcagctgcaggaatt<br>gtggttacaggagacaaagccgtcaacatatacacctcatccca<br>gacaggatcaatcatagttaagctcctcccgaatctgcccaagg<br>ataaggaggcatgtgcgaaagccccccttggatgcatacaacagg<br>acattgaccactttgctcacccccccttggtgactctatccgtag<br>gatacaagagtctgtgactacatctggagggggggagacaggggc<br>gccttataggcgccattattggcggtgtggctcttggggttgca<br>actgccgcacaaataacagcggccgcagctctgatacaagccaa<br>acaaaatgctgccaacatcctccgacttaaagagagcattgccg<br>caaccaatgaggctgtgcatgaggtcactgacggattatcgcaa<br>ctagcagtggcagttgggaagatgcagcagtttgttaatgacca<br>atttaataaaacagctcaggaattagactgcatcaaaattgcac<br>agcaagttggtgtagagctcaacctgtacctaaccgaattgact<br>acagtattcggaccacaaatcacttcacctgctttaaacaagct<br>gactattcaggcactttacaatctagctggtggaaatatggatt | |

TABLE 1-continued

| Human RSV F Sequences | | |
|---|---|---|
| Description | Sequence | SEQ ID NO. |
| | acttattgactaagttaggtgtagggaacaatcaactcagctca<br>ttaatcggtagcggcttaatcaccggtaaccctattctatacga<br>ctcacagactcaactcttgggtatacaggtaactctaccttcag<br>tcgggaacctaaataatatgcgtgccacctacttggaaacctta<br>tccgtaagcacaaccaggggatttgcctcggcacttgtcccAaa<br>agtggtgacacaggtcggttctgtgatagaagaacttgacacct<br>catactgtatagaaactgacttagatttatattgtacaagaata<br>gtaacgttccctatgtcccctggtatttattcctgcttgagcgg<br>caatacgtcggcctgtatgtactcaaagaccgaaggcgcactta<br>ctacaccatacatgactatcaaaggttcagtcatcgccaactgc<br>aagatgacaacatgtagatgtgtaaaccccccgggtatcatatc<br>gcaaaactatggagaagccgtgtctctaatagataaacaatcat<br>gcaatgttttatccttaggcgggataactttaaggctcagtggg<br>gaattcgatgtaacttatcagaagaatatctcaatacaagattc<br>tcaagtaataataacaggcaatcttgatatctcaactgagcttg<br>ggaatgtcaacaactcgatcagtaatgctttgaataagttagag<br>gaaagcaacagaaaactagacaaagtcaatgtcaaactgactag<br>cacatctgctctcattacctatatcgttttgactatcatatctc<br>ttgtttttggtatacttagcctgattctagcatgctacctaatg<br>tacaagcaaaaggcgcaacaaaagaccttattatggcttgggaa<br>taatactctagatcagatgagagccactacaaaaatgtgaacac<br>agatgaggaacgaaggtttccctaatagtaatttgtgtgaaagt<br>tctggtagtctgtcagttcagagagttaagaaaaaactaccggt<br>tgtagatgaccaaaggacgatatacgggtagaacggtaagagag<br>gccgcccctcaattgcgagccaggcttcacaacctccgttctac<br>cgcttcaccgacaacagtcctcaatcatggaccgcgccgttagc<br>caagttgcgttagagaatgatgaaagagaggcaaaaaatacatg<br>gcgcttgatattccggattgcaatcttattcttaacagtagtga<br>ccttggctatatctgtagcctcccttttatatagcatggggggct<br>agcacacctagcgatcttgtaggcataccgactaggatttccag<br>ggcagaagaaaagattacatctacacttggttccaatcaagatg<br>tagtagataggatatataagcaagtggcccttgagtctccgttg<br>gcattgttaaatactgagaccacaattatgaacgcaataacatc<br>tctctcttatcagattaatggagctgcaaacaacagtgggtggg<br>gggcacctatccatgacccagattatataggggggataggcaaa<br>gaactcattgtagatgatgctagtgatgtcacatcattctatcc<br>ctctgcatttcaagaacatctgaattttatcccggcgcctacta<br>caggatcaggttgcactcgaataccctcatttgacatgagtgct<br>acccattactgctacacccataatgtaatattgtctggatgcag<br>agatcactcacattcatatcagtatttagcacttggtgtgctcc<br>ggacatctgcaacagggagggtattcttttctactctgcgttcc<br>atcaacctggacgacacccaaaatcggaagtcttgcagtgtgag<br>tgcaactcccctgggttgtgatatgctgtgctcgaaagtcacgg<br>agacagaggaagaagattataactcagctgtccctacgcggatg<br>gtacatgggaggttagggttcgacggccagtaccacgaaaagga<br>cctagatgtcacaacattattcggggactgggtggccaactacc<br>caggagtaggggggtggatcttttattgacagccgcgtatggttc<br>tcagtctacggagggttaaaacccaattcacccagtgacactgt<br>acaggaagggaaatatgtgatatacaagcgatacaatgacacat<br>gcccagatgagcaagactaccagattcgaatggccaagtcttcg<br>tataagcctggacggtttggtgggaaacgcatacagcaggctat<br>cttatctatcaaggtgtcaacatccttaggcgaagacccggtac<br>tgactgtaccgcccaacacagtcacactcatgggggccgaaggc<br>agaattctcacagtagggacatctcatttcttgtatcaacgagg<br>gtcatcatacttctctcccgcgttattatatcctatgacagtca<br>gcaacaaaacagccactcttcatagtccttatacattcaatgcc<br>ttcactcggccaggtagtatcccttgccaggcttcagcaagatg<br>ccccaactcgtgtgttactggagtctatacagatccatatcccc<br>taatcttctatagaaaccacaccttgcgaggggtattcgggaca<br>atgcttgatggtgtacaagcaagacttaaccctgcgtctgcagt<br>attcgatagcacatcccgcagtcgcattactcgagtgagttcaa<br>gcagtaccaaagcagcatacacaacatcaacttgttttaaagtg<br>gtcaagactaataagacctattgtctcagcattgctgaaatatc<br>taatactctcttcggagaattcagaatcgtcccgttactagttg<br>agatcctcaaagatgacggggttagagaagccaggtctggctag<br>ttgagtcaattataaaggagttggaaagatggcattgtatcacc<br>tatcttctgcgacatcaagaatcaaaccgaatgccggcgcgtgc<br>tcgaattccatgttgccagttgaccacaatcagccagtgctcat<br>gcgatcagattaagccttgtcaAtaGtctcttgattaagaaaaa<br>atgtaagtggcaatgagatacaaggcaaaacagctcatggtTaa<br>Caatacgggtaggacatggcgagctccggtcctgaaagggcaga<br>gcatcagattatcctaccagagTcacacctgtcttcaccattgg<br>tcaagcacaaactactctattactggaaattaactgggctaccg<br>cttcctgatgaatgtgacttcgaccacctcattctcagccgaca<br>atggaaaaaaatacttgaatcggcctctcctgatactgagagaa | |

TABLE 1-continued

Human RSV F Sequences

| Description | Sequence | SEQ ID NO. |
|---|---|---|
| | tgataaaactcggaagggcagtacaccaaactcttaaccacaat | |
| | tccagaataaccggagtgctccaccccaggtgtttagaaGaact | |
| | ggctaatattgaggtcccagattcaaccaacaaatttcggaaga | |
| | ttgagaagaagatccaaattcacaacacgagatatggagaactg | |
| | ttcacaaggctgtgtacgcatatagagaagaaactgctggggtc | |
| | atcttggtctaacaatgtcccccggtcagaggagttcagcagca | |
| | ttcgtacggatccggcattctggtttcactcaaaatggtccaca | |
| | gccaagtttgcatggctccatataaaacagatccagaggcatct | |
| | gatggtggcagctaGgacaaggtctgcggccaacaaattggtga | |
| | tgctaacccataaggtaggccaagtctttgtcactcctgaactt | |
| | gtcgttgtgacgcatacgaatgagaacaagttcacatgtcttac | |
| | ccaggaacttgtattgatgtatgcagatatgatggagggcagag | |
| | atatggtcaacataatatcaaccacggcggtgcatctcagaagc | |
| | ttatcagagaaaattgatgacattttgcggttaatagacgctct | |
| | ggcaaaagacttgggtaatcaagtctacgatgttgtatcactaa | |
| | tggagggatttgcatacggagctgtccagctactcgagccgtca | |
| | ggtacatttgcaggagatttcttcgcattcaacctgcaggagct | |
| | taaagacattctaattggcctcctccccaatgatatagcagaat | |
| | ccgtgactcatgcaatcgctactgtattctctggtttagaacag | |
| | aatcaagcagctgagatgttgtgtctgttgcgtctgtggggtca | |
| | cccactgcttgagtcccgtattgcagcaaaggcagtcaggagcc | |
| | aaatgtgcgcaccgaaaatggtagactttgatatgatccttcag | |
| | gtactgtctttcttcaagggaacaatcatcaacgggtacagaaa | |
| | gaagaatgcaggtgtgtggccgcgagtcaaagtggatacaatat | |
| | atgggaaggtcattgggcaactacatgcagattcagcagagatt | |
| | tcacacgatatcatgttgagagagtataagagtttatctgcact | |
| | tgaatttgagccatgtatagaatatgaccctgtcaccaacctga | |
| | gcatgttcctaaaagacaaggcaatcgcacaccccaacgataat | |
| | tggcttgcctcgtttaggcggaaccttctctccgaagaccagaa | |
| | gaaacatgtaaaagaagcaacttcgactaatcgcctcttgatag | |
| | agtttttagagtcaaatgattttgatccatataaagagatggaa | |
| | tatctgacgacccttgagtaccttagagatgacaatgtggcagt | |
| | atcatactcgctcaaggagaaggaagtgaaagttaatggacgga | |
| | tcttcgctaagctgacaaagaagttaaggaactgtcaggtgatg | |
| | gcggaagggatcctagccgatcagattgcacctttctttcaggg | |
| | aaatggagtcattcaggatagcatatccttgaccaagagtatgc | |
| | tagcgatgagtcaactgtcttttaacagcaataagaaacgtatc | |
| | actgactgtaaagaaagagtatcttcaaaccgcaatcatgatcc | |
| | gaaaagcaagaaccgtcggagagttgcaaccttcataacaactg | |
| | acctgcaaaagtactgtcttaattggagatatcagacaatcaaa | |
| | ttgttcgctcatgccatcaatcagttgatgggcctacctcactt | |
| | cttcgaatggattcacctaagactgatggacactacgatgttcg | |
| | taggagaccctttcaatcctccaagtgaccctactgactgtgac | |
| | ctctcaagagtccctaatgatgacatatatattgtcagtgccag | |
| | agggggtatcgaaggattatgccagaagctatggacaatgatct | |
| | caattgctgcaatccaacttgctgcagctagatcgcattgtcgt | |
| | gttgcctgtatggtacagggtgataatcaagtaatagcagtaac | |
| | gagagaggtaagatcagacgactctccggagatggtgttgacac | |
| | agttgcatcaagccagtgataatttcttcaaggaattaattcat | |
| | gtcaatcatttgattggccataatttgaaggatcgtgaaaccat | |
| | caggtcagacacattcttcatatacagcaaacgaatcttcaaag | |
| | atggagcaatcctcagtcaagtcctcaaaaattcatctaaatta | |
| | gtgctagtgtcaggtgatctcagtgaaaacaccgtaatgtcctg | |
| | tgccaacattgcctctactgtagcacggctatgcgagaacgggc | |
| | ttcccaaagacttctgttactatttaaactatataatgagttgt | |
| | gtgcagacatactttgactctgagttctccatcaccaacaattc | |
| | gcaccccgatcttaatcagtcgtggattgaggacatctcttttg | |
| | tgcactcatatgttctgactcctgcccaattaggggactgagt | |
| | aaccttcaatactcaaggctctacactagaaatatcggtgaccc | |
| | ggggactactgcttttgcagagatcaagcgactagaagcagtgg | |
| | gattactgagtcctaacattatgactaatatcttaactaggccg | |
| | cctgggaatggagattgggccagtctgtgcaacgacccatactc | |
| | tttcaattttgagactgttgcaagcccaaatattgttcttaaga | |
| | aacatacgcaaagagtcctatttgaaacttgttcaaatccctta | |
| | ttgtctggagtgcacacagaggataatgaggcagaagagaaggc | |
| | attggctgaattcttgcttaatcaagaggtgattcatccccgcg | |
| | ttgcgcatgccatcatggaggcaagctctgtaggtaggagaaag | |
| | caaattcaagggcttgttgacacaacaaacaccgtaattaagat | |
| | tgcgcttactaggaggccattaggcatcaagaggctgatgcgga | |
| | tagtcaattattctagcatgcatgcaatgctgtttagagacgat | |
| | gtttttttcctccagtagatccaaccaccccttagtctcttctaa | |
| | tatgtgttctctgacactggcagactatgcacggaatagaagct | |
| | ggtcacctttgacgggaggcaggaaaatactgggtgtatctaat | |
| | cctgatacgatagaactcgtagagggtgagattcttagtgtaag | |
| | cggagggtgtacaagatgtgacagcggagatgaacaatttactt | |

TABLE 1-continued

Human RSV F Sequences

| Description | Sequence | SEQ ID NO. |
|---|---|---|
| | ggttccatcttccaagcaatatagaattgaccgatgacaccagc<br>aagaatcctccgatgagggtaccatatctcgggtcaaagacaca<br>ggagaggagagctgcctcacttgcaaaaatagctcatatgtcgc<br>cacatgtaaaggctgccctaagggcatcatccgtgttgatctgg<br>gcttatggggataatgaagtaaattggactgctgctcttacgat<br>tgcaaaatctcggtgtaatgtaaacttagagtatcttcggttac<br>tgtcccctttacccacggctgggaatcttcaacatagactagat<br>gatggtataactcagatgacattcaccccctgcatctctctacag<br>gGtgtcaccttacattcacatatccaatgattctcaaaggctgt<br>tcactgaagaaggagtcaaagaggggaatgtggtttaccaacag<br>atcatgctcttgggtttatctctaatcgaatcgatctttccaat<br>gacaacaaccaggacatatgatgagatcacactgcacctacata<br>gtaaatttagttgctgtatcagagaagcacctgttgcggttcct<br>ttcgagctacttggggtggtaccggaactgaggacagtgacctc<br>aaataagtttatgtatgatcctagccctgtatcggagggagact<br>ttgcgagacttgacttagctatcttcaagagttatgagcttaat<br>ctggagtcatatcccacgatagagctaatgaacattctttcaat<br>atccagcgggaagttgattggccagtctgtggtttcttatgatg<br>aagatacctccataaagaatgacgccataatagtgtatgacaat<br>acccgaaattggatcagtgaagctcagaattcagatgtggtccg<br>cctatttgaatatgcagcacttgaagtgctcctcgactgttctt<br>accaactctattacctgagagtaagaggcctGgacaatattgtc<br>ttatatatgggtgatttatacaagaatatgccaggaattctact<br>ttccaacattgcagctacaatatctcatcccgtcattcattcaa<br>ggttacatgcagtgggcctggtcaaccatgacggatcacaccaa<br>cttgcagatacggattttatcgaaatgtctgcaaaactattagt<br>atcttgcacccgacgtgtgatctccggcttatattcaggaaata<br>agtatgatctgctgttcccatctgtcttagatgataacctgaat<br>gagaagatgcttcagctgatatcccggttatgtgtctgtacac<br>ggtactctttgctacaacaagagaaatcccgaaaataagaggct<br>taactgcagaagagaaatgttcaatactcactgagtatttactg<br>tcggatgctgtgaaaccattacttagccccgatcaagtgagctc<br>tatcatgtctcctaacataattacattcccagctaatctgtact<br>acatgtctcggaagagcctcaatttgatcagggaaagggaggac<br>agggatactatcctggcgttgttgttcccccaagagccattatt<br>agagttcccttctgtgcaagatattggtgctcgagtgaaagatc<br>cattcacccgacaacctgcggcattttttgcaagagttagatttg<br>agtgctccagcaaggtatgacgcattcacacttagtcagattca<br>tcctgaactcacatctccaaatccggaggaagactacttagtac<br>gatacttgttcagagggatagggactgcatcttcctcttggtat<br>aaggcatctcatctcctttctgtacccgaggtaagatgtgcaag<br>acacgggaactccttatacttagctgaagggagcggagccatca<br>tgagtcttctcgaactgcatgtaccacatgaaactatctattac<br>aatacgctcttttcaaatgagatgaacccccccgcaacgacattt<br>cgggccgaccccaactcagtttttgaattcggttgtttatagga<br>atctacaggcggaggtaacatgcaaagatggatttgtccaagag<br>ttccgtccattatggagagaaaatacagaggaaagCgacctgac<br>ctcagataaagTagtggggtatattacatctgcagtgccctaca<br>gatctgtatcattgctgcattgtgacattgaaattcctccaggg<br>tccaatcaaagcttactagatcaactagctatcaatttatctct<br>gattgccatgcattctgtaagggagggcggggtagtaatcatca<br>aagtgttgtatgcaatgggatactactttcatctactcatgaac<br>ttgtttgctccgtgttccacaaaaggatatattctctctaatgg<br>ttatgcatgtcgaggagatatggagtgttacctggtatttgtca<br>tgggttacctgggcgggcctacatttgtacatgaggtggtgagg<br>atggcGaaaactctggtgcagcggcacggtacgctTttgtctaa<br>atcagatgagatcacactgaccaggttattcacctcacagcggc<br>agcgtgtgacagacatcctatccagtcctttaccaagattaata<br>aagtacttgaggaagaatattgacactgcgctgattgaagccgg<br>gggacagcccgtccgtccattctgtgcggagagtctggtgagca<br>cgctagcgaacataactcagataacccagatCatcgctagtcac<br>attgacacagttatccggtctgtgatatatatggaagctgaggg<br>tgatctcgctgacacagtatttctatttaccccttacaatctct<br>ctactgacgggaaaaagaggacatcacttaAacagtgcacgaga<br>cagatcctagaggttacaatactaggtcttagagtcgaaaatct<br>caataaaataggcgatataatcagcctagtgcttaaaggcatga<br>tctccatggaggaccttatcccactaaggacatacttgaagcat<br>agtacctgccctaaatatttgaaggctgtcctaggtattaccaa<br>actcaaagaaatgtttacagacacttctgtaCtgtacttgactc<br>gtgctcaacaaaaattctacatgaaaactataggcaatgcagtc<br>aaaggatattacagtaactgtgactcttaacgaaaatcacatat<br>taataggctcctttttttggccaattgtattcttgttgatttaat<br>catattatgttagaaaaaagttgaaccctgactccttaggactc<br>gaattcgaactcaaataaatgtcttaaaaaaaggttgcgcacaa<br>ttattcttgagtgtagtctcgtcattcaccaaatctttttttgg | |

TABLE 1-continued

Human RSV F Sequences

| Description | Sequence | SEQ ID NO. |
|---|---|---|
| | t | |
| Amino acid sequence of human RSV F protein of A2 strain (The transmembrane and cytoplasmic domains of the human RSV F protein are underlined. The amino acid sequence of the RSV F protein encoded by the wild-type nucleic acid sequence for the human RSV F protein (SEQ ID NO: 1) is identical to the amino acid sequence of the human RSV F protein encoded by the codon-optimized nucleic acid sequence for human RSV F protein. (SEQ ID NO: 2)) | MELLILKANAITTILTAVTFCFASGQNITEEFYQSTCSAVSK<br>GYLSALRTGWYTSVITIELSNIKENKCNGTDAKVKLIKQEL<br>DKYKNAVTELQLLMQSTPATNNRARRELPRFMNYTLNNA<br>KKTNVTLSKKRKRRFLGFLLGVGSAIASGVAVSKVLHLEG<br>EVNKIKSALLSTNKAVVSLSNGVSVLTSKVLDLKNYIDKQ<br>LLPIVNKQSCSISNIATVIEFQQKNNRLLEITREFSVNAGVT<br>TPVSTYMLTNSELLSLINDMPITNDQKKLMSNNVQIVRQQ<br>SYSIMSIIKEEVLAYVVQLPLYGVIDTPCWKLHTSPLCTTN<br>TKEGSNICLTRTDRGWYCDNAGSVSFFPQAETCKVQSNRV<br>FCDTMNSLTLPSEVNLCNVDIFNPKYDCKIMTSKTDVSSSV<br>ITSLGAIVSCYGKTKCTASNKNRGIIKTFSNGCDYVSNKGV<br>DTVSVGNTLYYVNKQEGKSLYVKGEPIINFYDPLVFPSDEF<br>DASISQVNEKINQSLAFIRKSDELLHNVNAGKSTINIMITTII<br>IVIIVILLSLIAVGLLLYCKARSTPVTLSKDQLSGINNIAFSN | 6 |
| Amino acid sequence of chimeric F protein encoded by SEQ ID NO: 4 (The transmembrane and cytoplasmic domains are underlined.) | MELLILKANAITTILTAVTFCFASGQNITEEFYQSTCSAVSK<br>GYLSALRTGWYTSVITIELSNIKENKCNGTDAKVKLIKQEL<br>DKYKNAVTELQLLMQSTPATNNRARRELPRFMNYTLNNA<br>KKTNVTLSKKRKRRFLGFLLGVGSAIASGVAVSKVLHLEG<br>EVNKIKSALLSTNKAVVSLSNGVSVLTSKVLDLKNYIDKQ<br>LLPIVNKQSCSISNIATVIEFQQKNNRLLEITREFSVNAGVT<br>TPVSTYMLTNSELLSLINDMPITNDQKKLMSNNVQIVRQQ<br>SYSIMSIIKEEVLAYVVQLPLYGVIDTPCWKLHTSPLCTTN<br>TKEGSNICLTRTDRGWYCDNAGSVSFFPQAETCKVQSNRV<br>FCDTMNSLTLPSEVNLCNVDIFNPKYDCKIMTSKTDVSSSV<br>ITSLGAIVSCYGKTKCTASNKNRGIIKTFSNGCDYVSNKGV<br>DTVSVGNTLYYVNKQEGKSLYVKGEPIINFYDPLVFPSDEF<br>DASISQVNEKINQSLAFIRKSDELLHNVNAGKSTINVNLITY<br>IVLTIISLVFGILSLILACYLMYKQKAQQKTLLWLGNNTLD<br>QMRATTKM | 7 |
| Wild-type nucleic acid sequence encoding human RSV F protein from strain RSVA/Homo sapiens/USA/TH_10656/2014 (transmembrane and cytoplasmic domains are underlined) | ATGGAGTTGCCAATCCTCAAAACAAATGCTATTACCAC<br>AATCCTTGCTGCAGTCACACTCTGTTTTGCTTCCAGTCA<br>AAACATCACTGAAGAATTTTATCAATCAACATGCAGTG<br>CAGTTAGCAAAGGCTATCTTAGTGCTCTAAGAACTGGTT<br>GGTATACTAGTGTTATAACTATAGAATTAAGTAATATCA<br>AGGAAAATAAGTGTAATGGTACAGACGCTAAGGTAAA<br>ATTAATAAAACAAGAATTAGATAAATATAAAAATGCTG<br>TAACAGAATTGCAGTTGCTCATGCAAAGCACACCAGCA<br>GCCAACAGTCGAGCCAGAAGAGAACTACCAAGATTTAT<br>GAATTATACACTCAACAATACCAAAAACACCAATGTAA<br>CATTAAGTAAGAAAAGGAAAAGAAGATTTCTTGGATTT<br>TTGTTAGGTGTTGGATCTGCAATCGCCAGTGGCATTGCC<br>GTATCCAAGGTCCTGCACCTAGAAGGGGAAGTGAACAA<br>AATCAAAAGTGCTCTACTATCCACAAACAAGGCTGTAG<br>TCAGCTTATCTAATGGAGTCAGTGTCTTAACCAGCAAG<br>GTGTTAGACCTCAAAAACTATATAGATAAACAGTTGTT<br>ACCTATTGTTAACAAGCAAAGCTGCAGCATATCAAACA<br>TTGAAACTGTGATAGAGTTCCAACAAAAGAACAACAGA<br>CTACTAGAGATTACCAGAGAATTTAGTGTTAATGCAGG<br>TGTAACTACACCTGTAAGCACTTATATGTTAACTAATAG<br>TGAGTTATTATCATTAATCAATGATATGCCTATAACAAA<br>TGATCAGAAAAAGTTAATGTCCAGCAATGTTCAAATAG<br>TTAGACAGCAAAGTTACTCTATCATGTCAATAATAAAA<br>GAGGAAGTCTTAGCATATGTAGTACAATTACCACTATA | 25 |

TABLE 1-continued

Human RSV F Sequences

| Description | Sequence | SEQ ID NO. |
|---|---|---|
| | TGGTGTAATAGATACTCCTTGTTGGAAACTACACACATC<br>CCCTCTATGTACAACCAACACAAAGGAAGGATCCAACA<br>TCTGCTTAACAAGAACCGACAGAGGATGGTACTGTGAC<br>AATGCAGGATCAGTATCCTTTTTCCCACAAGCTGAAAC<br>ATGTAAAGTTCAATCGAATCGGGTGTTTTGTGACACAAT<br>GAACAGTTTAACATTACCAAGTGAGGTAAATCTCTGCA<br>ACATTGACATATTCAACCCCAAATATGATTGCAAAATT<br>ATGACTTCAAAAACAGATGTAAGCAGCTCCGTTATCAC<br>ATCTCTAGGAGCCATTGTGTCATGCTATGGCAAAACCA<br>AATGTACAGCATCCAATAAAAATCGTGGGATCATAAAG<br>ACATTCTCTAACGGGTGTGATTATGTATCAAATAAGGG<br>GGTGGATACTGTGTCTGTAGGTAATACATTATATTATGT<br>AAATAAGCAAGAAGGCAAAAGTCTCTATGTAAAAGGTG<br>AACCAATAATAAATTTCTATGATCCATTAGTGTTCCCCT<br>CTGATGAATTTGATGCATCAATATCTCAAGTCAATGAG<br>AAAATTAATCAGAGTCTAGCATTTATCCGTAAATCAGA<br>TGAATTATTACATAATGTAAATGCTGGTAAATCCACCAC<br>AAATATCATGATAACTACCATAATTATAGTAATTATAGT<br>AATATTGTTAGCATTAATTGCAGTTGGACTGCTTCTATA<br>CTGCAAGGCCAGAAGCACACCAGTCACATTAAGTAAGG<br>ATCAACTGAGTGGTATAAATAACATTGCATTTAGTAACT<br>GA | |
| Codon optimized nucleic acid sequence encoding human RSV F protein from strain RSVA/Homo sapiens/USA/TH_10656/2014 | ATGGAGCTGCCCATCCTGAAGACCAACGCCATCACCAC<br>CATCCTGGCCGCCGTGACCCTGTGCTTCGCCAGCAGCCA<br>GAACATCACCGAGGAGTTCTACCAGAGCACCTGCAGCG<br>CCGTGAGCAAGGGCTACCTGAGCGCCCTGAGAACCGGC<br>TGGTACACCAGCGTGATCACCATCGAGCTGAGCAACAT<br>CAAGGAGAACAAGTGCAACGGCACCGACGCCAAGGTG<br>AAGCTGATCAAGCAGGAGCTGGACAAGTACAAGAACG<br>CCGTGACCGAGCTGCAGCTGCTGATGCAGAGCACCCCC<br>GCCGCCAACAGCAGAGCCAGAAGAGAGCTGCCCAGATT<br>CATGAACTACACCCTGAACAACACCAAGAACACCAACG<br>TGACCCTGAGCAAGAAGAGAAAGAGAAGATTCCTGGG<br>CTTCCTGCTGGGCGTGGGCAGCGCCATCGCCAGCGGCA<br>TCGCCGTGAGCAAGGTGCTGCACCTGGAGGGCGAGGTG<br>AACAAGATCAAGAGCGCCCTGCTGAGCACCAACAAGGC<br>CGTGGTGAGCCTGAGCAACGGCGTGAGCGTGCTGACCA<br>GCAAGGTGCTGGACCTGAAGAACTACATCGACAAGCAG<br>CTGCTGCCCATCGTGAACAAGCAGAGCTGCAGCATCAG<br>CAACATCGAGACCGTGATCGAGTTCCAGCAGAAGAACA<br>ACAGACTGCTGGAGATCACCAGAGAGTTCAGCGTGAAC<br>GCCGGCGTGACCACCCCCGTGAGCACCTACATGCTGAC<br>CAACAGCGAGCTGCTGAGCCTGATCAACGACATGCCCA<br>TCACCAACGACCAGAAGAAGCTGATGAGCAGCAACGTG<br>CAGATCGTGAGACAGCAGAGCTACAGCATCATGAGCAT<br>CATCAAGGAGGAGGTGCTGGCCTACGTGGTGCAGCTGC<br>CCCTGTACGGCGTGATCGACACCCCCTGCTGGAAGCTG<br>CACACCAGCCCCCTGTGCACCACCAACACCAAGGAGGG<br>CAGCAACATCTGCCTGACCAGAACCGACAGAGGCTGGT<br>ACTGCGACAACGCCGGCAGCGTGAGCTTCTTCCCCCAG<br>GCCGAGACCTGCAAGGTGCAGAGCAACAGAGTGTTCTG<br>CGACACCATGAACAGCCTGACCCTGCCCAGCGAGGTGA<br>ACCTGTGCAACATCGACATCTTCAACCCCAAGTACGAC<br>TGCAAGATCATGACCAGCAAGACCGACGTGAGCAGCAG<br>CGTGATCACCAGCCTGGGCGCCATCGTGAGCTGCTACG<br>GCAAGACCAAGTGCACCGCCAGCAACAAGAACAGAGG<br>CATCATCAAGACCTTCAGCAACGGCTGCGACTACGTGA<br>GCAACAAGGGCGTGGACACCGTGAGCGTGGGCAACAC<br>CCTGTACTACGTGAACAAGCAGGAGGGCAAGAGCCTGT<br>ACGTGAAGGGCGAGCCCATCATCAACTTCTACGACCCC<br>CTGGTGTTCCCCAGCGACGAGTTCGACGCCAGCATCAG<br>CCAGGTGAACGAGAAGATCAACCAGAGCCTGGCCTTCA<br>TCAGAAAGAGCGACGAGCTGCTGCACAACGTGAACGCC<br>GGCAAGAGCACCACCAACATCATGATCACCACCATCAT<br>CATCGTGATCATCGTGATCCTGCTGGCCCTGATCGCCGT<br>GGGCCTGCTGCTGTACTGCAAGGCCAGAAGCACCCCCG<br>TGACCCTGAGCAAGGACCAGCTGAGCGGCATCAACAAC<br>ATCGCCTTCAGCAAC | 26 |
| Amino acid sequence of human RSV F protein from the strain | MELPILKTNAITTILAAVTLCFASSQNITEEFYQSTCSAVSK<br>GYLSALRTGWYTSVITIELSNIKENKCNGTDAKVKLIKQEL<br>DKYKNAVTELQLLMQSTPAANSRARRELPRFMNYTLNNT<br>KNTNVTLSKKRKRRFLGFLLGVGSAIASGIAVSKVLHLEG<br>EVNKIKSALLSTNKAVVSLSNGVSVLTSKVLDLKNYIDKQ | 50 |

TABLE 1-continued

| Human RSV F Sequences | | |
|---|---|---|
| Description | Sequence | SEQ ID NO. |
| RSVA/Homo sapiens/USA/TH_10656/2014 | LLPIVNKQSCSISNIETVIEFQQKNNRLLEITREFSVNAGVTT<br>PVSTYMLTNSELLSLINDMPITNDQKKLMSSNVQIVRQQS<br>YSIMSIIKEEVLAYVVQLPLYGVIDTPCWKLHTSPLCTTNT<br>KEGSNICLTRTDRGWYCDNAGSVSFFPQAETCKVQSNRVF<br>CDTMNSLTLPSEVNLCNIDIFNPKYDCKIMTSKTDVSSSVIT<br>SLGAIVSCYGKTKCTASNKNRGIIKTFSNGCDYVSNKGVD<br>TVSVGNTLYYVNKQEGKSLYVKGEPIINFYDPLVFPSDEFD<br>ASISQVNEKINQSLAFIRKSDELLHNVNAGKSTTNIMITTIII<br>VIIVILLALIAVGLLLYCKARSTPVTLSKDQLSGINNIAFSN | |
| Wild-type nucleic acid sequence encoding human RSV F protein from strain RSVB/Homo sapiens/USA/LA2_82/2013 (transmembrane and cytoplasmic domains are underlined) | ATGGAGTTGCTGATCCATAGATCAAGTGTAATCTTCCTA<br>ACTCTTGCTATTAACGCATTGTACCTCACCTCAAGTCAG<br>AACATAACTGAGGAGTTTTACCAATCGACATGTAGTGC<br>AGTTAGCAGAGGTTACTTTAGTGCTTTAAGAACAGGTT<br>GGTATACTAGTGTCATAACAATAGAATTAAGTAATATA<br>AAAGAAACCAAATGCAATGGAACTGACACTAAAGTAA<br>AACTTATAAAACAAGAATTAGATAAGTATAAGAATGCA<br>GTAACAGAATTACAGTTACTTATGCAAAACATACCAGC<br>TGCCAACAACCGAGCCAGAAGAGAAGCACCACAGTAT<br>ATGAACTACACAATCAATACCACTAAAAACCTAAATGT<br>ATCAATAAGCAAGAAGAGGAAACGAAGATTTCTGGGCT<br>TCTTGTTAGGTGTAGGATCTGCAATAGCAAGTGGCATA<br>GCTGTATCCAAAGTTCTACACCTTGAAGGAGAAGTGAA<br>CAAGATCAAAAATGCTTTGCTGTCTACAAACAAAGCTG<br>TAGTCAGTCTATCAAATGGGGTCAGTGTTTTAACCAGCA<br>AAGTGTTAGATCTCAAGAATTATATAAACAACCAATTA<br>TTACCTATAGTAAATCAACAGAGTTGTCGCATCTCCAAC<br>ATTGAAACAGTTATAGAATTCCAGCAGAAGAACAGCAG<br>ATTGTTGGAAATCACCAGAGAATTTAGTGTCAATGCAG<br>GTGTAACGACACCTTTAAGCACTTACATGTTAACAAAC<br>AGTGAGTTGCTATCATTAATCAATGATATGCCTATAACA<br>AATGATCAGAAGAAATTAATGTCAAGCAATGTTCAGAT<br>AGTAAGGCAACAAAGTTATTCTATCATGTCTATAATAA<br>AGGAAGAAGTCCTCGCATATGTTGTACAGCTACCTATCT<br>ATGGTGTAATAGATACACCTTGCTGGAAATTACACACA<br>TCACCTCTGTGCACCACCAACATCAAGGAAGGTTCAAA<br>TATTTGTTTAACAAGGACTGATAGAGGATGGTACTGTG<br>ATAATGCAGGATCAGTATCCTTCTTTCCACAGGCTGACA<br>CTTGTAAAGTACAGTCCAATCGAGTATTTTGTGACACTA<br>TGAACAGTTTGACATTACCAAGTGAAGTCAGCCTTTGTA<br>ACACTGACATATTCAATTCCAAGTATGATTGCAAAATTA<br>TGACATCAAAAACAGACATAAGCAGCTCAGTAATTACT<br>TCTCTAGGAGCTATAGTGTCATGCTATGGTAAAACTAA<br>ATGCACTGCATCCAACAAAAATCGTGGAATTATAAAGA<br>CATTTTCTAATGGTTGTGATTATGTGTCAAACAAAGGAG<br>TAGATACTGTATCAGTGGGCAACACTTTATACTATGTCA<br>ACAAGCTGGAAGGCAAAAACCTTTATGTAAAAGGGGA<br>ACCTATAATAAATTACTATGACCCTCTAGTGTTTCCTTC<br>TGATGAGTTTGATGCATCAATATCTCAAGTCAATGAAA<br>AAATTAATCAAAGTTTAGCTTTTATTCGTAGATCCGATG<br>AATTATTACATAATGTAAATACTGGAAAATCTACTACA<br>AATATTATGATAACTGTAATTATTATAGTAATCATTGTA<br>GTATTGTTATCATTAATAGCTATTGGTTTACTGTTGTATT<br>GCAAAGCCAAAAACACACCAGTTACACTAAGCAAAGA<br>CCAACTAAGTGGAATCAATAATATTGCATTCAGCAAAT<br>AG | 27 |
| Codon optimized nucleic acid sequence encoding human RSV F protein from strain RSVB/Homo sapiens/USA/LA2_82/2013 | ATGGAGCTGCTGATCCACAGAAGCAGCGTGATCTTCCT<br>GACCCTGGCCATCAACGCCCTGTACCTGACCAGCAGCC<br>AGAACATCACCGAGGAGTTCTACCAGAGCACCTGCAGC<br>GCCGTGAGCAGAGGCTACTTCAGCGCCCTGAGAACCGG<br>CTGGTACACCAGCGTGATCACCATCGAGCTGAGCAACA<br>TCAAGGAGACCAAGTGCAACGGCACCGACACCAAGGT<br>GAAGCTGATCAAGCAGGAGCTGGACAAGTACAAGAAC<br>GCCGTGACCGAGCTGCAGCTGCTGATGCAGAACATCCC<br>CGCCGCCAACAACAGAGCCAGAAGAGAGGCCCCCCAG<br>TACATGAACTACACCATCAACACCACCAAGAACCTGAA<br>CGTGAGCATCAGCAAGAAGAGAAAGAGAAGATTCCTG<br>GGCTTCCTGCTGGGCGTGGGCAGCGCCATCGCCAGCGG<br>CATCGCCGTGAGCAAGGTGCTGCACCTGGAGGGCGAGG<br>TGAACAAGATCAAGAACGCCCTGCTGAGCACCAACAAG<br>GCCGTGGTGAGCCTGAGCAACGGCGTGAGCGTGCTGAC<br>CAGCAAGGTGCTGGACCTGAAGAACTACATCAACAACC<br>AGCTGCTGCCCATCGTGAACCAGCAGAGCTGCAGAATC<br>AGCAACATCGAGACCGTGATCGAGTTCCAGCAGAAGAA | 28 |

TABLE 1-continued

| Human RSV F Sequences | | |
|---|---|---|
| Description | Sequence | SEQ ID NO. |
| | CAGCAGACTGCTGGAGATCACCAGAGAGTTCAGCGTGA<br>ACGCCGGCGTGACCACCCCCCTGAGCACCTACATGCTG<br>ACCAACAGCGAGCTGCTGAGCCTGATCAACGACATGCC<br>CATCACCAACGACCAGAAGAAGCTGATGAGCAGCAAC<br>GTGCAGATCGTGAGACAGCAGAGCTACAGCATCATGAG<br>CATCATCAAGGAGGAGGTGCTGGCCTACGTGGTGCAGC<br>TGCCCATCTACGGCGTGATCGACACCCCCTGCTGGAAG<br>CTGCACACCAGCCCCCTGTGCACCACCAACATCAAGGA<br>GGGCAGCAACATCTGCCTGACCAGAACCGACAGAGGCT<br>GGTACTGCGACAACGCCGGCAGCGTGAGCTTCTTCCCC<br>CAGGCCGACACCTGCAAGGTGCAGAGCAACAGAGTGTT<br>CTGCGACACCATGAACAGCCTGACCCTGCCCAGCGAGG<br>TGAGCCTGTGCAACACCGACATCTTCAACAGCAAGTAC<br>GACTGCAAGATCATGACCAGCAAGACCGACATCAGCAG<br>CAGCGTGATCACCAGCCTGGGCGCCATCGTGAGCTGCT<br>ACGGCAAGACCAAGTGCACCGCCAGCAACAAGAACAG<br>AGGCATCATCAAGACCTTCAGCAACGGCTGCGACTACG<br>TGAGCAACAAGGGCGTGGACACCGTGAGCGTGGGCAA<br>CACCCTGTACTACGTGAACAAGCTGGAGGGCAAGAACC<br>TGTACGTGAAGGGCGAGCCCATCATCAACTACTACGAC<br>CCCCTGGTGTTCCCCAGCGACGAGTTCGACGCCAGCAT<br>CAGCCAGGTGAACGAGAAGATCAACCAGAGCCTGGCCT<br>TCATCAGAAGAAGCGACGAGCTGCTGCACAACGTGAAC<br>ACCGGCAAGAGCACCACCAACATCATGATCACCGTGAT<br>CATCATCGTGATCATCGTGGTGCTGCTGAGCCTGATCGC<br>CATCGGCCTGCTGCTGTACTGCAAGGCCAAGAACACCC<br>CCGTGACCCTGAGCAAGGACCAGCTGAGCGGCATCAAC<br>AACATCGCCTTCAGCAAG | |
| Amino acid sequence of RSV F protein from strain RSVB/Homo sapiens/USA/LA2_82/2013 | MELLIHRSSVIFLTLAINALYLTSSQNITEEFYQSTCSAVSR<br>GYFSALRTGWYTSVITIELSNIKETKCNGTDTKVKLIKQEL<br>DKYKNAVTELQLLMQNIPAANNRARREAPQYMNYTINTT<br>KNLNVSISKKRKRRFLGFLLGVGSAIASGIAVSKVLHLEGE<br>VNKIKNALLSTNKAVVSLSNGVSVLTSKVLDLKNYINNQL<br>LPIVNQQSCRISNIETVIEFQQKNSRLLEITREFSVNAGVTTP<br>LSTYMLTNSELLSLINDMPITNDQKKLMSSNVQIVRQQSYS<br>IMSIIKEEVLAYVVQLPIYGVIDTPCWKLHTSPLCTTNIKEG<br>SNICLTRTDRGWYCDNAGSVSFFPQADTCKVQSNRVFCDT<br>MNSLTLPSEVSLCNTDIFNSKYDCKIMTSKTDISSSVITSLG<br>AIVSCYGKTKCTASNKNRGIIKTFSNGCDYVSNKGVDTVS<br>VGNTLYYVNKLEGKNLYVKGEPIINYYDPLVFPSDEFDASI<br>SQVNEKINQSLAFIRRSDELLHNVNTGKSTTNIMITVIIIVII<br>VVLLSLIAIGLLLYCKAKNTPVTLSKDQLSGINNIAFSK | 58 |
| Wild-type nucleic acid sequence encoding human RSV F protein from strain HRSV-A-GZ08-18 (transmembrane and cytoplasmic domains are underlined) | ATGGAGTTGCCAATCCTCAAAGCAAATGCTATTACCAC<br>AATCCTTGCTGCAGTCACACTCTGTTTTGCTTCCAGTCA<br>AAACATCACTGAAGAATTTTATCAATCAACATGCAGTG<br>CAGTTAGCAAAGGCTATCTTAGTGCTCTAAGAACTGGTT<br>GGTATACTAGTGTTATAACTATAGAATTAAGTAATATCA<br>AGGAAAATAAGTGTAATGGAACAGATGCTAAGGTAAA<br>ATTGATAAAACAAGAATTAGATAAATACAAAAATGCTG<br>TAACAGAATTGCAGTTGCTCATGCAAAGCACACCAGCA<br>GCCAACAATCGAGCCAGAAGGGAATTACCAAGATTTAT<br>GAATTATACACTCAACAATACTGAAAACACCAATGTAA<br>CATTAAGCAAGAAAAGGAAAAGAAGATTTCTTGGCTTT<br>TTGTTAGGTGTTGGATCTGCAATCGCCAGTGGCATTGCC<br>GTATCCAAGGTCCTGCACCTAGAAGGGGAAGTGAACAA<br>AATCAAAAGTGCTCTACTATCCACAAACAAGGCTGTAG<br>TCAGCTTATCAAATGGAGTCAGTGTCTTAACCAGCAAA<br>GTGTTAGATCTCAAAAACTATATAGATAAACAGTTGTT<br>ACCTATTGTGAACAAGCAAAGCTGCAGCATATCAAACA<br>TTGAAACTGTAATAGAGTTCCAACAAAAGAACAACAGA<br>CTACTAGAGATTACCAGAGAATTTAGTGTTAATGCAGG<br>TGTAACTACACCTGTAAGCACTTATATGTTAACTAATAG<br>TGAATTATTATCATTAATCAATGATATGCCTATAACAAA<br>TGATCAGAAAAAGTTAATGTCCAACAATGTTCAAATAG<br>TTAGACAGCAAAGTTACTCTATCATGTCCATAATAAAA<br>GAGGAAGTCTTAGCATATGTAGTACAATTACCACTATA<br>TGGTGTAATAGATACACCTTGTTGGAAACTGCACACAT<br>CCCCTCTATGTACAACCAACACAAAGGAAGGGTCCAAC<br>ATCTGCTTAACAAGAACCGACAGAGGATGGTACTGTGA<br>CAATGCAGGATCAGTATCTTTCTTCCCACAAGCCGAAA<br>CATGTAAAGTTCAATCGAATCGGGTATTTTGTGACACA<br>ATGAACAGTTTAACATTACCAAGTGAGGTAAGTCTCTG<br>CAACGTTGACATATTCAACCCCAAATATGATTGCAAAA | 29 |

TABLE 1-continued

| Human RSV F Sequences | | |
|---|---|---|
| Description | Sequence | SEQ ID NO. |
| | TTATGACTTCAAAAACAGATGTAAGCAGCTCCGTTATC ACATCTCTGGGAGCCATTGTGTCATGCTATGGCAAAAC CAAATGTACAGCATCCAATAAAAATCGTGGGATCATAA AGACATTTTCTAACGGGTGTGATTATGTATCAAATAAG GGGGTGGATACTGTGTCTGTAGGTAATACATTATATTAT GTAAATAAGCAAGAAGGCAAAAATCTCTATGTAAAAGG TGAACCAATAATAAATTTCTATGACCCATTAGTGTTCCC CTCTGATGAATTTGATGCATCAATATCTCAAGTCAATGA GAAGATTAACCAGAGTCTAGCATTTATTCGTAAATCAG ATGAATTATTACATAATGTAAATGCTGTTAAATCCACTA CAAATATCATGATAACTACTATAATTATAGTGATTATAG TAATATTGTTATCATTAATTGTAGTTGGACTGCTTCTAT ACTGCAAGGCCAGAAGCACACCAGTCACACTAAGTAAG GATCAACTGAGTGGTATAAATAATATTGCATTTAGTAG CTGA | |
| Codon optimized nucleic acid sequence encoding human RSV F protein from RSV strain HRSV-A-GZ08-18 | ATGGAGCTGCCCATCCTGAAGGCCAACGCCATCACCAC CATCCTGGCCGCCGTGACCCTGTGCTTCGCCAGCAGCCA GAACATCACCGAGGAGTTCTACCAGAGCACCTGCAGCG CCGTGAGCAAGGGCTACCTGAGCGCCCTGAGAACCGGC TGGTACACCAGCGTGATCACCATCGAGCTGAGCAACAT CAAGGAGAACAAGTGCAACGGCACCGACGCCAAGGTG AAGCTGATCAAGCAGGAGCTGGACAAGTACAAGAACG CCGTGACCGAGCTGCAGCTGCTGATGCAGAGCACCCCC GCCGCCAACAACAGAGCCAGAAGAGAGCTGCCCAGATT CATGAACTACACCCTGAACAACACCGAGAACACCAACG TGACCCTGAGCAAGAAGAGAAAGAGAAGATTCCTGGG CTTCCTGCTGGGCGTGGGCAGCGCCATCGCCAGCGGCA TCGCCGTGAGCAAGGTGCTGCACCTGGAGGGCGAGGTG AACAAGATCAAGAGCGCCCTGCTGAGCACCAACAAGGC CGTGGTGAGCCTGAGCAACGGCGTGAGCGTGCTGACCA GCAAGGTGCTGGACCTGAAGAACTACATCGACAAGCAG CTGCTGCCCATCGTGAACAAGCAGAGCTGCAGCATCAG CAACATCGAGACCGTGATCGAGTTCCAGCAGAAGAACA ACAGACTGCTGGAGATCACCAGAGAGTTCAGCGTGAAC GCCGGCGTGACCACCCCCGTGAGCACCTACATGCTGAC CAACAGCGAGCTGCTGAGCCTGATCAACGACATGCCCA TCACCAACGACCAGAAGAAGCTGATGAGCAACAACGTG CAGATCGTGAGACAGCAGAGCTACAGCATCATGAGCAT CATCAAGGAGGAGGTGCTGGCCTACGTGGTGCAGCTGC CCCTGTACGGCGTGATCGACACCCCCTGCTGGAAGCTG CACACCAGCCCCCTGTGCACCACCAACACCAAGGAGGG CAGCAACATCTGCCTGACCAGAACCGACAGAGGCTGGT ACTGCGACAACGCCGGCAGCGTGAGCTTCTTCCCCCAG GCCGAGACCTGCAAGGTGCAGAGCAACAGAGTGTTCTG CGACACCATGAACAGCCTGACCCTGCCCAGCGAGGTGA GCCTGTGCAACGTGGACATCTTCAACCCCAAGTACGAC TGCAAGATCATGACCAGCAAGACCGACGTGAGCAGCAG CGTGATCACCAGCCTGGGCGCCATCGTGAGCTGCTACG GCAAGACCAAGTGCACCGCCAGCAACAAGAACAGAGG CATCATCAAGACCTTCAGCAACGGCTGCGACTACGTGA GCAACAAGGGCGTGGACACCGTGAGCGTGGGCAACAC CCTGTACTACGTGAACAAGCAGGAGGGCAAGAACCTGT ACGTGAAGGGCGAGCCCATCATCAACTTCTACGACCCC CTGGTGTTCCCCAGCGACGAGTTCGACGCCAGCATCAG CCAGGTGAACGAGAAGATCAACCAGAGCCTGGCCTTCA TCAGAAAGAGCGACGAGCTGCTGCACAACGTGAACGCC GTGAAGAGCACCACCAACATCATGATCACCACCATCAT CATCGTGATCATCGTGATCCTGCTGAGCCTGATCGTGGT GGGCCTGCTGCTGTACTGCAAGGCCAGAAGCACCCCCG TGACCCTGAGCAAGGACCAGCTGAGCGGCATCAACAAC ATCGCCTTCAGCAGC | 30 |
| Amino acid sequence of human RSV F protein from strain HRSV-A-GZ08-18 | MELPILKANAITTILAAVTLCFASSQNITEEFYQSTCSAVSKGYLSALRTGWYTSVI TIELSNIKENKCNGTDAKVKLIKQELDKYKNAVTELQLLMQSTPAANNRARREL PRFMNYTLNNTENTNVTLSKKRKRRFLGFLLGVGSAIASGIAVSKVLHLEGEVN KIKSALLSTNKAVVSLSNGVSVLTSKVLDLKNYIDKQLLPIVNKQSCSISNIETVIEF QQKNNRLLEITREFSVNAGVTTPVSTYMLTNSELLSLINDMPITNDQKKLMSN NVQIVRQQSYSIMSIIKEEVLAYVVQLPLYGVIDTPCWKLHTSPLCTTNTKEGSNI CLTRTDRGWYCDNAGSVSFFPQAETCKVQSNRVFCDTMNSLTLPSEVSLCNV DIFNPKYDCKIMTSKTDVSSSVITSLGAIVSCYGKTKCTASNKNRGIIKTFSNGCD YVSNKGVDTVSVGNTLYYVNKQEGKNLYVKGEPIINFYDPLVFPSDEFDASISQV NEKINQSLAFIRKSDELLHNVNAVKSTTNIMITTIIIVIIVILLSLIVVGLLLYCKARST PVTLSKDQLSGINNIAFSS | 49 |

TABLE 1-continued

Human RSV F Sequences

| Description | Sequence | SEQ ID NO. |
| --- | --- | --- |
| Nucleic acid sequence encoding chimeric F protein, wherein the nucleic acid sequence comprises a codon optimized nucleic acid sequence encoding the human RSV F protein ectodomain of strain RSVA/Homo sapiens/USA/TH_ 10656/2014 and a nucleic acid sequence encoding the transmembrane and cytoplasmic domains of F protein from NDV strain LaSota (transmembrane and cytoplasmic domains of NDV F are underlined) | ATGGAGCTGCCCATCCTGAAGACCAACGCCATCACCACCATCCTGGCCGCC<br>GTGACCCTGTGCTTCGCCAGCAGCCAGAACATCACCGAGGAGTTCTACCAG<br>AGCACCTGCAGCGCCGTGAGCAAGGGCTACCTGAGCGCCCTGAGAACCGG<br>CTGGTACACCAGCGTGATCACCATCGAGCTGAGCAACATCAAGGAGAACAA<br>GTGCAACGGCACCGACGCCAAGGTGAAGCTGATCAAGCAGGAGCTGGACA<br>AGTACAAGAACGCCGTGACCGAGCTGCAGCTGCTGATGCAGAGCACCCCC<br>GCCGCCAACAGCAGAGCCAGAAGAGAGCTGCCCAGATTCATGAACTACAC<br>CCTGAACAACACCAAGAACACCAACGTGACCCTGAGCAAGAAGAGAAAGA<br>GAAGATTCCTGGGCTTCCTGCTGGGCGTGGGCAGCGCCATCGCCAGCGGC<br>ATCGCCGTGAGCAAGGTGCTGCACCTGGAGGGCGAGGTGAACAAGATCAA<br>GAGCGCCCTGCTGAGCACCAACAAGGCCGTGGTGAGCCTGAGCAACGGCG<br>TGAGCGTGCTGACCAGCAAGGTGCTGGACCTGAAGAACTACATCGACAAG<br>CAGCTGCTGCCCATCGTGAACAAGCAGAGCTGCAGCATCAGCAACATCGAG<br>ACCGTGATCGAGTTCCAGCAGAAGAACAACAGACTGCTGGAGATCACCAG<br>AGAGTTCAGCGTGAACGCCGGCGTGACCACCCCCGTGAGCACCTACATGCT<br>GACCAACAGCGAGCTGCTGAGCCTGATCAACGACATGCCCATCACCAACGA<br>CCAGAAGAAGCTGATGAGCAGCAACGTGCAGATCGTGAGACAGCAGAGCT<br>ACAGCATCATGAGCATCATCAAGGAGGAGGTGCTGGCCTACGTGGTGCAG<br>CTGCCCCTGTACGGCGTGATCGACACCCCCTGCTGGAAGCTGCACACCAGC<br>CCCCTGTGCACCACCAACACCAAGGAGGGCAGCAACATCTGCCTGACCAGA<br>ACCGACAGAGGCTGGTACTGCGACAACGCCGGCAGCGTGAGCTTCTTCCCC<br>CAGGCCGAGACCTGCAAGGTGCAGAGCAACAGAGTGTTCTGCGACACCAT<br>GAACAGCCTGACCCTGCCCAGCGAGGTGAACCTGTGCAACATCGACATCTT<br>CAACCCCAAGTACGACTGCAAGATCATGACCAGCAAGACCGACGTGAGCA<br>GCAGCGTGATCACCAGCCTGGGCGCCATCGTGAGCTGCTACGGCAAGACC<br>AAGTGCACCGCCAGCAACAAGAACAGAGGCATCATCAAGACCTTCAGCAAC<br>GGCTGCGACTACGTGAGCAACAAGGGCGTGGACACCGTGAGCGTGGGCA<br>ACACCCTGTACTACGTGAACAAGCAGGAGGGCAAGAGCCTGTACGTGAAG<br>GGCGAGCCCATCATCAACTTCTACGACCCCCTGGTGTTCCCCAGCGACGAG<br>TTCGACGCCAGCATCAGCCAGGTGAACGAGAAGATCAACCAGAGCCTGGC<br>CTTCATCAGAAAGAGCGACGAGCTGCTGCACAACGTGAACGCCGGCAAGA<br>GCACCACCAACATCATGGgttaacCTCATTACCTATATCGTTTTGACTATCATAT<br>CTCTTGTTTTTGGTATACTTAGCCTGATTCTAGCATGCTACCTAATGTACAAG<br>CAAAAGGCGCAACAAAAGACCTTATTATGGCTTGGGAATAATACCCTAGAT<br>CAGATGAGAGCCACTACAAAAATGTGAccgcgg | 44 |
| Nucleic acid sequence encoding chimeric F protein, wherein the nucleic acid sequence comprises a codon optimized nucleic acid sequence encoding the human RSV F protein ectodomain of strain RSVB/Homo sapiens/USA/LA2_ 82/2013 and a nucleic acid sequence encoding the transmembrane and cytoplasmic domains of F protein from NDV strain LaSota (transmembrane and cytoplasmic domains of NDV F are underlined) | ATGGAGCTGCTGATCCACAGAAGCAGCGTGATCTTCCTGACCCTGGCCATC<br>AACGCCCTGTACCTGACCAGCAGCCAGAACATCACCGAGGAGTTCTACCAG<br>AGCACCTGCAGCGCCGTGAGCAGAGGCTACTTCAGCGCCCTGAGAACCGG<br>CTGGTACACCAGCGTGATCACCATCGAGCTGAGCAACATCAAGGAGACCAA<br>GTGCAACGGCACCGACACCAAGGTGAAGCTGATCAAGCAGGAGCTGGACA<br>AGTACAAGAACGCCGTGACCGAGCTGCAGCTGCTGATGCAGAACATCCCCG<br>CCGCCAACAACAGAGCCAGAAGAGAGGCCCCCCAGTACATGAACTACACC<br>ATCAACACCACCAAGAACCTGAACGTGAGCATCAGCAAGAAGAGAAAGAG<br>AAGATTCCTGGGCTTCCTGCTGGGCGTGGGCAGCGCCATCGCCAGCGGCAT<br>CGCCGTGAGCAAGGTGCTGCACCTGGAGGGCGAGGTGAACAAGATCAAGA<br>ACGCCCTGCTGAGCACCAACAAGGCCGTGGTGAGCCTGAGCAACGGCGTG<br>AGCGTGCTGACCAGCAAGGTGCTGGACCTGAAGAACTACATCAACAACCA<br>GCTGCTGCCCATCGTGAACCAGCAGAGCTGCAGAATCAGCAACATCGAGAC<br>CGTGATCGAGTTCCAGCAGAAGAACAGCAGACTGCTGGAGATCACCAGAG<br>AGTTCAGCGTGAACGCCGGCGTGACCACCCCCCTGAGCACCTACATGCTGA<br>CCAACAGCGAGCTGCTGAGCCTGATCAACGACATGCCCATCACCAACGACC<br>AGAAGAAGCTGATGAGCAGCAACGTGCAGATCGTGAGACAGCAGAGCTAC<br>AGCATCATGAGCATCATCAAGGAGGAGGTGCTGGCCTACGTGGTGCAGCT<br>GCCCATCTACGGCGTGATCGACACCCCCTGCTGGAAGCTGCACACCAGCCC<br>CCTGTGCACCACCAACATCAAGGAGGGCAGCAACATCTGCCTGACCAGAAC<br>CGACAGAGGCTGGTACTGCGACAACGCCGGCAGCGTGAGCTTCTTCCCCCA<br>GGCCGACACCTGCAAGGTGCAGAGCAACAGAGTGTTCTGCGACACCATGA<br>ACAGCCTGACCCTGCCCAGCGAGGTGAGCCTGTGCAACACCGACATCTTCA<br>ACAGCAAGTACGACTGCAAGATCATGACCAGCAAGACCGACATCAGCAGC<br>AGCGTGATCACCAGCCTGGGCGCCATCGTGAGCTGCTACGGCAAGACCAA<br>GTGCACCGCCAGCAACAAGAACAGAGGCATCATCAAGACCTTCAGCAACG<br>GCTGCGACTACGTGAGCAACAAGGGCGTGGACACCGTGAGCGTGGGCAAC<br>ACCCTGTACTACGTGAACAAGCTGGAGGGCAAGAACCTGTACGTGAAGGG<br>CGAGCCCATCATCAACTACTACGACCCCCTGGTGTTCCCCAGCGACGAGTTC<br>GACGCCAGCATCAGCCAGGTGAACGAGAAGATCAACCAGAGCCTGGCCTT<br>CATCAGAAGAAGCGACGAGCTGCTGCACAACGTGAACACCGGCAAGAGCA<br>CCACCAACATCATGGgttaacCTCATTACCTATATCGTTTTGACTATCATATCTCT<br>TGTTTTTGGTATACTTAGCCTGATTCTAGCATGCTACCTAATGTACAAGCAA<br>AAGGCGCAACAAAAGACCTTATTATGGCTTGGGAATAATACCCTAGATCAG<br>ATGAGAGCCACTACAAAAATGTGAccgcgg | 45 |
| Nucleic acid sequence encoding | ATGGAGCTGCCCATCCTGAAGGCCAACGCCATCACCACCATCCTGGCCGCC<br>GTGACCCTGTGCTTCGCCAGCAGCCAGAACATCACCGAGGAGTTCTACCAG<br>AGCACCTGCAGCGCCGTGAGCAAGGGCTACCTGAGCGCCCTGAGAACCGG | 46 |

TABLE 1-continued

Human RSV F Sequences

| Description | Sequence | SEQ ID NO. |
| --- | --- | --- |
| chimeric F protein, wherein the nucleic acid sequence comprises a codon optimized nucleic acid sequence encoding the human RSV F protein ectodomain of strain HRSV-A-GZ08-18 and a nucleic acid sequence encoding the transmembrane and cytoplasmic domains of F protein from NDV strain LaSota (transmembrane and cytoplasmic domains of NDV F are underlined) | CTGGTACACCAGCGTGATCACCATCGAGCTGAGCAACATCAAGGAGAACAA<br>GTGCAACGGCACCGACGCCAAGGTGAAGCTGATCAAGCAGGAGCTGGACA<br>AGTACAAGAACGCCGTGACCGAGCTGCAGCTGCTGATGCAGAGCACCCCC<br>GCCGCCAACAACAGAGCCAGAAGAGAGCTGCCCAGATTCATGAACTACACC<br>CTGAACAACACCGAGAACACCAACGTGACCCTGAGCAAGAAGAGAAAGAG<br>AAGATTCCTGGGCTTCCTGCTGGGCGTGGGCAGCGCCATCGCCAGCGGCAT<br>CGCCGTGAGCAAGGTGCTGCACCTGGAGGGCGAGGTGAACAAGATCAAGA<br>GCGCCCTGCTGAGCACCAACAAGGCCGTGGTGAGCCTGAGCAACGGCGTG<br>AGCGTGCTGACCAGCAAGGTGCTGGACCTGAAGAACTACATCGACAAGCA<br>GCTGCTGCCCATCGTGAACAAGCAGAGCTGCAGCATCAGCAACATCGAGAC<br>CGTGATCGAGTTCCAGCAGAAGAACAACAGACTGCTGGAGATCACCAGAG<br>AGTTCAGCGTGAACGCCGGCGTGACCACCCCCGTGAGCACCTACATGCTGA<br>CCAACAGCGAGCTGCTGAGCCTGATCAACGACATGCCCATCACCAACGACC<br>AGAAGAAGCTGATGAGCAACAACGTGCAGATCGTGAGACAGCAGAGCTAC<br>AGCATCATGAGCATCATCAAGGAGGAGGTGCTGGCCTACGTGGTGCAGCT<br>GCCCCTGTACGGCGTGATCGACACCCCCTGCTGGAAGCTGCACACCAGCCC<br>CCTGTGCACCACCAACACCAAGGAGGGCAGCAACATCTGCCTGACCAGAAC<br>CGACAGAGGCTGGTACTGCGACAACGCCGGCAGCGTGAGCTTCTTCCCCCA<br>GGCCGAGACCTGCAAGGTGCAGAGCAACAGAGTGTTCTGCGACACCATGA<br>ACAGCCTGACCCTGCCCAGCGAGGTGAGCCTGTGCAACGTGGACATCTTCA<br>ACCCCAAGTACGACTGCAAGATCATGACCAGCAAGACCGACGTGAGCAGC<br>AGCGTGATCACCAGCCTGGGCGCCATCGTGAGCTGCTACGGCAAGACCAA<br>GTGCACCGCCAGCAACAAGAACAGAGGCATCATCAAGACCTTCAGCAACG<br>GCTGCGACTACGTGAGCAACAAGGGCGTGGACACCGTGAGCGTGGGCAAC<br>ACCCTGTACTACGTGAACAAGCAGGAGGGCAAGAACCTGTACGTGAAGGG<br>CGAGCCCATCATCAACTTCTACGACCCCCTGGTGTTCCCCAGCGACGAGTTC<br>GACGCCAGCATCAGCCAGGTGAACGAGAAGATCAACCAGAGCCTGGCCTT<br>CATCAGAAAGAGCGACGAGCTGCTGCACAACGTGAACGCCGTGAAGAGCA<br>CCACCAACATCATGGgttaacCTCATTACCTATATCGTTTTGACTATCATATCTCT<br>TGTTTTTGGTATACTTAGCCTGATTCTAGCATGCTACCTAATGTACAAGCAA<br>AAGGCGCAACAAAAGACCTTATTATGGCTTGGGAATAATACCCTAGATCAG<br>ATGAGAGCCACTACAAAAATGTGAccgcgg | |
| Nucleic acid sequence encoding a chimeric F protein, wherein the chimeric F protein comprises the human RSV F protein ectodomain of RSV A2 strain and the transmembrane and cytoplasmic domains of NDV F protein of NDV LaSota strain | atggagttgctaatcctcaaagcaaatgcaattaccacaatcctcactgcagtcacat-<br>tttgttttgct<br>tctggtcaaaacatcactgaagaattttatcaatcaacatgcagtgcagttagcaaaggctatctta<br>gtgctctgagaactggttggtataccagtgttataactatagaattaagtaatatcaaggaaaataa<br>gtgtaatggaacagatgctaaggtaaaattgataaaacaagaattagataaatataaaaatgctgt<br>aacagaattgcagttgctcatgcaaagcacaccagcaacaaacaatcgagccagaagagaacta<br>ccaaggtttatgaattatacactcaacaatgccaaaaaaaccaatgtaacattaagcaagaaaag<br>gaaaagaagatttcttggtttttgttaggtgttg-<br>gatctgcaatcgccagtggcgttgctgtatctaa<br>ggtcctgcacctagaaggggaagtgaacaagatcaaaagtgctctactatccacaaacaaggctg<br>tagtcagcttatcaaatggagttagtgtcttaaccagcaaagtgttagacctcaaaaactatataga<br>taaacaattgttacctattgtgaacaagcaaagctgcagcatatcaaatatagcaactgtgataga<br>gttccaacaaaagaacaacagactactagagattaccagggaatttagtgttaatgcaggtgtaac<br>tacacctgtaagcacttacatgttaactaatagtgaattattgtcattaatcaatga-<br>tatgcctataac<br>aaatgatcagaaaaagttaatgtccaacaatgttcaaatagttagacagcaaagttactctatcatg<br>tccataataaaagaggaagtcttagcatatgtagtacaattaccactatatggtgttatagatacac<br>cctgttggaaactacacacatcccctctatgtacaaccaacacaaaagaagggtccaacatctgttt<br>aacaagaactgacagaggatggtactgtgacaatgcaggatcagtatctttcttcccacaagctga<br>aacatgtaaagttcaatcaaatcgagtattttgtgacacaatgaacagtttaacattaccaagtgaa<br>gtaaatctctgcaatgttgacatattcaaccccaaatatgattgtaaaattatgacttcaaaaacag<br>atgtaagcagctccgttatcacatctctaggagccattgtgtcatgctatggcaaaactaaatgtac<br>agcatccaataaaaatcgtggaatcataaagacattttctaacgggtgcgattatgtatcaaataaa<br>ggggtggacactgtgtctgtaggtaacacattatattatgtaaataagcaagaaggtaaaagtctct<br>atgtaaaaggtgaaccaataataaatttctatgacccattagtattcccctctgatgaatttgatgca<br>tcaatatctcaagtcaacgagaagattaaccagagcctagcatttattcgtaaatccgatgaattatt<br>acataatgtaaatgctggtaaatccaccataaatgttaacCTCATTACCTATATCGTTTTGA<br>CTATCATATCTCTTGTTTTTGGTATACTTAGCCTGATTCTAGCATGCTACCTA<br>ATGTACAAGCAAAAGGCGCAACAAAAGACCTTATTATGGCTTGGGAATAAT<br>ACCCTAGATCAGATGAGAGCCACTACAAAAATGTGA | 51 |

TABLE 2

| NDV LaSota F protein | | |
|---|---|---|
| Amino acid sequence of F protein of NDV strain LaSota (transmembrane domain is underlined and cytoplasmic domain is in bold) | MGSRPSTKNPAPMTLTIRVALVLSCICPANSIDGRPLAAAG<br>IVVTGDKAVNIYTSSQTGSIIVKLLPNLPKDKEACAKAPLD<br>AYNRTLTTLLTPLGDSIRRIQESVTTSGGGRQGRLIGAIIGG<br>VALGVATAAQITAAAALIQAKQNAANILRLKESIAATNEA<br>VHEVTDGLSQLAVAVGKMQQFVNDQFNKTAQELDCIKIA<br>QQVGVELNLYLTELTTVFGPQITSPALNKLTIQALYNLAG<br>GNMDYLLTKLGVGNNQLSSLIGSGLITGNPILYDSQTQLLG<br>IQVTLPSVGNLNNMRATYLETLSVSTTRGFASALVPKVVT<br>QVGSVIEELDTSYCIETDLDLYCTRIVTFPMSPGIYSCLSGN<br>TSACMYSKTEGALTTPYMTIKGSVIANCKMTTCRCVNPPG<br>IISQNYGEAVSLIDKQSCNVLSLGGITLRLSGEFDVTYQKNI<br>SIQDSQVIITGNLDISTELGNVNNSISNALNKLEESNRKLDK<br>VNVKLTSTSALITYIVLTIISLVFGILSLILACYL**MYKQKAQ**<br>**QKTLLWLGNNTLDQMRATTKM** | 8 |

TABLE 3

| Bovine RSV F Sequences | | |
|---|---|---|
| Wild-type Nucleic acid sequence encoding bovine RSV F protein of bovine RSV strain ATCC51908 (transmembrane and cytoplasmic domains underlined) | ATGGCGACAACAGCCATGAGGATGATCATCAGCATTATCTTCATCTCT<br>ACCTATGTGACACATATCACTTTATGCCAAAACATAACAGAAGAATTT<br>TATCAATCAACATGCAGTGCAGTTAGTAGAGGTTACCTTAGTGCATTA<br>AGAACTGGATGGTATACAAGTGTGGTAACAATAGAGTTGAGCAAAATA<br>CAAAAAAATGTGTGTAATAGTACTGATTCAAAAGTGAAATTAATAAAG<br>CAAGAACTAGAAAGATACAACAATGCAGTAGTGGAATTGCAGTCACTT<br>ATGCAAAATGAACCGGCCTCCTTCAGTAGAGCAAAAAGAGGGATACCA<br>GAGTTGATACATTATACAAGAAACTCTACAAAAAAGTTTTATGGGCTA<br>ATGGGCAAGAAGAGAAAAAGGAGATTTTTAGGATTCTTGCTAGGTATT<br>GGATCTGCTATTGCAAGTGGTGTAGCAGTGTCCAAAGTACTACACCTG<br>GAGGGAGAGGTGAATAAAATTAAAAATGCACTGCTATCCACAAATAAA<br>GCAGTAGTTAGTCTATCCAATGGAGTTAGTGTCCTTACTAGCAAAGTA<br>CTTGATCTAAAGAACTATATAGACAAAGAGCTTCTACCTAAAGTTAAC<br>AATCATGATTGTAGGATATCCAAAATAGAAACTGTGATAGAATTCCAA<br>CAAAAAAACAATAGATTGTTAGAAATTGCTAGGGAATTTAGTGTAAAT<br>GCTGGTATTACCACACCTCTCAGTACATACATGTTGACCAATAGTGAA<br>TTACTATCACTAATTAATGATATGCCTATAACGAATGACCAAAAAAAG<br>CTAATGTCAAGTAATGTTCAAATAGTCAGGCAACAGAGTTATTCCATT<br>ATGTCAGTGGTCAAAGAAGAAGTCATAGCTTATGTTGTACAATTGCCT<br>ATTTATGGAGTTATAGACACCCCCTGTTGGAAACTACACACCTCTCCG<br>TTATGCACCACTGATAATAAAGAAGGGTCAAACATCTGCTTAACTAGG<br>ACAGATCGTGGGTGGTATTGTGACAATGCAGGCTCTGTGTCTTTTTTC<br>CCACAGACAGAGACATGTAAGGTACAATCAAATAGAGTGTTCTGTGAC<br>ACAATGAACAGTTTAACTCTGCCTACTGACGTTAACTTATGCAACACT<br>GACATATTCAATACAAAGTATGACTGTAAAATAATGACATCTAAAACT<br>GACATAAGTAGCTCTGTGATAACTTCAATTGGAGCTATTGTATCATGC<br>TATGGGAAGACAAAATGTACAGCTTCTAATAAAAATCGTGGAATCATA<br>AAGACTTTTTCCAATGGGTGTGATTATGTATCAAACAAAGGAGTAGAT<br>ACTGTATCTGTTGGTAACACACTATATTATGTAAATAAGCTAGAGGGG<br>AAAGCACTCTATATAAAGGGTGAACCAATTATTAATTACTATGATCCA<br>CTAGTGTTTCCTTCTGATGAGTTTGATGCATCAATTGCCCAAGTAAAC<br>GCAAAAATAAACCAAAGCCTGGCCTTCATACGTCGATCTGATGAGTTA<br>CTTCACAGTGTAGATGTAGGAAAATCCACCACAAATGTAGTAATTACT<br>ACTATTATCATAGTGATAGTTGTAGTGATATTAATGTTAATAGCTGTA<br>GGATTACTGTTTTACTGTAAGACCAAGAGTACTCCTATCATGTTAGGG<br>AAGGATCAGCTCAGTGGTATCAACAATCTTTCCTTTAGTAAATGA | 9 |
| Amino acid sequence of bovine RSV F protein of bovine RSV strain ATCC51908 (transmembrane and cytoplasmic domains underlined. The amino acid sequence encoded by SEQ ID NO: 9) | MATTAMRMIISIIFISTYVTHITLCQNITEEFYQSTCSAVSRGY<br>LSALRTGWYTSVVTIELSKIQKNVCNSTDSKVKLIKQELERYNN<br>AVVELQSLMQNEPASFSRAKRGIPELIHYTRNSTKKFYGLMGKK<br>RKRRFLGFLLGIGSAIASGVAVSKVLHLEGEVNKIKNALLSTNK<br>AVVSLSNGVSVLTSKVLDLKNYIDKELLPKVNNHDCRISKIETV<br>IEFQQKNNRLLEIAREFSVNAGITTPLSTYMLTNSELLSLINDM<br>PITNDQKKLMSSNVQIVRQQSYSIMSVVKEEVIAYVVQLPIYGV<br>IDTPCWKLHTSPLCTTDNKEGSNICLTRTDRGWYCDNAGSVSFF<br>PQTETCKVQSNRVFCDTMNSLTLPTDVNLCNTDIFNTKYDCKIM<br>TSKTDISSSVITSIGAIVSCYGKTKCTASNKNRGIIKTESNGCD<br>YVSNKGVDTVSVGNTLYYVNKLEGKALYIKGEPIINYYDPLVFP<br>SDEFDASIAQVNAKINQSLAFIRRSDELLHSVDVGKSTTNVVIT<br>TIIIVIVVVILMLIAVGLLFYCKTKSTPIMLGKDQLSGINNLSF<br>SK | 10 |
| Codon optimized nucleic acid | ATGGCCACCACCGCCATGCGCATGATCATCAGCATCATCTTCAT<br>CAGCACCTACGTGACCCACATCACCCTGTGCCAGAACATCACCG<br>AGGAGTTCTACCAGAGCACCTGCAGCGCCGTGAGTCGCGGCTAC | 11 |

TABLE 3-continued

| Bovine RSV F Sequences | | |
|---|---|---|
| sequence<br>encoding bovine<br>RSV F protein<br>of bovine RSV<br>strain<br>ATCC51908 | CTGAGCGCCCTGCGCACCGGCTGGTACACCAGCGTGGTGACCAT<br>CGAGCTGAGCAAGATCCAGAAGAACGTGTGCAACAGCACCGACA<br>GCAAGGTGAAGCTGATCAAGCAGGAGCTGGAGCGCTACAACAAC<br>GCCGTGGTGGAGCTGCAGAGCCTGATGCAGAACGAGCCCGCCAG<br>CTTCAGCCGCGCCAAGCGCGGCATCCCCGAGCTGATCCACTACA<br>CCCGCAACAGCACCAAGAAGTTCTACGGCCTGATGGGCAAGAAG<br>CGCAAGCGCCGCTTCCTGGGCTTCCTGCTGGGCATCGGCAGCGC<br>CATCGCCAGCGGCGTGGCCGTGAGCAAGGTGCTGCACCTGGAGG<br>GCGAGGTGAACAAGATCAAGAACGCCCTGCTGAGCACCAACAAG<br>GCCGTGGTGAGCCTGAGCAACGGCGTGAGCGTGCTGACCAGCAA<br>GGTGCTGGACCTGAAGAACTACATCGACAAGGAGCTGCTGCCCA<br>AGGTGAACAACCACGACTGCCGCATCAGCAAGATCGAGACCGTG<br>ATCGAGTTCCAGCAGAAGAACAACCGCCTGCTGGAGATCGCCCG<br>CGAGTTCAGCGTGAACGCCGGCATCACCACCCCCCTGAGCACCT<br>ACATGCTGACCAACAGCGAGCTGCTGAGCCTGATCAACGACATG<br>CCCATCACCAACGACCAGAAGAAGCTGATGAGCAGCAACGTGCA<br>GATCGTGCGCCAGCAGAGCTACAGCATCATGAGCGTGGTGAAGG<br>AGGAGGTGATCGCCTACGTGGTGCAGCTGCCCATCTACGGCGTG<br>ATCGACACCCCCTGCTGGAAGCTGCACACCAGCCCCCTGTGCAC<br>CACCGACAACAAGGAGGGCAGCAACATCTGCCTGACCCGCACCG<br>ATCGCGGCTGGTACTGCGACAACGCCGGCAGCGTGAGCTTCTTC<br>CCCCAGACCGAGACCTGCAAGGTGCAGAGCAACCGCGTGTTCTG<br>CGACACCATGAACAGCCTGACCCTGCCCACCGACGTGAACCTGT<br>GCAACACCGACATCTTCAACACCAAGTACGACTGCAAGATCATG<br>ACCAGCAAGACCGACATCAGCAGCAGCGTGATCACCAGCATCGG<br>CGCCATCGTGAGCTGCTACGGCAAGACCAAGTGCACCGCCAGCA<br>ACAAGAATCGCGGCATCATCAAGACCTTCAGCAACGGCTGCGAC<br>TACGTGAGCAACAAGGGCGTGGACACCGTGAGCGTGGGCAACAC<br>CCTGTACTACGTGAACAAGCTGGAGGGCAAGGCCCTGTACATCA<br>AGGGCGAGCCCATCATCAACTACTACGACCCCCTGGTGTTCCCC<br>AGCGACGAGTTCGACGCCAGCATCGCCCAGGTGAACGCCAAGAT<br>CAACCAGAGCCTGGCCTTCATCCGCCGCAGCGACGAGCTGCTGC<br>ACAGCGTGGACGTGGGCAAGAGCACCACCAACGTGGTGATCACC<br>ACCATCATCATCGTGATCGTGGTGGTGATCCTGATGCTGATCGC<br>CGTGGGCCTGCTGTTCTACTGCAAGACCAAGAGCACCCCCATCA<br>TGCTGGGCAAGGACCAGCTGAGCGGCATCAACAACCTGAGCTTC<br>AGCAAGTAA | 12 |
| cDNA of<br>genomic<br>sequence of<br>NDV of LaSota<br>strain with the<br>nucleic acid<br>encoding bovine<br>RSV F protein<br>of strain<br>ATCC51908<br>(nucleic acid<br>sequence<br>encoding bovine<br>RSV F protein is<br>underlined) | accaaacagagaatccgtgagttacgataaaaggcgaaggagcaattg<br>aagtcgcacgggtagaaggtgtgaatctcgagtgcgagcccgaagcac<br>aaactcgagaaagccttctgccaacatgtcttccgtatttgatgagta<br>cgaacagctcctcgcggctcagactcgccccaatggagctcatggagg<br>gggagaaaaagggagtaccttaaaagtagacgtcccggtattcactct<br>taacagtgatgacccagaagatagatggagctttgtggtattctgcct<br>ccggattgctgttagcgaagatgccaacaaaccactcaggcaaggtgc<br>tctcatatctcttttatgctcccactcacaggtaatgaggaaccatgt<br>tgccCttgcagggaaacagaatgaagccacattggccgtgcttgagat<br>tgatggctttgccaacggcacgccccagttcaacaataggagtggagt<br>gtctgaagagagagcacagagatttgcgatgatagcaggatctctccc<br>tcgggcatgcagcaacggaaccccgttcgtcacagccggggcCgaaga<br>tgatgcaccagaagacatcaccgataccctggagaggatcctctctat<br>ccaggctcaagtatgggtcacagtagcaaaagccatgactgcgtatga<br>gactgcagatgagtcggaaacaaggcgaatcaataagtatatgcagca<br>aggcagggtccaaaagaaatacatcctctaccccgtatgcaggagcac<br>aatccaactcacgatcagacagtctcttgcagtccgcatctttttggt<br>tagcgagctcaagagaggccgcaacacggcaggtggtacctctactta<br>ttataacctggtaggggacgtagactcatacatcaggaataccgggct<br>tactgcattcttcttgacactcaagtacggaatcaacaccaagacatc<br>agcccttgcacttagtagcctctcaggcgacatccagaagatgaagca<br>gctcatgcgtttgtatcggatgaaaggagataatgcgccgtacatgac<br>attacttggtgatagtgaccagatgagctttgcgcctgccgagtatgc<br>acaactttactcctttgccatgggtatggcatcagtcctagataaagg<br>tactgggaaataccaatttgccagggactttatgagcacatcattctg<br>gagacttggagtagagtacgctcaggctcagggaagtagcattaacga<br>ggatatggctgccgagctaaagctaaccccagcagcaaGgaGgggcct<br>ggcagctgctgcccaacgggtctccgaGgaGaccagcagcataGacat<br>gcctactcaacaagtcggagtcctcactgggcttagcgagggggggtc<br>ccaagctctacaaggcggatcgaatagatcgcaagggcaaccagaagc<br>cggggatggggagacccaattcctggatctgatgagagcggtagcaaa<br>tagcatgagggaggcgccaaactctgcacagggcactccccaatcggg<br>gcctcccccaactcctgggccatcccaagataacgacaccgactgggg<br>gtattgatggacaaaacccagcctgcttccacaaaaacatcccaatgc<br>cctcacccgtagtcgacccctcgatttgcggctctatatgaccacacc<br>ctcaaacaaacatcccccctctttcctccctccccctgctgtacaactA<br>cgTacgccctagataccacaggcacaatgcggctcactaacaatcaaa<br>acagagccgagggaattagaaaaaagtacgggtagaagagggatattc<br>agagatcagggcaagtctcccgagtctctgctctctcctctacctgat<br>agaccaggacaaacatggccacctttacagatgcagagatcgacgagc | |

TABLE 3-continued

Bovine RSV F Sequences tatttgagacaagtggaactgtcattgacaacataattacagcccagg
gtaaaccagcagagactgttggaaggagtgcaatcccacaaggcaaga
ccaaggtgctgagcgcagcatgggagaagcatgggagcatccagccac
cggccagtcaagacaaccccgatcgacaggacagatctgacaaacaac
catccacacccgagcaaacgaccccgcatgacagcccgccggccacat
ccgccgaccagcccccccacccaggccacagacgaagccgtcgacacac
agCtcaggaccggagcaagcaactctctgctgttgatgcttgacaagc
tcagcaataaatcgtccaatgctaaaaagggcccatggtcgagccccc
aagaggggaatcaccaacgtccgactcaacagcaggggagtcaaccca
gtcgcggaaacagtcaggaaagaccgcagaaccaagtcaaggccgccc
ctggaaaccagggcacagacgtgaacacagcatatcatggacaatggg
aggagtcacaactatcagctggtgcaacccctcatgctctccgatcaa
ggcagagccaagacaatacccttgtatctgcggatcatgtccagccac
ctgtagactttgtgcaagcgatgatgtctatgatggaggcgatatcac
agagagtaagtaaggttgactatcagctagatcttgtcttgaaacaga
catcctccatccctatgatgcggtccgaaatccaacagctgaaaacat
ctgttgcagtcatggaagccaacttgggaatgatgaagattctggatc
ccggttgtgccaacatttcatctctgagtgatctacgggcagttgccc
gatctcacccggttttagtttcaggccctggagacccctctccctatg
tgacacaaggaggcgaaatggcacttaataaactttcgcaaccagtgc
cacatccatctgaattgattaaacccgccactgcatgcgggcctgata
taggagtggaaaaggacactgtccgtgcattgatcatgtcacgcccaa
tgcacccgagttcttcagccaagctcctaagcaagttagatgcagccg
ggtcgatcgaggaaatcaggaaaatcaagcgccttgctctaaatggct
aattactactgccacacgtagcgggtccctgtccactcggcatcacac
ggaatctgcaccgagttcccccccgcGgTTAGAAAAAATACGGGTAGA
ACCGCCACCATGGCGACAACAGCCATGAGGATGATCATCAGCATTATC
TTCATCTCTACCTATGTGACACATATCACTTTATGCCAAAACATAACA
GAAGAATTTTATCAATCAACATGCAGTGCAGTTAGTAGAGGTTACCTT
AGTGCATTAAGAACTGGATGGTATACAAGTGTGGTAACAATAGAGTTG
AGCAAAATACAAAAAAATGTGTGTAATAGTACTGATTCAAAAGTGAAA
TTAATAAAGCAAGAACTAGAAAGATACAACAATGCAGTAGTGGAATTG
CAGTCACTTATGCAAAATGAACCGGCCTCCTTCAGTAGAGCAAAAAGA
GGGATACCAGAGTTGATACATTATACAAGAAACTCTACAAAAAAGTTT
TATGGGCTAATGGGCAAGAAGAGAAAAAGGAGATTTTTAGGATTCTTG
CTAGGTATTGGATCTGCTATTGCAAGTGGTGTAGCAGTGTCCAAAGTA
CTACACCTGGAGGGAGAGGTGAATAAAATTAAAAATGCACTGCTATCC
ACAAATAAAGCAGTAGTTAGTCTATCCAATGGAGTTAGTGTCCTTACT
AGCAAAGTACTTGATCTAAAGAACTATATAGACAAAGAGCTTCTACCT
AAAGTTAACAATCATGATTGTAGGATATCCAAAATAGAAACTGTGATA
GAATTCCAACAAAAAAACAATAGATTGTTAGAAATTGCTAGGGAATTT
AGTGTAAATGCTGGTATTACCACACCTCTCAGTACATACATGTTGACC
AATAGTGAATTACTATCACTAATTAATGATATGCCTATAACGAATGAC
CAAAAAAAGCTAATGTCAAGTAATGTTCAAATAGTCAGGCAACAGAGT
TATTCCATTATGTCAGTGGTCAAAGAAGAAGTCATAGCTTATGTTGTA
CAATTGCCTATTTATGGAGTTATAGACACCCCCTGTTGGAAACTACAC
ACCTCTCCGTTATGCACCACTGATAATAAAGAAGGGTCAAACATCTGC
TTAACTAGGACAGATCGTGGGTGGTATTGTGACAATGCAGGCTCTGTG
TCTTTTTTCCCACAGACAGAGACATGTAAGGTACAATCAAATAGAGTG
TTCTGTGACACAATGAACAGTTTAACTCTGCCTACTGACGTTAACTTA
TGCAACACTGACATATTCAATACAAAGTATGACTGTAAAATAATGACA
TCTAAAACTGACATAAGTAGCTCTGTGATAACTTCAATTGGAGCTATT
GTATCATGCTATGGGAAGACAAAATGTACAGCTTCTAATAAAAATCGT
GGAATCATAAAGACTTTTTCCAATGGGTGTGATTATGTATCAAACAAA
GGAGTAGATACTGTATCTGTTGGTAACACACTATATTATGTAAATAAG
CTAGAGGGGAAAGCACTCTATATAAAGGGTGAACCAATTATTAATTAC
TATGATCCACTAGTGTTTCCTTCTGATGAGTTTGATGCATCAATTGCC
CAAGTAAACGCAAAAATAAACCAAAGCCTGGCCTTCATACGTCGATCT
GATGAGTTACTTCACAGTGTAGATGTAGGAAAATCCACCACAAATGTA
GTAATTACTACTATTATCATAGTGATAGTTGTAGTGATATTAATGTTA
ATAGCTGTAGGATTACTGTTTTACTGTAAGACCAAGAGTACTCCTATC
ATGTTAGGGAAGGATCAGCTCAGTGGTATCAACAATCTTTCCTTTAGT
AAATGAcccccccgcggacccaaggtccaactctccaagcggcaatcct
ctctcgcttcctcagccccactgaatgAtcgcgtaaccgtaattaatc
tagctacatttaagattaagaaaaaatacgggtagaattggagtgccc
caattgtgccaagatggactcatctaggacaattgggctgtactttga
ttctgcccattcttctagcaacctgttagcatttccgatcgtcctaca
agAcacaggagatgggaagaagcaaatcgccccgcaatataggatcca
gcgccttgacttgtggactgatagtaaggaggactcagtattcatcac
cacctatggattcatctttcaagttgggaatgaagaagccacCgtcgg
catgatcgatgataaacccaagcgcgagttactttccgctgcgatgct
ctgcctaggaagcgtcccaaataccggagaccttattgagctggcaag
ggcctgtctcactatgatagtcacatgcaagaagagtgcaactaatac
tgagagaatggttttctcagtagtgcaggcaccccaagtgctgcaaag
ctgtagggttgtggcaaacaaatactcatcagtgaatgcagtcaagca
cgtgaaagcgccagagaagattcccgggagtggaaccctagaatacaa
ggtgaactttgtctccttgactgtggtaccgaagaGggatgtctacaa
gatcccagctgcagtattgaaggtttctggctcgagtctgtacaatct TABLE 3-continued

| Bovine RSV F Sequences |
|---|
| tgcgctcaatgtcactattaatgtggaggtagacccgaggagtccttt<br>ggttaaatctCtgtctaagtctgacagcggatactatgctaacctctt<br>cttgcatattggacttatgaccacTgtagataggaaggggaagaaagt<br>gacatttgacaagctggaaaagaaaataaggagccttgatctatctgt<br>cgggctcagtgatgtgctcgggccttccgtgttggtaaaagcaagagg<br>tgcacggactaagcttttggcacctttcttctctagcagtgggacagc<br>ctgctatcccatagcaaatgcttctcctcaggtggccaagatactctg<br>gagtcaaaccgcgtgcctgcggagcgttaaaatcattatccaagcagg<br>tacccaacgcgctgtcgcagtgaccgccgaccacgaggttacctctac<br>taagctggagaaggggcacacccttgccaaatacaatccttttaagaa<br>ataagctgcgtctctgagattgcgctccgcccactcacccagatcatc<br>atgacacaaaaaactaatctgtcttgattatttacagttagtttacct<br>gtctatcaagttagaaaaaacacgggtagaagattctggatcccggtt<br>ggcgccctccaggtgcaagatgggctccagaccttctaccaagaaccc<br>agcacctatgatgctgactatccgggttgcgctggtactgagttgcat<br>ctgtccggcaaactccattgatggcaggcctcttgcagctgcaggaat<br>tgtggttacaggagacaaagccgtcaacatatacacctcatcccagac<br>aggatcaatcatagttaagctcctcccgaatctgcccaaggataagga<br>ggcatgtgcgaaagccccccttggatgcatacaacaggacattgaccac<br>tttgctcaccccccttggtgactctatccgtaggatacaagagtctgt<br>gactacatctggagggggagacaggggcgccttataggcgccattat<br>tggcggtgtggctcttggggttgcaactgccgcacaaataacagcggc<br>cgcagctctgatacaagccaaacaaaatgctgccaacatcctccgact<br>taaagagagcattgccgcaaccaatgaggctgtgcatgaggtcactga<br>cggattatcgcaactagcagtggcagttgggaagatgcagcagtttgt<br>taatgaccaatttaataaaacagctcaggaattagactgcatcaaaat<br>tgcacagcaagttggtgtagagctcaacctgtacctaaccgaattgac<br>tacagtattcggaccacaaatcacttcacctgctttaaacaagctgac<br>tattcaggcactttacaatctagctggtggaaatatggattacttatt<br>gactaagttaggtgtagggaacaatcaactcagctcattaatcggtag<br>cggcttaatcaccggtaaccctattctatacgactcacagactcaact<br>cttgggtatacaggtaactctaccttcagtcgggaacctaaataatat<br>gcgtgccacctacttggaaaccttatccgtaagcacaaccaggggatt<br>tgcctcggcacttgtcccAaaagtggtgacacaggtcggttctgtgat<br>agaagaacttgacacctcatactgtatagaaactgacttagatttata<br>ttgtacaagaatagtaacgttccctatgtcccctggtatttattcctg<br>cttgagcggcaatacgtcggcctgtatgtactcaaagaccgaaggcgc<br>acttactacaccatacatgactatcaaaggttcagtcatcgccaactg<br>caagatgacaacatgtagatgtgtaaaccccccgggtatcatatcgca<br>aaactatggagaagccgtgtctctaatagataaacaatcatgcaatgt<br>tttatccttaggcgggataactttaaggctcagtggggaattcgatgt<br>aacttatcagaagaatatctcaatacaagattctcaagtaataataac<br>aggcaatcttgatatctcaactgagcttgggaatgtcaacaactcgat<br>cagtaatgctttgaataagttagaggaaagcaacagaaaactagacaa<br>agtcaatgtcaaactgactagcacatctgctctcattacctatatcgt<br>tttgactatcatatctcttgtttttggtatacttagcctgattctagc<br>atgctacctaatgtacaagcaaaaggcgcaacaaaagaccttattatg<br>gcttgggaataatactctagatcagatgagagccactacaaaaatgtg<br>aacacagatgaggaacgaaggtttccctaatagtaatttgtgtgaaag<br>ttctggtagtctgtcagttcagagagttaagaaaaaactaccggttgt<br>agatgaccaaaggacgatatacgggtagaacggtaagagaggccgccc<br>ctcaattgcgagccaggcttcacaacctccgttctaccgcttcaccga<br>caacagtcctcaatcatggaccgcgccgttagccaagttgcgttagag<br>aatgatgaaagagaggcaaaaaatacatggcgcttgatattccggatt<br>gcaatcttattcttaacagtagtgaccttggctatatctgtagcctcc<br>cttttatatagcatgggggctagcacacctagcgatcttgtaggcata<br>ccgactaggatttccagggcagaagaaaagattacatctacacttggt<br>tccaatcaagatgtagtagataggatatataagcaagtggcccttgag<br>tctccgttggcattgttaaatactgagaccacaattatgaacgcaata<br>acatctctctcttatcagattaatggagctgcaaacaacagtgggtgg<br>ggggcacctatccatgacccagattatatagggggggataggcaaagaa<br>ctcattgtagatgatgctagtgatgtcacatcattctatccctctgca<br>tttcaagaacatctgaattttatcccggcgcctactacaggatcaggt<br>tgcactcgaataccctcatttgacatgagtgctacccattactgctac<br>acccataatgtaatattgtctggatgcagagatcactcacattcatat<br>cagtatttagcacttggtgtgctccggacatctgcaacagggagggta<br>ttcttttctactctgcgttccatcaacctggacgacacccaaaatcgg<br>aagtcttgcagtgtgagtgcaactcccctgggttgtgatatgctgtgc<br>tcgaaagtcacggagacagaggaagaagattataactcagctgtccct<br>acgcggatggtacatgggaggttagggttcgacggccagtaccacgaa<br>aaggacctagatgtcacaacattattcggggactgggggccaactac<br>ccaggagtagggggtggatcttttattgacagccgcgtatggttctca<br>gtctacggagggttaaaacccaattcacccagtgacactgtacaggaa<br>gggaaatatgtgatatacaagcgatacaatgacacatgcccagatgag<br>caagactaccagattcgaatggccaagtcttcgtataagcctggacgg<br>tttggtgggaaacgcatacagcaggctatcttatctatcaaggtgtca<br>acatccttaggcgaagacccggtactgactgtaccgcccaacacagtc<br>acactcatgggggccgaaggcagaattctcacagtagggacatctcat |

TABLE 3-continued

| Bovine RSV F Sequences |
| --- |
| ttcttgtatcaacgagggtcatcatacttctctcccgcgttattatat<br>cctatgacagtcagcaacaaaacagccactcttcatagtccttataca<br>ttcaatgccttcactcggccaggtagtatcccttgccaggcttcagca<br>agatgccccaactcgtgtgttactggagtctatacagatccatatccc<br>ctaatcttctatagaaaccacaccttgcgaggggtattcgggacaatg<br>cttgatggtgtacaagcaagacttaaccctgcgtctgcagtattcgat<br>agcacatcccgcagtcgcattactcgagtgagttcaagcagtaccaaa<br>gcagcatacacaacatcaacttgttttaaagtggtcaagactaataag<br>acctattgtctcagcattgctgaaatatctaatactctcttcggagaa<br>ttcagaatcgtcccgttactagttgagatcctcaaagatgacggggtt<br>agagaagccaggtctggctagttgagtcaattataaaggagttggaaa<br>gatggcattgtatcacctatcttctgcgacatcaagaatcaaaccgaa<br>tgccggcgcgtgctcgaattccatgttgccagttgaccacaatcagcc<br>agtgctcatgcgatcagattaagccttgtcaAtaGtctcttgattaag<br>aaaaaatgtaagtggcaatgagatacaaggcaaaacagctcatggtTa<br>aCaatacgggtaggacatggcgagctccggtcctgaaagggcagagca<br>tcagattatcctaccagagTcacacctgtcttcaccattggtcaagca<br>caaactactctattactggaaattaactgggctaccgcttcctgatga<br>atgtgacttcgaccacctcattctcagccgacaatggaaaaaaatact<br>tgaatcggcctctcctgatactgagagaatgataaaactcggaagggc<br>agtacaccaaactcttaaccacaattccagaataaccggagtgctcca<br>ccccaggtgtttagaaGaactggctaatattgaggtcccagattcaac<br>caacaaatttcggaagattgagaagaagatccaaattcacaacacgag<br>atatggagaactgttcacaaggctgtgtacgcatatagagaagaaact<br>gctggggtcatcttggtctaacaatgtcccccggtcagaggagttcag<br>cagcattcgtacggatccggcattctggtttcactcaaaatggtccac<br>agccaagtttgcatggctccatataaaacagatccagaggcatctgat<br>ggtggcagctaGgacaaggtctgcggccaacaaattggtgatgctaac<br>ccataaggtaggccaagtctttgtcactcctgaacttgtcgttgtgac<br>gcatacgaatgagaacaagttcacatgtcttacccaggaacttgtatt<br>gatgtatgcagatatgatggagggcagagatatggtcaacataatatc<br>aaccacggcggtgcatctcagaagcttatcagagaaaattgatgacat<br>tttgcggttaatagacgctctggcaaaagacttgggtaatcaagtcta<br>cgatgttgtatcactaatggagggatttgcatacggagctgtccagct<br>actcgagccgtcaggtacatttgcaggagatttcttcgcattcaacct<br>gcaggagcttaaagacattctaattggcctcctccccaatgatatagc<br>agaatccgtgactcatgcaatcgctactgtattctctggtttagaaca<br>gaatcaagcagctgagatgttgtgtctgttgcgtctgtggggtcaccc<br>actgcttgagtcccgtattgcagcaaaggcagtcaggagccaaatgtg<br>cgcaccgaaaatggtagactttgatatgatccttcaggtactgtcttt<br>cttcaagggaacaatcatcaacgggtacagaaagaagaatgcaggtgt<br>gtggccgcgagtcaaagtggatacaatatatgggaaggtcattgggca<br>actacatgcagattcagcagagatttcacacgatatcatgttgagaga<br>gtataagagtttatctgcacttgaatttgagccatgtatagaatatga<br>ccctgtcaccaacctgagcatgttcctaaaagacaaggcaatcgcaca<br>ccccaacgataattggcttgcctcgtttaggcggaaccttctctccga<br>agaccagaagaaacatgtaaaagaagcaacttcgactaatcgcctctt<br>gatagagtttttagagtcaaatgattttgatccatataaagagatgga<br>atatctgacgacccttgagtaccttagagatgacaatgtggcagtatc<br>atactcgctcaaggagaaggaagtgaaagttaatggacggatcttcgc<br>taagctgacaaagaagttaaggaactgtcaggtgatggcggaagggat<br>cctagccgatcagattgcacctttctttcagggaaatggagtcattca<br>ggatagcatatccttgaccaagagtatgctagcgatgagtcaactgtc<br>ttttaacagcaataagaaacgtatcactgactgtaaagaaagagtatc<br>ttcaaaccgcaatcatgatccgaaaagcaagaaccgtcggagagttgc<br>aaccttcataacaactgacctgcaaaagtactgtcttaattggagata<br>tcagacaatcaaattgttcgctcatgccatcaatcagttgatgggcct<br>acctcacttcttcgaatggattcacctaagactgatggacactacgat<br>gttcgtaggagaccctttcaatcctccaagtgaccctactgactgtga<br>cctctcaagagtccctaatgatgacatatatattgtcagtgccagagg<br>gggtatcgaaggattatgccagaagctatggacaatgatctcaattgc<br>tgcaatccaacttgctgcagctagatcgcattgtcgtgttgcctgtat<br>ggtacagggtgataatcaagtaatagcagtaacgagagaggtaagatc<br>agacgactctccggagatggtgttgacacagttgcatcaagccagtga<br>taatttcttcaaggaattaattcatgtcaatcatttgattggccataa<br>tttgaaggatcgtgaaaccatcaggtcagacacattcttcatatacag<br>caaacgaatcttcaaagatggagcaatcctcagtcaagtcctcaaaaa<br>ttcatctaaattagtgctagtgtcaggtgatctcagtgaaaacaccgt<br>aatgtcctgtgccaacattgcctctactgtagcacggctatgcgagaa<br>cgggcttcccaaagacttctgttactatttaaactatataatgagttg<br>tgtgcagacatactttgactctgagttctccatcaccaacaattcgca<br>ccccgatcttaatcagtcgtggattgaggacatctcttttgtgcactc<br>atatgttctgactcctgcccaattagggggactgagtaaccttcaata<br>ctcaaggctctacactagaaatatcggtgacccggggactactgcttt<br>tgcagagatcaagcgactagaagcagtgggattactgagtcctaacat<br>tatgactaatatcttaactaggccgcctgggaatggagattgggccag<br>tctgtgcaacgacccatactctttcaattttgagactgttgcaagccc<br>aaatattgttcttaagaaacatacgcaaagagtcctatttgaaacttg |

TABLE 3-continued

| Bovine RSV F Sequences |
| --- |
| ttcaaatcccttattgtctggagtgcacacagaggataatgaggcaga<br>agagaaggcattggctgaattcttgcttaatcaagaggtgattcatcc<br>ccgcgttgcgcatgccatcatggaggcaagctctgtaggtaggagaaa<br>gcaaattcaagggcttgttgacacaacaaacaccgtaattaagattgc<br>gcttactaggaggccattaggcatcaagaggctgatgcggatagtcaa<br>ttattctagcatgcatgcaatgctgtttagagacgatgtttttttcctc<br>cagtagatccaaccaccccttagtctcttctaatatgtgttctctgac<br>actggcagactatgcacggaatagaagctggtcacctttgacgggagg<br>caggaaaatactgggtgtatctaatcctgatacgatagaactcgtaga<br>gggtgagattcttagtgtaagcggagggtgtacaagatgtgacagcgg<br>agatgaacaatttacttggttccatcttccaagcaatatagaattgac<br>cgatgacaccagcaagaatcctccgatgagggtaccatatctcgggtc<br>aaagacacaggagaggagagctgcctcacttgcaaaaatagctcatat<br>gtcgccacatgtaaaggctgccctaagggcatcatccgtgttgatctg<br>ggcttatggggataatgaagtaaattggactgctgctcttacgattgc<br>aaaatctcggtgtaatgtaaacttagagtatcttcggttactgtcccc<br>tttacccacggctgggaatcttcaacatagactagatgatggtataac<br>tcagatgacattcaccccctgcatctctctacaggGtgtcaccttacat<br>tcacatatccaatgattctcaaaggctgttcactgaagaaggagtcaa<br>agaggggaatgtggtttaccaacagatcatgctcttgggtttatctct<br>aatcgaatcgatctttccaatgacaacaaccaggacatatgatgagat<br>cacactgcacctacatagtaaatttagttgctgtatcagagaagcacc<br>tgttgcggttcctttcgagctacttggggtggtaccggaactgaggac<br>agtgacctcaaataagtttatgtatgatcctagccctgtatcggaggg<br>agactttgcgagacttgacttagctatcttcaagagttatgagcttaa<br>tctggagtcatatcccacgatagagctaatgaacattctttcaatatc<br>cagcgggaagttgattggccagtctgtggtttcttatgatgaagatac<br>ctccataaagaatgacgccataatagtgtatgacaatacccgaaattg<br>gatcagtgaagctcagaattcagatgtggtccgcctatttgaatatgc<br>agcacttgaagtgctcctcgactgttcttaccaactctattacctgag<br>agtaagaggcctGgacaatattgtcttatatatgggtgatttatacaa<br>gaatatgccaggaattctactttccaacattgcagctacaatatctca<br>tcccgtcattcattcaaggttacatgcagtgggcctggtcaaccatga<br>cggatcacaccaacttgcagatacggattttatcgaaatgtctgcaaa<br>actattagtatcttgcacccgacgtgtgatctccggcttatattcagg<br>aaataagtatgatctgctgttcccatctgtcttagatgataacctgaa<br>tgagaagatgcttcagctgatatcccggttatgctgtctgtacacggt<br>actctttgctacaacaagagaaatcccgaaaataagaggcttaactgc<br>agaagagaaatgttcaatactcactgagtatttactgtcggatgctgt<br>gaaaccattacttagccccgatcaagtgagctctatcatgtctcctaa<br>cataattacattcccagctaatctgtactacatgtctcggaagagcct<br>caatttgatcagggaaagggaggacagggatactatcctggcgttgtt<br>gttcccccaagagccattattagagttcccttctgtgcaagatattgg<br>tgctcgagtgaaagatccattcacccgacaacctgcggcatttttgca<br>agagttagatttgagtgctccagcaaggtatgacgcattcacacttag<br>tcagattcatcctgaactcacatctccaaatccggaggaagactactt<br>agtacgatacttgttcagagggatagggactgcatcttcctcttggta<br>taaggcatctcatctcctttctgtacccgaggtaagatgtgcaagaca<br>cgggaactccttatacttagctgaagggagcggagccatcatgagtct<br>tctcgaactgcatgtaccacatgaaactatctattacaatacgctctt<br>ttcaaatgagatgaacccccgcaacgacatttcgggccgaccccaac<br>tcagtttttgaattcggttgtttataggaatctacaggcggaggtaac<br>atgcaaagatggatttgtccaagagttccgtccattatggagagaaaa<br>tacagaggaaagCgacctgacctcagataaagTagtggggtatattac<br>atctgcagtgccctacagatctgtatcattgctgcattgtgacattga<br>aattcctccagggtccaatcaaagcttactagatcaactagctatcaa<br>tttatctctgattgccatgcattctgtaagggagggcggggtagtaat<br>catcaaagtgttgtatgcaatgggatactactttcatctactcatgaa<br>cttgtttgctccgtgttccacaaaaggatatattctctctaatggtta<br>tgcatgtcgaggagatatggagtgttacctggtatttgtcatgggtta<br>cctgggcgggcctacatttgtacatgaggtggtgaggatggcGaaaac<br>tctggtgcagcggcacggtacgctTttgtctaaatcagatgagatcac<br>actgaccaggttattcacctcacagcggcagcgtgtgacagacatcct<br>atccagtcctttaccaagattaataaagtacttgaggaagaatattga<br>cactgcgctgattgaagccgggggacagcccgtccgtccattctgtgc<br>ggagagtctggtgagcacgctagcgaacataactcagataacccagat<br>Catcgctagtcacattgacacagttatccggtctgtgatatatatgga<br>agctgagggtgatctcgctgacacagtatttctatttaccccttacaa<br>tctctctactgacgggaaaaagaggacatcacttaAacagtgcacgag<br>acagatcctagaggttacaatactaggtcttagagtcgaaaatctcaa<br>taaaataggcgatataatcagcctagtgcttaaaggcatgatctccat<br>ggaggaccttatcccactaaggacatacttgaagcatagtacctgccc<br>taaatatttgaaggctgtcctaggtattaccaaactcaaagaaatgtt |

TABLE 3-continued

| Bovine RSV F Sequences | | |
|---|---|---|
| | tacagacacttctgtaCtgtacttgactcgtgctcaacaaaaattcta<br>catgaaaactataggcaatgcagtcaaaggatattacagtaactgtga<br>ctcttaacgaaaatcacatattaataggctccttttttggccaattgt<br>attcttgttgatttaatcatattatgttagaaaaaagttgaaccctga<br>ctccttaggactcgaattcgaactcaaataaatgtcttaaaaaaaggt<br>tgcgcacaattattcttgagtgtagtctcgtcattcaccaaatctttg<br>tttggt | |
| CDNA of genomic sequence of NDV LaSota strain with the codon optimized nucleic acid sequence encoding bovine RSV F protein of strain ATCC51908 inserted (codon optimized nucleic acid sequence of bovine RSV F protein is underlined) | accaaacagagaatccgtgagttacgataaaaggcgaaggagcaattg<br>aagtcgcacgggtagaaggtgtgaatctcgagtgcgagcccgaagcac<br>aaactcgagaaagccttctgccaacatgtcttccgtatttgatgagta<br>cgaacagctcctcgcggctcagactcgccccaatggagctcatggagg<br>gggagaaaaagggagtaccttaaaagtagacgtcccggtattcactct<br>taacagtgatgacccagaagatagatggagctttgtggtattctgcct<br>ccggattgctgttagcgaagatgccaacaaaccactcaggcaaggtgc<br>tctcatatctcttttatgctcccactcacaggtaatgaggaaccatgt<br>tgccCttgcagggaaacagaatgaagccacattggccgtgcttgagat<br>tgatggctttgccaacggcacgccccagttcaacaataggagtggagt<br>gtctgaagagagagcacagagatttgcgatgatagcaggatctctccc<br>tcgggcatgcagcaacggaaccccgttcgtcacagccggggcCgaaga<br>tgatgcaccagaagacatcaccgataccctggagaggatcctctctat<br>ccaggctcaagtatgggtcacagtagcaaaagccatgactgcgtatga<br>gactgcagatgagtcggaaacaaggcgaatcaataagtatatgcagca<br>aggcagggtccaaaagaaatacatcctctaccccgtatgcaggagcac<br>aatccaactcacgatcagacagtctcttgcagtccgcatcttttggt<br>tagcgagctcaagagaggccgcaacacggcaggtggtacctctactta<br>ttataacctggtaggggacgtagactcatacatcaggaataccgggct<br>tactgcattcttcttgacactcaagtacggaatcaacaccaagacatc<br>agcccttgcacttagtagcctctcaggcgacatccagaagatgaagca<br>gctcatgcgtttgtatcggatgaaaggagataatgcgccgtacatgac<br>attacttggtgatagtgaccagatgagctttgcgcctgccgagtatgc<br>acaactttactcctttgccatgggtatggcatcagtcctagataaagg<br>tactgggaaataccaatttgccagggactttatgagcacatcattctg<br>gagacttggagtagagtacgctcaggctcagggaagtagcattaacga<br>ggatatggctgccgagctaaagctaaccccagcagcaaGgaGgggcct<br>ggcagctgctgcccaacgggtctccgaGgaGaccagcagcataGacat<br>gcctactcaacaagtcggagtcctcactgggcttagcgagggggggtc<br>ccaagctctacaaggcggatcgaatagatcgcaagggcaaccagaagc<br>cggggatggggagacccaattcctggatctgatgagagcggtagcaaa<br>tagcatgagggaggcgccaaactctgcacagggcactccccaatcggg<br>gcctcccccaactcctgggccatcccaagataacgacaccgactgggg<br>gtattgatggacaaaacccagcctgcttccacaaaaacatcccaatgc<br>cctcacccgtagtcgacccctcgatttgcggctctatatgaccacacc<br>ctcaaacaaacatcccctctttcctccctcccctgctgtacaactA<br>cgTacgccctagataccacaggcacaatgcggctcactaacaatcaaa<br>acagagccgagggaattagaaaaaagtacgggtagaagagggatattc<br>agagatcagggcaagtctcccgagtctctgctctctcctctacctgat<br>agaccaggacaaacatggccacctttacagatgcagagatcgacgagc<br>tatttgagacaagtggaactgtcattgacaacataattacagcccagg<br>gtaaaccagcagagactgttggaaggagtgcaatcccacaaggcaaga<br>ccaaggtgctgagcgcagcatgggagaagcatgggagcatccagccac<br>cggccagtcaagacaaccccgatcgacaggacagatctgacaaacaac<br>catccacacccgagcaaacgaccccgcatgacagcccgccggccacat<br>ccgccgaccagcccccacccaggccacagacgaagccgtcgacacac<br>agCtcaggaccggagcaagcaactctctgctgttgatgcttgacaagc<br>tcagcaataaatcgtccaatgctaaaaagggcccatggtcgagccccc<br>aagaggggaatcaccaacgtccgactcaacagcaggggagtcaaccca<br>gtcgcggaaacagtcaggaaagaccgcagaaccaagtcaaggccgccc<br>ctggaaaccagggcacagacgtgaacacagcatatcatggacaatggg<br>aggagtcacaactatcagctggtgcaacccctcatgctctccgatcaa<br>ggcagagccaagacaatacccttgtatctgcggatcatgtccagccac<br>ctgtagactttgtgcaagcgatgatgtctatgatggaggcgatatcac<br>agagagtaagtaaggttgactatcagctagatcttgtcttgaaacaga<br>catcctccatccctatgatgcggtccgaaatccaacagctgaaaacat<br>ctgttgcagtcatggaagccaacttgggaatgatgaagattctggatc<br>ccggttgtgccaacatttcatctctgagtgatctacgggcagttgccc<br>gatctcacccggttttagtttcaggccctggagacccctctccctatg<br>tgacacaaggaggcgaaatggcacttaataaactttcgcaaccagtgc<br>cacatccatctgaattgattaaacccgccactgcatgcgggcctgata<br>taggagtggaaaaggacactgtccgtgcattgatcatgtcacgcccaa<br>tgcacccgagttcttcagccaagctcctaagcaagttagatgcagccg<br>ggtcgatcgaggaaatcaggaaaatcaagcgccttgctctaaatggct<br>aattactactgccacacgtagcgggtccctgtccactcggcatcacac<br>ggaatctgcaccgagttccccccgcGgTTAGAAAAAATACGGGTAGA<br>ACCGCCACCATGGCCACCACCGCCATGCGCATGATCATCAGCATCATC<br>TTCATCAGCACCTACGTGACCCACATCACCCTGTGCCAGAACATCACC<br>GAGGAGTTCTACCAGAGCACCTGCAGCGCCGTGAGTCGCGGCTACCTG<br>AGCGCCCTGCGCACCGGCTGGTACACCAGCGTGGTGACCATCGAGCTG | 13 |

TABLE 3-continued

| Bovine RSV F Sequences |
|---|
| AGCAAGATCCAGAAGAACGTGTGCAACAGCACCGACAGCAAGGTGAAG |
| CTGATCAAGCAGGAGCTGGAGCGCTACAACAACGCCGTGGTGGAGCTG |
| CAGAGCCTGATGCAGAACGAGCCCGCCAGCTTCAGCCGCGCCAAGCGC |
| GGCATCCCCGAGCTGATCCACTACACCCGCAACAGCACCAAGAAGTTC |
| TACGGCCTGATGGGCAAGAAGCGCAAGCGCCGCTTCCTGGGCTTCCTG |
| CTGGGCATCGGCAGCGCCATCGCCAGCGGCGTGGCCGTGAGCAAGGTG |
| CTGCACCTGGAGGGCGAGGTGAACAAGATCAAGAACGCCCTGCTGAGC |
| ACCAACAAGGCCGTGGTGAGCCTGAGCAACGGCGTGAGCGTGCTGACC |
| AGCAAGGTGCTGGACCTGAAGAACTACATCGACAAGGAGCTGCTGCCC |
| AAGGTGAACAACCACGACTGCCGCATCAGCAAGATCGAGACCGTGATC |
| GAGTTCCAGCAGAAGAACAACCGCCTGCTGGAGATCGCCCGCGAGTTC |
| AGCGTGAACGCCGGCATCACCACCCCCCTGAGCACCTACATGCTGACC |
| AACAGCGAGCTGCTGAGCCTGATCAACGACATGCCCATCACCAACGAC |
| CAGAAGAAGCTGATGAGCAGCAACGTGCAGATCGTGCGCCAGCAGAGC |
| TACAGCATCATGAGCGTGGTGAAGGAGGAGGTGATCGCCTACGTGGTG |
| CAGCTGCCCATCTACGGCGTGATCGACACCCCCTGCTGGAAGCTGCAC |
| ACCAGCCCCCTGTGCACCACCGACAACAAGGAGGGCAGCAACATCTGC |
| CTGACCCGCACCGATCGCGGCTGGTACTGCGACAACGCCGGCAGCGTG |
| AGCTTCTTCCCCCAGACCGAGACCTGCAAGGTGCAGAGCAACCGCGTG |
| TTCTGCGACACCATGAACAGCCTGACCCTGCCCACCGACGTGAACCTG |
| TGCAACACCGACATCTTCAACACCAAGTACGACTGCAAGATCATGACC |
| AGCAAGACCGACATCAGCAGCAGCGTGATCACCAGCATCGGCGCCATC |
| GTGAGCTGCTACGGCAAGACCAAGTGCACCGCCAGCAACAAGAATCGC |
| GGCATCATCAAGACCTTCAGCAACGGCTGCGACTACGTGAGCAACAAG |
| GGCGTGGACACCGTGAGCGTGGGCAACACCCTGTACTACGTGAACAAG |
| CTGGAGGGCAAGGCCCTGTACATCAAGGGCGAGCCCATCATCAACTAC |
| TACGACCCCCTGGTGTTCCCCAGCGACGAGTTCGACGCCAGCATCGCC |
| CAGGTGAACGCCAAGATCAACCAGAGCCTGGCCTTCATCCGCCGCAGC |
| GACGAGCTGCTGCACAGCGTGGACGTGGGCAAGAGCACCACCAACGTG |
| GTGATCACCACCATCATCATCGTGATCGTGGTGGTGATCCTGATGCTG |
| ATCGCCGTGGGCCTGCTGTTCTACTGCAAGACCAAGAGCACCCCCATC |
| ATGCTGGGCAAGGACCAGCTGAGCGGCATCAACAACCTGAGCTTCAGC |
| AAGTAAccccccgcggacccaaggtccaactctccaagcggcaatcct |
| ctctcgcttcctcagccccactgaatgAtcgcgtaaccgtaattaatc |
| tagctacatttaagattaagaaaaaatacgggtagaattggagtgccc |
| caattgtgccaagatggactcatctaggacaattgggctgtactttga |
| ttctgcccattcttctagcaacctgttagcatttccgatcgtcctaca |
| agAcacaggagatgggaagaagcaaatcgccccgcaatataggatcca |
| gcgccttgacttgtggactgatagtaaggaggactcagtattcatcac |
| cacctatggattcatctttcaagttgggaatgaagaagccacCgtcgg |
| catgatcgatgataaacccaagcgcgagttactttccgctgcgatgct |
| ctgcctaggaagcgtcccaaataccggagaccttattgagctggcaag |
| ggcctgtctcactatgatagtcacatgcaagaagagtgcaactaatac |
| tgagagaatggttttctcagtagtgcaggcaccccaagtgctgcaaag |
| ctgtagggttgtggcaaacaaatactcatcagtgaatgcagtcaagca |
| cgtgaaagcgccagagaagattcccgggagtggaaccctagaatacaa |
| ggtgaactttgtctccttgactgtggtaccgaagaGggatgtctacaa |
| gatcccagctgcagtattgaaggtttctggctcgagtctgtacaatct |
| tgcgctcaatgtcactattaatgtggaggtagacccgaggagtccttt |
| ggttaaatctCtgtctaagtctgacagcggatactatgctaacctctt |
| cttgcatattggacttatgaccacTgtagataggaaggggaagaaagt |
| gacatttgacaagctggaaaagaaaataaggagccttgatctatctgt |
| cgggctcagtgatgtgctcgggccttccgtgttggtaaaagcaagagg |
| tgcacggactaagcttttggcacctttcttctctagcagtgggacagc |
| ctgctatcccatagcaaatgcttctcctcaggtggccaagatactctg |
| gagtcaaaccgcgtgcctgcggagcgttaaaatcattatccaagcagg |
| tacccaacgcgctgtcgcagtgaccgccgaccacgaggttacctctac |
| taagctggagaaggggcacacccttgccaaatacaatccttttaagaa |
| ataagctgcgtctctgagattgcgctccgcccactcacccagatcatc |
| atgacacaaaaaactaatctgtcttgattatttacagttagtttacct |
| gtctatcaagttagaaaaaacacgggtagaagattctggatcccggtt |
| ggcgccctccaggtgcaagatgggctccagaccttctaccaagaaccc |
| agcacctatgatgctgactatccgggttgcgctggtactgagttgcat |
| ctgtccggcaaactccattgatggcaggcctcttgcagctgcaggaat |
| tgtggttacaggagacaaagccgtcaacatatacacctcatcccagac |
| aggatcaatcatagttaagctcctcccgaatctgcccaaggataagga |
| ggcatgtgcgaaagccccttggatgcatacaacaggacattgaccac |
| tttgctcaccccccttggtgactctatccgtaggatacaagagtctgt |
| gactacatctggagggggagacaggggcgccttataggcgccattat |
| tggcggtgtggctcttggggttgcaactgccgcacaaataacagcggc |
| cgcagctctgatacaagccaaacaaaatgctgccaacatcctccgact |
| taaagagagcattgccgcaaccaatgaggctgtgcatgaggtcactga |
| cggattatcgcaactagcagtggcagttgggaagatgcagcagtttgt |
| taatgaccaatttaataaaacagctcaggaattagactgcatcaaaat |
| tgcacagcaagttggtgtagagctcaacctgtacctaaccgaattgac |
| tacagtattcggaccacaaatcacttcacctgctttaaacaagctgac |
| tattcaggcactttacaatctagctggtggaaatatggattacttatt |
| gactaagttaggtgtagggaacaatcaactcagctcattaatcggtag |

TABLE 3-continued

| Bovine RSV F Sequences |
| --- |
| cggcttaatcaccggtaaccctattctatacgactcacagactcaact<br>cttgggtatacaggtaactctaccttcagtcgggaacctaaataatat<br>gcgtgccacctacttggaaaccttatccgtaagcacaaccaggggatt<br>tgcctcggcacttgtcccAaaagtggtgacacaggtcggttctgtgat<br>agaagaacttgacacctcatactgtatagaaactgacttagatttata<br>ttgtacaagaatagtaacgttccctatgtcccctggtatttattcctg<br>cttgagcggcaatacgtcggcctgtatgtactcaaagaccgaaggcgc<br>acttactacaccatacatgactatcaaaggttcagtcatcgccaactg<br>caagatgacaacatgtagatgtgtaaacccccgggtatcatatcgca<br>aaactatggagaagccgtgtctctaatagataaacaatcatgcaatgt<br>tttatccttaggcgggataactttaaggctcagtggggaattcgatgt<br>aacttatcagaagaatatctcaatacaagattctcaagtaataataac<br>aggcaatcttgatatctcaactgagcttgggaatgtcaacaactcgat<br>cagtaatgctttgaataagttagaggaaagcaacagaaaactagacaa<br>agtcaatgtcaaactgactagcacatctgctctcattacctatatcgt<br>tttgactatcatatctcttgtttttggtatacttagcctgattctagc<br>atgctacctaatgtacaagcaaaaggcgcaacaaaagaccttattatg<br>gcttgggaataatactctagatcagatgagagccactacaaaaatgtg<br>aacacagatgaggaacgaaggtttccctaatagtaatttgtgtgaaag<br>ttctggtagtctgtcagttcagagagttaagaaaaaactaccggttgt<br>agatgaccaaaggacgatatacgggtagaacggtaagagaggccgccc<br>ctcaattgcgagccaggcttcacaacctccgttctaccgcttcaccga<br>caacagtcctcaatcatggaccgcgccgttagccaagttgcgttagag<br>aatgatgaaagagaggcaaaaaatacatggcgcttgatattccggatt<br>gcaatcttattcttaacagtagtgaccttggctatatctgtagcctcc<br>cttttatatagcatgggggctagcacacctagcgatcttgtaggcata<br>ccgactaggatttccagggcagaagaaaagattacatctacacttggt<br>tccaatcaagatgtagtagataggatatataagcaagtggcccttgag<br>tctccgttggcattgttaaatactgagaccacaattatgaacgcaata<br>acatctctctcttatcagattaatggagctgcaaacaacagtgggtgg<br>ggggcacctatccatgacccagattatatagggggggataggcaaagaa<br>ctcattgtagatgatgctagtgatgtcacatcattctatccctctgca<br>tttcaagaacatctgaattttatcccggcgcctactacaggatcaggt<br>tgcactcgaataccctcatttgacatgagtgctacccattactgctac<br>acccataatgtaatattgtctggatgcagagatcactcacattcatat<br>cagtatttagcacttggtgtgctccggacatctgcaacagggagggta<br>ttctttttctactctgcgttccatcaacctggacgacacccaaaatcgg<br>aagtcttgcagtgtgagtgcaactcccctgggttgtgatatgctgtgc<br>tcgaaagtcacggagacagaggaagaagattataactcagctgtccct<br>acgcggatggtacatgggaggttagggttcgacggccagtaccacgaa<br>aaggacctagatgtcacaacattattcggggactgggtggccaactac<br>ccaggagtagggggtggatcttttattgacagccgcgtatggttctca<br>gtctacggagggttaaaacccaattcacccagtgacactgtacaggaa<br>gggaaatatgtgatatacaagcgatacaatgacacatgcccagatgag<br>caagactaccagattcgaatggccaagtcttcgtataagcctggacgg<br>tttggtgggaaacgcatacagcaggctatcttatctatcaaggtgtca<br>acatccttaggcgaagacccggtactgactgtaccgcccaacacagtc<br>acactcatgggggccgaaggcagaattctcacagtagggacatctcat<br>ttcttgtatcaacgagggtcatcatacttctctcccgcgttattatat<br>cctatgacagtcagcaacaaaacagccactcttcatagtccttataca<br>ttcaatgccttcactcggccaggtagtatcccttgccaggcttcagca<br>agatgccccaactcgtgtgttactggagtctatacagatccatatccc<br>ctaatcttctatagaaaccacaccttgcgaggggtattcgggacaatg<br>cttgatggtgtacaagcaagacttaaccctgcgtctgcagtattcgat<br>agcacatcccgcagtcgcattactcgagtgagttcaagcagtaccaaa<br>gcagcatacacaacatcaacttgttttaaagtggtcaagactaataag<br>acctattgtctcagcattgctgaaatatctaatactctcttcggagaa<br>ttcagaatcgtcccgttactagttgagatcctcaaagatgacggggtt<br>agagaagccaggtctggctagttgagtcaattataaaggagttggaaa<br>gatggcattgtatcacctatcttctgcgacatcaagaatcaaaccgaa<br>tgccggcgcgtgctcgaattccatgttgccagttgaccacaatcagcc<br>agtgctcatgcgatcagattaagccttgtcaAtaGtctcttgattaag<br>aaaaaatgtaagtggcaatgagatacaaggcaaaacagctcatggtTa<br>aCaatacgggtaggacatggcgagctccggtcctgaaagggcagagca<br>tcagattatcctaccagagTcacacctgtcttcaccattggtcaagca<br>caaactactctattactggaaattaactgggctaccgcttcctgatga<br>atgtgacttcgaccacctcattctcagccgacaatggaaaaaaatact<br>tgaatcggcctctcctgatactgagagaatgataaaactcggaagggc<br>agtacaccaaactcttaaccacaattccagaataaccggagtgctcca<br>ccccaggtgtttagaaGaactggctaatattgaggtcccagattcaac<br>caacaaatttcggaagattgagaagaagatccaaattcacaacacgag<br>atatggagaactgttcacaaggctgtgtacgcatatagagaagaaact<br>gctggggtcatcttggtctaacaatgtcccccggtcagaggagttcag<br>cagcattcgtacggatccggcattctggtttcactcaaaatggtccac<br>agccaagtttgcatggctccatataaaacagatccagaggcatctgat<br>ggtggcagctaGgacaaggtctgcggccaacaaattggtgatgctaac<br>ccataaggtaggccaagtctttgtcactcctgaacttgtcgttgtgac<br>gcatacgaatgagaacaagttcacatgtcttacccaggaacttgtatt |

TABLE 3-continued

| Bovine RSV F Sequences |
|---|
| gatgtatgcagatatgatggagggcagagatatggtcaacataatatc<br>aaccacggcggtgcatctcagaagcttatcagagaaaattgatgacat<br>tttgcggttaatagacgctctggcaaaagacttgggtaatcaagtcta<br>cgatgttgtatcactaatggagggatttgcatacggagctgtccagct<br>actcgagccgtcaggtacatttgcaggagatttcttcgcattcaacct<br>gcaggagcttaaagacattctaattggcctcctccccaatgatatagc<br>agaatccgtgactcatgcaatcgctactgtattctctggtttagaaca<br>gaatcaagcagctgagatgttgtgtctgttgcgtctgtggggtcaccc<br>actgcttgagtcccgtattgcagcaaaggcagtcaggagccaaatgtg<br>cgcaccgaaaatggtagactttgatatgatccttcaggtactgtcttt<br>cttcaagggaacaatcatcaacgggtacagaaagaagaatgcaggtgt<br>gtggccgcgagtcaaagtggatacaatatatgggaaggtcattgggca<br>actacatgcagattcagcagagatttcacacgatatcatgttgagaga<br>gtataagagtttatctgcacttgaatttgagccatgtatagaatatga<br>ccctgtcaccaacctgagcatgttcctaaaagacaaggcaatcgcaca<br>ccccaacgataattggcttgcctcgtttaggcggaaccttctctccga<br>agaccagaagaaacatgtaaaagaagcaacttcgactaatcgcctctt<br>gatagagtttttagagtcaaatgattttgatccatataaagagatgga<br>atatctgacgacccttgagtaccttagagatgacaatgtggcagtatc<br>atactcgctcaaggagaaggaagtgaaagttaatggacggatcttcgc<br>taagctgacaaagaagttaaggaactgtcaggtgatggcggaagggat<br>cctagccgatcagattgcacctttctttcagggaaatggagtcattca<br>ggatagcatatccttgaccaagagtatgctagcgatgagtcaactgtc<br>ttttaacagcaataagaaacgtatcactgactgtaaagaaagagtatc<br>ttcaaaccgcaatcatgatccgaaaagcaagaaccgtcggagagttgc<br>aaccttcataacaactgacctgcaaaagtactgtcttaattggagata<br>tcagacaatcaaattgttcgctcatgccatcaatcagttgatgggcct<br>acctcacttcttcgaatggattcacctaagactgatggacactacgat<br>gttcgtaggagaccctttcaatcctccaagtgaccctactgactgtga<br>cctctcaagagtccctaatgatgacatatatattgtcagtgccagagg<br>gggtatcgaaggattatgccagaagctatggacaatgatctcaattgc<br>tgcaatccaacttgctgcagctagatcgcattgtcgtgttgcctgtat<br>ggtacagggtgataatcaagtaatagcagtaacgagagaggtaagatc<br>agacgactctccggagatggtgttgacacagttgcatcaagccagtga<br>taatttcttcaaggaattaattcatgtcaatcatttgattggccataa<br>tttgaaggatcgtgaaaccatcaggtcagacacattcttcatatacag<br>caaacgaatcttcaaagatggagcaatcctcagtcaagtcctcaaaaa<br>ttcatctaaattagtgctagtgtcaggtgatctcagtgaaaacaccgt<br>aatgtcctgtgccaacattgcctctactgtagcacggctatgcgagaa<br>cgggcttcccaaagacttctgttactatttaaactatataatgagttg<br>tgtgcagacatactttgactctgagttctccatcaccaacaattcgca<br>ccccgatcttaatcagtcgtggattgaggacatctcttttgtgcactc<br>atatgttctgactcctgcccaattaggggactgagtaaccttcaata<br>ctcaaggctctacactagaaatatcggtgacccggggactactgcttt<br>tgcagagatcaagcgactagaagcagtgggattactgagtcctaacat<br>tatgactaatatcttaactaggccgcctgggaatggagattgggccag<br>tctgtgcaacgacccatactctttcaattttgagactgttgcaagccc<br>aaatattgttcttaagaaacatacgcaaagagtcctatttgaaacttg<br>ttcaaatcccttattgtctggagtgcacacagaggataatgaggcaga<br>agagaaggcattggctgaattcttgcttaatcaagaggtgattcatcc<br>ccgcgttgcgcatgccatcatggaggcaagctctgtaggtaggagaaa<br>gcaaattcaagggcttgttgacacaacaaacaccgtaattaagattgc<br>gcttactaggaggccattaggcatcaagaggctgatgcggatagtcaa<br>ttattctagcatgcatgcaatgctgtttagagacgatgtttttttcctc<br>cagtagatccaaccaccccttagtctcttctaatatgtgttctctgac<br>actggcagactatgcacggaatagaagctggtcacctttgacgggagg<br>caggaaaatactgggtgtatctaatcctgatacgatagaactcgtaga<br>gggtgagattcttagtgtaagcggagggtgtacaagatgtgacagcgg<br>agatgaacaatttacttggttccatcttccaagcaatatagaattgac<br>cgatgacaccagcaagaatcctccgatgagggtaccatatctcgggtc<br>aaagacacaggagaggagagctgcctcacttgcaaaaatagctcatat<br>gtcgccacatgtaaaggctgccctaagggcatcatccgtgttgatctg<br>ggcttatggggataatgaagtaaattggactgctgctcttacgattgc<br>aaaatctcggtgtaatgtaaacttagagtatcttcggttactgtcccc<br>tttacccacggctgggaatcttcaacatagactagatgatggtataac<br>tcagatgacattcacccctgcatctctctacaggGtgtcaccttacat<br>tcacatatccaatgattctcaaaggctgttcactgaagaaggagtcaa<br>agaggggaatgtggtttaccaacagatcatgctcttgggtttatctct<br>aatcgaatcgatctttccaatgacaacaaccaggacatatgatgagat<br>cacactgcacctacatagtaaatttagttgctgtatcagagaagcacc<br>tgttgcggttcctttcgagctacttggggtggtaccggaactgaggac<br>agtgacctcaaataagtttatgtatgatcctagccctgtatcggaggg<br>agactttgcgagacttgacttagctatcttcaagagttatgagcttaa<br>tctggagtcatatcccacgatagagctaatgaacattctttcaatatc<br>cagcgggaagttgattggccagtctgtggtttcttatgatgaagatac<br>ctccataaagaatgacgccataatagtgtatgacaatacccgaaattg<br>gatcagtgaagctcagaattcagatgtggtccgcctatttgaatatgc<br>agcacttgaagtgctcctcgactgttcttaccaactctattacctgag |

TABLE 3-continued

| Bovine RSV F Sequences | | |
|---|---|---|
| | agtaagaggcctGgacaatattgtcttatatatgggtgatttatacaa<br>gaatatgccaggaattctactttccaacattgcagctacaatatctca<br>tcccgtcattcattcaaggttacatgcagtgggcctggtcaaccatga<br>cggatcacaccaacttgcagatacggattttatcgaaatgtctgcaaa<br>actattagtatcttgcacccgacgtgtgatctccggcttatattcagg<br>aaataagtatgatctgctgttcccatctgtcttagatgataacctgaa<br>tgagaagatgcttcagctgatatcccggttatgctgtctgtacacggt<br>actctttgctacaacaagagaaatcccgaaaataagaggcttaactgc<br>agaagagaaatgttcaatactcactgagtatttactgtcggatgctgt<br>gaaaccattacttagccccgatcaagtgagctctatcatgtctcctaa<br>cataattacattcccagctaatctgtactacatgtctcggaagagcct<br>caatttgatcagggaaagggaggacagggatactatcctggcgttgtt<br>gttcccccaagagccattattagagttcccttctgtgcaagatattgg<br>tgctcgagtgaaagatccattcacccgacaacctgcggcattttttgca<br>agagttagatttgagtgctccagcaaggtatgacgcattcacacttag<br>tcagattcatcctgaactcacatctccaaatccggaggaagactactt<br>agtacgatacttgttcagagggatagggactgcatcttcctcttggta<br>taaggcatctcatctcctttctgtacccgaggtaagatgtgcaagaca<br>cgggaactccttatacttagctgaagggagcggagccatcatgagtct<br>tctcgaactgcatgtaccacatgaaactatctattacaatacgctctt<br>ttcaaatgagatgaacccccccgcaacgacatttcgggccgaccccaac<br>tcagtttttgaattcggttgtttataggaatctacaggcggaggtaac<br>atgcaaagatggatttgtccaagagttccgtccattatggagagaaaa<br>tacagaggaaagCgacctgacctcagataaagTagtggggtatattac<br>atctgcagtgccctacagatctgtatcattgctgcattgtgacattga<br>aattcctccagggtccaatcaaagcttactagatcaactagctatcaa<br>tttatctctgattgccatgcattctgtaagggagggcggggtagtaat<br>catcaaagtgttgtatgcaatgggatactactttcatctactcatgaa<br>cttgtttgctccgtgttccacaaaaggatatattctctctaatggtta<br>tgcatgtcgaggagatatggagtgttacctggtatttgtcatgggtta<br>cctgggcgggcctacatttgtacatgaggtggtgaggatggcGaaaac<br>tctggtgcagcggcacggtacgctTttgtctaaatcagatgagatcac<br>actgaccaggttattcacctcacagcggcagcgtgtgacagacatcct<br>atccagtcctttaccaagattaataaagtacttgaggaagaatattga<br>cactgcgctgattgaagccgggggacagcccgtccgtccattctgtgc<br>ggagagtctggtgagcacgctagcgaacataactcagataacccagat<br>Catcgctagtcacattgacacagttatccggtctgtgatatatatgga<br>agctgagggtgatctcgctgacacagtatttctatttaccccttacaa<br>tctctctactgacgggaaaaagaggacatcacttaAacagtgcacgag<br>acagatcctagaggttacaatactaggtcttagagtcgaaaatctcaa<br>taaaataggcgatataatcagcctagtgcttaaaggcatgatctccat<br>ggaggaccttatcccactaaggacatacttgaagcatagtacctgccc<br>taaatatttgaaggctgtcctaggtattaccaaactcaaagaaatgtt<br>tacagacacttctgtaCtgtacttgactcgtgctcaacaaaaattcta<br>catgaaaactataggcaatgcagtcaaaggatattacagtaactgtga<br>ctcttaacgaaaatcacatattaataggctcctttttttggccaattgt<br>attcttgttgatttaatcatattatgttagaaaaaagttgaaccctga<br>ctccttaggactcgaattcgaactcaaataaatgtcttaaaaaaaggt<br>tgcgcacaattattcttgagtgtagtctcgtcattcaccaaatctttg<br>tttggt | |
| Nucleic acid sequence encoding chimeric F protein comprising the ectodomain of bovine RSV F protein of strain ATCC51908 and the transmembrane and cytoplasmic domains of NDV F protein of NDV LaSota strain, wherein the nucleotide sequence encoding the ectodomain of the RSV F protein is codon optimized (transmembrane and cytoplasmic domains are | ATGGCCACCACCGCCATGCGCATGATCATCAGCATCAT<br>CTTCATCAGCACCTACGTGACCCACATCACCCTGTGCCA<br>GAACATCACCGAGGAGTTCTACCAGAGCACCTGCAGCG<br>CCGTGAGTCGCGGCTACCTGAGCGCCCTGCGCACCGGC<br>TGGTACACCAGCGTGGTGACCATCGAGCTGAGCAAGAT<br>CCAGAAGAACGTGTGCAACAGCACCGACAGCAAGGTG<br>AAGCTGATCAAGCAGGAGCTGGAGCGCTACAACAACGC<br>CGTGGTGGAGCTGCAGAGCCTGATGCAGAACGAGCCCG<br>CCAGCTTCAGCCGCGCCAAGCGCGGCATCCCCGAGCTG<br>ATCCACTACACCCGCAACAGCACCAAGAAGTTCTACGG<br>CCTGATGGGCAAGAAGCGCAAGCGCCGCTTCCTGGGCT<br>TCCTGCTGGGCATCGGCAGCGCCATCGCCAGCGGCGTG<br>GCCGTGAGCAAGGTGCTGCACCTGGAGGGCGAGGTGAA<br>CAAGATCAAGAACGCCCTGCTGAGCACCAACAAGGCCG<br>TGGTGAGCCTGAGCAACGGCGTGAGCGTGCTGACCAGC<br>AAGGTGCTGGACCTGAAGAACTACATCGACAAGGAGCT<br>GCTGCCCAAGGTGAACAACCACGACTGCCGCATCAGCA<br>AGATCGAGACCGTGATCGAGTTCCAGCAGAAGAACAAC<br>CGCCTGCTGGAGATCGCCCGCGAGTTCAGCGTGAACGC<br>CGGCATCACCACCCCCCTGAGCACCTACATGCTGACCA<br>ACAGCGAGCTGCTGAGCCTGATCAACGACATGCCCATC<br>ACCAACGACCAGAAGAAGCTGATGAGCAGCAACGTGC<br>AGATCGTGCGCCAGCAGAGCTACAGCATCATGAGCGTG<br>GTGAAGGAGGAGGTGATCGCCTACGTGGTGCAGCTGCC<br>CATCTACGGCGTGATCGACACCCCCTGCTGGAAGCTGC<br>ACACCAGCCCCCTGTGCACCACCGACAACAAGGAGGGC<br>AGCAACATCTGCCTGACCCGCACCGATCGCGGCTGGTA | 14 |

TABLE 3-continued

| Bovine RSV F Sequences | | |
|---|---|---|
| underlined) | CTGCGACAACGCCGGCAGCGTGAGCTTCTTCCCCCAGA | |
| | CCGAGACCTGCAAGGTGCAGAGCAACCGCGTGTTCTGC | |
| | GACACCATGAACAGCCTGACCCTGCCCACCGACGTGAA | |
| | CCTGTGCAACACCGACATCTTCAACACCAAGTACGACT | |
| | GCAAGATCATGACCAGCAAGACCGACATCAGCAGCAGC | |
| | GTGATCACCAGCATCGGCGCCATCGTGAGCTGCTACGG | |
| | CAAGACCAAGTGCACCGCCAGCAACAAGAATCGCGGC | |
| | ATCATCAAGACCTTCAGCAACGGCTGCGACTACGTGAG | |
| | CAACAAGGGCGTGGACACCGTGAGCGTGGGCAACACCC | |
| | TGTACTACGTGAACAAGCTGGAGGGCAAGGCCCTGTAC | |
| | ATCAAGGGCGAGCCCATCATCAACTACTACGACCCCCT | |
| | GGTGTTCCCCAGCGACGAGTTCGACGCCAGCATCGCCC | |
| | AGGTGAACGCCAAGATCAACCAGAGCCTGGCCTTCATC | |
| | CGCCGCAGCGACGAGCTGCTGCACAGCGTGGACGTGGG | |
| | CAAGAGCACCACCAACGTTAACCTCATTACCTATATCGT | |
| | TTTGACTATCATATCTCTTGTTTTTGGTATACTTAGCCTG | |
| | ATTCTAGCATGCTACCTAATGTACAAGCAAAAGGCGCA | |
| | ACAAAAGACCTTATTATGGCTTGGGAATAATACCCTAG | |
| | ATCAGATGAGAGCCACTACAAAAATGTGA | |
| Nucleic acid | ATGGCGACAACAGCCATGAGGATGATCATCAGCATTATCTTCATCTCTACCT | 31 |
| sequence | ATGTGACACATATCACTTTATGCCAAAACATAACAGAAGAATTTTATCAATC | |
| encoding a | AACATGCAGTGCAGTTAGTAGAGGTTACCTTAGTGCATTAAGAACTGGATG | |
| chimeric F | GTATACAAGTGTGGTAACAATAGAGTTGAGCAAAATACAAAAAAATGTGTG | |
| protein | TAATAGTACTGATTCAAAAGTGAAATTAATAAAGCAAGAACTAGAAAGATA | |
| comprising | CAACAATGCAGTAGTGGAATTGCAGTCACTTATGCAAAATGAACCGGCCTC | |
| bovine RSV F | CTTCAGTAGAGCAAAAAGAGGGATACCAGAGTTGATACATTATACAAGAAA | |
| protein | CTCTACAAAAAAGTITTATGGGCTAATGGGCAAGAAGAGAAAAAGGAGAT | |
| ectodomain of | TTTTAGGATTCTTGCTAGGTATTGGATCTGCTATTGCAAGTGGTGTAGCAGT | |
| bovine RSV | GTCCAAAGTACTACACCTGGAGGGAGAGGTGAATAAAATTAAAAATGCACT | |
| strain | GCTATCCACAAATAAAGCAGTAGTTAGTCTATCCAATGGAGTTAGTGTCCTT | |
| ATCC51908 and | ACTAGCAAAGTACTTGATCTAAAGAACTATATAGACAAAGAGCTTCTACCTA | |
| NDV F protein | AAGTTAACAATCATGATTGTAGGATATCCAAAATAGAAACTGTGATAGAAT | |
| transmembrane | TCCAACAAAAAAACAATAGATTGTTAGAAATTGCTAGGGAATTTAGTGTAA | |
| and cytoplasmic | ATGCTGGTATTACCACACCTCTCAGTACATACATGTTGACCAATAGTGAATT | |
| domains of the | ACTATCACTAATTAATGATATGCCTATAACGAATGACCAAAAAAAGCTAATG | |
| NDV LaSota | TCAAGTAATGTTCAAATAGTCAGGCAACAGAGTTATTCCATTATGTCAGTGG | |
| strain | TCAAAGAAGAAGTCATAGCTTATGTTGTACAATTGCCTATTTATGGAGTTAT | |
| (transmembrane | AGACACCCCCTGTTGGAAACTACACACCTCTCCGTTATGCACCACTGATAAT | |
| and cytoplasmic | AAAGAAGGGTCAAACATCTGCTTAACTAGGACAGATCGTGGGTGGTATTGT | |
| domains of NDV | GACAATGCAGGCTCTGTGTCTTTTTTCCCACAGACAGAGACATGTAAGGTA | |
| F protein are | CAATCAAATAGAGTGTTCTGTGACACAATGAACAGTTTAACTCTGCCTACTG | |
| underlined) | ACGTTAACTTATGCAACACTGACATATTCAATACAAAGTATGACTGTAAAAT | |
| | AATGACATCTAAAACTGACATAAGTAGCTCTGTGATAACTTCAATTGGAGCT | |
| | ATTGTATCATGCTATGGGAAGACAAAATGTACAGCTTCTAATAAAAATCGT | |
| | GGAATCATAAAGACTTTTTCCAATGGGTGTGATTATGTATCAAACAAAGGA | |
| | GTAGATACTGTATCTGTTGGTAACACACTATATTATGTAAATAAGCTAGAGG | |
| | GGAAAGCACTCTATATAAAGGGTGAACCAATTATTAATTACTATGATCCACT | |
| | AGTGTTTCCTTCTGATGAGTTTGATGCATCAATTGCCCAAGTAAACGCAAAA | |
| | ATAAACCAAAGCCTGGCCTTCATACGTCGATCTGATGAGTTACTTCACAGTG | |
| | TAGATGTAGGAAAATCCACCACAAATgttaacCTCATTACCTATATCGTTTTGA | |
| | CTATCATATCTCTTGTTTTTGGTATACTTAGCCTGATTCTAGCATGCTACCTA | |
| | ATGTACAAGCAAAAGGCGCAACAAAAGACCTTATTATGGCTTGGGAATAAT | |
| | ACCCTAGATCAGATGAGAGCCACTACAAAAATGTGA | |

| | | |
|---|---|---|
| Nucleic acid | ATGGCCACCACCGCCATGAGAATGATCATCAGCATCATCTTCATCAGCACCT | 38 |
| sequence | ACGTGACCCACATCACCCTGTGCCAGAACATCACCGAGGAGTTCTACCAGA | |
| encoding | GCACCTGCAGCGCCGTGAGCAGAGGCTACCTGAGCGCCCTGAGAACCGGC | |
| chimeric F | TGGTACACCAGCGTGGTGACCATCGAGCTGAGCAAGATCCAGAAGAACGT | |
| protein, wherein | GTGCAAGAGCACCGACAGCAAGGTGAAGCTGATCAAGCAGGAGCTGGAG | |
| the nucleic acid | AGATACAACAACGCCGTGGTGGAGCTGCAGAGCCTGATGCAGAACGAGCC | |
| sequence | CGCCAGCTTCAGCAGAGCCAAGAGAGGCATCCCCGAGCTGATCCACTACAC | |
| comprises a | CAGAAACAGCACCAAGAAGTTCTACGGCCTGATGGGCAAGAAGAGAAAGA | |
| codon optimized | GAAGATTCCTGGGCTTCCTGCTGGGCATCGGCAGCGCCGTGGCCAGCGGC | |
| nucleic acid | GTGGCCGTGAGCAAGGTGCTGCACCTGGAGGGCGAGGTGAACAAGATCA | |
| sequence | AGAACGCCCTGCTGAGCACCAACAAGGCCGTGGTGAGCCTGAGCAACGGC | |
| encoding the | GTGAGCGTGCTGACCAGCAAGGTGCTGGACCTGAAGAACTACATCGACAA | |
| bovine RSV F | GGAGCTGCTGCCCCAGGTGAACAACCACGACTGCAGAATCAGCAACATCG | |
| protein | AGACCGTGATCGAGTTCCAGCAGAAGAACAACAGACTGCTGGAGATCGCC | |
| ectodomain of | AGAGAGTTCAGCGTGAACGCCGGCATCACCACCCCCCTGAGCACCTACATG | |
| strain | CTGACCAACAGCGAGCTGCTGAGCCTGATCAACGACATGCCCATCACCAAC | |
| ATue51908 and | GACCAGAAGAAGCTGATGAGCAGCAACGTGCAGATCGTGAGACAGCAGA | |
| a nucleic acid | GCTACAGCATCATGAGCGTGGTGAAGGAGGAGGTGATCGCCTACGTGGTG | |
| sequence | CAGCTGCCCATCTACGGCGTGATCGACACCCCCTGCTGGAAGCTGCACACC | |

-continued

| | | |
|---|---|---|
| encoding the<br>transmembrane<br>and cytoplasmic<br>domains of F<br>protein from<br>NDV strain<br>LaSota<br>(transmembrane<br>and cytoplasmic<br>domains of NDV<br>F are underlined) | AGCCCCCTGTGCACCACCGACAACAAGGAGGGCAGCAACATCTGCCTGACC<br>AGAACCGACAGAGGCTGGTACTGCGACAACGCCGGCAGCGTGAGCTTCTT<br>CCCCCAGACCGAGACCTGCAAGGTGCAGAGCAACAGAGTGTTCTGCGACA<br>CCATGAACAGCCTGACCCTGCCCACCGACGTGAACCTGTGCAACACCGACA<br>TCTTCAACACCAAGTACGACTGCAAGATCATGACCAGCAAGACCGACATCA<br>GCAGCAGCGTGATCACCAGCATCGGCGCCATCGTGAGCTGCTACGGCAAG<br>ACCAAGTGCACCGCCAGCAACAAGAACAGAGGCATCATCAAGACCTTCAGC<br>AACGGCTGCGACTACGTGAGCAACAAGGGCGTGGACACCGTGAGCGTGG<br>GCAACACCCTGTACTACGTGAACAAGCTGGAGGGCAAGGCCCTGTACATCA<br>AGGGCGAGCCCATCATCAACTACTACGACCCCCTGGTGTTCCCCAGCGACG<br>AGTTCGACGCCAGCATCGCCCAGGTGAACGCCAAGATCAACCAGAGCCTG<br>GCCTTCATCAGAAGAAGCGACGAGCTGCTGCACAGCGTGGACGTGGGCAA<br>GAGCACCACCAACGTGGgttaacCTCATTACCTATATCGTTTTGACTATCATATC<br>TCTTGTTTTTGGTATACTTAGCCTGATTCTAGCATGCTACCTAATGTACAAGC<br>AAAAGGCGCAACAAAAGACCTTATTATGGCTTGGGAATAATACCCTAGATC<br>AGATGAGAGCCACTACAAAAATGTGAccgcgg | |
| Nucleic acid<br>sequence<br>encoding<br>chimeric F<br>protein, wherein<br>the nucleic acid<br>sequence<br>comprises a<br>codon optimized<br>nucleic acid<br>sequence<br>encoding the<br>bovine RSV F<br>protein<br>ectodomain of<br>strain snook and<br>a nucleic acid<br>sequence<br>encoding the<br>transmembrane<br>and cytoplasmic<br>domains of F<br>protein from<br>NDV strain<br>LaSota<br>(transmembrane<br>and cytoplasmic<br>domains of NDV<br>F are underlined) | ATGGCCACCACCGCCATGACCATGATCATCAGCATCATCTTCATCAGCACCT<br>ACGTGACCCACATCACCCTGTGCCAGAACATCACCGAGGAGTTCTACCAGA<br>GCACCTGCAGCGCCGTGAGCAGAGGCTACCTGAGCGCCCTGAGAACCGGC<br>TGGTACACCAGCGTGGTGACCATCGAGCTGAGCAAGATCCAGAAGAACGT<br>GTGCAAGAGCACCGACAGCAAGGTGAAGCTGATCAAGCAGGAGCTGGAG<br>AGATACAACAACGCCGTGGTGGAGCTGCAGAGCCTGATGCAGAACGAGCC<br>CGCCAGCTTCAGCAGAGCCAAGAGAAGCATCCCCGAGCTGATCCACTACAC<br>CAGAAACAGCACCAAGAAGTTCTACGGCCTGATGGGCAAGAAGAGAAAGA<br>GAAGATTCCTGGGCTTCCTGCTGGGCATCGGCAGCGCCATCGCCAGCGGCG<br>TGGCCGTGAGCAAGGTGCTGCACCTGGAGGGCGAGGTGAACAAGATCAA<br>GAACGCCCTGCTGAGCACCAACAAGGCCGTGGTGAGCCTGAGCAACGGCG<br>TGAGCGTGCTGACCAGCAAGGTGCTGGACCTGAAGAACTACATCGACAAG<br>GAGCTGCTGCCCAAGGTGAACAACCACGACTGCAGAATCAGCAACATCGCC<br>ACCGTGATCGAGTTCCAGCAGAAGAACAACAGACTGCTGGAGATCGCCAG<br>AGAGTTCAGCGTGAACGCCGGCATCACCACCCCCCTGAGCACCTACATGCT<br>GACCAACAGCGAGCTGCTGAGCCTGATCAACGACATGCCCATCACCAACGA<br>CCAGAAGAAGCTGATGAGCAGCAACGTGCAGATCGTGAGACAGCAGAGCT<br>ACAGCATCATGAGCGTGGTGAAGGAGGAGGTGATCGCCTACGTGGTGCAG<br>CTGCCCATCTACGGCGTGATCGACACCCCCTGCTGGAAGCTGCACACCAGC<br>CCCCTGTGCACCACCGACAACAAGGAGGGCAGCAACATCTGCCTGACCAGA<br>ACCGACAGAGGCTGGTACTGCGACAACGCCGGCAGCGTGAGCTTCTTCCCC<br>CAGGCCGAGACCTGCAAGGTGCAGAGCAACAGAGTGTTCTGCGACACCAT<br>GAACAGCCTGACCCTGCCCACCGACGTGAACCTGTGCAACACCGACATCTT<br>CAACACCAAGTACGACTGCAAGATCATGACCAGCAAGACCGACATCAGCAG<br>CAGCGTGATCACCAGCATCGGCGCCATCGTGAGCTGCTACGGCAAGACCAA<br>GTGCACCGCCAGCAACAAGAACAGAGGCATCATCAAGACCTTCAGCAACG<br>GCTGCGACTACGTGAGCAACAAGGGCGTGGACACCGTGAGCGTGGGCAAC<br>ACCCTGTACTACGTGAACAAGCTGGAGGGCAAGGCCCTGTACATCAAGGG<br>CGAGCCCATCATCAACTACTACGACCCCCTGGTGTTCCCCAGCGACGAGTTC<br>GACGCCAGCATCGCCCAGGTGAACGCCAAGATCAACCAGAGCCTGGCCTTC<br>ATCAGAAGAAGCGACGAGCTGCTGCACAGCGTGGACGTGGGCAAGAGCAC<br>CACCAACGTGGgttaacCTCATTACCTATATCGTTTTGACTATCATATCTCTTGTT<br>TTTGGTATACTTAGCCTGATTCTAGCATGCTACCTAATGTACAAGCAAAAGG<br>CGCAACAAAAGACCTTATTATGGCTTGGGAATAATACCCTAGATCAGATGA<br>GAGCCACTACAAAAATGTGAccgcgg | 39 |
| Wild-type<br>Nucleic acid<br>encoding bovine<br>RSV F protein<br>of strain<br>ATue51908 (the<br>transmembrane<br>and cytoplasmic<br>domains are<br>underlined) | ATGGCGACAACAGCCATGAGGATGATCATCAGCATTAT<br>CTTCATCTCTACCTATGTGACACATATCACTTTATGCCA<br>AAACATAACAGAAGAATTTTATCAATCAACATGCAGTG<br>CAGTTAGTAGAGGTTACCTTAGTGCATTAAGAACTGGA<br>TGGTATACAAGTGTGGTAACAATAGAGTTGAGCAAAAT<br>ACAAAAAAATGTGTGTAAAAGTACTGATTCAAAAGTGA<br>AATTAATAAAGCAAGAACTAGAAAGATACAACAATGC<br>AGTAGTGGAATTGCAGTCACTTATGCAAAATGAACCGG<br>CCTCCTTCAGTAGAGCAAAAAGAGGGATACCAGAGTTG<br>ATACATTATACAAGAAACTCTACAAAAAAGTTTTATGG<br>GCTAATGGGCAAGAAGAGAAAAAGGAGATTTTTAGGAT<br>TCTTGCTAGGTATTGGATCTGCTGTTGCAAGTGGTGTAG<br>CAGTGTCCAAAGTACTACACCTGGAGGGAGAGGTGAAT<br>AAAATTAAAAATGCACTGCTATCCACAAATAAAGCAGT<br>AGTTAGTCTATCCAATGGAGTTAGTGTCCTTACTAGCAA<br>AGTACTTGATCTAAAGAACTATATAGACAAAGAGCTTC<br>TACCTCAAGTTAACAATCATGATTGTAGGATATCCAAC<br>ATAGAAACTGTGATAGAATTCCAACAAAAAAACAATAG<br>ATTGTTAGAAATTGCTAGGGAATTTAGTGTAAATGCTG<br>GTATTACCACACCTCTCAGTACATACATGTTGACCAATA<br>GTGAATTACTATCACTAATTAATGATATGCCTATAACGA<br>ATGACCAAAAAAAGCTAATGTCAAGTAATGTTCAAATA<br>GTCAGGCAACAGAGTTATTCCATTATGTCAGTGGTCAA<br>AGAAGAAGTCATAGCTTATGTTGTACAATTGCCTATTTA<br>TGGAGTTATAGACACCCCCTGTTGGAAACTACACACCT<br>CTCCGTTATGCACCACTGATAATAAAGAAGGGTCAAAC | 40 |

-continued

| | | |
|---|---|---|
| | ATCTGCTTAACTAGGACAGATCGTGGGTGGTATTGTGA<br>CAATGCAGGCTCTGTGTCTTTTTTCCCACAGACAGAGAC<br>ATGTAAGGTACAATCAAATAGAGTGTTCTGTGACACAA<br>TGAACAGTTTAACTCTGCCTACTGACGTTAACTTATGCA<br>ACACTGACATATTCAATACAAAGTATGACTGTAAAATA<br>ATGACATCTAAAACTGACATAAGTAGCTCTGTGATAAC<br>TTCAATTGGAGCTATTGTATCATGCTATGGAAGACAA<br>AATGTACAGCTTCTAATAAAAATCGTGGAATCATAAAG<br>ACTTTTTCCAATGGGTGTGATTATGTATCAAACAAAGGA<br>GTAGATACTGTATCTGTTGGTAACACACTATATTATGTA<br>AATAAGCTAGAGGGGAAAGCACTCTATATAAAGGGTGA<br>ACCAATTATTAATTACTATGATCCACTAGTGTTTCCTTC<br>TGATGAGTTTGATGCATCAATTGCCCAAGTAAACGCAA<br>AAATAAACCAAAGCCTGGCCTTCATACGTCGATCTGAT<br>GAGTTACTTCACAGTGTAGATGTAGGAAAATCCACCAC<br>AAATGTAGTAATTACTACTATTATCATAGTGATAGTTGT<br>AGTGATATTAATGTTAATAGCTGTAGGATTACTGTTTTA<br>CTGTAAGACCAAGAGTACTCCTATCATGTTAGGGAAGG<br>ATCAGCTCAGTGGTATCAACAATCTTTCCTTTAGTAAAT<br>GA | |
| Codon optimized nucleic acid sequence encoding bovine RSV F protein of strain ATue51908 | ATGGCCACCACCGCCATGAGAATGATCATCAGCATCAT<br>CTTCATCAGCACCTACGTGACCCACATCACCCTGTGCCA<br>GAACATCACCGAGGAGTTCTACCAGAGCACCTGCAGCG<br>CCGTGAGCAGAGGCTACCTGAGCGCCCTGAGAACCGGC<br>TGGTACACCAGCGTGGTGACCATCGAGCTGAGCAAGAT<br>CCAGAAGAACGTGTGCAAGAGCACCGACAGCAAGGTG<br>AAGCTGATCAAGCAGGAGCTGGAGAGATACAACAACG<br>CCGTGGTGGAGCTGCAGAGCCTGATGCAGAACGAGCCC<br>GCCAGCTTCAGCAGAGCCAAGAGAGGCATCCCCGAGCT<br>GATCCACTACACCAGAAACAGCACCAAGAAGTTCTACG<br>GCCTGATGGGCAAGAAGAGAAAGAGAAGATTCCTGGG<br>CTTCCTGCTGGGCATCGGCAGCGCCGTGGCCAGCGGCG<br>TGGCCGTGAGCAAGGTGCTGCACCTGGAGGGCGAGGTG<br>AACAAGATCAAGAACGCCCTGCTGAGCACCAACAAGGC<br>CGTGGTGAGCCTGAGCAACGGCGTGAGCGTGCTGACCA<br>GCAAGGTGCTGGACCTGAAGAACTACATCGACAAGGAG<br>CTGCTGCCCCAGGTGAACAACCACGACTGCAGAATCAG<br>CAACATCGAGACCGTGATCGAGTTCCAGCAGAAGAACA<br>ACAGACTGCTGGAGATCGCCAGAGAGTTCAGCGTGAAC<br>GCCGGCATCACCACCCCCCTGAGCACCTACATGCTGAC<br>CAACAGCGAGCTGCTGAGCCTGATCAACGACATGCCCA<br>TCACCAACGACCAGAAGAAGCTGATGAGCAGCAACGTG<br>CAGATCGTGAGACAGCAGAGCTACAGCATCATGAGCGT<br>GGTGAAGGAGGAGGTGATCGCCTACGTGGTGCAGCTGC<br>CCATCTACGGCGTGATCGACACCCCCTGCTGGAAGCTG<br>CACACCAGCCCCCTGTGCACCACCGACAACAAGGAGGG<br>CAGCAACATCTGCCTGACCAGAACCGACAGAGGCTGGT<br>ACTGCGACAACGCCGGCAGCGTGAGCTTCTTCCCCCAG<br>ACCGAGACCTGCAAGGTGCAGAGCAACAGAGTGTTCTG<br>CGACACCATGAACAGCCTGACCCTGCCCACCGACGTGA<br>ACCTGTGCAACACCGACATCTTCAACACCAAGTACGAC<br>TGCAAGATCATGACCAGCAAGACCGACATCAGCAGCAG<br>CGTGATCACCAGCATCGGCGCCATCGTGAGCTGCTACG<br>GCAAGACCAAGTGCACCGCCAGCAACAAGAACAGAGG<br>CATCATCAAGACCTTCAGCAACGGCTGCGACTACGTGA<br>GCAACAAGGGCGTGGACACCGTGAGCGTGGGCAACAC<br>CCTGTACTACGTGAACAAGCTGGAGGGCAAGGCCCTGT<br>ACATCAAGGGCGAGCCCATCATCAACTACTACGACCCC<br>CTGGTGTTCCCCAGCGACGAGTTCGACGCCAGCATCGC<br>CCAGGTGAACGCCAAGATCAACCAGAGCCTGGCCTTCA<br>TCAGAAGAAGCGACGAGCTGCTGCACAGCGTGGACGTG<br>GGCAAGAGCACCACCAACGTGGTGATCACCACCATCAT<br>CATCGTGATCGTGGTGGTGATCCTGATGCTGATCGCCGT<br>GGGCCTGCTGTTCTACTGCAAGACCAAGAGCACCCCCA<br>TCATGCTGGGCAAGGACCAGCTGAGCGGCATCAACAAC<br>CTGAGCTTCAGCAAG | 41 |
| Wild-type Nucleic acid sequence encoding bovine RSV F protein of strain snook (transmembrane and cytoplasmic domains are underlined) | ATGGCGACAACAGCCATGACGATGATCATCAGCATTAT<br>CTTCATCTCTACCTATGTGACACATATCACTTTATGCCA<br>AAACATAACAGAAGAATTTTATCAATCAACATGCAGTG<br>CAGTTAGTAGAGGTTACCTTAGTGCATTAAGAACTGGA<br>TGGTATACAAGTGTGGTAACAATAGAGTTGAGCAAAAT<br>ACAAAAAAATGTGTGTAAAAGTACTGATTCGAAAGTGA<br>AATTAATAAAGCAAGAACTAGAAAGATACAACAATGC<br>AGTAGTGGAATTGCAGTCACTTATGCAAAATGAACCGG<br>CCTCCTTCAGTAGAGCAAAAAGAAGTATACCAGAGTTG<br>ATACATTATACAAGAAACTCTACAAAAAAGTTTTATGG<br>GCTAATGGGCAAGAAGAGAAAAAGGAGATTTTTAGGAT | 42 |

-continued

| | | |
|---|---|---|
| | TCTTACTAGGTATTGGATCTGCTATTGCAAGTGGTGTAG<br>CAGTGTCCAAAGTACTACACCTGGAGGGAGAGGTGAAT<br>AAAATTAAAAATGCACTGCTATCCACAAACAAAGCAGT<br>AGTTAGTCTATCCAATGGAGTTAGTGTCCTTACTAGCAA<br>AGTACTTGATCTAAAGAACTATATAGACAAAGAGCTTC<br>TACCTAAAGTTAACAATCATGATTGTAGGATATCCAAC<br>ATAGCAACTGTGATAGAATTCCAACAAAAAAACAATAG<br>ATTGTTAGAAATTGCTAGGGAATTTAGTGTAAATGCTG<br>GTATTACCACACCCCTCAGTACATACATGTTGACCAATA<br>GTGAATTACTATCACTAATTAATGATATGCCTATAACGA<br>ATGACCAAAAAAAGCTAATGTCAAGTAATGTTCAAATA<br>GTCAGGCAACAGAGTTATTCCATTATGTCAGTGGTCAA<br>AGAAGAGGTCATAGCTTATGTTGTACAATTGCCTATTTA<br>TGGAGTTATAGACACCCCCTGTTGGAAACTACACACTTC<br>TCCATTATGCACCACTGATAATAAAGAAGGGTCAAACA<br>TCTGCTTAACTAGGACAGATCGTGGGTGGTATTGTGAC<br>AATGCAGGCTCTGTATCTTTTTTCCCACAGGCAGAGACG<br>TGTAAGGTACAATCAAATAGAGTGTTCTGTGACACAAT<br>GAACAGTTTAACTCTGCCTACTGATGTTAACTTATGCAA<br>CACTGACATATTCAATACAAAGTATGACTGTAAAATAA<br>TGACATCTAAAACTGACATAAGTAGCTCTGTAATAACTT<br>CAATTGGAGCTATTGTATCATGCTATGGGAAGACAAAA<br>TGTACAGCTTCTAATAAAAATCGTGGAATCATAAAGAC<br>TTTTTCCAATGGGTGTGATTATGTATCAAACAAAGGAGT<br>TGATACTGTATCTGTTGGTAACACACTATATTATGTAAA<br>TAAGCTAGAGGGGAAAGCACTCTATATAAAGGGTGAAC<br>CAATTATTAATTACTATGATCCACTAGTGTTTCCTTCTG<br>ATGAGTTTGATGCATCAATTGCCCAAGTAAACGCAAAA<br>ATAAACCAAAGCCTGGCTTTCATACGTCGATCTGATGA<br>GTTACTTCACAGTGTAGATGTAGGAAAATCCACCACAA<br>ATGTAGTAATTACTACTATTATCATAGTGATAGTTGTAG<br>TGATATTAATGTTAATAGCTGTAGGATTACTGTTTTACT<br>GTAAGACCAGGAGTACTCCTATCATGTTAGGGAAGGAT<br>CAGCTTAGTGGTATCAACAATCTTTCCTTTAGTAAATGA | |
| Codon optimized nucleic acid sequence encoding bovine RSV F protein of strain snook | ATGGCCACCACCGCCATGACCATGATCATCAGCATCAT<br>CTTCATCAGCACCTACGTGACCCACATCACCCTGTGCCA<br>GAACATCACCGAGGAGTTCTACCAGAGCACCTGCAGCG<br>CCGTGAGCAGAGGCTACCTGAGCGCCCTGAGAACCGGC<br>TGGTACACCAGCGTGGTGACCATCGAGCTGAGCAAGAT<br>CCAGAAGAACGTGTGCAAGAGCACCGACAGCAAGGTG<br>AAGCTGATCAAGCAGGAGCTGGAGAGATACAACAACG<br>CCGTGGTGGAGCTGCAGAGCCTGATGCAGAACGAGCCC<br>GCCAGCTTCAGCAGAGCCAAGAGAAGCATCCCCGAGCT<br>GATCCACTACACCAGAAACAGCACCAAGAAGTTCTACG<br>GCCTGATGGGCAAGAAGAGAAAGAGAAGATTCCTGGG<br>CTTCCTGCTGGGCATCGGCAGCGCCATCGCCAGCGGCG<br>TGGCCGTGAGCAAGGTGCTGCACCTGGAGGGCGAGGTG<br>AACAAGATCAAGAACGCCCTGCTGAGCACCAACAAGGC<br>CGTGGTGAGCCTGAGCAACGGCGTGAGCGTGCTGACCA<br>GCAAGGTGCTGGACCTGAAGAACTACATCGACAAGGAG<br>CTGCTGCCCAAGGTGAACAACCACGACTGCAGAATCAG<br>CAACATCGCCACCGTGATCGAGTTCCAGCAGAAGAACA<br>ACAGACTGCTGGAGATCGCCAGAGAGTTCAGCGTGAAC<br>GCCGGCATCACCACCCCCCTGAGCACCTACATGCTGAC<br>CAACAGCGAGCTGCTGAGCCTGATCAACGACATGCCCA<br>TCACCAACGACCAGAAGAAGCTGATGAGCAGCAACGTG<br>CAGATCGTGAGACAGCAGAGCTACAGCATCATGAGCGT<br>GGTGAAGGAGGAGGTGATCGCCTACGTGGTGCAGCTGC<br>CCATCTACGGCGTGATCGACACCCCCTGCTGGAAGCTG<br>CACACCAGCCCCCTGTGCACCACCGACAACAAGGAGGG<br>CAGCAACATCTGCCTGACCAGAACCGACAGAGGCTGGT<br>ACTGCGACAACGCCGGCAGCGTGAGCTTCTTCCCCCAG<br>GCCGAGACCTGCAAGGTGCAGAGCAACAGAGTGTTCTG<br>CGACACCATGAACAGCCTGACCCTGCCCACCGACGTGA<br>ACCTGTGCAACACCGACATCTTCAACACCAAGTACGAC<br>TGCAAGATCATGACCAGCAAGACCGACATCAGCAGCAG<br>CGTGATCACCAGCATCGGCGCCATCGTGAGCTGCTACG<br>GCAAGACCAAGTGCACCGCCAGCAACAAGAACAGAGG<br>CATCATCAAGACCTTCAGCAACGGCTGCGACTACGTGA<br>GCAACAAGGGCGTGGACACCGTGAGCGTGGGCAACAC<br>CCTGTACTACGTGAACAAGCTGGAGGGCAAGGCCCTGT<br>ACATCAAGGGCGAGCCCATCATCAACTACTACGACCCC<br>CTGGTGTTCCCCAGCGACGAGTTCGACGCCAGCATCGC<br>CCAGGTGAACGCCAAGATCAACCAGAGCCTGGCCTTCA<br>TCAGAAGAAGCGACGAGCTGCTGCACAGCGTGGACGTG<br>GGCAAGAGCACCACCAACGTGGTGATCACCACCATCAT<br>CATCGTGATCGTGGTGGTGATCCTGATGCTGATCGCCGT<br>GGGCCTGCTGTTCTACTGCAAGACCAGAAGCACCCCCA | 43 |

-continued

| | | |
|---|---|---|
| | TCATGCTGGGCAAGGACCAGCTGAGCGGCATCAACAAC<br>CTGAGCTTCAGCAAG | |
| Amino acid sequence encoding chimeric F protein comprising the ectodomain of bovine RSV F protein of bovine RSV strain ATCC51908 and the transmembrane and cytoplasmic domains of NDV F protein of NDV LaSota strain (transmembrane and cytoplasmic domains of NDV F protein are underlined) | MATTAMRMIISIIFISTYVTHITLCQNITEEFYQSTCSAVSRG<br>YLSALRTGWYTSVVTIELSKIQKNVCNSTDSKVKLIKQELE<br>RYNNAVVELQSLMQNEPASFSRAKRGIPELIHYTRNSTKK<br>FYGLMGKKRKRRFLGFLLGIGSAIASGVAVSKVLHLEGEV<br>NKIKNALLSTNKAVVSLSNGVSVLTSKVLDLKNYIDKELL<br>PKVNNHDCRISKIETVIEFQQKNNRLLEIAREFSVNAGITTP<br>LSTYMLTNSELLSLINDMPITNDQKKLMSSNVQIVRQQSYS<br>IMSVVKEEVIAYVVQLPIYGVIDTPCWKLHTSPLCTTDNKE<br>GSNICLTRTDRGWYCDNAGSVSFFPQTETCKVQSNRVFCD<br>TMNSLTLPTDVNLCNTDIFNTKYDCKIMTSKTDISSSVITSI<br>GAIVSCYGKTKCTASNKNRGIIKTFSNGCDYVSNKGVDTV<br>SVGNTLYYVNKLEGKALYIKGEPIINYYDPLVFPSDEFDAS<br>IAQVNAKINQSLAFIRRSDELLHSVDVGKSTTNVNLITYIVL<br>TIISLVFGILSLILACYLMYKQKAQQKTLLWLGNNTLDQM<br>RATTKM | 33 |
| Genome of NDV LaSota with a chimeric F protein (underlined). Ectodomain is codon optimized from bovine RSV strain ATCC51908. Transmembrane and cytoplasmic domains are from the F protein of NDV strain LaSota | accaaacagagaatccgtgagttacgataaaaggcgaaggagcaattgaagtcgcacggg<br>tagaaggtgtgaatctcgagtgcgagcccgaagcacaaactcgagaaagccttctgccaac<br>atgtcttccgtatttgatgagtacgaacagctcctcgcggctcagactcgccccaatggagct<br>catggagggggagaaaaagggagtaccttaaaagtagacgtcccggtattcactcttaaca<br>gtgatgacccagaagatagatggagctttgtggtattctgcctccggattgctgttagcgaag<br>atgccaacaaaccactcaggcaaggtgctctcatatctcttttatgctcccactcacaggtaat<br>gaggaaccatgttgccCttgcagggaaacagaatgaagccacattggccgtgcttgagatt<br>gatggctttgccaacggcacgccccagttcaacaataggagtggagtgtctgaagagagag<br>cacagagatttgcgatgatagcaggatctctccctcgggcatgcagcaacggaaccccgttc<br>gtcacagccggggcCgaagatgatgcaccagaagacatcaccgataccctggagaggat<br>cctctctatccaggctcaagtatgggtcacagtagcaaaagccatgactgcgtatgagactg<br>cagatgagtcggaaacaaggcgaatcaataagtatatgcagcaaggcagggtccaaaaga<br>aatacatcctctaccccgtatgcaggagcacaatccaactcacgatcagacagtctcttgcag<br>tccgcatctttttggttagcgagctcaagagaggccgcaacacggcaggtggtacctctactt<br>attataacctggtaggggacgtagactcatacatcaggaataccgggcttactgcattcttctt<br>gacactcaagtacggaatcaacaccaagacatcagcccttgcacttagtagcctctcaggcg<br>acatccagaagatgaagcagctcatgcgtttgtatcggatgaaaggagataatgcgccgtac<br>atgacattacttggtgatagtgaccagatgagctttgcgcctgccgagtatgcacaactttact<br>cctttgccatgggtatggcatcagtcctagataaaggtactgggaaataccaatttgccaggg<br>actttatgagcacatcattctggagacttggagtagagtacgctcaggctcagggaagtagc<br>attaacgaggatatggctgccgagctaaagctaaccccagcagcaaGgaGgggcctggc<br>agctgctgcccaacgggtctccgaGgaGaccagcagcataGacatgcctactcaacaag<br>tcggagtcctcactgggcttagcgagggggggtcccaagctctacaaggcggatcgaata<br>gatcgcaagggcaaccagaagccggggatggggagacccaattcctggatctgatgaga<br>gcggtagcaaatagcatgagggaggcgccaaactctgcacagggcactccccaatcggg<br>gcctcccccaactcctgggccatcccaagataacgacaccgactgggggtattgatggaca<br>aaacccagcctgcttccacaaaaacatcccaatgccctcacccgtagtcgacccctcgatttg<br>cggctctatatgaccacaccctcaaacaaacatcccccctctttcctccctccccctgctgtaca<br>actAcgTacgccctagataccacaggcacaatgcggctcactaacaatcaaaacagagc<br>cgagggaattagaaaaaagtacgggtagaagagggatattcagagatcagggcaagtctc<br>ccgagtctctgctctctcctctacctgatagaccaggacaaacatggccacctttacagatgc<br>agagatcgacgagctatttgagacaagtggaactgtcattgacaacataattacagcccagg<br>gtaaaccagcagagactgttggaaggagtgcaatcccacaaggcaagaccaaggtgctga<br>gcgcagcatgggagaagcatgggagcatccagccaccggccagtcaagacaaccccgat<br>cgacaggacagatctgacaaacaaccatccacacccgagcaaacgaccccgcatgacag<br>cccgccggccacatccgccgaccagcccccacccaggccacagacgaagccgtcgac<br>acacagCtcaggaccggagcaagcaactctctgctgttgatgcttgacaagctcagcaata<br>aatcgtccaatgctaaaaagggcccatggtcgagcccccaagaggggaatcaccaacgtc<br>cgactcaacagcaggggagtcaacccagtcgcggaaacagtcaggaaagaccgcagaa<br>ccaagtcaaggccgcccctggaaaccagggcacagacgtgaacacagcatatcatggac<br>aatgggaggagtcacaactatcagctggtgcaacccctcatgctctccgatcaaggcagag<br>ccaagacaataccccttgtatctgcggatcatgtccagccacctgtagactttgtgcaagcgat<br>gatgtctatgatggaggcgatatcacagagagtaagtaaggttgactatcagctagatcttgtc<br>ttgaaacagacatcctccatccctatgatgcggtccgaaatccaacagctgaaaacatctgtt<br>gcagtcatggaagccaacttgggaatgatgaagattctggatcccggttgtgccaacatttca<br>tctctgagtgatctacgggcagttgcccgatctcacccggttttagtttcaggccctggagacc<br>cctctccctatgtgacacaaggaggcgaaatggcacttaataaactttcgcaaccagtgcca<br>catccatctgaattgattaaacccgccactgcatgcgggcctgatataggagtggaaaagga<br>cactgtccgtgcattgatcatgtcacgcccaatgcacccgagttcttcagccaagctcctaag<br>caagttagatgcagccgggtcgatcgaggaaatcaggaaaatcaagcgccttgctctaaat<br>ggctaattactactgccacacgtagcgggtccctgtccactcggcatcacacggaatctgca<br>ccgagttcccccccgcGgTTAGAAAAAATACGGGTAGAACCGCC | 37 |

-continued

ACCATGGCCACCACCGCCATGCGCATGATCATCAGCAT
CATCTTCATCAGCACCTACGTGACCCACATCACCCTGTG
CCAGAACATCACCGAGGAGTTCTACCAGAGCACCTGCA
GCGCCGTGAGTCGCGGCTACCTGAGCGCCCTGCGCACC
GGCTGGTACACCAGCGTGGTGACCATCGAGCTGAGCAA
GATCCAGAAGAACGTGTGCAACAGCACCGACAGCAAG
GTGAAGCTGATCAAGCAGGAGCTGGAGCGCTACAACAA
CGCCGTGGTGGAGCTGCAGAGCCTGATGCAGAACGAGC
CCGCCAGCTTCAGCCGCGCCAAGCGCGGCATCCCCGAG
CTGATCCACTACACCCGCAACAGCACCAAGAAGTTCTA
CGGCCTGATGGGCAAGAAGCGCAAGCGCCGCTTCCTGG
GCTTCCTGCTGGGCATCGGCAGCGCCATCGCCAGCGGC
GTGGCCGTGAGCAAGGTGCTGCACCTGGAGGGCGAGGT
GAACAAGATCAAGAACGCCCTGCTGAGCACCAACAAG
GCCGTGGTGAGCCTGAGCAACGGCGTGAGCGTGCTGAC
CAGCAAGGTGCTGGACCTGAAGAACTACATCGACAAGG
AGCTGCTGCCCAAGGTGAACAACCACGACTGCCGCATC
AGCAAGATCGAGACCGTGATCGAGTTCCAGCAGAAGAA
CAACCGCCTGCTGGAGATCGCCCGCGAGTTCAGCGTGA
ACGCCGGCATCACCACCCCCCTGAGCACCTACATGCTG
ACCAACAGCGAGCTGCTGAGCCTGATCAACGACATGCC
CATCACCAACGACCAGAAGAAGCTGATGAGCAGCAAC
GTGCAGATCGTGCGCCAGCAGAGCTACAGCATCATGAG
CGTGGTGAAGGAGGAGGTGATCGCCTACGTGGTGCAGC
TGCCCATCTACGGCGTGATCGACACCCCCTGCTGGAAG
CTGCACACCAGCCCCCTGTGCACCACCGACAACAAGGA
GGGCAGCAACATCTGCCTGACCCGCACCGATCGCGGCT
GGTACTGCGACAACGCCGGCAGCGTGAGCTTCTTCCCC
CAGACCGAGACCTGCAAGGTGCAGAGCAACCGCGTGTT
CTGCGACACCATGAACAGCCTGACCCTGCCCACCGACG
TGAACCTGTGCAACACCGACATCTTCAACACCAAGTAC
GACTGCAAGATCATGACCAGCAAGACCGACATCAGCAG
CAGCGTGATCACCAGCATCGGCGCCATCGTGAGCTGCT
ACGGCAAGACCAAGTGCACCGCCAGCAACAAGAATCG
CGGCATCATCAAGACCTTCAGCAACGGCTGCGACTACG
TGAGCAACAAGGGCGTGGACACCGTGAGCGTGGGCAA
CACCCTGTACTACGTGAACAAGCTGGAGGGCAAGGCCC
TGTACATCAAGGGCGAGCCCATCATCAACTACTACGAC
CCCCTGGTGTTCCCCAGCGACGAGTTCGACGCCAGCAT
CGCCCAGGTGAACGCCAAGATCAACCAGAGCCTGGCCT
TCATCCGCCGCAGCGACGAGCTGCTGCACAGCGTGGAC
GTGGGCAAGAGCACCACCAACGTTAACCTCATTACCTA
TATCGTTTTGACTATCATATCTCTTGTTTTTGGTATACTT
AGCCTGATTCTAGCATGCTACCTAATGTACAAGCAAAA
GGCGCAACAAAAGACCTTATTATGGCTTGGGAATAATA
CCCTAGATCAGATGAGAGCCACTACAAAAATGTGAGCT
TCAGCAAGTAAccccccgcggacccaaggtccaactctccaagcggcaatcctc
tctcgcttcctcagccccactgaatgAtcgcgtaaccgtaattaatctagctacatttaagatta
agaaaaaatacgggtagaattggagtgccccaattgtgccaagatggactcatctaggacaa
ttgggctgtactttgattctgcccattcttctagcaacctgttagcatttccgatcgtcctacaag
Acacaggagatgggaagaagcaaatcgccccgcaatataggatccagcgccttgacttgt
ggactgatagtaaggaggactcagtattcatcaccacctatggattcatctttcaagttgggaa
tgaagaagccacCgtcggcatgatcgatgataaacccaagcgcgagttactttccgctgcg
atgctctgcctaggaagcgtcccaaataccggagaccttattgagctggcaagggcctgtct
cactatgatagtcacatgcaagaagagtgcaactaatactgagagaatggttttctcagtagtg
caggcaccccaagtgctgcaaagctgtagggttgtggcaaacaaatactcatcagtgaatgc
agtcaagcacgtgaaagcgccagagaagattcccgggagtggaaccctagaatacaaggt
gaactttgtctccttgactgtggtaccgaagaGggatgtctacaagatcccagctgcagtatt
gaaggtttctggctcgagtctgtacaatcttgcgctcaatgtcactattaatgtggaggtagac
ccgaggagtcctttggttaaatctCtgtctaagtctgacagcggatactatgctaacctcttctt
gcatattggacttatgaccacTgtagataggaaggggaagaaagtgacatttgacaagctg
gaaaagaaaataaggagccttgatctatctgtcgggctcagtgatgtgctcgggccttccgtg
ttggtaaaagcaagaggtgcacggactaagcttttggcacctttcttctctagcagtgggaca
gcctgctatcccatagcaaatgcttctcctcaggtggccaagatactctggagtcaaaccgcg
tgcctgcggagcgttaaaatcattatccaagcaggtacccaacgcgctgtcgcagtgaccgc
cgaccacgaggttacctctactaagctggagaaggggcacacccttgccaaatacaatcctt
ttaagaaataagctgcgtctctgagattgcgctccgcccactcacccagatcatcatgacaca
aaaaactaatctgtcttgattatttacagttagtttacctgtctatcaagttagaaaaaacacggg
tagaagattctggatcccggttggcgccctccaggtgcaagatgggctccagaccttctacc
aagaacccagcacctatgatgctgactatccgggttgcgctggtactgagttgcatctgtccg
gcaaactccattgatggcaggcctcttgcagctgcaggaattgtggttacaggagacaaagc
cgtcaacatatacacctcatcccagacaggatcaatcatagttaagctcctcccgaatctgcc
caaggataaggaggcatgtgcgaaagccccttggatgcatacaacaggacattgaccact
ttgctcaccccccttggtgactctatccgtaggatacaagagtctgtgactacatctggaggg
gggagacaggggcgccttataggcgccattattggcggtgtggctcttggggttgcaactgc
cgcacaaataacagcggccgcagctctgatacaagccaaacaaaatgctgccaacatcctc
cgacttaaagagagcattgccgcaaccaatgaggctgtgcatgaggtcactgacggattatc
gcaactagcagtggcagttgggaagatgcagcagtttgttaatgaccaatttaataaaacagc
tcaggaattagactgcatcaaaattgcacagcaagttggtgtagagctcaacctgtacctaac -continued

```
cgaattgactacagtattcggaccacaaatcacttcacctgctttaaacaagctgactattcag
gcactttacaatctagctggtggaaatatggattacttattgactaagttaggtgtagggaacaa
tcaactcagctcattaatcggtagcggcttaatcaccggtaaccctattctatacgactcacag
actcaactcttgggtatacaggtaactctaccttcagtcgggaacctaaataatatgcgtgcca
cctacttggaaaccttatccgtaagcacaaccaggggatttgcctcggcacttgtcccAaaa
gtggtgacacaggtcggttctgtgatagaagaacttgacacctcatactgtatagaaactgac
ttagatttatattgtacaagaatagtaacgttccctatgtcccctggtatttattcctgcttgagcg
gcaatacgtcggcctgtatgtactcaaagaccgaaggcgcacttactacaccatacatgact
atcaaaggttcagtcatcgccaactgcaagatgacaacatgtagatgtgtaaaccccccggg
tatcatatcgcaaaactatggagaagccgtgtctctaatagataaacaatcatgcaatgttttat
ccttaggcgggataactttaaggctcagtggggaattcgatgtaacttatcagaagaatatctc
aatacaagattctcaagtaataataacaggcaatcttgatatctcaactgagcttgggaatgtc
aacaactcgatcagtaatgctttgaataagttagaggaaagcaacagaaaactagacaaagt
caatgtcaaactgactagcacatctgctctcattacctatatcgttttgactatcatatctcttgtttt
tggtatacttagcctgattctagcatgctacctaatgtacaagcaaaaggcgcaacaaaagac
cttattatggcttgggaataatactctagatcagatgagagccactacaaaaatgtgaacaca
gatgaggaacgaaggtttccctaatagtaatttgtgtgaaagttctggtagtctgtcagttcaga
gagttaagaaaaaactaccggttgtagatgaccaaaggacgatatacgggtagaacggtaa
gagaggccgcccctcaattgcgagccaggcttcacaacctccgttctaccgcttcaccgaca
acagtcctcaatcatggaccgcgccgttagccaagttgcgttagagaatgatgaaagagag
gcaaaaaatacatggcgcttgatattccggattgcaatcttattcttaacagtagtgaccttggc
tatatctgtagcctcccttttatatagcatgggggctagcacacctagcgatcttgtaggcatac
cgactaggatttccagggcagaagaaaagattacatctacacttggttccaatcaagatgtag
tagataggatatataagcaagtggcccttgagtctccgttggcattgttaaatactgagaccac
aattatgaacgcaataacatctctctcttatcagattaatggagctgcaaacaacagtgggtgg
ggggcacctatccatgacccagattatatagggggggataggcaaagaactcattgtagatga
tgctagtgatgtcacatcattctatccctctgcatttcaagaacatctgaattttatcccggcgcc
tactacaggatcaggttgcactcgaataccctcatttgacatgagtgctacccattactgctac
acccataatgtaatattgtctggatgcagagatcactcacattcatatcagtatttagcacttggt
gtgctccggacatctgcaacagggagggtattcttttctactctgcgttccatcaacctggacg
acacccaaaatcggaagtcttgcagtgtgagtgcaactcccctgggttgtgatatgctgtgct
cgaaagtcacggagacagaggaagaagattataactcagctgtccctacgcggatggtaca
tgggaggttagggttcgacggccagtaccacgaaaaggacctagatgtcacaacattattcg
gggactgggtggccaactacccaggagtagggggtggatcttttattgacagccgcgtatg
gttctcagtctacggagggttaaaacccaattcacccagtgacactgtacaggaagggaaat
atgtgatatacaagcgatacaatgacacatgcccagatgagcaagactaccagattcgaatg
gccaagtcttcgtataagcctggacggtttggtgggaaacgcatacagcaggctatcttatct
atcaaggtgtcaacatccttaggcgaagacccggtactgactgtaccgcccaacacagtcac
actcatgggggccgaaggcagaattctcacagtagggacatctcatttcttgtatcaacgagg
gtcatcatacttctctcccgcgttattatatcctatgacagtcagcaacaaaacagccactcttc
atagtccttatacattcaatgccttcactcggccaggtagtatcccttgccaggcttcagcaag
atgccccaactcgtgtgttactggagtctatacagatccatatcccctaatcttctatagaaacc
acaccttgcgaggggtattcgggacaatgcttgatggtgtacaagcaagacttaaccctgcg
tctgcagtattcgatagcacatcccgcagtcgcattactcgagtgagttcaagcagtaccaaa
gcagcatacacaacatcaacttgttttaaagtggtcaagactaataagacctattgtctcagcat
tgctgaaatatctaatactctcttcggagaattcagaatcgtcccgttactagttgagatcctcaa
agatgacggggttagagaagccaggtctggctagttgagtcaattataaaggagttggaaag
atggcattgtatcacctatcttctgcgacatcaagaatcaaaccgaatgccggcgcgtgctcg
aattccatgttgccagttgaccacaatcagccagtgctcatgcgatcagattaagccttgtca
AtaGtctcttgattaagaaaaaatgtaagtggcaatgagatacaaggcaaaacagctcatg
gtTaaCaatacgggtaggacatggcgagctccggtcctgaaagggcagagcatcagatta
tcctaccagagTcacacctgtcttcaccattggtcaagcacaaactactctattactggaaatt
aactgggctaccgcttcctgatgaatgtgacttcgaccacctcattctcagccgacaatggaa
aaaaatacttgaatcggcctctcctgatactgagagaatgataaaactcggaagggcagtac
accaaactcttaaccacaattccagaataaccggagtgctccaccccaggtgtttagaaGaa
ctggctaatattgaggtcccagattcaaccaacaaatttcggaagattgagaagaagatccaa
attcacaacacgagatatggagaactgttcacaaggctgtgtacgcatatagagaagaaact
gctggggtcatcttggtctaacaatgtcccccggtcagaggagttcagcagcattcgtacgg
atccggcattctggtttcactcaaaatggtccacagccaagtttgcatggctccatataaaaca
gatccagaggcatctgatggtggcagctaGgacaaggtctgcggccaacaaattggtgat
gctaacccataaggtaggccaagtctttgtcactcctgaacttgtcgttgtgacgcatacgaat
gagaacaagttcacatgtcttacccaggaacttgtattgatgtatgcagatatgatggagggc
agagatatggtcaacataatatcaaccacggcggtgcatctcagaagcttatcagagaaaatt
gatgacattttgcggttaatagacgctctggcaaaagacttgggtaatcaagtctacgatgttg
tatcactaatggagggatttgcatacggagctgtccagctactcgagccgtcaggtacatttg
caggagatttcttcgcattcaacctgcaggagcttaaagacattctaattggcctcctcccaa
tgatatagcagaatccgtgactcatgcaatcgctactgtattctctggtttagaacagaatcaag
cagctgagatgttgtgtctgttgcgtctgtggggtcacccactgcttgagtcccgtattgcagc
aaaggcagtcaggagccaaatgtgcgcaccgaaaatggtagactttgatatgatccttcagg
tactgtctttcttcaagggaacaatcatcaacgggtacagaaagaagaatgcaggtgtgtggc
cgcgagtcaaagtggatacaatatatgggaaggtcattgggcaactacatgcagattcagca
gagatttcacacgatatcatgttgagagagtataagagtttatctgcacttgaatttgagccatg
tatagaatatgaccctgtcaccaacctgagcatgttcctaaaagacaaggcaatcgcacacc
ccaacgataattggcttgcctcgtttaggcggaaccttctctccgaagaccagaagaaacatg
taaaagaagcaacttcgactaatcgcctcttgatagagtttttagagtcaaatgattttgatccat
ataaagagatggaatatctgacgacccttgagtaccttagagatgacaatgtggcagtatcat
actcgctcaaggagaaggaagtgaaagttaatggacggatcttcgctaagctgacaaagaa
gttaaggaactgtcaggtgatggcggaagggatcctagccgatcagattgcacctttctttca
gggaaatggagtcattcaggatagcatatccttgaccaagagtatgctagcgatgagtcaact
```

-continued

```
gtcttttaacagcaataagaaacgtatcactgactgtaaagaaagagtatcttcaaaccgcaat
catgatccgaaaagcaagaaccgtcggagagttgcaaccttcataacaactgacctgcaaa
agtactgtcttaattggagatatcagacaatcaaattgttcgctcatgccatcaatcagttgatg
ggcctacctcacttcttcgaatggattcacctaagactgatggacactacgatgttcgtaggag
accctttcaatcctccaagtgaccctactgactgtgacctctcaagagtccctaatgatgacat
atatattgtcagtgccagagggggtatcgaaggattatgccagaagctatggacaatgatctc
aattgctgcaatccaacttgctgcagctagatcgcattgtcgtgttgcctgtatggtacagggt
gataatcaagtaatagcagtaacgagagaggtaagatcagacgactctccggagatggtgtt
gacacagttgcatcaagccagtgataatttcttcaaggaattaattcatgtcaatcatttgattgg
ccataatttgaaggatcgtgaaaccatcaggtcagacacattcttcatatacagcaaacgaat
cttcaaagatggagcaatcctcagtcaagtcctcaaaaattcatctaaattagtgctagtgtca
ggtgatctcagtgaaaacaccgtaatgtcctgtgccaacattgcctctactgtagcacggctat
gcgagaacgggcttcccaaagacttctgttactatttaaactatataatgagttgtgtgcagac
atactttgactctgagttctccatcaccaacaattcgcaccccgatcttaatcagtcgtggattg
aggacatctcttttgtgcactcatatgttctgactcctgcccaattaggggggactgagtaacctt
caatactcaaggctctacactagaaatatcggtgacccggggactactgcttttgcagagatc
aagcgactagaagcagtgggattactgagtcctaacattatgactaatatcttaactaggccg
cctgggaatggagattgggccagtctgtgcaacgacccatactctttcaattttgagactgttg
caagcccaaatattgttcttaagaaacatacgcaaagagtcctatttgaaacttgttcaaatccc
ttattgtctggagtgcacacagaggataatgaggcagaagagaaggcattggctgaattcttg
cttaatcaagaggtgattcatccccgcgttgcgcatgccatcatggaggcaagctctgtaggt
aggagaaagcaaattcaagggcttgttgacacaacaaacaccgtaattaagattgcgcttact
aggaggccattaggcatcaagaggctgatgcggatagtcaattattctagcatgcatgcaat
gctgtttagagacgatgtttttcctccagtagatccaaccaccccttagtctcttctaatatgtgt
tctctgacactggcagactatgcacggaatagaagctggtcacctttgacgggaggcagga
aaatactgggtgtatctaatcctgatacgatagaactcgtagagggtgagattcttagtgtaag
cggagggtgtacaagatgtgacagcggagatgaacaatttacttggttccatcttccaagcaa
tatagaattgaccgatgacaccagcaagaatcctccgatgagggtaccatatctcgggtcaa
agacacaggagaggagagctgcctcacttgcaaaaatagctcatatgtcgccacatgtaaa
ggctgccctaagggcatcatccgtgttgatctgggcttatggggataatgaagtaaattggac
tgctgctcttacgattgcaaaatctcggtgtaatgtaaacttagagtatcttcggttactgtcccc
tttacccacggctgggaatcttcaacatagactagatgatggtataactcagatgacattcacc
cctgcatctctctacaggGtgtcaccttacattcacatatccaatgattctcaaaggctgttcac
tgaagaaggagtcaaagaggggaatgtggtttaccaacagatcatgctcttgggtttatctcta
atcgaatcgatctttccaatgacaacaaccaggacatatgatgagatcacactgcacctacat
agtaaatttagttgctgtatcagagaagcacctgttgcggttcctttcgagctacttggggtggt
accggaactgaggacagtgacctcaaataagtttatgtatgatcctagccctgtatcggaggg
agactttgcgagacttgacttagctatcttcaagagttatgagcttaatctggagtcatatccca
cgatagagctaatgaacattctttcaatatccagcgggaagttgattggccagtctgtggtttct
tatgatgaagatacctccataaagaatgacgccataatagtgtatgacaatacccgaaattgg
atcagtgaagctcagaattcagatgtggtccgcctatttgaatatgcagcacttgaagtgctcc
tcgactgttcttaccaactctattacctgagagtaagaggcctGgacaatattgtcttatatatg
ggtgatttatacaagaatatgccaggaattctactttccaacattgcagctacaatatctcatcc
cgtcattcattcaaggttacatgcagtgggcctggtcaaccatgacggatcacaccaacttgc
agatacggattttatcgaaatgtctgcaaaactattagtatcttgcacccgacgtgtgatctccg
gcttatattcaggaaataagtatgatctgctgttcccatctgtcttagatgataacctgaatgaga
agatgcttcagctgatatcccggttatgctgtctgtacacggtactctttgctacaacaagaga
aatcccgaaaataagaggcttaactgcagaagagaaatgttcaatactcactgagtatttactg
tcggatgctgtgaaaccattacttagccccgatcaagtgagctctatcatgtctcctaacataat
tacattcccagctaatctgtactacatgtctcggaagagcctcaatttgatcagggaaaggga
ggacagggatactatcctggcgttgttgttcccccaagagccattattagagttcccttctgtgc
aagatattggtgctcgagtgaaagatccattcacccgacaacctgcggcattttgcaagagtt
agatttgagtgctccagcaaggtatgacgcattcacacttagtcagattcatcctgaactcaca
tctccaaatccggaggaagactacttagtacgatacttgttcagagggatagggactgcatct
tcctcttggtataaggcatctcatctcctttctgtacccgaggtaagatgtgcaagacacggga
actccttatacttagctgaagggagcggagccatcatgagtcttctcgaactgcatgtaccac
atgaaactatctattacaatacgctcttttcaaatgagatgaacccccgcaacgacatttcgg
gccgaccccaactcagtttttgaattcggttgtttataggaatctacaggcggaggtaacatgc
aaagatggatttgtccaagagttccgtccattatggagagaaaatacagaggaaagCgacc
tgacctcagataaagTagtggggtatattacatctgcagtgccctacagatctgtatcattgct
gcattgtgacattgaaattcctccagggtccaatcaaagcttactagatcaactagctatcaatt
tatctctgattgccatgcattctgtaagggagggcggggtagtaatcatcaaagtgttgtatgc
aatgggatactactttcatctactcatgaacttgtttgctccgtgttccacaaaaggatatattctc
tctaatggttatgcatgtcgaggagatatggagtgttacctggtatttgtcatgggttacctggg
cgggcctacatttgtacatgaggtggtgaggatggcGaaaactctggtgcagcggcacggt
acgctTttgtctaaatcagatgagatcacactgaccaggttattcacctcacagcggcagcgt
gtgacagacatcctatccagtcctttaccaagattaataaagtacttgaggaagaatattgaca
ctgcgctgattgaagccgggggacagcccgtccgtccattctgtgcggagagtctggtgag
cacgctagcgaacataactcagataacccagatCatcgctagtcacattgacacagttatcc
ggtctgtgatatatatggaagctgagggtgatctcgctgacacagtatttctatttaccccttac
aatctctctactgacgggaaaaagaggacatcacttaAacagtgcacgagacagatcctag
aggttacaatactaggtcttagagtcgaaaatctcaataaaataggcgatataatcagcctagt
gcttaaaggcatgatctccatggaggaccttatcccactaaggacatacttgaagcatagtac
ctgccctaaatatttgaaggctgtcctaggtattaccaaactcaaagaaatgtttacagacactt
ctgtaCtgtacttgactcgtgctcaacaaaaattctacatgaaaactataggcaatgcagtcaa
aggatattacagtaactgtgactcttaacgaaaatcacatattaataggctcctttttttggccaat
tgtattcttgttgatttaatcatattatgttagaaaaaagttgaaccctgactccttaggactcgaa
ttcgaactcaaataaatgtcttaaaaaaaggttgcgcacaattattcttgagtgtagtctcgtcat
tcaccaaatctttgtttggt
```

-continued

Genome of NDV LaSota with a chimeric F protein (underlined). Ectodomain is NOT optimized from bovine RSV strain ATCC51908. Transmembrane and cytoplasmic domains are from the F protein of NDV strain LaSota

59 accaaacagagaatccgtgagttacgataaaaggcgaaggagcaattgaagtcgcacggg
tagaaggtgtgaatctcgagtgcgagcccgaagcacaaactcgagaaagccttctgccaac
atgtcttccgtatttgatgagtacgaacagctcctcgcggctcagactcgccccaatggagct
catggagggggagaaaaagggagtaccttaaaagtagacgtcccggtattcactcttaaca
gtgatgacccagaagatagatggagctttgtggtattctgcctccggattgctgttagcgaag
atgccaacaaaccactcaggcaaggtgctctcatatctcttttatgctcccactcacaggtaat
gaggaaccatgttgccCttgcagggaaacagaatgaagccacattggccgtgcttgagatt
gatggctttgccaacggcacgccccagttcaacaataggagtggagtgtctgaagagagag
cacagagatttgcgatgatagcaggatctctccctcgggcatgcagcaacggaaccccgttc
gtcacagccggggcCgaagatgatgcaccagaagacatcaccgataccctggagaggat
cctctctatccaggctcaagtatgggtcacagtagcaaaagccatgactgcgtatgagactg
cagatgagtcggaaacaaggcgaatcaataagtatatgcagcaaggcagggtccaaaaga
aatacatcctctaccccgtatgcaggagcacaatccaactcacgatcagacagtctcttgcag
tccgcatctttttggttagcgagctcaagagaggccgcaacacggcaggtggtacctctactt
attataacctggtaggggacgtagactcatacatcaggaataccgggcttactgcattcttctt
gacactcaagtacggaatcaacaccaagacatcagcccttgcacttagtagcctctcaggcg
acatccagaagatgaagcagctcatgcgtttgtatcggatgaaaggagataatgcgccgtac
atgacattacttggtgatagtgaccagatgagctttgcgcctgccgagtatgcacaactttact
cctttgccatgggtatggcatcagtcctagataaaggtactgggaaataccaatttgccaggg
actttatgagcacatcattctggagacttggagtagagtacgctcaggctcagggaagtagc
attaacgaggatatggctgccgagctaaagctaaccccagcagcaaGgaGgggcctggc
agctgctgcccaacgggtctccgaGgaGaccagcagcataGacatgcctactcaacaag
tcggagtcctcactgggcttagcgagggggggtcccaagctctacaaggcggatcgaata
gatcgcaagggcaaccagaagccggggatggggagacccaattcctggatctgatgaga
gcggtagcaaatagcatgagggaggcgccaaactctgcacagggcactccccaatcggg
gcctcccccaactcctgggccatcccaagataacgacaccgactgggggtattgatggaca
aaacccagcctgcttccacaaaaacatcccaatgccctcacccgtagtcgacccctcgatttg
cggctctatatgaccacaccctcaaacaaacatcccccctctttcctccctccccctgctgtaca
actAcgTacgccctagataccacaggcacaatgcggctcactaacaatcaaaacagagc
cgagggaattagaaaaaagtacgggtagaagagggatattcagagatcagggcaagtctc
ccgagtctctgctctctcctctacctgatagaccaggacaaacatggccacctttacagatgc
agagatcgacgagctatttgagacaagtggaactgtcattgacaacataattacagcccagg
gtaaaccagcagagactgttggaaggagtgcaatcccacaaggcaagaccaaggtgctga
gcgcagcatgggagaagcatgggagcatccagccaccggccagtcaagacaaccccgat
cgacaggacagatctgacaaacaaccatccacacccgagcaaacgaccccgcatgacag
cccgccggccacatccgccgaccagcccccacccaggccacagacgaagccgtcgac
acacagCtcaggaccggagcaagcaactctctgctgttgatgcttgacaagctcagcaata
aatcgtccaatgctaaaaagggcccatggtcgagcccccaagaggggaatcaccaacgtc
cgactcaacagcaggggagtcaacccagtcgcggaaacagtcaggaaagaccgcagaa
ccaagtcaaggccgcccctggaaaccagggcacagacgtgaacacagcatatcatggac
aatgggaggagtcacaactatcagctggtgcaacccctcatgctctccgatcaaggcagag
ccaagacaatacccttgtatctgcggatcatgtccagccacctgtagactttgtgcaagcgat
gatgtctatgatggaggcgatatcacagagagtaagtaaggttgactatcagctagatcttgtc
ttgaaacagacatcctccatccctatgatgcggtccgaaatccaacagctgaaaacatctgtt
gcagtcatggaagccaacttgggaatgatgaagattctggatcccggttgtgccaacatttca
tctctgagtgatctacgggcagttgcccgatctcacccggttttagtttcaggccctggagacc
cctctccctatgtgacacaaggaggcgaaatggcacttaataaactttcgcaaccagtgcca
catccatctgaattgattaaacccgccactgcatgcgggcctgatataggagtggaaaagga
cactgtccgtgcattgatcatgtcacgcccaatgcacccgagttcttcagccaagctcctaag
caagttagatgcagccgggtcgatcgaggaaatcaggaaaatcaagcgccttgctctaaat
ggctaattactactgccacacgtagcgggtccctgtccactcggcatcacacggaatctgca
ccgagttcccccccgcGgTTAGAAAAAATACGGGTAGAACCGCC
ACCATGGCGACAACAGCCATGAGGATGATCATCAGCAT
TATCTTCATCTCTACCTATGTGACACATATCACTTTATG
CCAAAACATAACAGAAGAATTTTATCAATCAACATGCA
GTGCAGTTAGTAGAGGTTACCTTAGTGCATTAAGAACT
GGATGGTATACAAGTGTGGTAACAATAGAGTTGAGCAA
AATACAAAAAAATGTGTGTAATAGTACTGATTCAAAAG
TGAAATTAATAAAGCAAGAACTAGAAAGATACAACAAT
GCAGTAGTGGAATTGCAGTCACTTATGCAAAATGAACC
GGCCTCCTTCAGTAGAGCAAAAAGAGGGATACCAGAGT
TGATACATTATACAAGAAACTCTACAAAAAAGTTTTAT
GGGCTAATGGGCAAGAAGAGAAAAAGGAGATTTTTAG
GATTCTTGCTAGGTATTGGATCTGCTATTGCAAGTGGTG
TAGCAGTGTCCAAAGTACTACACCTGGAGGGAGAGGTG
AATAAAATTAAAAATGCACTGCTATCCACAAATAAAGC
AGTAGTTAGTCTATCCAATGGAGTTAGTGTCCTTACTAG
CAAAGTACTTGATCTAAAGAACTATATAGACAAAGAGC
TTCTACCTAAAGTTAACAATCATGATTGTAGGATATCCA
AAATAGAAACTGTGATAGAATTCCAACAAAAAAACAAT
AGATTGTTAGAAATTGCTAGGGAATTTAGTGTAAATGC
TGGTATTACCACACCTCTCAGTACATACATGTTGACCAA
TAGTGAATTACTATCACTAATTAATGATATGCCTATAAC
GAATGACCAAAAAAAGCTAATGTCAAGTAATGTTCAAA
TAGTCAGGCAACAGAGTTATTCCATTATGTCAGTGGTCA
AAGAAGAAGTCATAGCTTATGTTGTACAATTGCCTATTT
ATGGAGTTATAGACACCCCCTGTTGGAAACTACACACC
TCTCCGTTATGCACCACTGATAATAAAGAAGGGTCAAA -continued CATCTGCTTAACTAGGACAGATCGTGGGTGGTATTGTG
ACAATGCAGGCTCTGTGTCTTTTTTCCCACAGACAGAGA
CATGTAAGGTACAATCAAATAGAGTGTTCTGTGACACA
ATGAACAGTTTAACTCTGCCTACTGACGTTAACTTATGC
AACACTGACATATTCAATACAAAGTATGACTGTAAAAT
AATGACATCTAAAACTGACATAAGTAGCTCTGTGATAA
CTTCAATTGGAGCTATTGTATCATGCTATGGGAAGACA
AAATGTACAGCTTCTAATAAAAATCGTGGAATCATAAA
GACTTTTTCCAATGGGTGTGATTATGTATCAAACAAAGG
AGTAGATACTGTATCTGTTGGTAACACACTATATTATGT
AAATAAGCTAGAGGGGAAAGCACTCTATATAAAGGGTG
AACCAATTATTAATTACTATGATCCACTAGTGTTTCCTT
CTGATGAGTTTGATGCATCAATTGCCCAAGTAAACGCA
AAAATAAACCAAAGCCTGGCCTTCATACGTCGATCTGA
TGAGTTACTTCACAGTGTAGATGTAGGAAAATCCACCA
CAAATgttaacCTCATTACCTATATCGTTTTGACTATCATAT
CTCTTGTTTTTGGTATACTTAGCCTGATTCTAGCATGCTA
CCTAATGTACAAGCAAAAGGCGCAACAAAAGACCTTAT
TATGGCTTGGGAATAATACCCTAGATCAGATGAGAGCC
ACTACAAAAATGTGAGCTTCAGCAAGTAAccccccgcggaccc
aaggtccaactctccaagcggcaatcctctctcgcttcctcagccccactgaatgAtcgcgt
aaccgtaattaatctagctacatttaagattaagaaaaaatacgggtagaattggagtgcccca
attgtgccaagatggactcatctaggacaattgggctgtactttgattctgcccattcttctagca
acctgttagcatttccgatcgtcctacaagAcacaggagatgggaagaagcaaatcgcccc
gcaatataggatccagcgccttgacttgtggactgatagtaaggaggactcagtattcatcac
cacctatggattcatctttcaagttgggaatgaagaagccacCgtcggcatgatcgatgataa
acccaagcgcgagttactttccgctgcgatgctctgcctaggaagcgtcccaaataccggag
accttattgagctggcaagggcctgtctcactatgatagtcacatgcaagaagagtgcaacta
atactgagagaatggttttctcagtagtgcaggcaccccaagtgctgcaaagctgtagggttg
tggcaaacaaatactcatcagtgaatgcagtcaagcacgtgaaagcgccagagaagattcc
cgggagtggaaccctagaatacaaggtgaactttgtctccttgactgtggtaccgaagaGg
gatgtctacaagatcccagctgcagtattgaaggtttctggctcgagtctgtacaatcttgcgct
caatgtcactattaatgtggaggtagacccgaggagtcctttggttaaatctCtgtctaagtct
gacagcggatactatgctaacctcttcttgcatattggacttatgaccacTgtagataggaag
gggaagaaagtgacatttgacaagctggaaaagaaaataaggagccttgatctatctgtcgg
gctcagtgatgtgctcgggccttccgtgttggtaaaagcaagaggtgcacggactaagctttt
ggcacctttcttctctagcagtgggacagcctgctatcccatagcaaatgcttctcctcaggtg
gccaagatactctggagtcaaaccgcgtgcctgcggagcgttaaaatcattatccaagcagg
tacccaacgcgctgtcgcagtgaccgccgaccacgaggttacctctactaagctggagaag
gggcacacccttgccaaatacaatccttttaagaaataagctgcgtctctgagattgcgctcc
gcccactcacccagatcatcatgacacaaaaaactaatctgtcttgattatttacagttagtttac
ctgtctatcaagttagaaaaaacacgggtagaagattctggatcccggttggcgccctccag
gtgcaagatgggctccagaccttctaccaagaacccagcacctatgatgctgactatccggg
ttgcgctggtactgagttgcatctgtccggcaaactccattgatggcaggcctcttgcagctgc
aggaattgtggttacaggagacaaagccgtcaacatatacacctcatcccagacaggatcaa
tcatagttaagctcctcccgaatctgcccaaggataaggaggcatgtgcgaaagccccccttg
gatgcatacaacaggacattgaccactttgctcacccccttggtgactctatccgtaggatac
aagagtctgtgactacatctggaggggggagacaggggcgccttataggcgccattattgg
cggtgtggctcttggggttgcaactgccgcacaaataacagcggccgcagctctgatacaa
gccaaacaaaatgctgccaacatcctccgacttaaagagagcattgccgcaaccaatgagg
ctgtgcatgaggtcactgacggattatcgcaactagcagtggcagttgggaagatgcagca
gtttgttaatgaccaatttaataaaacagctcaggaattagactgcatcaaaattgcacagcaa
gttggtgtagagctcaacctgtacctaaccgaattgactacagtattcggaccacaaatcactt
cacctgctttaaacaagctgactattcaggcactttacaatctagctggtggaaatatggattac
ttattgactaagttaggtgtagggaacaatcaactcagctcattaatcggtagcggcttaatca
ccggtaaccctattctatacgactcacagactcaactcttgggtatacaggtaactctaccttca
gtcgggaacctaaataatatgcgtgccacctacttggaaaccttatccgtaagcacaaccag
gggatttgcctcggcacttgtcccAaaagtggtgacacaggtcggttctgtgatagaagaac
ttgacacctcatactgtatagaaactgacttagatttatattgtacaagaatagtaacgttccctat
gtcccctggtatttattcctgcttgagcggcaatacgtcggcctgtatgtactcaaagaccgaa
ggcgcacttactacaccatacatgactatcaaaggttcagtcatcgccaactgcaagatgaca
acatgtagatgtgtaaaccccccgggtatcatatcgcaaaactatggagaagccgtgtctcta
atagataaacaatcatgcaatgttttatccttaggcgggataactttaaggctcagtggggaatt
cgatgtaacttatcagaagaatatctcaatacaagattctcaagtaataataacaggcaatcttg
atatctcaactgagcttgggaatgtcaacaactcgatcagtaatgctttgaataagttagagga
aagcaacagaaaactagacaaagtcaatgtcaaactgactagcacatctgctctcattaccta
tatcgttttgactatcatatctcttgtttttggtatacttagcctgattctagcatgctacctaatgta
caagcaaaaggcgcaacaaaagaccttattatggcttgggaataatactctagatcagatga
gagccactacaaaaatgtgaacacagatgaggaacgaaggtttccctaatagtaatttgtgtg
aaagttctggtagtctgtcagttcagagagttaagaaaaaactaccggttgtagatgaccaaa
ggacgatatacgggtagaacggtaagagaggccgcccctcaattgcgagccaggcttcac
aacctccgttctaccgcttcaccgacaacagtcctcaatcatggaccgcgccgttagccaagt
tgcgttagagaatgatgaaagagaggcaaaaaatacatggcgcttgatattccggattgcaat
cttattcttaacagtagtgaccttggctatatctgtagcctcccttttatatagcatgggggctag
cacacctagcgatcttgtaggcataccgactaggatttccagggcagaagaaaagattacat
ctacacttggttccaatcaagatgtagtagataggatatataagcaagtggcccttgagtctcc
gttggcattgttaaatactgagaccacaattatgaacgcaataacatctctctcttatcagattaa
tggagctgcaaacaacagtgggtgggggcacctatccatgacccagattatataggggg
gataggcaaagaactcattgtagatgatgctagtgatgtcacatcattctatccctctgcatttc -continued

```
aagaacatctgaattttatcccggcgcctactacaggatcaggttgcactcgaataccctcatt
tgacatgagtgctacccattactgctacacccataatgtaatattgtctggatgcagagatcact
cacattcatatcagtatttagcacttggtgtgctccggacatctgcaacagggagggtattcttt
tctactctgcgttccatcaacctggacgacacccaaaatcggaagtcttgcagtgtgagtgca
actcccctgggttgtgatatgctgtgctcgaaagtcacggagacagaggaagaagattataa
ctcagctgtccctacgcggatggtacatgggaggttagggttcgacggccagtaccacgaa
aaggacctagatgtcacaacattattcggggactgggtggccaactacccaggagtagggg
gtggatcttttattgacagccgcgtatggttctcagtctacggagggttaaaacccaattcacc
cagtgacactgtacaggaagggaaatatgtgatatacaagcgatacaatgacacatgccca
gatgagcaagactaccagattcgaatggccaagtcttcgtataagcctggacggtttggtgg
gaaacgcatacagcaggctatcttatctatcaaggtgtcaacatccttaggcgaagacccggt
actgactgtaccgcccaacacagtcacactcatgggggccgaaggcagaattctcacagta
gggacatctcatttcttgtatcaacgagggtcatcatacttctctcccgcgttattatatcctatga
cagtcagcaacaaaacagccactcttcatagtccttatacattcaatgccttcactcggccagg
tagtatcccttgccaggcttcagcaagatgccccaactcgtgtgttactggagtctatacagat
ccatatcccctaatcttctatagaaaccacaccttgcgaggggtattcgggacaatgcttgatg
gtgtacaagcaagacttaaccctgcgtctgcagtattcgatagcacatcccgcagtcgcatta
ctcgagtgagttcaagcagtaccaaagcagcatacacaacatcaacttgttttaaagtggtca
agactaataagacctattgtctcagcattgctgaaatatctaatactctcttcggagaattcaga
atcgtcccgttactagttgagatcctcaaagatgacggggttagagaagccaggtctggcta
gttgagtcaattataaaggagttggaaagatggcattgtatcacctatcttctgcgacatcaag
aatcaaaccgaatgccggcgcgtgctcgaattccatgttgccagttgaccacaatcagccag
tgctcatgcgatcagattaagccttgtcaAtaGtctcttgattaagaaaaaatgtaagtggca
atgagatacaaggcaaaacagctcatggtTaaCaatacgggtaggacatggcgagctcc
ggtcctgaaagggcagagcatcagattatcctaccagagTcacacctgtcttcaccattggt
caagcacaaactactctattactggaaattaactgggctaccgcttcctgatgaatgtgacttc
gaccacctcattctcagccgacaatggaaaaaaatacttgaatcggcctctcctgatactgag
agaatgataaaactcggaagggcagtacaccaaactcttaaccacaattccagaataaccg
gagtgctccaccccaggtgtttagaaGaactggctaatattgaggtcccagattcaaccaac
aaatttcggaagattgagaagaagatccaaattcacaacacgagatatggagaactgttcac
aaggctgtgtacgcatatagagaagaaactgctggggtcatcttggtctaacaatgtccccg
gtcagaggagttcagcagcattcgtacggatccggcattctggtttcactcaaaatggtccac
agccaagtttgcatggctccatataaaacagatccagaggcatctgatggtggcagctaGg
acaaggtctgcggccaacaaattggtgatgctaacccataaggtaggccaagtctttgtcact
cctgaacttgtcgttgtgacgcatacgaatgagaacaagttcacatgtcttacccaggaacttg
tattgatgtatgcagatatgatggagggcagagatatggtcaacataatatcaaccacggcg
gtgcatctcagaagcttatcagagaaaattgatgacattttgcggttaatagacgctctggcaa
aagacttgggtaatcaagtctacgatgttgtatcactaatggagggatttgcatacggagctgt
ccagctactcgagccgtcaggtacatttgcaggagatttcttcgcattcaacctgcaggagctt
aaagacattctaattggcctcctccccaatgatatagcagaatccgtgactcatgcaatcgcta
ctgtattctctggtttagaacagaatcaagcagctgagatgttgtgtctgttgcgtctgtggggt
cacccactgcttgagtcccgtattgcagcaaaggcagtcaggagccaaatgtgcgcaccga
aaatggtagactttgatatgatccttcaggtactgtctttcttcaagggaacaatcatcaacggg
tacagaaagaagaatgcaggtgtgtggccgcgagtcaaagtggatacaatatatgggaagg
tcattgggcaactacatgcagattcagcagagatttcacacgatatcatgttgagagagtataa
gagtttatctgcacttgaatttgagccatgtatagaatatgaccctgtcaccaacctgagcatgt
tcctaaaagacaaggcaatcgcacaccccaacgataattggcttgcctcgtttaggcggaac
cttctctccgaagaccagaagaaacatgtaaaagaagcaacttcgactaatcgcctcttgata
gagtttttagagtcaaatgattttgatccatataaagagatggaatatctgacgacccttgagta
ccttagagatgacaatgtggcagtatcatactcgctcaaggagaaggaagtgaaagttaatg
gacggatcttcgctaagctgacaaagaagttaaggaactgtcaggtgatggcggaagggat
cctagccgatcagattgcacctttctttcagggaaatggagtcattcaggatagcatatccttg
accaagagtatgctagcgatgagtcaactgtcttttaacagcaataagaaacgtatcactgact
gtaaagaaagagtatcttcaaaccgcaatcatgatccgaaaagcaagaaccgtcggagagt
tgcaaccttcataacaactgacctgcaaaagtactgtcttaattggagatatcagacaatcaaa
ttgttcgctcatgccatcaatcagttgatgggcctacctcacttcttcgaatggattcacctaag
actgatggacactacgatgttcgtaggagaccctttcaatcctccaagtgaccctactgactgt
gacctctcaagagtccctaatgatgacatatatattgtcagtgccagaggggggtatcgaagga
ttatgccagaagctatggacaatgatctcaattgctgcaatccaacttgctgcagctagatcgc
attgtcgtgttgcctgtatggtacagggtgataatcaagtaatagcagtaacgagagaggtaa
gatcagacgactctccggagatggtgttgacacagttgcatcaagccagtgataatttcttcaa
ggaattaattcatgtcaatcatttgattggccataatttgaaggatcgtgaaaccatcaggtcag
acacattcttcatatacagcaaacgaatcttcaaagatggagcaatcctcagtcaagtcctcaa
aaattcatctaaattagtgctagtgtcaggtgatctcagtgaaaacaccgtaatgtcctgtgcca
acattgcctctactgtagcacggctatgcgagaacgggcttcccaaagacttctgttactattta
aactatataatgagttgtgtgcagacatactttgactctgagttctccatcaccaacaattcgca
ccccgatcttaatcagtcgtggattgaggacatctcttttgtgcactcatatgttctgactcctgc
ccaattaggggggactgagtaaccttcaatactcaaggctctacactagaaatatcggtgaccc
ggggactactgcttttgcagagatcaagcgactagaagcagtgggattactgagtcctaaca
ttatgactaatatcttaactaggccgcctgggaatggagattgggccagtctgtgcaacgacc
catactctttcaattttgagactgttgcaagcccaaatattgttcttaagaaacatacgcaaaga
gtcctatttgaaacttgttcaaatcccttattgtctggagtgcacacagaggataatgaggcag
aagagaaggcattggctgaattcttgcttaatcaagaggtgattcatccccgcgttgcgcatg
ccatcatggaggcaagctctgtaggtaggagaaagcaaattcaagggcttgttgacacaac
aaacaccgtaattaagattgcgcttactaggaggccattaggcatcaagaggctgatgcgga
tagtcaattattctagcatgcatgcaatgctgtttagagacgatgtttttcctccagtagatccaa
ccaccccttagtctcttctaatatgtgttctctgacactggcagactatgcacggaatagaagct
ggtcacctttgacgggaggcaggaaaatactgggtgtatctaatcctgatacgatagaactc
gtagagggtgagattcttagtgtaagcggagggtgtacaagatgtgacagcggagatgaac
```

-continued

```
aatttacttggttccatcttccaagcaatatagaattgaccgatgacaccagcaagaatcctcc
gatgagggtaccatatctcgggtcaaagacacaggagaggagagctgcctcacttgcaaaa
atagctcatatgtcgccacatgtaaaggctgccctaagggcatcatccgtgttgatctgggctt
atggggataatgaagtaaattggactgctgctcttacgattgcaaaatctcggtgtaatgtaaa
cttagagtatcttcggttactgtcccctttacccacggctgggaatcttcaacatagactagatg
atggtataactcagatgacattcacccctgcatctctctacaggGtgtcaccttacattcacata
tccaatgattctcaaaggctgttcactgaagaaggagtcaaagaggggaatgtggtttaccaa
cagatcatgctcttgggtttatctctaatcgaatcgatctttccaatgacaacaaccaggacata
tgatgagatcacactgcacctacatagtaaatttagttgctgtatcagagaagcacctgttgcg
gttcctttcgagctacttggggtggtaccggaactgaggacagtgacctcaaataagtttatgt
atgatcctagccctgtatcggagggagactttgcgagacttgacttagctatcttcaagagttat
gagcttaatctggagtcatatcccacgatagagctaatgaacattctttcaatatccagcggga
agttgattggccagtctgtggtttcttatgatgaagatacctccataaagaatgacgccataata
gtgtatgacaatacccgaaattggatcagtgaagctcagaattcagatgtggtccgcctatttg
aatatgcagcacttgaagtgctcctcgactgttcttaccaactctattacctgagagtaagagg
cctGgacaatattgtcttatatatgggtgatttatacaagaatatgccaggaattctactttccaa
cattgcagctacaatatctcatcccgtcattcattcaaggttacatgcagtgggcctggtcaac
catgacggatcacaccaacttgcagatacggattttatcgaaatgtctgcaaaactattagtat
cttgcacccgacgtgtgatctccggcttatattcaggaaataagtatgatctgctgttcccatct
gtcttagatgataacctgaatgagaagatgcttcagctgatatcccggttatgctgtctgtacac
ggtactctttgctacaacaagagaaatcccgaaaataagaggcttaactgcagaagagaaat
gttcaatactcactgagtatttactgtcggatgctgtgaaaccattacttagccccgatcaagtg
agctctatcatgtctcctaacataattacattcccagctaatctgtactacatgtctcggaagag
cctcaatttgatcagggaaagggaggacagggatactatcctggcgttgttgttcccccaag
agccattattagagttcccttctgtgcaagatattggtgctcgagtgaaagatccattcacccg
acaacctgcggcattttttgcaagagttagatttgagtgctccagcaaggtatgacgcattcaca
cttagtcagattcatcctgaactcacatctccaaatccggaggaagactacttagtacgatactt
gttcagagggatagggactgcatcttcctcttggtataaggcatctcatctcctttctgtacccg
aggtaagatgtgcaagacacgggaactccttatacttagctgaagggagcggagccatcat
gagtcttctcgaactgcatgtaccacatgaaactatctattacaatacgctcttttcaaatgagat
gaacccccccgcaacgacatttcgggccgaccccaactcagtttttgaattcggttgtttatagg
aatctacaggcggaggtaacatgcaaagatggatttgtccaagagttccgtccattatggaga
gaaaatacagaggaaagCgacctgacctcagataaagTagtggggtatattacatctgca
gtgccctacagatctgtatcattgctgcattgtgacattgaaattcctccagggtccaatcaaag
cttactagatcaactagctatcaatttatctctgattgccatgcattctgtaagggaggggggg
tagtaatcatcaaagtgttgtatgcaatgggatactactttcatctactcatgaacttgtttgctcc
gtgttccacaaaaggatatattctctctaatggttatgcatgtcgaggagatatggagtgttacc
tggtatttgtcatgggttacctgggcgggcctacatttgtacatgaggtggtgaggatggcGa
aaactctggtgcagcggcacggtacgctTttgtctaaatcagatgagatcacactgaccagg
ttattcacctcacagcggcagcgtgtgacagacatcctatccagtcctttaccaagattaataa
agtacttgaggaagaatattgacactgcgctgattgaagccgggggacagcccgtccgtcc
attctgtgcggagagtctggtgagcacgctagcgaacataactcagataacccagatCatc
gctagtcacattgacacagttatccggtctgtgatatatatggaagctgagggtgatctcgctg
acacagtatttctatttaccccttacaatctctctactgacgggaaaaagaggacatcacttaA
acagtgcacgagacagatcctagaggttacaatactaggtcttagagtcgaaaatctcaataa
aataggcgatataatcagcctagtgcttaaaggcatgatctccatggaggaccttatcccact
aaggacatacttgaagcatagtacctgccctaaatatttgaaggctgtcctaggtattaccaaa
ctcaaagaaatgtttacagacacttctgtaCtgtacttgactcgtgctcaacaaaaattctacat
gaaaactataggcaatgcagtcaaaggatattacagtaactgtgactcttaacgaaaatcaca
tattaataggctcctttttttggccaattgtattcttgttgatttaatcatattatgttagaaaaaagttg
aaccctgactccttaggactcgaattcgaactcaaataaatgtcttaaaaaaaggttgcgcac
aattattcttgagtgtagtctcgtcattcaccaaatctttgtttggt
```

TABLE 4

| hMPV F Sequences | | |
|---|---|---|
| Wild-type Nucleic acid encoding hMPV-F protein of hMPV strain CAN00-16 (transmembrane and cytoplasmic domains are indicated by underlining) | ATGTCTTGGAAAGTGGTGATCATTTTTTCATTGCTAATAACACCTCAA<br>CACGGTCTTAAAGAGAGCTACCTAGAAGAATCATGTAGCACTATAACT<br>GAGGGATATCTTAGTGTTCTGAGGACAGGTTGGTATACCAACGTTTTT<br>ACATTAGAGGTGGGTGATGTAGAAAACCTTACATGTTCTGATGGACCT<br>AGCCTAATAAAAACAGAATTAGATCTGACCAAAAGTGCACTAAGAGAG<br>CTCAAAACAGTCTCTGCTGACCAATTGGCAAGAGAGGAACAAATTGAG<br>AATCCCAGACAATCTAGGTTTGTTCTAGGAGCAATAGCACTCGGTGTT<br>GCAACAGCAGCTGCAGTCACAGCAGGTGTTGCAATTGCCAAAACCATC<br>CGGCTTGAGAGTGAAGTCACAGCAATTAAGAATGCCCTCAAAACGACC<br>AATGAAGCAGTATCTACATTGGGGAATGGAGTTCGAGTGTTGGCAACT<br>GCAGTGAGAGAGCTGAAAGACTTTGTGAGCAAGAATTTAACTCGTGCA<br>ATCAACAAAAACAAGTGCGACATTGATGACCTAAAAATGGCCGTTAGC<br>TTCAGTCAATTCAACAGAAGGTTTCTAAATGTTGTGCGGCAATTTTCA<br>GACAATGCTGGAATAACACCAGCAATATCTTTGGACTTAATGACAGAT<br>GCTGAACTAGCCAGGGCCGTTTCTAACATGCCGACATCTGCAGGACAA<br>ATAAAATTGATGTTGGAGAACCGCGCGATGGTGCGAAGAAAGGGGTTC<br>GGAATCCTGATAGGGGTCTACGGGAGCTCTGTAATTTACATGGTGCAG<br>CTGCCAATCTTTGGCGTTATAGACACGCCTTGCTGGATAGTAAAAGCA<br>GCCCCTTCTTGTTCCGAAAAAAAGGGAAACTATGCTTGCCTCTTAAGA<br>GAAGACCAAGGGTGGTATTGTCAGAATGCAGGGTCAACTGTTTACTAC | 16 |

TABLE 4-continued

| hMPV F Sequences | | |
|---|---|---|
| | CCAAATGAGAAAGACTGTGAAACAAGAGGAGACCATGTCTTTTGCGAC<br>ACAGCAGCAGGAATTAATGTTGCTGAGCAATCAAAGGAGTGCAACATC<br>AACATATCCACTACAAATTACCCATGCAAAGTCAGCACAGGAAGACAT<br>CCTATCAGTATGGTTGCACTGTCTCCTCTTGGGGCTCTGGTTGCTTGC<br>TACAAAGGAGTAAGCTGTTCCATTGGCAGCAACAGAGTAGGGATCATC<br>AAGCAGCTGAACAAAGGTTGCTCCTATATAACCAACCAAGATGCAGAC<br>ACAGTGACAATAGACAACACTGTATATCAGCTAAGCAAAGTTGAGGGT<br>GAACAGCATGTTATAAAAGGCAGACCAGTGTCAAGCAGCTTTGATCCA<br>ATCAAGTTTCCTGAAGATCAATTCAATGTTGCACTTGACCAAGTTTTT<br>GAGAGCATTGAAAACAGCCAGGCCTTGGTAGATCAATCAAACAGAATC<br>CTAAGCAGTGCAGAGAAAGGGAATACTGGCTTCATCATTGTAATAATT<br>CTAATTGCTGTCCTTGGCTCTAGCATGATCCTAGTGAGCATCTTCATT<br>ATAATCAAGAAAACAAAGAAACCAACGGGAGCACCTCCAGAGCTGAGT<br>GGTGTCACAAACAATGGCTTCATACCACACAGTTAG | |
| Amino acid sequence of huMPV-F protein of hMPV strain CAN00-16 (transmembrane and cytoplasmic domains are underlined; SEQ ID No: 16 or 18 encode this amino acid sequence) | MSWKVVIIFSLLITPQHGLKESYLEESCSTITEGYLSVLRTGWYTNVE<br>TLEVGDVENLTCSDGPSLIKTELDLTKSALRELKTVSADQLAREEQIE<br>NPRQSRFVLGAIALGVATAAAVTAGVAIAKTIRLESEVTAIKNALKTT<br>NEAVSTLGNGVRVLATAVRELKDFVSKNLTRAINKNKCDIDDLKMAVS<br>FSQFNRRELNVVRQFSDNAGITPAISLDLMTDAELARAVSNMPTSAGQ<br>IKLMLENRAMVRRKGFGILIGVYGSSVIYMVQLPIFGVIDTPCWIVKA<br>APSCSEKKGNYACLLREDQGWYCQNAGSTVYYPNEKDCETRGDHVFCD<br>TAAGINVAEQSKECNINISTTNYPCKVSTGRHPISMVALSPLGALVAC<br>YKGVSCSIGSNRVGIIKQLNKGCSYITNQDADTVTIDNTVYQLSKVEG<br>EQHVIKGRPVSSSFDPIKFPEDQFNVALDQVFESIENSQALVDQSNRI<br>LSSAEKGNTGFIIVIILIAVLGSSMILVSIFIIIKKTKKPTGAPPELS<br>GVTNNGFIPHS | 17 |
| Codon optimized nucleic acid encoding hMPV-F protein of hMPV strain CAN00-16 (transmembrane and cytoplasmic domains are underlined) | ATGAGCTGGAAGGTGGTGATCATCTTCAGCCTGCTGATCACCCCCCAG<br>CACGGCCTGAAGGAGAGCTACCTGGAGGAGAGCTGCAGCACCATCACC<br>GAGGGCTACCTGAGCGTGCTGAGAACCGGCTGGTACACCAACGTGTTC<br>ACCCTGGAGGTGGGCGACGTGGAGAACCTGACCTGCAGCGACGGCCCC<br>AGCCTGATCAAGACCGAGCTGGACCTGACCAAGAGCGCCCTGAGAGAG<br>CTGAAGACCGTGAGCGCCGACCAGCTGGCCAGAGAGGAGCAGATCGAG<br>AACCCCAGACAGAGCAGATTCGTGCTGGGCGCCATCGCCCTGGGCGTG<br>GCCACCGCCGCCGCCGTGACCGCCGGCGTGGCCATCGCCAAGACCATC<br>AGACTGGAGAGCGAGGTGACCGCCATCAAGAACGCCCTGAAGACCACC<br>AACGAGGCCGTGAGCACCCTGGGCAACGGCGTGAGAGTGCTGGCCACC<br>GCCGTGAGAGAGCTGAAGGACTTCGTGAGCAAGAACCTGACCAGAGCC<br>ATCAACAAGAACAAGTGCGACATCGACGACCTGAAGATGGCCGTGAGC<br>TTCAGCCAGTTCAACAGAAGATTCCTGAACGTGGTGAGACAGTTCAGC<br>GACAACGCCGGCATCACCCCCGCCATCAGCCTGGACCTGATGACCGAC<br>GCCGAGCTGGCCAGAGCCGTGAGCAACATGCCCACCAGCGCCGGCCAG<br>ATCAAGCTGATGCTGGAGAACAGAGCCATGGTGAGAAGAAAGGGCTTC<br>GGCATCCTGATCGGCGTGTACGGCAGCAGCGTGATCTACATGGTGCAG<br>CTGCCCATCTTCGGCGTGATCGACACCCCCTGCTGGATCGTGAAGGCC<br>GCCCCCAGCTGCAGCGAGAAGAAGGGCAACTACGCCTGCCTGCTGAGA<br>GAGGACCAGGGCTGGTACTGCCAGAACGCCGGCAGCACCGTGTACTAC<br>CCCAACGAGAAGGACTGCGAGACCAGAGGCGACCACGTGTTCTGCGAC<br>ACCGCCGCCGGCATCAACGTGGCCGAGCAGAGCAAGGAGTGCAACATC<br>AACATCAGCACCACCAACTACCCCTGCAAGGTGAGCACCGGCAGACAC<br>CCCATCAGCATGGTGGCCCTGAGCCCCCTGGGCGCCCTGGTGGCCTGC<br>TACAAGGGCGTGAGCTGCAGCATCGGCAGCAACAGAGTGGGCATCATC<br>AAGCAGCTGAACAAGGGCTGCAGCTACATCACCAACCAGGACGCCGAC<br>ACCGTGACCATCGACAACACCGTGTACCAGCTGAGCAAGGTGGAGGGC<br>GAGCAGCACGTGATCAAGGGCAGACCCGTGAGCAGCAGCTTCGACCCC<br>ATCAAGTTCCCCGAGGACCAGTTCAACGTGGCCCTGGACCAGGTGTTC<br>GAGAGCATCGAGAACAGCCAGGCCCTGGTGGACCAGAGCAACAGAATC<br>CTGAGCAGCGCCGAGAAGGGCAACACCGGCTTCATCATCGTGATCATC<br>CTGATCGCCGTGCTGGGCAGCAGCATGATCCTGGTGAGCATCTTCATC<br>ATCATCAAGAAGACCAAGAAGCCCACCGGCGCCCCCCCCGAGCTGAGC<br>GGCGTGACCAACAACGGCTTCATCCCCCACAGCTGA | 18 |
| Nucleic acid encoding chimeric hMPV F protein comprising the ectodomain of the F protein of hMPV strain CAN00-16 and the transmembrane and cytoplasmic domains of the | ATGAGCTGGAAGGTGGTGATCATCTTCAGCCTGCTGAT<br>CACCCCCCAGCACGGCCTGAAGGAGAGCTACCTGGAGG<br>AGAGCTGCAGCACCATCACCGAGGGCTACCTGAGCGTG<br>CTGAGAACCGGCTGGTACACCAACGTGTTCACCCTGGA<br>GGTGGGCGACGTGGAGAACCTGACCTGCAGCGACGGCC<br>CCAGCCTGATCAAGACCGAGCTGGACCTGACCAAGAGC<br>GCCCTGAGAGAGCTGAAGACCGTGAGCGCCGACCAGCT<br>GGCCAGAGAGGAGCAGATCGAGAACCCCAGACAGAGC<br>AGATTCGTGCTGGGCGCCATCGCCCTGGGCGTGGCCAC<br>CGCCGCCGCCGTGACCGCCGGCGTGGCCATCGCCAAGA<br>CCATCAGACTGGAGAGCGAGGTGACCGCCATCAAGAAC<br>GCCCTGAAGACCACCAACGAGGCCGTGAGCACCCTGGG<br>CAACGGCGTGAGAGTGCTGGCCACCGCCGTGAGAGAGC | 19 |

TABLE 4-continued

| hMPV F Sequences | | |
|---|---|---|
| F protein of NDV LaSota strain, wherein the nucleotide sequence encoding the ectodomain of the F protein of the hMPV is codon optimized | TGAAGGACTTCGTGAGCAAGAACCTGACCAGAGCCATC<br>AACAAGAACAAGTGCGACATCGACGACCTGAAGATGG<br>CCGTGAGCTTCAGCCAGTTCAACAGAAGATTCCTGAAC<br>GTGGTGAGACAGTTCAGCGACAACGCCGGCATCACCCC<br>CGCCATCAGCCTGGACCTGATGACCGACGCCGAGCTGG<br>CCAGAGCCGTGAGCAACATGCCCACCAGCGCCGGCCAG<br>ATCAAGCTGATGCTGGAGAACAGAGCCATGGTGAGAAG<br>AAAGGGCTTCGGCATCCTGATCGGCGTGTACGGCAGCA<br>GCGTGATCTACATGGTGCAGCTGCCCATCTTCGGCGTGA<br>TCGACACCCCCTGCTGGATCGTGAAGGCCGCCCCCAGC<br>TGCAGCGAGAAGAAGGGCAACTACGCCTGCCTGCTGAG<br>AGAGGACCAGGGCTGGTACTGCCAGAACGCCGGCAGC<br>ACCGTGTACTACCCCAACGAGAAGGACTGCGAGACCAG<br>AGGCGACCACGTGTTCTGCGACACCGCCGCCGGCATCA<br>ACGTGGCCGAGCAGAGCAAGGAGTGCAACATCAACATC<br>AGCACCACCAACTACCCCTGCAAGGTGAGCACCGGCAG<br>ACACCCCATCAGCATGGTGGCCCTGAGCCCCCTGGGCG<br>CCCTGGTGGCCTGCTACAAGGGCGTGAGCTGCAGCATC<br>GGCAGCAACAGAGTGGGCATCATCAAGCAGCTGAACA<br>AGGGCTGCAGCTACATCACCAACCAGGACGCCGACACC<br>GTGACCATCGACAACACCGTGTACCAGCTGAGCAAGGT<br>GGAGGGCGAGCAGCACGTGATCAAGGGCAGACCCGTG<br>AGCAGCAGCTTCGACCCCATCAAGTTCCCCGAGGACCA<br>GTTCAACGTGGCCCTGGACCAGGTGTTCGAGAGCATCG<br>AGAACAGCCAGGCCCTGGTGGACCAGAGCAACAGAAT<br>CCTGAGCAGCGCCGAGAAGGGCAACACCGGCGTTAACC<br>TCATTACCTATATCGTTTTGACTATCATATCTCTTGTTTT<br>TGGTATACTTAGCCTGATTCTAGCATGCTACCTAATGTA<br>CAAGCAAAAGGCGCAACAAAAGACCTTATTATGGCTTG<br>GGAATAATACCCTAGATCAGATGAGAGCCACTACAAAA<br>ATGTGA | |
| Amino acid sequence of the chimeric F protein comprising the ectodomain of hMPV F protein of CAN00-16 strain and LaSota strain NDV F protein transmembrane and cytoplasmic domains | MSWKVVIIFSLLITPQHGLKESYLEESCSTITEGYLSVLRTGWYTNVF<br>TLEVGDVENLTCSDGPSLIKTELDLTKSALRELKTVSADQLAREEQIE<br>NPRQSRFVLGAIALGVATAAAVTAGVAIAKTIRLESEVTAIKNALKTT<br>NEAVSTLGNGVRVLATAVRELKDFVSKNLTRAINKNKCDIDDLKMAVS<br>FSQFNRRFLNVVRQFSDNAGITPAISLDLMTDAELARAVSNMPTSAGQ<br>IKLMLENRAMVRRKGFGILIGVYGSSVIYMVQLPIFGVIDTPCWIVKA<br>APSCSEKKGNYACLLREDQGWYCQNAGSTVYYPNEKDCETRGDHVFCD<br>TAAGINVAEQSKECNINISTTNYPCKVSTGRHPISMVALSPLGALVAC<br>YKGVSCSIGSNRVGIIKQLNKGCSYITNQDADTVTIDNTVYQLSKVEG<br>EQHVIKGRPVSSSFDPIKFPEDQFNVALDQVFESIENSQALVDQSNRI<br>LSSAEKGNTGVNLITYIVLTIISLVFGILSLILACYLMYKQKAQQKTL<br>LWLGNNTLDQMRATTKM | 15 |
| cDNA of genomic sequence of NDV LaSota strain with the nucleic acid encoding hMPV F protein of hMPV strain CAN00-16 inserted (nucleic acid sequence encoding hMPV F protein is indicated by underlining; Sac II restriction site is indicated by double underlining) | accaaacagagaatccgtgagttacgataaaaggcgaaggagcaattg<br>aagtcgcacgggtagaaggtgtgaatctcgagtgcgagcccgaagcac<br>aaactcgagaaagccttctgccaacatgtcttccgtatttgatgagta<br>cgaacagctcctcgcggctcagactcgccccaatggagctcatggagg<br>gggagaaaaagggagtaccttaaaagtagacgtcccggtattcactct<br>taacagtgatgacccagaagatagatggagctttgtggtattctgcct<br>ccggattgctgttagcgaagatgccaacaaaccactcaggcaaggtgc<br>tctcatatctcttttatgctcccactcacaggtaatgaggaaccatgt<br>tgccCttgcagggaaacagaatgaagccacattggccgtgcttgagat<br>tgatggctttgccaacggcacgccccagttcaacaataggagtggagt<br>gtctgaagagagagcacagagatttgcgatgatagcaggatctctccc<br>tcgggcatgcagcaacggaaccccgttcgtcacagccggggcCgaaga<br>tgatgcaccagaagacatcaccgataccctggagaggatcctctctat<br>ccaggctcaagtatgggtcacagtagcaaaagccatgactgcgtatga<br>gactgcagatgagtcggaaacaaggcgaatcaataagtatatgcagca<br>aggcagggtccaaaagaaatacatcctctaccccgtatgcaggagcac<br>aatccaactcacgatcagacagtctcttgcagtccgcatctttttggt<br>tagcgagctcaagagaggccgcaacacggcaggtggtacctctactta<br>ttataacctggtaggggacgtagactcatacatcaggaataccgggct<br>tactgcattcttcttgacactcaagtacggaatcaacaccaagacatc<br>agcccttgcacttagtagcctctcaggcgacatccagaagatgaagca<br>gctcatgcgtttgtatcggatgaaaggagataatgcgccgtacatgac<br>attacttggtgatagtgaccagatgagctttgcgcctgccgagtatgc<br>acaactttactcctttgccatgggtatggcatcagtcctagataaagg<br>tactgggaaataccaatttgccagggactttatgagcacatcattctg<br>gagacttggagtagagtacgctcaggctcagggaagtagcattaacga<br>ggatatggctgccgagctaaagctaaccccagcagcaaGgaGgggcct<br>ggcagctgctgcccaacgggtctccgaGgaGaccagcagcataGacat<br>gcctactcaacaagtcggagtcctcactgggcttagcgaggggggtc<br>ccaagctctacaaggcggatcgaatagatcgcaagggcaaccagaagc | 20 |

TABLE 4-continued

| hMPV F Sequences |
|---|
| cggggatggggagacccaattcctggatctgatgagagcggtagcaaa<br>tagcatgagggaggcgccaaactctgcacagggcactccccaatcggg<br>gcctcccccaactcctgggccatcccaagataacgacaccgactgggg<br>gtattgatggacaaaacccagcctgcttccacaaaaacatcccaatgc<br>cctcacccgtagtcgacccctcgatttgcggctctatatgaccacacc<br>ctcaaacaaacatccccctctttcctccctccccctgctgtacaactA<br>cgTacgccctagataccacaggcacaatgcggctcactaacaatcaaa<br>acagagccgagggaattagaaaaaagtacgggtagaagagggatattc<br>agagatcagggcaagtctcccgagtctctgctctctcctctacctgat<br>agaccaggacaaacatggccacctttacagatgcagagatcgacgagc<br>tatttgagacaagtggaactgtcattgacaacataattacagcccagg<br>gtaaaccagcagagactgttggaaggagtgcaatcccacaaggcaaga<br>ccaaggtgctgagcgcagcatgggagaagcatgggagcatccagccac<br>cggccagtcaagacaaccccgatcgacaggacagatctgacaaacaac<br>catccacacccgagcaaacgaccccgcatgacagcccgccggccacat<br>ccgccgaccagcccccacccaggccacagacgaagccgtcgacacac<br>agCtcaggaccggagcaagcaactctctgctgttgatgcttgacaagc<br>tcagcaataaatcgtccaatgctaaaaagggcccatggtcgagccccc<br>aagaggggaatcaccaacgtccgactcaacagcaggggagtcaaccca<br>gtcgcggaaacagtcaggaaagaccgcagaaccaagtcaaggccgccc<br>ctggaaaccagggcacagacgtgaacacagcatatcatggacaatggg<br>aggagtcacaactatcagctggtgcaacccctcatgctctccgatcaa<br>ggcagagccaagacaatacccttgtatctgcggatcatgtccagccac<br>ctgtagactttgtgcaagcgatgatgtctatgatggaggcgatatcac<br>agagagtaagtaaggttgactatcagctagatcttgtcttgaaacaga<br>catcctccatccctatgatgcggtccgaaatccaacagctgaaaacat<br>ctgttgcagtcatggaagccaacttgggaatgatgaagattctggatc<br>ccggttgtgccaacatttcatctctgagtgatctacgggcagttgccc<br>gatctcacccggttttagtttcaggccctggagacccctctccctatg<br>tgacacaaggaggcgaaatggcacttaataaactttcgcaaccagtgc<br>cacatccatctgaattgattaaacccgccactgcatgcgggcctgata<br>taggagtggaaaaggacactgtccgtgcattgatcatgtcacgcccaa<br>tgcacccgagttcttcagccaagctcctaagcaagttagatgcagccg<br>ggtcgatcgaggaaatcaggaaaatcaagcgccttgctctaaatggct<br>aattactactgccacacgtagcgggtccctgtccactcggcatcacac<br>ggaatctgcaccgagttcccccccgcGgTTAGAAAAAATACGGGTAGA<br>ACCGCCACCATGTCTTGGAAAGTGGTGATCATTTTTCATTGCTAATA<br>ACACCTCAACACGGTCTTAAAGAGAGCTACCTAGAAGAATCATGTAGC<br>ACTATAACTGAGGGATATCTTAGTGTTCTGAGGACAGGTTGGTATACC<br>AACGTTTTTACATTAGAGGTGGGTGATGTAGAAAACCTTACATGTTCT<br>GATGGACCTAGCCTAATAAAAACAGAATTAGATCTGACCAAAAGTGCA<br>CTAAGAGAGCTCAAAACAGTCTCTGCTGACCAATTGGCAAGAGAGGAA<br>CAAATTGAGAATCCCAGACAATCTAGGTTTGTTCTAGGAGCAATAGCA<br>CTCGGTGTTGCAACAGCAGCTGCAGTCACAGCAGGTGTTGCAATTGCC<br>AAAACCATCCGGCTTGAGAGTGAAGTCACAGCAATTAAGAATGCCCTC<br>AAAACGACCAATGAAGCAGTATCTACATTGGGGAATGGAGTTCGAGTG<br>TTGGCAACTGCAGTGAGAGAGCTGAAAGACTTTGTGAGCAAGAATTTA<br>ACTCGTGCAATCAACAAAAACAAGTGCGACATTGATGACCTAAAAATG<br>GCCGTTAGCTTCAGTCAATTCAACAGAAGGTTTCTAAATGTTGTGCGG<br>CAATTTTCAGACAATGCTGGAATAACACCAGCAATATCTTTGGACTTA<br>ATGACAGATGCTGAACTAGCCAGGGCCGTTTCTAACATGCCGACATCT<br>GCAGGACAAATAAAATTGATGTTGGAGAACCGCGCGATGGTGCGAAGA<br>AAGGGGTTCGGAATCCTGATAGGGGTCTACGGGAGCTCTGTAATTTAC<br>ATGGTGCAGCTGCCAATCTTTGGCGTTATAGACACGCCTTGCTGGATA<br>GTAAAAGCAGCCCCTTCTTGTTCCGAAAAAAAGGGAAACTATGCTTGC<br>CTCTTAAGAGAAGACCAAGGGTGGTATTGTCAGAATGCAGGGTCAACT<br>GTTTACTACCCAAATGAGAAAGACTGTGAAACAAGAGGAGACCATGTC<br>TTTTGCGACACAGCAGCAGGAATTAATGTTGCTGAGCAATCAAAGGAG<br>TGCAACATCAACATATCCACTACAAATTACCCATGCAAAGTCAGCACA<br>GGAAGACATCCTATCAGTATGGTTGCACTGTCTCCTCTTGGGGCTCTG<br>GTTGCTTGCTACAAAGGAGTAAGCTGTTCCATTGGCAGCAACAGAGTA<br>GGGATCATCAAGCAGCTGAACAAAGGTTGCTCCTATATAACCAACCAA<br>GATGCAGACACAGTGACAATAGACAACACTGTATATCAGCTAAGCAAA<br>GTTGAGGGTGAACAGCATGTTATAAAAGGCAGACCAGTGTCAAGCAGC<br>TTTGATCCAATCAAGTTTCCTGAAGATCAATTCAATGTTGCACTTGAC<br>CAAGTTTTTGAGAGCATTGAAAACAGCCAGGCCTTGGTAGATCAATCA<br>AACAGAATCCTAAGCAGTGCAGAGAAAGGGAATACTGGCTTCATCATT<br>GTAATAATTCTAATTGCTGTCCTTGGCTCTAGCATGATCCTAGTGAGC<br>ATCTTCATTATAATCAAGAAAACAAAGAAACCAACGGGAGCACCTCCA<br>GAGCTGAGTGGTGTCACAAACAATGGCTTCATACCACACAGTTAGGcc<br>gcggacccaaggtccaactctccaagcggcaatcctctctcgcttcct<br>cagccccactgaatgAtcgcgtaaccgtaattaatctagctacattta<br>agattaagaaaaaatacgggtagaattggagtgccccaattgtgccaa<br>gatggactcatctaggacaattgggctgtactttgattctgcccattc<br>ttctagcaacctgttagcatttccgatcgtcctacaagAcacaggaga<br>tgggaagaagcaaatcgccccgcaatataggatccagcgccttgactt<br>gtggactgatagtaaggaggactcagtattcatcaccacctatggatt<br>catctttcaagttgggaatgaagaagccacCgtcggcatgatcgatga |

TABLE 4-continued

| hMPV F Sequences |
| --- |
| taaacccaagcgcgagttactttccgctgcgatgctctgcctaggaag<br>cgtcccaaataccggagaccttattgagctggcaagggcctgtctcac<br>tatgatagtcacatgcaagaagagtgcaactaatactgagagaatggt<br>tttctcagtagtgcaggcaccccaagtgctgcaaagctgtagggttgt<br>ggcaaacaaatactcatcagtgaatgcagtcaagcacgtgaaagcgcc<br>agagaagattcccgggagtggaaccctagaatacaaggtgaactttgt<br>ctccttgactgtggtaccgaagaGggatgtctacaagatcccagctgc<br>agtattgaaggtttctggctcgagtctgtacaatcttgcgctcaatgt<br>cactattaatgtggaggtagacccgaggagtcctttggttaaatctCt<br>gtctaagtctgacagcggatactatgctaacctcttcttgcatattgg<br>acttatgaccacTgtagataggaaggggaagaaagtgacatttgacaa<br>gctggaaaagaaaataaggagccttgatctatctgtcgggctcagtga<br>tgtgctcgggccttccgtgttggtaaaagcaagaggtgcacggactaa<br>gcttttggcacctttcttctctagcagtgggacagcctgctatcccat<br>agcaaatgcttctcctcaggtggccaagatactctggagtcaaaccgc<br>gtgcctgcggagcgttaaaatcattatccaagcaggtacccaacgcgc<br>tgtcgcagtgaccgccgaccacgaggttacctctactaagctggagaa<br>ggggcacacccttgccaaatacaatccttttaagaaataagctgcgtc<br>tctgagattgcgctccgcccactcacccagatcatcatgacacaaaaa<br>actaatctgtcttgattatttacagttagtttacctgtctatcaagtt<br>agaaaaaacacgggtagaagattctggatcccggttggcgccctccag<br>gtgcaagatgggctccagaccttctaccaagaacccagcacctatgat<br>gctgactatccgggttgcgctggtactgagttgcatctgtccggcaaa<br>ctccattgatggcaggcctcttgcagctgcaggaattgtggttacagg<br>agacaaagccgtcaacatatacacctcatcccagacaggatcaatcat<br>agttaagctcctcccgaatctgcccaaggataaggaggcatgtgcgaa<br>agccccttggatgcatacaacaggacattgaccactttgctcacccc<br>ccttggtgactctatccgtaggatacaagagtctgtgactacatctgg<br>agggggagacaggggcgccttataggcgccattattggcggtgtggc<br>tcttggggttgcaactgccgcacaaataacagcggccgcagctctgat<br>acaagccaaacaaaatgctgccaacatcctccgacttaaagagagcat<br>tgccgcaaccaatgaggctgtgcatgaggtcactgacggattatcgca<br>actagcagtggcagttgggaagatgcagcagtttgttaatgaccaatt<br>taataaaacagctcaggaattagactgcatcaaaattgcacagcaagt<br>tggtgtagagctcaacctgtacctaaccgaattgactacagtattcgg<br>accacaaatcacttcacctgctttaaacaagctgactattcaggcact<br>ttacaatctagctggtggaaatatggattacttattgactaagttagg<br>tgtagggaacaatcaactcagctcattaatcggtagcggcttaatcac<br>cggtaaccctattctatacgactcacagactcaactcttgggtataca<br>ggtaactctaccttcagtcgggaacctaaataatatgcgtgccaccta<br>cttggaaaccttatccgtaagcacaaccaggggatttgcctcggcact<br>tgtcccAaaagtggtgacacaggtcggttctgtgatagaagaacttga<br>cacctcatactgtatagaaactgacttagatttatattgtacaagaat<br>agtaacgttccctatgtcccctggtatttattcctgcttgagcggcaa<br>tacgtcggcctgtatgtactcaaagaccgaaggcgcacttactacacc<br>atacatgactatcaaaggttcagtcatcgccaactgcaagatgacaac<br>atgtagatgtgtaaacccccgggtatcatatcgcaaaactatggaga<br>agccgtgtctctaatagataaacaatcatgcaatgttttatccttagg<br>cgggataactttaaggctcagtggggaattcgatgtaacttatcagaa<br>gaatatctcaatacaagattctcaagtaataataacaggcaatcttga<br>tatctcaactgagcttgggaatgtcaacaactcgatcagtaatgcttt<br>gaataagttagaggaaagcaacagaaaactagacaaagtcaatgtcaa<br>actgactagcacatctgctctcattacctatatcgttttgactatcat<br>atctcttgtttttggtatacttagcctgattctagcatgctacctaat<br>gtacaagcaaaaggcgcaacaaaagaccttattatggcttgggaataa<br>tactctagatcagatgagagccactacaaaaatgtgaacacagatgag<br>gaacgaaggtttccctaatagtaatttgtgtgaaagttctggtagtct<br>gtcagttcagagagttaagaaaaaactaccggttgtagatgaccaaag<br>gacgatatacgggtagaacggtaagagaggccgcccctcaattgcgag<br>ccaggcttcacaacctccgttctaccgcttcaccgacaacagtcctca<br>atcatggaccgcgccgttagccaagttgcgttagagaatgatgaaaga<br>gaggcaaaaaatacatggcgcttgatattccggattgcaatcttattc<br>ttaacagtagtgaccttggctatatctgtagcctcccttttatatagc<br>atgggggctagcacacctagcgatcttgtaggcataccgactaggatt<br>tccagggcagaagaaaagattacatctacacttggttccaatcaagat<br>gtagtagataggatatataagcaagtggcccttgagtctccgttggca<br>ttgttaaatactgagaccacaattatgaacgcaataacatctctctct<br>tatcagattaatggagctgcaaacaacagtgggtgggggcacctatc<br>catgacccagattatatagggggataggcaaagaactcattgtagat<br>gatgctagtgatgtcacatcattctatccctctgcatttcaagaacat<br>ctgaattttatcccggcgcctactacaggatcaggttgcactcgaata<br>ccctcatttgacatgagtgctacccattactgctacacccataatgta<br>atattgtctggatgcagagatcactcacattcatatcagtatttagca<br>cttggtgtgctccggacatctgcaacagggagggtattcttttctact<br>ctgcgttccatcaacctggacgacacccaaaatcggaagtcttgcagt<br>gtgagtgcaactcccctgggttgtgatatgctgtgctcgaaagtcacg<br>gagacagaggaagaagattataactcagctgtccctacgcggatggta<br>catgggaggttagggttcgacggccagtaccacgaaaaggacctagat |

TABLE 4-continued

| hMPV F Sequences |
|---|
| gtcacaacattattcggggactgggtggccaactacccaggagtaggg<br>ggtggatcttttattgacagccgcgtatggttctcagtctacggaggg<br>ttaaaacccaattcacccagtgacactgtacaggaagggaaatatgtg<br>atatacaagcgatacaatgacacatgcccagatgagcaagactaccag<br>attcgaatggccaagtcttcgtataagcctggacggtttggtgggaaa<br>cgcatacagcaggctatcttatctatcaaggtgtcaacatccttaggc<br>gaagacccggtactgactgtaccgcccaacacagtcacactcatgggg<br>gccgaaggcagaattctcacagtagggacatctcatttcttgtatcaa<br>cgagggtcatcatacttctctcccgcgttattatatcctatgacagtc<br>agcaacaaaacagccactcttcatagtccttatacattcaatgccttc<br>actcggccaggtagtatcccttgccaggcttcagcaagatgccccaac<br>tcgtgtgttactggagtctatacagatccatatcccctaatcttctat<br>agaaaccacaccttgcgaggggtattcgggacaatgcttgatggtgta<br>caagcaagacttaaccctgcgtctgcagtattcgatagcacatcccgc<br>agtcgcattactcgagtgagttcaagcagtaccaaagcagcatacaca<br>acatcaacttgttttaaagtggtcaagactaataagacctattgtctc<br>agcattgctgaaatatctaatactctcttcggagaattcagaatcgtc<br>ccgttactagttgagatcctcaaagatgacggggttagagaagccagg<br>tctggctagttgagtcaattataaaggagttggaaagatggcattgta<br>tcacctatcttctgcgacatcaagaatcaaaccgaatgccggcgcgtg<br>ctcgaattccatgttgccagttgaccacaatcagccagtgctcatgcg<br>atcagattaagccttgtcaAtaGtctcttgattaagaaaaaatgtaag<br>tggcaatgagatacaaggcaaaacagctcatggtTaaCaatacgggta<br>ggacatggcgagctccggtcctgaaagggcagagcatcagattatcct<br>accagagTcacacctgtcttcaccattggtcaagcacaaactactcta<br>ttactggaaattaactgggctaccgcttcctgatgaatgtgacttcga<br>ccacctcattctcagccgacaatggaaaaaaatacttgaatcggcctc<br>tcctgatactgagagaatgataaaactcggaagggcagtacaccaaac<br>tcttaaccacaattccagaataaccggagtgctccaccccaggtgttt<br>agaaGaactggctaatattgaggtcccagattcaaccaacaaatttcg<br>gaagattgagaagaagatccaaattcacaacacgagatatggagaact<br>gttcacaaggctgtgtacgcatatagagaagaaactgctggggtcatc<br>ttggtctaacaatgtcccccggtcagaggagttcagcagcattcgtac<br>ggatccggcattctggtttcactcaaaatggtccacagccaagtttgc<br>atggctccatataaaacagatccagaggcatctgatggtggcagctaG<br>gacaaggtctgcggccaacaaattggtgatgctaacccataaggtagg<br>ccaagtctttgtcactcctgaacttgtcgttgtgacgcatacgaatga<br>gaacaagttcacatgtcttacccaggaacttgtattgatgtatgcaga<br>tatgatggagggcagagatatggtcaacataatatcaaccacggcggt<br>gcatctcagaagcttatcagagaaaattgatgacattttgcggttaat<br>agacgctctggcaaaagacttgggtaatcaagtctacgatgttgtatc<br>actaatggagggatttgcatacggagctgtccagctactcgagccgtc<br>aggtacatttgcaggagatttcttcgcattcaacctgcaggagcttaa<br>agacattctaattggcctcctccccaatgatatagcagaatccgtgac<br>tcatgcaatcgctactgtattctctggtttagaacagaatcaagcagc<br>tgagatgttgtgtctgttgcgtctgtggggtcacccactgcttgagtc<br>ccgtattgcagcaaaggcagtcaggagccaaatgtgcgcaccgaaaat<br>ggtagactttgatatgatccttcaggtactgtctttcttcaagggaac<br>aatcatcaacgggtacagaaagaagaatgcaggtgtgtggccgcgagt<br>caaagtggatacaatatatgggaaggtcattgggcaactacatgcaga<br>ttcagcagagatttcacacgatatcatgttgagagagtataagagttt<br>atctgcacttgaatttgagccatgtatagaatatgaccctgtcaccaa<br>cctgagcatgttcctaaaagacaaggcaatcgcacaccccaacgataa<br>ttggcttgcctcgtttaggcggaaccttctctccgaagaccagaagaa<br>acatgtaaaagaagcaacttcgactaatcgcctcttgatagagttttt<br>agagtcaaatgattttgatccatataaagagatggaatatctgacgac<br>ccttgagtaccttagagatgacaatgtggcagtatcatactcgctcaa<br>ggagaaggaagtgaaagttaatggacggatcttcgctaagctgacaaa<br>gaagttaaggaactgtcaggtgatggcggaagggatcctagccgatca<br>gattgcacctttctttcagggaaatggagtcattcaggatagcatatc<br>cttgaccaagagtatgctagcgatgagtcaactgtcttttaacagcaa<br>taagaaacgtatcactgactgtaaagaaagagtatcttcaaaccgcaa<br>tcatgatccgaaaagcaagaaccgtcggagagttgcaaccttcataac<br>aactgacctgcaaaagtactgtcttaattggagatatcagacaatcaa<br>attgttcgctcatgccatcaatcagttgatgggcctacctcacttctt<br>cgaatggattcacctaagactgatggacactacgatgttcgtaggaga<br>ccctttcaatcctccaagtgaccctactgactgtgacctctcaagagt<br>ccctaatgatgacatatatattgtcagtgccagagggggtatcgaagg<br>attatgccagaagctatggacaatgatctcaattgctgcaatccaact<br>tgctgcagctagatcgcattgtcgtgttgcctgtatggtacagggtga<br>taatcaagtaatagcagtaacgagagaggtaagatcagacgactctcc<br>ggagatggtgttgacacagttgcatcaagccagtgataatttcttcaa<br>ggaattaattcatgtcaatcatttgattggccataatttgaaggatcg<br>tgaaaccatcaggtcagacacattcttcatatacagcaaacgaatctt<br>caaagatggagcaatcctcagtcaagtcctcaaaaattcatctaaatt<br>agtgctagtgtcaggtgatctcagtgaaaacaccgtaatgtcctgtgc<br>caacattgcctctactgtagcacggctatgcgagaacgggcttcccaa<br>agacttctgttactatttaaactatataatgagttgtgtgcagacata |

TABLE 4-continued

| hMPV F Sequences |
|---|
| ctttgactctgagttctccatcaccaacaattcgcaccccgatcttaa |
| tcagtcgtggattgaggacatctcttttgtgcactcatatgttctgac |
| tcctgcccaattaggggactgagtaaccttcaatactcaaggctcta |
| cactagaaatatcggtgacccggggactactgcttttgcagagatcaa |
| gcgactagaagcagtgggattactgagtcctaacattatgactaatat |
| cttaactaggccgcctgggaatggagattgggccagtctgtgcaacga |
| cccatactctttcaattttgagactgttgcaagcccaaatattgttct |
| taagaaacatacgcaaagagtcctatttgaaacttgttcaaatccctt |
| attgtctggagtgcacacagaggataatgaggcagaagagaaggcatt |
| ggctgaattcttgcttaatcaagaggtgattcatccccgcgttgcgca |
| tgccatcatggaggcaagctctgtaggtaggagaaagcaaattcaagg |
| gcttgttgacacaacaaacaccgtaattaagattgcgcttactaggag |
| gccattaggcatcaagaggctgatgcggatagtcaattattctagcat |
| gcatgcaatgctgtttagagacgatgtttttcctccagtagatccaa |
| ccaccccttagtctcttctaatatgtgttctctgacactggcagacta |
| tgcacggaatagaagctggtcacctttgacgggaggcaggaaaatact |
| gggtgtatctaatcctgatacgatagaactcgtagagggtgagattct |
| tagtgtaagcggagggtgtacaagatgtgacagcggagatgaacaatt |
| tacttggttccatcttccaagcaatatagaattgaccgatgacaccag |
| caagaatcctccgatgagggtaccatatctcgggtcaaagacacagga |
| gaggagagctgcctcacttgcaaaaatagctcatatgtcgccacatgt |
| aaaggctgccctaagggcatcatccgtgttgatctgggcttatgggga |
| taatgaagtaaattggactgctgctcttacgattgcaaaatctcggtg |
| taatgtaaacttagagtatcttcggttactgtcccctttacccacggc |
| tgggaatcttcaacatagactagatgatggtataactcagatgacatt |
| caccccctgcatctctctacaggGtgtcaccttacattcacatatccaa |
| tgattctcaaaggctgttcactgaagaaggagtcaaagaggggaatgt |
| ggtttaccaacagatcatgctcttgggtttatctctaatcgaatcgat |
| ctttccaatgacaacaaccaggacatatgatgagatcacactgcacct |
| acatagtaaatttagttgctgtatcagagaagcacctgttgcggttcc |
| tttcgagctacttggggtggtaccggaactgaggacagtgacctcaaa |
| taagtttatgtatgatcctagccctgtatcggagggagactttgcgag |
| acttgacttagctatcttcaagagttatgagcttaatctggagtcata |
| tcccacgatagagctaatgaacattctttcaatatccagcgggaagtt |
| gattggccagtctgtggtttcttatgatgaagatacctccataaagaa |
| tgacgccataatagtgtatgacaatacccgaaattggatcagtgaagc |
| tcagaattcagatgtggtccgcctatttgaatatgcagcacttgaagt |
| gctcctcgactgttcttaccaactctattacctgagagtaagaggcct |
| Ggacaatattgtcttatatatgggtgatttatacaagaatatgccagg |
| aattctactttccaacattgcagctacaatatctcatcccgtcattca |
| ttcaaggttacatgcagtgggcctggtcaaccatgacggatcacacca |
| acttgcagatacggattttatcgaaatgtctgcaaaactattagtatc |
| ttgcacccgacgtgtgatctccggcttatattcaggaaataagtatga |
| tctgctgttcccatctgtcttagatgataacctgaatgagaagatgct |
| tcagctgatatcccggttatgctgtctgtacacggtactctttgctac |
| aacaagagaaatcccgaaaataagaggcttaactgcagaagagaaatg |
| ttcaatactcactgagtatttactgtcggatgtgtgaaaccattact |
| tagccccgatcaagtgagctctatcatgtctcctaacataattacatt |
| cccagctaatctgtactacatgtctcggaagagcctcaatttgatcag |
| ggaaagggaggacagggatactatcctggcgttgttgttcccccaaga |
| gccattattagagttcccttctgtgcaagatattggtgctcgagtgaa |
| agatccattcacccgacaacctgcggcatttttgcaagagttagattt |
| gagtgctccagcaaggtatgacgcattcacacttagtcagattcatcc |
| tgaactcacatctccaaatccggaggaagactacttagtacgatactt |
| gttcagagggatagggactgcatcttcctcttggtataaggcatctca |
| tctcctttctgtacccgaggtaagatgtgcaagacacgggaactcctt |
| atacttagctgaagggagcggagccatcatgagtcttctcgaactgca |
| tgtaccacatgaaactatctattacaatacgctcttttcaaatgagat |
| gaacccccccgcaacgacatttcgggccgaccccaactcagtttttgaa |
| ttcggttgtttataggaatctacaggcggaggtaacatgcaaagatgg |
| atttgtccaagagttccgtccattatggagagaaaatacagaggaaag |
| CgacctgacctcagataaagTagtggggtatattacatctgcagtgcc |
| ctacagatctgtatcattgctgcattgtgacattgaaattcctccagg |
| gtccaatcaaagcttactagatcaactagctatcaatttatctctgat |
| tgccatgcattctgtaagggagggcggggtagtaatcatcaaagtgtt |
| gtatgcaatgggatactactttcatctactcatgaacttgtttgctcc |
| gtgttccacaaaaggatatattctctctaatggttatgcatgtcgagg |
| agatatggagtgttacctggtatttgtcatgggttacctgggcgggcc |
| tacatttgtacatgaggtggtgaggatggcGaaaactctggtgcagcg |
| gcacggtacgctTttgtctaaatcagatgagatcacactgaccaggtt |
| attcacctcacagcggcagcgtgtgacagacatcctatccagtccttt |
| accaagattaataaagtacttgaggaagaatattgacactgcgctgat |
| tgaagccgggggacagcccgtccgtccattctgtgcggagagtctggt |
| gagcacgctagcgaacataactcagataacccagatCatcgctagtca |
| cattgacacagttatccggtctgtgatatatatggaagctgagggtga |
| tctcgctgacacagtatttctatttaccccttacaatctctctactga |
| cgggaaaaagaggacatcacttaAacagtgcacgagacagatcctaga |
| ggttacaatactaggtcttagagtcgaaaatctcaataaaataggcga |

TABLE 4-continued

| hMPV F Sequences | | |
|---|---|---|
| | tataatcagcctagtgcttaaaggcatgatctccatggaggaccttat<br>cccactaaggacatacttgaagcatagtacctgccctaaatatttgaa<br>ggctgtcctaggtattaccaaactcaaagaaatgtttacagacacttc<br>tgtaCtgtacttgactcgtgctcaacaaaaattctacatgaaaactat<br>aggcaatgcagtcaaaggatattacagtaactgtgactcttaacgaaa<br>atcacatattaataggctcctttttggccaattgtattcttgttgat<br>ttaatcatattatgttagaaaaaagttgaaccctgactccttaggact<br>cgaattcgaactcaaataaatgtcttaaaaaaaggttgcgcacaatta<br>ttcttgagtgtagtctcgtcattcaccaaatctttgtttggt | |
| cDNA of genomic sequence of NDV LaSota strain with the codon optimized nucleic acid encoding hMPV F protein of CAN00-16 inserted (Sac II restriction sites used to insert the codon optimized hMPV F protein are shown by double underlining. The initiation and stop codons of the codon optimized hMPV F are underlined. The open reading frame of the codon optimized hMPV F is in bold.) | accaaacagagaatccgtgagttacgataaaaggcgaaggagcaattg<br>aagtcgcacgggtagaaggtgtgaatctcgagtgcgagcccgaagcac<br>aaactcgagaaagccttctgccaacatgtcttccgtatttgatgagta<br>cgaacagctcctcgcggctcagactcgccccaatggagctcatggagg<br>gggagaaaaagggagtaccttaaaagtagacgtcccggtattcactct<br>taacagtgatgacccagaagatagatggagctttgtggtattctgcct<br>ccggattgctgttagcgaagatgccaacaaaccactcaggcaaggtgc<br>tctcatatctcttttatgctcccactcacaggtaatgaggaaccatgt<br>tgccCttgcagggaaacagaatgaagccacattggccgtgcttgagat<br>tgatggctttgccaacggcacgccccagttcaacaataggagtggagt<br>gtctgaagagagagcacagagatttgcgatgatagcaggatctctccc<br>tcgggcatgcagcaacggaaccccgttcgtcacagccggggcCgaaga<br>tgatgcaccagaagacatcaccgataccctggagaggatcctctctat<br>ccaggctcaagtatgggtcacagtagcaaaagccatgactgcgtatga<br>gactgcagatgagtcggaaacaaggcgaatcaataagtatatgcagca<br>aggcagggtccaaaagaaatacatcctctaccccgtatgcaggagcac<br>aatccaactcacgatcagacagtctcttgcagtccgcatctttttggt<br>tagcgagctcaagagaggccgcaacacggcaggtggtacctctactta<br>ttataacctggtaggggacgtagactcatacatcaggaataccgggct<br>tactgcattcttcttgacactcaagtacggaatcaacaccaagacatc<br>agcccttgcacttagtagcctctcaggcgacatccagaagatgaagca<br>gctcatgcgtttgtatcggatgaaaggagataatgcgccgtacatgac<br>attacttggtgatagtgaccagatgagctttgcgcctgccgagtatgc<br>acaactttactcctttgccatgggtatggcatcagtcctagataaagg<br>tactgggaaataccaatttgccagggactttatgagcacatcattctg<br>gagacttggagtagagtacgctcaggctcagggaagtagcattaacga<br>ggatatggctgccgagctaaagctaaccccagcagcaaGgaGgggcct<br>ggcagctgctgcccaacgggtctccgaGgaGaccagcagcataGacat<br>gcctactcaacaagtcggagtcctcactgggcttagcgagggggggtc<br>ccaagctctacaaggcggatcgaatagatcgcaagggcaaccagaagc<br>cggggatggggagacccaattcctggatctgatgagagcggtagcaaa<br>tagcatgagggaggcgccaaactctgcacagggcactccccaatcggg<br>gcctcccccaactcctgggccatcccaagataacgacaccgactgggg<br>gtattgatggacaaaacccagcctgcttccacaaaaacatcccaatgc<br>cctcacccgtagtcgacccctcgatttgcggctctatatgaccacacc<br>ctcaaacaaacatcccccctctttcctccctcccccctgctgtacaactA<br>cgTacgccctagataccacaggcacaatgcggctcactaacaatcaaa<br>acagagccgagggaattagaaaaaagtacgggtagaagagggatattc<br>agagatcagggcaagtctcccgagtctctgctctctcctctacctgat<br>agaccaggacaaacatggccacctttacagatgcagagatcgacgagc<br>tatttgagacaagtggaactgtcattgacaacataattacagcccagg<br>gtaaaccagcagagactgttggaaggagtgcaatcccacaaggcaaga<br>ccaaggtgctgagcgcagcatgggagaagcatgggagcatccagccac<br>cggccagtcaagacaaccccgatcgacaggacagatctgacaaacaac<br>catccacacccgagcaaacgaccccgcatgacagcccgccggccacat<br>ccgccgaccagcccccacccaggccacagacgaagccgtcgacacac<br>agCtcaggaccggagcaagcaactctctgctgttgatgcttgacaagc<br>tcagcaataaatcgtccaatgctaaaaagggcccatggtcgagccccc<br>aagaggggaatcaccaacgtccgactcaacagcaggggagtcaaccca<br>gtcgcggaaacagtcaggaaagaccgcagaaccaagtcaaggccgccc<br>ctggaaaccagggcacagacgtgaacacagcatatcatggacaatggg<br>aggagtcacaactatcagctggtgcaacccctcatgctctccgatcaa<br>ggcagagccaagacaatacccttgtatctgcggatcatgtccagccac<br>ctgtagactttgtgcaagcgatgatgtctatgatggaggcgatatcac<br>agagagtaagtaaggttgactatcagctagatcttgtcttgaaacaga<br>catcctccatccctatgatgcggtccgaaatccaacagctgaaaacat<br>ctgttgcagtcatggaagccaacttgggaatgatgaagattctggatc<br>ccggttgtgccaacatttcatctctgagtgatctacgggcagttgccc<br>gatctcacccggttttagtttcaggccctggagacccctctccctatg<br>tgacacaaggaggcgaaatggcacttaataaactttcgcaaccagtgc<br>cacatccatctgaattgattaaacccgccactgcatgcgggcctgata<br>taggagtggaaaaggacactgtccgtgcattgatcatgtcacgcccaa<br>tgcacccgagttcttcagccaagctcctaagcaagttagatgcagccg<br>ggtcgatcgaggaaatcaggaaaatcaagcgccttgctctaaatggct<br>aattactactgccacacgtagcgggtccctgtccactcggcatcacac<br>ggaatctgcaccgagttcccccccgcGgTTAGAAAAAATACGGGTAGA<br>ACCGCCACC**ATGAGCTGGAAGGTGGTGATCATCTTCAGCCTGCTGATC**<br>**ACCCCCCAGCACGGCCTGAAGGAGAGCTACCTGGAGGAGAGCTGCAGC** | 21 |

TABLE 4-continued hMPV F Sequences

ACCATCACCGAGGGCTACCTGAGCGTGCTGAGAACCGGCTGGTACACC
AACGTGTTCACCCTGGAGGTGGGCGACGTGGAGAACCTGACCTGCAGC
GACGGCCCCAGCCTGATCAAGACCGAGCTGGACCTGACCAAGAGCGCC
CTGAGAGAGCTGAAGACCGTGAGCGCCGACCAGCTGGCCAGAGAGGAG
CAGATCGAGAACCCCAGACAGAGCAGATTCGTGCTGGGCGCCATCGCC
CTGGGCGTGGCCACCGCCGCCGCCGTGACCGCCGGCGTGGCCATCGCC
AAGACCATCAGACTGGAGAGCGAGGTGACCGCCATCAAGAACGCCCTG
AAGACCACCAACGAGGCCGTGAGCACCCTGGGCAACGGCGTGAGAGTG
CTGGCCACCGCCGTGAGAGAGCTGAAGGACTTCGTGAGCAAGAACCTG
ACCAGAGCCATCAACAAGAACAAGTGCGACATCGACGACCTGAAGATG
GCCGTGAGCTTCAGCCAGTTCAACAGAAGATTCCTGAACGTGGTGAGA
CAGTTCAGCGACAACGCCGGCATCACCCCCGCCATCAGCCTGGACCTG
ATGACCGACGCCGAGCTGGCCAGAGCCGTGAGCAACATGCCCACCAGC
GCCGGCCAGATCAAGCTGATGCTGGAGAACAGAGCCATGGTGAGAAGA
AAGGGCTTCGGCATCCTGATCGGCGTGTACGGCAGCAGCGTGATCTAC
ATGGTGCAGCTGCCCATCTTCGGCGTGATCGACACCCCCTGCTGGATC
GTGAAGGCCGCCCCCAGCTGCAGCGAGAAGAAGGGCAACTACGCCTGC
CTGCTGAGAGAGGACCAGGGCTGGTACTGCCAGAACGCCGGCAGCACC
GTGTACTACCCCAACGAGAAGGACTGCGAGACCAGAGGCGACCACGTG
TTCTGCGACACCGCCGCCGGCATCAACGTGGCCGAGCAGAGCAAGGAG
TGCAACATCAACATCAGCACCACCAACTACCCCTGCAAGGTGAGCACC
GGCAGACACCCCATCAGCATGGTGGCCCTGAGCCCCCTGGGCGCCCTG
GTGGCCTGCTACAAGGGCGTGAGCTGCAGCATCGGCAGCAACAGAGTG
GGCATCATCAAGCAGCTGAACAAGGGCTGCAGCTACATCACCAACCAG
GACGCCGACACCGTGACCATCGACAACACCGTGTACCAGCTGAGCAAG
GTGGAGGGCGAGCAGCACGTGATCAAGGGCAGACCCGTGAGCAGCAGC
TTCGACCCCATCAAGTTCCCCGAGGACCAGTTCAACGTGGCCCTGGAC
CAGGTGTTCGAGAGCATCGAGAACAGCCAGGCCCTGGTGGACCAGAGC
AACAGAATCCTGAGCAGCGCCGAGAAGGGCAACACCGGCTTCATCATC
GTGATCATCCTGATCGCCGTGCTGGGCAGCAGCATGATCCTGGTGAGC
ATCTTCATCATCATCAAGAAGACCAAGAAGCCCACCGGCGCCCCCCCC
GAGCTGAGCGGCGTGACCAACAACGGCTTCATCCCCCACAGCTGAGcc
gcggacccaaggtccaactctccaagcggcaatcctctctcgcttcct
cagccccactgaatgAtcgcgtaaccgtaattaatctagctacattta
agattaagaaaaaatacgggtagaattggagtgccccaattgtgccaa
gatggactcatctaggacaattgggctgtactttgattctgcccattc
ttctagcaacctgttagcatttccgatcgtcctacaagAcacaggaga
tgggaagaagcaaatcgccccgcaatataggatccagcgccttgactt
gtggactgatagtaaggaggactcagtattcatcaccacctatggatt
catctttcaagttgggaatgaagaagccacCgtcggcatgatcgatga
taaacccaagcgcgagttactttccgctgcgatgctctgcctaggaag
cgtcccaaataccggagaccttattgagctggcaagggcctgtctcac
tatgatagtcacatgcaagaagagtgcaactaatactgagagaatggt
tttctcagtagtgcaggcaccccaagtgctgcaaagctgtagggttgt
ggcaaacaaatactcatcagtgaatgcagtcaagcacgtgaaagcgcc
agagaagattcccgggagtggaaccctagaatacaaggtgaactttgt
ctccttgactgtggtaccgaagaGggatgtctacaagatcccagctgc
agtattgaaggtttctggctcgagtctgtacaatcttgcgctcaatgt
cactattaatgtggaggtagacccgaggagtcctttggttaaatctCt
gtctaagtctgacagcggatactatgctaacctcttcttgcatattgg
acttatgaccacTgtagataggaaggggaagaaagtgacatttgacaa
gctggaaaagaaaataaggagccttgatctatctgtcgggctcagtga
tgtgctcgggccttccgtgttggtaaaagcaagaggtgcacggactaa
gcttttggcacctttcttctctagcagtgggacagcctgctatcccat
agcaaatgcttctcctcaggtggccaagatactctggagtcaaaccgc
gtgcctgcggagcgttaaaatcattatccaagcaggtacccaacgcgc
tgtcgcagtgaccgccgaccacgaggttacctctactaagctggagaa
ggggcacacccttgccaaatacaatccttttaagaaataagctgcgtc
tctgagattgcgctccgcccactcacccagatcatcatgacacaaaaa
actaatctgtcttgattatttacagttagtttacctgtctatcaagtt
agaaaaaacacgggtagaagattctggatcccggttggcgccctccag
gtgcaagatgggctccagaccttctaccaagaacccagcacctatgat
gctgactatccgggttgcgctggtactgagttgcatctgtccggcaaa
ctccattgatggcaggcctcttgcagctgcaggaattgtggttacagg
agacaaagccgtcaacatatacacctcatcccagacaggatcaatcat
agttaagctcctcccgaatctgcccaaggataaggaggcatgtgcgaa
agccccttggatgcatacaacaggacattgaccactttgctcacccc
ccttggtgactctatccgtaggatacaagagtctgtgactacatctgg
agggggagacaggggcgccttataggcgccattattggcggtgtggc
tcttggggttgcaactgccgcacaaataacagcggccgcagctctgat
acaagccaaacaaaatgctgccaacatcctccgacttaaagagagcat
tgccgcaaccaatgaggctgtgcatgaggtcactgacggattatcgca
actagcagtggcagttgggaagatgcagcagtttgttaatgaccaatt
taataaaacagctcaggaattagactgcatcaaaattgcacagcaagt
tggtgtagagctcaacctgtacctaaccgaattgactacagtattcgg
accacaaatcacttcacctgctttaaacaagctgactattcaggcact
ttacaatctagctggtggaaatatggattacttattgactaagttagg
tgtagggaacaatcaactcagctcattaatcggtagcggcttaatcac TABLE 4-continued

| hMPV F Sequences |
|---|
| cggtaaccctattctatacgactcacagactcaactcttgggtataca<br>ggtaactctaccttcagtcgggaacctaaataatatgcgtgccaccta<br>cttggaaaccttatccgtaagcacaaccaggggatttgcctcggcact<br>tgtcccAaaagtggtgacacaggtcggttctgtgatagaagaacttga<br>cacctcatactgtatagaaactgacttagatttatattgtacaagaat<br>agtaacgttccctatgtcccctggtatttattcctgcttgagcggcaa<br>tacgtcggcctgtatgtactcaaagaccgaaggcgcacttactacacc<br>atacatgactatcaaaggttcagtcatcgccaactgcaagatgacaac<br>atgtagatgtgtaaaccccccgggtatcatatcgcaaaactatggaga<br>agccgtgtctctaatagataaacaatcatgcaatgttttatccttagg<br>cgggataactttaaggctcagtggggaattcgatgtaacttatcagaa<br>gaatatctcaatacaagattctcaagtaataataacaggcaatcttga<br>tatctcaactgagcttgggaatgtcaacaactcgatcagtaatgcttt<br>gaataagttagaggaaagcaacagaaaactagacaaagtcaatgtcaa<br>actgactagcacatctgctctcattacctatatcgttttgactatcat<br>atctcttgtttttggtatacttagcctgattctagcatgctacctaat<br>gtacaagcaaaaggcgcaacaaaagaccttattatggcttgggaataa<br>tactctagatcagatgagagccactacaaaaatgtgaacacagatgag<br>gaacgaaggtttccctaatagtaatttgtgtgaaagttctggtagtct<br>gtcagttcagagagttaagaaaaaactaccggttgtagatgaccaaag<br>gacgatatacgggtagaacggtaagagaggccgcccctcaattgcgag<br>ccaggcttcacaacctccgttctaccgcttcaccgacaacagtcctca<br>atcatggaccgcgccgttagccaagttgcgttagagaatgatgaaaga<br>gaggcaaaaaatacatggcgcttgatattccggattgcaatcttattc<br>ttaacagtagtgaccttggctatatctgtagcctcccttttatatagc<br>atgggggctagcacacctagcgatcttgtaggcataccgactaggatt<br>tccagggcagaagaaaagattacatctacacttggttccaatcaagat<br>gtagtagataggatatataagcaagtggcccttgagtctccgttggca<br>ttgttaaatactgagaccacaattatgaacgcaataacatctctctct<br>tatcagattaatggagctgcaaacaacagtgggtgggggcacctatc<br>catgacccagattatataggggggataggcaaagaactcattgtagat<br>gatgctagtgatgtcacatcattctatccctctgcatttcaagaacat<br>ctgaattttatcccggcgcctactacaggatcaggttgcactcgaata<br>ccctcatttgacatgagtgctacccattactgctacacccataatgta<br>atattgtctggatgcagagatcactcacattcatatcagtatttagca<br>cttggtgtgctccggacatctgcaacagggagggtattcttttctact<br>ctgcgttccatcaacctggacgacacccaaaatcggaagtcttgcagt<br>gtgagtgcaactcccctgggttgtgatatgctgtgctcgaaagtcacg<br>gagacagaggaagaagattataactcagctgtccctacgcggatggta<br>catgggaggttagggttcgacggccagtaccacgaaaaggacctagat<br>gtcacaacattattcggggactgggtggccaactacccaggagtaggg<br>ggtggatcttttattgacagccgcgtatggttctcagtctacggaggg<br>ttaaaacccaattcacccagtgacactgtacaggaagggaaatatgtg<br>atatacaagcgatacaatgacacatgcccagatgagcaagactaccag<br>attcgaatggccaagtcttcgtataagcctggacggtttggtgggaaa<br>cgcatacagcaggctatcttatctatcaaggtgtcaacatccttaggc<br>gaagacccggtactgactgtaccgcccaacacagtcacactcatgggg<br>gccgaaggcagaattctcacagtagggacatctcatttcttgtatcaa<br>cgagggtcatcatacttctctcccgcgttattatatcctatgacagtc<br>agcaacaaaacagccactcttcatagtccttatacattcaatgccttc<br>actcggccaggtagtatcccttgccaggcttcagcaagatgccccaac<br>tcgtgtgttactggagtctatacagatccatatcccctaatcttctat<br>agaaaccacaccttgcgaggggtattcgggacaatgcttgatggtgta<br>caagcaagacttaaccctgcgtctgcagtattcgatagcacatcccgc<br>agtcgcattactcgagtgagttcaagcagtaccaaagcagcatacaca<br>acatcaacttgttttaaagtggtcaagactaataagacctattgtctc<br>agcattgctgaaatatctaatactctcttcggagaattcagaatcgtc<br>ccgttactagttgagatcctcaaagatgacggggttagagaagccagg<br>tctggctagttgagtcaattataaaggagttggaaagatggcattgta<br>tcacctatcttctgcgacatcaagaatcaaaccgaatgccggcgcgtg<br>ctcgaattccatgttgccagttgaccacaatcagccagtgctcatgcg<br>atcagattaagccttgtcaAtaGtctcttgattaagaaaaaatgtaag<br>tggcaatgagatacaaggcaaaacagctcatggtTaaCaatacgggta<br>ggacatggcgagctccggtcctgaaagggcagagcatcagattatcct<br>accagagTcacacctgtcttcaccattggtcaagcacaaactactcta<br>ttactggaaattaactgggctaccgcttcctgatgaatgtgacttcga<br>ccacctcattctcagccgacaatggaaaaaaatacttgaatcggcctc<br>tcctgatactgagagaatgataaaactcggaagggcagtacaccaaac<br>tcttaaccacaattccagaataaccggagtgctccaccccaggtgttt<br>agaaGaactggctaatattgaggtcccagattcaaccaacaaatttcg<br>gaagattgagaagaagatccaaattcacaacacgagatatggagaact<br>gttcacaaggctgtgtacgcatatagagaagaaactgctggggtcatc<br>ttggtctaacaatgtcccccggtcagaggagttcagcagcattcgtac<br>ggatccggcattctggtttcactcaaaatggtccacagccaagtttgc<br>atggctccatataaaacagatccagaggcatctgatggtggcagctaG<br>gacaaggtctgcggccaacaaattggtgatgctaacccataaggtagg<br>ccaagtctttgtcactcctgaacttgtcgttgtgacgcatacgaatga<br>gaacaagttcacatgtcttacccaggaacttgtattgatgtatgcaga |

TABLE 4-continued

| hMPV F Sequences |
| --- |
| tatgatggagggcagagatatggtcaacataatatcaaccacggcggt<br>gcatctcagaagcttatcagagaaaattgatgacattttgcggttaat<br>agacgctctggcaaaagacttgggtaatcaagtctacgatgttgtatc<br>actaatggagggatttgcatacggagctgtccagctactcgagccgtc<br>aggtacatttgcaggagatttcttcgcattcaacctgcaggagcttaa<br>agacattctaattggcctcctccccaatgatatagcagaatccgtgac<br>tcatgcaatcgctactgtattctctggtttagaacagaatcaagcagc<br>tgagatgttgtgtctgttgcgtctgtggggtcacccactgcttgagtc<br>ccgtattgcagcaaaggcagtcaggagccaaatgtgcgcaccgaaaat<br>ggtagactttgatatgatccttcaggtactgtctttcttcaagggaac<br>aatcatcaacgggtacagaaagaagaatgcaggtgtgtggccgcgagt<br>caaagtggatacaatatatgggaaggtcattgggcaactacatgcaga<br>ttcagcagagatttcacacgatatcatgttgagagagtataagagttt<br>atctgcacttgaatttgagccatgtatagaatatgaccctgtcaccaa<br>cctgagcatgttcctaaaagacaaggcaatcgcacaccccaacgataa<br>ttggcttgcctcgtttaggcggaaccttctctccgaagaccagaagaa<br>acatgtaaaagaagcaacttcgactaatcgcctcttgatagagttttt<br>agagtcaaatgattttgatccatataaagagatggaatatctgacgac<br>ccttgagtaccttagagatgacaatgtggcagtatcatactcgctcaa<br>ggagaaggaagtgaaagttaatggacggatcttcgctaagctgacaaa<br>gaagttaaggaactgtcaggtgatggcggaagggatcctagccgatca<br>gattgcacctttctttcagggaaatggagtcattcaggatagcatatc<br>cttgaccaagagtatgctagcgatgagtcaactgtcttttaacagcaa<br>taagaaacgtatcactgactgtaaagaaagagtatcttcaaaccgcaa<br>tcatgatccgaaaagcaagaaccgtcggagagttgcaaccttcataac<br>aactgacctgcaaaagtactgtcttaattggagatatcagacaatcaa<br>attgttcgctcatgccatcaatcagttgatgggcctacctcacttctt<br>cgaatggattcacctaagactgatggacactacgatgttcgtaggaga<br>ccctttcaatcctccaagtgaccctactgactgtgacctctcaagagt<br>ccctaatgatgacatatatattgtcagtgccagaggggggtatcgaagg<br>attatgccagaagctatggacaatgatctcaattgctgcaatccaact<br>tgctgcagctagatcgcattgtcgtgttgcctgtatggtacagggtga<br>taatcaagtaatagcagtaacgagagaggtaagatcagacgactctcc<br>ggagatggtgttgacacagttgcatcaagccagtgataatttcttcaa<br>ggaattaattcatgtcaatcatttgattggccataatttgaaggatcg<br>tgaaaccatcaggtcagacacattcttcatatacagcaaacgaatctt<br>caaagatggagcaatcctcagtcaagtcctcaaaaattcatctaaatt<br>agtgctagtgtcaggtgatctcagtgaaaacaccgtaatgtcctgtgc<br>caacattgcctctactgtagcacggctatgcgagaacgggcttcccaa<br>agacttctgttactatttaaactatataatgagttgtgtgcagacata<br>ctttgactctgagttctccatcaccaacaattcgcaccccgatcttaa<br>tcagtcgtggattgaggacatctcttttgtgcactcatatgttctgac<br>tcctgcccaattaggggggactgagtaaccttcaatactcaaggctcta<br>cactagaaatatcggtgacccggggactactgcttttgcagagatcaa<br>gcgactagaagcagtgggattactgagtcctaacattatgactaatat<br>cttaactaggccgcctgggaatggagattgggccagtctgtgcaacga<br>cccatactctttcaattttgagactgttgcaagcccaaatattgttct<br>taagaaacatacgcaaagagtcctatttgaaacttgttcaaatccctt<br>attgtctggagtgcacacagaggataatgaggcagaagagaaggcatt<br>ggctgaattcttgcttaatcaagaggtgattcatccccgcgttgcgca<br>tgccatcatggaggcaagctctgtaggtaggagaaagcaaattcaagg<br>gcttgttgacacaacaaacaccgtaattaagattgcgcttactaggag<br>gccattaggcatcaagaggctgatgcggatagtcaattattctagcat<br>gcatgcaatgctgtttagagacgatgtttttcctccagtagatccaa<br>ccaccccttagtctcttctaatatgtgttctctgacactggcagacta<br>tgcacggaatagaagctggtcacctttgacgggaggcaggaaaatact<br>gggtgtatctaatcctgatacgatagaactcgtagagggtgagattct<br>tagtgtaagcggagggtgtacaagatgtgacagcggagatgaacaatt<br>tacttggttccatcttccaagcaatatagaattgaccgatgacaccag<br>caagaatcctccgatgagggtaccatatctcgggtcaaagacacagga<br>gaggagagctgcctcacttgcaaaaatagctcatatgtcgccacatgt<br>aaaggctgccctaagggcatcatccgtgttgatctgggcttatgggga<br>taatgaagtaaattggactgctgctcttacgattgcaaaatctcggtg<br>taatgtaaacttagagtatcttcggttactgtcccctttacccacggc<br>tgggaatcttcaacatagactagatgatggtataactcagatgacatt<br>cacccctgcatctctctacaggGtgtcaccttacattcacatatccaa<br>tgattctcaaaggctgttcactgaagaaggagtcaaagaggggaatgt<br>ggtttaccaacagatcatgctcttgggtttatctctaatcgaatcgat<br>ctttccaatgacaacaaccaggacatatgatgagatcacactgcacct<br>acatagtaaatttagttgctgtatcagagaagcacctgttgcggttcc<br>tttcgagctacttggggggtaccggaactgaggacagtgacctcaaa<br>taagtttatgtatgatcctagccctgtatcggagggagactttgcgag<br>acttgacttagctatcttcaagagttatgagcttaatctggagtcata<br>tcccacgatagagctaatgaacattctttcaatatccagcgggaagtt<br>gattggccagtctgtggtttcttatgatgaagatacctccataaagaa<br>tgacgccataatagtgtatgacaatacccgaaattggatcagtgaagc<br>tcagaattcagatgtggtccgcctatttgaatatgcagcacttgaagt<br>gctcctcgactgttcttaccaactctattacctgagagtaagaggcct |

TABLE 4-continued

| hMPV F Sequences | | |
|---|---|---|
| | Ggacaatattgtcttatatatgggtgatttatacaagaatatgccagg | |
| | aattctactttccaacattgcagctacaatatctcatcccgtcattca | |
| | ttcaaggttacatgcagtgggcctggtcaaccatgacggatcacacca | |
| | acttgcagatacggattttatcgaaatgtctgcaaaactattagtatc | |
| | ttgcacccgacgtgtgatctccggcttatattcaggaaataagtatga | |
| | tctgctgttcccatctgtcttagatgataacctgaatgagaagatgct | |
| | tcagctgatatcccggttatgctgtctgtacacggtactctttgctac | |
| | aacaagagaaatcccgaaaataagaggcttaactgcagaagagaaatg | |
| | ttcaatactcactgagtatttactgtcggatgctgtgaaaccattact | |
| | tagccccgatcaagtgagctctatcatgtctcctaacataattacatt | |
| | cccagctaatctgtactacatgtctcggaagagcctcaatttgatcag | |
| | ggaaagggaggacagggatactatcctggcgttgttgttcccccaaga | |
| | gccattattagagttcccttctgtgcaagatattggtgctcgagtgaa | |
| | agatccattcacccgacaacctgcggcattttttgcaagagttagattt | |
| | gagtgctccagcaaggtatgacgcattcacacttagtcagattcatcc | |
| | tgaactcacatctccaaatccggaggaagactacttagtacgatactt | |
| | gttcagagggatagggactgcatcttcctcttggtataaggcatctca | |
| | tctcctttctgtacccgaggtaagatgtgcaagacacgggaactcctt | |
| | atacttagctgaagggagcggagccatcatgagtcttctcgaactgca | |
| | tgtaccacatgaaactatctattacaatacgctcttttcaaatgagat | |
| | gaacccccgcaacgacatttcgggccgaccccaactcagtttttgaa | |
| | ttcggttgtttataggaatctacaggcggaggtaacatgcaaagatgg | |
| | atttgtccaagagttccgtccattatggagagaaaatacagaggaaag | |
| | CgacctgacctcagataaagTagtggggtatattacatctgcagtgcc | |
| | ctacagatctgtatcattgctgcattgtgacattgaaattcctccagg | |
| | gtccaatcaaagcttactagatcaactagctatcaatttatctctgat | |
| | tgccatgcattctgtaagggagggcggggtagtaatcatcaaagtgtt | |
| | gtatgcaatgggatactactttcatctactcatgaacttgtttgctcc | |
| | gtgttccacaaaaggatatattctctctaatggttatgcatgtcgagg | |
| | agatatggagtgttacctggtatttgtcatgggttacctgggggcc | |
| | tacatttgtacatgaggtggtgaggatggcGaaaactctggtgcagcg | |
| | gcacggtacgctTttgtctaaatcagatgagatcacactgaccaggtt | |
| | attcacctcacagcggcagcgtgtgacagacatcctatccagtccttt | |
| | accaagattaataaagtacttgaggaagaatattgacactgcgctgat | |
| | tgaagccgggggacagcccgtccgtccattctgtgcggagagtctggt | |
| | gagcacgctagcgaacataactcagataacccagatCatcgctagtca | |
| | cattgacacagttatccggtctgtgatatatatggaagctgagggtga | |
| | tctcgctgacacagtatttctatttaccccttacaatctctctactga | |
| | cgggaaaaagaggacatcacttaAacagtgcacgagacagatcctaga | |
| | ggttacaatactaggtcttagagtcgaaaatctcaataaaataggcga | |
| | tataatcagcctagtgcttaaaggcatgatctccatggaggaccttat | |
| | cccactaaggacatacttgaagcatagtacctgccctaaatatttgaa | |
| | ggctgtcctaggtattaccaaactcaaagaaatgtttacagacacttc | |
| | tgtaCtgtacttgactcgtgctcaacaaaaattctacatgaaaactat | |
| | aggcaatgcagtcaaaggatattacagtaactgtgactcttaacgaaa | |
| | atcacatattaataggctcctttttggccaattgtattcttgttgat | |
| | ttaatcatattatgttagaaaaaagttgaaccctgactccttaggact | |
| | cgaattcgaactcaaataaatgtcttaaaaaaaggttgcgcacaatta | |
| | ttcttgagtgtagtctcgtcattcaccaaatctttgtttggt | |

| | | |
|---|---|---|
| Nucleic acid | ATGTCTTGGAAAGTGGTGATCATTTTTTCATTGCTAATAACACCTCAACACG | 32 |
| sequence | GTCTTAAAGAGAGCTACCTAGAAGAATCATGTAGCACTATAACTGAGGGAT | |
| encoding a | ATCTTAGTGTTCTGAGGACAGGTTGGTATACCAACGTTTTTACATTAGAGGT | |
| chimeric F | GGGTGATGTAGAAAACCTTACATGTTCTGATGGACCTAGCCTAATAAAAAC | |
| protein | AGAATTAGATCTGACCAAAAGTGCACTAAGAGAGCTCAAAACAGTCTCTGC | |
| comprising | TGACCAATTGGCAAGAGAGGAACAAATTGAGAATCCCAGACAATCTAGGTT | |
| hMPV F | TGTTCTAGGAGCAATAGCACTCGGTGTTGCAACAGCAGCTGCAGTCACAGC | |
| protein | AGGTGTTGCAATTGCCAAAACCATCCGGCTTGAGAGTGAAGTCACAGCAAT | |
| ectodomain of | TAAGAATGCCCTCAAAACGACCAATGAAGCAGTATCTACATTGGGGAATGG | |
| hMPV strain | AGTTCGAGTGTTGGCAACTGCAGTGAGAGAGCTGAAAGACTTTGTGAGCA | |
| CAN00-16 and | AGAATTTAACTCGTGCAATCAACAAAAACAAGTGCGACATTGATGACCTAA | |
| NDV F protein | AAATGGCCGTTAGCTTCAGTCAATTCAACAGAAGGTTTCTAAATGTTGTGCG | |
| transmembrane | GCAATTTTCAGACAATGCTGGAATAACACCAGCAATATCTTTGGACTTAATG | |
| and cytoplasmic | ACAGATGCTGAACTAGCCAGGGCCGTTTCTAACATGCCGACATCTGCAGGA | |
| domains of the | CAAATAAAATTGATGTTGGAGAACCGCGCGATGGTGCGAAGAAAGGGGTT | |
| LaSota strain | CGGAATCCTGATAGGGGTCTACGGGAGCTCTGTAATTTACATGGTGCAGCT | |
| (transmembrane | GCCAATCTTTGGCGTTATAGACACGCCTTGCTGGATAGTAAAAGCAGCCCC | |
| and cytoplasmic | TTCTTGTTCCGAAAAAAAGGGAAACTATGCTTGCCTCTTAAGAGAAGACCA | |
| domains of NDV | AGGGTGGTATTGTCAGAATGCAGGGTCAACTGTTTACTACCCAAATGAGAA | |
| F protein are | AGACTGTGAAACAAGAGGAGACCATGTCTTTTGCGACACAGCAGCAGGAA | |
| underlined) | TTAATGTTGCTGAGCAATCAAAGGAGTGCAACATCAACATATCCACTACAA | |
| | ATTACCCATGCAAAGTCAGCACAGGAAGACATCCTATCAGTATGGTTGCAC | |
| | TGTCTCCTCTTGGGGCTCTGGTTGCTTGCTACAAAGGAGTAAGCTGTTCCAT | |
| | TGGCAGCAACAGAGTAGGGATCATCAAGCAGCTGAACAAAGGTTGCTCCT | |

-continued

| | | |
|---|---|---|
| | ATATAACCAACCAAGATGCAGACACAGTGACAATAGACAACACTGTATATC<br>AGCTAAGCAAAGTTGAGGGTGAACAGCATGTTATAAAAGGCAGACCAGTG<br>TCAAGCAGCTTTGATCCAATCAAGTTTCCTGAAGATCAATTCAATGTTGCAC<br>TTGACCAAGTTTTTGAGAGCATTGAAAACAGCCAGGCCTTGGTAGATCAAT<br>CAAACAGAATCCTAAGCAGTGCAGAGAAAGGAATACTGGCgttaacCTCAT<br>TACCTATATCGTTTTGACTATCATATCTCTTGTTTTTGGTATACTTAGCCTGAT<br>TCTAGCATGCTACCTAATGTACAAGCAAAAGGCGCAACAAAAGACCTTATT<br>ATGGCTTGGGAATAATACCCTAGATCAGATGAGAGCCACTACAAAAATGTG<br>A | |
| Nucleic acid sequence encoding chimeric F protein, wherein the nucleic acid sequence comprises a codon optimized nucleic acid sequence encoding the hMPV F protein ectodomain of strain HMPV/Homo sapiens/PER/FPP 00726/2011/A and a nucleic acid sequence encoding the transmembrane and cytoplasmic domains of F protein from NDV strain LaSota (transmembrane and cytoplasmic domains of NDV F are underlined) | ATGAGCTGGAAGGTGGTGATCATCTTCAGCCTGCTGATCACCCCCCAGCAC<br>GGCCTGAAGGAGAGCTACCTGGAGGAGAGCTGCAGCACCATCACCGAGGG<br>CTACCTGAGCGTGCTGAGAACCGGCTGGTACACCAACGTGTTCACCCTGGA<br>GGTGGGCGACGTGGAGAACCTGACCTGCGCCGACGGCCCCAGCCTGATCA<br>AGACCGAGCTGGACCTGACCAAGAGCGCCCTGAGAGAGCTGAAGACCGTG<br>AGCGCCGACCAGCTGGCCAGAGAGGAGCAGATCGAGAACCCCAGACAGA<br>GCAGATTCGTGCTGGGCGCCATCGCCCTGGGCGTGGCCACCGCCGCCGCC<br>GTGACCGCCGGCGTGGCCATCGCCAAGACCATCAGACTGGAGAGCGAGGT<br>GACCGCCATCAAGAACGCCCTGAAGAAGACCAACGAGGCCGTGAGCACCC<br>TGGGCAACGGCGTGAGAGTGCTGGCCACCGCCGTGAGAGAGCTGAAGGA<br>CTTCGTGAGCAAGAACCTGACCAGAGCCATCAACAAGAACAAGTGCGACAT<br>CGACGACCTGAAGATGGCCGTGAGCTTCAGCCAGTTCAACAGAAGATTCCT<br>GAACGTGGTGAGACAGTTCAGCGACAACGCCGGCATCACCCCCGCCATCAG<br>CCTGGACCTGATGACCGACGCCGAGCTGGCCAGAGCCGTGAGCAACATGC<br>CCACCAGCGCCGGCCAGATCAAGCTGATGCTGGAGAACAGAGCCATGGTG<br>AGAAGAAAGGGCTTCGGCATCCTGATCGGCGTGTACGGCAGCAGCGTGAT<br>CTACATGGTGCAGCTGCCCATCTTCGGCGTGATCGACACCCCCTGCTGGATC<br>GTGAAGGCCGCCCCCAGCTGCAGCGAGAAGAAGGGCAACTACGCCTGCCT<br>GCTGAGAGAGGACCAGGGCTGGTACTGCCAGAACGCCGGCAGCACCGTGT<br>ACTACCCCAACGAGAAGGACTGCGAGACCAGAGGCGACCACGTGTTCTGC<br>GACACCGCCGCCGGCATCAACGTGGCCGAGCAGAGCAAGGAGTGCAACAT<br>CAACATCAGCACCACCAACTACCCCTGCAAGGTGAGCACCGGCAGACACCC<br>CATCAGCATGGTGGCCCTGAGCCCCCTGGGCGCCCTGGTGGCCTGCTACAA<br>GGGCGTGAGCTGCAGCATCGGCAGCAACAGAGTGGGCATCATCAAGCAGC<br>TGAACAAGGGCTGCAGCTACATCACCAACCAGGACGCCGACACCGTGACCA<br>TCGACAACACCGTGTACCAGCTGAGCAAGGTGGAGGGCGAGCAGCACGTG<br>ATCAAGGGCAGACCCGTGAGCAGCAGCTTCGACCCCGTGAAGTTCCCCGA<br>GGACCAGTTCAACGTGGCCCTGGACCAGGTGTTCGAGAACATCGAGAACA<br>GCCAGGCCCTGGTGGACCAGAGCAACAGAATCCTGAGCAGCGCCGAGAAG<br>GGCAACACCGGCgttaacCTCATTACCTATATCGTTTTGACTATCATATCTCTT<br>GTTTTTGGTATACTTAGCCTGATTCTAGCATGCTACCTAATGTACAAGCAAA<br>AGGCGCAACAAAAGACCTTATTATGGCTTGGGAATAATACCCTAGATCAGA<br>TGAGAGCCACTACAAAAATGTGAccgcgg | 34 |
| Nucleic acid sequence encoding chimeric F protein, wherein the nucleic acid sequence comprises a codon optimized nucleic acid sequence encoding the hMPV F protein ectodomain of strain HMPV/USA/C2-175/2005/B and a nucleic acid sequence encoding the transmembrane and cytoplasmic domains of F protein from NDV strain LaSota (transmembrane and cytoplasmic domains of NDV F are underlined) | ATGAGCTGGAAGGTGATGATCATCATCAGCCTGCTGAT<br>CACCCCCCAGCACGGCCTGAAGGAGAGCTACCTGGAGG<br>AGAGCTGCAGCACCATCACCGAGGGCTACCTGAGCGTG<br>CTGAGAACCGGCTGGTACACCAACGTGTTCACCCTGGA<br>GGTGGGCGACGTGGAGAACCTGACCTGCACCGACGGCC<br>CCAGCCTGATCAAGACCGAGCTGGACCTGACCAAGAGC<br>GCCCTGAGAGAGCTGAAGACCGTGAGCGCCGACCAGCT<br>GGCCAGAGAGGAGCAGATCGAGAACCCCAGACAGAGC<br>AGATTCGTGCTGGGCGCCATCGCCCTGGGCGTGGCCAC<br>CGCCGCCGCCGTGACCGCCGGCATCGCCATCGCCAAGA<br>CCATCAGACTGGAGAGCGAGGTGAACGCCATCAAGGGC<br>GCCCTGAAGCAGACCAACGAGGCCGTGAGCACCCTGGG<br>CAACGGCGTGAGAGTGCTGGCCACCGCCGTGAGAGAGC<br>TGAAGGAGTTCGTGAGCAAGAACCTGACCAGCGCCATC<br>AACAGAAACAAGTGCGACATCGCCGACCTGAAGATGGC<br>CGTGAGCTTCAGCCAGTTCAACAGAAGATTCCTGAACG<br>TGGTGAGACAGTTCAGCGACAACGCCGGCATCACCCCC<br>GCCATCAGCCTGGACCTGATGACCGACGCCGAGCTGGC<br>CAGAGCCGTGAGCTACATGCCCACCAGCGCCGGCCAGA<br>TCAAGCTGATGCTGGAGAACAGAGCCATGGTGAGAAGA<br>AAGGGCTTCGGCATCCTGATCGGCGTGTACGGCAGCAG<br>CGTGATCTACATGGTGCAGCTGCCCATCTTCGGCGTGAT<br>CGACACCCCCTGCTGGATCATCAAGGCCGCCCCCAGCT<br>GCAGCGAGAAGAACGGCAACTACGCCTGCCTGCTGAGA<br>GAGGACCAGGGCTGGTACTGCAAGAACGCCGGCAGCA<br>CCGTGTACTACCCCAACGAGAAGGACTGCGAGACCAGA<br>GGCGACCACGTGTTCTGCGACACCGCCGCCGGCATCAA<br>CGTGGCCGAGCAGAGCAGAGAGTGCAACATCAACATCA<br>GCACCACCAACTACCCCTGCAAGGTGAGCACCGGCAGA<br>CACCCCATCAGCATGGTGGCCCTGAGCCCCCTGGGCGC<br>CCTGGTGGCCTGCTACAAGGGCGTGAGCTGCAGCATCG<br>GCAGCAACAGAGTGGGCATCATCAAGCAGCTGCCCAAG<br>GGCTGCAGCTACATCACCAACCAGGACGCCGACACCGT<br>GACCATCGACAACACCGTGTACCAGCTGAGCAAGGTGG<br>AGGGCGAGCAGCACGTGATCAAGGGCAGACCCGTGAG | 35 |

-continued

| | | |
|---|---|---|
| | CAGCAGCTTCGACCCCATCAGATTCCCCGAGGACCAGT<br>TCAACGTGGCCCTGGACCAGGTGTTCGAGAGCATCGAG<br>AACAGCCAGGCCCTGGTGGAGCAGAGCAACAAGATCCT<br>GAACAGCGCCGAGAAGGGCAACACCGGCgttaacCTCATT<br>ACCTATATCGTTTTGACTATCATATCTCTTGTTTTTGGTA<br>TACTTAGCCTGATTCTAGCATGCTACCTAATGTACAAGC<br>AAAAGGCGCAACAAAAGACCTTATTATGGCTTGGGAAT<br>AATACCCTAGATCAGATGAGAGCCACTACAAAAATGTG<br>Accgcgg | |
| Nucleic acid sequence encoding chimeric F protein, wherein the nucleic acid sequence comprises a codon optimized nucleic acid sequence encoding the hMPV F protein ectodomain of strain HMPV/ARG/107/2002/A and a nucleic acid sequence encoding the transmembrane and cytoplasmic domains of F protein from NDV strain LaSota (transmembrane and cytoplasmic domains of NDV F are underlined) | ATGAGCTGGAAGGTGGTGATCATCTTCAGCCTGCTGATCACCCCCCAGCAC<br>GGCCTGAAGGAGAGCTACCTGGAGGAGAGCTGCAGCACCATCACCGAGGG<br>CTACCTGAGCGTGCTGAGAACCGGCTGGTACACCAACGTGTTCACCCTGGA<br>GGTGGGCGACGTGGAGAACCTGACCTGCAGCGACGGCCCCAGCCTGATCA<br>AGACCGAGCTGGACCTGACCAAGAGCGCCCTGAGAGAGCTGAAGACCGTG<br>AGCGCCGACCAGCTGGCCAGAGAGGAGCAGATCGAGAACCCCAGACAGA<br>GCAGATTCGTGCTGGGCGCCATCGCCCTGGGCGTGGCCACCGCCGCCGCC<br>GTGACCGCCGGCGTGGCCATCGCCAAGACCATCAGACTGGAGAGCGAGGT<br>GACCGCCATCAAGAACGCCCTGAAGACCACCAACGAGGCCGTGAGCACCCT<br>GGGCAACGGCGTGAGAGTGCTGGCCACCGCCGTGAGAGAGCTGAAGGAC<br>TTCGTGAGCAAGAACCTGACCAGAGCCATCAACAAGAACAAGTGCGACATC<br>GACGACCTGAAGATGGCCGTGAGCTTCAGCCAGTTCAACAGAAGATTCCTG<br>AACGTGGTGAGACAGTTCAGCGACAACGCCGGCATCACCCCCGCCATCAGC<br>CTGGACCTGATGACCGACGCCGAGCTGGCCAGAGCCGTGAGCAACATGCC<br>CACCAGCGCCGGCCAGATCAAGCTGATGCTGGAGAACAGAGCCATGGTGA<br>GAAGAAAGGGCTTCGGCATCCTGATCGGCGTGTACGGCAGCAGCGTGATC<br>TACATGGTGCAGCTGCCCATCTTCGGCGTGATCGACACCCCCTGCTGGATC<br>GTGAAGGCCGCCCCCAGCTGCAGCGAGAAGAAGGGCAACTACGCCTGCCT<br>GCTGAGAGAGGACCAGGGCTGGTACTGCCAGAACGCCGGCAGCACCGTGT<br>ACTACCCCAACGAGAAGGACTGCGAGACCAGAGGCGACCACGTGTTCTGC<br>GACACCGCCGCCGGCATCAACGTGGCCGAGCAGAGCAAGGAGTGCAACAT<br>CAACATCAGCACCACCAACTACCCCTGCAAGGTGAGCACCGGCAGACACCC<br>CATCAGCATGGTGGCCCTGAGCCCCCTGGGCGCCCTGGTGGCCTGCTACAA<br>GGGCGTGAGCTGCAGCATCGGCAGCAACAGAGTGGGCATCATCAAGCAGC<br>TGAACAAGGGCTGCAGCTACATCACCAACCAGGACGCCGACACCGTGACCA<br>TCGACAACACCGTGTACCAGCTGAGCAAGGTGGAGGGCGAGCAGCACGTG<br>ATCAAGGGCAGACCCGTGAGCAGCAGCTTCGACCCCATCAAGTTCCCCGAG<br>GACCAGTTCAACGTGGCCCTGGACCAGGTGTTCGAGAACATCGAGAACAG<br>CCAGGCCCTGGTGGACCAGAGCAACAGAATCCTGAGCAGCGCCGAGAAGG<br>GCAACACCGGCgttaacCTCATTACCTATATCGTTTTGACTATCATATCTCTTG<br>TTTTTGGTATACTTAGCCTGATTCTAGCATGCTACCTAATGTACAAGCAAAA<br>GGCGCAACAAAAGACCTTATTATGGCTTGGGAATAATACCCTAGATCAGAT<br>GAGAGCCACTACAAAAATGTGAccgcgg | 36 |
| cDNA of genomic sequence of NDV LaSota strain with the nucleic acid encoding a chimeric F protein, wherein the chimeric F protein comprises ectodomain of hMPV F protein of hMPV CAN00-16 strain and the transmembrane and cytoplasmic domains of the NDV F protein of LaSota strain inserted (Sac II (CCGCGG) restriction sites used to insert the chimeric RSV-F sequence are double underlined and the open reading frame for hMPVF protein is underlined) | accaaacagagaatccgtgagttacgataaaaggcgaaggagcaattg<br>aagtcgcacgggtagaaggtgtgaatctcgagtgcgagcccgaagcac<br>aaactcgagaaagccttctgccaacatgtcttccgtatttgatgagta<br>cgaacagctcctcgcggctcagactcgccccaatggagctcatggagg<br>gggagaaaaagggagtaccttaaaagtagacgtcccggtattcactct<br>taacagtgatgacccagaagatagatggagctttgtggtattctgcct<br>ccggattgctgttagcgaagatgccaacaaaccactcaggcaaggtgc<br>tctcatatctcttttatgctcccactcacaggtaatgaggaaccatgt<br>tgccCttgcagggaaacagaatgaagccacattggccgtgcttgagat<br>tgatggctttgccaacggcacgccccagttcaacaataggagtggagt<br>gtctgaagagagagcacagagatttgcgatgatagcaggatctctccc<br>tcgggcatgcagcaacggaaccccgttcgtcacagccggggcCgaaga<br>tgatgcaccagaagacatcaccgataccctggagaggatcctctctat<br>ccaggctcaagtatgggtcacagtagcaaaagccatgactgcgtatga<br>gactgcagatgagtcggaaacaaggcgaatcaataagtatatgcagca<br>aggcagggtccaaaagaaatacatcctctaccccgtatgcaggagcac<br>aatccaactcacgatcagacagtctcttgcagtccgcatctttttggt<br>tagcgagctcaagagaggccgcaacacggcaggtggtacctctactta<br>ttataacctggtaggggacgtagactcatacatcaggaataccgggct<br>tactgcattcttcttgacactcaagtacggaatcaacaccaagacatc<br>agcccttgcacttagtagcctctcaggcgacatccagaagatgaagca<br>gctcatgcgtttgtatcggatgaaaggagataatgcgccgtacatgac<br>attacttggtgatagtgaccagatgagctttgcgcctgccgagtatgc<br>acaactttactcctttgccatgggtatggcatcagtcctagataaagg<br>tactgggaaataccaatttgccagggactttatgagcacatcattctg<br>gagacttggagtagagtacgctcaggctcagggaagtagcattaacga<br>ggatatggctgccgagctaaagctaaccccagcagcaaGgaGgggcct<br>ggcagctgctgcccaacgggtctccgaGgaGaccagcagcataGacat<br>gcctactcaacaagtcggagtcctcactgggcttagcgagggggggtc<br>ccaagctctacaaggcggatcgaatagatcgcaagggcaaccagaagc<br>cggggatggggagacccaattcctggatctgatgagagcggtagcaaa<br>tagcatgagggaggcgccaaactctgcacagggcactccccaatcggg<br>gcctcccccaactcctgggccatcccaagataacgacaccgactgggg<br>gtattgatggacaaaacccagcctgcttccacaaaaacatcccaatgc<br>cctcacccgtagtcgacccctcgatttgcggctctatatgaccacacc | 22 |

-continued

```
ctcaaacaaacatcccccctctttcctccctccccctgctgtacaactA
cgTacgccctagataccacaggcacaatgcggctcactaacaatcaaa
acagagccgagggaattagaaaaaagtacgggtagaagagggatattc
agagatcagggcaagtctcccgagtctctgctctctcctctacctgat
agaccaggacaaacatggccacctttacagatgcagagatcgacgagc
tatttgagacaagtggaactgtcattgacaacataattacagcccagg
gtaaaccagcagagactgttggaaggagtgcaatcccacaaggcaaga
ccaaggtgctgagcgcagcatgggagaagcatgggagcatccagccac
cggccagtcaagacaaccccgatcgacaggacagatctgacaaacaac
catccacacccgagcaaacgaccccgcatgacagcccgccggccacat
ccgccgaccagcccccccacccaggccacagacgaagccgtcgacacac
agCtcaggaccggagcaagcaactctctgctgttgatgcttgacaagc
tcagcaataaatcgtccaatgctaaaaagggcccatggtcgagccccc
aagaggggaatcaccaacgtccgactcaacagcaggggagtcaaccca
gtcgcggaaacagtcaggaaagaccgcagaaccaagtcaaggccgccc
ctggaaaccagggcacagacgtgaacacagcatatcatggacaatggg
aggagtcacaactatcagctggtgcaacccctcatgctctccgatcaa
ggcagagccaagacaatacccttgtatctgcggatcatgtccagccac
ctgtagactttgtgcaagcgatgatgtctatgatggaggcgatatcac
agagagtaagtaaggttgactatcagctagatcttgtcttgaaacaga
catcctccatccctatgatgcggtccgaaatccaacagctgaaaacat
ctgttgcagtcatggaagccaacttgggaatgatgaagattctggatc
ccggttgtgccaacatttcatctctgagtgatctacgggcagttgccc
gatctcacccggttttagtttcaggccctggagacccctctccctatg
tgacacaaggaggcgaaatggcacttaataaactttcgcaaccagtgc
cacatccatctgaattgattaaacccgccactgcatgcgggcctgata
taggagtggaaaaggacactgtccgtgcattgatcatgtcacgcccaa
tgcacccgagttcttcagccaagctcctaagcaagttagatgcagccg
ggtcgatcgaggaaatcaggaaaatcaagcgccttgctctaaatggct
aattactactgccacacgtagcgggtccctgtccactcggcatcacac
ggaatctgcaccgagttccccccgcGgacccaaggtccaactctcca
agcggcaatcctctctcgcttcctcagccccactgaatgAtcgcgtaa
ccgtaattaatctagctacatttaagattaagaaaaaatacgggtaga
attggagtgccccaCtAgtTTTgccaCCATGTCTTGGAAAGTGGTGAT
CATTTTTTCATTGCTAATAACACCTCAACACGGTCTTAAAGAGAGCTA
CCTAGAAGAATCATGTAGCACTATAACTGAGGGATATCTTAGTGTTCT
GAGGACAGGTTGGTATACCAACGTTTTTACATTAGAGGTGGGTGATGT
AGAAAACCTTACATGTTCTGATGGACCTAGCCTAATAAAAACAGAATT
AGATCTGACCAAAAGTGCACTAAGAGAGCTCAAAACAGTCTCTGCTGA
CCAATTGGCAAGAGAGGAACAAATTGAGAATCCCAGACAATCTAGGTT
TGTTCTAGGAGCAATAGCACTCGGTGTTGCAACAGCAGCTGCAGTCAC
AGCAGGTGTTGCAATTGCCAAAACCATCCGGCTTGAGAGTGAAGTCAC
AGCAATTAAGAATGCCCTCAAAACGACCAATGAAGCAGTATCTACATT
GGGGAATGGAGTTCGAGTGTTGGCAACTGCAGTGAGAGAGCTGAAAGA
CTTTGTGAGCAAGAATTTAACTCGTGCAATCAACAAAAACAAGTGCGA
CATTGATGACCTAAAAATGGCCGTTAGCTTCAGTCAATTCAACAGAAG
GTTTCTAAATGTTGTGCGGCAATTTTCAGACAATGCTGGAATAACACC
AGCAATATCTTTGGACTTAATGACAGATGCTGAACTAGCCAGGGCCGT
TTCTAACATGCCGACATCTGCAGGACAAATAAAATTGATGTTGGAGAA
CCGCGCGATGGTGCGAAGAAAGGGGTTCGGAATCCTGATAGGGGTCTA
CGGGAGCTCTGTAATTTACATGGTGCAGCTGCCAATCTTTGGCGTTAT
AGACACGCCTTGCTGGATAGTAAAAGCAGCCCCTTCTTGTTCCGAAAA
AAAGGGAAACTATGCTTGCCTCTTAAGAGAAGACCAAGGGTGGTATTG
TCAGAATGCAGGGTCAACTGTTTACTACCCAAATGAGAAAGACTGTGA
AACAAGAGGAGACCATGTCTTTTGCGACACAGCAGCAGGAATTAATGT
TGCTGAGCAATCAAAGGAGTGCAACATCAACATATCCACTACAAATTA
CCCATGCAAAGTCAGCACAGGAAGACATCCTATCAGTATGGTTGCACT
GTCTCCTCTTGGGGCTCTGGTTGCTTGCTACAAAGGAGTAAGCTGTTC
CATTGGCAGCAACAGAGTAGGGATCATCAAGCAGCTGAACAAAGGTTG
CTCCTATATAACCAACCAAGATGCAGACACAGTGACAATAGACAACAC
TGTATATCAGCTAAGCAAAGTTGAGGGTGAACAGCATGTTATAAAAGG
CAGACCAGTGTCAAGCAGCTTTGATCCAATCAAGTTTCCTGAAGATCA
ATTCAATGTTGCACTTGACCAAGTTTTTGAGAGCATTGAAAACAGCCA
GGCCTTGGTAGATCAATCAAACAGAATCCTAAGCAGTGCAGAGAAAGG
GAATACTGGCGTTAACCTCATTACCTATATCGTTTTGACTATCATATC
TCTTGTTTTTGGTATACTTAGCCTGATTCTAGCATGCTACCTAATGTA
CAAGCAAAAGGCGCAACAAAAGACCTTATTATGGCTTGGGAATAATAC
CCTAGATCAGATGAGAGCCACTACAAAAATGTGAccgcggacccaagg
tccaactctccaagcggcaatcctctctcgcttcctcagccccactga
atgAtcgcgtaaccgtaattaatctagctacatttaagattaagaaaa
aatacgggtagaattggagtgccccaattgtgccaagatggactcatc
taggacaattgggctgtactttgattctgcccattcttctagcaacct
gttagcatttccgatcgtcctacaagAcacaggagatgggaagaagca
aatcgccccgcaatataggatccagcgccttgacttgtggactgatag
taaggaggactcagtattcatcaccacctatggattcatctttcaagt
tgggaatgaagaagccacCgtcggcatgatcgatgataaacccaagcg
cgagttactttccgctgcgatgctctgcctaggaagcgtcccaaatac
cggagaccttattgagctggcaagggcctgtctcactatgatagtcac
atgcaagaagagtgcaactaatactgagagaatggttttctcagtagt
```

-continued

```
gcaggcaccccaagtgctgcaaagctgtagggttgtggcaaacaaata
ctcatcagtgaatgcagtcaagcacgtgaaagcgccagagaagattcc
cgggagtggaaccctagaatacaaggtgaactttgtctccttgactgt
ggtaccgaagaGggatgtctacaagatcccagctgcagtattgaaggt
ttctggctcgagtctgtacaatcttgcgctcaatgtcactattaatgt
ggaggtagacccgaggagtcctttggttaaatctCtgtctaagtctga
cagcggatactatgctaacctcttcttgcatattggacttatgaccac
Tgtagataggaaggggaagaaagtgacatttgacaagctggaaaagaa
aataaggagccttgatctatctgtcgggctcagtgatgtgctcgggcc
ttccgtgttggtaaaagcaagaggtgcacggactaagcttttggcacc
tttcttctctagcagtgggacagcctgctatcccatagcaaatgcttc
tcctcaggtggccaagatactctggagtcaaaccgcgtgcctgcggag
cgttaaaatcattatccaagcaggtacccaacgcgctgtcgcagtgac
cgccgaccacgaggttacctctactaagctggagaaggggcacaccct
tgccaaatacaatccttttaagaaataagctgcgtctctgagattgcg
ctccgcccactcacccagatcatcatgacacaaaaaactaatctgtct
tgattatttacagttagtttacctgtctatcaagttagaaaaaacacg
ggtagaagattctggatcccggttggcgccctccaggtgcaagatggg
ctccagaccttctaccaagaacccagcacctatgatgctgactatccg
ggttgcgctggtactgagttgcatctgtccggcaaactccattgatgg
caggcctcttgcagctgcaggaattgtggttacaggagacaaagccgt
caacatatacacctcatcccagacaggatcaatcatagttaagctcct
cccgaatctgcccaaggataaggaggcatgtgcgaaagccccccttgga
tgcatacaacaggacattgaccactttgctcaccccccttggtgactc
tatccgtaggatacaagagtctgtgactacatctggagggggagaca
ggggcgccttataggcgccattattggcggtgtggctcttggggttgc
aactgccgcacaaataacagcggccgcagctctgatacaagccaaaca
aaatgctgccaacatcctccgacttaaagagagcattgccgcaaccaa
tgaggctgtgcatgaggtcactgacggattatcgcaactagcagtggc
agttgggaagatgcagcagtttgttaatgaccaatttaataaaacagc
tcaggaattagactgcatcaaaattgcacagcaagttggtgtagagct
caacctgtacctaaccgaattgactacagtattcggaccacaaatcac
ttcacctgctttaaacaagctgactattcaggcactttacaatctagc
tggtggaaatatggattacttattgactaagttaggtgtagggaacaa
tcaactcagctcattaatcggtagcggcttaatcaccggtaaccctat
tctatacgactcacagactcaactcttgggtatacaggtaactctacc
ttcagtcgggaacctaaataatatgcgtgccacctacttggaaacctt
atccgtaagcacaaccaggggatttgcctcggcacttgtcccAaaagt
ggtgacacaggtcggttctgtgatagaagaacttgacacctcatactg
tatagaaactgacttagatttatattgtacaagaatagtaacgttccc
tatgtcccctggtatttattcctgcttgagcggcaatacgtcggcctg
tatgtactcaaagaccgaaggcgcacttactacaccatacatgactat
caaaggttcagtcatcgccaactgcaagatgacaacatgtagatgtgt
aaacccccccgggtatcatatcgcaaaactatggagaagccgtgtctct
aatagataaacaatcatgcaatgttttatccttaggcgggataacttt
aaggctcagtggggaattcgatgtaacttatcagaagaatatctcaat
acaagattctcaagtaataataacaggcaatcttgatatctcaactga
gcttgggaatgtcaacaactcgatcagtaatgctttgaataagttaga
ggaaagcaacagaaaactagacaaagtcaatgtcaaactgactagcac
atctgctctcattacctatatcgttttgactatcatatctcttgtttt
tggtatacttagcctgattctagcatgctacctaatgtacaagcaaaa
ggcgcaacaaaagaccttattatggcttgggaataatactctagatca
gatgagagccactacaaaaatgtgaacacagatgaggaacgaaggttt
ccctaatagtaatttgtgtgaaagttctggtagtctgtcagttcagag
agttaagaaaaaactaccggttgtagatgaccaaaggacgatatacgg
gtagaacggtaagagaggccgcccctcaattgcgagccaggcttcaca
acctccgttctaccgcttcaccgacaacagtcctcaatcatggaccgc
gccgttagccaagttgcgttagagaatgatgaaagagaggcaaaaaat
acatggcgcttgatattccggattgcaatcttattcttaacagtagtg
accttggctatatctgtagcctcccttttatatagcatgggggctagc
acacctagcgatcttgtaggcataccgactaggatttccagggcagaa
gaaaagattacatctacacttggttccaatcaagatgtagtagatagg
atatataagcaagtggcccttgagtctccgttggcattgttaaatact
gagaccacaattatgaacgcaataacatctctctcttatcagattaat
ggagctgcaaacaacagtgggtgggggcacctatccatgacccagat
tatataggggggataggcaaagaactcattgtagatgatgctagtgat
gtcacatcattctatccctctgcatttcaagaacatctgaattttatc
ccggcgcctactacaggatcaggttgcactcgaataccctcatttgac
atgagtgctacccattactgctacacccataatgtaatattgtctgga
tgcagagatcactcacattcatatcagtatttagcacttggtgtgctc
cggacatctgcaacagggagggtattcttttctactctgcgttccatc
aacctggacgacacccaaaatcggaagtcttgcagtgtgagtgcaact
cccctgggttgtgatatgctgtgctcgaaagtcacggagacagaggaa
gaagattataactcagctgtccctacgcggatggtacatgggaggtta
gggttcgacggccagtaccacgaaaaggacctagatgtcacaacatta
ttcggggactgggtggccaactacccaggagtagggggggatctttt
attgacagccgcgtatggttctcagtctacggagggttaaaacccaat
tcacccagtgacactgtacaggaagggaaatatgtgatatacaagcga
tacaatgacacatgcccagatgagcaagactaccagattcgaatggcc
```

-continued aagtcttcgtataagcctggacggtttggtgggaaacgcatacagcag
gctatcttatctatcaaggtgtcaacatccttaggcgaagacccggta
ctgactgtaccgcccaacacagtcacactcatgggggccgaaggcaga
attctcacagtagggacatctcatttcttgtatcaacgagggtcatca
tacttctctcccgcgttattatatcctatgacagtcagcaacaaaaca
gccactcttcatagtccttatacattcaatgccttcactcggccaggt
agtatcccttgccaggcttcagcaagatgccccaactcgtgtgttact
ggagtctatacagatccatatcccctaatcttctatagaaaccacacc
ttgcgaggggtattcgggacaatgcttgatggtgtacaagcaagactt
aaccctgcgtctgcagtattcgatagcacatcccgcagtcgcattact
cgagtgagttcaagcagtaccaaagcagcatacacaacatcaacttgt
tttaaagtggtcaagactaataagacctattgtctcagcattgctgaa
atatctaatactctcttcggagaattcagaatcgtcccgttactagtt
gagatcctcaaagatgacggggttagagaagccaggtctggctagttg
agtcaattataaaggagttggaaagatggcattgtatcacctatcttc
tgcgacatcaagaatcaaaccgaatgccggcgcgtgctcgaattccat
gttgccagttgaccacaatcagccagtgctcatgcgatcagattaagc
cttgtcaAtaGtctcttgattaagaaaaaatgtaagtggcaatgagat
acaaggcaaaacagctcatggtTaaCaatacgggtaggacatggcgag
ctccggtcctgaaagggcagagcatcagattatcctaccagagTcaca
cctgtcttcaccattggtcaagcacaaactactctattactggaaatt
aactgggctaccgcttcctgatgaatgtgacttcgaccacctcattct
cagccgacaatggaaaaaaatacttgaatcggcctctcctgatactga
gagaatgataaaactcggaagggcagtacaccaaactcttaaccacaa
ttccagaataaccggagtgctccaccccaggtgtttagaaGaactggc
taatattgaggtcccagattcaaccaacaaatttcggaagattgagaa
gaagatccaaattcacaacacgagatatggagaactgttcacaaggct
gtgtacgcatatagagaagaaactgctggggtcatcttggtctaacaa
tgtcccccggtcagaggagttcagcagcattcgtacggatccggcatt
ctggtttcactcaaaatggtccacagccaagtttgcatggctccatat
aaaacagatccagaggcatctgatggtggcagctaGgacaaggtctgc
ggccaacaaattggtgatgctaacccataaggtaggccaagtctttgt
cactcctgaacttgtcgttgtgacgcatacgaatgagaacaagttcac
atgtcttacccaggaacttgtattgatgtatgcagatatgatggaggg
cagagatatggtcaacataatatcaaccacggcggtgcatctcagaag
cttatcagagaaaattgatgacattttgcggttaatagacgctctggc
aaaagacttgggtaatcaagtctacgatgttgtatcactaatggaggg
atttgcatacggagctgtccagctactcgagccgtcaggtacatttgc
aggagatttcttcgcattcaacctgcaggagcttaaagacattctaat
tggcctcctccccaatgatatagcagaatccgtgactcatgcaatcgc
tactgtattctctggtttagaacagaatcaagcagctgagatgttgtg
tctgttgcgtctgtggggtcacccactgcttgagtcccgtattgcagc
aaaggcagtcaggagccaaatgtgcgcaccgaaaatggtagactttga
tatgatccttcaggtactgtctttcttcaagggaacaatcatcaacgg
gtacagaaagaagaatgcaggtgtgtggccgcgagtcaaagtggatac
aatatatgggaaggtcattgggcaactacatgcagattcagcagagat
ttcacacgatatcatgttgagagagtataagagtttatctgcacttga
atttgagccatgtatagaatatgaccctgtcaccaacctgagcatgtt
cctaaaagacaaggcaatcgcacaccccaacgataattggcttgcctc
gtttaggcggaaccttctctccgaagaccagaagaaacatgtaaaaga
agcaacttcgactaatcgcctcttgatagagtttttagagtcaaatga
ttttgatccatataaagagatggaatatctgacgacccttgagtacct
tagagatgacaatgtggcagtatcatactcgctcaaggagaaggaagt
gaaagttaatggacggatcttcgctaagctgacaaagaagttaaggaa
ctgtcaggtgatggcggaagggatcctagccgatcagattgcaccttt
ctttcagggaaatggagtcattcaggatagcatatccttgaccaagag
tatgctagcgatgagtcaactgtcttttaacagcaataagaaacgtat
cactgactgtaaagaaagagtatcttcaaaccgcaatcatgatccgaa
aagcaagaaccgtcggagagttgcaaccttcataacaactgacctgca
aaagtactgtcttaattggagatatcagacaatcaaattgttcgctca
tgccatcaatcagttgatgggcctacctcacttcttcgaatggattca
cctaagactgatggacactacgatgttcgtaggagaccctttcaatcc
tccaagtgaccctactgactgtgacctctcaagagtccctaatgatga
catatatattgtcagtgccagagggggtatcgaaggattatgccagaa
gctatggacaatgatctcaattgctgcaatccaacttgctgcagctag
atcgcattgtcgtgttgcctgtatggtacagggtgataatcaagtaat
agcagtaacgagagaggtaagatcagacgactctccggagatggtgtt
gacacagttgcatcaagccagtgataatttcttcaaggaattaattca
tgtcaatcatttgattggccataatttgaaggatcgtgaaaccatcag
gtcagacacattcttcatatacagcaaacgaatcttcaaagatggagc
aatcctcagtcaagtcctcaaaaattcatctaaattagtgctagtgtc
aggtgatctcagtgaaaacaccgtaatgtcctgtgccaacattgcctc
tactgtagcacggctatgcgagaacgggcttcccaaagacttctgtta
ctatttaaactatataatgagttgtgtgcagacatactttgactctga
gttctccatcaccaacaattcgcaccccgatcttaatcagtcgtggat
tgaggacatctcttttgtgcactcatatgttctgactcctgcccaatt
agggggactgagtaaccttcaatactcaaggctctacactagaaatat
cggtgacccggggactactgcttttgcagagatcaagcgactagaagc
agtgggattactgagtcctaacattatgactaatatcttaactaggcc -continued

```
gcctgggaatggagattgggccagtctgtgcaacgacccatactcttt
caattttgagactgttgcaagcccaaatattgttcttaagaaacatac
gcaaagagtcctatttgaaacttgttcaaatcccttattgtctggagt
gcacacagaggataatgaggcagaagagaaggcattggctgaattctt
gcttaatcaagaggtgattcatccccgcgttgcgcatgccatcatgga
ggcaagctctgtaggtaggagaaagcaaattcaagggcttgttgacac
aacaaacaccgtaattaagattgcgcttactaggaggccattaggcat
caagaggctgatgcggatagtcaattattctagcatgcatgcaatgct
gtttagagacgatgtttttcctccagtagatccaaccaccccttagt
ctcttctaatatgtgttctctgacactggcagactatgcacggaatag
aagctggtcacctttgacgggaggcaggaaaatactgggtgtatctaa
tcctgatacgatagaactcgtagagggtgagattcttagtgtaagcgg
agggtgtacaagatgtgacagcggagatgaacaatttacttggttcca
tcttccaagcaatatagaattgaccgatgacaccagcaagaatcctcc
gatgagggtaccatatctcgggtcaaagacacaggagaggagagctgc
ctcacttgcaaaaatagctcatatgtcgccacatgtaaaggctgccct
aagggcatcatccgtgttgatctgggcttatggggataatgaagtaaa
ttggactgctgctcttacgattgcaaaatctcggtgtaatgtaaactt
agagtatcttcggttactgtcccctttacccacggctgggaatcttca
acatagactagatgatggtataactcagatgacattcacccctgcatc
tctctacaggGtgtcaccttacattcacatatccaatgattctcaaag
gctgttcactgaagaaggagtcaaagaggggaatgtggtttaccaaca
gatcatgctcttgggtttatctctaatcgaatcgatctttccaatgac
aacaaccaggacatatgatgagatcacactgcacctacatagtaaatt
tagttgctgtatcagagaagcacctgttgcggttcctttcgagctact
tggggtggtaccggaactgaggacagtgacctcaaataagtttatgta
tgatcctagccctgtatcggagggagactttgcgagacttgacttagc
tatcttcaagagttatgagcttaatctggagtcatatcccacgataga
gctaatgaacattctttcaatatccagcgggaagttgattggccagtc
tgtggtttcttatgatgaagatacctccataaagaatgacgccataat
agtgtatgacaatacccgaaattggatcagtgaagctcagaattcaga
tgtggtccgcctatttgaatatgcagcacttgaagtgctcctcgactg
ttcttaccaactctattacctgagagtaagaggcctGgacaatattgt
cttatatatgggtgatttatacaagaatatgccaggaattctactttc
caacattgcagctacaatatctcatcccgtcattcattcaaggttaca
tgcagtgggcctggtcaaccatgacggatcacaccaacttgcagatac
ggattttatcgaaatgtctgcaaaactattagtatcttgcacccgacg
tgtgatctccggcttatattcaggaaataagtatgatctgctgttccc
atctgtcttagatgataacctgaatgagaagatgcttcagctgatatc
ccggttatgctgtctgtacacggtactctttgctacaacaagagaaat
cccgaaaataagaggcttaactgcagaagagaaatgttcaatactcac
tgagtatttactgtcggatgctgtgaaaccattacttagccccgatca
agtgagctctatcatgtctcctaacataattacattcccagctaatct
gtactacatgtctcggaagagcctcaatttgatcagggaaagggagga
cagggatactatcctggcgttgttgttcccccaagagccattattaga
gttcccttctgtgcaagatattggtgctcgagtgaaagatccattcac
ccgacaacctgcggcattttgcaagagttagatttgagtgctccagc
aaggtatgacgcattcacacttagtcagattcatcctgaactcacatc
tccaaatccggaggaagactacttagtacgatacttgttcagagggat
agggactgcatcttcctcttggtataaggcatctcatctcctttctgt
acccgaggtaagatgtgcaagacacgggaactccttatacttagctga
agggagcggagccatcatgagtcttctcgaactgcatgtaccacatga
aactatctattacaatacgctcttttcaaatgagatgaacccccgca
acgacatttcgggccgaccccaactcagtttttgaattcggttgttta
taggaatctacaggcggaggtaacatgcaaagatggatttgtccaaga
gttccgtccattatggagagaaaatacagaggaaagCgacctgacctc
agataaagTagtggggtatattacatctgcagtgccctacagatctgt
atcattgctgcattgtgacattgaaattcctccagggtccaatcaaag
cttactagatcaactagctatcaatttatctctgattgccatgcattc
tgtaagggagggcggggtagtaatcatcaaagtgttgtatgcaatggg
atactactttcatctactcatgaacttgtttgctccgtgttccacaaa
aggatatattctctctaatggttatgcatgtcgaggagatatggagtg
ttacctggtatttgtcatgggttacctgggcgggcctacatttgtaca
tgaggtggtgaggatggcGaaaactctggtgcagcggcacggtacgct
Tttgtctaaatcagatgagatcacactgaccaggttattcacctcaca
gcggcagcgtgtgacagacatcctatccagtcctttaccaagattaat
aaagtacttgaggaagaatattgacactgcgctgattgaagccgggg
acagcccgtccgtccattctgtgcggagagtctggtgagcacgctagc
gaacataactcagataacccagatCatcgctagtcacattgacacagt
tatccggtctgtgatatatatggaagctgagggtgatctcgctgacac
agtatttctatttaccccttacaatctctctactgacgggaaaaagag
gacatcacttaAacagtgcacgagacagatcctagaggttacaatact
aggtcttagagtcgaaaatctcaataaaataggcgatataatcagcct
agtgcttaaaggcatgatctccatggaggaccttatcccactaaggac
atacttgaagcatagtacctgccctaaatatttgaaggctgtcctagg
tattaccaaactcaaagaaatgtttacagacacttctgtaCtgtactt
gactcgtgctcaacaaaaattctacatgaaaactataggcaatgcagt
caaaggatattacagtaactgtgactcttaacgaaaatcacatattaa
taggctcctttttggccaattgtattcttgttgatttaatcatatta
```

-continued

| | | |
|---|---|---|
| | tgttagaaaaaagttgaaccctgactccttaggactcgaattcgaact<br>caaataaatgtcttaaaaaaaggttgcgcacaattattcttgagtgta<br>gtctcgtcattcaccaaatctttgtttggt | |
| Wild-type Nucleic acid sequence encoding hMPV F protein of strain HMPV/Homo sapiens/PER/FPP 00726/2011/A | ATGTCTTGGAAAGTGGTGATCATTTTTTCATTGCTAATA<br>ACACCTCAACACGGTCTTAAAGAGAGCTACTTAGAAGA<br>ATCATGTAGCACTATAACTGAGGGATATCTCAGTGTTCT<br>GAGGACAGGTTGGTATACCAACGTTTTTACATTAGAAG<br>TGGGTGATGTAGAAAACCTCACATGTGCTGATGGACCT<br>AGCCTAATAAAAACAGAATTAGATCTGACCAAAAGTGC<br>ACTAAGAGAGCTCAAAACAGTTTCTGCTGACCAATTGG<br>CAAGAGAGGAACAGATTGAGAATCCCAGACAATCTAG<br>ATTTGTTCTAGGAGCAATAGCACTCGGTGTTGCGACAG<br>CAGCTGCAGTTACAGCAGGTGTTGCAATTGCCAAAACT<br>ATCCGACTTGAGAGTGAAGTTACAGCAATTAAGAATGC<br>CCTTAAAAAGACTAATGAAGCAGTGTCTACATTGGGGA<br>ATGGAGTTCGAGTGTTAGCAACTGCAGTGAGGGAACTG<br>AAAGATTTTGTGAGCAAGAATTTAACTCGTGCAATCAA<br>CAAAAACAAGTGCGACATTGATGACCTAAAAATGGCTG<br>TTAGCTTCAGTCAATTCAACAGAAGGTTTCTAAATGTTG<br>TGCGGCAATTTTCAGACAATGCTGGAATAACACCAGCA<br>ATATCTTTAGACTTAATGACAGATGCTGAACTAGCCAG<br>GGCCGTTTCCAACATGCCGACATCTGCAGGACAAATAA<br>AATTGATGTTGGAAAACCGTGCAATGGTGCGAAGGAAG<br>GGGTTCGGAATCCTGATCGGGGTCTACGGGAGCTCCGT<br>AATTTACATGGTGCAGCTGCCAATCTTTGGCGTTATAGA<br>CACGCCTTGCTGGATAGTAAAAGCAGCCCCTTCTTGTTC<br>CGAAAAAAAGGGAAACTATGCTTGCCTCTTAAGAGAAG<br>ACCAAGGGTGGTATTGTCAGAATGCAGGGTCAACTGTT<br>TACTACCCAAATGAGAAGGACTGTGAAACAAGAGGAG<br>ACCATGTCTTTTGCGACACAGCAGCAGGAATTAATGTT<br>GCTGAGCAATCAAAGGAGTGCAACATCAATATATCCAC<br>CACAAATTACCCGTGCAAAGTCAGCACAGGAAGGCATC<br>CCATCAGTATGGTTGCACTGTCCCCTCTTGGGGCTCTGG<br>TTGCCTGTTACAAGGGAGTAAGCTGTTCCATTGGCAGC<br>AATAGAGTAGGGATCATCAAGCAGCTGAACAAAGGTTG<br>CTCTTATATAACCAACCAAGATGCAGACACAGTGACAA<br>TAGACAACACTGTATATCAGCTGAGCAAAGTTGAGGGT<br>GAACAGCATGTTATAAAAGGCAGACCAGTGTCAAGCAG<br>CTTTGATCCAGTCAAGTTTCCTGAAGATCAATTCAATGT<br>TGCACTTGATCAAGTTTTTGAAAACATTGAAAACAGCC<br>AGGCCTTGGTAGATCAATCAAACAGAATCCTAAGCAGT<br>GCAGAGAAAGGGAACACTGGCTTCATCATTGTGATAAT<br>TCTAATTGCTGTCCTTGGCTCTAGCATGATCCTGGTGAG<br>CGTCTTTATTATAATCAAGAAAACAAAGAAACCAACAG<br>GAGCACCTCCAGAGCTAAGCGGTGTCACAAACAATGGC<br>TTCATACCGCACAGTTAG | 52 |
| Codon optimized nucleic acid encoding hMPV F protein of HMPV/Homo sapiens/PER/ FPP00726/2011/A | ATGAGCTGGAAGGTGGTGATCATCTTCAGCCTGCTGATCACCCC<br>CCAGCACGGCCTGAAGGAGAGCTACCTGGAGGAGAGCTGCAGCA<br>CCATCACCGAGGGCTACCTGAGCGTGCTGAGAACCGGCTGGTAC<br>ACCAACGTGTTCACCCTGGAGGTGGGCGACGTGGAGAACCTGAC<br>CTGCGCCGACGGCCCCAGCCTGATCAAGACCGAGCTGGACCTGA<br>CCAAGAGCGCCCTGAGAGAGCTGAAGACCGTGAGCGCCGACCAG<br>CTGGCCAGAGAGGAGCAGATCGAGAACCCCAGACAGAGCAGATT<br>CGTGCTGGGCGCCATCGCCCTGGGCGTGGCCACCGCCGCCGCCG<br>TGACCGCCGGCGTGGCCATCGCCAAGACCATCAGACTGGAGAGC<br>GAGGTGACCGCCATCAAGAACGCCCTGAAGAAGACCAACGAGGC<br>CGTGAGCACCCTGGGCAACGGCGTGAGAGTGCTGGCCACCGCCG<br>TGAGAGAGCTGAAGGACTTCGTGAGCAAGAACCTGACCAGAGCC<br>ATCAACAAGAACAAGTGCGACATCGACGACCTGAAGATGGCCGT<br>GAGCTTCAGCCAGTTCAACAGAAGATTCCTGAACGTGGTGAGAC<br>AGTTCAGCGACAACGCCGGCATCACCCCCGCCATCAGCCTGGAC<br>CTGATGACCGACGCCGAGCTGGCCAGAGCCGTGAGCAACATGCC<br>CACCAGCGCCGGCCAGATCAAGCTGATGCTGGAGAACAGAGCCA<br>TGGTGAGAAGAAAGGGCTTCGGCATCCTGATCGGCGTGTACGGC<br>AGCAGCGTGATCTACATGGTGCAGCTGCCCATCTTCGGCGTGAT<br>CGACACCCCCTGCTGGATCGTGAAGGCCGCCCCCAGCTGCAGCG<br>AGAAGAAGGGCAACTACGCCTGCCTGCTGAGAGAGGACCAGGGC<br>TGGTACTGCCAGAACGCCGGCAGCACCGTGTACTACCCCAACGA<br>GAAGGACTGCGAGACCAGAGGCGACCACGTGTTCTGCGACACCG<br>CCGCCGGCATCAACGTGGCCGAGCAGAGCAAGGAGTGCAACATC<br>AACATCAGCACCACCAACTACCCCTGCAAGGTGAGCACCGGCAG<br>ACACCCCATCAGCATGGTGGCCCTGAGCCCCCTGGGCGCCCTGG<br>TGGCCTGCTACAAGGGCGTGAGCTGCAGCATCGGCAGCAACAGA<br>GTGGGCATCATCAAGCAGCTGAACAAGGGCTGCAGCTACATCAC<br>CAACCAGGACGCCGACACCGTGACCATCGACAACACCGTGTACC<br>AGCTGAGCAAGGTGGAGGGCGAGCAGCACGTGATCAAGGGCAGA | 53 |

-continued

CCCGTGAGCAGCAGCTTCGACCCCGTGAAGTTCCCCGAGGACCA
GTTCAACGTGGCCCTGGACCAGGTGTTCGAGAACATCGAGAACA
GCCAGGCCCTGGTGGACCAGAGCAACAGAATCCTGAGCAGCGCC
GAGAAGGGCAACACCGGCTTCATCATCGTGATCATCCTGATCGC
CGTGCTGGGCAGCAGCATGATCCTGGTGAGCGTGTTCATCATCA
TCAAGAAGACCAAGAAGCCCACCGGCGCCCCCCCCGAGCTGAGC
GGCGTGACCAACAACGGCTTCATCCCCCACAGCTGA

Wild-type Nucleic acid sequence encoding hMPV F protein of strain HMPV/USA/C2-175/2005/B — 54

ATGTCTTGGAAAGTGATGATCATCATTTCGTTACTCATA
ACACCCCAGCACGGGCTAAAGGAGAGTTATTTGGAAGA
ATCATGCAGTACTATAACTGAGGGATACCTCAGTGTTTT
AAGAACAGGCTGGTACACCAATGTCTTCACATTAGAAG
TTGGTGATGTTGAAAATCTTACATGTACTGATGGACCTA
GCTTAATCAAAACAGAACTTGACCTAACAAAAAGTGCT
TTAAGGGAACTCAAAACAGTCTCTGCTGATCAGTTAGC
GAGAGAGGAGCAAATTGAAAATCCCAGACAATCAAGA
TTTGTCCTAGGTGCAATAGCTCTCGGAGTTGCTACAGCA
GCAGCAGTCACAGCAGGCATTGCAATAGCCAAAACCAT
AAGGCTTGAGAGTGAGGTGAATGCAATTAAAGGTGCTC
TCAAACAAACTAATGAAGCAGTATCCACATTAGGAAAT
GGTGTGCGGGTCCTAGCCACTGCAGTGAGAGAGCTAAA
AGAATTTGTGAGCAAAAATCTGACTAGTGCAATCAACA
GGAACAAATGTGACATTGCTGATCTGAAGATGGCTGTC
AGCTTCAGTCAATTCAACAGAAGATTTCTAAATGTTGTG
CGGCAGTTTTCAGACAATGCAGGGATAACACCAGCAAT
ATCATTGGACCTAATGACTGATGCTGAATTGGCCAGAG
CTGTATCATACATGCCAACATCTGCAGGACAGATAAAA
CTGATGTTGGAGAACCGCGCAATGGTAAGGAGAAAAG
GATTTGGAATCCTAATAGGGGTCTACGGAAGCTCTGTG
ATTTACATGGTTCAATTGCCGATCTTTGGTGTCATAGAT
ACACCTTGTTGGATAATCAAGGCAGCTCCCTCTTGCTCA
GAAAAAAACGGGAATTATGCTTGCCTCCTAAGAGAGGA
TCAAGGGTGGTATTGTAAAAATGCAGGATCCACTGTTT
ACTACCCAAACGAAAAAGACTGTGAAACAAGAGGTGA
TCATGTTTTTTGTGACACAGCAGCAGGGATCAATGTTGC
TGAGCAATCAAGAGAATGCAACATCAACATATCTACTA
CCAACTACCCATGCAAAGTCAGCACAGGAAGACACCCT
ATAAGCATGGTTGCACTATCACCTCTCGGTGCTTTGGTG
GCTTGCTATAAAGGGGTAAGCTGCTCGATTGGCAGCAA
TCGGGTTGGAATCATCAAACAATTACCTAAAGGCTGCT
CATACATAACTAACCAGGATGCAGACACTGTAACAATT
GACAATACCGTGTATCAACTAAGCAAAGTTGAAGGTGA
ACAGCATGTAATAAAAGGGAGACCAGTTTCAAGCAGTT
TTGACCCAATCAGGTTTCCTGAGGATCAGTTCAATGTTG
CACTTGATCAAGTCTTCGAAAGCATTGAGAACAGTCAG
GCACTGGTGGAACAGTCAAACAAAATTCTAAACAGTGC
AGAAAAAGGAAACACTGGCTTCATTATTGTAATAATTT
TGGTTGCTGTTCTTGGTTTAACCATGATTTCAGTGAGCA
TCATCATCATAATCAAGAAAACAAGGAAGCCCACAGGA
GCACCTCCAGAGCTGAATGGTGTCACCAACGGCGGTTT
CATACCACATAGTTAG

Codon optimized nucleic acid sequence encoding hMPV F protein of strain HMPV/USA/C2-175/2005/B — 55

ATGAGCTGGAAGGTGATGATCATCATCAGCCTGCTGATCACCCC
CCAGCACGGCCTGAAGGAGAGCTACCTGGAGGAGAGCTGCAGCA
CCATCACCGAGGGCTACCTGAGCGTGCTGAGAACCGGCTGGTAC
ACCAACGTGTTCACCCTGGAGGTGGGCGACGTGGAGAACCTGAC
CTGCACCGACGGCCCCAGCCTGATCAAGACCGAGCTGGACCTGA
CCAAGAGCGCCCTGAGAGAGCTGAAGACCGTGAGCGCCGACCAG
CTGGCCAGAGAGGAGCAGATCGAGAACCCCAGACAGAGCAGATT
CGTGCTGGGCGCCATCGCCCTGGGCGTGGCCACCGCCGCCGCCG
TGACCGCCGGCATCGCCATCGCCAAGACCATCAGACTGGAGAGC
GAGGTGAACGCCATCAAGGGCGCCCTGAAGCAGACCAACGAGGC
CGTGAGCACCCTGGGCAACGGCGTGAGAGTGCTGGCCACCGCCG
TGAGAGAGCTGAAGGAGTTCGTGAGCAAGAACCTGACCAGCGCC
ATCAACAGAAACAAGTGCGACATCGCCGACCTGAAGATGGCCGT
GAGCTTCAGCCAGTTCAACAGAAGATTCCTGAACGTGGTGAGAC
AGTTCAGCGACAACGCCGGCATCACCCCCGCCATCAGCCTGGAC
CTGATGACCGACGCCGAGCTGGCCAGAGCCGTGAGCTACATGCC
CACCAGCGCCGGCCAGATCAAGCTGATGCTGGAGAACAGAGCCA
TGGTGAGAAGAAAGGGCTTCGGCATCCTGATCGGCGTGTACGGC
AGCAGCGTGATCTACATGGTGCAGCTGCCCATCTTCGGCGTGAT
CGACACCCCCTGCTGGATCATCAAGGCCGCCCCCAGCTGCAGCG
AGAAGAACGGCAACTACGCCTGCCTGCTGAGAGAGGACCAGGGC
TGGTACTGCAAGAACGCCGGCAGCACCGTGTACTACCCCAACGA
GAAGGACTGCGAGACCAGAGGCGACCACGTGTTCTGCGACACCG
CCGCCGGCATCAACGTGGCCGAGCAGAGCAGAGAGTGCAACATC
AACATCAGCACCACCAACTACCCCTGCAAGGTGAGCACCGGCAG
ACACCCCATCAGCATGGTGGCCCTGAGCCCCCTGGGCGCCCTGG
TGGCCTGCTACAAGGGCGTGAGCTGCAGCATCGGCAGCAACAGA

-continued

| | | |
|---|---|---|
| | GTGGGCATCATCAAGCAGCTGCCCAAGGGCTGCAGCTACATCAC<br>CAACCAGGACGCCGACACCGTGACCATCGACAACACCGTGTACC<br>AGCTGAGCAAGGTGGAGGGCGAGCAGCACGTGATCAAGGGCAGA<br>CCCGTGAGCAGCAGCTTCGACCCCATCAGATTCCCCGAGGACCA<br>GTTCAACGTGGCCCTGGACCAGGTGTTCGAGAGCATCGAGAACA<br>GCCAGGCCCTGGTGGAGCAGAGCAACAAGATCCTGAACAGCGCC<br>GAGAAGGGCAACACCGGCTTCATCATCGTGATCATCCTGGTGGC<br>CGTGCTGGGCCTGACCATGATCAGCGTGAGCATCATCATCATCA<br>TCAAGAAGACCAGAAAGCCCACCGGCGCCCCCCCCGAGCTGAAC<br>GGCGTGACCAACGGCGGCTTCATCCCCCACAGCTGA | |
| Wild-type Nucleic acid sequence encoding hMPV F protein of strain HMPV/ARG/107/2002/A | ATGTCTTGGAAAGTGGTGATCATTTTTTCATTGCTAATAACACC<br>TCAACACGGTCTTAAAGAAAGCTACCTAGAAGAATCATGTAGCA<br>CTATAACTGAGGGATATCTTAGTGTTCTGAGGACAGGTTGGTAT<br>ACCAACGTTTTTACATTAGAGGTGGGTGATGTAGAAAACCTTAC<br>ATGTTCTGATGGACCTAGCCTAATAAAAACAGAATTAGATCTGA<br>CCAAAAGTGCACTAAGAGAGCTCAAAACAGTCTCTGCTGACCAA<br>TTGGCAAGAGAGGAACAAATTGAGAATCCCAGACAATCTAGGTT<br>TGTTCTAGGAGCAATAGCACTCGGTGTTGCAACAGCAGCTGCAG<br>TCACAGCAGGTGTTGCAATTGCCAAAACCATCCGGCTTGAGAGT<br>GAAGTCACAGCAATTAAGAATGCCCTCAAAACGACCAATGAAGC<br>AGTATCTACATTGGGGAATGGAGTTCGAGTGTTAGCAACTGCAG<br>TGAGAGAGCTGAAAGACTTTGTGAGCAAGAATTTAACCCGTGCA<br>ATCAACAAAAACAAGTGTGACATTGATGACCTAAAAATGGCCGT<br>TAGCTTCAGTCAATTCAACAGAAGGTTTCTAAATGTTGTGCGGC<br>AATTTTCAGACAATGCTGGAATAACACCAGCAATATCTCTGGAC<br>TTAATGACAGATGCTGAACTAGCCAGGGCCGTTTCTAACATGCC<br>GACATCTGCAGGACAAATAAAATTGATGTTGGAGAACCGTGCGA<br>TGGTGCGAAGAAAGGGGTTCGGAATCCTGATAGGGGTCTACGGG<br>AGCTCCGTAATTTACATGGTGCAGCTGCCAATCTTTGGCGTTAT<br>AGACACGCCTTGCTGGATAGTAAAAGCAGCCCCTTCTTGTTCCG<br>AAAAAAAGGGAAACTATGCTTGCCTCTTAAGAGAAGACCAAGGG<br>TGGTATTGTCAGAATGCAGGGTCAACTGTTTACTACCCAAATGA<br>GAAAGACTGTGAAACAAGAGGAGACCATGTCTTTTGCGACACAG<br>CAGCAGGAATTAATGTTGCTGAGCAATCAAAGGAGTGCAACATC<br>AACATATCCACTACAAATTACCCATGCAAAGTCAGCACAGGAAG<br>ACATCCTATCAGTATGGTTGCACTGTCTCCTCTTGGGGCTCTGG<br>TTGCTTGCTACAAAGGAGTAAGCTGTTCCATTGGCAGCAACAGA<br>GTAGGGATCATCAAGCAGCTGAACAAAGGTTGCTCCTATATAAC<br>CAACCAAGATGCAGACACAGTGACAATAGACAACACTGTATATC<br>AGCTAAGCAAAGTTGAGGGTGAACAGCATGTTATAAAAGGCAGA<br>CCAGTGTCAAGCAGCTTTGATCCAATCAAGTTTCCTGAAGATCA<br>ATTCAATGTTGCACTTGACCAAGTTTTTGAGAACATTGAAAACA<br>GCCAGGCCTTGGTAGATCAATCAAACAGAATCCTAAGCAGTGCA<br>GAGAAAGGGAACACTGGCTTCATCATTGTAATAATTCTAATTGC<br>TGTCCTTGGCTCTAGCATGATCCTAGTGAGCATCTTCATTATAA<br>TCAAGAAAACAAAGAAACCAACGGGAGCACCTCCAGAGCTGAGT<br>GGTGTCACAAACAATGGCTTCATACCACACAGTTAG | 56 |
| Codon optimized nucleic acid sequence encoding hMPV F protein of strain HMPV/ARG/107/2002/A | ATGAGCTGGAAGGTGGTGATCATCTTCAGCCTGCTGAT<br>CACCCCCCAGCACGGCCTGAAGGAGAGCTACCTGGAGG<br>AGAGCTGCAGCACCATCACCGAGGGCTACCTGAGCGTG<br>CTGAGAACCGGCTGGTACACCAACGTGTTCACCCTGGA<br>GGTGGGCGACGTGGAGAACCTGACCTGCAGCGACGGCC<br>CCAGCCTGATCAAGACCGAGCTGGACCTGACCAAGAGC<br>GCCCTGAGAGAGCTGAAGACCGTGAGCGCCGACCAGCT<br>GGCCAGAGAGGAGCAGATCGAGAACCCCAGACAGAGC<br>AGATTCGTGCTGGGCGCCATCGCCCTGGGCGTGGCCAC<br>CGCCGCCGCCGTGACCGCCGGCGTGGCCATCGCCAAGA<br>CCATCAGACTGGAGAGCGAGGTGACCGCCATCAAGAAC<br>GCCCTGAAGACCACCAACGAGGCCGTGAGCACCCTGGG<br>CAACGGCGTGAGAGTGCTGGCCACCGCCGTGAGAGAGC<br>TGAAGGACTTCGTGAGCAAGAACCTGACCAGAGCCATC<br>AACAAGAACAAGTGCGACATCGACGACCTGAAGATGG<br>CCGTGAGCTTCAGCCAGTTCAACAGAAGATTCCTGAAC<br>GTGGTGAGACAGTTCAGCGACAACGCCGGCATCACCCC<br>CGCCATCAGCCTGGACCTGATGACCGACGCCGAGCTGG<br>CCAGAGCCGTGAGCAACATGCCCACCAGCGCCGGCCAG<br>ATCAAGCTGATGCTGGAGAACAGAGCCATGGTGAGAAG<br>AAAGGGCTTCGGCATCCTGATCGGCGTGTACGGCAGCA<br>GCGTGATCTACATGGTGCAGCTGCCCATCTTCGGCGTGA<br>TCGACACCCCCTGCTGGATCGTGAAGGCCGCCCCCAGC<br>TGCAGCGAGAAGAAGGGCAACTACGCCTGCCTGCTGAG<br>AGAGGACCAGGGCTGGTACTGCCAGAACGCCGGCAGC<br>ACCGTGTACTACCCCAACGAGAAGGACTGCGAGACCAG<br>AGGCGACCACGTGTTCTGCGACACCGCCGCCGGCATCA<br>ACGTGGCCGAGCAGAGCAAGGAGTGCAACATCAACATC<br>AGCACCACCAACTACCCCTGCAAGGTGAGCACCGGCAG<br>ACACCCCATCAGCATGGTGGCCCTGAGCCCCCTGGGCG | 57 |

-continued

```
CCCTGGTGGCCTGCTACAAGGGCGTGAGCTGCAGCATC
GGCAGCAACAGAGTGGGCATCATCAAGCAGCTGAACA
AGGGCTGCAGCTACATCACCAACCAGGACGCCGACACC
GTGACCATCGACAACACCGTGTACCAGCTGAGCAAGGT
GGAGGGCGAGCAGCACGTGATCAAGGGCAGACCCGTG
AGCAGCAGCTTCGACCCCATCAAGTTCCCCGAGGACCA
GTTCAACGTGGCCCTGGACCAGGTGTTCGAGAACATCG
AGAACAGCCAGGCCCTGGTGGACCAGAGCAACAGAAT
CCTGAGCAGCGCCGAGAAGGGCAACACCGGCTTCATCA
TCGTGATCATCCTGATCGCCGTGCTGGGCAGCAGCATG
ATCCTGGTGAGCATCTTCATCATCATCAAGAAGACCAA
GAAGCCCACCGGCGCCCCCCCCGAGCTGAGCGGCGTGA
CCAACAACGGCTTCATCCCCCACAGCTGA
```

TABLE 5

| Signal Sequences | | |
|---|---|---|
| Human RSV F signal sequence of the F protein of RSV strain A2 (first 25 amino acids of SEQ ID NO: 6) | MELLILKANAITTILTAVTFCFASG | 23 |
| hMPV F signal sequence of the F protein of hMPV strains CAN00-16 (SEQ ID NO: 16), HMPV/*Homo sapiens*/PER/FPP 00726/2011/A (SEQ ID NO: 52) and HMPV/ARG/10 7/2002/A (SEQ ID NO: 56) | MSWKVVIIFSLLITPQHG | 24 |
| Bovine RSV F signal sequence of the F protein of ATCC51908 strain (SEQ ID NO: 33) | MATTAMRMIISIIFISTYVTHITLC | 60 |

TABLE 6

| cDNA of genome of NDV Strains | | |
|---|---|---|
| cDNA of genomic sequence of NDV strain LaSota | accaaacagagaatccgtgagttacgataaaaggcgaaggagcaattgaagtcgcacggg<br>tagaaggtgtgaatctcgagtgcgagcccgaagcacaaactcgagaaagccttctgccaac<br>atgtcttccgtatttgatgagtacgaacagctcctcgcggctcagactcgccccaatggagct<br>catggagggggagaaaaagggagtaccttaaaagtagacgtcccggtattcactcttaaca<br>gtgatgacccagaagatagatggagctttgtggtattctgcctccggattgctgttagcgaag<br>atgccaacaaaccactcaggcaaggtgctctcatatctcttttatgctcccactcacaggtaat<br>gaggaaccatgttgccCttgcagggaaacagaatgaagccacattggccgtgcttgagatt<br>gatggctttgccaacggcacgccccagttcaacaataggagtggagtgtctgaagagagag<br>cacagagatttgcgatgatagcaggatctctccctcgggcatgcagcaacggaaccccgttc<br>gtcacagccggggcCgaagatgatgcaccagaagacatcaccgataccctggagaggat<br>cctctctatccaggctcaagtatgggtcacagtagcaaaagccatgactgcgtatgagactg<br>cagatgagtcggaaacaaggcgaatcaataagtatatgcagcaaggcagggtccaaaaga<br>aatacatcctctaccccgtatgcaggagcacaatccaactcacgatcagacagtctcttgcag<br>tccgcatctttttggttagcgagctcaagagaggccgcaacacggcaggtggtacctctactt<br>attataacctggtaggggacgtagactcatacatcaggaataccgggcttactgcattcttctt<br>gacactcaagtacggaatcaacaccaagacatcagcccttgcacttagtagcctctcaggcg<br>acatccagaagatgaagcagctcatgcgtttgtatcggatgaaaggagataatgcgccgtac<br>atgacattacttggtgatagtgaccagatgagctttgcgcctgccgagtatgcacaactttact<br>cctttgccatgggtatggcatcagtcctagataaaggtactgggaaataccaatttgccaggg<br>actttatgagcacatcattctggagacttggagtagagtacgctcaggctcagggaagtagc<br>attaacgaggatatggctgccgagctaaagctaaccccagcagcaaGgaGgggcctggc<br>agctgctgcccaacgggtctccgaGgaGaccagcagcataGacatgcctactcaacaag<br>tcggagtcctcactgggcttagcgagggggggtcccaagctctacaaggcggatcgaata<br>gatcgcaagggcaaccagaagccggggatggggagacccaattcctggatctgatgaga<br>gcggtagcaaatagcatgagggaggcgccaaactctgcacagggcactccccaatcggg<br>gcctcccccaactcctgggccatcccaagataacgacaccgactgggggtattgatggaca<br>aaacccagcctgcttccacaaaaacatcccaatgccctcacccgtagtcgacccctcgatttg<br>cggctctatatgaccacaccctcaaacaaacatcccccctctttcctccctcccccctgctgtaca<br>actAcgTacgccctagataccacaggcacaatgcggctcactaacaatcaaaacagagc<br>cgagggaattagaaaaaagtacgggtagaagagggatattcagagatcagggcaagtctc<br>ccgagtctctgctctctcctctacctgatagaccaggacaaacatggccacctttacagatgc<br>agagatcgacgagctatttgagacaagtggaactgtcattgacaacataattacagcccagg<br>gtaaaccagcagagactgttggaaggagtgcaatcccacaaggcaagaccaaggtgctga<br>gcgcagcatgggagaagcatgggagcatccagccaccggccagtcaagacaaccccgat<br>cgacaggacagatctgacaaacaaccatccacacccgagcaaacgaccccgcatgacag<br>cccgccggccacatccgccgaccagccccccacccaggccacagacgaagccgtcgac<br>acacagCtcaggaccggagcaagcaactctctgctgttgatgcttgacaagctcagcaata<br>aatcgtccaatgctaaaaagggcccatggtcgagcccccaagaggggaatcaccaacgtc | 47 |

TABLE 6-continued

| cDNA of genome of NDV Strains |
|---|
| cgactcaacagcaggggagtcaacccagtcgcggaaacagtcaggaaagaccgcagaa<br>ccaagtcaaggccgcccctggaaaccagggcacagacgtgaacacagcatatcatggac<br>aatgggaggagtcacaactatcagctggtgcaacccctcatgctctccgatcaaggcagag<br>ccaagacaatacccttgtatctgcggatcatgtccagccacctgtagactttgtgcaagcgat<br>gatgtctatgatggaggcgatatcacagagagtaagtaaggttgactatcagctagatcttgtc<br>ttgaaacagacatcctccatccctatgatgcggtccgaaatccaacagctgaaaacatctgtt<br>gcagtcatggaagccaacttgggaatgatgaagattctggatcccggttgtgccaacatttca<br>tctctgagtgatctacgggcagttgcccgatctcacccggttttagtttcaggccctggagacc<br>cctctccctatgtgacacaaggaggcgaaatggcacttaataaactttcgcaaccagtgcca<br>catccatctgaattgattaaacccgccactgcatgcgggcctgatataggagtggaaaagga<br>cactgtccgtgcattgatcatgtcacgcccaatgcacccgagttcttcagccaagctcctaag<br>caagttagatgcagccgggtcgatcgaggaaatcaggaaaatcaagcgccttgctctaaat<br>ggctaattactactgccacacgtagcgggtccctgtccactcggcatcacacggaatctgca<br>ccgagttcccccccgcGgacccaaggtccaactctccaagcggcaatcctctctcgcttcct<br>cagccccactgaatgAtcgcgtaaccgtaattaatctagctacatttaagattaagaaaaaat<br>acgggtagaattggagtgccccaattgtgccaagatggactcatctaggacaattgggctgt<br>actttgattctgcccattcttctagcaacctgttagcatttccgatcgtcctacaagAcacagga<br>gatgggaagaagcaaatcgccccgcaatataggatccagcgccttgacttgtggactgata<br>gtaaggaggactcagtattcatcaccacctatggattcatctttcaagttgggaatgaagaagc<br>cacCgtcggcatgatcgatgataaacccaagcgcgagttactttccgctgcgatgctctgcc<br>taggaagcgtcccaaataccggagaccttattgagctggcaagggcctgtctcactatgata<br>gtcacatgcaagaagagtgcaactaatactgagagaatggttttctcagtagtgcaggcacc<br>ccaagtgctgcaaagctgtagggttgtggcaaacaaatactcatcagtgaatgcagtcaagc<br>acgtgaaagcgccagagaagattcccgggagtggaaccctagaatacaaggtgaactttgt<br>ctccttgactgtggtaccgaagaGggatgtctacaagatcccagctgcagtattgaaggtttc<br>tggctcgagtctgtacaatcttgcgctcaatgtcactattaatgtggaggtagacccgaggagt<br>cctttggttaaatctCtgtctaagtctgacagcggatactatgctaacctcttcttgcatattgga<br>cttatgaccacTgtagataggaaggggaagaaagtgacatttgacaagctggaaaagaaa<br>ataaggagccttgatctatctgtcgggctcagtgatgtgctcgggccttccgtgttggtaaaag<br>caagaggtgcacggactaagcttttggcacctttcttctctagcagtgggacagcctgctatc<br>ccatagcaaatgcttctcctcaggtggccaagatactctggagtcaaaccgcgtgcctgcgg<br>agcgttaaaatcattatccaagcaggtacccaacgcgctgtcgcagtgaccgccgaccacg<br>aggttacctctactaagctggagaaggggcacacccttgccaaatacaatccttttaagaaat<br>aagctgcgtctctgagattgcgctccgcccactcacccagatcatcatgacacaaaaaacta<br>atctgtcttgattatttacagttagtttacctgtctatcaagttagaaaaaacacgggtagaagatt<br>ctggatcccggttggcgccctccaggtgcaagatgggctccagaccttctaccaagaaccc<br>agcacctatgatgctgactatccgggttgcgctggtactgagttgcatctgtccggcaaactc<br>cattgatggcaggcctcttgcagctgcaggaattgtggttacaggagacaaagccgtcaaca<br>tatacacctcatcccagacaggatcaatcatagttaagctcctcccgaatctgcccaaggata<br>aggaggcatgtgcgaaagccccttggatgcatacaacaggacattgaccactttgctcacc<br>ccccttggtgactctatccgtaggatacaagagtctgtgactacatctggagggggagaca<br>ggggcgccttataggcgccattattggcggtgtggctcttggggttgcaactgccgcacaaa<br>taacagcggccgcagctctgatacaagccaaacaaaatgctgccaacatcctccgacttaaa<br>gagagcattgccgcaaccaatgaggctgtgcatgaggtcactgacggattatcgcaactag<br>cagtggcagttgggaagatgcagcagtttgttaatgaccaatttaataaaacagctcaggaat<br>tagactgcatcaaaattgcacagcaagttggtgtagagctcaacctgtacctaaccgaattga<br>ctacagtattcggaccacaaatcacttcacctgctttaaacaagctgactattcaggcactttac<br>aatctagctggtggaaatatggattacttattgactaagttaggtgtagggaacaatcaactca<br>gctcattaatcggtagcggcttaatcaccggtaaccctattctatacgactcacagactcaact<br>cttgggtatacaggtaactctaccttcagtcgggaacctaaataatatgcgtgccacctacttg<br>gaaaccttatccgtaagcacaaccaggggatttgcctcggcacttgtcccAaaagtggtga<br>cacaggtcggttctgtgatagaagaacttgacacctcatactgtatagaaactgacttagattta<br>tattgtacaagaatagtaacgttccctatgtcccctggtatttattcctgcttgagcggcaatacg<br>tcggcctgtatgtactcaaagaccgaaggcgcacttactacaccatacatgactatcaaaggt<br>tcagtcatcgccaactgcaagatgacaacatgtagatgtgtaaacccccgggtatcatatcg<br>caaaactatggagaagccgtgtctctaatagataaacaatcatgcaatgttttatccttaggcg<br>ggataactttaaggctcagtggggaattcgatgtaacttatcagaagaatatctcaatacaaga<br>ttctcaagtaataataacaggcaatcttgatatctcaactgagcttgggaatgtcaacaactcg<br>atcagtaatgctttgaataagttagaggaaagcaacagaaaactagacaaagtcaatgtcaa<br>actgactagcacatctgctctcattacctatatcgttttgactatcatatctcttgtttttggtatactt<br>agcctgattctagcatgctacctaatgtacaagcaaaaggcgcaacaaaagaccttattatgg<br>cttgggaataatactctagatcagatgagagccactacaaaaatgtgaacacagatgaggaa<br>cgaaggtttccctaatagtaatttgtgtgaaagttctggtagtctgtcagttcagagagttaaga<br>aaaaactaccggttgtagatgaccaaaggacgatatacgggtagaacggtaagagaggcc<br>gcccctcaattgcgagccaggcttcacaacctccgttctaccgcttcaccgacaacagtcctc<br>aatcatggaccgcgccgttagccaagttgcgttagagaatgatgaaagagaggcaaaaaat<br>acatggcgcttgatattccggattgcaatcttattcttaacagtagtgaccttggctatatctgta<br>gcctcccttttatatagcatgggggctagcacacctagcgatcttgtaggcataccgactagg<br>atttccagggcagaagaaaagattacatctacacttggttccaatcaagatgtagtagatagg<br>atatataagcaagtggcccttgagtctccgttggcattgttaaatactgagaccacaattatgaa<br>cgcaataacatctctctcttatcagattaatggagctgcaaacaacagtgggtgggggcac<br>ctatccatgacccagattatataggggggataggcaaagaactcattgtagatgatgctagtg<br>atgtcacatcattctatccctctgcatttcaagaacatctgaattttatcccggcgcctactacag<br>gatcaggttgcactcgaataccctcatttgacatgagtgctacccattactgctacacccataat<br>gtaatattgtctggatgcagagatcactcacattcatatcagtatttagcacttggtgtgctccg<br>gacatctgcaacagggagggtattcttttctactctgcgttccatcaacctggacgacaccca<br>aaatcggaagtcttgcagtgtgagtgcaactcccctgggttgtgatatgctgtgctcgaaagt<br>cacggagacagaggaagaagattataactcagctgtccctacgcggatggtacatgggag |

TABLE 6-continued

| cDNA of genome of NDV Strains |
| --- |
| gttagggttcgacggccagtaccacgaaaaggacctagatgtcacaacattattcggggact<br>gggtggccaactacccaggagtagggggtggatcttttattgacagccgcgtatggttctca<br>gtctacggagggttaaaacccaattcacccagtgacactgtacaggaagggaaatatgtgat<br>atacaagcgatacaatgacacatgcccagatgagcaagactaccagattcgaatggccaag<br>tcttcgtataagcctggacggtttggtgggaaacgcatacagcaggctatcttatctatcaagg<br>tgtcaacatccttaggcgaagacccggtactgactgtaccgcccaacacagtcacactcatg<br>ggggccgaaggcagaattctcacagtagggacatctcatttcttgtatcaacgagggtcatca<br>tacttctctcccgcgttattatatcctatgacagtcagcaacaaaacagccactcttcatagtcct<br>tatacattcaatgccttcactcggccaggtagtatcccttgccaggcttcagcaagatgcccca<br>actcgtgtgttactggagtctatacagatccatatcccctaatcttctatagaaaccacaccttg<br>cgaggggtattcgggacaatgcttgatggtgtacaagcaagacttaaccctgcgtctgcagt<br>attcgatagcacatcccgcagtcgcattactcgagtgagttcaagcagtaccaaagcagcat<br>acacaacatcaacttgttttaaagtggtcaagactaataagacctattgtctcagcattgctgaa<br>atatctaatactctcttcggagaattcagaatcgtcccgttactagttgagatcctcaaagatga<br>cggggttagagaagccaggtctggctagttgagtcaattataaaggagttggaaagatggca<br>ttgtatcacctatcttctgcgacatcaagaatcaaaccgaatgccggcgcgtgctcgaattcca<br>tgttgccagttgaccacaatcagccagtgctcatgcgatcagattaagccttgtcaAtaGtct<br>cttgattaagaaaaaatgtaagtggcaatgagatacaaggcaaaacagctcatggtTaaCa<br>atacgggtaggacatggcgagctccggtcctgaaagggcagagcatcagattatcctacca<br>gagTcacacctgtcttcaccattggtcaagcacaaactactctattactggaaattaactggg<br>ctaccgcttcctgatgaatgtgacttcgaccacctcattctcagccgacaatggaaaaaaata<br>cttgaatcggcctctcctgatactgagagaatgataaaactcggaagggcagtacaccaaac<br>tcttaaccacaattccagaataaccggagtgctccaccccaggtgtttagaaGaactggcta<br>atattgaggtcccagattcaaccaacaaatttcggaagattgagaagaagatccaaattcaca<br>acacgagatatggagaactgttcacaaggctgtgtacgcatatagagaagaaactgctggg<br>gtcatcttggtctaacaatgtcccccggtcagaggagttcagcagcattcgtacggatccggc<br>attctggtttcactcaaaatggtccacagccaagtttgcatggctccatataaaacagatccag<br>aggcatctgatggtggcagctaGgacaaggtctgcggccaacaaattggtgatgctaaccc<br>ataaggtaggccaagtctttgtcactcctgaacttgtcgttgtgacgcatacgaatgagaacaa<br>gttcacatgtcttacccaggaacttgtattgatgtatgcagatatgatggagggcagagatatg<br>gtcaacataatatcaaccacggcggtgcatctcagaagcttatcagagaaaattgatgacattt<br>tgcggttaatagacgctctggcaaaagacttgggtaatcaagtctacgatgttgtatcactaat<br>ggagggatttgcatacggagctgtccagctactcgagccgtcaggtacatttgcaggagattt<br>cttcgcattcaacctgcaggagcttaaagacattctaattggcctcctccccaatgatatagca<br>gaatccgtgactcatgcaatcgctactgtattctctggtttagaacagaatcaagcagctgaga<br>tgttgtgtctgttgcgtctgtggggtcacccactgcttgagtcccgtattgcagcaaaggcagt<br>caggagccaaatgtgcgcaccgaaaatggtagactttgatatgatccttcaggtactgtctttc<br>ttcaagggaacaatcatcaacgggtacagaaagaagaatgcaggtgtgtggccgcgagtc<br>aaagtggatacaatatatgggaaggtcattgggcaactacatgcagattcagcagagatttca<br>cacgatatcatgttgagagagtataagagtttatctgcacttgaatttgagccatgtatagaatat<br>gaccctgtcaccaacctgagcatgttcctaaaagacaaggcaatcgcacaccccaacgata<br>attggcttgcctcgtttaggcggaaccttctctccgaagaccagaagaaacatgtaaaagaa<br>gcaacttcgactaatcgcctcttgatagagtttttagagtcaaatgatttgatccatataaagag<br>atggaatatctgacgacccttgagtaccttagagatgacaatgtggcagtatcatactcgctca<br>aggagaaggaagtgaaagttaatggacggatcttcgctaagctgacaaagaagttaaggaa<br>ctgtcaggtgatggcggaagggatcctagccgatcagattgcacctttctttcagggaaatgg<br>agtcattcaggatagcatatccttgaccaagagtatgctagcgatgagtcaactgtcttttaaca<br>gcaataagaaacgtatcactgactgtaaagaaagagtatcttcaaaccgcaatcatgatccga<br>aaagcaagaaccgtcggagagttgcaaccttcataacaactgacctgcaaaagtactgtctt<br>aattggagatatcagacaatcaaattgttcgctcatgccatcaatcagttgatgggcctacctc<br>acttcttcgaatggattcacctaagactgatggacactacgatgttcgtaggagaccctttcaat<br>cctccaagtgaccctactgactgtgacctctcaagagtccctaatgatgacatatatattgtca<br>gtgccagagggggtatcgaaggattatgccagaagctatggacaatgatctcaattgctgca<br>atccaacttgctgcagctagatcgcattgtcgtgttgcctgtatggtacagggtgataatcaag<br>taatagcagtaacgagagaggtaagatcagacgactctccggagatggtgttgacacagttg<br>catcaagccagtgataatttcttcaaggaattaattcatgtcaatcatttgattggccataatttga<br>aggatcgtgaaaccatcaggtcagacacattcttcatatacagcaaacgaatcttcaaagatg<br>gagcaatcctcagtcaagtcctcaaaaattcatctaaattagtgctagtgtcaggtgatctcagt<br>gaaaacaccgtaatgtcctgtgccaacattgcctctactgtagcacggctatgcgagaacgg<br>gcttcccaaagacttctgttactatttaaactatataatgagttgtgtgcagacatactttgactct<br>gagttctccatcaccaacaattcgcaccccgatcttaatcagtcgtggattgaggacatctcttt<br>tgtgcactcatatgttctgactcctgcccaattaggggggactgagtaaccttcaatactcaagg<br>ctctacactagaaatatcggtgacccggggactactgcttttgcagagatcaagcgactaga<br>agcagtgggattactgagtcctaacattatgactaatatcttaactaggccgcctgggaatgg<br>agattgggccagtctgtgcaacgacccatactctttcaattttgagactgttgcaagcccaaat<br>attgttcttaagaaacatacgcaaagagtcctatttgaaacttgttcaaatcccttattgtctgga<br>gtgcacacagaggataatgaggcagaagagaaggcattggctgaattcttgcttaatcaaga<br>ggtgattcatccccgcgttgcgcatgccatcatggaggcaagctctgtaggtaggagaaag<br>caaattcaagggcttgttgacacaacaaacaccgtaattaagattgcgcttactaggaggcca<br>ttaggcatcaagaggctgatgcggatagtcaattattctagcatgcatgcaatgctgtttagag<br>acgatgtttttcctccagtagatccaaccaccccttagtctcttctaatatgtgttctctgacact<br>ggcagactatgcacggaatagaagctggtcacctttgacgggaggcaggaaaatactgggt<br>gtatctaatcctgatacgatagaactcgtagagggtgagattcttagtgtaagcggagggtgt<br>acaagatgtgacagcggagatgaacaatttacttggttccatcttccaagcaatatagaattga<br>ccgatgacaccagcaagaatcctccgatgagggtaccatatctcgggtcaaagacacagga<br>gaggagagctgcctcacttgcaaaaatagctcatatgtcgccacatgtaaaggctgccctaa<br>gggcatcatccgtgttgatctgggcttatggggataatgaagtaaattggactgctgctcttac<br>gattgcaaaatctcggtgtaatgtaaacttagagtatcttcggttactgtcccctttacccacgg |

TABLE 6-continued

| cDNA of genome of NDV Strains | | |
|---|---|---|
| | ctgggaatcttcaacatagactagatgatggtataactcagatgacattcaccccctgcatctct<br>ctacaggGtgtcaccttacattcacatatccaatgattctcaaaggctgttcactgaagaagg<br>agtcaaagaggggaatgtggtttaccaacagatcatgctcttgggtttatctctaatcgaatcg<br>atctttccaatgacaacaaccaggacatatgatgagatcacactgcacctacatagtaaattta<br>gttgctgtatcagagaagcacctgttgcggttcctttcgagctacttggggtggtaccggaact<br>gaggacagtgacctcaaataagtttatgtatgatcctagccctgtatcggagggagactttgc<br>gagacttgacttagctatcttcaagagttatgagcttaatctggagtcatatcccacgatagag<br>ctaatgaacattctttcaatatccagcgggaagttgattggccagtctgtggtttcttatgatgaa<br>gatacctccataaagaatgacgccataatagtgtatgacaatacccgaaattggatcagtgaa<br>gctcagaattcagatgtggtccgcctatttgaatatgcagcacttgaagtgctcctcgactgttc<br>ttaccaactctattacctgagagtaagaggcctGgacaatattgtcttatatatgggtgatttata<br>caagaatatgccaggaattctactttccaacattgcagctacaatatctcatcccgtcattcattc<br>aaggttacatgcagtgggcctggtcaaccatgacggatcacaccaacttgcagatacggatt<br>ttatcgaaatgtctgcaaaactattagtatcttgcacccgacgtgtgatctccggcttatattcag<br>gaaataagtatgatctgctgttcccatctgtcttagatgataacctgaatgagaagatgcttcag<br>ctgatatcccggttatgctgtctgtacacggtactctttgctacaacaagagaaatcccgaaaa<br>taagaggcttaactgcagaagagaaatgttcaatactcactgagtatttactgtcggatgctgt<br>gaaaccattacttagccccgatcaagtgagctctatcatgtctcctaacataattacattcccag<br>ctaatctgtactacatgtctcggaagagcctcaatttgatcagggaaagggaggacagggat<br>actatcctggcgttgttgttcccccaagagccattattagagttcccttctgtgcaagatattggt<br>gctcgagtgaaagatccattcacccgacaacctgcggcatttttgcaagagttagatttgagt<br>gctccagcaaggtatgacgcattcacacttagtcagattcatcctgaactcacatctccaaatc<br>cggaggaagactacttagtacgatacttgttcagagggatagggactgcatcttcctcttggta<br>taaggcatctcatctcctttctgtacccgaggtaagatgtgcaagacacgggaactccttatac<br>ttagctgaagggagcggagccatcatgagtcttctcgaactgcatgtaccacatgaaactatc<br>tattacaatacgctcttttcaaatgagatgaacccccccgcaacgacatttcgggccgacccca<br>actcagtttttgaattcggttgtttataggaatctacaggcggaggtaacatgcaaagatggatt<br>tgtccaagagttccgtccattatggagagaaaatacagaggaaagCgacctgacctcagat<br>aaagTagtggggtatattacatctgcagtgccctacagatctgtatcattgctgcattgtgaca<br>ttgaaattcctccagggtccaatcaaagcttactagatcaactagctatcaatttatctctgattg<br>ccatgcattctgtaagggagggcggggtagtaatcatcaaagtgttgtatgcaatgggatact<br>actttcatctactcatgaacttgtttgctccgtgttccacaaaaggatatattctctctaatggttat<br>gcatgtcgaggagatatggagtgttacctggtatttgtcatgggttacctgggcgggcctaca<br>tttgtacatgaggtggtgaggatggcGaaaactctggtgcagcggcacggtacgctTttgt<br>ctaaatcagatgagatcacactgaccaggttattcacctcacagcggcagcgtgtgacagac<br>atcctatccagtcctttaccaagattaataaagtacttgaggaagaatattgacactgcgctgat<br>tgaagccgggggacagcccgtccgtccattctgtgcggagagtctggtgagcacgctagc<br>gaacataactcagataacccagatCatcgctagtcacattgacacagttatccggtctgtgat<br>atatatggaagctgagggtgatctcgctgacacagtatttctatttaccccttacaatctctctac<br>tgacgggaaaaagaggacatcacttaAacagtgcacgagacagatcctagaggttacaat<br>actaggtcttagagtcgaaaatctcaataaaataggcgatataatcagcctagtgcttaaagg<br>catgatctccatggaggaccttatcccactaaggacatacttgaagcatagtacctgccctaa<br>atatttgaaggctgtcctaggtattaccaaactcaaagaaatgtttacagacacttctgtaCtgt<br>acttgactcgtgctcaacaaaaattctacatgaaaactataggcaatgcagtcaaaggatatta<br>cagtaactgtgactcttaacgaaaatcacatattaataggctcctttttttggccaattgtattcttgt<br>tgatttaatcatattatgttagaaaaaagttgaaccctgactccttaggactcgaattcgaactca<br>aataaatgtcttaaaaaaaggttgcgcacaattattcttgagtgtagtctcgtcattcaccaaatc<br>tttgtttggt | |
| cDNA of<br>genomic<br>sequence of<br>NDV strain<br>Hitchner B1 | ACCAAACAGAGAATCCGTAAGTTACGATAAAAGGCGA<br>AGGAGCAATTGAAGTCGCACGGGTAGAAGGTGTGAATC<br>TCGAGTGCGAGCCCGAAGCACAAACTCGAGGAAGCCTT<br>CTGCCAACATGTCTTCCGTATTCGACGAGTACGAACAG<br>CTCCTCGCGGCTCAGACTCGCCCCAATGGAGCTCATGG<br>AGGGGGGGAGAAAGGGAGTACCTTAAAAGTAGACGTC<br>CCGGTATTCACTCTTAACAGTGATGACCCAGAAGATAG<br>GTGGAGCTTTGTGGTATTCTGCCTCCGGATTGCTGTTAG<br>CGAAGATGCCAACAAACCACTCAGGCAAGGTGCTCTCA<br>TATCTCTTTTATGCTCCCACTCACAGGTAATGAGGAACC<br>ATGTTGCCCTTGCAGGGAAACAGAATGAAGCCACATTG<br>GCCGTGCTTGAGATTGATGGCTTTGCCAACGGCACGCC<br>CCAGTTCAACAATAGGAGTGGAGTGTCTGAAGAGAGAG<br>CACAGAGATTTGCGATGATAGCAGGATCTCTCCCTCGG<br>GCATGCAGCAACGGCACCCCGTTCGTCACAGCCGGGGC<br>TGAAGATGATGCACCAGAAGACATCACCGATACCCTGG<br>AGAGGATCCTCTCTATCCAGGCTCAAGTATGGGTCACA<br>GTAGCAAAAGCCATGACTGCGTATGAGACTGCAGATGA<br>GTCGGAAACAAGGCGAATCAATAAGTATATGCAGCAAG<br>GCAGGGTCCAAAAGAAATACATCCTCTACCCCGTATGC<br>AGGAGCACAATCCAACTCACGATCAGACAGTCTCTTGC<br>AGTCCGCATCTTTTTGGTTAGCGAGCTCAAGAGAGGCC<br>GCAACACGGCAGGTGGTACCTCTACTTATTATAACCTA<br>GTAGGGGACGTAGACTCATATATCAGGAATACCGGGCT<br>TACTGCATTCTTCTTGACACTCAAGTACGGAATCAACAC<br>CAAGACATCAGCCCTTGCACTTAGTAGCCTCTCAGGCG<br>ACATCCAGAAGATGAAGCAGCTCATGCGTTTGTATCGG<br>ATGAAAGGAGATAATGCGCCGTACATGACATTACTTGG<br>TGATAGTGACCAGATGAGCTTTGCGCCTGCCGAGTATG | 48 |

TABLE 6-continued

| cDNA of genome of NDV Strains |
| --- |
| CACAACTTTACTCCTTTGCCATGGGTATGGCATCAGTCC<br>TAGATAAAGGTACTGGGAAATACCAATTTGCCAGGGAC<br>TTTATGAGCACATCATTCTGGAGACTTGGAGTAGAGTA<br>CGCTCAGGCTCAGGGAAGTAGCATTAACGAGGATATGG<br>CTGCCGAGCTAAAGCTAACCCCGGCAGCAAGGAGGGGC<br>CTGGCAGCTGCTGCCCAACGAGTCTCCGAGGTGACCAG<br>CAGCATAGACATGCCTACTCAACAAGTCGGAGTCCTCA<br>CTGGGCTTAGCGAGGGGGGATCCCAAGCCCTACAAGGC<br>GGATCGAATAGATCGCAAGGGCAACCAGAAGCCGGGG<br>ATGGGGAGACCCAATTCCTGGATCTGATGAGAGCGGTA<br>GCAAATAGCATGAGGGAGGCGCCAAACTCTGCACAGG<br>GCACTCCCCAATCGGGGCCTCCCCCAACTCCTGGGCCAT<br>CCCAAGATAACGACACCGACTGGGGGTATTGATTGACA<br>AAACCCAGCCTGCTTCTACAAGAACATCCCAATGCTCTC<br>ACCCGTAGTCGACCCCTCGATTTGCGGCTCTATATGACC<br>ACACCCTCAAACAAACATCCCCCTCTTTCCTCCCTCCCC<br>CTGCTGTACAACTCCGCACGCCCTAGATACCACAGGCA<br>CACCGCGGCTCACTAACAATCAAAACAGAGCCGAGGGA<br>ATTAGAAAAAAGTACGGGTAGAAGAGGGATATTCAGA<br>GATCAGGGCAAGTCTCCCGAGTCTCTGCTCTCTCCTCTA<br>CCTGATAGACCAGGACAAACATGGCCACCTTTACAGAT<br>GCAGAGATCGACGAGCTATTTGAGACAAGTGGAACTGT<br>CATTGACAACATAATTACAGCCCAGGGTAAACCAGCAG<br>AGACTGTTGGAAGGAGTGCAATCCCACAGGGCAAGACC<br>AAGGTGCTGAGCGCAGCATGGGAGAAGCATGGGAGCA<br>TCCAGCCACCGGCCAGTCAAGACAACCTCGATCGACAG<br>GACAGATCTGACAAACAACCATCCACACCCGAGCAAAC<br>GACCCCGCACGACAGCCCGCCGGCCACATCCGCTGACC<br>AGCCCCCCACCCAGGCCACAGACGAAGCCGTCGACACA<br>CAGCTCAGGACCGGAGCAAGCAACTCTCTGCTGTTGAT<br>GCTTGACAAGCTCAGCAATAAATCGTCCAATGCTAAAA<br>AGGGCCCATGGTCGAGCCCCCAAGAGGGGAATCACCAA<br>CGTCCGACTCAACAGCAGGGGAGTCAACCCAGTCGCGG<br>AAACAGCCAGGAAAGACTGCAGAACCAAGTCAAGGCC<br>GCCCCTGGAAACCAGGGCACAGACGTGAACACAGCATA<br>TCATGGACAATGGGAGGAGTCACAACTATCAGCTGGTG<br>CAACCCCTCATGCTCTCCGATCAAGGCAGAGCCAAGAC<br>AATACCCTTGTATCTGCGGATCATGTCCAGCCACCTGTA<br>GACTTTGTGCAAGCGATGATGTCTATGATGGGGGCGAT<br>ATCACAGAGAGTAAGTAAGGTTGACTATCAGCTAGATC<br>TTGTCTTGAAACAGACATCCTCCATCCCTATGATGCGGT<br>CCGAAATCCAACAGCTGAAAACATCTGTTGCAGTCATG<br>GAAGCCAACTTGGGAATGATGAAGATTCTGGATCCCGG<br>TTGTGCCAACATTTCATCTCTGAGTGATCTACGGGCAGT<br>TGCCCGATCTCACCCGGTTTTAGTTTCAGGCCCTGGAGA<br>CCCATCTCCCTATGTGATACAAGGAGGCGAAATGGCAC<br>TTAATAAACTTTCGCAACCAGTGCCACATCCATCTGAAT<br>TGATTAAACCCGCCACTGCATGCGGGCCTGATATAGGA<br>GTGGAGAGGGACACTGTCCGTGCATTGATCATGTCACG<br>CCCAATGCACCCGAGTTCTTCAGCCAAGCTCCTAAGCA<br>AGTTAGATGCAGCCGGGTCGATCGAGGAAATCAGGAAA<br>ATCAAGCGCCTTGCTCTAAATGGCTAATTACTACTGCCA<br>CACGTAGCGGGTCCCTGTCCACTCGGCATCACACGGAA<br>TCTGCACCGAGTTCCCCCCCGCAGACCCAAGGTCCAAC<br>TCTAGAAGCGGCAATCCTCTCTCGCTTCCTCAGCCCCAC<br>TGAATGATCGCGTAACCGTAATTAATCTAGCTACATTAA<br>GGATTAAGAAAAAATACGGGTAGAATTGGAGTGCCCCA<br>ATTGTGCCAAGATGGACTCATCTAGGACAATTGGGCTG<br>TACTTTGATTCTGCCCATTCTTCTAGCAACCTGTTAGCA<br>TTTCCGATCGTCCTACAAGACACAGGAGATGGGAAGAA<br>GCAAATCGCCCCGCAATATAGGATCCAGCGCCTTGACT<br>CGTGGACTGATAGTAAGGAAGACTCAGTATTCATCACC<br>ACCTATGGATTCATCTTTCAAGTTGGGAATGAGGAAGC<br>CACTGTCGGCATGATCGATGATAAACCCAAGCGCGAGT<br>TACTTTCCGCTGCGATGCTCTGCCTAGGAAGCGTCCCAA<br>ATACCGGAGACCTTGTTGAGCTGGCAAGGGCCTGTCTC<br>ACTATGATGGTCACATGCAAGAAGAGTGCAACTAATAC<br>TGAGAGAATGGTTTTCTCAGTAGTGCAGGCACCCCAAG<br>TGCTGCAAAGCTGTAGGGTTGTGGCAAATAAATACTCA<br>TCAGTGAATGCAGTCAAGCACGTGAAAGCGCCAGAGAA<br>GATCCCCGGGAGTGGAACCCTAGAATACAAGGTGAACT<br>TTGTCTCCTTGACTGTGGTACCGAAGAAGGATGTCTACA<br>AGATCCCAGCTGCAGTATTGAAGATTTCTGGCTCGAGTC<br>TGTACAATCTTGCGCTCAATGTCACTATTAATGTGGAGG<br>TAGACCCGAGGAGTCCTTTGGTTAAATCTCTGTCTAAGT<br>CTGACAGCGGATACTATGCTAACCTCTTCTTGCATATTG<br>GACTTATGACCACCGTAGATAGGAAGGGGAAGAAAGT<br>GACATTTGACAAGCTGGAAAAGAAAATAAGGAGCCTTG |

TABLE 6-continued

| cDNA of genome of NDV Strains |
|---|
| ATCTATCTGTCGGGCTCAGTGATGTGCTCGGGCCTTCCG<br>TGTTGGTAAAAGCAAGAGGTGCACGGACTAAGCTTTTG<br>GCACCTTTCTTCTCTAGCAGTGGGACAGCCTGCTATCCC<br>ATAGCAAATGCTTCTCCTCAGGTGGCCAAGATACTCTG<br>GAGTCAAACCGCGTGCCTGCGGAGCGTTAAAATCATTA<br>TCCAAGCAGGTACCCAACGCGCTGTCGCAGTGACCGCT<br>GACCACGAGGTTACCTCTACTAAGCTGGAGAAGGGGCA<br>CACCCTTGCCAAATACAATCCTTTTAAGAAATAAGCTGC<br>GTCTCTGAGATTGCGCTCCGCCCACTCACCCAGATCATC<br>ATGACACAAAAAACTAATCTGTCTTGATTATTTACAGTT<br>AGTTTACCTGTCCATCAAGTTAGAAAAAACACGGGTAG<br>AAGATTCTGGATCCCGGTTGGCGCCCTCCAGGTGCAGG<br>ATGGGCTCCAGACCTTCTACCAAGAACCCAGCACCTAT<br>GATGCTGACTATCCGGGTCGCGCTGGTACTGAGTTGCAT<br>CTGCCCGGCAAACTCCATTGATGGCAGGCCTCTTGCAG<br>CTGCAGGAATTGTGGTTACAGGAGACAAAGCAGTCAAC<br>ATATACACCTCATCCCAGACAGGATCAATCATAGTTAA<br>GCTCCTCCCGAATCTGCCCAAGGATAAGGAGGCATGTG<br>CGAAAGCCCCCTTGGATGCATACAACAGGACATTGACC<br>ACTTTGCTCACCCCCCTTGGTGACTCTATCCGTAGGATA<br>CAAGAGTCTGTGACTACATCTGGAGGGGGAGACAGGG<br>GCGCCTTATAGGCGCCATTATTGGCGGTGTGGCTCTTGG<br>GGTTGCAACTGCCGCACAAATAACAGCGGCCGCAGCTC<br>TGATACAAGCCAAACAAAATGCTGCCAACATCCTCCGA<br>CTTAAAGAGAGCATTGCCGCAACCAATGAGGCTGTGCA<br>TGAGGTCACTGACGGATTATCGCAACTAGCAGTGGCAG<br>TTGGGAAGATGCAGCAGTTTGTTAATGACCAATTTAAT<br>AAAACAGCTCAGGAATTAGACTGCATCAAAATTGCACA<br>GCAAGTTGGTGTAGAGCTCAACCTGTACCTAACCGAAT<br>TGACTACAGTATTCGGACCACAAATCACTTCACCTGCCT<br>TAAACAAGCTGACTATTCAGGCACTTTACAATCTAGCTG<br>GTGGGAATATGGATTACTTATTGACTAAGTTAGGTATA<br>GGGAACAATCAACTCAGCTCATTAATCGGTAGCGGCTT<br>AATCACCGGTAACCCTATTCTATACGACTCACAGACTCA<br>ACTCTTGGGTATACAGGTAACTCTACCTTCAGTCGGGAA<br>CCTAAATAATATGCGTGCCACCTACTTGGAAACCTTATC<br>CGTAAGCACAACCAGGGGATTTGCCTCGGCACTTGTCC<br>CAAAAGTGGTGACACAGGTCGGTTCTGTGATAGAAGAA<br>CTTGACACCTCATACTGTATAGAAACTGACTTAGATTTA<br>TATTGTACAAGAATAGTAACGTTCCCTATGTCCCCTGGT<br>ATTTACTCCTGCTTGAGCGGCAATACATCGGCCTGTATG<br>TACTCAAAGACCGAAGGCGCACTTACTACACCATATAT<br>GACTATCAAAGGCTCAGTCATCGCTAACTGCAAGATGA<br>CAACATGTAGATGTGTAAACCCCCCGGGTATCATATCG<br>CAAAACTATGGAGAAGCCGTGTCTCTAATAGATAAACA<br>ATCATGCAATGTTTTATCCTTAGGCGGGATAACTTTAAG<br>GCTCAGTGGGGAATTCGATGTAACTTATCAGAAGAATA<br>TCTCAATACAAGATTCTCAAGTAATAATAACAGGCAAT<br>CTTGATATCTCAACTGAGCTTGGGAATGTCAACAACTCG<br>ATCAGTAATGCTTTGAATAAGTTAGAGGAAAGCAACAG<br>AAAACTAGACAAAGTCAATGTCAAACTGACCAGCACAT<br>CTGCTCTCATTACCTATATCGTTTTGACTATCATATCTCT<br>TGTTTTTGGTATACTTAGCCTGATTCTAGCATGCTACCT<br>AATGTACAAGCAAAAGGCGCAACAAAAGACCTTATTAT<br>GGCTTGGGAATAATACCCTAGATCAGATGAGAGCCACT<br>ACAAAAATGTGAACACAGATGAGGAACGAAGGTTTCCC<br>TAATAGTAATTTGTGTGAAAGTTCTGGTAGTCTGTCAGT<br>TCGGAGAGTTAAGAAAAAACTACCGGTTGTAGATGACC<br>AAAGGACGATATACGGGTAGAACGGTAAGAGAGGCCG<br>CCCCTCAATTGCGAGCCAGACTTCACAACCTCCGTTCTA<br>CCGCTTCACCGACAACAGTCCTCAATCATGGACCGCGC<br>CGTTAGCCAAGTTGCGTTAGAGAATGATGAAAGAGAGG<br>CAAAAAATACATGGCGCTTGATATTCCGGATTGCAATC<br>TTATTCTTAACAGTAGTGACCTTGGCTATATCTGTAGCC<br>TCCCTTTTATATAGCATGGGGGCTAGCACACCTAGCGAT<br>CTTGTAGGCATACCGACTAGGATTTCCAGGGCAGAAGA<br>AAAGATTACATCTACACTTGGTTCCAATCAAGATGTAGT<br>AGATAGGATATATAAGCAAGTGGCCCTTGAGTCTCCAT<br>TGGCATTGTTAAATACTGAGACCACAATTATGAACGCA<br>ATAACATCTCTCTCTTATCAGATTAATGGAGCTGCAAAC<br>AACAGCGGGTGGGGGGCACCTATTCATGACCCAGATTA<br>TATAGGGGGGATAGGCAAAGAACTCATTGTAGATGATG<br>CTAGTGATGTCACATCATTCTATCCCTCTGCATTTCAAG<br>AACATCTGAATTTTATCCCGGCGCCTACTACAGGATCAG<br>GTTGCACTCGAATACCCTCATTTGACATGAGTGCTACCC<br>ATTACTGCTACACCCATAATGTAATATTGTCTGGATGCA<br>GAGATCACTCACACTCACATCAGTATTTAGCACTTGGTG<br>TGCTCCGGACATCTGCAACAGGGAGGGTATTCTTTTCTA |

TABLE 6-continued

| cDNA of genome of NDV Strains |
| --- |
| CTCTGCGTTCCATCAACCTGGACGACACCCAAAATCGG<br>AAGTCTTGCAGTGTGAGTGCAACTCCCCTGGGTTGTGAT<br>ATGCTGTGCTCGAAAGCCACGGAGACAGAGGAAGAAG<br>ATTATAACTCAGCTGTCCCTACGCGGATGGTACATGGG<br>AGGTTAGGGTTCGACGGCCAATATCACGAAAAGGACCT<br>AGATGTCACAACATTATTCGGGGACTGGGTGGCCAACT<br>ACCCAGGAGTAGGGGGTGGATCTTTTATTGACAGCCGC<br>GTATGGTTCTCAGTCTACGGAGGGTTAAAACCCAATAC<br>ACCCAGTGACACTGTACAGGAAGGGAAATATGTGATAT<br>ACAAGCGATACAATGACACATGCCCAGATGAGCAAGAC<br>TACCAGATTCGAATGGCCAAGTCTTCGTATAAGCCTGG<br>ACGGTTTGGTGGGAAACGCATACAGCAGGCTATCTTAT<br>CTATCAAAGTGTCAACATCCTTAGGCGAAGACCCGGTA<br>CTGACTGTACCGCCCAACACAGTCACACTCATGGGGGC<br>CGAAGGCAGAATTCTCACAGTAGGGACATCCCATTTCT<br>TGTATCAGCGAGGGTCATCATACTTCTCTCCCGCGTTAT<br>TATATCCTATGACAGTCAGCGACAAAACAGCCACTCTT<br>CATAGTCCTTATACATTCAATGCCTTCACTCGGCCAGGT<br>AGTATCCCTTGCCAGGCTTCAGCAAGATGCCCCAACTC<br>GTGTGTTACTGGAGTCTATACAGATCCATATCCCCTAAT<br>CTTCTATAGAAACCACACCTTGCGAGGGGTATTCGGGA<br>CAATGCTTGATGGTGAACAAGCAAGACTTAACCCTGCG<br>TCTGCAGTATTCGATAGCACATCCCGCAGTCGCATAACT<br>CGAGTGAGTTCAAGCAGCATCAAAGCAGCATACACAAC<br>ATCAACTTGTTTTAAAGTGGTCAAGACCAATAAGACCT<br>ATTGTCTCAGCATTGCTGAAATATCTAATACTCTCTTCG<br>GAGAATTCAGAATCGTCCCGTTACTAGTTGAGATCCTCA<br>AAGATGACGGGGTTAGAGAAGCCAGGTCTGGCTAGTTG<br>AGTCAACTATGAAAGAGTTGGAAAGATGGCATTGTATC<br>ACCTATCTTCTGCGACATCAAGAATCAAACCGAATGCC<br>GGCGCGTGCTCGAATTCCATGTCGCCAGTTGACCACAA<br>TCAGCCAGTGCTCATGCGATCAGATTAAGCCTTGTCAAT<br>AGTCTCTTGATTAAGAAAAAATGTAAGTGGCAATGAGA<br>TACAAGGCAAAACAGCTCACGGTAAATAATACGGGTAG<br>GACATGGCGAGCTCCGGTCCTGAAAGGGCAGAGCATCA<br>GATTATCCTACCAGAGTCACACCTGTCTTCACCATTGGT<br>CAAGCACAAACTACTCTATTATTGGAAATTAACTGGGC<br>TACCGCTTCCTGATGAATGTGACTTCGACCACCTCATTC<br>TCAGCCGACAATGGAAAAAAATACTTGAATCGGCCTCT<br>CCTGATACTGAGAGAATGATAAAACTCGGAAGGGCAGT<br>ACACCAAACTCTTAACCACAATTCCAGAATAACCGGAG<br>TACTCCACCCCAGGTGTTTAGAAGAACTGGCTAATATTG<br>AGGTCCCTGATTCAACCAACAAATTTCGGAAGATTGAG<br>AAGAAGATCCAAATTCACAACACGAGATATGGAGAACT<br>GTTCACAAGGCTGTGTACGCATATAGAGAAGAAACTGC<br>TGGGGTCATCTTGGTCTAACAATGTCCCCCGGTCAGAG<br>GAGTTCAGCAGCATTCGTACGGATCCGGCATTCTGGTTT<br>CACTCAAAATGGTCCACAGCCAAGTTTGCATGGCTCCA<br>TATAAAACAGATCCAGAGGCATCTGATTGTGGCAGCTA<br>GGACAAGGTCTGCGGCCAACAAATTGGTGATGCTAACC<br>CATAAGGTAGGCCAAGTCTTTGTCACTCCTGAACTTGTT<br>GTTGTGACGCATACGAATGAGAACAAGTTCACATGTCT<br>TACCCAGGAACTTGTATTGATGTATGCAGATATGATGG<br>AGGGCAGAGATATGGTCAACATAATATCAACCACGGCG<br>GTGCATCTCAGAAGCTTATCAGAGAAAATTGATGACAT<br>TTTGCGGTTAATAGACGCTCTGGCAAAAGACTTGGGTA<br>ATCAAGTCTACGATGTTGTATCACTAATGGAGGGATTTG<br>CATACGGAGCTGTCCAGCTACTCGAGCCGTCAGGTACA<br>TTTGCGGGAGATTTCTTCGCATTCAACCTGCAGGAGCTT<br>AAAGACATTCTAATTGGCCTCCTCCCCAATGATATAGCA<br>GAATCCGTGACTCATGCAATCGCTACTGTATTCTCTGGT<br>TTAGAACAGAATCAAGCAGCTGAGATGTTGTGCCTGTT<br>GCGTCTGTGGGGTCACCCACTGCTTGAGTCCCGTATTGC<br>AGCAAAGGCAGTCAGGAGCCAAATGTGCGCACCGAAA<br>ATGGTAGACTTTGATATGATCCTTCAGGTACTGTCTTTC<br>TTCAAGGGAACAATCATCAACGGATACAGAAAGAAGA<br>ATGCAGGTGTGTGGCCGCGAGTCAAAGTGGATACAATA<br>TATGGGAAGGTCATTGGGCAACTACATGCAGATTCAGC<br>AGAGATTTCACACGATATCATGTTGAGAGAGTATAAGA<br>GTTTATCTGCACTTGAATTTGAGCCATGTATAGAATACG<br>ACCCTGTCACTAACCTGAGCATGTTCCTAAAAGACAAG<br>GCAATCGCACACCCCAACGATAATTGGCTTGCCTCGTTT<br>AGGCGGAACCTTCTCTCCGAAGACCAGAAGAAACATGT<br>AAAGGAAGCGACTTCGACTAACCGCCTCTTGATAGAGT<br>TTTTAGAGTCAAATGATTTTGATCCATATAAAGAGATGG<br>AATATCTGACGACCCTTGAGTACCTTAGAGATGACAAT<br>GTGGCAGTATCATACTCGCTCAAAGAGAAGGAAGTGAA<br>AGTTAATGGACGGATCTTCGCTAAGCTGACAAAGAAGT |

TABLE 6-continued

| cDNA of genome of NDV Strains |
|---|
| TAAGGAACTGTCAGGTGATGGCGGAAGGGATCCTAGCC<br>GATCAGATTGCACCTTTCTTTCAGGGAAATGGAGTCATT<br>CAGGATAGCATATCCTTGACCAAGAGTATGCTAGCGAT<br>GAGTCAACTGTCTTTTAACAGCAATAAGAAACGTATCA<br>CTGACTGTAAAGAAAGAGTATGTTCAAACCGCAATCAT<br>GATCCGAAAAGCAAGAACCGTCGGAGAGTTGCAACCTT<br>CATAACAACTGACCTGCAAAAGTACTGTCTTAATTGGA<br>GATATCAGACGATCAAATTGTTCGCTCATGCCATCAATC<br>AGTTGATGGGCCTACCTCATTTCTTCGAGTGGATTCACC<br>TAAGACTGATGGACACTACGATGTTCGTAGGAGACCCT<br>TTCAATCCTCCAAGTGACCCTACTGACTGTGACCTCTCA<br>AGAGTCCCTAATGATGACATATATATTGTCAGTGCCAG<br>AGGGGGTATCGAAGGATTATGCCAGAAGCTATGGACAA<br>TGATCTCAATTGCTGCAATCCAACTTGCTGCAGCTAGAT<br>CGCATTGTCGTGTTGCCTGTATGGTACAGGGTGATAATC<br>AAGTAATAGCAGTAACGAGAGAGGTAAGATCAGATGA<br>CTCTCCGGAGATGGTGTTGACACAGTTGCATCAAGCCA<br>GTGATAATTTCTTCAAGGAATTAATCCATGTCAATCATT<br>TGATTGGCCATAATTTGAAGGATCGTGAAACCATCAGG<br>TCAGACACATTCTTCATATACAGCAAACGAATCTTCAA<br>AGATGGAGCAATCCTCAGTCAAGTCCTCAAAAATTCAT<br>CTAAATTAGTGCTAGTGTCAGGTGATCTCAGTGAAAAC<br>ACCGTAATGTCCTGTGCCAACATTGCCTCTACTGTAGCA<br>CGGCTATGCGAGAACGGGCTTCCCAAAGACTTCTGTTA<br>CTATTTAAACTATATAATGAGTTGTGTGCAGACATACTT<br>TGACTCTGAGTTCTCCATCACCAACAATTCGCACCCCGA<br>TCTTAATCAGTCGTGGATTGAGGACATCTCTTTTGTGCA<br>CTCATATGTTCTGACTCCTGCCCAATTAGGGGGACTGAG<br>TAACCTTCAATACTCAAGGCTCTACACTAGAAATATCG<br>GTGACCCGGGGACTACTGCTTTTGCAGAGATCAAGCGA<br>CTAGAAGCAGTGGGACTACTGAGTCCTAACATTAGGAC<br>TAATATCTTAACTAGGCCGCCTGGGAATGGAGATTGGG<br>CCAGTCTGTGCAACGACCCATACTCTTTCAATTTTGAGA<br>CTGTTGCAAGCCCAAACATTGTTCTTAAGAAACATACG<br>CAAAGAGTCCTATTTGAAACTTGTTCAAATCCCTTATTG<br>TCTGGAGTGCACACAGAGGATAATGAGGCAGAAGAGA<br>AGGCATTGGCTGAATTCTTGCTTAATCAAGAGGTGATTC<br>ATCCCCGCGTTGCGCATGCCATCATGGAGGCAAGCTCT<br>GTAGGTAGGAGAAAGCAAATTCAAGGGCTTGTTGACAC<br>AACAAACACTGTAATTAAGATTGCGCTTACTAGGAGGC<br>CATTAGGCATCAAGAGGCTGATGCGGATAGTCAATTAT<br>TCTAGCATGCATGCAATGCTGTTTAGAGACGATGTTTTT<br>TCCTCTAGTAGATCCAACCACCCCTTAGTCTCTTCTAAT<br>ATGTGTTCTCTGACACTGGCAGACTATGCACGGAATAG<br>AAGCTGGTCACCTTTGACGGGAGGCAGGAAAATACTGG<br>GTGTATCTAATCCTGATACGATAGAACTCGTAGAGGGT<br>GAGATTCTTAGTGTAAGCGGAGGGTGTACAAGATGTGA<br>CAGCGGAGATGAACAATTTACTTGGTTCCATCTTCCAAG<br>CAATATAGAATTGACCGATGACACCAGCAAGAATCCTC<br>CGATGAGGGTACCATATCTCGGGTCAAAGACACAGGAG<br>AGGAGAGCTGCCTCACTTGCGAAAATAGCTCATATGTC<br>GCCACATGTGAAGGCTGCCCTAAGGGCATCATCCGTGT<br>TGATCTGGGCTTATGGGGATAATGAAGTAAATTGGACT<br>GCTGCTCTTACGATTGCAAAATCTCGGTGTAATGTAAAC<br>TTAGAGTATCTTCGGTTACTGTCCCCTTTACCCACGGCT<br>GGGAATCTTCAACATAGACTAGATGATGGTATAACTCA<br>GATGACATTCACCCCTGCATCTCTCTACAGGGTGTCACC<br>TTACATTCACATATCCAATGATTCTCAAAGGCTGTTCAC<br>TGAAGAAGGAGTCAAAGAGGGGAATGTGGTTTACCAAC<br>AGATCATGCTCTTGGGTTTATCTCTAATCGAATCGATCT<br>TTCCAATGACAACAACCAGAACATATGATGAGATCACA<br>CTGCACCTACATAGTAAATTTAGTTGCTGTATCAGGGAA<br>GCACCTGTTGCGGTTCCTTTCGAGCTACTTGGGGTGGCA<br>CCGGAACTGAGGACAGTGACCTCAAATAAGTTTATGTA<br>TGATCCTAGCCCTGTATCGGAGGGAGACTTTGCGAGAC<br>TTGACTTAGCTATCTTCAAGAGTTATGAGCTTAATCTGG<br>AGTCATATCCCACGATAGAGCTAATGAACATTCTTTCAA<br>TATCCAGCGGGAAGTTGATTGGCCAGTCTGTGGTTTCTT<br>ATGATGAAGATACCTCCATAAAGAATGATGCCATAATA<br>GTGTATGACAATACCCGAAATTGGATCAGTGAAGCTCA<br>GAATTCAGATGTGGTCCGCCTATTTGAATATGCAGCACT<br>TGAAGTGCTCCTCGACTGTTCTTACCAACTCTATTACCT<br>GAGAGTAAGAGACCTAGACAATATTGTCTTATATATGG<br>GTGATTTATACAAGAATATGCCAGGAATTCTACTTTCCA<br>ACATTGCAGCTACAATATCTCATCCTGTCATTCATTCAA<br>GGTTACATGCAGTGGGCCTGGTCAACCATGACGGATCA<br>CACCAACTTGCAGATACGGATTTTATCGAAATGTCTGCA<br>AAACTGTTAGTATCTTGCACCCGACGTGTGATCTCCGGC |

TABLE 6-continued

| cDNA of genome of NDV Strains |
|---|
| TTATATTCAGGAAATAAGTATGATCTGCTGTTCCCATCT<br>GTCTTAGATGATAACCTGAATGAGAAGATGCTTCAGCT<br>GATATCCCGGTTATGCTGTCTGTACACGGTACTCTTTGC<br>TACAACAAGAGAAATCCCGAAAATAAGAGGCTTAACTG<br>CAGAAGAGAAATGTTCAATACTCACTGAGTATTTACTG<br>TCGGATGCTGTGAAACCATTACTTAGCCCCGATCAAGT<br>GAGCTCTATCATGTCTCCTAACATAATTACATTCCCAGC<br>TAATCTGTACTACATGTCTCGGAAGAGCCTCAATTTGAT<br>CAGGGAAAGGGAGGACAGGGATACTATCCTGGCGTTGT<br>TGTTCCCCCAAGAGCCATTATTAGAGTTCCCTTCTGTGC<br>AAGATATTGGTGCTCGAGTGAAAGATCCATTCACCCGA<br>CAACCTGCGGCATTTTTGCAAGAGTTAGATTTGAGTGCT<br>CCAGCAAGGTATGACGCATTCACACTTAGTCAGATTCA<br>TCCTGAACTCACATCTCCAAATCCGGAGGAAGACTACT<br>TAGTACGATACTTGTTCAGAGGGATAGGGACTGCATCT<br>TCCTCTTGGTATAAGGCATCCCATCTCCTTTCTGTACCC<br>GAGGTAAGATGTGCAAGACACGGGAACTCCTTATACTT<br>GGCTGAAGGAAGCGGAGCCATCATGAGTCTTCTTGAAC<br>TGCATGTACCACATGAAACTATCTATTACAATACGCTCT<br>TTTCAAATGAGATGAACCCCCCGCAACGACATTTCGGG<br>CCGACCCCAACTCAGTTTTTGAATTCGGTTGTTTATAGG<br>AATCTACAGGCGGAGGTAACATGCAAGGATGGATTTGT<br>CCAAGAGTTCCGTCCATTATGGAGAGAAAATACAGAGG<br>AAAGTGACCTGACCTCAGATAAAGCAGTGGGGTATATT<br>ACATCTGCAGTACCCTACAGATCTGTATCATTGCTGCAT<br>TGTGACATTGAAATTCCTCCAGGGTCCAATCAAAGCTTA<br>CTAGATCAACTAGCTATCAATTTATCTCTGATTGCCATG<br>CATTCTGTAAGGGAGGGCGGGGTAGTAATCATCAAAGT<br>GTTGTATGCAATGGGATACTACTTTCATCTACTCATGAA<br>CTTGTTTGCTCCGTGTTCCACAAAAGGATATATTCTCTC<br>TAATGGTTATGCATGTCGAGGGGATATGGAGTGTTACC<br>TGGTATTTGTCATGGGTTACCTGGGCGGGCCTACATTTG<br>TACATGAGGTGGTGAGGATGGCAAAAACTCTGGTGCAG<br>CGGCACGGTACGCTTTTGTCTAAATCAGATGAGATCAC<br>ACTGACCAGGTTATTCACCTCACAGCGGCAGCGTGTGA<br>CAGACATCCTATCCAGTCCTTTACCAAGATTAATAAAGT<br>ACTTGAGGAAGAATATTGACACTGCGCTGATTGAAGCC<br>GGGGGACAGCCCGTCCGTCCATTCTGTGCGGAGAGTCT<br>GGTGAGCACGCTAGCGAACATAACTCAGATAACCCAGA<br>TCATCGCTAGTCACATTGACACAGTCATCCGGTCTGTGA<br>TATATATGGAAGCTGAGGGTGATCTCGCTGACACAGTA<br>TTTCTATTTACCCCTTACAATCTCTCTACTGACGGGAAA<br>AAGAGGACATCACTTAAACAGTGCACGAGACAGATCCT<br>AGAGGTTACAATACTAGGTCTTAGAGTCGAAAATCTCA<br>ATAAAATAGGCGATATAATCAGCCTAGTGCTTAAAGGC<br>ATGATCTCCATGGAGGACCTTATCCCACTAAGGACATA<br>CTTGAAGCATAGTACCTGCCCTAAATATTTGAAGGCTGT<br>CCTAGGTATTACCAAACTCAAAGAAATGTTTACAGACA<br>CTTCTGTACTGTACTTGACTCGTGCTCAACAAAAATTCT<br>ACATGAAAACTATAGGCAATGCAGTCAAAGGATATTAC<br>AGTAACTGTGACTCCTAACGAAAATCACATATTAATAG<br>GCTCCTTTTTTGGCCAATTGTATTCTTGTTGATTTAATTA<br>TATTATGTTAGAAAAAAGTTGAACTCTGACTCCTTAGGA<br>CTCGAATTCGAACTCAAATAAATGTCTTTAAAAAAGGT<br>TGCGCACAATTATTCTTGAGTGTAGTCTCGTCATTCACC<br>AAATCTTTGTTTGGT |

6. EXAMPLES

6.1 Example 1: Viral Vectored RSV Vaccine Induces Long-Lived Humoral Immunity in Cotton Rats This example demonstrates that vaccination with a recombinant Newcastle disease virus-vectored vaccine that expresses the F glycoprotein of RSV (rNDV-F) protects cotton rats from RSV challenge and induces long-lived neutralizing antibody production, even in RSV immune animals. In addition, this example demonstrates that the pulmonary eosinophilia induced by RSV infection of unvaccinated cotton rats is prevented by rNDV-F vaccination. Overall, these example demonstrates enhanced protective immunity to RSV F when this protein is presented in the context of an abortive NDV infection.

6.1.1 Materials & Methods

6.1.1.1 Animals 6-10 week old female cotton rats (*Sigmodon hispidus*) were used in this study (Sigmovir Biosystems, Inc., Bethesda, MD, USA). Animals were housed in groups of 3 in a BSL 2 facility and were offered a commercial pelleted rat chow and water ad libitum. Animals were acclimated for 7 to 10 days prior to vaccination or viral challenge. All procedures used here were conducted humanely. Data were collected from 3-5 cotton rats per cohort per time point, unless otherwise specified. All cotton rat studies were approved by the Institutional Animal Care and Use Committees of New York University School of Medicine (protocol 100504-02) and Rutgers-New Jersey Medical School.

6.1.1.2 Generation rNDV-F Construct rNDV-F was constructed as previously described [6]. Briefly, the sequence coding for the F protein of RSV (strain Long; SEQ ID NO:1) was inserted in the cDNA of the full length genome of NDV strain Hitchner B1 (a non-virulent vaccine strain of NDV), between the P and M genes. The inserted sequence contained NDV gene end and gene start sequences to make it a functional transcription unit, and a Kozak sequence for efficient translation. The cDNA sequence of the full length genome of NDV strain Hitchner B1 with the nucleic acid sequence encoding the RSV F protein inserted.

6.1.1.3 Vaccination rNDV-F was constructed as previously described [6] then amplified in 10-day-old embryonated chicken eggs. While under isoflurane anesthesia, cotton rats were intranasally (i.n.) vaccinated with $1\times10^6$ pfu rNDV-F, $1\times10^6$ pfu NDV vector alone, or allantoic fluid as a mock control in a 100 μl total volume divided equally between nares. Twenty-eight days after the priming vaccination, cotton rats were boosted in the same manner.

6.1.1.4 RSV Challenge

Human RSV strain A2, originally obtained from ATCC (VR-1540), was passaged on murine $STAT1^{-/-}$ fibroblast monolayers as previously described [12]. The challenge dose of $1\times10^6$ pfu RSV was instilled into the nasal cavities of cotton rats under isoflurane anesthesia in a 50 μl total volume, divided equally between nares. The inoculum was delivered slowly, over approximately 15 seconds, to restrict initial virus infection to the upper airway.

6.1.1.5 Plaque Assay

Cotton rats were euthanized by $CO_2$ asphyxiation, and nasal wash fluids and lungs were collected immediately after euthanasia and stored at −80° C. until use in viral plaque assay. Viral plaque assay was performed on murine STAT1−/− fibroblast monolayers as previously described [13].

6.1.1.6 Histology and Immunohistochemistry

Nasal cavities and lung were collected immediately following $CO_2$ asphyxiation. Nasal cavities were fixed in neutral buffered formalin then decalcified with 0.35M EDTA in 0.1M Tris (pH 6.95). The lung and decalcified nasal cavities were processed routinely, paraffin-embedded and sectioned at 5 μm. Tissues sections were stained with hematoxylin and eosin (H&E) or were left unstained for immunohistochemistry (IHC). For IHC, tissue sections were incubated with goat polyclonal RSV antiserum (Biodesign, Saco, Maine, USA) diluted 1:500 followed by incubation with biotinylated rabbit anti-goat IgG antibody then HRP (ScyTek, Logan, UT, USA). Virus detection was accomplished with the streptavidin link and AEC chromagen (Scytek, Logan, UT, USA). IHC-labeled tissue sections were counterstained with hematoxylin.

6.1.1.7 RSV F-Specific ELISA

Purified RSV F glycoprotein, whose transmembrane anchor was replaced with a 6His tag (SEQ ID NO:61), was produced by transfection of HEK293F cells and purified as described [14]. For RSV F-specific ELISA, Nunc maxisorb immunoplates (ThermoScientific, Waltham, MA, USA) were coated overnight at 4° C. with 0.3 μg purified F protein diluted in 0.1M sodium carbonate buffer. Plates were washed with PBS containing 0.05% Tween 20 (PBS-T) then blocked with PBS containing 10% fetal calf serum (PBS-F). Plates were washed with PBS-T then samples, serially diluted in PBS-F, were added followed by incubation at 25° C. for 60 minutes. Wells were washed with PBS-T and secondary antibody diluted in PBS-F was added (chicken anti-cotton rat IgG, Immunology Consultants Laboratory, Inc., Portland, OR, USA). Plates were incubated at 25° C. for 60 minutes. After washing with PBS-T, tertiary antibody diluted in PBS-F was added (goat anti-chicken IgG conjugated to HRP, Southern Biotech, Birmingham, AL, USA). Following a second incubation at 25° C. for 60 minutes, plates were again washed with PBS-T followed by the addition of tetramethylbenzidine peroxidase substrate (ScyTek, Logan, UT, USA). After incubation at 25° C. for 30 minutes, the reaction was stopped by addition of 2N $H_2SO_4$. Absorbance at 450 nm ($A_{450}$) was determined using an Epoch Microplate Spectrophotomer (BioTek, Winooki, VT, USA). Titers were defined as the highest dilution of the sample resulting in $A_{450}$ four-fold greater than background (PBS-F alone).

6.1.1.8 Serum Neutralization Assay

Two different methods were used for detection of RSV neutralizing antibody. Data shown in FIG. 4D were collected using a standard plaque reduction assay. Serum dilutions pre-incubated with 200 pfu RSV were used as the inoculum for plaque assay on murine $STAT1^{-/-}$ fibroblast monolayers as previously described [13].

For a more quantitative approach to determining neutralizing antibody titer, a flow cytometric assay was devised. For data shown in FIG. 7A, serum samples at a 1/800 dilution were incubated with rg-RSV [8] at a concentration of $3\times10^5$ pfu/ml. in DMEM+5% fetal calf serum for 1 hour at 37° C. The serum-virus mixture was then used to inoculate, in duplicate, monolayers of Vero cells ($10^5$ cells plated in 2 $cm^2$ wells). After a 20 hour incubation, cells were resuspended and analyzed by flow cytometry. Only infected cells will express gfp. Percent neutralization was calculated as 100 $(1-f_s/f_0)$ where $f_s$=fraction of gfp+ cells in the sample, and $f_0$=the fraction of gfp+ cells in the no-serum control.

6.1.1.9 Enumeration of RSV F-Specific B Cells

For T cell depletion, mouse anti-cotton rat CD8 and mouse anti-cotton rat CD4 monoclonal antibodies (r&d systems) were labeled with DSB-X according to the manufacturer's protocol (Dynabeads FlowComp Flexi, Invitrogen Life Technologies, Grand Island, NY, USA). Single cell suspensions of cervical lymph nodes, pooled by cohort, were incubated with 0.5 μg each of CD8 and CD4 DSB-X labeled antibody per sample, then T cells were depleted according to the manufacturer's protocol (Dynabeads FlowComp Flexi, Invitrogen Life Technologies, Grand Island, NY, USA). Cervical lymph node single cell suspensions, depleted of T cells and pooled by cohort, were used in ELISpot assays.

For F-specific ELISpot, multiscreen HTS HA plates (Millipore, Jaffrey, NH, USA) were coated overnight at 4° C. with 0.3 μg purified F protein diluted in 0.1M sodium carbonate buffer. Plates were washed with RPMI supplemented with 10% fetal calf serum (cRPMI) and then were blocked with cRPMI for 1 hr at 37° C. in a 5% C02 incubator. Plates were washed with RPMI then cervical lymph node single cell suspensions were added in duplicate. Plates were incubated 4-6 hrs at 37° C. in 5% C02. Plates were then washed with PBS containing 0.05% Tween-20 (PBS-T). Secondary antibody diluted in PBS-T (chicken anti-cotton rat IgG, Immunology Consultants Laboratory, Inc., Portland, OR, USA) was added and plates were incubated overnight at 4° C. Plates were washed with PBS-T. Tertiary antibody diluted in PBS-T was added (goat anti-chicken AP, Southern Biotech, Birmingham, AL, USA) and plates were incubated at 25° C. for 60 minutes. Plates were again washed with PBS-T. NBT/BCIP substrate (Millipore, Jaffrey, NH, USA) was added and plates were incubated in the dark for 30 minutes at 25° C. Plates were washed with tap water. Spots were counted visually.

6.1.1.10 BAL Fluid Analysis

BAL fluids were collected from cotton rats immediately after C02 asphyxiation by washing the lung with 2 ml of sterile saline. BAL fluid cell counts were determined by hemocytometer and BAL differentials were determined on Wright-Giemsa stained CytoSpin preparations (ThermoScientific, Waltham, MA, USA). For the 1 month time point, BAL fluid data was available for only 2 NDV vaccinated animals as BAL fluid collected from one NDV vaccinated animals was of poor quality and thus excluded. For the 2 month time point, BAL fluid data was available for only 2 mock vaccinated animals because one of the mock vaccinated animals died prior to sampling. For the 4 days after secondary RSV infection time point, BAL fluid data was available for only 2 mock vaccinated animals as necropsy of a third mock-vaccinated animal revealed pyometra, an abdominal mass and fibrinous pericarditis. BAL fluid analysis was not performed on that animal.

6.1.1.11 Statistical Analysis

SigmaPlot 12.0 (Systat Software, Inc., San Jose, CA, USA) and GraphPad (GraphPad Software, Inc., La Jolla, CA USA) were used to perform ANOVA and t-test where appropriate. A p-value<0.05 was considered statistically significant.

6.1.2 Results 6.1.2.1 rNDV-F Vaccination Induces a Mild Inflammatory Response

The immunization regimen involved intranasal delivery of $10^6$ pfu of rNDV-F into the nasal cavity of cotton rats. To determine the effect of inoculation, the nasal cavity and lung tissues were examined following each of the two i.n. vaccine doses. Histologic sections from the upper airway taken 24 hours, 48 hours, 72 hours and 7 days following intranasal instillation of $10^6$ pfu of rNDV-F showed minimal signs of inflammation, indistinguishable from similar sections taken from untreated cotton rats (Data not shown).

The nasal cavities of inoculated animals were also examined 28 days following priming, and 28 days following boost, for any evidence of disease secondary to immunization alone. No histologic changes were observed at this time point following delivery of allantoic fluid (FIGS. 3A and 3B) or the NDV vector alone (FIGS. 3E and 3F), but nasal cavity tissues collected from rNDV-F vaccinated animals showed submucosal lymphoplasmacytic infiltrates (FIGS. 1C and 1D), indicative of an acquired immune response. A more pronounced infiltrate was observed following rNDV-F boosting (FIGS. 1G and 1H).

No histologic changes were observed in the lung following delivery of allantoic fluid or a priming dose of NDV vector alone (FIGS. 1I, 1L, and 1J). However, in response to rNDV-F priming, submucosal lymphoplasmacytic infiltrates similar to those observed in the nasal cavity mucosa, were observed surrounding bronchioles (FIG. 1K), with an increased number of lymphocytes and plasma cells surrounding bronchioles following rNDV-F boosting (FIG. 1N). Similar peribronchiolar infiltrates were observed in response to a boosting dose of NDV vector alone (FIG. 1M), but these were less cellular than those that accompanied rNDV-F vaccination. Additionally, following a second dose with NDV vector alone, or either dose of rNDV-F, rare eosinophils were observed intermixed with the lymphocytic and plasma cell infiltrates surrounding bronchioles (FIGS. 1K, 1M and 1N). Based on these studies it appears that intranasal immunization with rNDV-F causes no acute injury to the upper or lower airway, but does induce a mucosal lymphocytic response. The basis for the enhanced, though still mild, inflammatory response to rNDV-F when compared with the NDV vector alone is not clear, but is consistent with the ability to boost immunity with a second, boosting vaccine dose.

6.1.2.2 rNDV-F Vaccination Protects Against RSV Infection and Reinfection

Tissues were harvested 4 days after RSV challenge of animals that had been immunized with two i.n. doses of allantoic fluid, NDV vector alone, or rNDV-F. In the nasal cavity and lung tissue of animals receiving allantoic fluid or NDV vector alone prior to RSV challenge, primary RSV infection was associated with mucosal and submucosal inflammatory infiltrates composed primarily of lymphocytes (FIGS. 2A and 2B). The lungs from these mock-immunized cotton rats had sparse peribronchiolar lymphohistiocytic infiltrates, with mucus and inflammatory cells in small airways (FIGS. 2D and 2E). In contrast, both lung and nasal cavity tissues collected from RSV-challenged, rNDV-F vaccinated cotton rats exhibited changes similar to those observed in response to vaccination alone (FIGS. 2C and 2F), with a more pronounced lymphocytic infiltrate, but lacking the mucus production and mixed inflammatory infiltrate.

Figure 3G:
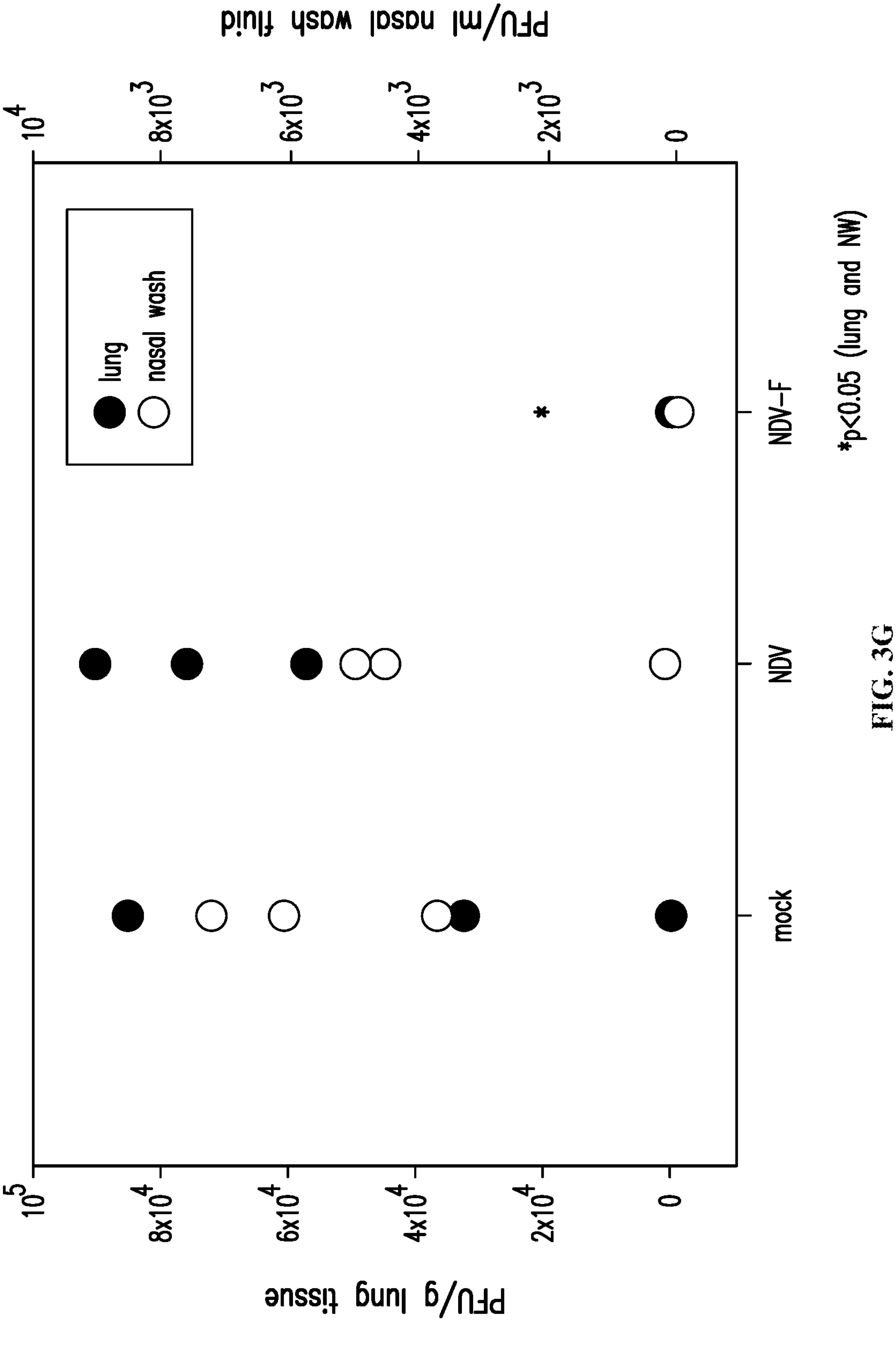

Viral load following challenge was assayed by immunohistochemistry (IHC) and by plaque assay. IHC staining with a polyclonal antiviral serum revealed diffuse RSV antigen staining in the nasal cavities and small foci of infected cells in the lower airways of mock and NDV vaccinated animals. In contrast, only rare RSV antigen positive cells were detected in the nasal cavities of the rNDV-F vaccinated cotton rats, and none in the lower airways of the immunized animals (FIGS. 3A-3F). In support of IHC findings, viable virions were not detected by plaque assay of nasal mucosa and lung collected from animals that had received rNDV-F vaccination prior to RSV challenge (FIG. 3G).

Following a second RSV challenge delivered 6 months after the first RSV challenge of mock-vaccinated or rNDV-F vaccinated animals, lung and nasal tissues were collected. IHC of nasal cavity and lung collected 4 days after secondary RSV challenge revealed rare, scattered antigen-positive cells in the nasal mucosa of cohorts primed with allantoic fluid or NDV vector only. No RSV antigen was detected in the lungs or nasal cavities of rNDV-F vaccinated animals. Plaque assay of nasal cavity mucosa and lung tissues collected after secondary RSV challenge was negative in all animals (not shown).

6.1.2.3 rNDV-F Vaccination Induces a Long-Lived Mucosal Antibody Response

Serum, bronchoalveolar lavage (BAL) fluid and nasal wash (NW) fluid were collected at multiple time points after vaccination and RSV challenge for determination of RSV F-specific IgG levels by ELISA (FIG. 4). rNDV-F vaccination induced robust, F-specific IgG responses that were boosted following RSV challenge and then maintained at high levels. While serum antibody levels were similar amongst cohorts 1-2 months after RSV challenge, mucosal F-specific antibody responses remained significantly elevated in BAL and NW fluid samples collected from rNDV-F vaccinated animals compared to controls up to 6 months after RSV infection, the latest time point examined. Serum neutralization, assayed by plaque reduction, demonstrated that antibodies produced in response to rNDV-F vaccination were neutralizing (FIG. 4D).

Cervical lymph nodes were collected 4 days or 5 months after RSV challenge of mock and rNDV-F primed and boosted animals, and RSV F-specific IgG antibody secreting cells (ASCs) were enumerated by ELISpot (FIG. 4E). While a response was not detected, or was minimal, by cells harvested from cervical lymph nodes of mock or NDV vaccinated animals, robust F-specific ASC responses were observed in cervical lymph nodes collected from rNDV-F vaccinated animals at both the 4 day and 5 month time points. This is a significant finding given the short-lived mucosal protection that follows natural infection, and the importance of augmenting this protection by any RSV vaccine candidate [5]. Reagents to assay IgA in the cotton rat model are not yet available.

6.1.2.4 rNDV-F Vaccination Prevents Eosinophilic Lung Inflammation

The cellularity of BAL fluid collected at multiple time points after vaccination and RSV challenge was determined by cell counts, and evaluated for cell type by examination of Wright-Giemsa stained cytospin preparations (FIGS. 5A and 5B). While vaccination alone did not increase total BAL fluid cellularity, a small, but not statistically significant, increase in total BAL fluid cellularity was detected in all cohorts after primary RSV challenge. After secondary RSV infection this increase in cellularity was again detected in BAL fluid collected from animals that had been vaccinated with allantoic fluid or NDV vector alone, but not present in BAL fluids collected from rNDV-F vaccinated animals.

As previously described [7], eosinophils are present in the lungs of naïve cotton rats, in the absence of pulmonary pathology, and the composition of the BAL fluid was not altered by vaccination alone. Consistent with these prior observations, eosinophils were significantly increased one month after primary RSV challenge of control animals [7], but this increase did not occur in animals vaccinated with rNDV-F (FIG. 5). The number of pulmonary eosinophils decreased nearly to baseline 2 months after primary RSV infection, but rose again in response to secondary RSV challenge of control animals that had received only allantoic fluid or NDV vector. This increase in BAL eosinophils following secondary RSV infection, while striking, did not reach statistical significance (p=0.06). Thus, in the cotton rat model, rNDV-F vaccination confers long-lasting protection, but also inhibits eosinophilic inflammation in response to RSV infection and reinfection.

6.1.2.5 Immunization of RSV-Immune Animals

Figure 6:
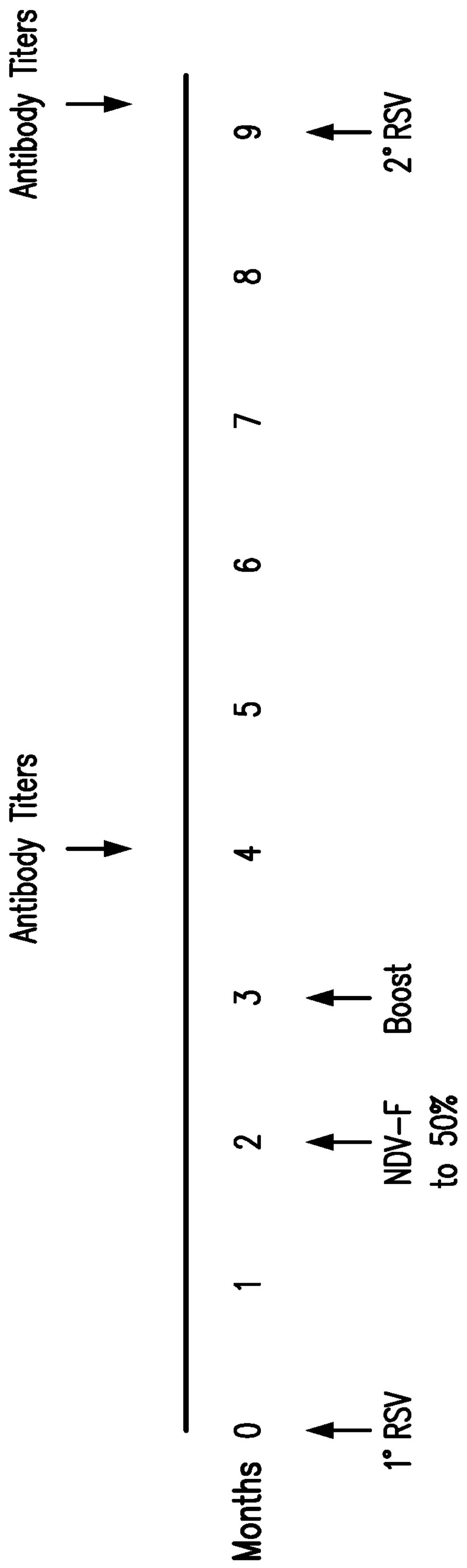

Based on the vaccination strategy wherein the RSV F protein is expressed only in rNDV-F infected cells, it was hypothesized that it might be possible to immunize animals previously exposed to RSV. To test this possibility, 20 cotton rats were infected with RSV, and half of these were immunized with $10^6$ pfu of rNDV-F administered i.n. at 2 months, and again at 3 months, after primary RSV infection (FIG. 6). The 2 month time point for vaccination was chosen to ensure that RSV F protein specific antibodies would be present in serum and at the mucosal surface of the respiratory tree (see FIG. 4). Serum antibody titers were determined at 4 months, and again at 9 months after primary RSV infection as outlined in FIG. 6. All remaining animals were re-challenged with RSV at the 9 month time point, and no virus was detected in the lungs or noses of animals in either cohort at 2 or 4 days post virus instillation.

RSV F-specific IgG levels in all animals were measured by an F-protein specific ELISA assay which demonstrated an approximately 3-fold increase in animals that had received rNDV-F (1/2500 versus 1/7500), a level maintained for 6 months after the boosting dose of vaccine was administered (FIG. 7B). Neutralizing antibody was assessed by incubating serum samples with rg-RSV, a recombinant virus expressing eGFP [8], and determining % of Vero cell infection by flow cytometry. The result of this assay is shown in FIG. 7A, demonstrating an enhancement of neutralizing antibody in animals immunized with rNDV-F in the presence of RSV-neutralizing antibody, an enhancement which remained stable at the 9 month time point. This study suggests that, in addition to the ability of this vaccine to give long-lasting protection, rNDV-F is also efficacious in those with pre-existing antibody.

6.1.3 Discussion

The data presented in this example demonstrates that a Newcastle disease virus vectored RSV vaccine, designed to stimulate robust IFN production simultaneous with RSV F protein presentation to the immune system, protects against RSV infection and induces a long-lived humoral immune response. Delivery of a protective dose of rNDV-F was not associated with adverse histopathology. Lymphoplasmacytic infiltrates observed in immunized animals in response to the boosting rNDV-F dose and subsequent challenge are consistent with an appropriate adaptive immune response (FIG. 1). Additionally, the increase in lung eosinophils detected in cotton rats that been mock vaccinated prior to primary and secondary RSV challenge was not detected in the lungs of rNDV-F vaccinated cotton rats. This finding is of particular interest when considered in light of mounting evidence that severe RSV lung disease during infancy is associated with asthma and recurrent wheezing later in childhood [1-4].

As shown here, the eosinophilic response to RSV infection in the cotton rat was abrogated by rNDV-F vaccination. Without being bound by any theory, the adjuvant effect of the type I IFN induction, in addition to the prolongation of antibody responses by the rNDV-F vaccines described in this example, may also decrease $T_H2$ responses to inhaled allergens encountered during RSV infections in young children.

RSV-specific secretory and serum antibodies have been correlated with protection of the upper and lower airways, respectively, against re-infection with RSV [9, 10]. A recent study suggests that the ability of this virus to re-infect immunocompetent adults is correlated with a defect in B cell memory. Neutralizing serum and nasal antibody levels in experimentally infected healthy adult volunteers increased post-infection, but returned to baseline levels 6 months later [5]. This differs markedly from the lifelong persistence of influenza specific IgG that follows this infection [11]. Thus, it is essential that any RSV vaccine candidate induce both systemic and mucosal RSV-specific antibodies, but do so in a manner that induces a B cell memory response superior to that induced by RSV infection. It is this requirement that recommends consideration of a vectored RSV vaccine.

In this example, rNDV-F vaccination induced serum and mucosal F-specific antibodies that were maintained for at least 7 months. Importantly, the mucosal F-specific antibody response, which correlates most closely with protection against reinfection [5], was more robust and longer lived in rNDV-F immunized cotton rats than that induced by RSV infection alone. The ability of NDV-F to boost neutralizing antibody titers in RSV seropositive animals indicates that vaccination of older children and adults may provide an avenue for protecting a population while avoiding the difficulties associated with vaccination of young infants.

6.1.4 REFERENCES CITED IN THIS EXAMPLE 6.1

1. Korppi M, Piippo-Savolainen E, Korhonen K, Remes S. Respiratory morbidity 20 years after RSV infection in infancy. Pediatric pulmonology. 2004; 38(2):155-60. Epub 2004/06/24. doi: 10.1002/ppul.20058. PubMed PMID: 15211700.

2. Pelaia G, Vatrella A, Gallelli L, Renda T, Cazzola M, Maselli R, et al. Respiratory infections and asthma. Respiratory medicine. 2006; 100(5):775-84. Epub 2005/11/18. doi: 10.1016/j.rmed.2005.08.025. PubMed PMID: 16289785.
3. Sigurs N, Bjarnason R, Sigurbergsson F, Kjellman B. Respiratory syncytial virus bronchiolitis in infancy is an important risk factor for asthma and allergy at age 7. American journal of respiratory and critical care medicine. 2000; 161(5):1501-7. Epub 2000/05/12. PubMed PMID: 10806145.
4. Sigurs N, Gustafsson P M, Bjarnason R, Lundberg F, Schmidt S, Sigurbergsson F, et al. Severe respiratory syncytial virus bronchiolitis in infancy and asthma and allergy at age 13. American journal of respiratory and critical care medicine. 2005; 171(2):137-41. Epub 2004/11/02. doi: 10.1164/rccm.200406-7300C. PubMed PMID: 15516534.
5. Habibi M S, Jozwik A, Makris S, Dunning J, Paras A, DeVincenzo J P, et al. Impaired Antibody-mediated Protection and Defective IgA B-Cell Memory in Experimental Infection of Adults with Respiratory Syncytial Virus. American journal of respiratory and critical care medicine. 2015; 191(9):1040-9. doi: 10.1164/rccm.201412-2256OC. PubMed PMID: 25730467; PubMed Central PMCID: PMCPMC4435460.
6. Martinez-Sobrido L, Gitiban N, Fernandez-Sesma A, Cros J, Mertz S E, Jewell N A, et al. Protection against respiratory syncytial virus by a recombinant Newcastle disease virus vector. Journal of virology. 2006; 80(3): 1130-9. Epub 2006/01/18. doi: 10.1128/JVI.80.3.1130-1139.2006. PubMed PMID: 16414990; PubMed Central PMCID: PMC1346968.
7. Grieves J L, Yin Z, Durbin R K, Durbin J E. Acute and Chronic Airway Disease After Human Respiratory Syncytial Virus Infection in Cotton Rats (*Sigmodon hispidus*). Comp Med. 2015; 65(4):315-26. PubMed PMID: 26310461; PubMed Central PMCID: PMCPMC4549677.
8. Hallak L K, Collins P L, Knudson W, Peeples M E. Iduronic acid-containing glycosaminoglycans on target cells are required for efficient respiratory syncytial virus infection. Virology. 2000; 271(2):264-75. doi: 10.1006/viro.2000.0293. PubMed PMID: 10860881.
9. Shinoff J J, O'Brien K L, Thumar B, Shaw J B, Reid R, Hua W, et al. Young infants can develop protective levels of neutralizing antibody after infection with respiratory syncytial virus. The Journal of infectious diseases. 2008; 198(7):1007-15. Epub 2008/08/16. doi: 10.1086/591460. PubMed PMID: 18702606.
10. Walsh E E, Falsey A R. Humoral and mucosal immunity in protection from natural respiratory syncytial virus infection in adults. The Journal of infectious diseases. 2004; 190(2):373-8. Epub 2004/06/25. doi: 10.1086/421524. PubMed PMID: 15216475.
11. Fujimoto C, Takeda N, Matsunaga A, Sawada A, Tanaka T, Kimoto T, et al. Induction and maintenance of anti-influenza antigen-specific nasal secretory IgA levels and serum IgG levels after influenza infection in adults. Influenza Other Respir Viruses. 2012; 6(6):396-403. doi: 10.1111/j.1750-2659.2011.00330.x. PubMed PMID: 22226319; PubMed Central PMCID: PMCPMC4941696.
12. Durbin J E, Hackenmiller R, Simon M C, Levy D E. Targeted disruption of the mouse Stat1 gene results in compromised innate immunity to viral disease. Cell. 1996; 84(3):443-50. Epub 1996/02/09. PubMed PMID: 8608598.
13. Gitiban N, Jurcisek J A, Harris R H, Mertz S E, Durbin R K, Bakaletz L O, et al. Chinchilla and murine models of upper respiratory tract infections with respiratory syncytial virus. Journal of virology. 2005; 79(10):6035-42. Epub 2005/04/29. doi: 10.1128/JVI.79.10.6035-6042.2005. PubMed PMID: 15857989; PubMed Central PMCID: PMC1091680.
14. Chaiwatpongsakorn S, Epand R F, Collins P L, Epand R M, Peeples M E. Soluble respiratory syncytial virus fusion protein in the fully cleaved, pretriggered state is triggered by exposure to low-molarity buffer. Journal of virology. 2011; 85(8):3968-77. doi: 10.1128/JVI.01813-10. PubMed PMID: 21307202; PubMed Central PMCID: PMCPMC3126149.

6.2 Example 2: Optimized Recombinant Ndv Constructs

This example demonstrates the production of optimized recombinant NDV constructs. In particular, the example demonstrates the enhanced expression of RSV F protein by the optimized recombinant NDV constructs.

6.2.1 Materials & Methods 6.2.1.1 Generation of Recombinant Newcastle Disease Virus (rNDV) Expressing the F Protein of Human Respiratory Syncytial Virus.

The generation and characterization of the first version of rNDV-RSV-F has been described in detail in reference Martinez-Sobrido et al. (Journal of virology. 2006; 80(3): 1130-9). This first version will be referred here as rNDV-F. Briefly, the sequence coding for the F protein of RSV (strain Long) was inserted in the cDNA of the full length genome of NDV strain Hitchner B1 (a non-virulent vaccine strain of NDV), between the P and M genes. The inserted sequence contained NDV gene end and gene start sequences to make it a functional transcription unit, and a Kozak sequence for efficient translation.

The plasmid obtained was used to rescue an infectious rNDV-F following a well-established protocol that has been recently described in Ayllon et al. (J Vis Exp. 80:50830 (2013)). The next versions of rNDV—RSV-F were prepared in a similar way, but using a full length cDNA of NDV vaccine strain LaSota and a codon optimized sequence of the RSV-F protein. The codon optimized sequence was purchased from Genewiz (see the website for Genewiz) and used to generate 2 different versions of rNDV-RSV-F that will be referred here as rNDV-Fopt and rNDV-F$_{chim}$ and are described in detail in the following paragraphs. NDV-Fopt was generated in a similar way to the original rNDV-F. The synthetic, codon optimized, sequence of RSV-F was used as template to PCR amplify an insert that contained the F open reading frame flanked by the necessary restriction sites, gene end and gene start regulatory sequences, and a Kozak sequence for efficient translation. The codon-optimized sequence of RSV-F sequence is shown in SEQ ID NO:2. The PCR product was directly cloned into the plasmid containing the full length NDV cDNA, between the P and M genes, and used to rescue an infectious rNDV-Fopt as previously described. The full length NDV cDNA sequence of the NDV strain LaSota with the codon-optimized RSV-F sequence inserted is shown in SEQ ID NO:3.

rNDV-F$_{chim}$ was designed to express a chimeric F protein with the transmembrane and cytoplasmic domains of the RSV F protein replaced by the corresponding sequences of the NDV F protein. The rationale for this was that the chimeric F protein is predicted to be efficiently incorporated in the envelope of the viral particle and result in better immunogenicity. To obtain the rescue plasmid for rNDV-$F_{chim}$ we proceeded in two steps, summarized in FIG. 8. First, the codon optimized synthetic sequence was used as template to PCR amplify the ectodomain, flanked by the appropriate restriction sites and Kozak sequence. The PCR product was cloned into plasmid pShuttle LaSota that contained the required gene end and gene start sequences, as well as the sequence coding for the transmembrane and cytoplasmic domains of the NDV F protein. The fusion in frame of the RSV-F ectodomain and rNDV-F transmembrane and cytoplasmic domains resulted in the chimeric F protein. In the second step, after sequence confirmation, the insert in plasmid pShuttle LaSota was excised and cloned into the plasmid containing the full length NDV cDNA, between the P and M genes, and used to rescue the infectious rNDV-chimF. The chimeric RSV-F sequence is shown in SEQ ID NO:4. The full length NDV cDNA sequence of the NDV strain LaSota with the codon-optimized RSV-F sequence inserted is shown in SEQ ID NO:5. A schematic representation of the different rNDV-F, rNDV-$F_{opt}$, rNDV-$F_{chim}$ are shown in FIG. 9.

6.2.1.2 Animals 6-10 week old female cotton rats (*Sigmodon hispidus*) were used in this study (Sigmovir Biosystems, Inc., Bethesda, MD, USA). Animals were housed in groups of 3 in a BSL 2 facility and were offered a commercial pelleted rat chow and water ad libitum. Animals were acclimated for 7 to 10 days prior to vaccination or viral challenge. Animal housing and experimental procedures were approved by the Institutional Animal Care and Use Committee at the New York University School of Medicine and the Rutgers—New Jersey Medical School. All procedures used here were conducted humanely. Data were collected from 3-5 cotton rats per cohort per time point, unless otherwise specified.

6.2.1.3 Vaccination

NDV-F was constructed as previously described (33) then amplified in 10-day-old embryonated chicken eggs. While under isoflurane anesthesia, cotton rats were intranasally (i.n.) vaccinated with $1\times10^6$ pfu NDV-F, $1\times10^6$ pfu NDV vector alone, or allantoic fluid as a mock control in a 100 µl total volume divided equally between nares. Twenty-eight days after the priming vaccination, cotton rats were boosted in the same manner.

6.2.1.4 RSV Challenge

Human RSV strain A2, originally obtained from ATCC (VR-1540), was passaged on murine $STAT1^{-/-}$ fibroblast monolayers as previously described (54). The challenge dose of $1\times10^6$ pfu RSV was instilled into the nasal cavities of cotton rats under isoflurane anesthesia in a 50 µl total volume, divided equally between nares. The inoculum was delivered slowly, over approximately 15 seconds, to restrict initial virus infection to the upper airway.

6.2.1.5 Plaque Assay

Cotton rats were euthanized by $CO_2$ asphyxiation, and lungs were collected immediately after euthanasia and stored at −80° C. until use in viral plaque assay. Viral plaque assay was performed on murine STAT1−/−fibroblast monolayers as previously described (Gitiban et al., Journal of Virology 2005; 79(10):6035-42).

6.2.1.6 Flow Cytometry Assay

With respect to the data shown in FIG. 18: Vero cells growing in 6 well plates were infected with dilutions of the viral stocks by adding 250 µl of virus diluted in PBS per well. After 1 h adsorption, 2 ml of complete medium (DMEM supplemented with 1% antibiotics and 10% fetal bovine serum) was added per well and cells were incubated at 37° C. in a CO2 incubator. At 24 h post infection cells were resuspended by trypsin treatment and fixed with 4% formaldehyde for 30 min. at room temperature. After fixation, approximately $10^5$ cells (1/10 of the sample) were labelled with RSV F specific humanized monoclonal antibody Synagis followed by fluorescently labelled anti-human secondary antibody. Fluorescently labelled cells were detected using a flow cytometer Canto II.

With respect to the data shown in FIGS. 9A-9B: Serum samples at a 1/800 dilution were incubated with rg-RSV [37] at a concentration of $3\times10^5$ pfu/ml. in DMEM+5% fetal calf serum for 1 hour at 37° C. The serum-virus mixture was then used to inoculate, in duplicate, monolayers of Vero cells ($10^5$ cells plated in 2 cm2 wells). After a 20 hour incubation, cells were resuspended and analyzed by flow cytometry. Only infected cells will express gfp. Percent neutralization was calculated as 100 (1−fs/f0) where fs=fraction of gfp+ cells in the sample, and f0=the fraction of gfp+ cells in the no-serum control.

6.2.1.7 Rt-PCR and Immunofluorescence Assay

RT-PCR: Viral RNA was purified from the viral stocks using the kit E.Z.N.A. viral RNA kit (OMEGA bio-tek) and conditions recommended by the manufacturer. 5 µl of purified RNA were used as template in a 50 µl RT-PCR reaction using the kit Superscript III high-fidelity RT-PCR kit (Invitrogen, 12574-035) and the following primers specific for NDV genome sequences flanking the insert site. pNDV/3102+5'-CTGTCCACTCGGCATCACAC-3' (SEQ ID NO:62) and pNDV/3231-5'-CTAGATTAATTACGGT-TACGC-3' (SEQ ID NO:63). The amplified band was purified from an agarose gel using the kit E.Z.N.A. gel extraction kit (OMEGA bio-tek) and sequenced using the same primers.

Immunofluorescence Microscopy: Vero cells growing in 96 well plates were infected with dilutions of the viral stocks by adding 50 µl of virus diluted in PBS per well. After 1 h adsorption, 200 µl of complete medium (DMEM supplemented with 1% antibiotics and 10% fetal bovine serum) was added per well and cells were incubated at 37° C. in a C02 incubator. At 24 h post infection cells were fixed with 4% formaldehyde for 30 min. at room temperature and then labelled with RSV F specific humanized monoclonal antibody Synagis and/or NDV specific mouse serum, followed by fluorescently labelled anti-human and/or anti-mouse secondary antibodies. Fluorescently labelled cells were observed and photographed in a fluorescent microscope.

6.2.1.8 RSV-F Specific ELISA

Purified RSV F glycoprotein, whose transmembrane anchor was replaced with a 6His tag (SEQ ID NO:61), was produced by transfection of HEK293F cells and purified as described (56). For RSV F-specific ELISA, Nunc maxisorb immunoplates (ThermoScientific, Waltham, MA, USA) were coated overnight at 4° C. with 0.3 µg purified F protein diluted in 0.1M sodium carbonate buffer. Plates were washed with PBS containing 0.05% Tween 20 (PBS-T) then blocked with PBS containing 10% fetal calf serum (PBS-F). Plates were washed with PBS-T then samples, serially diluted in PBS-F, were added followed by incubation at 25° C. for 60 minutes. Wells were washed with PBS-T and secondary antibody diluted in PBS-F was added (chicken anti-cotton rat IgG, Immunology Consultants Laboratory, Inc., Portland, OR, USA). Plates were incubated at 25° C. for 60 minutes. After washing with PBS-T, tertiary antibody diluted in PBS-F was added (goat anti-chicken IgG conjugated to HRP, Southern Biotech, Birmingham, AL, USA). Following a second incubation at 25° C. for 60 minutes, plates were again washed with PBS-T followed by the addition of tetramethylbenzidine peroxidase substrate (ScyTek, Logan, UT, USA). After incubation at 25° C. for 30 minutes, the reaction was stopped by addition of 2N $H_2SO_4$. Absorbance at 450 nm ($A_{450}$) was determined using an Epoch Microplate Spectrophotomer (BioTek, Winooki, VT, USA). Titers were defined as the highest dilution of the sample resulting in $A_{450}$ four-fold greater than background (PBS-F alone).

6.2.1.9 RSV Neutralization Assay

The potent RSV neutralizing monoclonal antibody Synagis® (concentration 100 mg/ml) was serially diluted in tissue culture medium (DMEM supplemented with 1% fetal bovine serum and 1% antibiotics). Dilutions tested were 1:1000, 1:5000, 1:25000, 1:125000, 1:625000, as indicated in FIGS. 14 and 15.

Next, the antibody dilutions were distributed in 96 well plates, (50 µl per well), and the indicated viruses were added, in duplicate rows (see table below). Viral stocks were diluted in tissue culture medium to give an approximate titer of $10^2$-$10^3$ infectious particles per 50 µl. Virus and antibody dilutions were mixed by pipetting up and down and incubated at 37° C. for 2 h. After the 2 h incubation, 100 µl of medium containing $10^4$ cells was added to each well and the plates were incubated at 37° C. for 24 h. For the RSV-GFP virus cells were the HEp2 cell line, for all the recombinant NDVs we used Vero cells.

At 24 h post infection cells were fixed with 10% paraformaldehyde in PBS for 15 minutes at room temperature and then overlaid with 1×PBS.

Cells infected with GFP expressing viruses (RSV-GFP and NDV-GFP) were visualized directly by fluorescence microscopy. For the recombinant NDV viruses, infected cells were visualized by immuno-fluorescence using a commercial monoclonal antibody that recognizes the NDV HN protein followed by a fluorescent anti-mouse secondary antibody. Representative microscopic fields were photographed to prepare FIGS. 14 and 15.

RSV-F. After rescue, all of the recombinant NDVs were amplified by inoculation in 8-10 old embryonated chicken eggs and characterized by RT-PCR and immunofluorescence (FIG. 13).

While inflammation is a necessary adjuvant in any vaccination strategy, it is important to limit inflammation in the respiratory tree when the vaccine is administered by the intranasal route. Both primary immunization and challenge with the optimized constructs, rNDV-$F_{opt}$ and rNDV-$F_{chim}$, showed a decreased acute inflammatory response when compared with the original rNDV-F construct. In addition, the optimized constructs, rNDV-$F_{opt}$ and rNDV-$F_{chim}$, show enhanced RSV F protein expression (FIG. 10). Expression of the RSV F protein is enhanced in both NDV-$F_{opt}$ and NDV-$F_{chim}$ when compared with the original NDV-F construct. With being bound by any theory, it is possible that the relative reduction in RSV-F protein expression in the original NDV-F is related to the instability of the original rNDV-F construct. Initial observations indicate that the optimized constructs, NDV-$F_{opt}$ and NDV-$F_{chim}$, appear to be much more stable than the original rNDV-F construct. The initial observations indicate that the original rNDV-F construct loses the RSV sequence upon passage.

Cotton rats were mock treated or given priming and boosting doses of NDV, rNDV-F, rNDV-$F_{opt}$ or rNDV-$F_{chim}$. Following RSV challenge, no RSV was detected in lung homogenates from animals receiving either rNDV-$F_{opt}$ or rNDV-$F_{chim}$. Thus, the administration of rNDV-$F_{opt}$ and rNDV-$F_{chim}$ prior to challenge with RSV infection inhibited RSV replication. The administration of rNDV-Fopt to cotton rats resulted in a better protection against RSV challenge than administration rNDV-F to cotton rats.

Another important measure of efficacy is the longevity of antibody protection. To determine whether rNDV-$F_{opt}$ and rNDV-$F_{chim}$ could also induce long-lived RSV-F specific antibody, animals were given allantoic fluid, rNDV vector, rNDV-$F_{opt}$ or rNDV-$F_{chim}$, boosted one month later, and challenged with RSV on day 0. Serum samples were taken at day—31, and days 6, 13, 91 and 147 post-RSV challenge. The data in FIG. 12 demonstrates that the optimized constructs, unlike natural infection, can induce high titers of

TABLE 2 distribution of virus and antibody dilutions in the plate. Each virus was added to two replicate rows.

| | dilution 1:1000 | dilution 1:5000 | dilution 1:25000 | dilution 1:125000 | dilution 1:625000 | no antibody |
|---|---|---|---|---|---|---|
| RSV-GFP[1] | | | | | | |
| NDV-GFP[2] | | | | | | |
| NDV-F[3] | | | | | | |
| NDV-Fopt[4] | | | | | | |
| NDV-Fchim[5] | | | | | | |
| NDV-LaSota wt[6] | | | | | | |
| NDV-boFopt[7] | | | | | | |
| NDV-boFchim[8] | | | | | | |

[1]SV-GFP: recombinant RSV expressing the Green Fluorescent Protein, kindly provided by Dr. Megan Shaw (Mount Sinai). Positive control for neutralization.
[2]NDV-GFP: recombinant NDV (strain LaSota) expressing the Green Fluorescent Protein. Negative control for neutralization.
[3]NDV-F: original recombinant NDV (strain Hitchner B1) expressing the wild type version of the human RSV F protein.
[4]NDV-Fopt: recombinant NDV (strain LaSota) expressing a codon optimized full length version of the human RSV F protein.
[5]NDV-Fchim: recombinant NDV (strain LaSota) expressing a codon optimized chimeric version of the human RSV F protein ectodomain fused to the transmembrane and cytoplasmic domains of the NDV F protein.
[6]NDV-LaSota wt: recombinant NDV with no insert. Negative control for neutralization.
[7]NDV-boFopt: recombinant NDV (strain LaSota) expressing a codon optimized full length version of the bovine RSV F protein.
[8]NDV-boFchim: recombinant NDV (strain LaSota) expressing a codon optimized chimeric version of the bovine RSV F protein ectodomain fused to the transmembrane and cytoplasmic domains of the NDV F protein.

6.2.2 Results

Optimized versions of the rNDV-F construct have been produced as described in Section 6.2.1.1. These constructs are named rNDV-$F_{opt}$ and rNDV-$F_{chim}$. FIG. 9 summarizes the main differences in the 3 recombinant NDVs expressing RSV F specific antibody that persist for 6 months after immunization. Titers are boosted by virus challenge, while protecting the host from infection, in the absence of disease.

To assess the ability of Synagis®, a monoclonal antibody that binds to RSV F protein, to neutralize the recombination NDV constructs. As shown in FIG. 14, the recombinant RSV-GFP was neutralized by Synagis®, but NDV-GFP was not inhibited. Similarly, the recombinant NDV constructs, rNDV-F, rNDV-Fopt, and rNDV-Fchim as well as wild-type NDV were not neutralized by Synagis® (FIG. 15). For all the recombinant NDVs, no reduction in the percentage of infected cells at any of the dilutions tested was observed.

6.3 Example 3: Stability Assays for Recombinant NDV Constructs

Stability of the recombinant NDVs expressing the F protein of RSV is evaluated by the ability to retain expression of the inserted gene after passage in eggs. The percentage of viruses retaining RSV-F expression is measured by simultaneous detection of the NDV protein HN and the RSV F protein by double immunofluorescence in cells infected with the different passages.

Based on initial observations, the optimized versions (rNDV-$F_{opt}$ and rNDV-$F_{chim}$) will retain a high percentage of cells with double labelling, while the original version (rNDV-F) will lose expression of the F protein in a high percentage of the infected cells after a few passages.

Viruses rNDV-F, rNDV-$F_{opt}$ and rNDV-$F_{chim}$ are inoculated in triplicate at a 1:10000 dilution in chicken embryonated eggs (100 μl per egg). At 3 days post-infection the allantoic fluid is harvested, evaluated for hemagglutination and used to inoculate new eggs at 1:10000 dilution, as described above. This strategy is repeated for several passages.

Serial dilutions of the harvested allantoic fluids is used to infect Vero cells in 96 well plates. At 24 hours post infection cells are fixed and co-stained with a commercial mouse monoclonal antibody that recognizes the NDV HN protein and a humanized monoclonal antibody that recognize the RSV-F protein. Single and doubly labelled cells are quantified using a fluorescence plate reader (Celigo).

6.4 Example 4: Recombinant NDV Encoding Bovine RSV F Protein 6.4.1 Materials & Methods 6.4.1.1 Generation of Recombinant Newcastle Disease Virus (rNDV) Expressing the F Protein of Human Respiratory Syncytial Virus.

6.4.1.2 RSV Neutralization Assay

This assay was performed as described in Section 6.2.1.9.

6.4.1.3 Generation of the Recombinant NDVs Expressing Bovine RSV F Proteins.

The generation of the recombinant NDVs (LaSota strain) expressing a full length codon optimized F protein from bovine RSV (strain ATCC51908) (see SEQ ID NO:11 for the codon optimized nucleic acid sequence encoding bovine RSV F protein) and a chimeric F protein with the codon optimized ectodomain from bovine RSV (strain ATCC51908) fused to the transmembrane and cytoplasmic domains of NDV (strain LaSota) (see SEQ ID NO:14 for the nucleic acid sequence encoding chimeric F protein) was performed as described for the construction of the recombinant NDVs expressing the full length and chimeric F proteins from human RSV, respectively.

6.4.1.4 Characterization of the Recombinant NDVs Expressing Bovine RSV F Proteins.

The presence of the inserted gene in the genome of the recombinant NDVs was confirmed by RT-PCR using viral RNA as template and primers flanking the insertion site. The amplified product was confirmed by sequencing.

Expression of the recombinant bovine RSV F proteins was confirmed by double immunofluorescence in Vero cells infected with the recombinant NDVs as described for the human RSV F expressing NDVs, using the same antibodies (monoclonal antibodies Synagis recognizes the F protein from both human and bovine RSV).

Absence of neutralization of the recombinant NDVs expressing bovine RSV F proteins by the potent RSV neutralizing Synagis antibody was performed as described for the recombinant NDVs expressing human RSV F proteins.

6.4.2 Results

To assess the ability of Synagis®, a monoclonal antibody that binds to RSV F protein, to neutralize the recombination NDV constructs. As shown in FIG. 14, the recombinant RSV-GFP was neutralized by Synagis®, but NDV-GFP was not inhibited. Similarly, the recombinant NDV constructs, rNDV-bovine RSV-Fopt, and rNDV-bovine RSV-Fchim as well as wild-type NDV were not neutralized by Synagis® (FIGS. 14 and 18). For all the recombinant NDVs, no reduction in the percentage of infected cells at any of the dilutions tested was observed.

6.5 Example 5: Recombinant NDV Encoding Human Metapneumovirus F Protein 6.5.1 Generation of the Recombinant NDVs Expressing Human Metapneumovirus F Proteins.

The generation of the recombinant NDVs expressing a full length codon optimized F protein from human MPV (strain CAN00-16) (see SEQ ID NO:18 for the codon optimized nucleic acid sequence encoding hMPV F protein) and a chimeric F protein with the codon optimized ectodomain from human MPV (strain CAN00-16) fused to the transmembrane and cytoplasmic domains of NDV (strain LaSota) (see SEQ ID NO:9 for the nucleic acid sequence encoding chimeric F protein) was performed as described for the construction of the recombinant NDVs expressing the full length and chimeric F proteins from human RSV, respectively.

6.5.2 Characterization of the Recombinant NDVs Expressing Human Metapneumovirus F Proteins.

The presence of the inserted gene in the genome of the recombinant NDVs was confirmed by RT-PCR using viral RNA as template and primers flanking the insertion site. The amplified product was confirmed by sequencing.

Expression of the human MPV F protein by the recombinant NDVs was confirmed by double immunofluorescence in Vero cells infected with the recombinant NDVs as described for the human RSV F expressing NDVs, using human monoclonal antibody MPE8 to detect huMPV F protein and a commercial mouse monoclonal antibody to detect the NDV HN protein.

7. Embodiments

Provided herein are the following exemplary embodiments:

1. A recombinant Newcastle disease virus (NDV) comprising a packaged genome comprising a transgene encoding a human respiratory syncytial virus ("RSV") F protein, wherein the transgene comprises an RNA sequence corresponding to the negative sense of the cDNA sequence of SEQ ID NO:2, 26, 28, or 30.

2. A recombinant NDV comprising a packaged genome comprising a transgene encoding a chimeric F protein, wherein the chimeric F protein comprises a human RSV F protein ectodomain and an NDV F protein transmembrane and cytoplasmic domains, wherein the transgene comprises an RNA sequence corresponding to the negative sense of the cDNA sequence of SEQ ID NO:4, 44, 45, or 46.

3. The recombinant NDV of embodiment 1, wherein the RSV F protein comprises the amino acid sequence set forth in SEQ ID NO:6.

4. The recombinant NDV of embodiment 2, wherein the chimeric F protein comprises the ectodomain of the amino acid sequence set forth in SEQ ID NO:7.

5. The recombinant NDV of embodiment 2 or 4, wherein the NDV virion comprises the chimeric F protein.

6. The recombinant NDV of embodiment 1 or 3, wherein the transgene is inserted between two transcription units of the packaged genome.

7. The recombinant NDV of embodiment 6, wherein the two transcription units of the packaged genome are the transcription units for the NDV P gene and the NDV M gene.

8. The recombinant NDV of embodiment 2, 4 or 5, wherein the transgene is inserted between two transcription units of the packaged genome.

9. The recombinant NDV of embodiment 8, wherein the two transcription units of the packaged genome are the transcription units for the NDV P gene and the NDV M gene.

10. The recombinant NDV of any one of embodiments 1 to 9 which comprises an NDV backbone which is lentogenic.

11. The recombinant NDV of any one of embodiments 1 to 9 which comprises an NDV backbone of LaSota strain.

12. The recombinant NDV of any one of embodiments 1 to 9 which comprises an NDV backbone of Hitchner B1 strain.

13. The recombinant NDV of embodiment 1 or 3, wherein the genome comprises a negative sense RNA sequence transcribed from the cDNA sequence set forth in SEQ ID NO:3.

14. The recombinant NDV of embodiment 2, 4 or 5, wherein the genome comprises a negative sense RNA sequence transcribed from the cDNA sequence set forth in SEQ ID NO:5.

15. An immunogenic composition comprising the recombinant NDV of any one of embodiments 1 to 14.

16. A method for inducing an immune response to RSV F protein, comprising administering the immunogenic composition of embodiment 15 to a subject.

17. A method for preventing an RSV disease, comprising administering the immunogenic composition of embodiment 15 to a subject.

18. A method for immunizing a subject against RSV, comprising administering the immunogenic composition of embodiment 15 to the subject.

19. The method of any one of embodiment 16 to 18, wherein the composition is administered to the subject intranasally.

20. The method of any one of embodiments 16 to 19, wherein the subject is seropositive for anti-RSV F antibodies.

21. The method of any one of embodiments 16 to 19, wherein the subject is seronegative for anti-RSV F antibodies.

22. The method of any one of embodiments 16 to 21, wherein the subject is a human.

23. The method of any one of embodiments 16 to 21, wherein the subject is a human infant six months old or older.

24. The method of any one of embodiments 16 to 21, wherein the subject is a human child.

25. The method of any one of embodiments 16 to 21, wherein the subject is a human adult or an elderly human.

26. A recombinant NDV comprising a packaged genome comprising a transgene encoding a bovine respiratory syncytial virus ("RSV") F protein.

27. The recombinant NDV of embodiment 26, wherein bovine RSV F protein comprises the amino acid sequence of SEQ ID NO:10.

28. The recombinant NDV of embodiment 26 or 27, wherein the transgene comprises an RNA sequence corresponding to the negative sense of the cDNA sequence of SEQ ID NO:9 or 11.

29. The recombinant NDV of embodiment 26, wherein the transgene comprises an RNA sequence corresponding to the negative sense of the cDNA sequence of SEQ ID NO:40, 41, 42, or 43.

30. A recombinant NDV comprising a packaged genome comprising a transgene encoding a chimeric F protein, wherein the chimeric F protein comprises a bovine RSV F protein ectodomain and an NDV F protein transmembrane and cytoplasmic domains.

31. The recombinant NDV of embodiment 30, wherein the transgene comprises an RNA sequence corresponding to the negative sense of the cDNA sequence of SEQ ID NO:14, 31, 38 or 39.

32. The recombinant NDV of embodiment 30, wherein the chimeric F protein comprises the ectodomain of the amino acid sequence set forth in SEQ ID NO:10.

33. The recombinant NDV of embodiment 30, wherein the chimeric F protein comprises the amino acid sequence set forth in SEQ ID NO:33.

34. The recombinant NDV of any one of embodiments 30 to 33, wherein the NDV virion comprises the chimeric F protein.

35. The recombinant NDV of any one of embodiments 26 to 29, wherein the transgene is inserted between two transcription units of the packaged genome.

36. The recombinant NDV of embodiment 35, wherein the two transcription units of the packaged genome are the transcription units for the NDV P gene and the NDV M gene.

37. The recombinant NDV of any one of embodiments 30 to 34, wherein the transgene is inserted between two transcription units of the packaged genome.

38. The recombinant NDV of embodiment 37, wherein the two transcription units of the packaged genome are the transcription units for the NDV P gene and the NDV M gene.

39. The recombinant NDV of any one of embodiments 26 to 38 which comprises an NDV backbone which is lentogenic.

40. The recombinant NDV of any one of embodiments 26 to 39 which comprises an NDV backbone of LaSota strain.

41. The recombinant NDV of any one of embodiments 26 to 39 which comprises an NDV backbone of Hitchner B1 strain.

42. The recombinant NDV of embodiment 26, wherein the genome comprises a negative sense RNA sequence transcribed from the cDNA sequence set forth in SEQ ID NO:12 or 13.

43. The recombinant NDV of embodiment 30, wherein the genome comprises a negative sense RNA sequence transcribed from the cDNA sequence set forth in SEQ ID NO: 37 or 59.

44. An immunogenic composition comprising the recombinant NDV of any one of embodiments 26 to 43.

45. A method for inducing an immune response to RSV F protein, comprising administering the immunogenic composition of embodiment 44 to a bovine subject.

46. A method for preventing an RSV disease, comprising administering the immunogenic composition of embodiment 44 to a bovine subject.

47. A method for immunizing a subject against RSV, comprising administering the immunogenic composition of embodiment 44 to the bovine subject.

48. The method of any one of embodiment 45 to 47, wherein the composition is administered to the subject intranasally.

49. The method of any one of embodiments 45 to 48, wherein the subject is seropositive for anti-RSV F antibodies.

50. The method of any one of embodiments 45 to 48, wherein the subject is seronegative for anti-RSV F antibodies.

51. A method for inducing an immune response to RSV F protein in a human subject seropositive for anti-RSV F antibodies, comprising administering to the subject a recombinant NDV, wherein the recombinant NDV comprises a packaged genome comprising a transgene, wherein the transgene encodes a human RSV F protein.

52. A method for preventing an RSV disease in a human subject seropositive for anti-RSV F antibodies, comprising administering to the subject a recombinant NDV, wherein the recombinant NDV comprises a packaged genome comprising a transgene, wherein the transgene encodes a human RSV F protein.

53. A method for immunizing a subject against RSV in a human subject seropositive for anti-RSV F antibodies, comprising administering to the subject a recombinant NDV, wherein the recombinant NDV comprises a packaged genome comprising a transgene, wherein the transgene encodes a human RSV F protein.

54. The method of any one of embodiments 51 to 53, wherein the human RSV F protein comprises the amino acid sequence set forth in SEQ ID NO:6, 49, 50 or 58.

55. The method of embodiment 54, wherein the transgene comprises an RNA sequence corresponding to the negative sense of the cDNA sequence set forth in SEQ ID NO:1 or 2.

56. The method of embodiment 54, wherein the transgene comprises a codon optimized nucleic acid sequence encoding the RSV F protein.

57. The method of any one of embodiments 51 to 53, wherein the transgene comprises an RNA sequence corresponding to the negative sense of the cDNA sequence set forth in SEQ ID NO: 25, 26, 27, 28, 29 or 30.

58. The method of any one of embodiments 53 to 57, wherein the transgene is inserted between two transcription units of the packaged genome.

59. The method of embodiment 58, wherein the two transcription units of the packaged genome are the transcription units for the NDV P gene and the NDV M gene.

60. The method of any one of embodiments 51 to 59, wherein the recombinant NDV comprises an NDV backbone which is lentogenic.

61. The method of any one of embodiments 51 to 59, wherein the recombinant NDV comprises an NDV backbone of LaSota strain.

62. The method of any one of embodiments 51 to 59, wherein the recombinant NDV comprises an NDV backbone of Hitchner B1 strain.

63. The method of any one of embodiments 51 to 54, wherein the genome comprises a negative sense RNA sequence transcribed from the cDNA sequence set forth in SEQ ID NO:3.

64. The method of any one of embodiments 51 to 63, wherein the composition is administered to the subject intranasally.

65. The method of any one of embodiments 51 to 64, wherein the human subject is an elderly human.

66. The method of any one of embodiments 51 to 64, wherein the human subject is a human adult.

67. The method of any one of embodiments 51 to 64, wherein the human subject is a human child.

68. A recombinant NDV comprising a packaged genome comprising a transgene encoding a human metapneumovirus ("hMPV") F protein.

69. The recombinant NDV of embodiment 68, wherein the hMPV F protein comprises the amino acid sequence set forth in SEQ ID NO: 17.

70. The recombinant NDV of embodiment 68 or 69, wherein the transgene comprises an RNA sequence corresponding to the negative sense of the cDNA sequence of SEQ ID NO:16 or 18.

71. The recombinant NDV of embodiment 68, wherein the transgene comprises an RNA sequence corresponding to the negative sense of the cDNA sequence of SEQ ID NO:52, 53, 54, 55, 56, or 57.

72. A recombinant Newcastle disease virus (NDV) comprising a packaged genome comprising a transgene encoding a chimeric F protein, wherein the chimeric F protein comprises an hMPV F protein ectodomain and an NDV F protein transmembrane and cytoplasmic domains.

73. The recombinant NDV of embodiment 72, wherein the chimeric F protein comprises the amino acid sequence of SEQ ID NO:15.

74. The recombinant NDV of embodiment 72, wherein the transgene comprises an RNA sequence corresponding to the negative sense of the cDNA sequence of SEQ ID NO: 19, 32, 34, 35 or 36.

75. The recombinant NDV of embodiment 72, 73 or 74, wherein the NDV virion comprises the chimeric F protein.

76. The recombinant NDV of any one of embodiments 68 to 71, wherein the transgene is inserted between two transcription units of the packaged genome.

77. The recombinant NDV of embodiment 76, wherein the two transcription units of the packaged genome are the transcription units for the NDV P gene and the NDV M gene.

78. The recombinant NDV of any one of embodiments 72 to 75, wherein the transgene is inserted between two transcription units of the packaged genome.

79. The recombinant NDV of embodiment 78, wherein the two transcription units of the packaged genome are the transcription units for the NDV P gene and the NDV M gene.

80. The recombinant NDV of any one of embodiments 68 to 79 which comprises an NDV backbone which is lentogenic.

81. The recombinant NDV of any one of embodiments 68 to 79 which comprises an NDV backbone of LaSota strain.

82. The recombinant NDV of any one of embodiments 68 to 78 which comprises an NDV backbone of Hitchner B1 strain.

83. The recombinant NDV of embodiment 68, wherein the genome comprises a negative sense RNA sequence transcribed from the cDNA sequence set forth in SEQ ID NO:20 or 21.

84. The recombination NDV of embodiment 72, wherein the genome comprises a negative sense RNA sequence transcribed from the cDNA sequence set forth in SEQ ID NO: 22.

85. An immunogenic composition comprising the recombinant NDV of any one of embodiments 68 to 84.

86. A method for inducing an immune response to hMPV F protein, comprising administering the immunogenic composition of embodiment 85 to a human subject.

87. A method for preventing an hMPV disease, comprising administering the immunogenic composition of embodiment 85 to a human subject.

88. A method for immunizing a subject against hMPV, comprising administering the immunogenic composition of embodiment 85 to a human subject.

89. The method of any one of embodiments 86 to 88, wherein the composition is administered to the subject intranasally.

90. The method of any one of embodiments 86 to 89, wherein the subject is seropositive for anti-hMPV F antibodies.

91. The method of any one of embodiments 86 to 89, wherein the subject is seronegative for anti-hMPV F antibodies.

92. The method of any one of embodiments 86 to 91, wherein the subject is a human infant.

93. The method of any one of embodiments 86 to 91, wherein the subject is an elderly human.

94. A kit comprising the recombinant NDV of any one of embodiments 1 to 14, 26 to 43, or 68 to 84.

95. A cell line or chicken embryonated egg comprising the propagating the recombinant NDV of any one of embodiments 1 to 14, 26 to 43, or 68 to 84.

96. A method for propagating the recombinant NDV of any one of embodiments 1 to 14, 26 to 43, or 68 to 84, the method comprising culturing the cell or embryonated egg of embodiment 95.

97. The method of embodiment 96, wherein the method further comprises isolating the recombinant NDV from the egg or embryonated egg.

The invention is not to be limited in scope by the specific embodiments described herein. Indeed, various modifications of the invention in addition to those described will become apparent to those skilled in the art from the foregoing description and accompanying Figures. Such modifications are intended to fall within the scope of the appended claims.

All references cited herein are incorporated herein by reference in their entirety and for all purposes to the same extent as if each individual publication or patent or patent application was specifically and individually indicated to be incorporated by reference in its entirety for all purposes.

What is claimed:

1. A recombinant Newcastle disease virus (NDV) comprising a packaged genome comprising (a) a transgene encoding a fusion (F) protein of a human virus of the family Pneumoviridae, wherein the transgene comprises (i) a ribonucleic acid (RNA) sequence corresponding to the negative sense of the complementary deoxyribonucleic acid (cDNA) sequence of SEQ ID NO: 2, 26, 28, or 30, or (ii) an RNA sequence corresponding to the negative sense of the cDNA sequence of SEQ ID NO: 18, 53, 55, or 57;

(b) a transgene encoding a chimeric protein comprising an ectodomain of a F protein of a human virus of the family Pneumoviridae and a transmembrane domain and a cytoplasmic domain of a NDV F protein, wherein:

(i) the human virus of the family Pneumoviridae is human respiratory syncytial virus ("RSV"), and the chimeric protein comprises the ectodomain of the amino acid sequence set forth in SEQ ID NO:7, (ii) the transgene comprises an RNA sequence corresponding to the negative sense of the cDNA sequence of SEQ ID NO: 19, 32, 34, 35, or 36, or (iii) the transgene comprises an RNA sequence corresponding to the negative sense of the cDNA sequence of SEQ ID NO: 4, 44, 45, or 46; or (c) a transgene encoding a bovine respiratory syncytial virus ("RSV") F protein, wherein the transgene comprises an RNA sequence corresponding to the negative sense of the cDNA sequence of SEQ ID NO: 11, 41, or 43; or (d) a transgene encoding a chimeric protein comprising a bovine Respiratory Syncytial Virus (RSV) F protein ectodomain and a transmembrane domain and a cytoplasmic domain of a NDV F protein, wherein:

(i) the chimeric protein comprises the amino acid sequence set forth in SEQ ID NO:33, or (ii) the transgene comprises an RNA sequence corresponding to the negative sense of the cDNA sequence of SEQ ID NO: 14, 31, 38, or 39.

2. The recombinant NDV of claim 1, wherein the human virus of the family Pneumoviridae is the RSV, and the chimeric protein comprises the ectodomain of the amino acid sequence set forth in SEQ ID NO:7.

3. The recombinant NDV of claim 1, wherein the genome comprises a negative sense RNA sequence transcribed from the cDNA sequence set forth in SEQ ID NO: 3, 5, 13, 37 or 59.

4. An immunogenic composition comprising the recombinant NDV of claim 1.

5. A method for inducing an immune response to an F protein of a human virus of the family Pneumoviridae in a subject, preventing a human virus of the family Pneumoviridae disease in a subject, or immunizing a subject against a human virus of the family Pneumoviridae, comprising administering the immunogenic composition of claim 4 to the subject.

6. The recombinant NDV of claim 1, wherein the chimeric protein comprises the amino acid sequence set forth in SEQ ID NO:33.

7. The recombinant NDV of claim 1, wherein the transgene comprises an RNA sequence corresponding to the negative sense of the cDNA sequence of SEQ ID NO: 11, 14, 31, 38, 39, 41, or 43.

8. A method for inducing an immune response to RSV F protein to a bovine subject, preventing an RSV disease in a bovine subject, or immunizing a bovine subject against RSV, the method comprising administering the immunogenic composition of claim 1 to the bovine subject.

9. A method for inducing an immune response to RSV F protein in a human subject seropositive for anti-RSV F antibodies, preventing an RSV disease in a human subject seropositive for anti-RSV F antibodies, or immunizing a subject against RSV in a human subject seropositive for anti-RSV F antibodies, the method comprising administering the immunogenic composition of claim 1 to the human subject.

10. The recombinant NDV of claim 1, wherein (a) the F protein of a human virus of the family Pneumoviridae is a human metapneumovirus ("hMPV") F protein; or (b) the ectodomain of a fusion (F) protein of a human virus of the family Pneumoviridae is a human metapneumovirus (hMPV) fusion (F) protein ectodomain.

11. The recombinant NDV of claim 10, wherein the transgene comprises an RNA sequence corresponding to the negative sense of the cDNA sequence of SEQ ID NO: 18, 53, 55, 57, 19, 32, 34, 35 or 36.

12. The recombinant NDV of claim 10, wherein the genome comprises a negative sense RNA sequence transcribed from the cDNA sequence set forth in SEQ ID NO: 21, or 22.

13. An immunogenic composition comprising the recombinant NDV of claim 10.

14. A method for inducing an immune response to hMPV F protein, preventing an hMPV disease, or immunizing a subject against hMPV, the method comprising administering the immunogenic composition of claim 13 to a human subject.

15. A cell line or chicken embryonated egg comprising the propagating the recombinant NDV of claim 1.

16. A method for propagating the recombinant NDV of claim 1, the method comprising culturing the cell or embryonated egg of claim 15.

17. The recombinant NDV of claim 1, wherein the transgene comprises an RNA sequence corresponding to the negative sense of the cDNA sequence of SEQ ID NO: 2, 26, 28, or 30.

18. The recombinant NDV of claim 1, wherein the transgene comprises an RNA sequence corresponding to the negative sense of the cDNA sequence of SEQ ID NO: 4, 44, 45, or 46.

* * * * *